US007255989B1

(12) United States Patent
Jeannin et al.

(10) Patent No.: US 7,255,989 B1
(45) Date of Patent: Aug. 14, 2007

(54) METHOD FOR OBTAINING NUCLEIC ACIDS FROM AN ENVIRONMENT SAMPLE, RESULTING NUCLEIC ACIDS AND USE IN SYNTHESIS OF NOVEL COMPOUNDS

(75) Inventors: Pascale Jeannin, Clamart (FR); Jean-Luc Pernodet, Cachan (FR); Michel Guerineau, Paris (FR); Pascal Simonet, Villeurbanne (FR); Sophie Courtois, Charenton le Pont (FR); Camela Cappellano, Fontenay sous Bois (FR); François Francou, Palaiseau (FR); Alain Raynal, Bures sur Yvette (FR); Maria Ball, Merida (VE); Guennadi Sezonov, Paris (FR); Karine Tuphile, Orsay (FR); Asa Frostegard, Nesoddtangen (NO)

(73) Assignee: Aventis Pharma S.A., Antony (FR)

( * ) Notice: Subject to any disclaimer, the term of this patent is extended or adjusted under 35 U.S.C. 154(b) by 382 days.

(21) Appl. No.: 10/148,328

(22) PCT Filed: Nov. 27, 2000

(86) PCT No.: PCT/FR00/03311

§ 371 (c)(1),
(2), (4) Date: Dec. 20, 2002

(87) PCT Pub. No.: WO01/40497

PCT Pub. Date: Jun. 7, 2001

Related U.S. Application Data

(60) Provisional application No. 60/209,800, filed on Jun. 7, 2000.

(30) Foreign Application Priority Data

Nov. 29, 1999 (FR) .................................. 99 15032

(51) Int. Cl.
*C12N 15/52* (2006.01)
*C12N 15/10* (2006.01)
*C12Q 1/68* (2006.01)

(52) U.S. Cl. ......................................... 435/6; 435/69.1

(58) Field of Classification Search ..................... None
See application file for complete search history.

(56) References Cited

U.S. PATENT DOCUMENTS

| | | | |
|---|---|---|---|
| 4,900,677 | A | 2/1990 | Hewitt |
| 5,688,689 | A | 11/1997 | Smokvina et al. |
| 5,824,485 | A | 10/1998 | Thompson et al. |

FOREIGN PATENT DOCUMENTS

| | | | |
|---|---|---|---|
| WO | WO 96/34112 | | 10/1996 |
| WO | WO96/34112 | * | 10/1996 |
| WO | WO 99/20799 | | 4/1999 |
| WO | WO 99/67374 | | 12/1999 |

OTHER PUBLICATIONS

Jacobsen CS and Rasmussen OF, "Development and application of a new method to extract bacterial DNA from soil based on separation of bacteria from soil with cation-exchange resin", Applied and Environmental 6Microbiology, 1992, p. 2458-62.*

Simonet P, et al. "Identification of Frankia strains in nodules by hybridization of polymerase chain reaction products with strain-specific oligonucleotide probes", 1990, Arch Microbiol, 153: 235-240.*

Ezaki, T. et al. "Achromopeptidase for lysis of anaerobic gram-positive cocci", J of Clin Micro. 1982, p. 844-846.*

Higuchi, R, et al. "A general method for cloning eukaryotic structural gene sequences", PNAS, 1976, vol. 73, p. 3146-3150.*

Ullrich, A. et al. "Rat insulin genes: construction of plasmids containing the coding sequences", 1977, 196(4296), p. 1313-1319.*

Bakken, LR, "Separation and purification of bacteria from soil", Applied and Environmental Microbiology, 1985, p. 1482-1487.*

Steffan RJ, et al. "Recovery of DNA from soils and sediments", Applied and Environmental Microbiology, 1988, p. 2908-2915.*

Nesme, H et al. "Specific DNA Sequences for detection of Soil Bacteria", Nucleic Acids in the Environment (Trevors, et al. Eds), Springer-Verlag, Heidelberg, 1995, p. 111-139.

Seow, K-T, et al. "A study of iterative Type II polyketide synthases: using bacterial genes cloned from soil DNA: a means to access and use genes from uncultured microorganisms" Journal of Bacteriology, 1997, p. 7360-7368.*

Nesme, H et al. "Specific DNA sequences for detection of Soil Bacteria", Nucleic Acids in the Environment (Trevors, et al., Eds), Springer-Verlag, Heidelberg, 1995, p. 111-139.*

Amann et al., Phylogenetic Identification and in Situ Detection of Individual Microbial Cells without Cultivation, *Microbiol. Rev.*, 59:143-169, 1995. *

Bakken, Separation and Purification of Bacteria from Soil, *Appl. Environ. Microbiol.*, 49: 1482-1487, 1985.

Clegg et al., Direct Extraction of Microbial Community DNA from Humified Upland Soils, *Lett. Appl. Microbiol.*, 25: 30-33, 1997.

(Continued)

*Primary Examiner*—Jeffrey Fredman
*Assistant Examiner*—Stephanie Mummert

(57) ABSTRACT

The invention concerns a method for preparing nucleic acids from an environment sample, more particularly a method for obtaining a library of nucleic acids from a sample. The invention also concerns nucleic acids of nucleic acid libraries obtained by said method their use in the synthesis of novel compounds, in particular novel compounds of therapeutic interest. The invent further concerns novel means used in the method for obtaining said nucleic acids, such as novel vectors and novel processes for preparing such vectors or recombinant host cells containing said nucleic acid. Finally, the invention concerns methods for detecting a nucleic acid of interest within a library of nucleic acids resulting from said method, and nucleic acids detected by said method and polypeptides encoded by said nucleic acids.

4 Claims, 39 Drawing Sheets

OTHER PUBLICATIONS

Clerc et al., Efficiency of The Transfer of a pSAM2-Derivative Plasmid between Two Strains of *Streptomyces lividans* in Conditions Ranging from Agar Slants to Non-Serile Soil Microcosms, *FEMS Microbilogy Ecology*, 21: 157-165, 1996.

Frostegärd et al., Microbial Biomass Measured as Total Lipid Phosphate In Soils of Different Organic Content, *J. Microbiol. Meth.*, 14: 151-163, 1991.

Frostegärd et al., Quantification of Bias Related to The Extraction of DNA Directly from Soils, *Appl. Environ. Microbiol.*, 65: 5409-5420, 1999.

Fu et al., Antibiotic Activity of Polyketide Products Derived from Combinatorial Biosynthesis: Implications for Directed Evolution, *Molecular Diversity*, 1: 121-124, 1995.

Holben et al., DNA Probe Method for the Detection of Specific Microorganisms in The Soil Bacterial Community, *Appl. Environ. Microbiol.*, 54: 703-711, 1988.

Jacobsen et al., Development and Application of a New Method To Extract Bacterial DNA from Soil Based on Separation of Bacteria from Soil with Cation-Exchange Resin, *Appl. Environ. Microbiol.*, 58: 2458-2462, 1992.

Kuske et al., Small-Scale DNA Sample Preparation Method for Field PCR Detection of Microbial Cells and Spores in Soil, *Appl. Environ. Microbiol.*, 64: 2463-2472, 1998.

Leff et al., Comparison of Methods of DNA Extraction from Stream Sediments, *Appl. Environ. Microbiol.*, 61: 1141-1143, 1995.

Liesack et al., Occurrence of Novel Groups of The Domain Bacteria as Revealed by Analysis of Genetic Material Isolated from An Australian Terrestrial Environment, *J. Bacteriol.*, 174: 5072-5078, 1992.

Liesack et al., Microbial Diversity in Soil: The Need for A Combined Approach Using Moleular and Cultivation Techniques, *in Modern Soil Microbiology* (van Elsas et al., Eds.), Marcel Dekker, Inc., New York, 1997, pp. 375-439.

Maidak et al., A New Version of the RDP (Ribosomal Database Project), *Nucleic Acids Research*, 27: 171-173, 1999.

Miller et al., Evaluation and Optimization of DNA Extraction and Purification Procedures for Soil and Ediment Samples, *Appl. Environ. Microbiol.*, 65: 4715-4724, 1999.

Moré et al., Quantitative Cell Lysis of Indigenous Microorganisms and Rapid Extraction of Microbial DNA from Sediment, *Appl. Environ. Microbiol.*, 60: 1572-1580, 1994.

Nesme et al., Specific DNA Sequences for Detection of Soil Bacteria, *in* Nucleic Acids in the Environment, (Trevors et al., Eds.), Springer-Verlag, Heidelberg, 1995, pp. 111-139.

Ogram et al., Effects of DNA Polymer Length on Its Adsorption to Soils, *Appl. Environ. Microbiol.*, 60: 393-396, 1994.

Ogram et al., The Extraction and Purification of Microbial DNA from Sediments, *J. Microbiol. Methods*, 7: 57-66, 1987.

Paget et al., Adsorption of DNA on Clay Minerals: Protection against DNaseI and Influence on Gene Transfer, *FEMS Microbiol. Lett.*, 97: 31-40, 1992.

Paget et al., The Fate of Recombinant Plant DNA in Soil, *Eur. J. Soil. Biol.*, 34: 81-88, 1998.

Picard et al., Detection and Enumeration of Bacteria in Soil by Direct DNA Extraction and Polymerase Chain Reaction, *Appl. Environ. Microbiol.*, 58: 2717-2722, 1992.

Raynal et al. Structure of The Chromosomal Insertion Site for pSAM2: Function Analysis in *Escherichia coli, Molecular Microbiology*, 28: 333-342, 1998.

Seow et al., A Study of Iterative Type II Polyketide Synthases, Using Bacterial Genes Cloned from Soil DNA: A Means to Access and Use Genes from Uncultured Microorganisms, *J. Bacteriol.*, 179: 7360-7368, 1997.

Smalla et al., Rapid DNA Extraction Protocol from Soil for Polymerase Chain Reaction-Mediated Amplification, *J. Appl. Bacteriol*, 74: 78-85, 1993.

Stein et al., Characterization of Uncultivated Prokaryotes: Isolation and Analysis of A 40-Kilobase-Pair Genome Fragment from A Planktonic Marine Archaeon, *J. Bacteriol.*, 178: 591-599, 1996.

Steffan et al., Recovery of DNA from Soils and Sediments, *Appl. Environ. Microbiol.*, 54: 2908-2915, 1988.

Tebbe et al., Interference of Humic Acids and DNA Extracted Directly from Soil in Detection and Transformation of Recombinant DNA from Bacteria and A Yeast, *Appl. Environ. Microbiol.*, 59: 2657-2665, 1993.

Torsvik, Isolation of Bacterial DNA from Soil, *Soil Biol. Biochem.*, 12: 15-21, 1980.

Tsai et al., Rapid Method for Direct Extraction of DNA from Soil and Sediments, *Appl. Environ. Microbiol.*, 57: 1070-1074, 1991.

van Elsas et al., Microbiological and Molecular Biological Methods for Monitoring Microbial Inoculants and Their Effects in The Soil Environment, *J. Microbiol. Methods*, 32: 133-154, 1998.

van Elsas et al., Soil DNA Extraction and Assessment of The Fate of Mycobacterium Chlorophenolicum Strain PCP-1 in Different Soils by 16S Ribosomal RNA Gene Sequence Based Most-Probable-Number PCR and Immunofluorescence, *Biol. Fertl. Soils*, 24: 188-195, 1997.

Volossiouk et al., Direct DNA Extraction for PCR-Mediated Assays of Soil Organisms, *Appl. Environ. Microbiol.*, 61: 3972-3976, 1995.

Ward, et al., 16S rRNA Sequences Reveal Numerous Uncultured Microorganisms in A Natural Community, *Nature*, 345: 63-65, 1990.

Widmer, et al., Sensitive Detection of Transgenic Plant Marker Gene Persistence in Soil Microcosms, *Mol. Ecol.*, 5: 603-613, 1996.

Zhou, et al., DNA Recoverty from Soils of Diverse Composition, *Appl. Environ. Microbiol.*, 62: 316-322, 1996.

Handelsman, et al., "Molecular Biological Access To The Chemistry of Unknown Soil Microbes: A New Frontier For Natural Products," *Chemistry & Biology*, 5: R245-249, 1998.

* cited by examiner

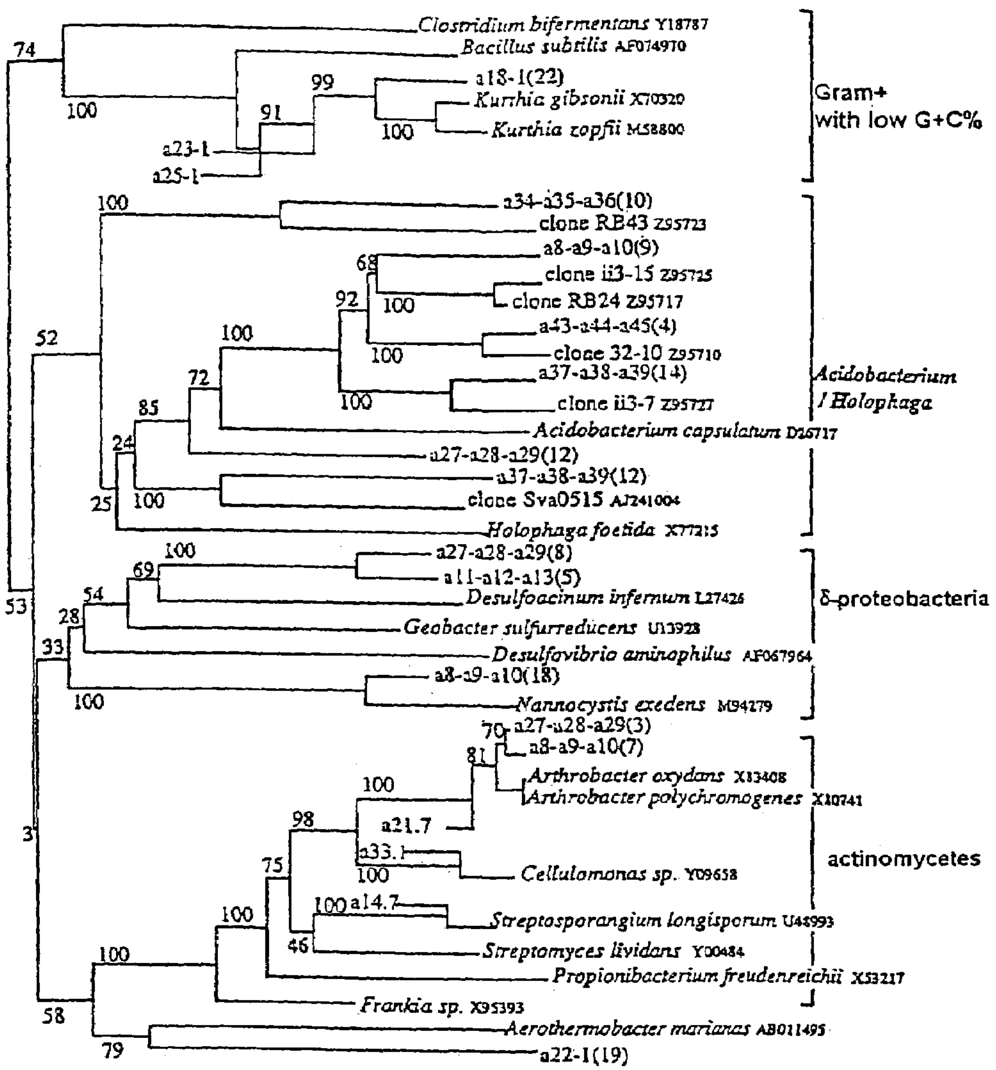
Figure 7- a)

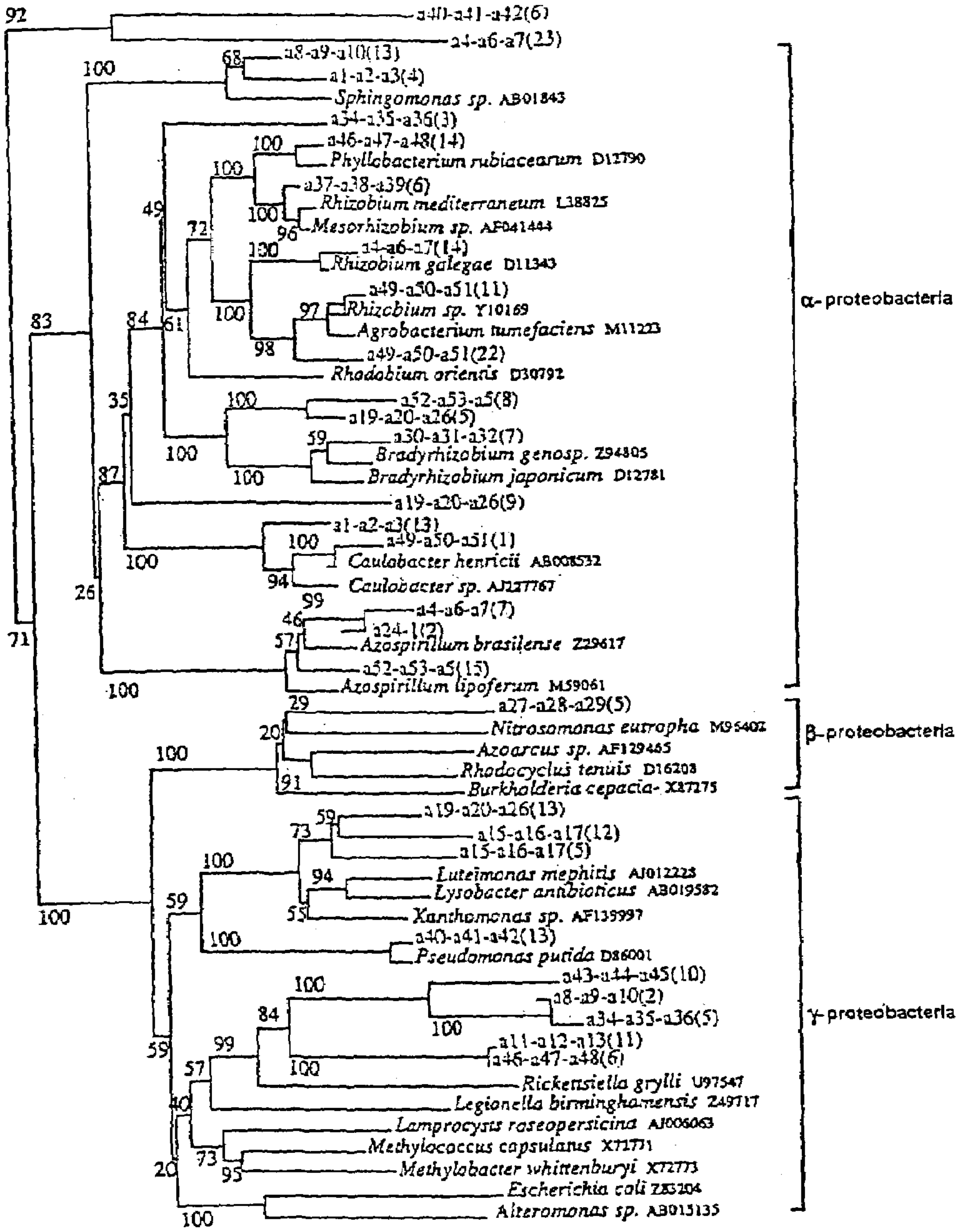
Figure 7 – b)

PCR COS

```
101                                                                   150
sol_a26G1-1        KDFLATRVSY KLNLRGPSLT VQTACSTSLV SVVMACESLQ RGASDIALAG
sol_a46B5-31       KDYLPTRVSY KLNLRGPSLA VQSACSTGLV AVCQAIQNLQ TYQCDMALAG
sol_a9B12-3        KDFIATRTAY KLNLRGPAMA VGTACSTSLV AVHEACQALR LGECDMALAG
sol_a49F1-32       KDFLATRTAY KLNLRGPAMT VQTACSSSLV AVHVAAQSLL AGECDIALAG
B. subtilis        SGTIPTMISH KLGLRGPSYF VHANCSSSLI GLHSAYKSLL SGESDYALVG
stramb12           GSVLSGRIAY TFGLQGPAVT VDTACSSSLV ALHLAAQALP AGECELALVG
stramb9            AAVLSGRVSY AFGLEGPAVT VDTACSSSLV ALHLAAQALR RGECDLALAG
EryA (module 1)    TSVASGRIAY TLGLEGPAIS VDTACSSSLV AVHLACQSLR RGESSLAMAG
sol_a26G1-2        FSTAAGRISY LLGLQGPNFP VDTACSSSLV AVHLACRSLQ SRECSMALAG
sol_a53F11-13      LNAAAGRLSY VLGLQGPSMA VDTACPSSLV AIHLACQSLR NRECRMALAG
sol_a53F11-14      HSIAAGRLAY VLGLQGPAMA VDTACSSSLV AIHLACQSLR NDDCRVAVAG
sol_a26G1-10       HSMLANRISY LLDLRGPSMA VDTACSSALV AVHLACQSLR RRECDAAFAG
sol_a36E8-1        LSIAANRLSY TFDFRGPSLA VDTACSSSLV AIHLACQSVR RGEAELAVAA
M. tuberculosis    MSIIANRLSY FLDLRGPSVA VDTACSSSLV AIHLACQSLR TQDCHLAIAA
saceryl9           LSIIPARIAY FLGLRGPDMT LNTACSSALV AMHQARQSIL LGESSVALVG
sol_a17D2-3        LAVVANRISY IYDLRGPSLT VDTACSSSLV ALHQAVEALR SGRIETAIVG
human fas          RAMMANRLSF FFDFRGPSIA LDTACSSSLM ALQNAYQAIH SGQCPAAIVG
```

Figure 24

METHOD FOR OBTAINING NUCLEIC ACIDS FROM AN ENVIRONMENT SAMPLE, RESULTING NUCLEIC ACIDS AND USE IN SYNTHESIS OF NOVEL COMPOUNDS

This application claims priority to French Application No. 99/15032, filed Nov. 29, 1999, and claims the benefit of U.S. Provisional Application No. 60/209,800, filed Jun. 7, 2000, each of which are herein incorporated by reference.

The present invention relates to a process for preparing nucleic acids from an environmental sample, more particularly a process for obtaining a collection of nucleic acids from a sample. The invention also relates to the nucleic acids or to the collections of nucleic acids obtained according to the process and to their use in the synthesis of novel compounds, in particular novel compounds of therapeutic interest.

The invention also relates to the novel means used in the above process for obtaining nucleic acids, such as novel vectors and novel processes for preparing such vectors or alternatively recombinant host cells comprising a nucleic acid of the invention.

The invention also relates to processes for detecting a nucleic acid of interest in a collection of nucleic acids obtained according to the above process, as well as to the nucleic acids detected by such a process and to the polypeptides encoded by such nucleic acids.

The invention also relates to nucleic acids obtained and detected according to the above processes, in particular nucleic acids encoding an enzyme which participates in the pathway for the biosynthesis of antibiotics such as β-lactams, aminoglycosides, heterocyclic nucleotides or polyketides, as well as the enzyme encoded by these nucleic acids, the polyketides produced by means of the expression of these nucleic acids and, finally, pharmaceutical compositions comprising a pharmacologically active amount of a polyketide produced by means of the expression of such nucleic acids.

Since the discovery of the production of streptomycin by actinomycetes, the search for novel compounds of therapeutic interest, and most particularly of novel antibiotics, has made increasing use of methods for screening the metabolites produced by soil microorganisms.

Such methods consist mainly in isolating the organisms of the telluric microflora, in culturing them on specially adapted nutrient media and then in detecting a pharmacological activity in the products found in the culture supernatants or in the cell lysates which have, where appropriate, undergone one or more prior separation and/or purification steps.

Thus, the methods for the in vitro isolation and culturing of the organisms constituting the telluric microflora have, to date, enabled the characterization of about 40,000 molecules, about half of which show biological activity.

Major products have been characterized according to such in vitro culture methods, such as antibiotics (penicillin, erythromycin, actinomycin, tetracycline, cephalosporin), anticancer agents, anti-cholesterolaemiants or pesticides.

The products of therapeutic interest of microbial origin which are known to date originate in the majority (about 70%) from the actinomycetes and more particularly from the *Streptomyces* genus. However, other therapeutic compounds, such as teicoplanins, gentamycin and spinosins, have been isolated from microorganisms of genera that are more difficult to culture, such as *Micromonospora, Actinomadura, Actinoplanes, Nocardia, Streptosporangium, Kitasatosporia* or *Saccharomonospora.*

However, the practice illustrates the fact that the characterization of novel natural products synthesized by the microorganisms of soil microflora remains limited, partly on account of the fact that the in vitro culturing step usually results in a selection of organisms that are already previously known.

The methods for in vitro separation and culturing of telluric organisms in order to identify novel compounds of interest thus have many limitations.

For example, in actinomycetes, the level of rediscovery of antibiotics that are already previously known is about 99%. Specifically, fluorescence microscopy techniques have made it possible to count more than $10^{10}$ bacterial cells in 1 g of soil, whereas only 0.1 to 1% of these bacteria can be isolated after inoculation on culture media.

With the aid of DNA recombination kinetics techniques, it has been possible to show that between 12,000 and 18,000 bacterial species can be contained in 1 g of soil, whereas, to date, only 5000 non-eukaryotic microorganisms have been described, all habitats considered.

Molecular ecology studies have made it possible to amplify and clone many novel sequences of 16S rDNA from environmental DNA.

The results of these studies have led to a trebling of the number of bacterial divisions previously characterized.

At the present time, bacteria are subdivided into 40 divisions, some of which consist only of bacteria which cannot be cultured. These latest results bear witness to the breadth of microbial biodiversity which remains unexploited to date.

Recent studies have attempted to overcome the many obstacles to gaining access to the biodiversity of the soil microflora, in particular including the step of in vitro culturing prior to the isolation and characterization of compounds of industrial interest, especially of therapeutic interest.

Methods have thus been developed which include a step of extracting the DNA from telluric organisms, where appropriate after a prior isolation of the organisms contained in the soil samples.

The DNA thus extracted, after lysis of the bacterial cells without prior in vitro culturing, is cloned into vectors used to transfect host organisms, in order to constitute libraries of DNA originating from soil bacteria.

These libraries of recombinant clones are used to detect the presence of genes encoding compounds of therapeutic interest or alternatively to detect the production of compounds of therapeutic interest by these recombinant clones.

However, the methods for gaining direct access to the DNA of soil microflora, described in the prior art, present drawbacks during the implementation of each of the steps described above, these drawbacks being of a nature to considerably affect the quantity and quality of the genetic material obtained and exploitable.

The prior art regarding each of the steps for constructing libraries of DNA originating from soil samples is detailed below, along with the technical drawbacks identified by the Applicant and which have been overcome according to the present invention.

1. Step of Extracting DNA from a Soil Sample 1.1 Direct Extraction of Environmental DNA This is essentially a process using DNA extraction techniques performed directly on the environmental sample, usually after a prior in situ lysis of the organisms in the sample.

Such techniques have been used on samples originating from aquatic media, both from freshwater and marine water.

They comprise a first step of preconcentrating the cells present in free form or in the form of particles, which generally consists of a filtration of large volumes of water on different filtration devices, for example conventional membrane filtration, tangential or rotational filtration or alternatively ultrafiltration.

The pore size is between 0.22 and 0.45 mm and often requires a prefiltration in order to avoid blockages due to the treatment of large volumes.

In a second stage, the cells harvested are lysed directly on the filters in small volumes of solutions, by enzymatic and/or chemical treatment.

This technique is illustrated for example by the studies by Stein et al., 1996, Journal of Bacteriology, Vol. 178 (3): 591-599 who describes the cloning of genes encoding ribosomal DNA and encoding a transcription elongation factor (EF 2) from *Archaebacteria* of marine plankton.

Techniques of direct extraction of DNA from samples of soil or sediment have also been described, which are based on protocols of physical, chemical or enzymatic lysis performed in situ.

For example, U.S. Pat. No. 5,824,485 (Chromaxome Corporation) describes a chemical lysis of bacteria directly on the sample taken by addition of a hot lysis buffer based on guanidium isothiocyanate.

International patent application No. WO 99/20799 (Wisconsin Alumni Research Foundation) describes a step of in situ lysis of bacteria using an extraction buffer containing a protease and SDS.

Other techniques have also been used, such as carrying out several cycles of freezing-thawing on the sample followed by high-pressure pressing of the thawed sample. Techniques of bacterial lysis using a succession of steps of sonication, heating with microwaves and heat shocks have also been used (Picard et al. 1992).

However, the techniques of the prior art described above for the direct extraction of DNA have very variable efficacy in quantitative and qualitative terms.

Thus, in situ chemical or enzymatic treatments of the sample have the drawback of lysing only certain categories of microorganisms on account of the selective resistance of the various microorganisms indigenous to the lysis step due to their heterogeneous morphology.

Thus, Gram-positive bacteria withstand a treatment with hot SDS detergent whereas virtually all Gram-negative cells are lysed.

In addition, some of the direct extraction protocols described above promote the adsorption of the nucleic acids extracted onto the mineral particles of the sample, thus significantly reducing the amount of available DNA.

Moreover, although some of the protocols of the prior art disclose a mechanical treatment step to lyse the microorganisms in the sample taken, such a mechanical lysis step is systematically carried out in liquid medium in an extraction buffer, which does not allow good homogenization of the starting sample in the form of fine particles enabling maximum accessibility to the diversity of organisms present in the sample. Grinding tests have also been carried out on crude soil samples using glass beads, but the amount of DNA extracted was low.

It has been observed according to the invention that a first step of in situ mechanical lysis in liquid medium has negative effects on the amount of DNA which can be extracted.

The amount of DNA which can be used directly for cloning in recombinant vectors is also dependent on the purification steps subsequent to its extraction.

In the prior art, the DNA extracted is then purified, for example by using polyvinylpolypyrrolidone, by a precipitation in the presence of ammonium acetate or potassium acetate, by centrifugations on a caesium chloride gradient, or by chromatographic techniques, in particular on a hydroxyapatite support, on an ion-exchange column or molecular sieving, or by electrophoresis techniques on agarose gel.

The DNA purification techniques previously described, especially when combined with the abovementioned techniques for extracting environmental DNA, are liable to lead to a co-purification of the DNA with inhibitory compounds, originating from the initial sample, that are difficult to remove.

The co-extraction of inhibitory compounds with the DNA necessitates the multiplication of the number of purification steps, which leads to considerable losses of the DNA initially extracted and simultaneously reduces the diversity of the genetic material initially contained in the sample, as well as its quantity.

Another aim of the invention was to overcome the drawbacks of the prior purification protocols and to develop a DNA purification step which makes it possible to maintain an optimum level of diversity of the DNA in the initial sample, on the one hand, and to promote quantitatively its production, on the other hand.

Most particularly, the qualitative and quantitative improvements to the purification of DNA are at a maximum when they make use of a combination of a direct DNA extraction process according to the invention and a subsequent purification process, as will be described hereinbelow.

1.2. Indirect Extraction of Environmental DNA

Such techniques involve a first step of separation of the various organisms in the telluric microflora from the other constituents of the starting sample, prior to the actual DNA extraction step.

In the state of the art, the prior separation of a microbial fraction from a soil sample usually comprises a physical dispersion of the sample by grinding it in liquid medium, for example using devices such as a Waring Blender or a mortar.

Chemical dispersions have also been described, for example dispersions on ion-exchange resins or dispersions using non-specific detergents such as sodium deoxycholate or polyethylene glycol. Whatever the mode of dispersion, the solid sample should be suspended in water, phosphate buffer or a saline solution.

The physical or chemical dispersion step can be followed by a centrifugation on a density gradient allowing the separation of the cells contained in the sample and of the particles of this sample, it being understood that bacteria have lower densities than those of most soil particles.

The physical dispersion step can also alternatively be followed by a step of low-speed centrifugation or a step of cell elutriation.

The DNA can then be extracted from the separated cells by any available method of lysis and can be purified by many methods, including the purification methods described in paragraph 1.1 above. In particular, the inclusion of the cells in low-melting agarose can be carried out in order to control the lysis.

However, the methods described in the prior art that are known to the Applicant are unsatisfactory on account of the presence, in the fractions containing the extracted DNA, of unwanted constituents of the starting sample which have a significant influence on the final quality and quantity of DNA.

The present invention proposes to solve the technical difficulties encountered in the processes of the prior art, as will be described hereinbelow.

2. Molecular Characterization of the Extracted DNA

When it is desired to construct a DNA library from an environmental sample, in particular from a soil sample, it is advantageous to check the quality and diversity of the source of DNA extracted and purified before it is inserted into suitable vectors.

The object of such a molecular characterization of the DNA extracted and purified is to obtain profiles representing the proportions of the various bacterial taxons present in this DNA extract. The molecular characterization of the DNA extracted and purified makes it possible to determine whether or not artifacts have been introduced during the implementation of the various extraction and purification steps and, where appropriate, whether or not the original diversity of the DNA extracted and purified is representative of the microbial diversity initially present in the sample, in particular in the soil sample.

To the Applicant's knowledge, the prior art makes use of quantitative hybridization processes using oligonucleotide probes that are specific for different bacterial groups, applied directly to the DNA extracted from the environment.

Unfortunately, such an approach is relatively insensitive and does not make it possible to detect taxonomic groups or genera that are present in low abundance.

The prior art also describes quantitative PCR processes, such as MPN-PCR or competitive quantitative PCR. However, these techniques have major drawbacks.

Thus, MPN-PCR is complicated to carry out on account of the multiplication of the dilutions and repetitions, making it unsuitable for a large number of samples or for primer couples.

Moreover, competitive quantitative PCR is, difficult to carry out on account of the need to construct a competitor which is specific to the target DNA and which, in addition, does not induce any bias or artifacts into the competition itself.

According to the invention, a process is thus proposed for prescreening a library of DNA originating from an environmental sample, which is both quick, simple and reliable and which makes it possible to test the quality of the DNA extracted and purified beforehand and thus to determine the value of constructing a library of clones prepared from this purified starting DNA.

3. Vectors for Cloning DNA Extracted and Purified from an Environmental Sample

Many vectors have already been described in the prior art for cloning DNA preextracted from an environmental sample.

Thus, according to the description of international patent application No. WO 99/20799, viral vectors, phages, plasmids, phagemids, cosmids, phosmids, vectors of the BAC (bacterial artificial chromosome) type or bacteriophage P1, vectors of PAC type (artificial chromosome based on bacteriophage P1), vectors of the YAC (yeast artificial chromosome) type, yeast plasmids or any other vector capable of maintaining and expressing a genomic DNA in a stable manner can be used.

Example 1 of PCT patent application No. WO 99/20799 describes the construction of a genomic DNA library by cloning into a vector of the BAC type.

To the Applicant's knowledge, no DNA library originating from an environmental sample has yet been effectively produced with vectors of conjugative type, such a technique being made available to and reproducible by those skilled in the art for the first time by virtue of the teaching of the present invention.

4. Host Cells

In the prior art, many host cells have been described as being able to be used in order to accommodate vectors containing inserts of DNA originating from the DNA extracted and purified from an environmental sample.

Thus, PCT patent application No. WO 99/20799 cites many suitable host cells, such as *Escherichia coli*, in particular the strain DH 10B or the strain 294 (ATCC 31446, the strain *E. coli* B, *E. Coli* X 1776 (ATCC No. 31.537), *E. coli* DH5α and *E. coli* W3110 (ATCC No. 27.325).

This PCT patent application also cites other suitable host cells such as *Enterobacter, Erwinia, Klebsiella, Proteus, Salmonella, Serratia, Schigella* or strains of the *bacillus* type such as *B. subtilis* and *B. licheniformis* as well as bacteria of the genus *Pseudomonas, Streptomyces* or *Actinomyces.*

U.S. Pat. No. 5,824,485 in particular cites the *Streptomyces lividans* TK66 strain or yeast cells such as those of *Saccharomyces pombe.*

5. Characterization of Genes of Interest in DNA Libraries Originating from an Environmental Sample PCT patent application No. WO 99/20799 describes an identification of the phenotype of different clones belonging to the DNA library of *B. cereus*, respectively a clone producing haemolysin, a clone hydrolysing esculin or a clone producing an orange pigment.

Mutagenesis techniques based on the use of a transposon encoding the pho A enzyme made it possible subsequently to isolate mutated clones and to characterize the sequences responsible for the phenotypes observed.

The abovementioned article by Stein et al. (1996) describes the use of specific primers for ribosomal DNA in order to amplify the DNA inserted into the vectors harboured by certain clones of a genomic DNA library of marine plankton *Archaebacteria* and the identification of several coding sequences in the DNA thus amplified.

The article by Borschert S. et al. (1992) describes the screening of a genomic DNA library of *Bacillus subtilis* using pairs of primers which hybridize with conserved regions of known peptide synthetases in order to identify one or more corresponding genes in the genome of *Bacillus subtilis.*

This technique made it possible to detect a chromosomal DNA fragment of about 26 kb carrying a portion of the surfactin biosynthesis operon.

The article by Kah-Tong S. et al. (1997) describes the screening of a library of DNA originating from the soil with the aid of primers which hybridize with conserved sequences of the operon responsible for the biosynthetic pathway of type II polyketides and shows the identification, in this DNA library, of sequences belonging to the PKS-β gene. This article also describes the construction of hybrid expression cassettes in which the sequence of the PKS-β subunit, found naturally in the operon responsible for polyketide biosynthesis, has been replaced with various similar sequences found in the DNA library.

Similarly, the article by Hong-Fu et al. (1995) describes the construction of expression cassettes containing the various open reading frames of the operon responsible for polyketide biosynthesis, the various expression cassettes having been constructed artificially by combining the open reading frames which are not found together naturally in the genome of *Streptomyces coelicolor*. This article shows that the combination, in the artificial expression cassettes, of open reading frames originating from different bacterial strains allows the production of polyketides that have different structural characteristics and relatively large antibiotic activities with respect to *Bacillus subtilis* and *Bacillus cereus*.

Polyketides form part of a large family of natural products of variable structure having great diversity of biological activity. Among the polyketides are, for example, tetracyclines and erythromycin (antibiotics), FK506 (immunosuppressant), doxorubicin (anticancer agent), monensin (a coccidiostatic agent) and avermectin (an antiparasitic agent).

These molecules are synthesized by means of multifunctional enzymes known as polyketide synthases, which catalyse repeated cycles of condensation between acyl thioesters (in general acetyl, propionyl, malonyl or methylmalonyl thioesters). Each condensation cycle results in the formation, on a growing carbon chain, of a β-keto group which can then undergo, where appropriate, one or more series of reductive steps.

Given the major clinical interest of polyketides, their common mechanism of biosynthesis and the high degree of conservation observed between the groups of genes encoding polyketide synthases, increased interest has developed for the development of novel polyketides by genetic engineering.

Novel artificial polyketides have thus been produced by genetic engineering, such as mederrhodin A or dihydrogranatirhodin. The vast majority of the novel polyketide molecules obtained by genetic engineering are very different, in structural terms, from the corresponding natural polyketides.

From the prior art, it thus emerges that there is a need to obtain novel polyketides of interest and most particularly polyketides of therapeutic interest which have in particular, relative to their natural homologues, an increased level of antibiotic activity or a different spectrum of antibiotic activity, either which is broader than that of the known polyketides, or which is, on the other hand, more selective.

As will be described below, this need is partly fulfilled according to the present invention.

DESCRIPTION OF THE INVENTION

The invention relates firstly to a process for constructing libraries of DNA originating from an environmental sample, such a sample possibly being, without discrimination, an aquatic medium (fresh water or marine water), a sample of soil (surface layer of soil, subsoil or sediments), or a sample of eukaryotic organisms containing an associated microflora, such as, for example, a sample originating from plants, insects or marine organisms and having an associate microflora.

The development of a process for constructing a library of DNA from an environmental sample, and most particularly from a soil sample, comprises critical steps whose implementation must necessarily be optimized in order to obtain a library of DNA whose content of nucleic acids of interest satisfies the objectives initially set.

A first critical step consists in extracting and subsequently purifying the nucleic acids initially contained in the sample, i.e. mainly the nucleic acids contained in the various organisms of which the microflora of this sample is composed.

The quality of purification of the extracted DNA is a factor which determines the result obtained.

A second important step of a process for constructing a library of nucleic acids originating from an environmental sample is the evaluation of the genetic diversity of the nucleic acids extracted and purified. The development of a step for the simple and reliable pre-screening of the DNA extracted and purified in order to check that it takes account, at least partially, of the phylogenetic diversity of the organisms initially present in the starting sample effectively makes it possible to determine the value or otherwise of using the initial source of extracted and purified DNA for the construction of the nucleic acid library itself or, on the contrary, to not continue the construction of the nucleic acid library on account of excessive artifacts introduced at the time of the extraction and purification of the nucleic acids. It has also been identified, according to the invention, that the quality of the inserts introduced into the vectors to construct the library is a determining factor. It has thus been determined that the use of restriction enzymes to cleave the DNA extracted and purified from the environmental sample was of a nature to introduce artifacts or "bias" into the structure of the inserts obtained. Specifically, the DNA extracted from the soil or from other environments, originating in the vast majority of cases from unculturable organisms, is composed of molecules whose content of G and C bases is by definition unknown and furthermore variable as a function of the origin of these organisms.

A third critical step is the insertion of the extracted and purified nucleic acids into vectors capable of integrating nucleic acids of chosen length, on the one hand, and to allow their transfection or integration into the genome of given host cells, on the other hand, as well as, where appropriate, to allow their expression in such host cells.

Vectors capable of integrating large nucleic acids, i.e. larger than 100 kb in size, constitute vectors of interest when the objective pursued consists in cloning and identifying a complete operon capable of directing a complete biosynthetic pathway of a compound of industrial interest, in particular of a compound of pharmaceutical or agronomic interest.

Definitions

For the purposes of the present invention, the terms "nucleic acids", "polynucleotides" and "oligonucleotides" mean not only DNA and RNA sequences but also hybrid RNA/DNA sequences of more than 2 nucleotides, in either single-stranded or double-stranded form.

The term "library" or "collection" is used in the present description with reference either to a set of extracted, and where appropriate purified, nucleic acids originating from an environmental sample, to a set of recombinant vectors, each of the recombinant vectors of the set comprising a nucleic acid originating from the set of abovementioned extracted, and where appropriate purified, nucleic acids, or to a set of recombinant host cells comprising one or more nucleic acids originating from the set of abovementioned extracted, and where appropriate purified, nucleic acids, the said nucleic acids being either carried by one or more recombinant vectors or integrated into the genome of the said recombinant host cells.

The expression "environmental sample" denotes, without discrimination, a sample of aquatic origin, for example from fresh or salt water, or a telluric sample originating from the surface layer of a soil, from sediments or from lower layers of the soil (subsoil), as well as samples of eukaryotic organisms, which may be multicellular, of plant origin, originating from marine organisms or from insects and having an associated microflora, this associated microflora constituting organisms of interest.

According to the invention, the term "operon" means a set of open reading frames whose transcription and/or translation is co-regulated by a unique set of signals for regulating the transcription and/or translation. According to the invention, an operon can also comprise the said signals for regulating the transcription and/or translation.

For the purposes of the invention, the expression "metabolic pathway" or "biosynthetic pathway" means a set of anabolic or catabolic biochemical reactions which results in the conversion of a first chemical species into a second chemical species.

For example, a biosynthetic pathway for an antibiotic consists of the set of biochemical reactions converting primary metabolites into intermediate products of the antibiotics, and then subsequently into antibiotics.

The expression "regulation sequence which is operably linked relative to a nucleotide sequence whose expression is desired" means that the transcription regulation sequence(s) is (are) located, relative to the nucleotide sequence of interest whose expression is desired, so as to allow the expression of the said sequence of interest, the regulation of the said expression being dependent on factors which interact with the regulatory nucleotide sequences.

According to another terminology, it may also be said that the nucleotide sequence of interest whose expression is desired is placed "under the control" of the transcription-regulating nucleotide sequences.

For the purposes of the present invention, the term "isolated" denotes a biological material which has been abstracted from its original environment (the environment in which it is naturally located).

For example, a polynucleotide or a polypeptide present in the natural state in an organism (virus, bacterium, fungus, yeast, plant or animal) is not isolated. The same polypeptide separated from its natural environment or the same polynucleotide separated from the adjacent nucleic acids within which it is naturally inserted in the genome of the organism, is isolated.

Such a polynucleotide can be included into a vector and/or such a polynucleotide can be included into a composition and nevertheless remain in isolated form, due to the fact that the vector or composition does not constitute its natural environment.

The term "purified" does not require the material to be present in a form of absolute purity, exclusive of the presence of other compounds. Rather, this is a relative definition.

A polypeptide or polynucleotide is in purified form after purification of the starting material by at least one order of magnitude, preferably two or three and preferentially four or five orders of magnitude.

For the purposes of the present invention, the "percentage of identity" between two sequences of nucleotides or of amino acids can be determined by comparing two optimally aligned sequences across a comparison window.

The portion of the nucleotide or polypeptide sequence in the comparison window can thus comprise additions or deletions (for example "gaps") relative to the reference sequence (which does not comprise these additions or deletions) so as to obtain an optimum alignment of the two sequences.

The percentage is calculated by determining the number of positions at which an identical nucleic base or an identical amino acid residue is observed for the two compared sequences (nucleic acid or peptide), followed by dividing the number of positions at which there is identity between the two bases or amino acid residues by the total number of positions in the comparison window, followed by multiplying the result by 100 in order to obtain the percentage of sequence identity.

The optimum alignment of the sequences for the comparison can be achieved by computer with the aid of known algorithms contained in the package from the company Wisconsin Genetics Software Package, Genetics Computer Group (GCG), 575 Science Doctor, Madison, Wis.

By way of illustration, the percentage of sequence identity may be determined using the BLAST software (BLAST versions 1.4.9 of March 1996, BLAST 2.0.4. of February 1998 and BLAST 2.0.6. of September 1998), exclusively using the default parameters (S. F. Altschul et al., J. Mol. Biol. 1990 215: 403-410, S. F. Altschul et al., Nucleic Acids Res. 1997 25: 3389-3402). Blast recherche des séquences similaires/homologues à une séquence "requête" de référence, à l'aide de l'algorithme [Blast search for sequences similar/homologous to a reference "request" sequence, with the aid of the algorithm] from Altschul et al. The request sequence and the databases used can be of peptide or nucleic nature, any combination being possible.

Extraction and Purification of Nucleic Acids Originating from an Environmental Sample 1. Direct Extraction of Nucleic Acids It has been shown according to the present invention that, in order to obtain a library of nucleic acids originating from organisms contained in a sample of soil, it was important to create conditions under which, on the one hand, the various organisms in the sample are made accessible to the subsequent steps for extracting the nucleic acids, and, on the other hand, that the initial step of treatment of the sample of soil allows a maximum mechanical lysis of the organisms in the sample, which is of a nature to make the nucleic acids of these organisms directly accessible, mainly the genomic and plasmid DNA, to the buffers used for the subsequent extraction steps.

It has thus been demonstrated according to the invention that maximum accessibility of nucleic acids originating from microorganisms from a sample of soil was achieved by a thorough dry-grinding of the pre-dried soil sample in order to obtain microparticles. The Applicant has thus determined that the drying of the soil sample prior to any subsequent treatment brings about a significant reduction in the cohesion of the crude soil sample and consequently promotes its subsequent disintegration in the form of microparticles, when a suitable grinding treatment is carried out.

Surprisingly, the Applicant has shown that microparticles of dry soil samples combined physicochemical properties that are favourable to the extraction of an optimum quantity of nucleic acids which, in their nature, could be representative of the genetic diversity of the organisms initially present in the starting soil sample. It has been shown in particular that the process of direct extraction of nucleic acids according to the invention allows the extraction of DNA originating from rare microorganisms, such as certain rare *Streptomyces* or sporulated microorganisms.

For the purposes of the present invention, the term "microparticles" of the soil sample means particles derived from the sample which have an average size of about 50 μm, i.e. on average between 45 and 55 μm.

According to the invention, the microparticles are obtained from soil samples that are pre-dried or pre-desiccated and then ground until microparticles with an average size of between 2 μm and 50 μm are obtained, before resuspension of the microparticles obtained in a liquid buffer medium.

Such a liquid buffer medium can consist of a nucleic acid extraction buffer, in particular a conventional DNA extraction buffer which is well known to those skilled in the art.

The grinding of the soil sample into microparticles has the twin function of mechanically lysing most of the organisms present in the initial soil sample and of making the organisms that are not lysed by this mechanical treatment accessible to optional subsequent steps of chemical and/or enzymatic lysis.

Thus, a first subject of the invention consists of a process for preparing a collection of nucleic acids from a soil sample containing organisms, the said process comprising a first step (I-a)) of obtaining microparticles by grinding the pre-dried or pre-desiccated soil sample, followed by suspending the microparticles in a liquid buffer medium.

In an entirely preferred manner, the grinding step is carried out using a device with agate or tungsten beads or alternatively using a device with tungsten rings. These devices are preferred since the hardness of materials such as agate or tungsten significantly facilitates the production of microparticles of the size specified above. For this reason, use of a grinding device with glass beads, which is found to be much less efficient, will preferably not be chosen, or will be avoided.

The drying or classification of the soil sample can be carried out by any method known to those skilled in the art. For example, the crude soil sample can be dried at room temperature for a period of 24 to 48 hours.

As indicated previously, the liquid buffer medium can consist of a medium for extracting the DNA present in the microparticles. An extraction buffer known as TENP containing, respectively, 50 mM Tris, 20 mM EDTA, 100 mM NaCl and 1% (weight/volume) of polyvinylpolypyrrolidone, at pH 9.0, will most preferably be used.

The process for preparing a collection of nucleic acids from a soil sample is also characterized in that the step for obtaining microparticles by grinding the pre-dried or pre-desiccated soil sample is followed by a step I-(b) of extracting the nucleic acids present in the microparticles.

It is common ground that the extraction of the nucleic acids is accompanied by a co-extraction of unwanted soil constituents and/or compounds, thus necessitating the subsequent purification of the nucleic acids extracted, such a subsequent purification step needing to be both selective enough to allow the removal of the unwanted soil constituents and/or compounds, and of a yield which is sufficient to entail a small loss in terms of the amount of pre-extracted DNA.

It has been shown according to the invention that a step of purifying the DNA extracted from the microparticles of the soil sample which satisfies the selectivity and yield criteria defined above comprises a treatment of the extracted DNA with a combination of two successive chromatography steps, a chromatography on molecular sieves and an anion-exchange chromatography, respectively.

According to another characteristic of the above process, step I-(b) of extracting the nucleic acids is followed by a step I-(c) of purifying the extracted nucleic acids with the aid of the following two chromatography steps:

passing the solution containing the nucleic acids over a molecular sieve, followed by recovery of the elution fractions enriched in nucleic acids;

passing the elution fractions enriched in nucleic acids over an anion-exchange chromatography support, followed by recovery of the elution fractions containing the nucleic acids.

The nature and order of the above chromatography steps are essential for good selectivity and an excellent yield for the step of purifying the DNA pre-extracted from the microparticles of the pre-dried or pre-desiccated soil sample.

In a very advantageous manner, the chromatographic support of the "molecular sieve" type in the above nucleic acid purification step consists of a chromatographic support of Sephacryl® S400 HR type or a chromatographic support of equivalent characteristics.

In an entirely preferred manner, the anion-exchange chromatographic support used in the second step for purifying the extracted DNA is a support of Elutip® d type, or a chromatographic support of equivalent characteristics.

By combining the steps I-(a) of obtaining microparticles of the dry soil sample, I-(b) of extracting the nucleic acids present in the microparticles and I-(c) of purification by the chromatography steps described above, it is possible according to the invention to extract the DNA from the soil directly without prior purification of the cells of the organisms initially contained in the sample, while at the same time avoiding the co-extraction of soil contaminants, such as, for example, humic acids, which is observed with the processes of the prior art.

The contaminants, such as humic acids, severely impair the analyses and the subsequent uses of the nucleic acids whose purification is desired.

According to the above process, it is also possible to gain access to the nucleic acids contained in the organisms which have not been lysed mechanically during step I-(a) of obtaining microparticles of the soil sample, with the aim of obtaining a virtually exhaustive collection of the genetic diversity of nucleic acids initially present in the soil sample. Thus, the microparticles of the soil sample can undergo subsequent steps of chemical, enzymatic or physical lysis treatment, or alternatively a combination of chemical, enzymatic or physical treatments.

According to a first aspect, the process for preparing a collection of nucleic acids from a soil sample according to the invention can also be characterized in that step I-(a) is followed by the following steps:

treatment of the soil suspension in a liquid buffer medium by sonication;

extraction and recovery of the nucleic acids.

In a preferred manner, for a treatment by sonication, use will be made of a device of titanium micro-point type, such as the 600 W Vibracell Ultrasonicator device sold by the company Bioblock or a sonicator of Cup Horn type.

In an entirely preferred manner, the sonication step is carried out at a power of 15 W for a duration of 7 to 10 minutes and comprises successive cycles of sonication, the sonication itself being carried out for 50% of the duration of each cycle.

According to a second aspect, the above process can also be characterized in that step I-(a) is followed by the following steps:

treatment of the soil suspension in a liquid buffer medium by sonication;

incubation of the suspension at 37° C. after sonication in the presence of lysozyme and achromopeptidase;

addition of SDS before centrifugation and precipitation of the nucleic acids;

recovery of the precipitated nucleic acids.

Preferably, the step of incubation in the presence of lysozyme and achromopeptidase will be carried out at a final concentration of 0.3 mg/ml of each of the two enzymes, preferably for 30 minutes at 37° C.

Preferably, the SDS will be used at a final concentration of 1% and for an incubation time of 1 hour at a temperature of 60° C. before centrifugation and precipitation.

According to a third aspect, the process for preparing a collection of nucleic acids from a soil sample above is also characterized in that step I-(a) is followed by the following steps:

homogenization of the soil suspension with a step of vigorous mixing (vortex) followed by a step of simple stirring;

freezing of the homogeneous suspension followed by thawing;

treatment of the suspension by sonication after thawing;

incubation of the suspension at 37° C. after sonication in the presence of lysozyme and achromopeptidase;

addition of SDS before centrifugation and precipitation of the nucleic acids;

recovery of the nucleic acids.

Preferably, the suspensions of soil microparticles are mixed on the vortex machine and then homogenized by gentle stirring on a stirrer with circular rotation for a duration of two hours, after which they are frozen at −20° C.

Preferably, the suspensions are again vigorously stirred with a vortex machine for 10 minutes, after thawing and before the sonication step.

It goes without saying that the nucleic acids extracted by the embodiments of the process described above for the direct extraction of nucleic acids are preferably purified according to the purification step consisting of a first passage over molecular sieves and then a subsequent passage, of the elution fractions obtained after the chromatography on molecular sieves, over an anion-exchange chromatographic support.

2. Indirect Extraction of Nucleic Acids

According to a second embodiment of the process for preparing a collection of nucleic acids from an environmental sample, according to the invention, the said environmental sample undergoes a first treatment which is of a nature to allow separation of the organisms, contained in this sample, from the other macro-constituents of the sample.

This second embodiment of the process for preparing a collection of nucleic acids according to the invention promotes the production of large nucleic acids, which are virtually impossible to obtain according to the first embodiment of the process according to the invention described above, the mechanical lysis step performed in order to obtain the microparticles also having the effect of physically breaking the nucleic acids in the soil sample or the nucleic acids contained in the organisms in the soil sample.

The production of large nucleic acids has been sought by the Applicant for the purpose of isolating and characterizing nucleic acids comprising, at least partially, all of the coding sequences belonging to the same operon capable of directing the biosynthesis of a compound of industrial interest.

Preferably, by carrying out the second embodiment of the process for preparing a collection of nucleic acids from a soil sample according to the invention, nucleic acids are obtained which are greater than 100 kb in size, preferably greater than 200, 250 or 300 kb, and most preferably nucleic acids greater than 400, 500 or even 600 kb in size.

This second embodiment of a process for preparing a collection of nucleic acids from an environmental sample according to the invention consists of a combination of four successive steps intended to obtain nucleic acids having the characteristics described above.

When the environmental sample is a soil sample, it has been shown according to the invention that a first step for obtaining a suspension by dispersing the soil sample in liquid medium promotes the accessibility of the organisms contained in the sample without bringing about any significant mechanical lysis of the cells.

The first step of obtaining a dispersion of the above soil sample makes the organisms in the sample accessible to the external medium and also allows a partial dissociation of the organisms in the sample and of the macro-constituents. It thus makes possible a subsequent separation of the organisms initially contained in the sample from the other constituents of this sample.

When the environmental sample originates, for example, from plants, from marine organisms or from insects, a pretreatment by grinding is necessary in order to make the organisms of the associated microflora accessible to the subsequent steps of the process.

Thus, the present process comprises a step of separating the organisms from the other inorganic and/or organic constituents obtained above by means of centrifugation on a density gradient. The organisms thus separated are then subjected to a step of lysis and then of extraction of the nucleic acids.

The step of centrifugation on a density gradient makes it possible, surprisingly, to separate the cells of organisms in the soil particles contained in the sample suspension. In point of fact, it might have been expected that a proportion of the cells would be entrained with the macroparticles in the gradient phase. In addition, it had never been demonstrated hitherto that a centrifugation of a soil sample on a density gradient made it possible to find, at the aqueous phase/gradient interface, a population of organisms representative of the diversity of the organisms present in the starting sample, due to the fact that these organisms are extremely variable in volume, density and shape. It could reasonably be assumed that they would be found either in the aqueous phase, at the aqueous phase/density gradient interface or in the density gradient itself.

Thus, a person skilled in the art could expect that organisms with densities less than or greater than the density of the density gradient used (density of the density gradient of between 1.2 and 1.5 g/ml, preferably 1.3 g/ml) could not be recovered, the effect of which would have been to introduce a bias into the representativeness of the organisms effectively separated and, consequently, also into the diversity of the nucleic acids extracted.

Also, in one specific embodiment of the process, a step of germination of spores, in particular of actinomycetes, is carried out, the effect of which is to significantly increase the amount of actinomycete DNA recovered.

The final step consists of a step of purifying the nucleic acids thus extracted on a caesium chloride gradient.

Surprisingly, the purification of the nucleic acids on the caesium chloride gradient allows a substantial or even complete removal of the substances of which the density gradient is composed. This characteristic is a determining factor as regards the subsequent use of the purified nucleic acids, since the density gradient is known as being a powerful enzymatic inhibitor, capable where appropriate of inhibiting the catalytic activity of the enzymes used to prepare the insertion of extracted nucleic acids into vectors.

According to this second embodiment, the process for preparing a collection of nucleic acids from an environmental sample containing organisms according to the invention comprises the succession of steps below:

(i) production of a suspension by dispersing the environmental sample in liquid medium and then homogenizing the suspension obtained by gentle stirring;

(ii) separating the organisms from the other inorganic and/or organic constituents of the homogeneous suspension obtained in step (i) by centrifugation on a density gradient;

(iii) lysis of the microorganisms separated in step (ii) and extraction of the nucleic acids;

(iv) purification of the nucleic acids on a caesium chloride gradient.

Preferably, the suspension of the soil sample is obtained by dispersing this sample by grinding with the aid of a device such as a Waring Blender or a device of equivalent characteristics. In an entirely preferred manner, the sample suspension is obtained after three successive grinding operations each lasting one minute in a device such as a Waring Blender. Preferably, the ground sample will be cooled in ice between each of the grinding operations.

Preferably, the organisms are then separated from the soil particles by centrifugation on a density cushion of the "Nycodenz" type, sold by the company Nycomed Pharma AS. (Oslo, Norway). The preferred centrifugation conditions are 10,000×g for 40 minutes at 4° C., advantageously in a rotor with swing-out buckets of the "rotor TST 28.38" type sold by the company Kontron.

The ring of organisms located, after centrifugation, at the interphase of the upper aqueous phase and the lower Nycodenz phase is then removed and washed by centrifugation before taking up the cell pellet in a suitable buffer.

Step (iii) of lysis of the organisms separated out in step (ii) described above can be carried out in any manner known to those skilled in the art.

Advantageously, the cells are lysed in a 10 mM Tris-100 mM EDTA solution at pH 8.0 in the presence of lysozyme and achromopeptidase, advantageously for one hour at 37° C.

The actual extraction of the DNA can advantageously be carried out by adding a solution of lauryl sarcosyl (1% of the final weight of the solution) in the presence of proteinase K and incubation of the final solution at 37° C. for 30 minutes.

The nucleic acids extracted in step (iii) are then purified on a caesium chloride gradient. Preferably, the step of purifying the nucleic acids on a caesium chloride gradient is carried out by centrifugation at 35,000 rpm for 36 hours, for example on a rotor of the Kontron 65.13 type.

According to one specific aspect of the process for preparing a collection of nucleic acids from a soil sample containing organisms according to the invention, the said nucleic acids consist predominantly, if not exclusively, of DNA molecules.

According to another aspect, the nucleic acids can be recovered after inclusion of the organisms, separated on a density gradient, in an agarose block and lysis, for example chemical and/or enzymatic lysis, or the organisms included in the agarose block.

Another subject of the invention consists of a collection of nucleic acids consisting of the nucleic acids obtained in step II-(iv) of the process for preparing a collection of nucleic acids according to the invention, or alternatively obtained in step (c) or a subsequent step of the process for preparing a collection of nucleic acids according to the invention.

The invention also relates to a nucleic acid which is characterized in that it is contained in a collection of nucleic acids as defined above.

According to a first aspect, such a nucleic acid constituting a collection of nucleic acids according to the invention is characterized in that it comprises a nucleotide sequence encoding at least one operon, or part of an operon.

Most preferably, such an operon encodes all or part of a metabolic pathway.

Example 9 describes the construction of a genomic DNA library from a strain of *Streptomyces alboniger* and its cloning into the shuttle cosmids pOS700I and pOS700R, respectively. It has been shown according to the invention that, in the DNA library prepared in the integrative vector pOS700I, new clones contain nucleotide sequences belonging to the operon responsible for the puromyocin biosynthetic pathway. Similarly, twelve clones containing nucleotide sequences of the operon responsible for the puromycin biosynthetic pathway have been identified in the DNA library prepared in the replicative vector pOS 700R.

In particular, certain integrative and replicative cosmids of the libraries produced have, after digestion with the restriction endonucleases ClaI and EcoRV, a 12-kb fragment capable of containing all of the sequences of the operon responsible for the puromycin biosynthetic pathway.

Thus, according to another aspect, a nucleic acid according to the invention contains, at least partially, nucleotide sequences of the operon responsible for the puromycin biosynthetic pathway.

Example 2 below describes the construction of a DNA library according to a process in accordance with the present invention, in a pBluescript $SK^-$ vector starting with a soil contaminated with lindane.

The recombinant vectors were transfected into *Escherichia coli* DH10B cells and the transformed cells were then cultured in a suitable culture medium in the presence of lindane. Screening of the clones on transformed cells of the library made it possible to show that, out of 10,000 screened clones, 35 of them had a lindane degradation phenotype. The presence of the linA gene in these clones was confirmed by PCT amplification by means of primers specific for this gene.

Thus, according to another aspect, the invention also relates to a nucleic acid containing a nucleotide sequence for the metabolic pathway which brings about the biodegradation of lindane.

It is thus clearly demonstrated, as described above, that a process for preparing a collection of nucleic acids from a soil sample containing organisms according to the invention and a process for preparing a collection of recombinant vectors containing the constituent nucleic acids of the collection of abovementioned nucleic acids was entirely suitable for the isolation and characterization of nucleotide sequences included in an operon.

An additional demonstration of the ability of a process according to the invention to identify coding nucleotide sequences involved in a biosynthetic pathway regulated in the form of an operon is also described later: this concerns the cloning and characterization of sequences encoding polyketide synthases involved in the pathway for the biosynthesis of polyketides, which belong to a family of molecules certain representatives of which are of major therapeutic interest, in particular antibiotic interest.

A subject of the present invention is thus also a constituent nucleic acid of a collection of nucleic acids according to the invention, characterized in that it comprises all of a nucleotide sequence encoding a polypeptide.

According to a first aspect, a constituent nucleic acid of a collection of nucleic acids according to the invention is of prokaryotic origin.

According to a second aspect, a constituent nucleic acid of a collection of nucleic acids according to the invention originates from a bacterium or from a virus.

According to a third aspect, a constituent nucleic acid of a collection of nucleic acids according to the invention is of eukaryotic origin.

In particular, such a nucleic acid is characterized in that it originates from a fungus, a yeast, a plant or an animal.

Molecular Characterization of the Collection of Nucleic Acids Extracted from the Soil In order to overcome the various technical drawbacks of the methods for characterizing libraries of DNA extracted and purified from an environmental sample which have been described in the section of the description relating to the prior art, the Applicant has developed a simple and reliable process for qualitatively and semi-quantitatively characterizing the nucleic acids obtained from the process described above.

The process according to the invention thus consists in universally amplifying a 700 bp fragment located inside a sequence of ribosomal DNA of 16S type, and then in hybridizing the amplified DNA with an oligonucleotide probe of variable specificity and finally in comparing the hybridization intensity of the sample relative to an external calibration range of DNA of known sequence or origin.

The amplification prior to the hybridization with the oligonucleotide probe makes it possible to quantify relatively scarce microorganism genera or species. Furthermore, the amplification with universal primers makes it possible, during the hybridization, to use a broad series of oligonucleotide probes.

Thus, a subject of the invention is also a process for determining the diversity of nucleic acids contained in a collection of nucleic acids, and most particularly of a collection of nucleic acids originating from an environmental sample, preferably from a soil sample, the said process comprising the following steps:

- placing the nucleic acids of the collection of nucleic acids to be tested in contact with a pair of oligonucleotide primers hybridizing at any sequence of bacterial 16S ribosomal DNA;
- carrying out at least three amplification cycles;
- detection of the amplified nucleic acids using an oligonucleotide probe or a plurality of oligonucleotide probes, each probe hybridizing specifically with a 16S ribosomal DNA sequence common to a bacterial kingdom, order, subclass or genus;
- where appropriate, comparison of the results from the preceding detection step with the detection results, using the probe or the plurality of probes of nucleic acids of known sequence constituting a calibration range.

Preferably, a first pair of primers hybridizing with universally conserved regions of the gene for the 16S ribosomal RNA consists, respectively, of the primers FGPS 612 (SEQ ID No 12) and FGPS 669 (SEQ ID No 13).

A second embodiment of a preferred pair of primers according to the invention consists of the pair of universal primers 63 f (SEQ ID No 22) and 1387 r (SEQ ID No 23).

According to one specific embodiment of a process for determining the diversity of nucleic acids in a collection of nucleic acids, the amplification step using a pair of universal primers can be carried out on a collection of recombinant vectors into each of which has been inserted a nucleic acid from the collection of nucleic acids under consideration, prior to the step of hybridization with the oligonucleotide probes specific for a particular bacterial kingdom, order, subclass or genus.

Such a process for determining the diversity of the nucleic acids contained in a collection is most particularly applicable to the collections of nucleic acids obtained in accordance with the teaching of the present description.

Thus, Example 3 details a process for preparing a collection of nucleic acids from a soil sample containing organisms, comprising a step of indirect extraction of DNA by dispersion of a soil sample prior to the separation of the cells on a Nycodenz gradient, lysis of the cells and then purification of the DNA on a caesium chloride gradient.

The collection of nucleic acids thus obtained was used as obtained or in the form of inserts into vectors of cosmid type in an amplification process using the abovementioned universal primers for 16S rDNA, and the amplified DNA was then subjected to a step of detection using oligonucleotide probes of sequences SEQ ID No 14 to SEQ ID No 21 which are presented in Table 4.

The results show that a process for preparing a collection of nucleic acids starting with a soil sample containing organisms according to the invention makes it possible to gain access to the DNA of more than 14% of the total telluric microflora, i.e. $2\times10^8$ cells per gram of soil, whereas the total microflora which can be cultured represents barely 2% of the total microbial population.

In order to determine the phylogenetic diversity of a collection of nucleic acids prepared in accordance with the invention, 47 sequences of the 16S rRNA gene were isolated and sequenced. These sequences correspond, respectively, to the nucleotide sequences SEQ ID No 60 to SEQ ID No 106.

The nucleic acids comprising the sequences SEQ ID No 60 to SEQ ID No 106 also form part of the invention, as do nucleic acids possessing at least 99%, preferably 99.5% or 99.8%, nucleic acid identity with the nucleic acids comprising the sequences SEQ ID No 60 to SEQ ID No 106. Such sequences can be used in particular as probes for screening clones of a DNA library and for thus identifying those, among the clones of the library, which contain such sequences, these sequences being liable to be close to coding sequences of interest, such as sequences encoding enzymes involved in the biosynthetic pathway of antibiotic metabolites, for example polyketides.

Comparison of the sequences of 16S rRNA from a DNA library prepared in accordance with the invention, with the sequences listed in the RDP database (Maidak B. L., Cole J. R., Parker C. T., Garrity G. M., Larsen N., Li B., Lilburn T. G., McCaughey, M. J., Olsen G. J., Overbeek R., Pramanik S., Schmidt T. M., Tiedje J. M., Woese C. R. (1999) "A new project of the RDP (Ribosomal Database Project)" Nucleic Acids Research Vol. 27: 171-173) made it possible to determine that the nucleic acids contained in a collection of nucleic acids according to the invention originate from α-proteobacteria, from β-proteobacteria, from δ-proteobacteria, from γ-proteobacteria, from actinomycetes and from a genus related to acidobacterium. These results, presented in Table 7 and in the phylogenetic tree in FIG. 7, take account of the huge phylogenetic diversity of the nucleic acids contained in a DNA library prepared in accordance with the process according to the invention.

Cloning and/or Expression Vectors

Each of the nucleic acids contained in a collection of nucleic acids prepared in accordance with the invention can be inserted into a cloning and/or expression vector.

For this purpose, any type of vector known in the prior art can be used, such as viral vectors, phages, plasmids, phagemids, cosmids, phosmids, vectors of BAC type, P1 bacteriophages, vectors of BAC type, vectors of YAC type, yeast plasmids or any other vector known in the prior art to a person skilled in the art.

Use will advantageously be made according to the invention of vectors which allow a stable expression of the nucleic acids of a DNA library. To this end, such vectors preferentially include transcription-regulation sequences which are operably linked with the genomic insert so as to allow the initiation and/or regulation of the expression of at least a portion of the said DNA insert.

It results from the text hereinabove that the invention also relates to a process for preparing a collection of recombinant vectors, characterized in that the nucleic acids obtained in step II-(iv) or in step I-(c) or any other subsequent step of a process for preparing a collection of nucleic acids from a soil sample containing organisms according to the invention are inserted into a cloning and/or expression vector.

Prior to their insertion into a cloning and/or expression vector, the constituent nucleic acids of a collection of nucleic acids according to the invention can be separated as a function of their size, for example by electrophoresis on an agarose gel, where appropriate after digestion with a restriction endonuclease.

According to another aspect, the average size of the constituent nucleic acids of a collection of nucleic acids according to the invention can be rendered into a substantially uniform size by carrying out a step of physical rupture prior to their insertion into the cloning and/or expression vector.

Such a step of physical or mechanical rupture of nucleic acids can consist of successive passages of these nucleic acids, in solution, in a metal channel about 0.4 mm in diameter, for example the channel of a syringe needle having such a diameter.

The average size of the nucleic acids can be, in this case, between 30 and 40 kb in length.

The construction of the vectors that are preferred according to the invention is represented schematically in FIGS. 25 (conjugative integrative cosmid) and 26 (integrative BAC).

Cloning and/or expression vectors which can be used advantageously for the purposes of inserting nucleic acids contained in a DNA library or collection according to the invention are, in particular, the vectors described in European patent No EP 0 350 341 and in U.S. Pat. No. 5,688,689, such vectors being especially suitable for the transformation of actinomycete strains. Such vectors contain, besides an insert DNA sequence, an attachment sequence att and a DNA sequence encoding an integrase (<u>int</u> sequence) which is functional in actinomycete strains.

However, it has been observed according to the invention that certain cloning and/or expression vectors had drawbacks and that their theoretical functional capacity was not achieved in practice.

Thus, it was seen that the integration system contained in vectors of the prior art, and in particular in the vectors described in European patent No EP 0 350 341, do not in reality allow good integration of the DNA insert from the library into the bacterial chromosome.

Starting from the hypothesis that the functional defects in the integration of such vectors into the bacterial chromosome were due to a defect in the expression of the integrase gene present in these vectors, the Applicant first attempted to increase the expression of the integrase gene by replacing the initial transcription promoter with a transcription promoter capable of significantly increasing the number of integrase transcripts.

The results were disappointing and the function of integration of these vectors into the chromosome was not improved.

Surprisingly, it has been shown according to the invention that the integrase expression difficulties contained in this family of integrative vectors did not lie in the amount of transcript expression, but in the stability of the transcripts.

According to a second hypothesis, the Applicant was able to show that the stability defect of the integrase transcripts was caused by defects in termination of the transcription of the corresponding messenger RNA.

The Applicant thus inserted a stop site placed downstream of the sequence encoding the integrase of the vector so as to obtain a messenger RNA of given size. The insertion of an additional termination signal downstream of the nucleotide sequence encoding the integrase of the vector made it possible to obtain a family of integrative vectors of cosmid type and of BAC type.

Preferentially, the stop site is placed downstream of the attachment site att.

In addition, the Applicant has developed novel conjugative vectors and novel replicative vectors of cosmid type and novel conjugative vectors of BAC type which can be used advantageously to insert constituent nucleic acids of a collection of nucleic acids prepared according to the process of the invention.

When the insertion of DNA fragments of average size is desired, vectors of the cosmid type, capable of receiving inserts having a maximum size of about 50 kb, are preferably used.

Such cosmid vectors are most particularly suitable for inserting constituent nucleic acids of a collection of nucleic acids obtained according to the process of the invention comprising a first step of direct DNA extraction by mechanical lysis of the organisms contained in the initial soil sample.

When the insertion of large nucleic acids, in particular of nucleic acids greater than 100 kb in size, or even greater than 200, 300, 400, 500 or 600 kb, is desired, use will then preferentially be made of vectors of the BAC type which are capable of receiving DNA inserts of such a size.

Such vectors of BAC type are most particularly suitable for inserting constituent nucleic acids of a collection of nucleic acids obtained in accordance with the process according to the invention, in which the first step consists of an indirect extraction of the DNA by prior separation of the organisms contained in the initial soil sample and removal of the macro-constituents from the said soil sample.

In particular, vectors of the BAC type are advantageously used to insert large nucleic acids containing, at least partially, the nucleotide sequence of an operon.

Thus, the process for preparing a collection of recombinant cloning and/or expression vectors according to the invention is also characterized in that the cloning and/or expression vector is of the plasmid type.

According to another aspect, such a process is characterized in that the cloning and/or expression vector is of the cosmid type.

According to a first aspect, it can be a cosmid which is replicative in *E. coli* and integrative in *Streptomyces*. An entirely preferred cosmid corresponding to such a definition is the cosmid pOS7001 described in Example 3.

According to yet another aspect, the cosmid vector is conjugative and integrative in *Streptomyces*.

In general, conjugative vectors of cosmid type or of BAC type, which comprise in their nucleotide sequences a unit recognized by the cellular enzymatic machinery known as a "conjugation origin", are used whenever it is desired to avoid resorting to laborious transformation techniques that are difficult to automate.

For example, the transfection of vectors initially harboured by *E. coli* cells into *Streptomyces* cells conventionally requires a step of recovering the recombinant vector contained in the *Escherichia coli* cells, and purifying it prior to the step of transforming *Streptomyces* protoplasts. It is commonly accepted that a transfection of an assembly of 1000 *Escherichia coli* clones into *Streptomyces* requires the production of about 8000 clones in order for each *E. coli* clone to have a chance of being represented.

Conversely, a step of transfection by conjugating a vector harboured by *E. coli* into *Streptomyces* cells requires the same number of clones of each of the microorganisms, the conjugation step taking place "clone to clone" and moreover not comprising the technical difficulties associated with the step for transferring genetic material by transformation of protoplasts, for example in the presence of polyethylene glycol.

In order to optimize the construction of a DNA library in *Streptomyces*, novel conjugative vectors of cosmid type and of BAC type which are of a nature to allow maximum efficacy of the conjugation step have been developed according to the invention.

In particular, the novel conjugative vectors according to the invention have been constructed by placing a selection marker gene at the end of the DNA of the vector which is transferred into the recipient bacterium at the end. This improvement to the conjugative vectors of the prior art makes it possible to positively select only the recipient bacteria which have received all of the vector DNA and, consequently, all of the insert DNA of interest.

Cosmids which are conjugative and integrative in *Streptomyces* and which are preferred according to the invention are the cosmids pOSV303, pOSV306 and pOSV307 described in Example 5.

According to another aspect, a process for preparing a collection of recombinant vectors according to the invention is carried out using a cosmid which is replicative both in *E. coli* and in *Streptomyces*. Such a cosmid is advantageously the cosmid pOS700R described in Example 6.

According to yet another aspect, the above process can be carried out with a cosmid which is replicative in *E. coli* and *Streptomyces* and conjugative in *Streptomyces*.

Such a replicative and conjugative cosmid can be obtained from a replicative cosmid in accordance with the invention, by inserting a suitable transfer origin, such as RK2, as described in Example 5 for the construction of the vector pOSV303.

According to another advantageous embodiment of the process for preparing a collection of recombinant vectors according to the invention, use is made of a cloning and/or expression vector of BAC type.

According to a first aspect, the vector of the BAC type is integrative and conjugative in *Streptomyces*.

In an entirely preferred manner, such a BAC vector which is integrative and conjugative in *Streptomyces* is the vector BAC pOSV403 described in Example 8 or else the vectors BAC pMBD-1, pMBD-2, pMBD-3, pMBD-4, pMBD-5 and pMBD-6 described in Example 15.

A subject of the invention is also a recombinant vector, characterized in that it is chosen from the following recombinant vectors:

a) a vector comprising a constituent nucleic acid of a collection of nucleic acids according to the invention;

b) a vector as obtained according to a process which avoids any involvement of the action of a restriction endonuclease on the DNA fragment to be inserted, as described previously.

In an entirely preferable manner, the invention also relates to a vector chosen from the following vectors:
- the cosmid pOS700I;
- the cosmid pOSV303;
- the cosmid pOSV306;
- the cosmid pQSV307;
- the cosmid pOS700R;
- the vector BAC pOSV403;
- the vector BAC pMBD-1;
- the vector BAC pMBD-2;
- the vector BAC pMBD-3;
- the vector BAC pMBD-4;
- the vector BAC pMBD-5;
- the vector BAC pMBD-6.

The invention also relates to a collection of recombinant vectors as obtained according to any one of the processes according to the invention.

Process for Preparing a Recombinant Cloning and/or Expression Vector According to the Invention The conventional techniques for inserting DNA into a vector in order to prepare a recombinant cloning and/or expression vector conventionally involve a first step in which a restriction endonuclease is incubated both with the DNA to be inserted and with the recipient vector, thus creating compatible ends between the DNA to be inserted and the vector DNA, allowing the assembly of the two DNAs before a final ligation step allowing the production of the recombinant vector.

However, such a conventional technique has notable drawbacks, most particularly when it is desired to insert large nucleic acids into a cloning and/or expression vector.

Specifically, the prior action of a restriction enzyme on the DNA fragments intended to be inserted into a vector is liable to appreciably reduce the size of this DNA prior to its insertion into the vector. It goes without saying that a significant reduction in the size of the DNA prior to its insertion into a vector is a situation that is particularly unfavourable when it is desired to clone large fragments of DNA liable to contain all of the coding sequences and, where appropriate, also the regulatory sequences, of an operon whose expression constitutes a complete biosynthetic pathway of a metabolite of industrial interest, and most particularly of a compound of therapeutic interest.

To overcome the drawbacks of the prior art, two processes have been developed according to the invention, for preparing a recombinant cloning and/or expression vector which do not use a restriction endonuclease on the DNA to be inserted prior to its introduction into the vector. Such processes are consequently entirely suitable for cloning long DNA fragments liable to contain, at least partially, all of the coding sequences and, where appropriate, also the regulatory sequences, of a complete operon responsible for a biosynthetic pathway.

According to a first aspect, one process for preparing a recombinant cloning and/or expression vector according to the invention is characterized in that the insertion of a nucleic acid into the cloning and/or expression vector comprises the following steps:
- opening the cloning and/or expression vector at a chosen cloning site, using a suitable restriction endonuclease;
- adding a first homopolymeric nucleic acid at the free 3' end of the open vector;
- adding a second homopolymeric nucleic acid, whose sequence is complementary to the first homopolymeric nucleic acid, at the free 3' end of the nucleic acid to be inserted into the vector;

assembling the nucleic acid of the vector and the nucleic acid by hybridizing the first and second homopolymeric nucleic acids of mutually complementary sequence;

closing the vector by ligation.

Such a process is described in Examples 10 and 13 below.

Advantageously, the above process can comprise the following characteristics, separately or in combination:

the first homopolymeric nucleic acid is of poly(A) or poly(T) sequence;

the second homopolymeric nucleic acid is of poly(T) or poly(A) sequence.

In an entirely preferred manner, the homopolymeric nucleic acids have a length of between 25 and 100 nucleotide bases, preferably between 25 and 70 nucleotide bases.

The process for preparing a recombinant cloning and/or expression vector described above is particularly suitable for the construction of DNA libraries in vectors of BAC type. Thus, according to one advantageous embodiment of the process for preparing a recombinant vector described above, the said process is also characterized in that the size of the nucleic acid to be inserted is at least 100 kb and preferably at least 200, 300, 400, 500 or 600 kb.

Such a preparation process is thus particularly suited to the insertion of nucleic acids contained in a collection of nucleic acids obtained according to the process of the invention.

In order to allow the insertion of large DNA fragments into cloning and/or expression vectors, a second process has been developed according to the invention, which makes it possible to dispense with any use of a restriction endonuclease on the DNA intended to be inserted into the vector.

Such a process for preparing a recombinant cloning and/or expression vector according to the invention is characterized in that the step of inserting a nucleic acid into the said cloning and/or expression vector comprises the following steps:

creation of blunt ends on the ends of the nucleic acid of the collection by removing the protruding 3' sequences and filling in the protruding 5' sequences;

opening the cloning and/or expression vector at a chosen cloning site using a suitable restriction endonuclease;

adding complementary oligonucleotide adapters;

creation of blunt ends at the ends of the vector nucleic acid by removing the protruding 3' sequences and filling in the protruding 5' sequences, then dephosphorylating the 5' ends in order to prevent a recircularization of the vector;

inserting the nucleic acid of the collection into the vector by ligation.

Preferably, the removal of the protruding 3' sequences is carried out using an exonuclease, such as the Klenow enzyme.

Preferably, the filling in of the protruding 5' sequences is carried out using a polymerase, and most preferably T4 polymerase, in the presence of the four nucleotide triphosphates.

A process for preparing a recombinant cloning and/or expression vector by removing the protruding 3' sequences and filling in the protruding 5' sequences as described above is particularly suitable for the construction of DNA libraries from vectors of cosmid type.

Such a process for obtaining recombinant vectors is described in Example 12.

In one specific method for preparing a recombinant vector according to the invention, oligonucleotides comprising one or more rare restriction sites are added to the vector in the cloning site of the DNA to be inserted, in accordance with the teaching of Example 10. This addition of oligonucleotides facilitates the subsequent recovery of the inserts without cleavage thereof.

Host Cells

Although any type of host cell can be used for the transfection or transformation with a nucleic acid or a recombinant vector according to the invention, in particular a prokaryotic or eukaryotic host cell, host cells whose physiological, biochemical and genetic properties are well characterized, which can be cultured easily on a large scale and whose culturing conditions for the production of metabolites are well known will preferably be used.

Preferably, the host cell receiving a nucleic acid or a recombinant vector according to the invention is phylogenetically close to the donor organisms initially contained in the environmental sample from which the nucleic acids originate.

In a most preferred manner, a host cell according to the invention should have a similar, or at least close, codon usage in the donor organisms initially present in the environmental sample, most particularly in the soil sample.

The size of the DNA fragments liable to carry the desired nucleotide sequences of interest can be variable. Thus, enzymes encoded by genes with an average size of 1 kb may be expressed using inserts of small size, while the expression of secondary metabolites will require the maintenance in the host organism of much larger fragments, for example from 40 kb to more than 100 kb, 200 kb, 300 kb, 400 kb or 600 kb.

Thus, the host cells of *Escherichia coli* constitute a preferred choice for cloning large DNA fragments.

In a most preferred manner, use will be made of the *Escherichia coli* strain known as DH10B and described by Shizuya et al. (1992), for which protocols for cloning into BAC vectors have been optimized.

However, other strains of *Escherichia coli* can be used advantageously to construct a DNA library according to the invention, such as the strains *E. coli* Sure, *E. coli* DH5α, or *E. coli* 294 (ATCC No. 31446).

In addition, the construction of a DNA library by transfecting *E. coli* cells with recombinant vectors according to the invention is also possible, the expression of genes of various prokaryotes such as *Bacillus, Thermotoga, Corynebacterium, Lactobacillus* or *Clostridium* having been described in PCT patent application No WO 99/20799.

In general, *E. coli* host cells can in all cases constitute transient hosts in which recombinant vectors according to the invention may be maintained highly effectively, it being possible for the genetic material to be handled easily and archived stably.

For the purposes of expressing the widest possible molecular diversity, other host cells may also advantageously be used, such as *Bacillus, Pseudomonas, Streptomyces, Myxococcus, Aspergillus nidulans* or *Neurospora crassa* cells.

It has also been shown according to the present invention that *Streptomyces lividans* cells can be used successfully and constitute expression systems complementary to *Escherichia coli.*

*Streptomyces lividans* constitutes a model for studying the genetics of *Streptomyces* and has also been used as a host for the heterologous expression of many secondary metabolites. *Streptomyces lividans* has, in common with other actinomycetes such as *Streptomyces coelicolor, Streptomyces griseus, Streptomyces fradiae* and *Streptomyces griseochromo-*

*genes*, the precursor molecules and the regulatory systems required for the expression of all or part of complex biosynthetic pathways, such as, for example, the polyketide biosynthetic pathway or the pathway for the biosynthesis of non-ribosomal polypeptides representing classes of molecules of very diverse structure.

*Streptomyces lividans* also has the advantage of accepting foreign DNA with high transformation efficacies.

Thus, the invention also relates to a recombinant host cell comprising a nucleic acid according to the invention, which is a constituent of a collection of nucleic acids prepared according to a process in accordance with the invention, or alternatively a recombinant host cell comprising a recombinant vector as defined above.

According to a first aspect, it may be a recombinant host cell of prokaryotic or eukaryotic origin.

Advantageously, a recombinant cell according to the invention is a bacterium, and most preferably a bacterium chosen from *E. coli* and *Streptomyces.*

According to another aspect, a recombinant host cell according to the invention is characterized in that it is a yeast or a filamentous fungus.

The invention also relates to a collection of recombinant host cells, each of the constituent host cells of the collection comprising a nucleic acid originating from a collection of nucleic acids prepared in accordance with a process for preparing a collection of nucleic acids from a soil sample containing organisms as described above.

The invention also relates to a collection of recombinant host cells, each of the constituent host cells of the collection comprising a recombinant vector according to the invention.

On account of the large size of the inserts, it is necessary to have maximum transformation efficacy. With this aim, a recipient strain of *Streptomyces lividans* constitutively expressing the pSAM2 integrase in order to promote the site-specific integration of the vector is preferred. For this, the int gene under the control of a strong promoter is integrated into the chromosome. The overproduction of integrase does not induce any excision phenomena (Raynal et al., 1998).

The production of a novel metabolite from the insert might be toxic for *Streptomyces* if the insert does not contain genes for resistance to the antibiotic produced or if this gene is not expressed or only expressed to a small extent. The capacity of the various genes for allowing *Streptomyces ambofaciens* to resist the antibiotic that it produces has been studied (Gourmelen et al., 1998; Pernodet et al., 1999). Some of these genes encode transporters of ABC type which are liable to impart a broad spectrum of resistance. These genes can be introduced into and overexpressed in the *Streptomyces lividans* host strain.

Conversely, a strain that is hypersensitive to antibiotics can be used (Pernodet et al., 1996) in order to detect the presence of resistance genes in the library. Specifically, in antibiotic-producing microorganisms, these resistance genes are often associated with the genes for the biosynthetic pathway of the antibiotic. The selection of resistance clones can make it possible to carry out a first sorting easily before the more complex tests for detecting a novel metabolite produced by the clone.

Isolation and Characterization of Novel Nucleotide Sequences Encoding Polyketide Synthases According to the invention, a collection of recombinant host cells was obtained after transfecting host cells with a collection of recombinant vectors each containing a nucleic acid insert originating from a collection of nucleic acids prepared in accordance with the process according to the invention.

More specifically, the DNA fragments obtained according to the process of the invention, in which a step of indirect extraction of DNA from the organisms contained in the soil sample is carried out, were first cloned into the integrative cosmid pOS700I.

The step of inserting DNA fragments into the integrative cosmid pOS700I was carried out according to the process of the invention in which homopolymeric polynucleotide tails poly(A) and poly(T) were added to the 3' end of the vector nucleic acid and of the DNA fragments to be inserted, respectively.

The recombinant vectors thus constructed were encapsidated in lambda phage heads and the phages obtained were used to infect *E. coli* cells-according to techniques that are well known to those skilled in the art.

A library of about 5000 *Escherichia coli* clones was obtained.

This library of clones was screened with pairs of primers specific for a nucleotide sequence encoding an enzyme involved in the polyketide biosynthetic pathway, the type I PKS enzyme, also known as β-ketoacyl synthase.

It is recalled here that polyketides constitute a chemical category of wide structural diversity comprising a large number of molecules of pharmaceutical interest such as tylosin, monensin, vermectin, erythromycin, doxorubicin or FK506.

Polyketides are synthesized by condensation of acetate molecules under the action of enzymes known as polyketide synthases (PKSs). Two types of polyketide synthase exist. The type II polyketide synthases are generally involved in the synthesis of polycyclic aromatic antibiotics and catalyze the iterative condensation of acetate units.

The type I polyketide synthases are involved in the synthesis of macrocyclic or macrolide polyketides and constitute modular multifunctional enzymes.

Given their therapeutic interest, there is a need in the state of the art to isolate and characterize novel polyketide synthases which can be used for the production of novel pharmaceutical compounds, in particular novel pharmaceutical compounds with antibiotic activity.

The screening of the library of recombinant clones described above using PCR primers which selectively amplify nucleotide sequences encoding type I polyketide synthases has made it possible to identify recombinant clones containing DNA inserts comprising a nucleotide sequence encoding novel polyketide synthases. The nucleotide sequences encoding these novel polyketide synthases are referenced as the sequences SEQ ID No 33 to SEQ ID No 44 and SEQ ID No. 115 to SEQ ID No. 120.

Another subject of the invention consists of a nucleic acid encoding a novel polyketide synthase I, characterized in that it comprises one of the nucleotide sequences SEQ ID No 34 to SEQ ID No 44 and SEQ ID No. 115 to SEQ ID No. 120.

Preferably, such a nucleic acid is in isolated and/or purified form.

The invention also relates to a recombinant vector comprising a polynucleotide comprising one of the sequences SEQ ID No 34 to SEQ ID No 44 and SEQ ID No. 115 to SEQ ID No. 120.

The invention also relates to a recombinant host cell comprising a nucleic acid chosen from polynucleotides comprising one of the nucleotide sequences SEQ ID No 34 to SEQ ID No 44 and SEQ ID No. 115 to SEQ ID No. 120 as well as to a recombinant host cell comprising a recombinant vector into which is inserted a polynucleotide comprising one of the nucleotide sequences SEQ ID No 34 to SEQ ID No 44 and SEQ ID No. 115 to SEQ ID No. 120.

Advantageously, the recombinant vectors containing a DNA insert encoding a novel type I polyketide synthase according to the invention are cloning and expression vectors.

Preferably, a recombinant host cell as described above is a bacterium, a yeast or a filamentous fungus.

The amino acid sequences of novel polyketide synthases originating from organisms contained in a soil sample were deduced from the nucleotide sequences SEQ ID No 34 to SEQ ID No 44 and SEQ ID No. 115 to SEQ ID No. 120 above. They are polypeptides comprising one of the amino acid sequences SEQ ID No 48 to SEQ ID No 59 and SEQ ID No. 121 to 126.

The invention also relates to novel polyketide synthases comprising an amino acid sequence chosen from the sequences SEQ ID No 48 to SEQ ID No 59 and SEQ ID No. 121 to SEQ ID No. 126.

The nucleotide sequence SEQ ID No. 114 which comprises six open reading frames respectively encoding the polypeptides of sequences SEQ ID No. 121 to SEQ ID No. 126 also forms part of the invention.

The nucleotide sequence SEQ ID No. 113 of the a26G1 cosmid, which contains the sequence complementary to the sequence SEQ ID No. 114 also forms part of the invention.

Genomic DNA originating from pure bacterial strains, such as *Streptomyces coelicolor* (ATCC No. 101.478), *Streptomyces ambofaciens* (NRRL No. 2.420), *Streptomyces lactamandurans* (ATCC No. 27.382), *Streptomyces rimosus* (ATCC No. 109.610), *Bacillus subtilis* (ATCC No. 6633) or *Bacillus lichenifornis* and *Saccharopolyspora erythrea*, was also extracted and amplified according to the invention.

A PCR amplification of DNA from each of the bacterial strains described above was carried out using pairs of primers specific for the nucleic acid sequences of type I polyketide synthase.

Novel bacterial type I polyketide synthase genes were thus able to be isolated and characterized. These are the nucleic acid sequences SEQ ID No 30 to SEQ ID No 32.

A subject of the invention is also, therefore, nucleotide sequences encoding novel type I polyketide synthases chosen from the polynucleotides comprising one of the nucleotide sequences SEQ ID No 30 to SEQ ID No 32.

Recombinant vectors comprising the nucleotide sequences encoding novel type I polyketide synthases defined above also form part of the invention.

The invention also relates to recombinant host cells, characterized in that they contain a nucleic acid encoding a novel type I polyketide synthase comprising a nucleotide sequence chosen from the sequences SEQ ID No 30 to SEQ ID No 32 and recombinant host cells comprising a recombinant vector as defined above.

A subject of the invention is also polypeptides encoded by sequences comprising the nucleic acids SEQ ID No 30 to 32, and more specifically polypeptides comprising the amino acid sequences SEQ ID No 47 to SEQ ID No 50.

A subject of the invention is also a process for producing a type I polyketide synthase according to the invention, the said production process comprising the following steps:

production of a recombinant host cell comprising a nucleic acid encoding a type I polyketide synthase comprising a nucleotide sequence chosen from the sequences SEQ ID No 33 to SEQ ID No 44 and SEQ ID No 30 to SEQ ID No 32 and SEQ ID No. 115 to SEQ ID No. 120;

culturing of the recombinant host cells in a suitable culture medium;

recovery and, where appropriate, purification of the type I polyketide synthase from the culture supernatant or from the cell lysate.

The novel type I polyketide synthases obtained according to the process described above can be characterized by binding to an immunoaffinity chromatography column onto which antibodies recognizing these polyketide synthases have been pre-immobilized.

The type I polyketide synthases according to the invention, and more particularly the recombinant polyketide synthases described above, can also be purified by high performance liquid chromatography (HPLC) techniques such as, for example, reverse-phase chromatography techniques or anion-exchange or cation-exchange chromatography techniques, that are well known to those skilled in the art.

The recombinant or non-recombinant polyketide synthases according to the invention can be used for the preparation of antibodies.

According to another aspect, a subject of the invention is also an antibody which specifically recognizes a type I polyketide synthase according to the invention or a peptide fragment of such a polyketide synthase.

The antibodies according to the invention may be monoclonal or polyclonal. The monoclonal antibodies can be prepared from hybridoma cells according to the technique described by Kohler and Milstein C. (1975), Nature, Vol. 256:495.

The polyclonal antibodies can be prepared by immunizing a mammal, in particular mice, rats or rabbits, with a type I polyketide synthase according to the invention, where appropriate in the presence of an immunity-adjuvant compound, such as complete Freund's adjuvant, incomplete Freund's adjuvant, aluminium hydroxide or a compound from the muramyl peptide family.

For the purposes of the present invention, antibody fragments such as the Fab, Fab', F(ab')$_2$, or single-chain antibody fragments containing the variable portion (ScFv) described by Martineau et al. (1998) J. Mol. Biol., Vol. 280 (1):117-127 or in U.S. Pat. No. 4,946,778, and the humanized antibodies described by Reinmann K A et al. (1997), AIDS Res. Hum. Retroviruses, Vol. 13(11):933-943 or by Leger O. J et al. (1997), Hum. Antibodies, Vol. 8 (1): 3-16, also constitute "antibodies".

The antibody preparations according to the invention are useful in particular in qualitative or quantitative immunological tests intended either simply to detect the presence of a type I polyketide synthase according to the invention or to quantify the amount of this polyketide synthase, for example in the culture supernatant or the cell lysate of a bacterial strain capable of producing such an enzyme.

Another subject of the invention consists of a process for detecting a type I polyketide synthase according to the invention or a peptide fragment of this enzyme, in a sample, the said process comprising the steps of:

a) placing an antibody according to the invention in contact with the sample to be tested;

b) detecting the antigen/antibody complex possibly formed.

The invention also relates to a kit or equipment for detecting a type I polyketide synthase according to the invention in a sample, comprising:

a) an antibody according to the invention;

b) where appropriate, reagents required for detecting the antigen/antibody complex possibly formed.

An antibody directed against a type I polyketide synthase according to the invention can be labelled using an isotopic or non-isotopic detectable label, according to processes that are well known to those skilled in the art.

Screening of a DNA library according to the invention using a pair of primers which hybridize with target sequences whose presence is desired, such as sequences of the puromycin biosynthetic pathway, sequences of the linA gene involved in the biodegradation of lindane or sequences encoding type I polyketide synthases, have been detailed hereinabove.

A subject of the invention is thus a process for detecting a nucleic acid of given nucleotide sequence, or whose nucleotide sequence is structurally similar to a given nucleotide sequence, in a collection of recombinant host cells according to the invention, characterized in that it comprises the following steps:

placing the collection of recombinant host cells in contact with a pair of primers which hybridize with the given nucleotide sequence or which hybridize with the nucleotide sequence that is structurally similar to a given nucleotide sequence;

carrying out at least three amplification cycles;

detecting any nucleic acid amplified.

For the amplification conditions that are appropriate as a function of the desired target sequences, a person skilled in the art may advantageously refer to the examples below.

According to another aspect, the invention also relates to a process for detecting a nucleic acid, given nucleotide sequences or nucleotide sequences that are structurally similar to a given nucleotide sequence, in a collection of recombinant host cells according to the invention, characterized in that it comprises the following steps:

placing the collection of recombinant host cells in contact with a probe which hybridizes with the given nucleotide sequence or which hybridizes with a nucleotide sequence that is structurally similar to the given nucleotide sequence;

detecting the hybrid possibly formed between the probe and the nucleic acids included in the vectors of the collection.

To carry out the screening of a DNA library according to the invention in order to detect the presence of a nucleotide sequence encoding a polypeptide capable of degrading lindane, the recombinant clones of interest were detected on the basis of their phenotype corresponding to their capacity to degrade lindane. With this aim, the clones isolated and/or sets of clones of the DNA library prepared were cultured in a culture medium in the presence of lindane and the lindane degradation was observed by the formation of a cloudy halo in the immediate environment of the cells.

The invention also relates to a process for identifying the production of a compound of interest by one or more recombinant host cells in a collection of recombinant host cells according to the invention, characterized in that it comprises the following steps:

culturing the recombinant host cells of the collection in a suitable culture medium;

detecting the compound of interest in the culture supernatant or in the cell lysate of one or more of the recombinant cells cultured.

A subject of the invention is also a process for selecting a recombinant host cell which produces a compound of interest in a collection of recombinant host cells according to the invention, characterized in that it comprises the following steps:

culturing recombinant host cells of the collection in a suitable culture medium;

detecting the compound of interest in the culture supernatant or in the cell lysate of one or more of the recombinant host cells cultured;

selecting recombinant host cells which produce the compound of interest.

The invention also relates to a process for producing a compound of interest, characterized in that it comprises the following steps:

culturing a recombinant host cell selected according to the process described above;

recovering and, where appropriate, purifying the compound produced by the said recombinant host cell.

The invention also relates to a compound of interest, characterized in that it is obtained according to the process described above.

A compound of interest according to the invention can consist of a polyketide produced by means of expressing at least one nucleotide sequence comprising a sequence chosen from the sequences SEQ ID No 33 to 44 and SEQ ID No 30 to 32 and SEQ ID No. 115 to SEQ ID No. 120.

The invention also relates to a composition comprising a polyketide produced by means of expressing at least one nucleotide sequence comprising a sequence chosen from the sequences SEQ ID No 33 to SEQ ID No 44 and SEQ ID No 30 to SEQ ID No 32 and SEQ ID No. 115 to SEQ ID No. 120.

A polyketide produced by means of expressing at least one nucleotide sequence above is preferentially the product of the activity of several coding sequences included in a functional operon whose translation products are the various enzymes required for the synthesis of a polyketide, one of the above sequences being included and expressed in the said operon. Such an operon comprising a nucleic acid sequence according to the invention encoding a polyketide synthase can be constructed, for example, according to the teaching of Borchert et al. (1992).

The invention also relates to a pharmaceutical composition comprising a pharmacologically active amount of a polyketide according to the invention, where appropriate in combination with a pharmaceutically compatible vehicle.

Such pharmaceutical compositions will advantageously be adapted for the administration, for example parenteral administration, of an amount of a polyketide synthesized by a type I polyketide synthase according to the invention ranging from 1 μg/kg per day to 10 mg/kg per day, preferably at least 0.01 mg/kg per day and most preferably between 0.01 and 1 mg/kg per day.

The pharmaceutical compositions according to the invention can be administered either orally, rectally, parenterally, intravenously, subcutaneously or intradermally.

The invention also relates to the use of a polyketide obtained by means of expressing a type I polyketide synthase according to the invention, for the manufacture of a medicinal product, in particular a medicinal product with antibiotic activity.

The invention will also be illustrated, without however being limited, by the figures and examples below.

FIG. 1 illustrates the scheme of the various lysis steps carried out according to protocols 1, 2, 3n, 4a, 4b, 5a and 5b described in Example 1.

FIG. 2 illustrates an electrophoresis on 0.8% agarose gel of the DNAs extracted from 300 mg of soil No 3 (St André coast) after various lysis treatments (protocols 1 to 5, cf. FIG. 1). M: lambda phage molecular weight marker.

FIG. 3 illustrates the proportion of various genera of actinomycetes cultured after treatments 1 to 5 (cf. FIG. 1). The cfu (colony-forming unit) number was determined on a medium which is selective for this group of bacteria. A total number of about 400 colonies was analysed.

FIG. 4 illustrates the recovery of lambda phage DNA digested with HindIII added to the soils at different concentrations before (G) or after (G*) grinding. The treatments T (heat shocks) and S (sonication) are additional lysis treatments. The quantification was carried out by analysis with a phospho-imager after dot-blot hybridization. A sample of each soil was used for each concentration of lambda phage added. The characteristics of the soils are given in Table 1. The samples corresponding to 10 and 15 µg of DNA added were not treated.

FIG. 5 illustrates the PCR amplification of the DNAs extracted from soil No 3 according to protocols 1, 2, 3, 5a and 5b. The primers FGPS 122 and FGPS 350 (Table 2) were used to target indigenous *Streptosporangium* spp. The DNAs extracted were used undiluted or at 10-fold and 100-fold dilutions. M: 123 bp molecular weight marker (Gibco BRL), C: DNA-free amplification control.

FIG. 6 illustrates the amounts of DNA extracted after inoculating spores (a) or mycelium (b) of *S. lividans* OS48.3 inoculated into the soils at different concentrations. The amounts of mycelium added to the soil correspond to the number of spores inoculated in the germination medium. About 50% of the spores germinated and the number of cells or genomes contained in the germinated spore hyphae was not determined. The amounts of spores and of mycelium inoculated are thus not directly comparable. The extraction protocol was carried out according to protocol 6 (cf. materials and methods section). Symbol (') indicates that RNA was included in the extraction buffer. The target DNA was amplified by PCR with the primers FGPS 516 and FGPS 517, and the quantification was carried out with a phospho-imager after dot-blot hybridization using the probe FGPS 518. A sample of each soil was used for each concentration of hyphae or of spores. The characteristics of the soils are described in Table 1.

FIG. 7 represents the phylogenetic tree obtained with the Neighbour Joining algorithm, positioning the 16S rDNA sequences contained in the soil DNA library, relative to cultured reference bacteria. In grey: the sequences obtained from the pools of clones of the library.

The bootstrap values are indicated at the nodes, after re-sampling of 100 repetitions. The scale bar indicates the number of substitutions per site. The access number of the sequences in the Genbank database is indicated in parentheses.

FIG. 24 illustrates the alignment of soil PKSs with the conserved active sites of other PKSs. The references for each peptide are indicated. The beta-ketoacyl synthase domains were aligned using the GCG PILEUP program (Wisconsin Package Version 9.1, Genetics Computer Group, Madison, Wis.).

Figure 25:
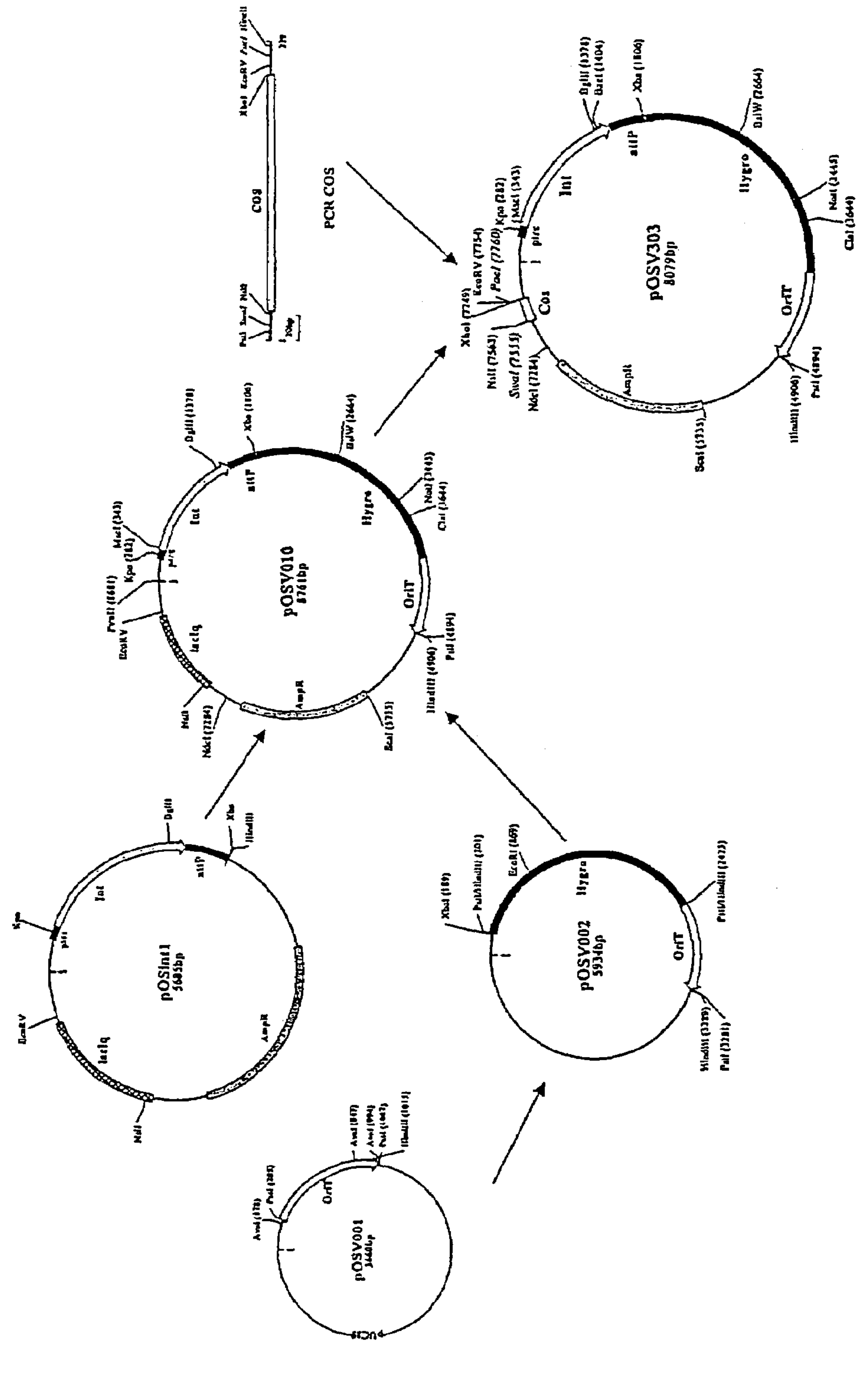

FIG. 25 illustrates the construction of an integrative conjugative cosmid.

Figure 26:
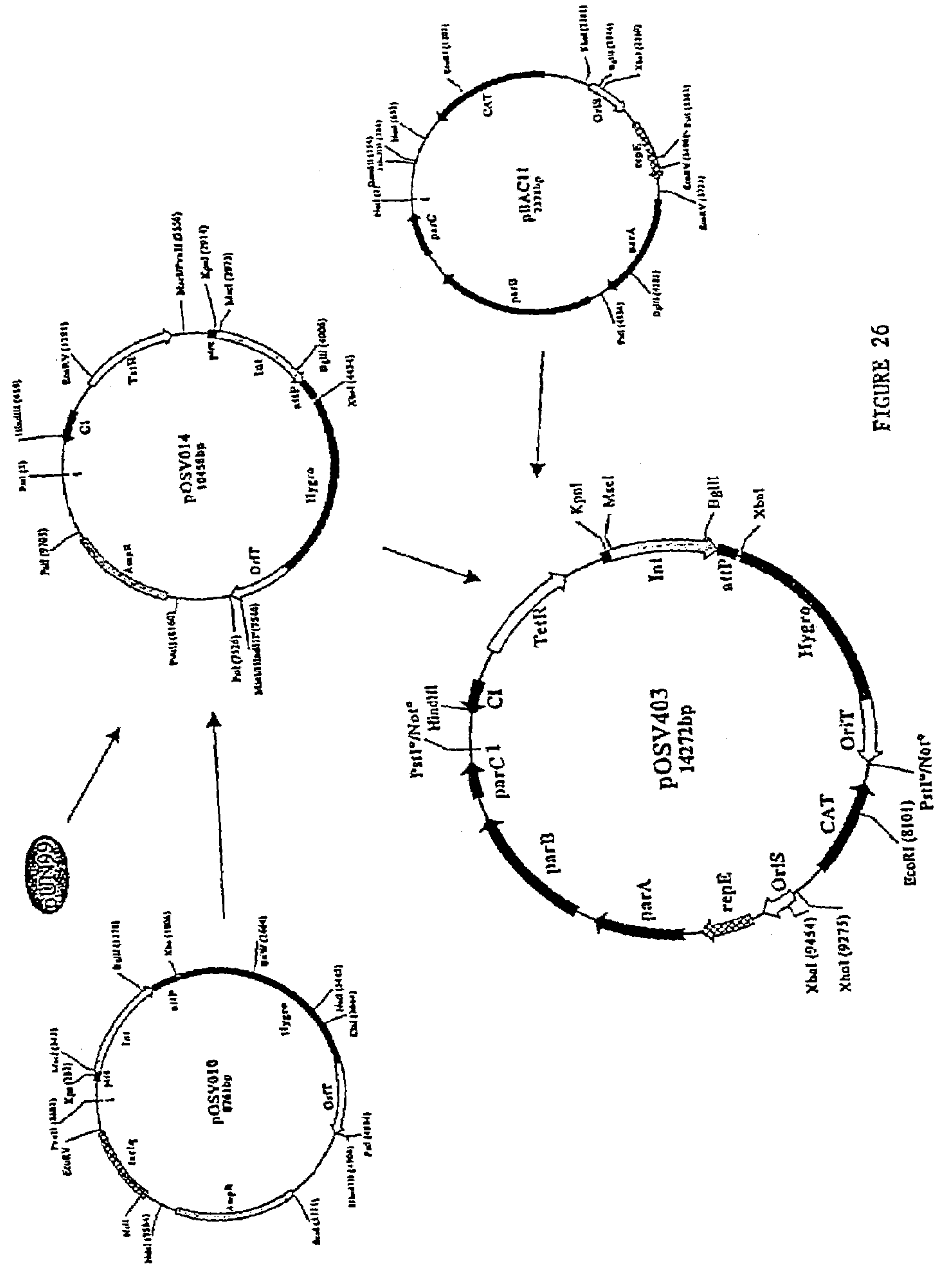

FIG. 26 illustrates the construction of an integrative conjugative BAC.

Figure 27:
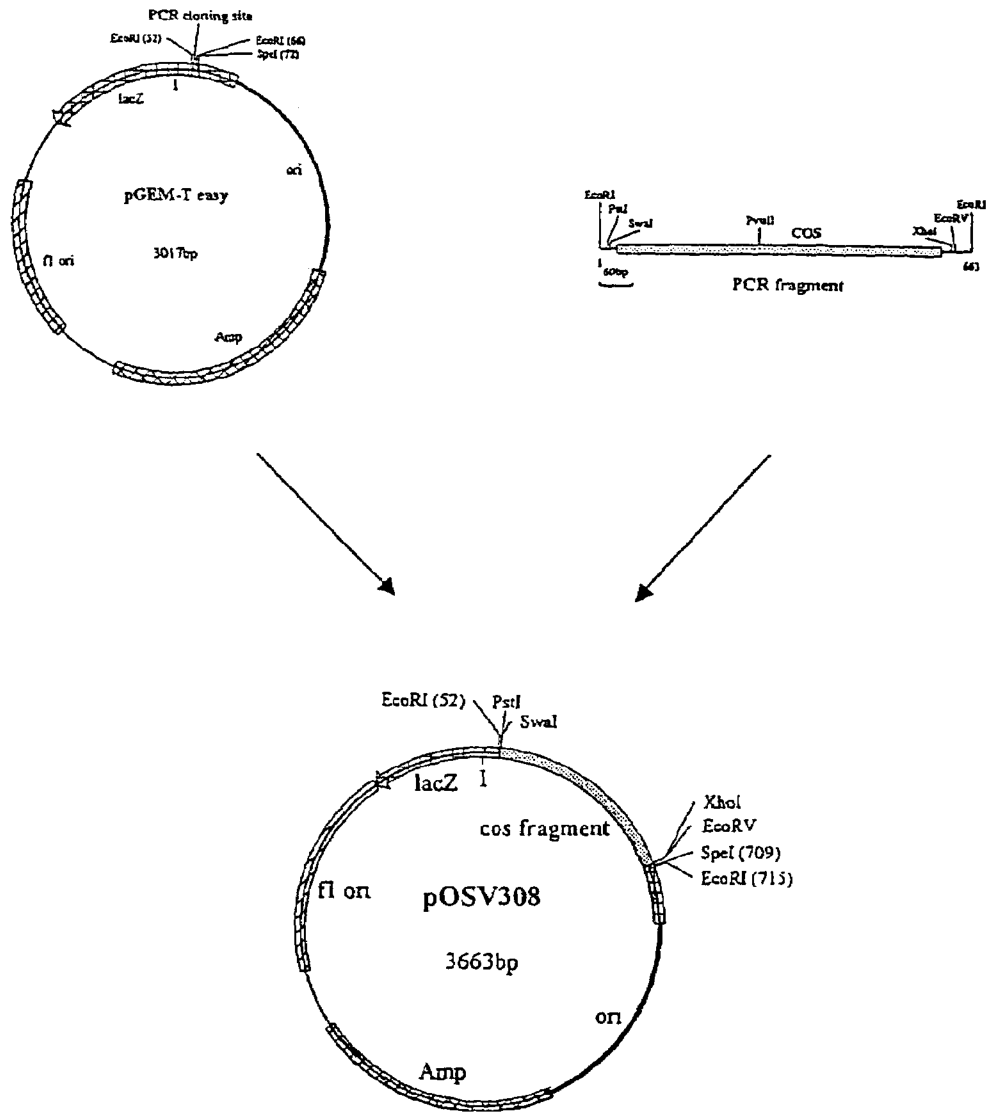

FIG. 27 illustrates the scheme for constructing the vector pOSV308.

Figure 28:
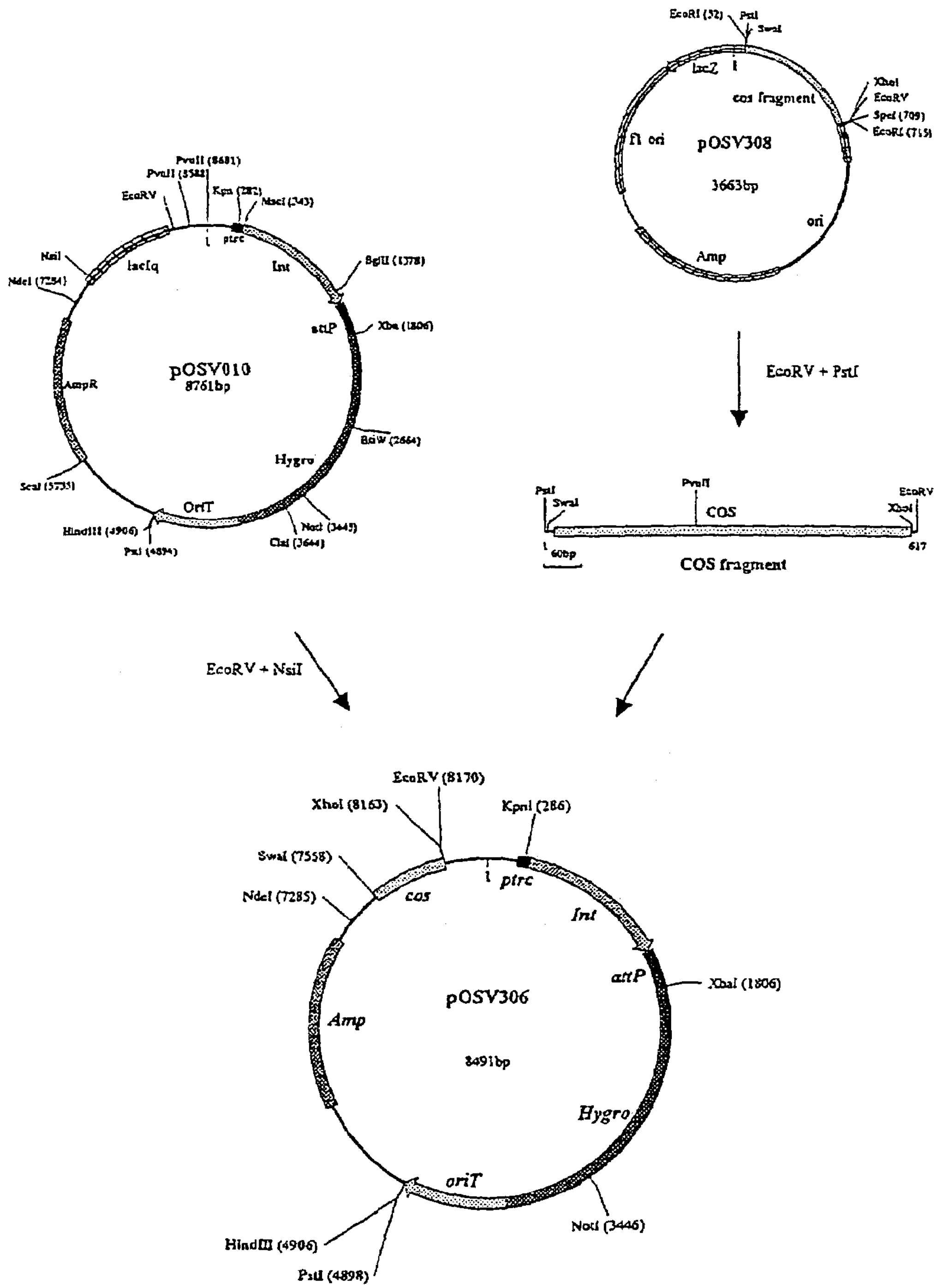

FIG. 28 illustrates the scheme for constructing the vector pOSV306.

Figure 29:
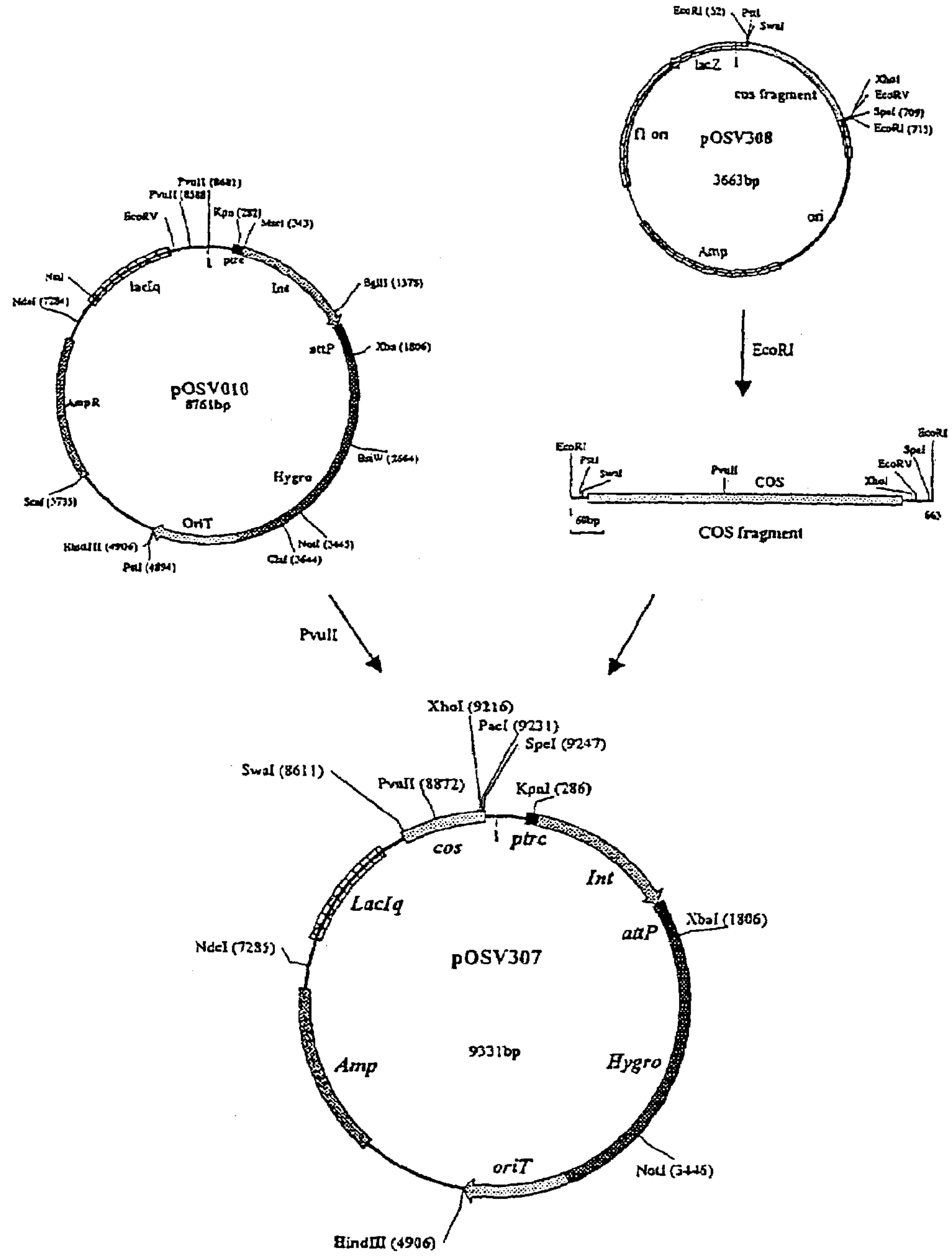

FIG. 29 illustrates the scheme for constructing the vector pOSV307.

Figure 30:
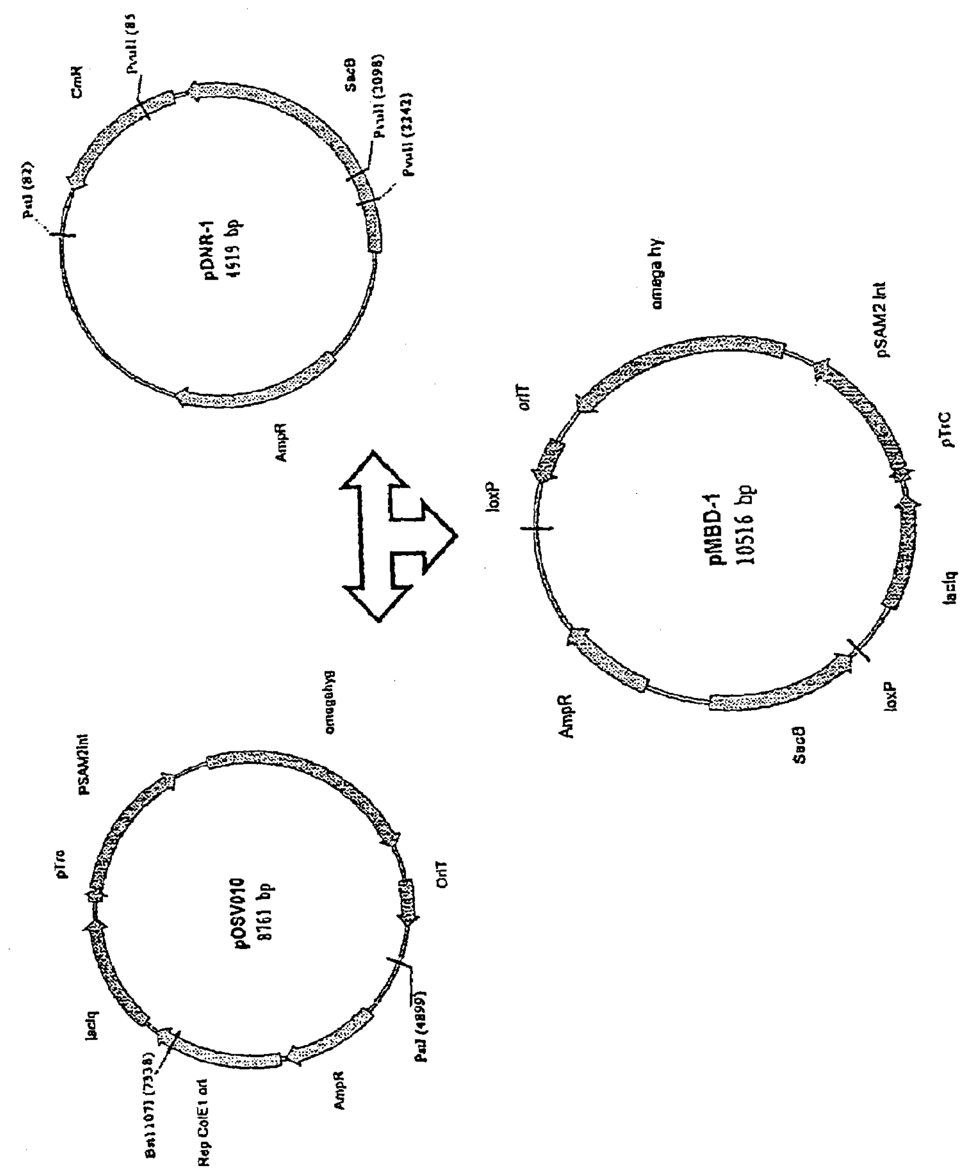

FIG. 30 illustrates the scheme for constructing the vector PMBD-1.

Figure 31:
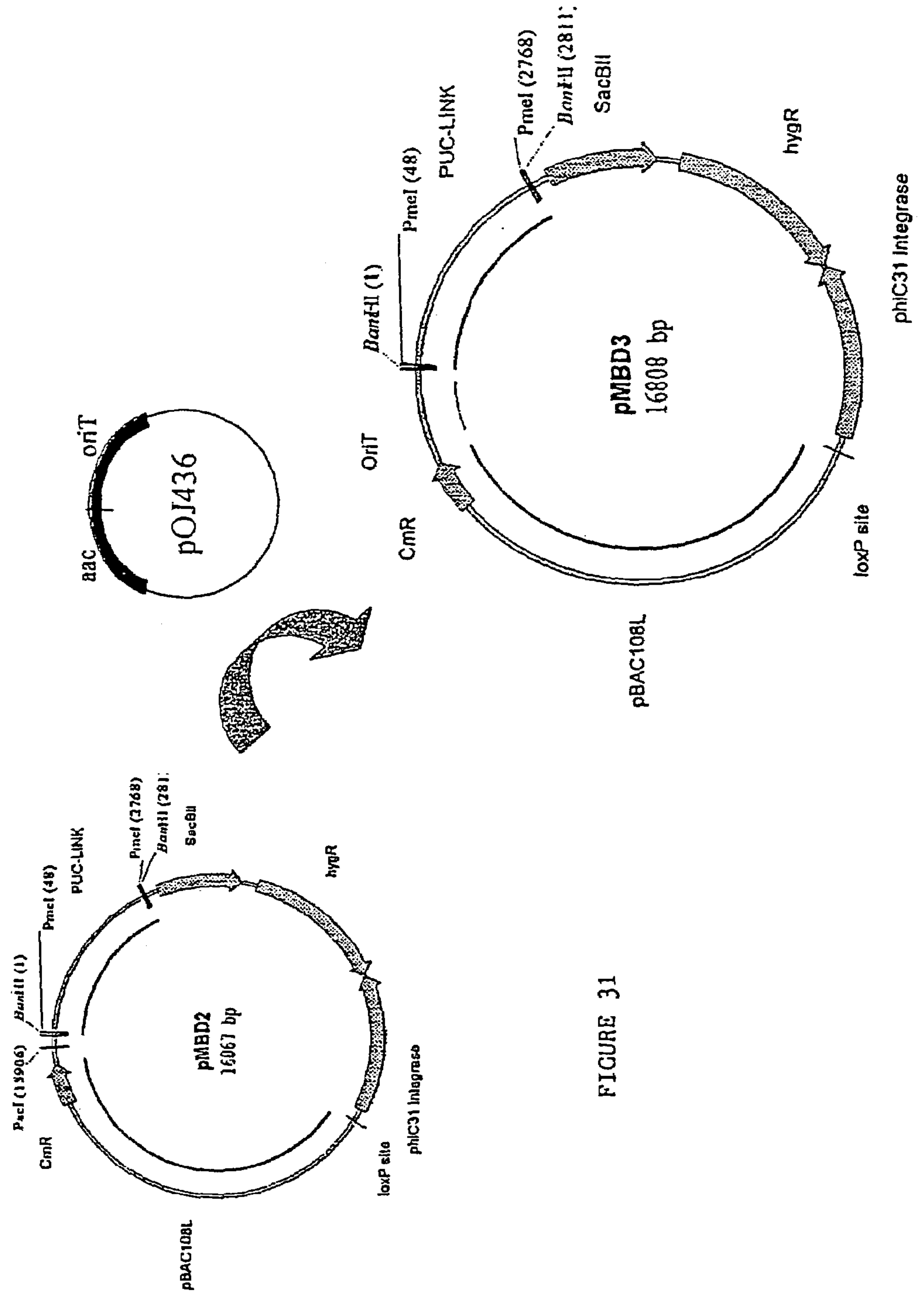

FIG. 31 shows a detailed map of the plasmid pMBD-2 and also a scheme for constructing the vector pMBD-3.

Figure 32:
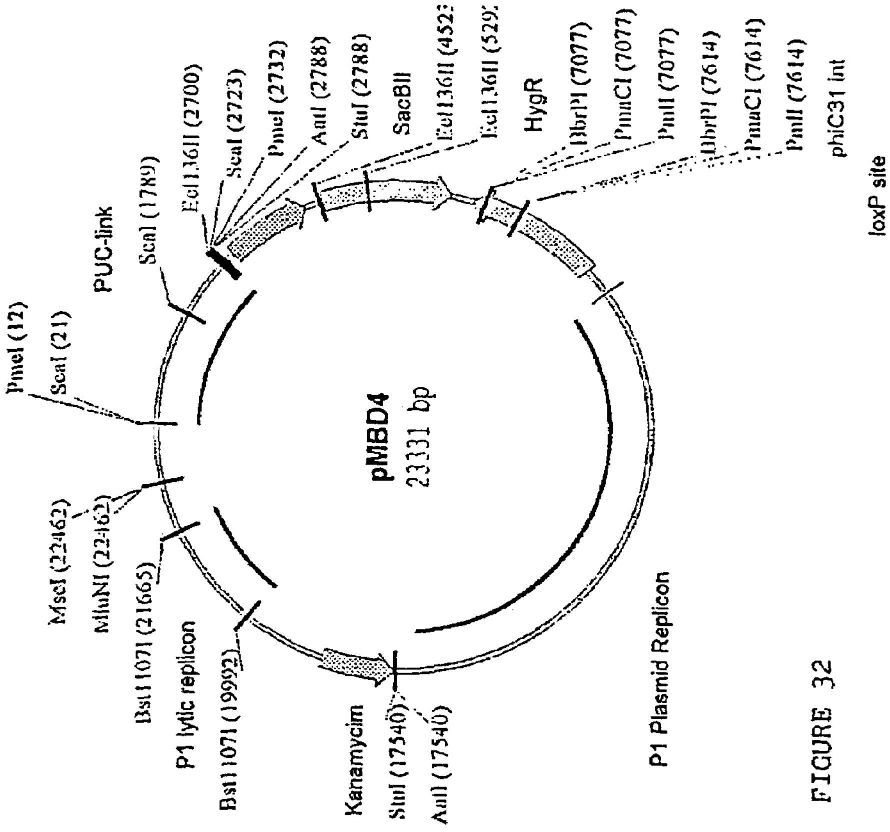

FIG. 32 illustrates a detailed map of the plasmid pMBD-4.

Figure 33:
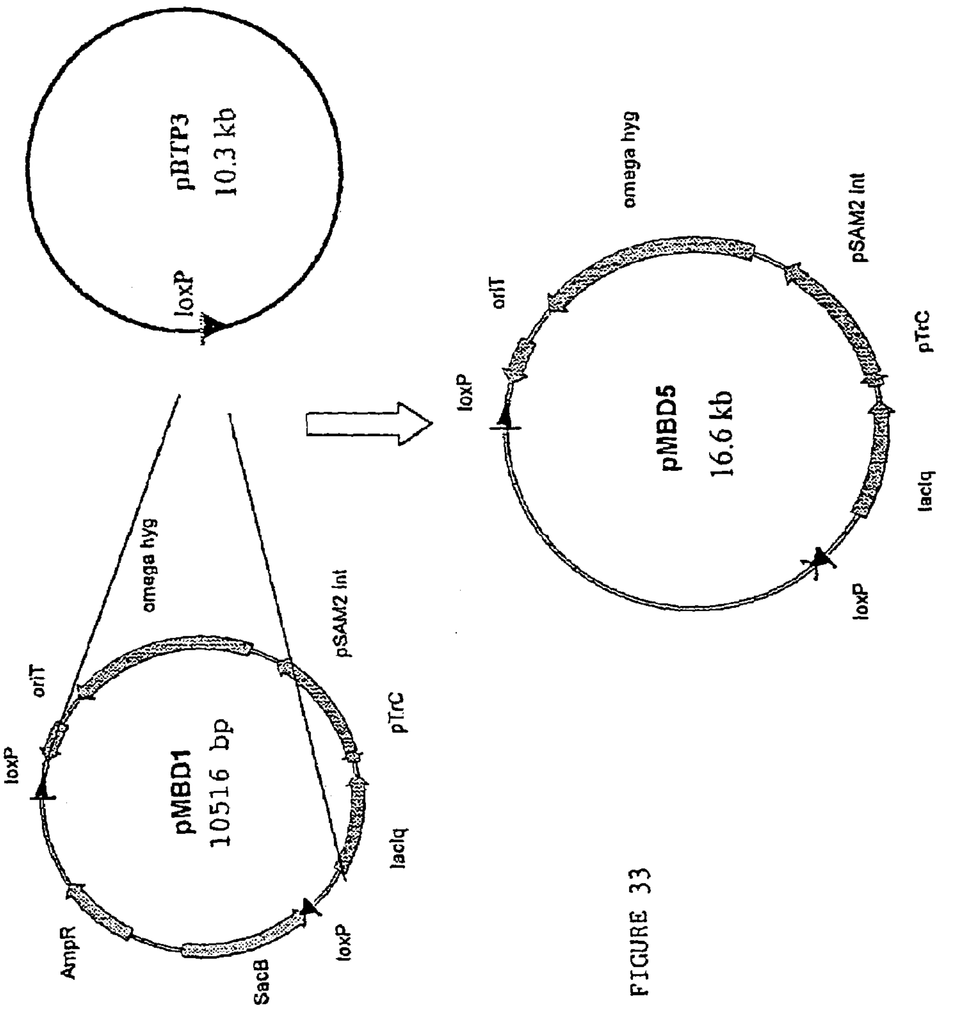

FIG. 33 illustrates the scheme for constructing the plasmid pMBD-5 from the plasmid pMBD-1.

Figure 34:
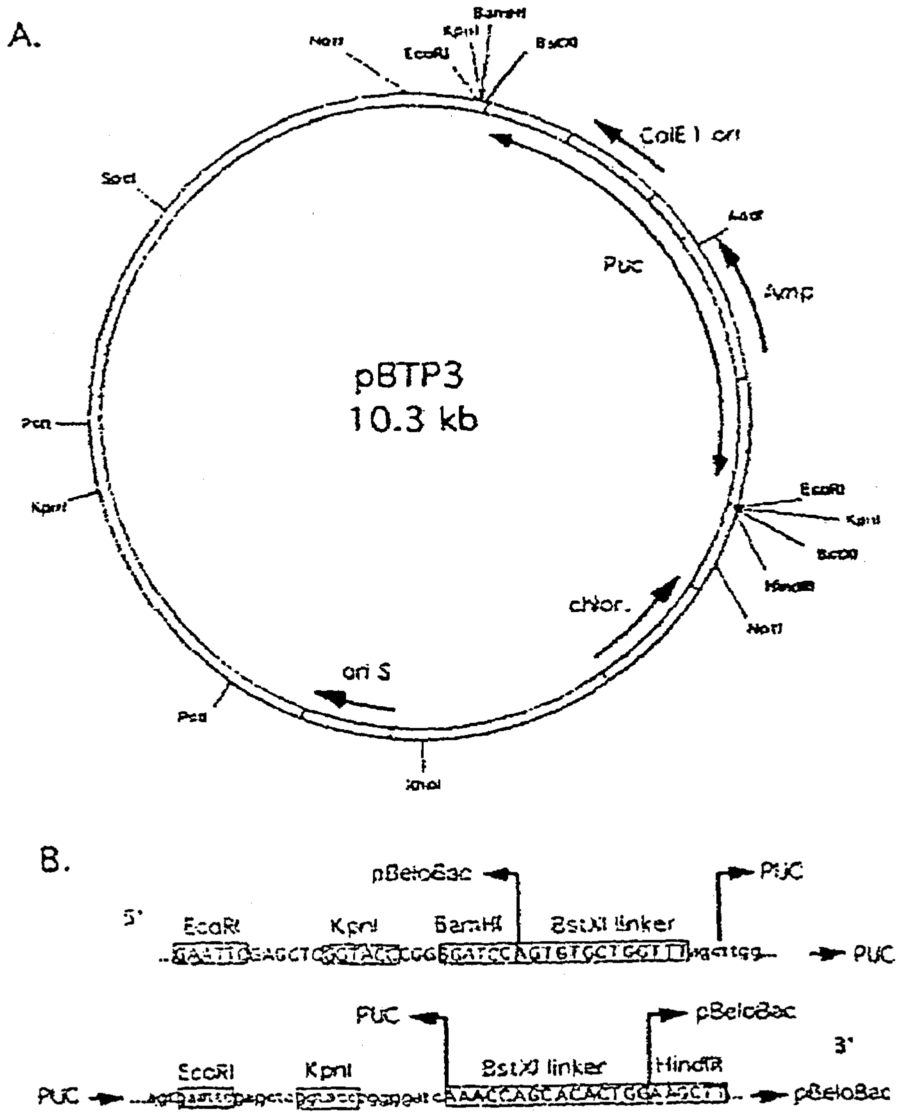

FIG. 34 illustrates the detailed map of the vector pBTP-3.

Figure 35:
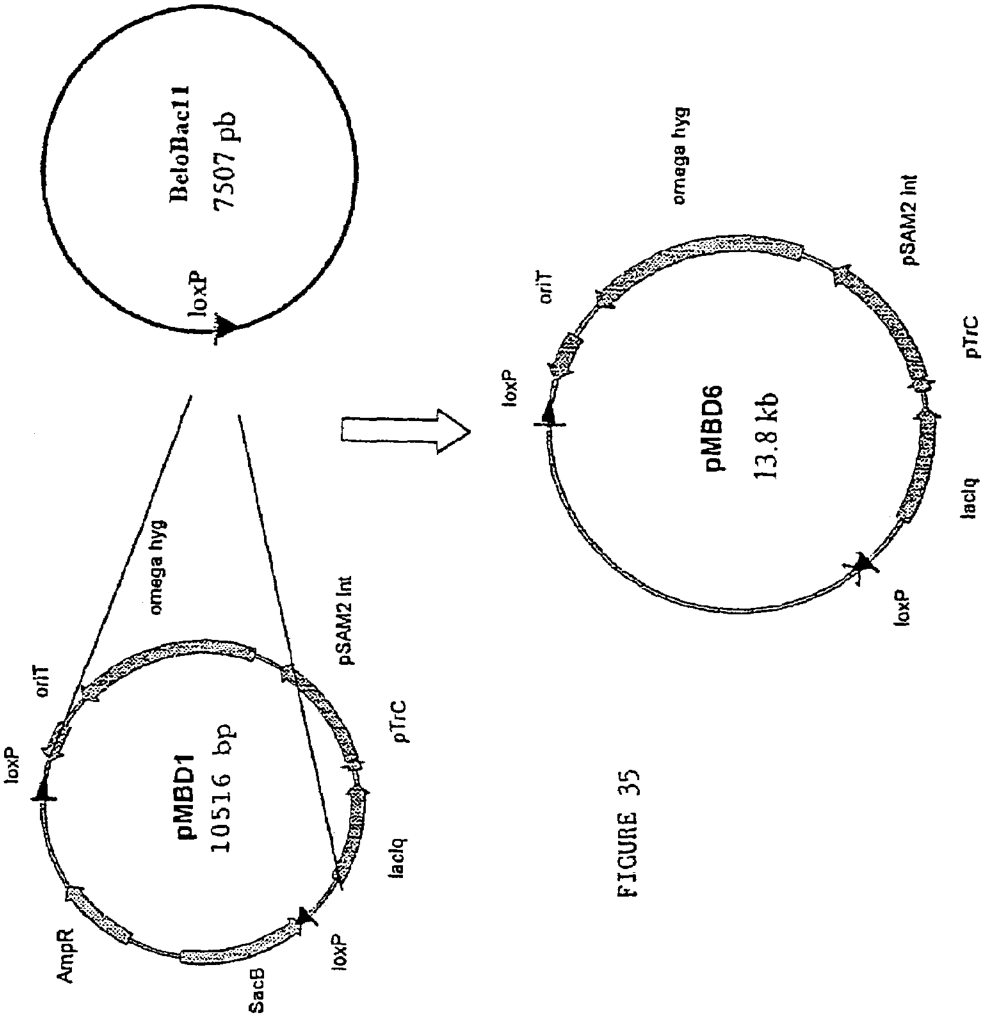

FIG. 35 illustrates the scheme for constructing the vector pMBD-6 from the vector pMBD-1.

Figure 36:
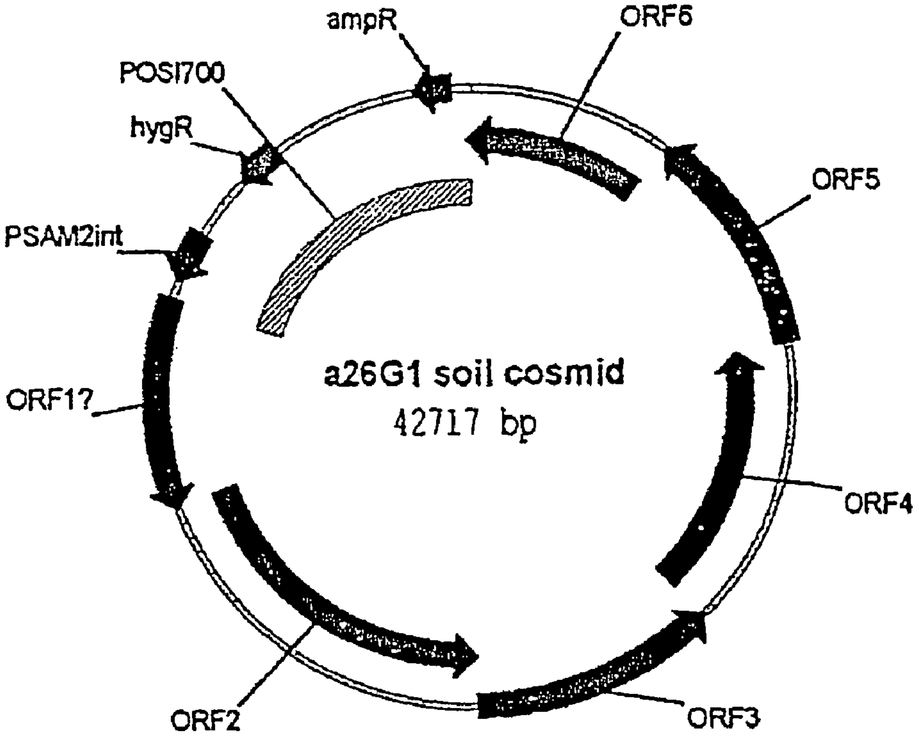

FIG. 36 illustrates the map of the cosmid a26G1 whose DNA insertion contains open reading frames encoding several polyketide synthases.

Figure 37:
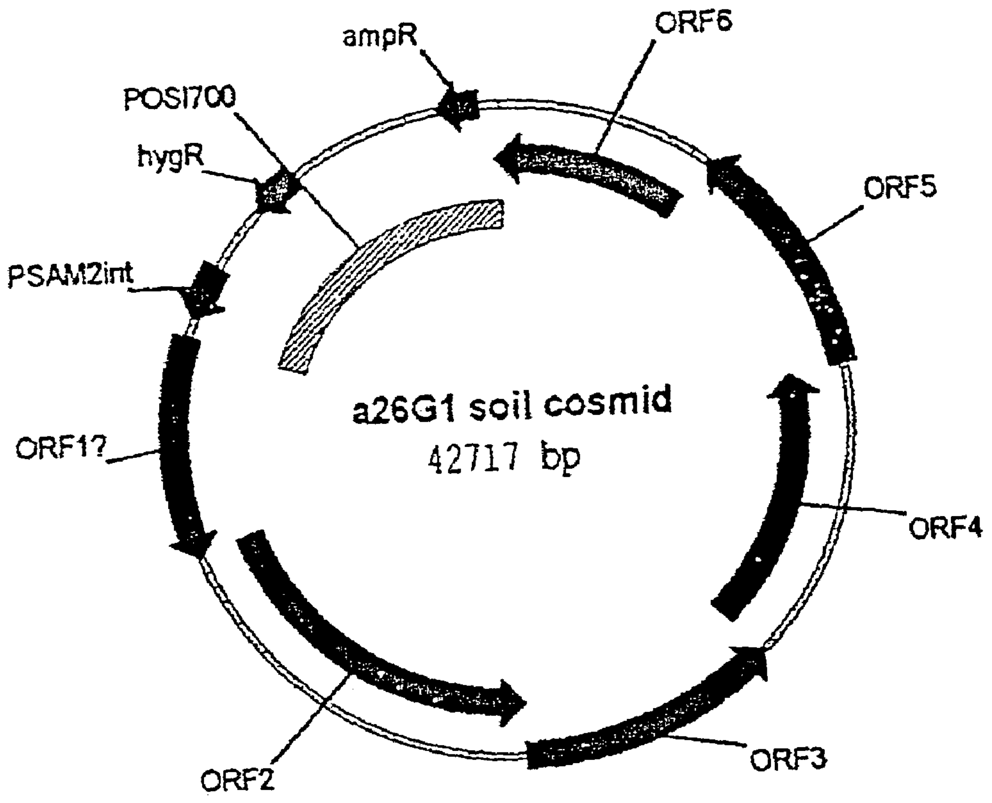
Figure 37:
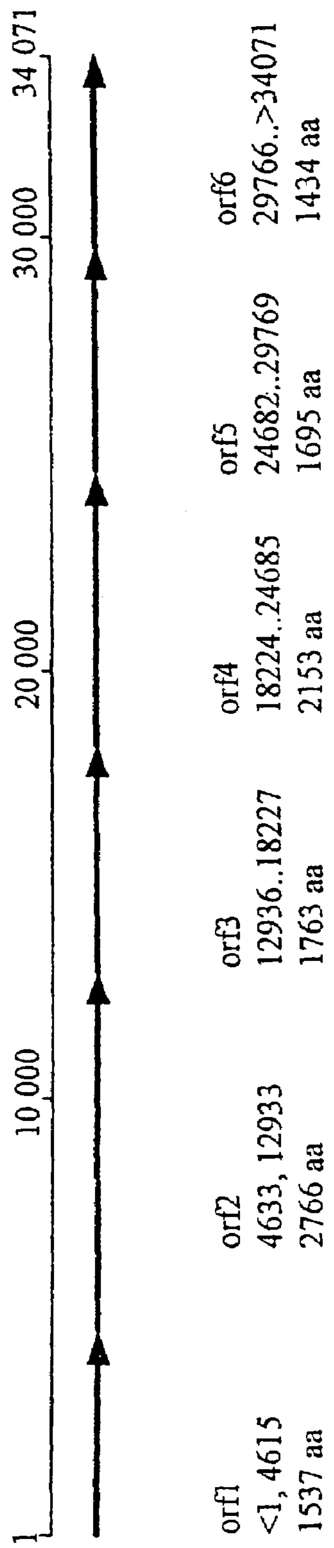

FIG. 37 is a scheme representing the DNA insertion (+strand) of the cosmid a26G1, on which are positioned the various reading frames encoding several polyketide synthases.

EXAMPLES

Example 1

Process for Preparing a Collection of Nucleic Acids from a Soil Sample Containing Organisms, Comprising a Step of Direct Extraction of DNA from the Soil Sample 1. Material and Methods 1.1 SOILS: The characteristics of the six soils used in this study are listed in Table 1.

The clay content and organic matter content range, respectively, from 9 to 47% and from 1.7 to 4.7%, the pH ranging from 4.3 to 5.8.

Soil samples were collected from the surface layer of 5 to 10 cm in depth. All the visible roots were removed and the soils were stored at 4° C. for a few days if necessary, after which they were dried for 24 hours at room temperature and screened (average mesh size: 2 mm) and then stored for up to several months at 4° C.

1.2 BACTERIAL STRAIN AND CULTURE CONDITIONS: The extracellular DNA and the bacterial strains supplying vegetative cells, spores or hyphae, used to inoculate the soil samples, were chosen such that their presence could be specifically monitored.

In order to obtain large amounts of extracellular DNA, the lysogenic strain of *E. coli* 1192 Hfr P4X (metB), containing the lambda phage CI857 Sam7, was cultured on Luria-Bertani (LB) medium for two hours at 30° C., then for 30 minutes at 40° C., and then for 3 hours at 37° C. The lambda phage DNA was extracted according to the technique described by Sambrook J. et al. (1989) Molecular Cloning: A Laboratory Manual, 2nd, ed. Cold Spring Harbor Laboratory, Cold Spring Harbor N.Y.

The avirulent strain of *Bacillus anthracis* (STERNE 7700) was used as bacterial cell inoculum. *Bacillus anthracis* was multiplied on a "trypticase soy broth" (TSB) (Biomérieux, Lyons, France) culture broth for about 6 hours, checking that the $OD_{600}$ was maintained below 0.6. These conditions allow the growth of vegetative cells without formation of spores (Patra et al., (1996), FEMS Immunol. Medical Microbiology, vol. 15:223-231). The spores of *Streptomyces lividans* OS48.3 (Clerc-Bardin et al., unpublished) were removed mechanically from the organism cultures on a R2YE medium (Hopwood et al., (1985), Genetic Manipulation of *Streptomyces*-A Laboratory Manual. The John Innes Foundation, Norwich, United Kingdom). The hyphae of *S. lividans* OS48.3 were obtained from pre-germination spores, since it was expected that the use of short hyphae would minimize the rupture and subsequent loss of DNA. The spores were suspended in TES buffer (N-tris[hydroxymethyl]methyl-2-aminoethane-sulphonic acid; Sigma-Aldrich Chimie, France) (0.05 M; pH 8) (Holben W E et al., (1988), APPL. Environ. Microbiol. vol. 54:703-711), and were then subjected to a heat shock (50° C. for 10 minutes followed by cooling under cold running water and then addition to an equal volume of pre-germination medium (1% yeast extract, 1% casamino acids, 0.01 M $CaCl_2$).

The solution was incubated at 37° C. on an agitator. The proportion of germinated spores was estimated at about 50%, in accordance with the results of Hopwood et al. (1985). After centrifugation, the pellets were resuspended in TES buffer, added to 3% TSB medium and incubated at 37° C. until an $OD_{450}$ of 0.15 was obtained (Hopwood et al., (1985)). *Streptomyces hygroscopicus* SWN 736 and *Streptosporangium fragile* AC1296 (Institute Pushino, Moscow) were cultured according to techniques described by Hickey and Tresner (1952).

The DNA of the spores and hyphae of *S. lividans* was extracted from pure cultures according to the lysis protocol 6 described below (except that no grinding was carried out), while the spores of *S. hygroscopicus* and *S. fragile* were extracted by chemical/enzymatic lysis (Hintermann et al., 1981).

1.3 CHOICE OF THE EXTRACTION BUFFER: A TENP buffer (50 mM Tris, 20 mM EDTA, 100 mM NaCl, 1% wt/vol of polyvinylpolypyrrolidone) developed by Picard (1992) was used. Similar buffers were subsequently used by other authors (Clegg et al., 1997; Kuske et al., 1998; Zhou et al., 1996).

The Tris and the EDTA protect the DNA from the nuclease activity, the NaCl provides a dispersant effect and the PVPP absorbs the humic acids and the other phenolic compounds (Holben et al. (1988); Picard et al., (1992)).

In this study, the extraction efficacy of this buffer was evaluated at different pH values (6.0-10.0) using 20 different soils having a pH range from 5.8 to 8.3 and an organic matter content of between 0.2 and 6.3%. These twenty soils (the other characteristics are not indicated) were used only in this experiment. The amount of DNA was determined by calorimetric means as described by Richard (1974), and detailed below.

1.4 PROTOCOL OF IN SITU LYSIS AND OF DNA EXTRACTION: Several protocols using an increasing number of steps were tested in order to evaluate the efficacy of various techniques for lysing the soil microbes in situ. For these experiments, the indigenous soil microflora was targeted in six soils. Additional experiments were carried out in order to study the effects of the lysis treatments on the DNA released, by analysing the quantities and quality of DNA recovered originating from a lambda phage DNA added beforehand to the soils.

Once an optimized protocol (referred to as protocol 6) had been developed, this protocol was used to quantify the DNA originating from indigenous *Actinomycetes* and of DNA originating from gram-positive bacteria inoculated in the selected soils. In all cases, the soil samples were dried and screened as described above.

After grinding, 0.5 ml of TENP buffer was added to 200 mg dry weight of soil, except for protocol 1 in which the buffer was added to an unground soil.

For the various lysis treatments (see below), the soil suspensions were vortexed for 10 minutes and centrifuged (4000×g for five minutes), after which an aliquot fraction (25 µl) of the supernatant was analysed by gel electrophoresis (0.8% agarose).

Another aliquot fraction of the supernatant representing a known volume, generally 350 µl, was precipitated with isopropanol.

Five aliquot fractions (representing the DNA derived from 1 g of soil) were combined and resuspended in 100 µl of a sterile TE buffer (10 mM Tris, 1 mM EDTA, pH 8.0) before purification (protocol D, see below) and quantification, either by hybridization (Dot-Blot) of the total DNA, or by hybridization (Dot-Blot) of the PCR amplification products (see below).

The hybridization signals were quantified by phosphorescence imaging ("phospho-imaging" technique, see below).

1.5 EVALUATION OF THE METHODS OF IN SITU CELL LYSIS: The quality and quantity of DNA extracted after an increasing number of lysis treatment steps (protocol 2-5b) were compared with those of the extracellular DNA obtained after washing the soil with an extraction buffer (protocol 1; see also FIG. 1).

Protocol 1: No Lysis Treatment.

The TENP buffer was added to an unground soil, and a DNA extraction step was carried out as described above.

Protocol 2: Grinding of the Soil Followed by a DNA Extraction.

Two different types of device were used to grind the soil.

In order to compare their respective efficacy, 5 g of dry soil were ground for 30 seconds in a grinder containing tungsten rings, or for times varying up to 60 minutes in a soil grinder containing a mortar and agate beads (20 mm in diameter).

The TENP buffer was then added and the DNA was extracted as described above.

The gel electrophoresis results showed that grinding for 40 minutes using agate beads was necessary in order to obtain amounts of extracted DNA equivalent to those obtained after grinding for 30 seconds using tungsten rings.

The size distribution of the DNA fragments is similar whatever the method used.

Thus, these treatments were considered as equivalent and the one which is used in the protocols described below will consequently not be specified.

In protocols 3 to 5, the efficacy of several other lysis treatments subsequent to the grinding of the soil was tested, either separately or in different combinations.

Protocol 3:

This protocol is identical to protocol 2, except that it comprises a step of homogenization using an Ultra-turrax type mixer (Janker and Kunkel, IKA Labortechnik, Germany) set at half the maximum speed for 5 minutes.

Protocols 4a and 4b:

These protocols are identical to protocol 3, except for an additional sonication step.

Two types of sonicator device were compared: a titanium micropoint sonicator (600W Vibracell Ultrasonicator, Bioblock, Illkirch, France) (Protocol 4a) and a sonicator of Cup Horn type (protocol 4b).

The Vibracell micropoint producing ultrasound is in direct contact with the soil solution.

As regards the device of Cup Horn type, the soil solution is stored in tubes which are placed in a water bath through which the ultrasound passes.

Preliminary experiments were carried out in order to determine the optimum conditions for the two sonicators (results not presented).

The best compromise, in terms of amount of DNA extracted and fragment size, consists of a sonication with the titanium micropoint and the sonicator of Cup Horn type for 7 and 10 minutes respectively, adjusting the power to 15 W and with 50% active cycles.

Protocols 5a and 5b:

After sonication with a titanium micropoint or a device of Cup Horn type (protocols 4a and 4b respectively), lysozyme and achromopeptidase were added to each of the enzymes at a final concentration of 0.3 mg/ml.

The soil suspensions were incubated for 30 minutes at 37° C., after which lauryl sulphate at a final concentration of 1% was added, and the suspensions were then incubated for 1 hour at 60° C. before centrifugation and precipitation as described above.

In addition to the protocols described above, the effect of the sonication (Cup. Horn, see protocol 4b) and heat shocks (30 seconds in liquid nitrogen followed by three minutes in boiling water, the treatments being repeated three times) on lambda phage DNA digested with HindIII added beforehand to the soil, were examined (see below).

Heat shocks were suggested in the prior art as means for in situ cell lysis (Picard et al. (1992)). However, due to the fact that such a treatment has a harmful effect on the free DNA (see the results section) it was not included in the protocols described above.

Optimized Protocol

After evaluation of the various lysis treatments, an optimized protocol was defined, which is referred to as protocol 6. Protocol 6 is identical to protocol 5b except that, before sonication, the soil suspensions are subjected to a vortexing treatment and then agitated by rotation on a wheel for two hours before being frozen at −20° C.

After thawing, the soil suspensions were vortexed for 10 minutes before sonication. Protocol 6 was used in the experiments in which the soils were inoculated with bacterial cells, as well as in the experiments in which the indigenous actinomycetes were quantified (see below).

1.6 COUNTING BY MICROSCOPE: The efficacy of grinding of the soil as a method for lysing bacterial cells was examined by microscope.

5 g of dried crude soil were mixed in a Waring Blender device with 50 ml of ultrapure sterilized water for 1.5 minutes; simultaneously, 1 g (dry weight) of ground soil (protocol 2) was suspended in 10 ml by agitation for 10 minutes. The soil suspensions were serially diluted and acridine orange was added to a final concentration of 0.001%.

After 2 minutes, the suspensions were filtered through a Nucleopore brand membrane of 0.2 μm black type. Each filter was rinsed with lysed sterile water, treated with 1 ml of isopropanol for 1 minute in order to fix the bacterial cells, and then rinsed again.

The bacterial cells were counted using a Zeiss Universal epifluorescence microscope with a 100× objective lens. For each of the types of soil, three filters were counted, and at least 200 cells were counted on each of the filters.

1.7 COUNTING OF THE CULTURABLE ACTINOMYCETES AND TOTAL NUMBER OF COLONY-FORMING UNITS (CFU): The actinomycetes which survived the lysis treatments (protocols 1-5) were examined specifically with soil No. 3 (Saint André coast, see Table 1).

After a 10-fold dilution of a solution of yeast extract (6% weight/volume) and of SDS (0.05%) in order to induce germination (Hayakawa et al. (1988)), the soil suspensions were serially diluted in sterile water, incubated at 40° C. for 20 minutes and inoculated on HV medium (Hayakawa et al., 1987).

The HV medium was supplemented with actidione (50 mg/l) and nystatin (50 mg/l).

The actinomycete colonies were counted after incubation for 15 days at 28° C.

In total, about 400 colonies were examined. The identification was carried out on the basis of the macro- and microscopic morphological characteristics as well as on the analysis of the diaminopimelic acid content of the isolates (Shirling et al., 1966); Staneck et al., 1974; Williams et al., 1993).

The total amount of culturable bacteria (total CFU) was also determined for each of the lysis protocols 1 to 5. The soil suspensions were serially diluted and inoculated in triplicate on a Bennett agar medium (Waksman et al., 1961) supplemented with nystatin and actidione (each at 50 mg/l).

Each Petri dish was covered with a cellulose nitrate filter (Millipore) and incubated for three days at 28° C. After counting the colonies on the membranes, the filters were removed and the Petri dishes were reincubated for 7 days at 28° C. and then counted again.

1.8 RECOVERY OF THE LAMBDA PHAGE DNA ADDED TO THE SOILS: The lambda phage DNA was digested with HindIII extracted with a phenol-chloroform mixture, precipitated and then resuspended in ultrapure sterile water according to standard protocols (Sambrook et al., 1989).

Dilutions corresponding, respectively, to 0, 2.5, 5, 7.5, 10 and 15 μg of DNA/g of dry weight of soil were prepared in 60 μl volumes. These DNA dilutions were added to 5 g batches of dry soil which were subsequently vortexed vigorously for 5 minutes before grinding.

The lambda phage DNA was also added to a soil before grinding at concentrations corresponding to 0, 10 and 15 μg of DNA/g of dry weight of soil.

After grinding, the extraction buffer was added and the DNA was extracted according to protocol 2 (see above).

1.9 SATURATION OF THE ADSORPTION SITES WITH RNA: In order to determined whether or not the saturation of the nucleic acid adsorption sites of the soil colloids could increase the level of recovery of the DNA, the sandy compost (soil No. 4) and the clayey soil (soil No. 5) were incubated with an RNA solution before any other treatment.

Commercial *Saccharomyces cerevisiae* RNA (Boehringer Mannheim, Meylan, France) was diluted in phosphate buffer (pH 7.1) and added to the dry, screened soil samples (2 ml/g of soil) at final concentrations of 20, 50 and 100 mg of RNA/g of dry weight of soil.

The tubes containing the soil suspensions were agitated by rotation for two hours at room temperature. After centrifugation, the soil pellets were dried in an oven (50° C.) overnight. The lambda phage DNA was then added to the soils (0, 20 or 50 μg/g of dry weight of soil) in order to simulate the fate of the DNA released after cell lysis.

The DNA was extracted according to protocol 2. It was determined thereafter that an identical effect of addition of RNA on the recovery of DNA could be achieved by adding the RNA directly to the extraction buffer.

This simplified procedure was used for the clayey soil No. 5 in the experiments in which the microorganisms were inoculated in the soils.

The RNA was then added at a concentration corresponding to 50 mg of RNA/g of dry weight of soil.

1.10 QUALITATIVE AND QUANTITATIVE DETERMINATION OF THE EFFICACY OF THE EXTRACTION PROTOCOLS: The quality of the DNA (absence of degradation) was estimated on the basis of the size of the DNA fragments or the relative position of the DNA migration bands after electrophoresis of an aliquot fraction of a DNA solution on a 0.8% agarose gel.

The fluorescence intensity allowed a semi-quantitative estimation of the extraction yields.

Another aliquot fraction was used for quantitative determinations of the DNA content by hybridization (Dot-Blot) and analysis with a phospho-imager. The Dot Blot hybridization protocol has been described by Simonet et al. (1990).

The hybridization membranes (GeneScreen plus, Life Science Products, Boston, USA) were prehybridized for at least 2 hours in 20 ml of a solution containing 6 ml of 20×SSC, 1 ml of Denhardt's solution, 1 ml of 10% SDS and 5 mg of salmon sperm DNA.

The hybridization was carried out overnight in the same solution in the presence of a labelled probe prior to two washes of the membranes in an SSC 2× buffer for 5 minutes at room temperature, followed by a third wash in a SSC 2×, 0.1% SDS buffer and a fourth wash in an SSC 1×, 0.1% SDS buffer for 30 minutes at the hybridization temperature.

The hybridization signals were quantified with a Biorad radioanalytical imaging system (Molecular Analyst Software, BIORAD, Ivry-sur-Seine, France).

In order to quantify the total amount of DNA derived from the indigenous microflora, the various soils were extracted according to protocols 1 to 5. The non-amplified DNA was applied to the Dot-Blot membranes and hybridized using the universal probe FGPS431 (Table 2).

This probe, which hybridizes to positions 1392-1406 of the *E. coli* 16S rDNA gene (Amann et al. (1995)) was labelled at its ends with a $^{32}$P ATPα using a polynucleotide T4 kinase (Boehringer Mannheim, Melan, France).

A calibration curve was prepared using *E. coli* DH5α DNA. The conversion of the calculations to the soil bacteria required a simplification, starting from the hypothesis that the average number of copies (rrn) is 7, as for *E. coli.*

The lambda phage DNA digested with HindIII was used to quantify the recovery of the extracellular DNA. Non-amplified extracts from soils, to which lambda phage DNA had been added, were hybridized with lambda phage DNA digested with HindIII and labelled at random using the Klenow fragment (Boehringer Mannheim, Melan, France).

The amounts of DNA were calculated by interpolation using a calibration curve prepared with the purified DNA.

The total amount of DNA extracted from soils 1, 2, 3, 4 and 6 according to protocol 2 (grinding) was also quantified by calorimetric means according to the technique described by Richard (1974).

Briefly, the DNA was mixed with concentrated $HClO_4$ (the final concentration of $HClO_4$ was 1.5 N). 2.5 volumes of this solution were mixed with 1.5 volumes of DPA (diphenylamine, Sigma-Aldrich, France) and the mixture was left to incubate at room temperature for 18 hours, prior to determination of the OD at 600 nm. The soil DNA extracts were quantified relative to a standard curve prepared with the DNA extracted from *E. coli* DH5α according to the standard protocols (Sambrook et al., (1989)).

1.11 DEVELOPMENT OF A DNA QUANTIFICATION TECHNIQUE USING PCR AMPLIFICATION AND HYBRIDIZATION: For the PCR amplifications, DNA Taq polymerase (Appligene Oncor, France) was used according to the manufacturer's instructions.

The PCR programme used for all the amplifications is as follows: initial denaturing for 3 minutes at 95° C., followed by 35 cycles consisting of 1 minute at 95° C., 1 minute at 55° C. and 1 minute at 72° C. and then a final extension at 72° C. for 3 minutes.

The DNA isolated and purified from *Streptosporangium fragile* was used as control at concentrations ranging from 100 fg to 100 ng.

In order to amplify specifically the DNA of this bacterial genus, the primers FGPS122 and FGPS350 (Table 2) were selected, which are complementary to a portion of the 16S rDNA, after alignment of the sequences of actinomycetes 16S rDNA. Their specificity was tested on a collection of actinomycetes strains (*Streptomyces, Streptosporangium* and other highly similar genera).

The PCR products were hybridized with the oligonucleotide probe FGPS643 (Table 2). In order to simulate the level of purity routinely obtained with DNA extracted from the soil, controls of pure DNA from *S. fragile* were mixed with the soil extracts obtained after treatments according to the lysis protocols 4b and 5b and then purified according to protocol D.

Before use, the soil extracts were treated with DNase (one unit of DNase/ml, Gibco BRL) for 30 minutes at room temperature. The DNase was then inactivated by heating at 65° C. for 10 minutes. Verification of the inactivation was carried out by PCR. The humic acid concentrations were measured by spectrophotometry ($OD_{280}$ nm) against a standard curve of commercial humic acids (Sigma).

Soil solutions treated with undiluted, 10-fold diluted and 100-fold diluted DNase were mixed with from 100 fg to 100 ng of *S. fragile* DNA before the PCR amplification. In another series of experiments, the increasing concentrations of *Streptomyces hygroscopicus* DNA (from 100 pg to 1 μg) were added to the *S. fragile* DNA in order to simulate the presence of non-target DNA and its influence on the PCR process.

1.12 PURIFICATION OF THE CRUDE DNA EXTRACTS: Four DNA purification methods were compared. The DNA was extracted from 1 g (dry weight of soil) according to protocol 4a and resuspended in 100 μl of buffer TE8 (50 mM Tris, 20 mM EDTA, pH 8.0).

Protocol A

Elution through two successive Elutip d columns (Schleicher and Schuell, Dassel, Germany) (Picard et al., (1992)).

Protocol B

Elution through a Sephacryl S200 column (Pharmacia Biotech, Uppsala, Sweden) followed by an elution through an Elutip d column (Nesme et al. (1995)).

Protocol C

Separation using a two-phase aqueous system with 17.9% (weight/weight) of PEG 8000 (Merck, Darmstadt, Germany) and 14.3% (weight/weight) of $(NH_4)_2SO_4$ (Zaslavsky, (1995)).

After vigorous vortex mixing, the two phases were left at room temperature to separate.

1 ml of each of the phases was transferred into another tube, mixed with 100 μl of the sample and left at 4° C. overnight to allow separation.

The lower phase was dialysed for one hour through a Millipore membrane in the presence of an excess of a TE 7.5 buffer (10 mM Tris, 1 mM EDTA at pH 7.5 and 1M $MgCl_2$) in order to remove the excess salts.

Protocol D

Elution through a Microspin Sephacryl S400 HR column (Pharmacia Biotech, Uppsala, Sweden), followed by elution through an Elutip d column.

Each protocol is completed by a step of precipitation with ethanol and the DNA is resuspended in 10 μl of TE 7.5 buffer. The efficacy of the purification protocols was checked by PCR amplification of undiluted aliquot fractions of the DNA solutions and of 10-fold and 100-fold diluted aliquot fractions, using standard protocols (see below).

1.13 Recovery of the DNA from Inoculated Microorganisms:

The cells, spores and hyphae were washed twice and counted by counting on a plate or by direct microscopic counting. 5 g batches of dry, screened soil (soils 2, 3 and 5) were inoculated with 100 μl of a suspension of *S. lividans* spores and hyphae at concentrations corresponding to 0, $10^3$, $10^5$, $10^7$ and $10^9$ spores/g of dry weight of soil, or with *B. anthracis* vegetative cells at concentrations corresponding to 0, $10^7$ and $10^9$ cells per gram of dry weight of soil.

The amounts of *S. lividans* hyphae were calculated on the basis of the number of spores from which they originate. After addition of the bacterial suspensions, the soil samples were vortexed vigorously for 5 minutes before grinding. The DNA was extracted according to protocol 6 (see below).

PCR amplification followed by Dot-Blot hybridization and phosphorescence imaging (phospho-imaging) was used in order to quantify the amounts of DNA recovered from the cells and spores and from the bacterial mycelium inoculated in the soils.

The DNA extraction was carried out according to lysis protocol 6. The PCR amplification and the hybridization were carried out as described above. The primers and probes are targeted on chromosome regions located outside the 16S region, and are highly specific for the respective organisms, so as to avoid background signals.

For the soils inoculated with *B. anthracis*, the primers R499 and R500 were used (Patra et al. (1996)) and the amplification products were hybridized with the oligonucleotide probe C501 (Table 2).

For the soils inoculated with *S. lividans*, the PCR reactions were carried out using the primers FGPS516 and FGPS517, and the amplification products were hybridized with the oligonucleotide probe FGPS518 (Table 2).

The amplified region is a portion of the cassette constructed specifically to obtain the strain OS48.3 (Clerc-Bardin et al., unpublished).

The calibration counts were obtained in all cases using the purified DNA from the target organism.

2. Results 2.1 Choice of the Extraction Buffer 20 different soils were used in order to determine the optimum pH of the DNA extraction buffer. For all the soils, the DNA yield increases as the buffer pH increases. The yield for each pH (±sd), calculated as the percentage of the highest value for each of the soil, is as follows: pH 6.0: 31±13; pH 7.0: 43±16; pH 8.0: 60±14; pH 9.0: 82±12; pH 10.0: 98±3.

For 16 out of the 20 soils, the highest yield was obtained at pH 10.0, whereas for the other four soils, the highest yield was obtained at pH 9.0. However, at pH 10.0, larger amounts of humic material were released, compared with pH 9.0 (results not presented). Consequently, pH 9.0 was chosen for all the experiments presented below.

Figure 1:
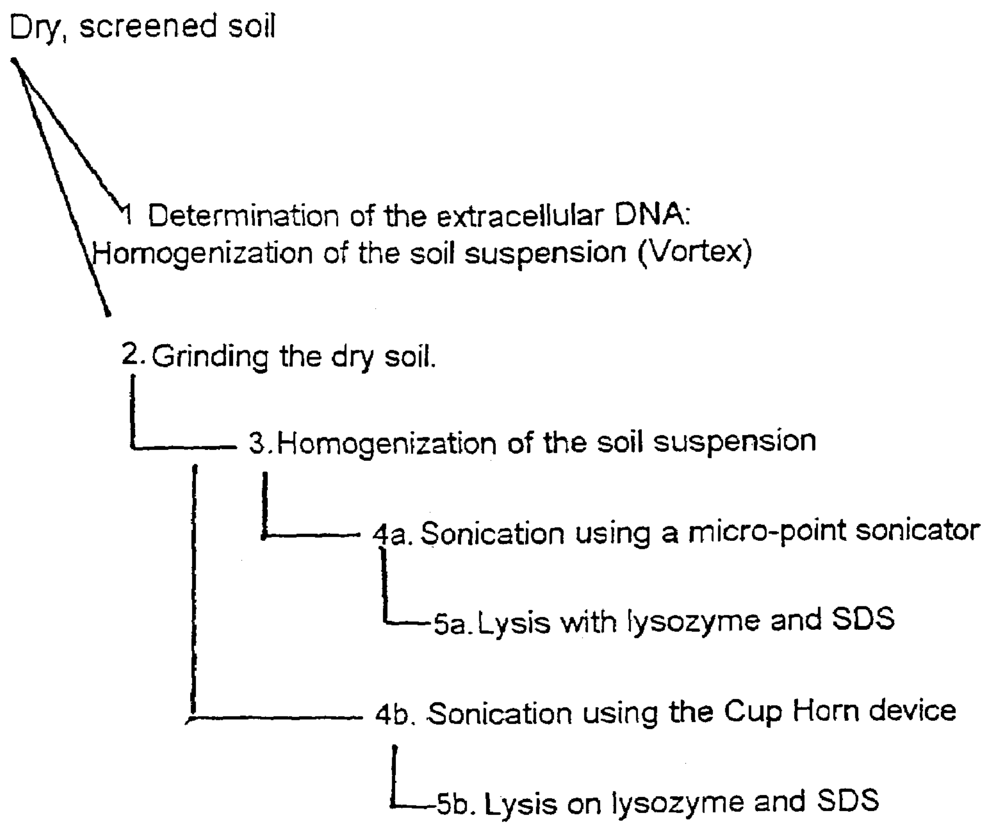

2.2 Efficacy of the DNA Extraction Protocols:

The total DNA from the indigenous soil organisms was extracted and quantified so as to evaluate the efficacy of several in situ cell lysis protocols. Soil samples 1-6 (Table 1) were treated according to protocols 1 to 5 described in the Materials and Methods section (FIG. 1).

After the DNA extraction, the soil suspensions were precipitated with isopropanol, and aliquot fractions of the resuspended pellets were analysed by gel electrophoresis, in a first step, in order to estimate the quality and quantity of the DNA released.

However, the colour of the DNA extract turned darker and darker as the number of lysis steps increased, due to the co-extraction of compounds, such as humic acids, with the DNA.

Some of these dark-coloured crude extracts do not migrate in the expected manner in the agarose gels.

Figure 2:
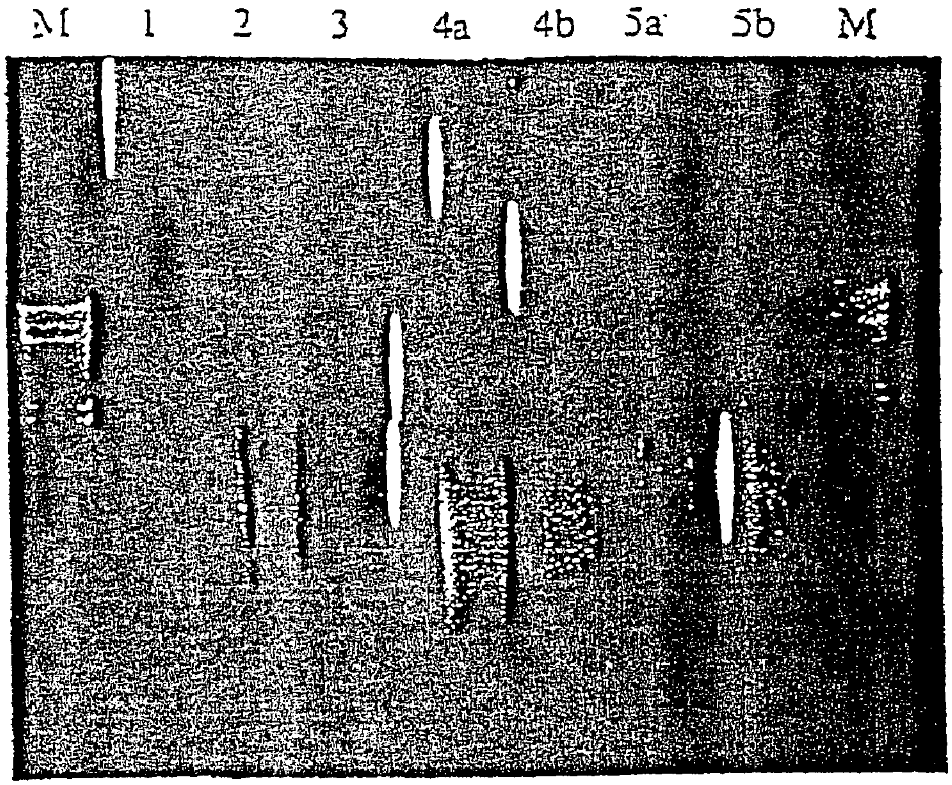

Consequently, the crude DNA solutions were purified (protocol B) before quantification. The gel electrophoreses of the purified solutions obtained after the various lysis treatments are given as examples on soil 3 (FIG. 2).

A visual comparison by ultraviolet radiation of the intensities of the coloured DNA allowed a semi-quantitative estimation of the efficacy of the treatments. Furthermore, the presence of migration profiles of multiple sizes of DNA fragments (discrete bands) and the disappearance of the long fragments indicates that a degradation of the DNA has taken place.

No DNA could be extracted from the clayey soil No. 5.

A more precise quantification of the DNA from all the soils, extracted according to protocols 1 to 5, was carried out by Dot-Blot hybridization without a prior PCR amplification step and using an oligonucleotide probe complementary to a highly conserved sequence of the 16S rDNA region (probe FGPS 431, Table 2).

The DNA was detected in the extracts of all the soils after each of the various lysis steps, except for the clayey soil No. 5.

The results agree with the estimations made after gel electrophoresis.

In order to compare with an independent quantification method, the DNA extracted according to protocol 2 (from all the soils except soil No. 5) was also quantified using a colorimetric DNA detection method (Richard, 1974).

Good correlation was found (r=0.88) between the DNA quantified using this calorimetric technique and the results obtained by Dot-Blot hybridization/radio-imaging, confirming the hypothesis that the average number of copies of the soil bacteria (rrn) is 7.

The hybridization (Dot-Blot) showed that the amounts of extracellular DNA, as determined by extraction without a lysis treatment (protocol 1), ranged from 4 μg/g for the acidic soil (No. 6) to 36 μg/g for soil No. 3 (Table 3).

Grinding of the soil (protocol 2) increased the amounts of DNA extracted from all the soils (e.g. 26 μg/g of soil for soil No. 6 and 59 μg/g of soil for soil No. 3) (Table 3; FIG. 2).

For the two grinding treatments (see the Materials and Methods section), the discrete DNA migration was detected on the agarose gels, indicating that the DNA molecules were partially degraded (FIG. 2).

The size of the DNA fragments is between 20 and 0.2 kb. The band intensity of the smallest fragments is very low, indicating that most of the fragments are much bigger than 1 kb.

Protocol 3 comprises a step of homogenization in an Ultra-turrax mixing device after addition of the extraction buffer to the soil samples. This step leads to an increase in the amounts of DNA extracted, as determined by Dot-Blot hybridization for two of the soils (the sandy soil No. 3 and the acidic soil No. 6), whereas the two soils rich in organic matter (soils No. 1 and No. 2) led to the production of smaller amounts of DNA.

Protocols 4a and 4b made it possible to evaluate the effect of two types of sonication on the yields of DNA from pre-ground and pre-homogenized soils.

The sonication had no positive effect on the DNA yield, compared with protocol 3, except for soil No. 6. However, the lysis efficacy for the two types of sonicator differs. For soils 2, 3 and 4, the largest amounts of DNA extracted were obtained using the titanium micropoint (Table 3; FIG. 2), whereas for soils Nos. 1 and 6, the DNA yield was higher using the Cup Horn device.

Contradictory results were also obtained when a step of enzymatic/chemical lysis was added (protocols 5a and 5b) after the sonication step; in certain cases, the amounts of DNA extracted were larger than those recovered according to protocols 4a and 4b, whereas in other cases the yields were lower (Table 3).

2.3 Direct Counting of the Microorganisms:

Counting by microscope of the total number of bacterial cells after staining with acridine orange was carried out for all the soils, before and after grinding.

Before grinding, the number of bacteria per gram of dry weight of soil ranged from $1.4\times10^9$ (±0.4) in the tropical soil No. 5, to $10\times10^9$ (±0.7) in the soil obtained from the Saint-André coast (soil No. 3) (Table 1).

After grinding, the number of cells were, respectively, 45, 74, 75, 54, 34 and 75% of the initial values for soils Nos. 1 to 6.

Figure 3:
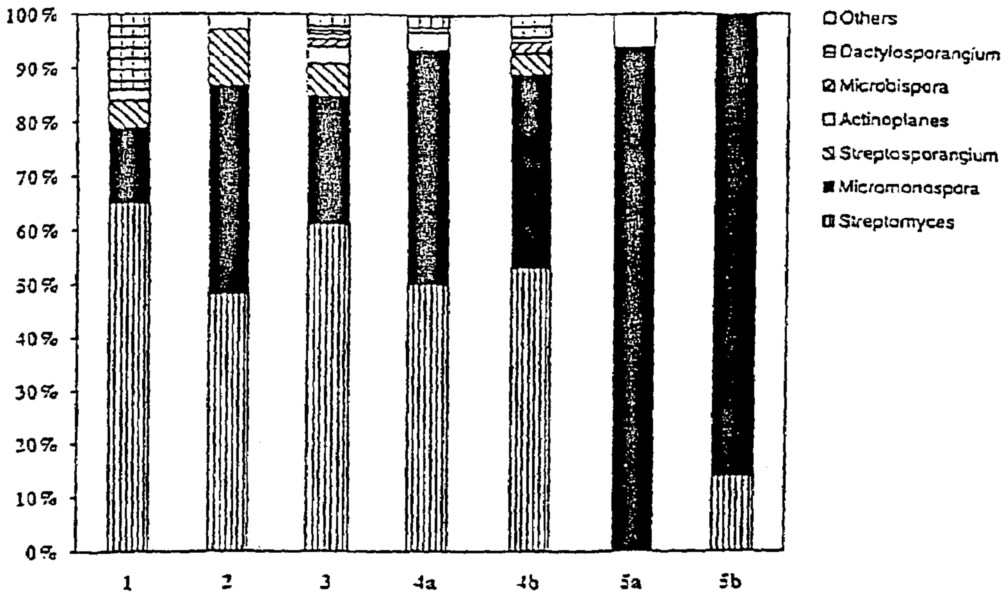
Figure 4:
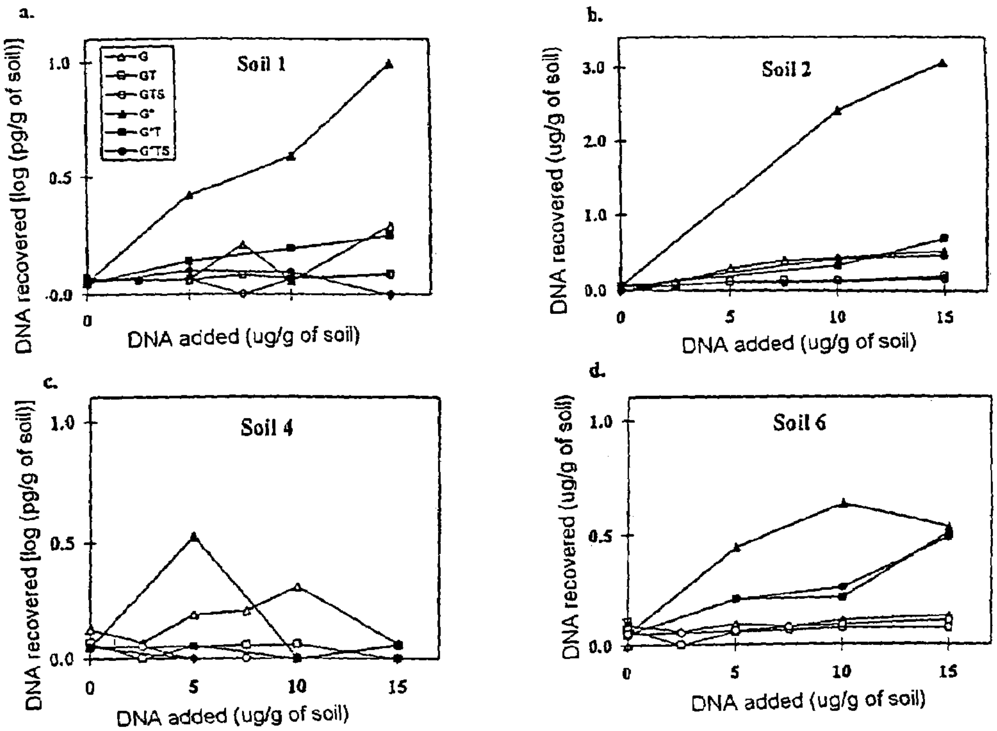

2.4 Counting of the Culturable Actinomycetes Belonging to Different Genera:

A modification in the populations of actinomycetes in soil No. 3 was noted after the various lysis treatments (FIG. 3).

For example, the colonies of *Streptomyces* sp. dominated the viable actinomycetes flora when no lysis treatment was applied (protocol 1) and represented 65% of the total number of colonies identified. After grinding, the percentage of *Streptomyces* colonies fell to 51%, whereas the proportion of colonies belonging to the *Micromonospora* genus increased by 14% to 41%.

The chemical/enzymatic lysis (protocols 5a and 5b) appeared to be particularly effective for the lysis of *Streptomycetes*. When all the lysis treatments were applied, including a chemical/enzymatic lysis (protocols 5a and 5b), the actinomycetes microflora, which still comprised more than $10^6$ cfu/g of soil, was dominated by the species belonging to the *Micromonospora* genus, while few or no *Streptomyces* colonies were recovered.

The organisms belonging to genera such as *Streptosporangium, Actinomadura, Microbispora, Dactilosporangium* and *Actinoplanes* appeared in small number on the plates (2-8% of the total number of colonies identified) after grinding, homogenization with the Ultra-turrax device and sonication, but were generally absent when these treatments were combined with a chemical/enzymatic lysis.

The total number of culturable bacteria remaining after each lysis treatment (protocols 2 to 5) was also investigated for soil No. 4. The results indicate that the number of culturable bacteria does not decrease with the intensity of the lysis treatments (about $2\times10^6$ cfu/g of soil in all cases, and also when a treatment is not applied, such as according to protocol 1).

The production of these low cfu values is probably due to the fact that dry soil was used and that only the most resistant bacteria multiplied on the plates. The number of actinomycetes forming colonies was generally greater than that of the total cfu (all the bacteria) due to the fact that a spore-germination step, included in the actinomycetes detection protocol, was missing during the control of the total bacteria.

2.5 Recovery of the Lambda Phage DNA Added:

The aim of these experiments was to estimate the way in which successive lysis treatments might affect the recovery of naked DNA, and whether or not these successive lysis treatments contributed to its degradation.

The DNA could be either a fraction of extracellular DNA released from already-dead organisms, which can persist in the soil for months (Ward et al., 1990), or DNA released from organisms readily lysed during the first steps of the treatment. In order to simulate this situation, lambda phage DNA digested with HindIII was added, at various concentrations, to the soils before and after grinding. In addition to grinding, a combination of the other lysis treatments was tested, including sonication (Cup Horn device, see protocol 4b) and heat shocks (see the Materials and Methods section).

After extraction, aliquot fractions which theoretically needed to contain from 25 to 150 ng of lambda phage DNA were analysed by gel electrophoresis. No DNA fragment specific for the lambda phage could be observed when the DNA was inoculated into the soil samples prior to grinding, independently of the dose or of the type of soil.

When the DNA was added after grinding, and extracted without an additional lysis treatment step, the specific lambda phage DNA profiles were detected in the extracts of four out of the five soils tested.

In all these cases, a direct cause-and-effect relationship was obtained between the amount of DNA added and the intensity of the signals on the agarose gels. However, the signal intensities were less than the signal intensities expected when compared with those of the molecular standards.

Furthermore, the band at 23 kb was absent in several cases, indicating that the long fragments were preferentially adsorbed onto the soil particles, or were more sensitive to degradation, compared with the short fragments.

No band was detected in the samples of tropical soil No. 5 which is characterized by a very high clay content (Table 1).

For a more precise quantification, the recovery of DNA was determined on a phosphorescence imaging device (phospho-imager) after Dot-Blot hybridization. According to this technique, the DNA was detected in all the samples, including those which had been inoculated before grinding, except for soil No. 5 in which no DNA could be detected.

In all the other soils, the amount of DNA extracted increases as the size of the inoculum increases (FIGS. 4*a-d*).

However, the recoveries of lambda phage DNA were low. When grinding was the only lysis treatment applied, the recoveries were between 0.6 and 5.9% of the DNA added when this DNA was added before grinding, and from 3.6 to 24% of the DNA added when the latter was added after grinding. The highest levels of recovery were obtained from soil No. 2.

Gel electrophoresis of aliquot fractions of samples treated by heat shock and sonication did not allow any DNA bands to be observed in any of the samples, including the tests in which the DNA had been added after grinding. The Dot-Blot hybridization experiments confirmed these results.

The hybridization signals obtained from soil suspensions which were treated with heat shocks and sonications were, at best, low.

The sample showing the largest amount of DNA (15 μg of DNA/g of dry weight of soil) was the only one for which the signal obtained was substantially different from the background level.

No difference (or only small differences) was observed between the samples treated with heat shock and those treated with heat shocks and sonication, indicating that the heat shocks have a harmful effect on the DNA. The best recoveries were observed for soil No. 2, which has the highest organic matter content (Table 1), whereas no DNA was recovered from the clayey soil No. 5.

Additional experiments were carried out with non-ground samples of soils No. 4 and No. 5, which were inoculated with 20 and 50 μg of lambda phage DNA per gram of soil.

The samples were extracted immediately or after an incubation period of one hour at 28° C., and the DNA extracts were then purified and analysed by gel electrophoresis.

The incubation of soil No. 4 for one hour after the inoculation did not give profiles that were qualitatively or quantitatively different from those obtained without incubation or from those observed previously when the DNA was added after grinding.

These results indicate that the enzymatic degradation by the soil nucleases is not thought to be involved in the low level of DNA recovery. Furthermore, the absence of a grinding step does not allow an increase in the recovery of the DNA from soil No. 5, indicating that the changes to the structure of the soil due to the grinding do not significantly increase the adsorption of the nucleic acids onto the colloids.

2.6 Saturation of the Adsorption Sites with RNA:

Most of the profiles obtained on the agarose gels do not differ significantly from the previous profiles in which the RNA treatment was not carried out.

For example, no band was detected from the clay-rich soil No. 5, independently of the RNA concentrations and of the lambda phage DNA concentrations used.

Furthermore, the specific bands of lambda phage DNA digested with HindIII remained undetectable in the sandy compost treated with RNA (soil No. 4) when the RNA is added before grinding.

The intensity of the bands obtained from samples inoculated with DNA after grinding increases as the RNA concentration increases, indicating that the treatment might have a positive effect.

However, the results after hybridization and analysis by phosphorescence imaging did not confirm the electrophoresis results. For example, the positive effect of the RNA treatment on the recovery of DNA from the clayey compost, when DNA was added after grinding, did not appear clearly.

On the other hand, a positive effect of the RNA was found for the clay-rich soil (No. 5) when the DNA was added after grinding.

Although the hybridization signals for the control samples do not differ from the background noise levels, significant amounts of DNA were released from the samples treated with RNA, and the signals increased as the amount of DNA added increased and as the RNA concentration increased.

However, even for the highest RNA concentration (100 mg/g of weight of dry soil), the recovery level never exceeded 3%.

2.7 Purification of the Crude DNA Extracts:

Of the four protocols tested, the best amplification of the undiluted DNA extracts (1 μl of extract in 50 μl of PCR mixture) was observed after elution through Microspin S400 columns followed by an elution through an Elutip d column as shown by the gel electrophoresis of the PCR products.

The DNA purified by the two-phase aqueous system (protocol C) gave smaller amounts of PCR products after amplification starting with undiluted DNA extract.

No amplification product could be obtained from the undiluted extracts after amplification following the use of protocols A or B. Consequently, protocol B (see Materials and Methods section) was used for all the experiments in which the PCR amplifications and/or the Dot-Blot hybridizations were performed.

2.8 Quantification by PCR and Hybridization:

The first step was to determine whether or not the amounts of PCR product were proportional to the number of target DNA molecules initially present in the reaction tube. DNA from *Streptosporangium fragile* was used as target (see Materials and Methods section).

The primers used were the primers FGPS122 and FGPS350 (Table 2). Gel electrophoresis of the PCR products showed that the band intensity increases as the concentration of the targets increases. The PCR products were hybridized with the oligonucleotide probe FGPS643 (Table 2), and the signals were quantified by phosphorescence imaging (phospho-imaging).

A good correlation ($r^2=0.98$) was found between the log [number of targets] and the log [intensity of the hybridization signal].

An investigation was then carried out to see whether or not the efficacy of the PCR amplification was affected by the humic acids and the non-target DNA. When analysed by gel electrophoresis, the increased intensity of the bands for the PCR products, corresponding to the various amounts of target DNA, were conserved when the amplification was carried out with DNA solutions to which extracts of soil treated with DNase had been added, containing humic acids at concentrations ranging up to 8 ng in 50 μl of the PCR mixture.

With 20 ng of humic acid in the PCR mixture, the bands corresponding to the small levels of target DNA disappeared, and at humic acid concentrations of 80 ng and at higher concentrations, no band was visible.

The varied amounts of target DNA from *S. fragile* made it possible to supply the expected amounts of PCR product when, before amplification, the *S. fragile* DNA was mixed with *Streptomyces hygroscopicus* DNA and added to 50 μl of the PCR mixture in a range from 100 pg to 1 μg in order to simulate the non-target DNA released from the soil microflora.

Figure 5:
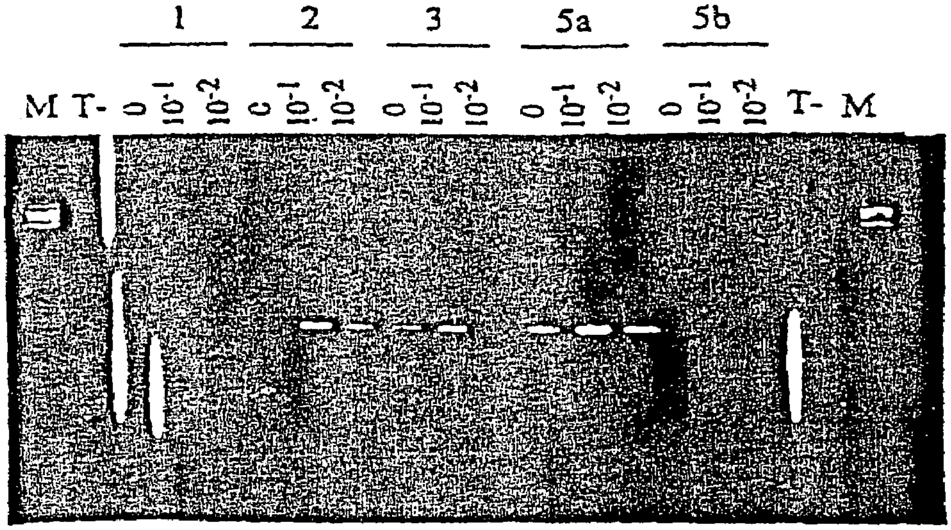

2.9 Quantification of the Indigenous Soil Actinomycetes after Different Lysis Treatments:

Purification protocol D was applied, followed by a PCR amplification as described above, in order to quantify the actinomycetes belonging to the *Streptosporangium* genus in soil No. 3 after extraction in accordance with protocols 1, 2, 3, 5a and 5b (FIG. 5).

After grinding (protocol 2), the amount of target DNA originating from this actinomycete was estimated by hybridization (Dot-Blot) and radio-imaging as being 2.5±1.3 ng/g of weight of dry soil.

If it is, postulated that the DNA content is 10 fg per cell, as for *Streptomyces* (Gladek et al., 1984), this value corresponds to approximately $2.5\times10^5$ genomes. Similar values were obtained after the other lysis treatments (2.6±1.1 and 1.8±1.3 ng of DNA/g of dry soil, respectively, using protocols 3 and 4b, respectively).

2.10 Efficacy of the Recovery of DNA from Soils Pre-Inoculated with Bacteria:

Three soils (Nos. 2, 3 and 5) were inoculated with different concentrations of *Streptomyces lividans* spores or hyphae (see Materials and Methods section). The amounts of mycelium added to the soil (FIG. 6*b*) correspond to the number of spores inoculated in the germination medium. Approximately 50% of these spores germinated. The exact number of cells in the hyphae of the germinated spores was not determined. Consequently, the amounts of spores and mycelium inoculated in the soils are not directly comparable.

For each soil sample, the extraction protocol No. 6, the purification method D and PCR amplification combined with Dot-Blot hybridization and phosphorescence imaging (phospho-imaging) were used to count the specific target DNAs which had been released. The DNA extracted can be clearly distinguished from the background noise only when the number of spores added exceeds $10^5$ for soils No. 3 and No. 5 and $10^7$ for soil No. 2 (FIG. 6*a*).

When the mycelium is added, the DNA extracted can be detected at and above an amount corresponding to $10^3$ spores/g of soil for soils No. 2 and No. 3, and at and above $10^7$ spores/g of soil No. 5 (Figure b).

Above the detection level, the hybridization signal increases as the amounts of inoculated cells increases.

Figure 6:
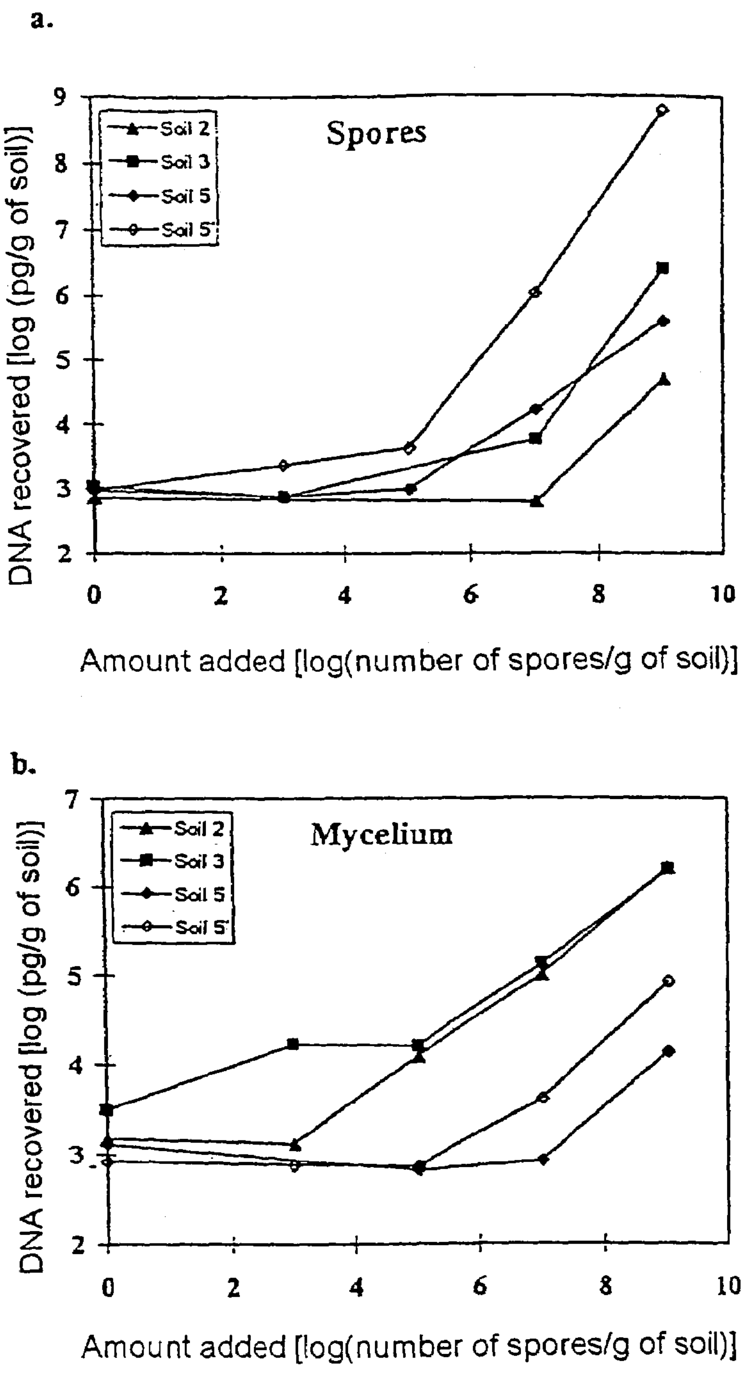

For the spore inoculum, a 100-fold increase in the number of cells inoculated leads to a close to 100-fold increase in the DNA yield. This increase is clearly less than when the hyphae are inoculated, particularly into soils No. 2 and No. 3 (FIG. 6).

In contrast, in the results obtained when lambda phage DNA was used as the inoculum, the DNA was also recovered from the clay-rich soil (No. 5) when the bacterial cells were used as the inoculum. However, for the latter inoculum also, the treatment with RNA increased the recovery of *Streptomyces* DNA from this soil both for the spores and the mycelium (FIG. 6).

Inoculating the soils with vegetative *Bacillus anthracis* cells gave recovery levels similar to those obtained for *Streptomyces.*

Furthermore, the levels of DNA recovery from soil No. 5 increased after treatment with RNA for this inoculum also.

Example 2

Construction of a Library of Low Molecular Weight DNA (<10 kb) Using a Soil Contaminated with Lindane, and Cloning and Expression of the linA Gene This example describes the construction of a DNA library of the *E. coli*. It demonstrates the cloning and expression of small genes obtained from a non-culturable microflora.

Lindane is an organochlorine pesticide, which is recalcitrant to degradation and persistent in the environment. Under aerobic conditions, biodegradation is catalyzed by a dehydrochlorinase, encoded by the linA gene, allowing lindane to be converted into 1,2,4-trichlorobenzene. The linA gene has been identified only from two strains isolated from soil: *Sphingomonas paucimobilis*, isolated in Japan (Seeno and Wada 1989; Imai et al., 1991; Nagata et al., 1993) and *Rhodanobacter lindaniclasticus* isolated in France (Thomas et al., 1996, Nalin et al., 1999).

However, the degradation potential of lindane, demonstrated by assaying the chloride ions released and PCR amplification of the linA gene from soils which have been in contact with lindane or otherwise, appears to be more widespread in the environment (Biesiekierska-Galguen, 1997).

1. Direct Extraction of Soil DNA

The dry soils are ground for 10 minutes in a Restch centrifugal-force grinder equipped with 6 tungsten beads. 10 grams of ground soil are suspended in 50 ml of pH 9 TENP buffer (50 mM Tris, 20 mM EDTA, 100 mM NaCl, 1% w/v polyvinylpolypyrrolidone), and homogenized by vortexing for 10 min.

After centrifuging for 5 min, at 4000×g and 4° C., the supernatant is precipitated with sodium acetate (3M, pH 5.2) and with isopropanol, then taken up in sterile TE buffer (10 mM Tris, 1 mM EDTA, pH 8.0). The DNA extracted is then purified on an S400 molecular sieve column (Pharmacia) and on an Elutip d ion-exchange column (Schleicher and Schuell), according to the manufacturers' instructions, then stored in TE.

2. Construction of the Library of DNA Extracted from the Soil in the Vector pBluescript SK−

The vector pBluescript SK− and the DNA extracted from the soil are each digested with the enzymes HindIII and BamHI (Roche), at a rate of 10 units of enzymes per 1 μg of DNA (incubation for 2 hours at 37° C.). The DNAs are then ligated by the action of T4 DNA ligase (Roche) overnight at 15° C., at a rate of one enzyme unit per 300 ng of DNA (about 200 ng of DNA insert and 100 ng of digested vector). Electrocompetent *Escherichia coli* cells, ElectroMAX DH10B™ (Gibco BRL) are transformed with the ligation mixture (2 μl) by electroporation (25 μF, 200 and 500Ω, 2.5 kV) (Biorad Gene Pulser).

After one hour of incubation in the LB medium, the transformed cells are diluted so as to obtain about 100 colonies per dish, and then plated out on LB medium (10 g/l tryptone, 5 g/l yeast extract, 5 g/l NaCl) supplemented with Ampicillin (100 mg/l), γ-HCH (500 mg/l), X-gal (5-bromo-4-chloro-3-indolyl-α-D-galactoside, 60 mg/l), and IPTG (isopropylthio-β-D-galactoside, 40 mg/l) and incubated overnight at 37° C. Since γ-hexachlorocyclohexane (Merck-Schuchardt) is insoluble in water, a 50 g/l solution is prepared in DMSO (dimethyl sulphoxide) (Sigma).

A library of 10,000 clones was thus obtained.

3. Cloning and Expression of the linA Gene

Screening of the library was carried out by visualization of a lindane degradation halo around the colony (the lindane precipitating in the culture media). Out of 10,000 clones screened, 35 thus exhibited lindane-degrading activity. The presence of the linA gene in these clones was confirmed by PCR with the aid of specific primers, described by Thomas et al. (1996). Digestions carried out on the inserts and on the amplification products showed identical profiles between all the clones screened and the reference control, *R. lindaniclasticus*. The clones carrying the linA gene also had an insert of the same size (about 4 kb).

It was thus demonstrated that the soil DNA could be cloned and expressed in a heterologous host: *E. coli*, and that genes derived from a microflora that is difficult to culture could be expressed. Libraries prepared by partial digestion of DNA extracted from soil, with restriction enzymes such as Sau3AI, can thus be envisaged also.

Example 3

Process for Preparing a Collection of Nucleic Acids from a Soil Sample, Comprising a Step of Indirect DNA Extraction 1. Materials and Methods 1.1 Extraction of the Bacterial Fraction of the Soil 5 g of soil are dispersed in 50 ml of sterile 0.8% NaCl, by grinding in a Waring Blender for 3×1 minute, with cooling in ice between each grinding. The bacterial cells are then separated from the soil particles by centrifugation on a density cushion of Nycodenz (Nycomed Pharma AS, Oslo, Norway). In a centrifugation tube, 11.6 ml of a Nycodenz solution with a density of 1.3 $g \cdot ml^{-1}$ (8 g of Nycodenz suspended in 10 ml of sterile water) are placed below 25 ml of the soil suspension previously obtained. After centrifugation at 10,000×g in a rotor with swing-out buckets (TST 28.38 rotor, Kontron) for 40 minutes at 4° C., the cellular ring, located at the interphase between the aqueous phase and the Nycodenz phase, is taken, washed in 25 ml of sterile water and centrifuged at 10,000×g for 20 minutes. The cell pellet is then taken up in a 10 mM Tris; 100 mMn EDTA pH 8.0 solution.

Prior to dispersion of the soil in the Waring Blender, a step of enrichment of the soil in a solution of yeast extract can be included in order in particular to allow the germination of the soil bacterial spores. 5 g of soil are thus incubated in 50 ml of a sterile solution of 0.8% NaCL-6% yeast extract, for 30 minutes at 40° C. The yeast extract is removed by centrifugation at 5000 rpm for 10 minutes in order to avoid the formation of a foam during the grinding.

1.2 Lysis of the Soil Bacterial Cells

Lysis of the Cells in Liquid Medium and Purification on a Caesium Chloride Gradient The cells are lysed in a 10 mM Tris, 100 mM EDTA, pH 8.0 solution containing 5 $mg \cdot ml^{-1}$ of lysozyme and 0.5 $mg \cdot ml^{-1}$ of achromopeptidase for 1 hour at 37° C. A solution of lauryl sarcosyl (1% final) and proteinase K (2 $mg \cdot ml^{-1}$) is then added and incubated at 37° C. for 30 minutes. The DNA solution is then purified on a density gradient of caesium chloride by centrifugation at 35,000 rpm for 36 hours on a Kontron 65.13 rotor. The caesium chloride gradient used is a gradient at 1 g/ml of CsCl, with a refractive index of 1.3860 (Sambrook et al., 1989).

Lysis of the Cells after Inclusion in an Agarose Block

The cells are mixed with an equal volume of agarose containing 1.5% (weight/volume) Seaplaque (Agarose Seaplaque FMC Products. TEBU, Le Perray en Yvelines, France) at low melting point and poured into a 100 µl block. The blocks are then incubated in a lysis solution: 250 mM EDTA, 10.3% sucrose, 5 $mg \cdot ml^{-1}$ lysozyme and 0.5 $mg \cdot ml^{-1}$ achromopeptidase at 37° C. for 3 hours. The blocks are then washed in a 10 mM Tris-500 mM EDTA solution and incubated overnight at 37° C. in 500 mM EDTA containing 1 $mg \cdot ml^{-1}$ of proteinase K and 1% lauryl sarcosyl. After washing several times in Tris-EDTA, the blocks are stored in 500 mM EDTA.

The quality of the DNAs thus extracted is checked by pulse-field electrophoresis.

The amount of DNA extracted was evaluated on electrophoresis gel relative to a calibration range of calf thymus DNA.

1.3 Molecular Characterization of the DNA Extracted from Soil

The DNAs extracted from the soil are characterized by PCR hybridization, this method consisting in a first stage in amplifying the DNAs using primers located on universally conserved regions of the 16S rRNA gene, and then in hybridizing the amplified DNAs with different oligonucleotide probes of known specificity (Table 4), with the aim of quantifying the intensity of the hybridization signal relative to an external calibration range of genomic DNA.

The DNAs extracted from the soil and the genomic DNAs extracted from pure cultures are amplified with the primers FGPS 612-669 (Table 1) under the standard PCR amplification conditions. The amplification products are then denatured with an equal volume of 1N NaOH, deposited on a Nylon membrane (GeneScreen Plus, Life Science Products) and hybridized with an oligonucleotide probe labelled at its end with $g^{32}P$ ATP by the action of T4 polynucleotide kinase. After pre-hybridization of the membrane in a solution of 20 ml containing 6 ml of SSC 20×, 1 ml of Denhardt's solution, 1 ml of 10% SDS and 5 mg of heterologous salmon sperm DNA, the hybridizations are carried out overnight at the temperature defined by the probe. The membranes are washed twice in SSC 2× for 5 minutes at room temperature, then once in SSC 2×0.1% SDS and a second time in SSC 1×, 0.1% SDS for 30 minutes at the hybridization temperature. The hybridization signals are quantified using the Molecular Analyst software (Biorad, Ivry sur Seine, France) and the amounts of DNA are estimated by interpolation of the calibration curves obtained from the genomic DNAs.

2. Results and Discussion 2.1 Extraction and Lysis of the Bacterial Fraction of the Soil Separation of the microbial cells from the soil particles, prior to extraction of the DNA, is an alternative which has many advantages over the methods of direct extraction of the DNA in the soil. Specifically, extraction of the microbial fraction limits the contamination of the DNA extract with extracellular DNA freely present in the soil or with DNA of eukaryotic origin. Above all though, the DNA extracted from the microbial fraction of the soil has fragments of longer size and better integrity than the DNA extracted by direct lysis (Jacobson and Rasmussen (1992)). Furthermore, separation of the soil particles makes it possible to avoid contamination of the DNA extract with humic and phenolic compounds, it being possible thereafter for these compounds to seriously impair the cloning efficacies.

One of the steps which is a determining factor for the extraction of the cells from the soil is the dispersion of the soil sample in order to dissociate the cells which adhere to the surface or to the inside of aggregates of soil particles. Three successive cycles of grinding for one minute each make it possible to obtain better cell extraction efficacy and a larger amount of DNA recovered, compared with a single cycle of grinding for one minute 30 seconds.

Table 5 reports the extraction efficacies obtained after centrifugation on a Nycodenz gradient, on the total viable microflora (counted by microscopy after staining with acridine orange), on the total culturable microflora (counted on solid 10% Trypticase-Soja medium), and on the actinomycetes microflora culturable on HV agar medium (after incubation at 40° C. in a solution of 6% yeast extract-0.05% SDS in order to bring about germination of the spores). Moreover, the extracted DNA was quantified either after lysing the cells in liquid medium (without purification on a caesium chloride gradient) or after lysing the cells included in an agarose block (after digesting the agarose with a β-agarase).

The results show that more than 14% of the total telluric microflora is recovered by this method (i.e. $2\times10^8$ cells per gram of soil) and that the total culturable microflora represents barely 2% of the total microbial population.

Moreover, the amount of DNA extracted from the cells is 330 ng per gram of dry soil. Estimating the DNA content per soil microbial cell to be between 1.6 and 2.4 fg, and given the amount of cells extracted ($2\times10^8$ cells per gram of soil), it can be estimated that virtually all of the cells are lysed and that this lysis does not place any major bias on this approach.

The pulsed-field electrophoreses show that the DNA from the soil extracted after Nycodenz and CsCl gradients could be up to 150 kb in size and that the agarose block lysis allowed fragments of more than 600 kb to be extracted.

These results confirm the advantage of this approach independent of culture for the construction of environmental DNA libraries, as an alternative to the methods of direct DNA extraction.

2.2 Molecular Characterization of the DNA Extracted from the Soil

The aim of the molecular characterization of the DNA extracted from the soil is to obtain profiles representing the proportions of the various bacterial taxons present in the DNA extract. It also involves the matter of knowing the extraction biases induced by the prior separation of the cellular reaction of the soil, in comparison with a direct extraction method in the absence of a direct visualization of the microbial diversity present in the soils. Specifically, little information has been collected on the extraction of cells on a Nycodenz gradient as a function of their morphological structure (cell diameter, filamentous or sporulated forms).

The methods in place hitherto were based on:

- quantitative hybridizations using oligonucleotide probes specific for different bacterial groups, applied directly to DNA extracted from the environment. Unfortunately, this approach is not very sensitive and does not allow taxonomic groups or genera present in low abundance to be detected (Amann (1995)).
- quantitative PCR such as MPN-PCR (Most Probable Number) (Sykes et al. (1992)) or competitive quantitative PCR (Diviacco et. al. (1993)). The respective drawbacks of each of these approaches are (i) the laborious nature due to the multiplication of the dilutions and repetitions, thus making the technique unsuitable for a large number of samples or pairs of primers, and (ii) the need to construct a competitor which is specific for the target DNA and which does not induce any bias in the competition.

The method introduced according to the present invention consists in universally amplifying a 700 pb fragment inside the 16S rDNA sequence, in hybridizing this amplificate with an oligonucleotide probe of variable specificity (as regards the kingdom, order, subclass or genus) and in comparing the hybridization intensity of the sample relative to an external calibration range. The amplification prior to the hybridization makes it possible to quantify genera or species of microorganisms that are relatively sparse. Furthermore, the amplification with universal primers makes it possible, during the hybridization, to use a wide series of oligonucleotide probes. It allows a comparison between different modes of lysis (direct or indirect extraction) on well defined taxonomic groups.

The results are collated in Table 6.

They show similar profiles between the two extraction methods (direct and indirect). Thus, it appears that prior extraction of the telluric microbial fraction does not introduce any genuine bias among the taxons tested. The only significant difference between the two extraction approaches would appear to be the greater abundance of rDNA sequences belonging to γ-proteobacteria in the extract by the indirect extraction method.

Furthermore, a significant effect of incubating the soil sample in a solution of yeast extract is observed on the sporulated soil populations (Gram$^+$, low percentage of GC and actinomycetes). This step brings about germination of the spores and, firstly, definitely allows better recovery of cells of this type, and, secondly, allows greater lysis efficacy on germinating cells.

This approach allows a semi-quantitative analysis, targeted on the main taxons defined using microorganisms cultured and usually found in the soils. Only molecular tools make it possible to estimate the magnitude of the various taxons, since culture methods are too restrictive and are dependent on the specificity of the medium used.

The results show that a large proportion of the microbial population is not represented in the phylogenetic groups described, thus demonstrating the existence of novel groups made up of microorganisms which have not been cultured hitherto, or which are not culturable.

Thus, novel probes can be defined using given sequences starting with DNA extracted from the soil (novel phyla composed of non-cultured microorganisms, Ludwig et al. (1997)) in order to obtain a more exact image of the composition of the DNA extract.

Example 4

Construction of the Cosmid pOS700I

Characteristics of pOS700I:

Replicative in *E. coli*

Integrative in *Streptomyces*

Selectable in *E. coli* AmpR, HygroR and *Streptomyces* HygroR

The properties of the cosmid make it possible to insert large DNA fragments of between 30 and 40 kb.

It comprises

1—The inducible promoter tipA of *Streptomyces lividans*

2—The integration system specific for the element pSAM2

3—The hygromycin-resistance gene

4—The cosmid pWED1, derived from pWED15

1)—The Inducible Promoter of the Tip A Gene of *S. lividans*

The tipA gene encodes a 19 KD protein whose transcription is induced by the antibiotic thiostrepton or nosiheptide. The tipA is well regulated: induction in exponential phase and in stationary phase (200×) (Murakami T, Holt T G, Thompson C J., J. Bacteriol 1989; 171: 1459-66).

2)—The Hygromycin-Resistance Gene

Hygromycin: antibiotic produced by *S. hygroscopicus*

The resistance gene encodes a phosphotransferase (hph)

The gene used originates from a cassette constructed by Blondelet et al., in which the hyg gene is under the control of its own promoter and of the IPTG-inducible plac promoter (Blondelet-Rouault et al.; Gene 1997; 190: 315-7)

3)—The Site-Specific Integration System

The element pSAM2 integrates into the chromosome by means of a site-specific integration mechanism. The recombination takes place between two identical 58 bp sequences present on the plasmid (attP) and on the chromosome (attB).

The int gene, located close to the attP site, is involved in the site-specific integration of pSAM2, and its product has similarities with the integrases of the temperate bacteriophages of enterobacteria. It has been demonstrated that a pSAM2 fragment containing only the attP attachment site as well as the int gene was capable of integrating in the same manner as the entire element (see French patent No. 88 06638 of 18 May 1988 and Raynal A et al., Mol. Microbiol. 1998 28: 333-42).

4)—Construction of the Cosmid pOS700I

Step 1/The promoter TipA was isolated from the plasmid pPM927 (Smokvina et al., Gene 1990; 94:53-9) on a 700-base pair HindIII-BamHI fragment and cloned into the vector pUC18 (Yannish-Perron et al., 1985) digested with HindIII/BamHI.

Step 2/This HindIII-BamHI fragment was subsequently transferred from pUC18 to pUC19 (Yannish-Perron et al., 1985).

Figure 8:
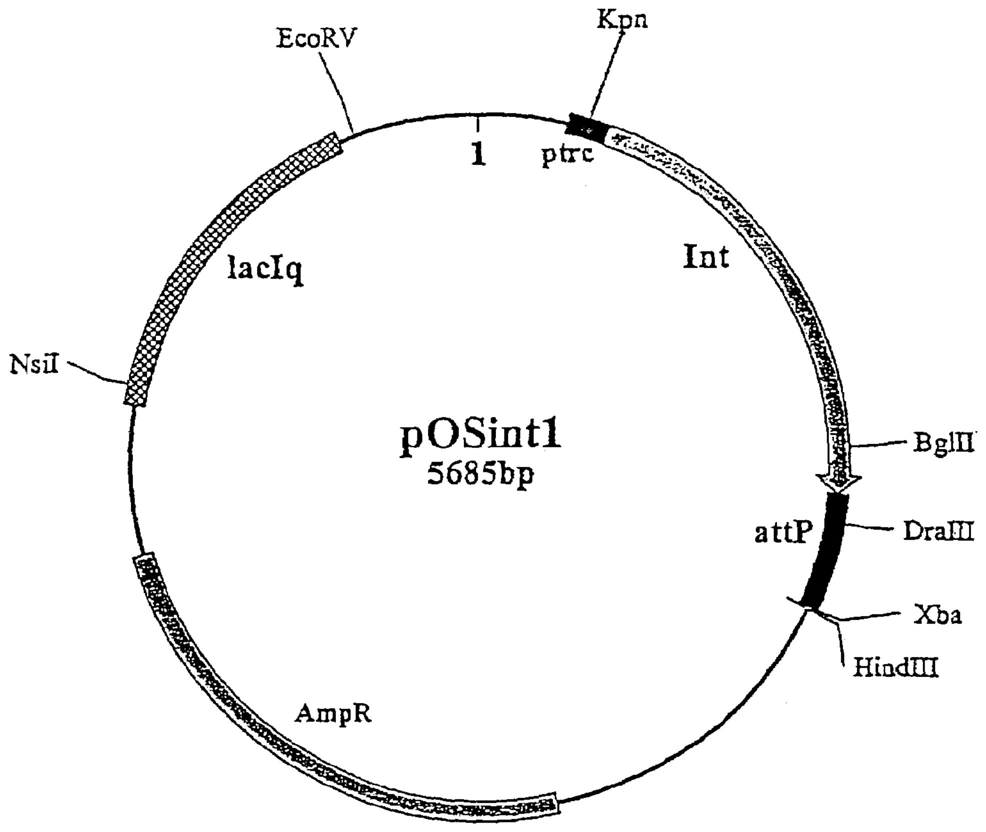
FIG. 8 represents a scheme of the vector pOSint 1.

Step 3/A 1500-base pair BamHI-BamHI insert carrying the int gene and the attP site of pSAM2 was isolated from the pOSint1, represented in FIG. 8 (Raynal A et al. Mol Microbiol 1998 28: 333-42) and cloned into the BamHI site of the preceding vector (pUC19/TipA), in the orientation which allows the int gene to be placed under the control of the promoter TipA.

Step 4/The BamHI site located on the 5' side of the int gene was deleted by partial digestion with BamHI followed by treatment with the Klenow enzyme. A HindIII-BamHI fragment carrying TipA-int-attP was thus isolated from pUC19 and transferred into pBR322 HindIII/BamHI.

Step 5/The hygromycin cassette isolated from pHP45Ωhyg (Blondelet-Rouault et al., 1997) on a HindIII-HindIII fragment was cloned into the HindIII site located upstream of the promoter TipA.

Step 6/The HindIII site located between the ΩHyg cassette and the promoter TipA was deleted by Klenow treatment after partial HindIII digestion.

Figure 9:
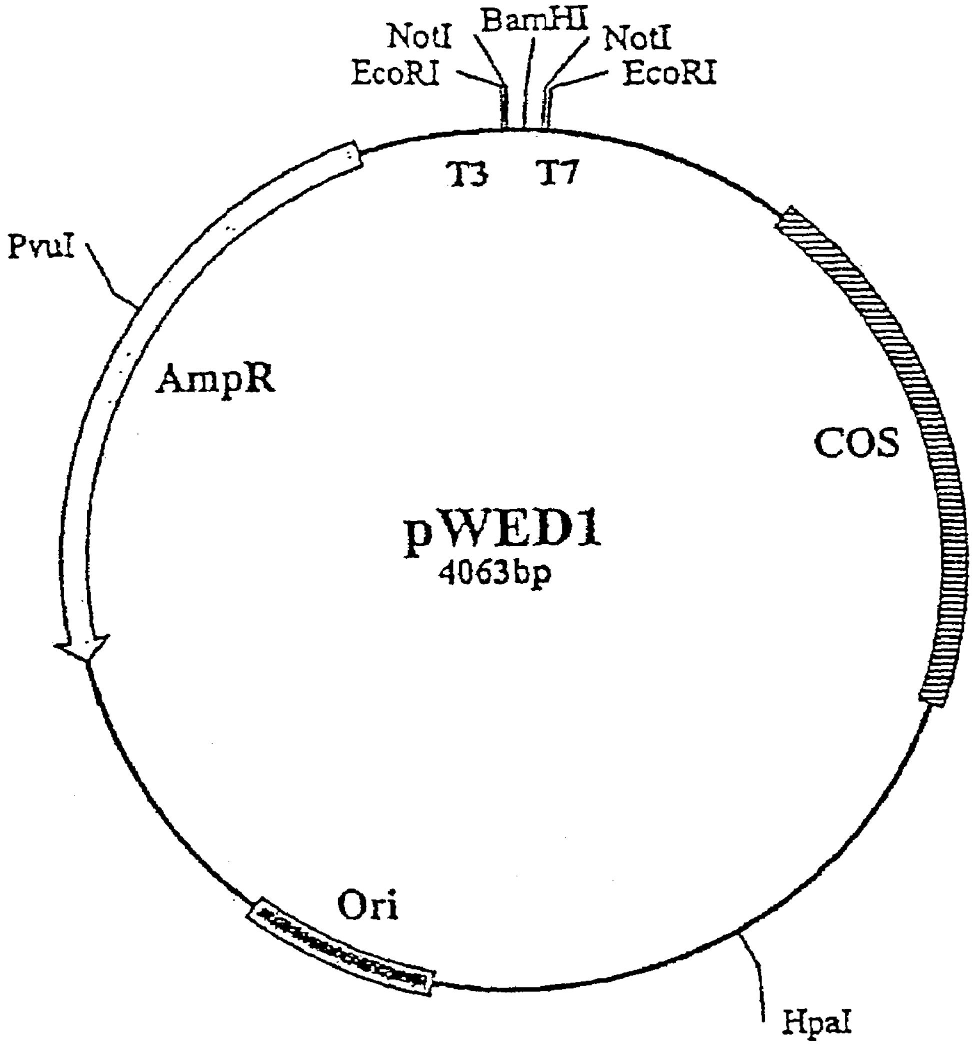
FIG. 9 represents a scheme of the vector pWED 1.
Figure 10:
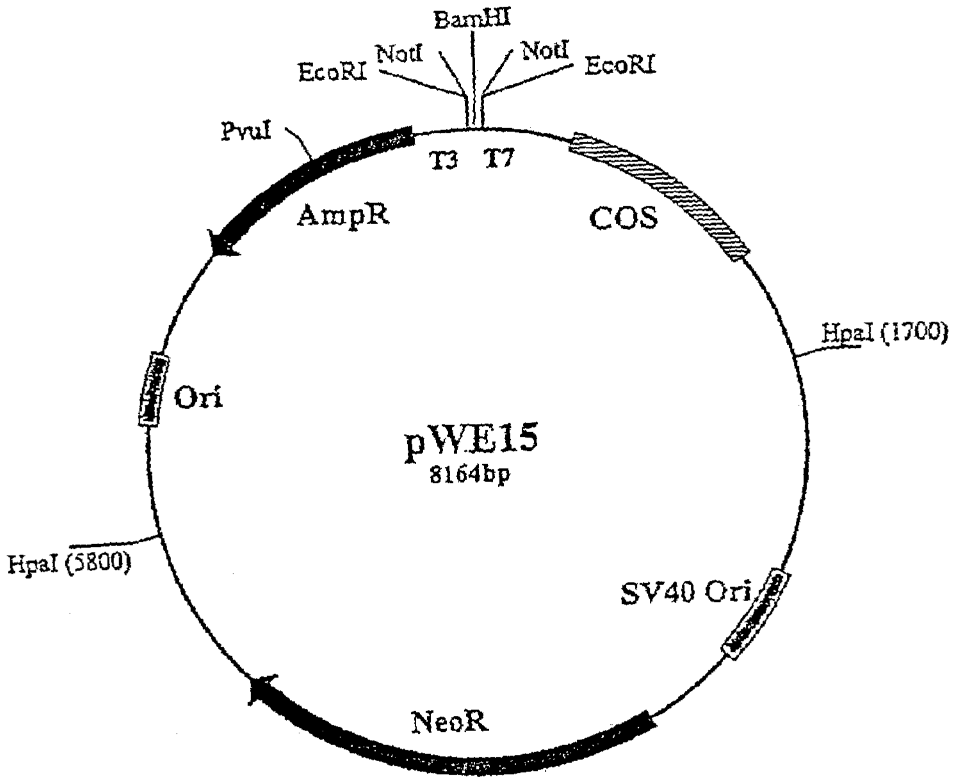
FIG. 10 represents a scheme of the vector pWE15 (ATCC No 37503).

Step 7/The plasmid obtained after the preceding step makes it possible to isolate a single HindIII-BamHI fragment, carrying all the ΩHyg/TipA/int attP elements, which was cloned after Klenow treatment into the EcoRV site of the cosmid pWED1. The cosmid pWED1, represented in FIG. 9, derived from the cosmid pWE15, represented in FIG. 10 (Wahl G M, et al., Proc. Natl. Acad. Sci. USA 1987 84:2160-4) by deletion of an HpaI-HpaI fragment carrying the Neomycin gene and the SV40 origin.

Figure 11:
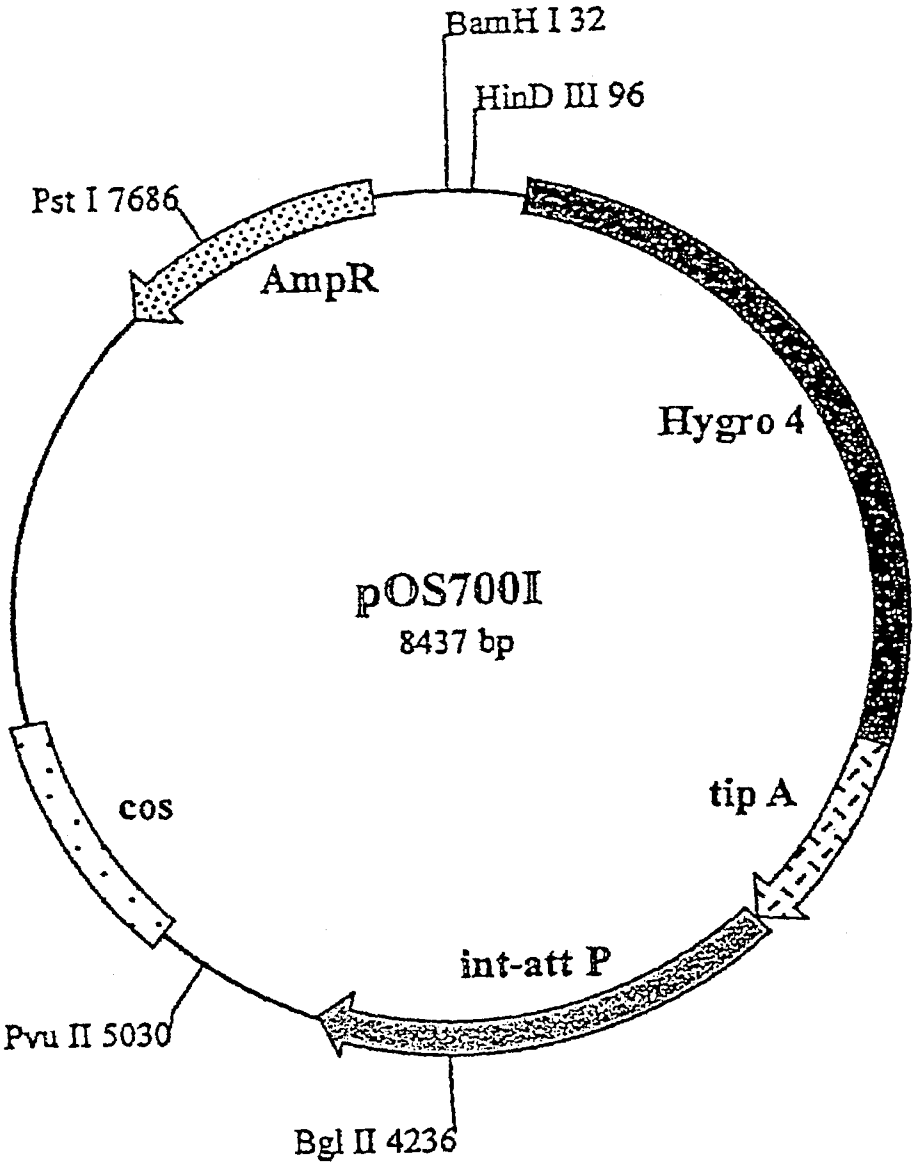
FIG. 11 represents a scheme of the vector pOS700I.

A map of the vector pOS 700I is represented in FIG. 11.

Example 5

Construction of the Cosmid which is Conjugative and Integrative in *Streptomyces*, the Vectors POSV 303, pOSV306 and pOSV307

5.1 Construction of the Vector pOSV303

Given that the packaging selects clones larger than 30 kb, only 10 to 15% of the clones contain no insert, and it is thus not really necessary to have a system for selecting recombinants, thus allowing a smaller vector to be constructed.

Construction:

Step 1: The Vector pOSV001

Cloning of an 800 base pair PstI-PstI fragment carrying the transfer origin OriT of the replicon R K2 (Guiney et al., 1983), into the plasmid pUC19 opened with PstI. This cloning step makes it possible to obtain a vector which is transferable from *E. coli* to *Streptomyces* by conjugation.

Figure 17:
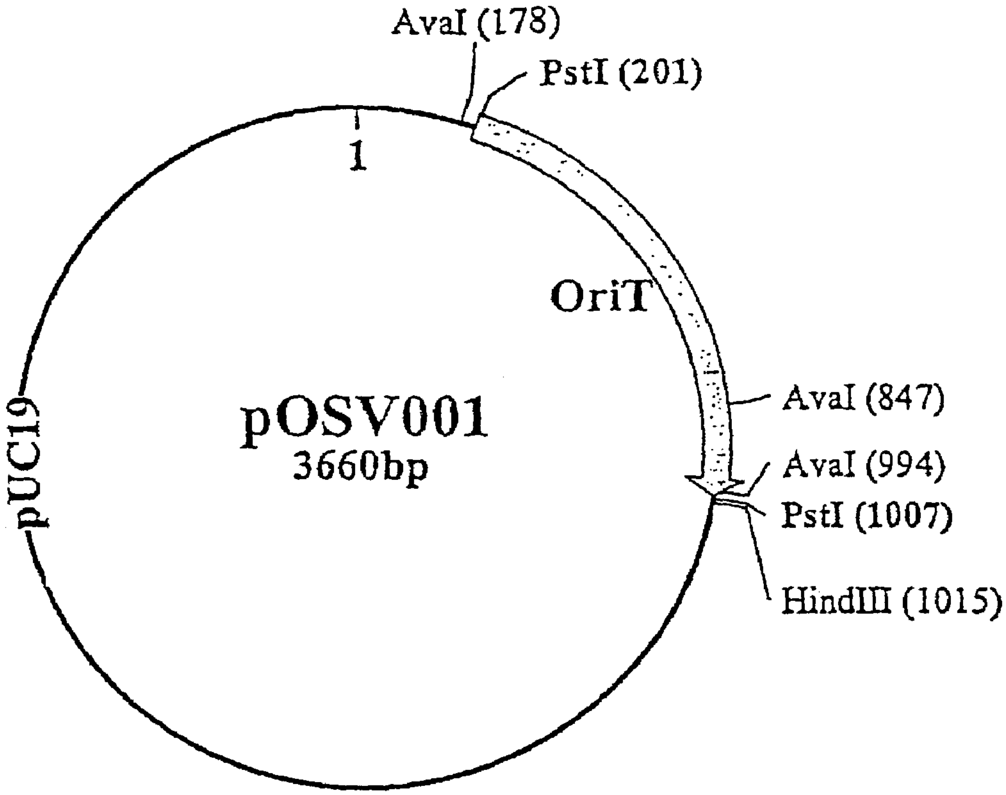
FIG. 17 represents a scheme of the vector pOSV001.

The map of the vector pOSV 001 is represented in FIG. 17.

Step 2: The Vector pOSV002

Insertion of the hygromycin marker (Ωhyg cassette), which is selectable in *Streptomyces*, such that the hygromycin-resistance gene is transferred last, thus making it possible to ensure complete transfer of the BAC with the soil DNA insert.

Cloning of the hygromycin cassette isolated from pHP45Ωhyg on a HindIII-HindIII fragment carrying the hygromycin-resistance gene. This fragment is cloned into the PstI site (position 201) of the vector pOSV001. This PstI site was chosen, given the direction of the transfer, such that the Hygro marker is transferred last during the conjugation. The PstI and HindIII ends are made compatible after treatment with the Klenow fragment of DNA polymerase, allowing “blunt ends” to be generated. The orientation of the Ωhyg fragment is determined at the end of construction.

Figure 18:
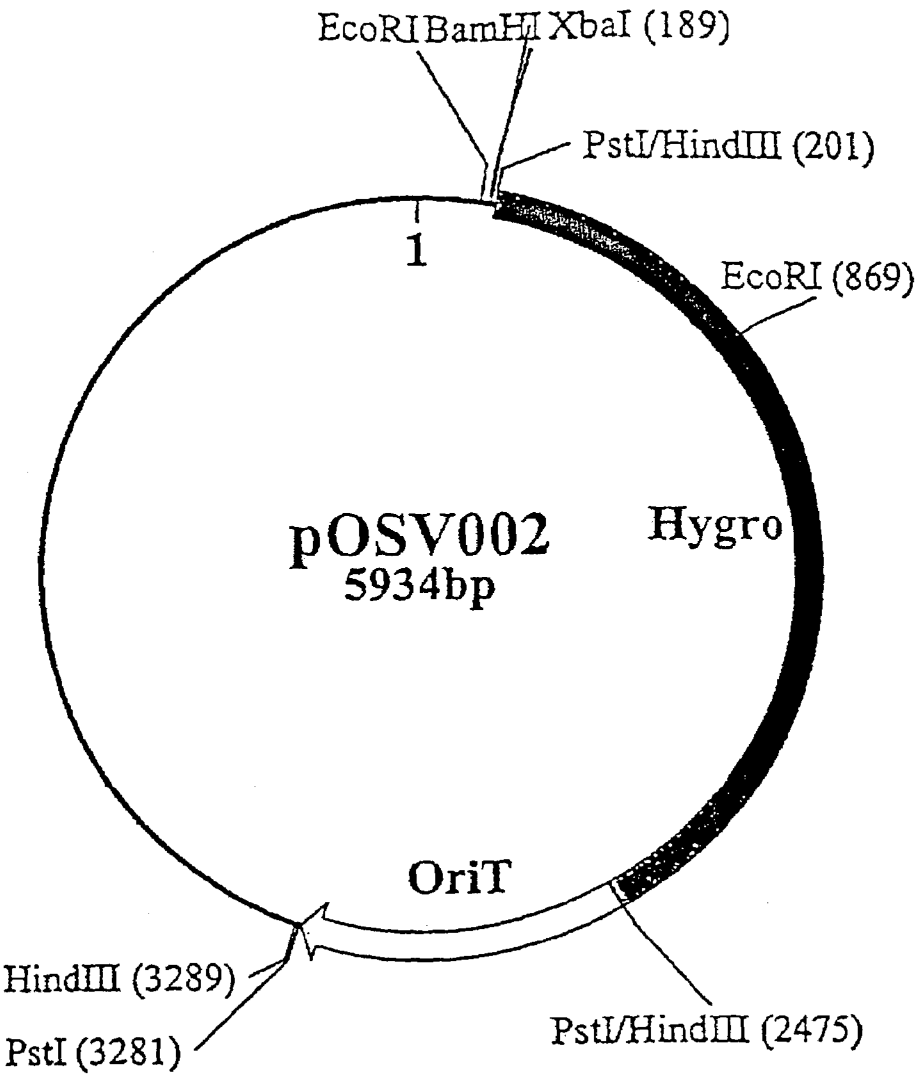
FIG. 18 represents a scheme of the vector pOSV002.

The map of the vector pOSV002 is represented in FIG. 18.

Step 3: The Vector pOSV010

The XbaI-HindIII fragment isolated from the plasmid pOSV002 and containing the hygromycin-resistance marker and the transfer origin is cloned into the plasmid pOSint1 digested with XbaI and HindIII. The orientation of the sites is such that the hygromycin marker will always be transferred last.

The plasmid pOSint1, represented in FIG. 8, was described in the article by Raynal et al. (Raynal A et al., Mol. Microbiol. 1998 28: 333-42).

This construct allows the expression of the integrase in *E. coli* and *Streptomyces*.

Step 4: Insertion of the “cos” Site

Figure 12:
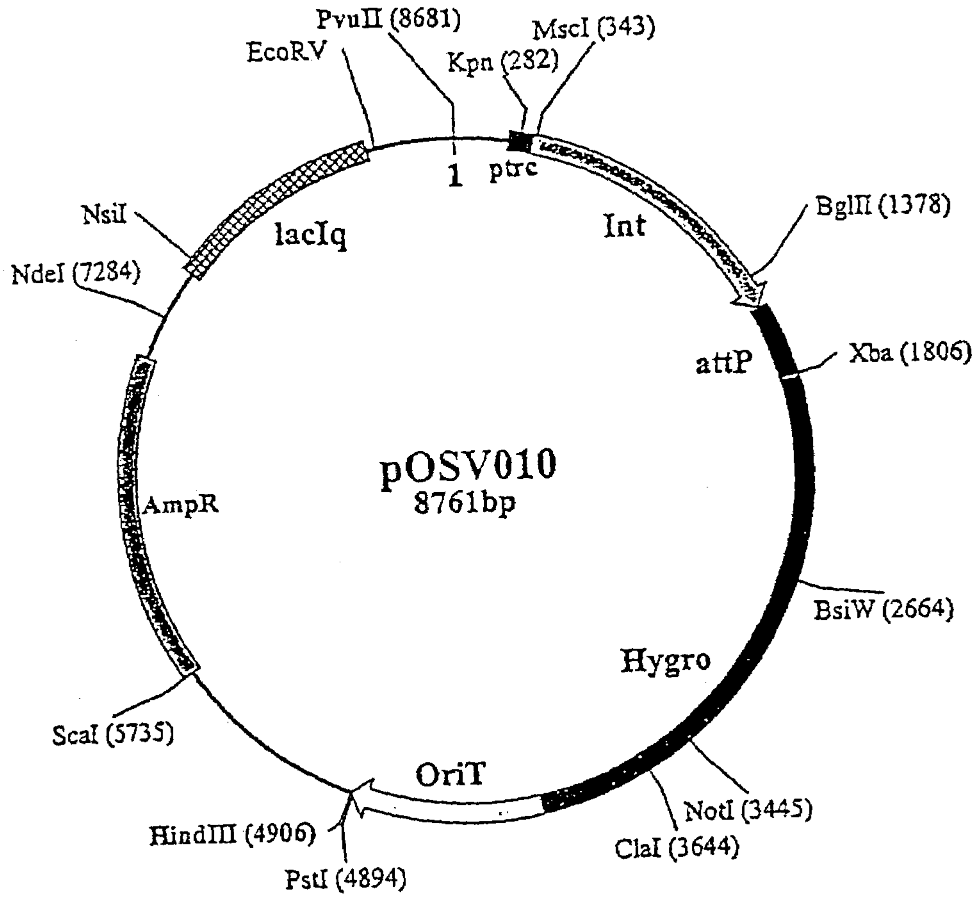
FIG. 12 represents a scheme of the vector pOSV010.

The principle is to insert a “cos” site into the plasmid pOSV010, allowing packaging into the plasmid pOSV010, represented in FIG. 12.

Figure 13:
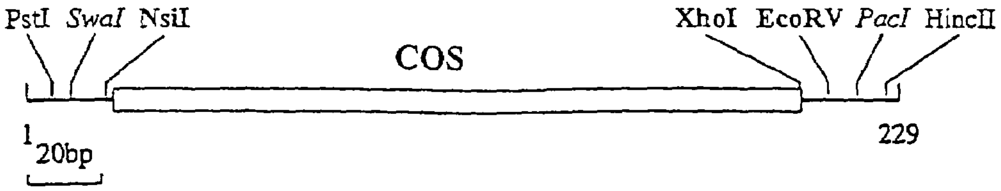
FIG. 13 represents the fragment containing a "cos" site inserted into the plasmid pOSV010 during construction of the vector pOSV303.

The production of the “cos” fragment is represented in FIG. 13.

This fragment is obtained by PCR. Starting with a fragment carrying the cohesive ends (cos) of λ (bacteriophage lambda or cosmid pHC79), a PCR amplification is carried out using oligonucleotides corresponding to the sequences −50/+130 relative to the cos site. These oligonucleotides also contain the NsiI cloning sites, PstI compatible, the XhoI site, SalI compatible, and EcoRV, site for obtaining "blunt ends".

Addition of the rare SwaI and PacI sites makes it possible to isolate and/or map the insert cloned.

The PCR fragment is delimited by a PstI site at the 5' end and by a HincII site at the 3' end, allowing cloning into the vector pOSV010 (FIG. 12) predigested with the enzymes NsiI and EcoRV, bringing about deletion of the lacIq repressor.

Figure 14:
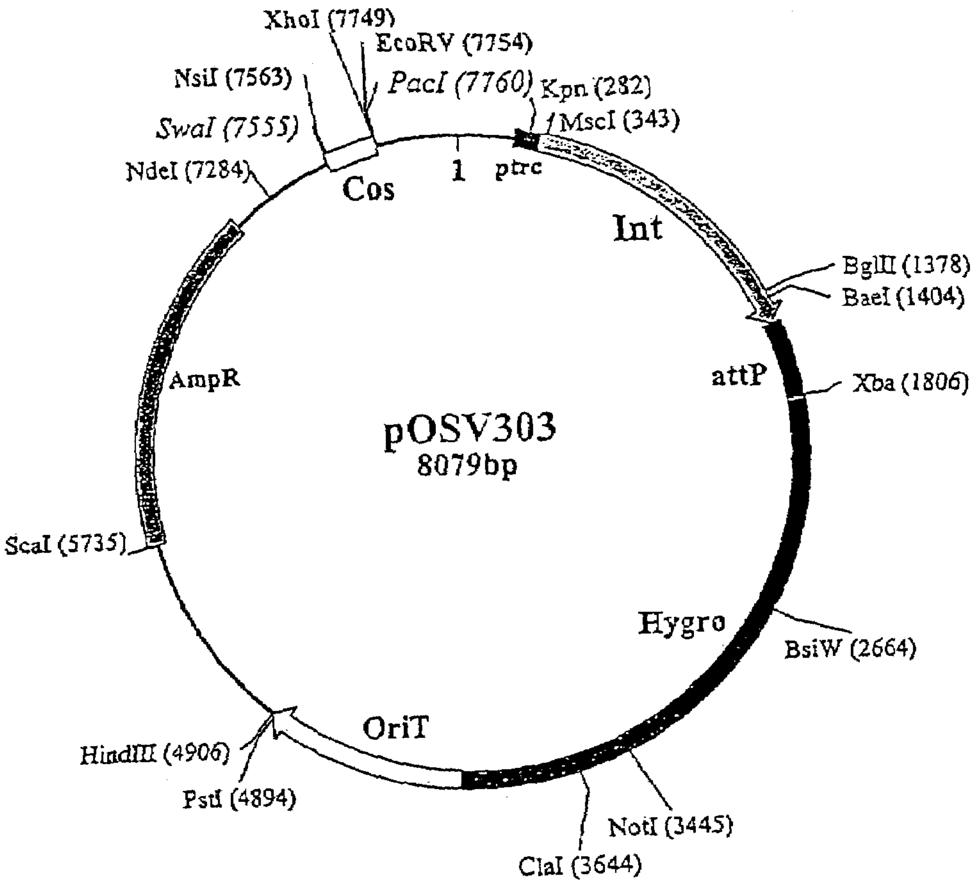
FIG. 14 represents a scheme of the vector pOSV303.

The map of the vector pOSV303 is represented in FIG. 14. The vector pOSV303 contains cloning sites such as the NsiI site, PstI compatible, the XhoI site, SalI compatible or the EcoRV site for obtaining "blunt ends".

5.2 Construction of the Vector pOSV306

Step 1: Construction of the Vector pOSV308

The vector pOSV308 was constructed according to the process illustrated in FIG. 27. A 643-bp: fragment containing the cos region was amplified using a pair of primers of sequences SEQ ID No. 107 and SEQ ID No. 108 from the cosmid vector pHc79 described by Hohm B and Collins (1980).

This amplified nucleotide fragment was cloned directly into the pGEMT-easy vector sold by the company Promega, as illustrated in FIG. 27, so as to produce the vector pOSV308.

Step 2: Construction of the Vector pOSV306

The vector pOSV010 was constructed as described in step 3 of construction of the vector pOSV303, as described in paragraph 5.1 of the present example.

The vector pOSV10 was digested with the enzymes EcoRV and NsiI in order to excise a 7874-bp fragment, which was subsequently purified, as illustrated in FIG. 28.

Next, the vector pOSV308 obtained in step 1) above was digested with the enzymes EcORV and PstI in order to excise a 617-bp fragment, which was subsequently purified.

Next, the 617-bp cos fragment obtained from the vector pOSV308 was integrated by ligation into the vector pOSV10, so as to obtain the vector pOSV306, as illustrated in FIG. 28.

5.3 Construction of the Vector pOSV307

The cosmid pOSV307 still contains the LacIq gene so as to improve the stability of the cosmid in *Streptomyces*, for example in the S17-1 strain of *Streptomyces.*

In order to construct the vector pOSV307, the vector pOSV010 was subjected to a digestion with the enzyme PvuII, to obtain an 8761-bp fragment which was purified and then dephosphorylated.

Next, the vector pOSV308, obtained as described in step 1) of paragraph 5.2 above, was digested with the enzyme EcoRI so as to obtain a 663-bp fragment, which was then purified and treated with the Klenow enzyme.

The nucleotide fragment thus treated was integrated into the vector pOSV010 after ligation so as to obtain the vector pOSV307, as illustrated in FIG. 29.

Example 6

Figure 15:
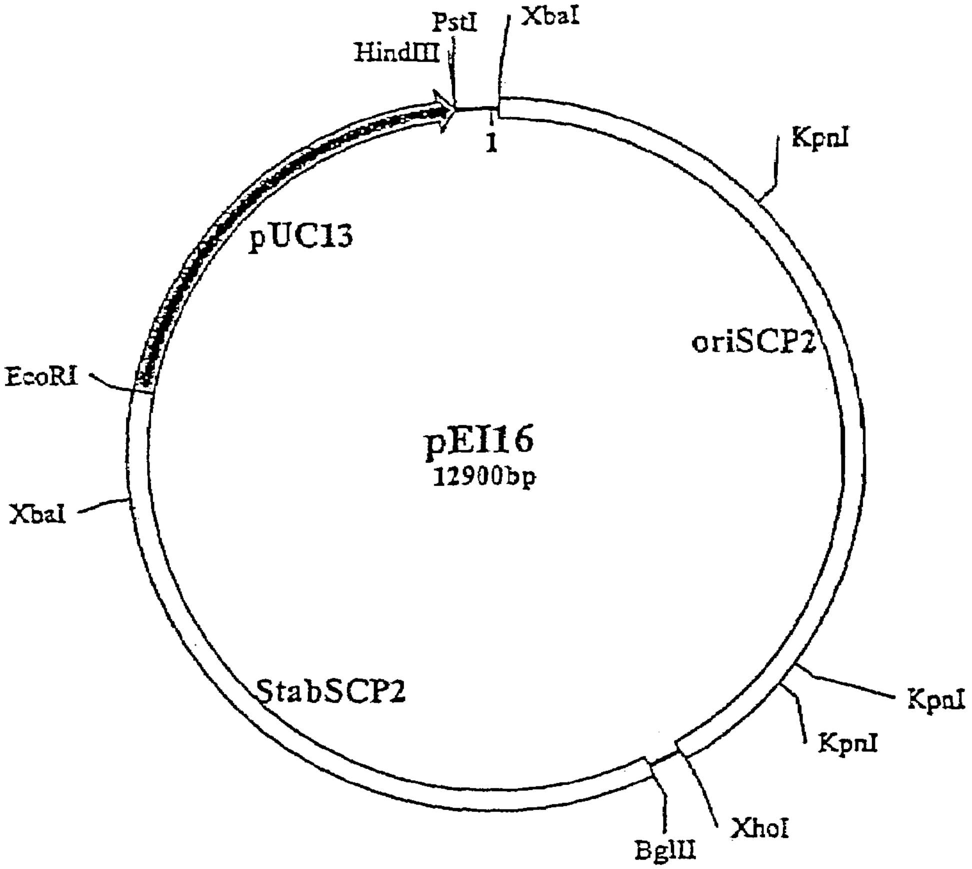
FIG. 15 represents a scheme of the vector pE116.

Construction of the *E. coli-Streptomyces* Replicative Shuttle Cosmid pOS700R The fragments of the plasmid pEI16 (Voliff et al., 1996) represented in FIG. 15 were isolated and Klenow-treated. These fragments contain the sequences required for replication and stability originating from the plasmid SCP2.

These two fragments are inserted separately into the EcoRV site of the cosmid pWED1, leading to 2 different clones.

The hygromycin cassette isolated from pHP45Ωhyg on a HindIII-HindIII fragment was cloned into the HindIII site of the pWED1 cosmids containing the ScP2 insert in the form of PstI-EcoRI or XbaI fragments. It imparts hygromycin resistance which can be selected both in *E. coli* and in *Streptomyces.*

Transformation of *S. lividans* and determination of the transformation efficacy.

It was found that the cosmid containing the XbaI insert was less stable than that containing the PstI EcoRI fragment. It is therefore the latter cosmid which was selected under the name pOS700R.

Figure 16:
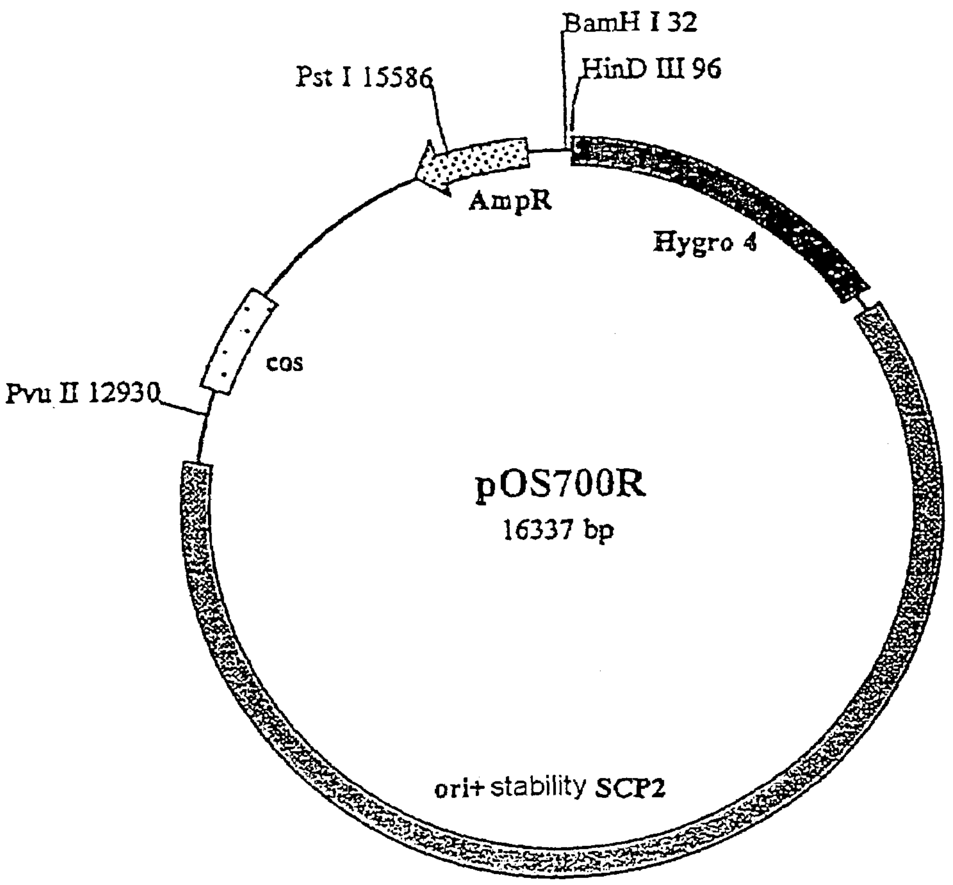
FIG. 16 represents a scheme of the vector pOS700R.

The map of the vector pOS 700R is represented in FIG. 16.

Example 7

Transformation Efficacy of the Integrative (pOS700I) and Replicative Vectors Possibilities To render the strain of *S. lividans* resistant to thiostrepton by integrating the plasmid pTO1 carrying the thiostrepton-resistance marker.

Preparation of protoplasts from *S. lividans* cultured in the presence of thiostrepton.

With the pOS700I vector, the transformation efficacy is about 3000 transformants per μg of DNA.

With the vector pOS700R, the transformation efficacy is about 30,000 transformants per μg of DNA.

Example 8

Construction of a BAC Vector which is Integrative in *Streptomyces* and Conjugative Characteristics:

Replicative in *E. coli*

Transferable by conjugation of *E. coli* with *Streptomyces*

Integrative in *Streptomyces*

Selectable in *E. coli* and *Streptomyces*

Capable of inserting large DNA fragments; it should be pointed out that it is necessary to have available soil DNA which is between 100 and 300 kb in size and which is not contaminated with small fragments. The reason for this is that the small fragments are very preferably integrated.

Endowed with a screen for selecting plasmids carrying an insert. This screen makes it possible, by removing the vectors which are closed on themselves and which are not digested, to work with a higher ratio between the vector and the DNA to be inserted, thus making it possible to have better cloning efficacy for making libraries.

Construction:

Step 1: The Vector pOSV001

Cloning of an 800 base pair PstI-PstI fragment carrying the transfer origin OriT of the replicon RK2 (Guiney et al., 1983), into the plasmid pUC19 opened with PstI. This cloning step makes it possible to obtain a vector which is transferable from *E. coli* to *Streptomyces* by conjugation.

The map of the vector pOSV 001 is represented in FIG. 17.

Step 2: The Vector pOSV002

Insertion of the hygromycin marker (Ωhyg cassette), which is selectable in *Streptomyces*, such that the hygromycin-resistance gene is transferred last, thus making it possible to ensure complete transfer of the BAC with the soil DNA insert.

Cloning of the hygromycin cassette isolated from pHP45Ωhyg on a HindIII-HindIII fragment carrying the hygromycin-resistance gene. This fragment is cloned into the PstI site (position 201) of the vector pOSV001. This PstI site was chosen, given the direction of the transfer, such that the Hygro marker is transferred last during the conjugation. The PstI and HindIII ends are made compatible after treatment with the Klenow fragment of DNA polymerase for generating "blunt ends". The orientation of the Ωhyg fragment is determined at the end of construction.

The map of the vector pOSV002 is represented in FIG. 18.

Step 3: The Vector pOSV010

The XbaI-HindIII fragment isolated from the plasmid pOSV002 and containing the hygromycin-resistance marker and the transfer origin is cloned into the plasmid pOSint1 digested with XbaI and HindIII. The orientation of the sites is such that the hygromycin marker will always be transferred last.

The plasmid pOSint1, represented in FIG. 8, was described in the article by Raynal et al. (Raynal A et al., Mol. Microbiol. 1998 28: 333-42).

This construct allows the expression of the integrase in *E. coli* and *Streptomyces.*

Step 4: The Vector pOSV014

Addition of a "cassette" making it possible at the end to select in the final construct the plasmids which have foreign DNA inserted.

This "cassette" carries the gene encoding the λ phage Cl repressor and the tetracycline-resistance gene. This gene carried the target sequence of the repressor in its non-coding 5' region. The insertion of DNA into the HindIII site located in the coding sequence of Cl leads to the non-production of the repressor and thus to the expression of tetracycline resistance.

It is carried by the plasmid pUN99 described in the article: Nilsson et al. (Nucleic Acids Res. 1983, 11:8019-30).

A PvuII-HindIII fragment isolated from pOSV010 and containing the sequences Int, attP, Hygro and oriT is cloned into the MscI site of pUN99.

Figure 19:
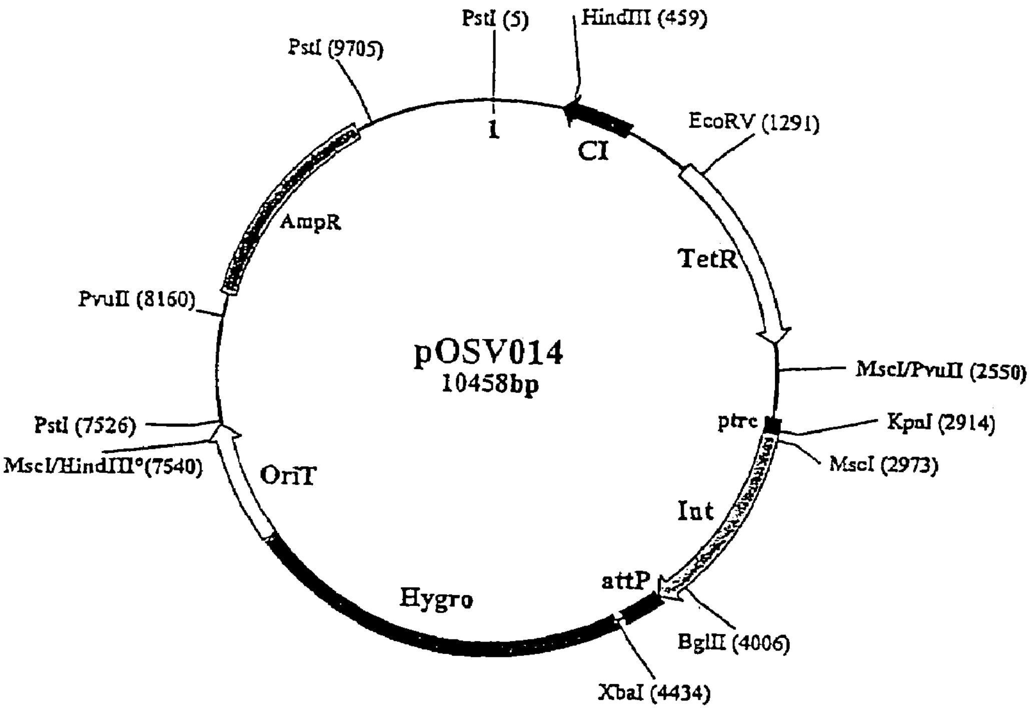
FIG. 19 represents a scheme of the vector pOSV014.

The map of the vector pOSV014 is represented in FIG. 19.

Step 5: The Vector POSV 403, and Integrative and Conjugative BAC Vector

Figure 20:
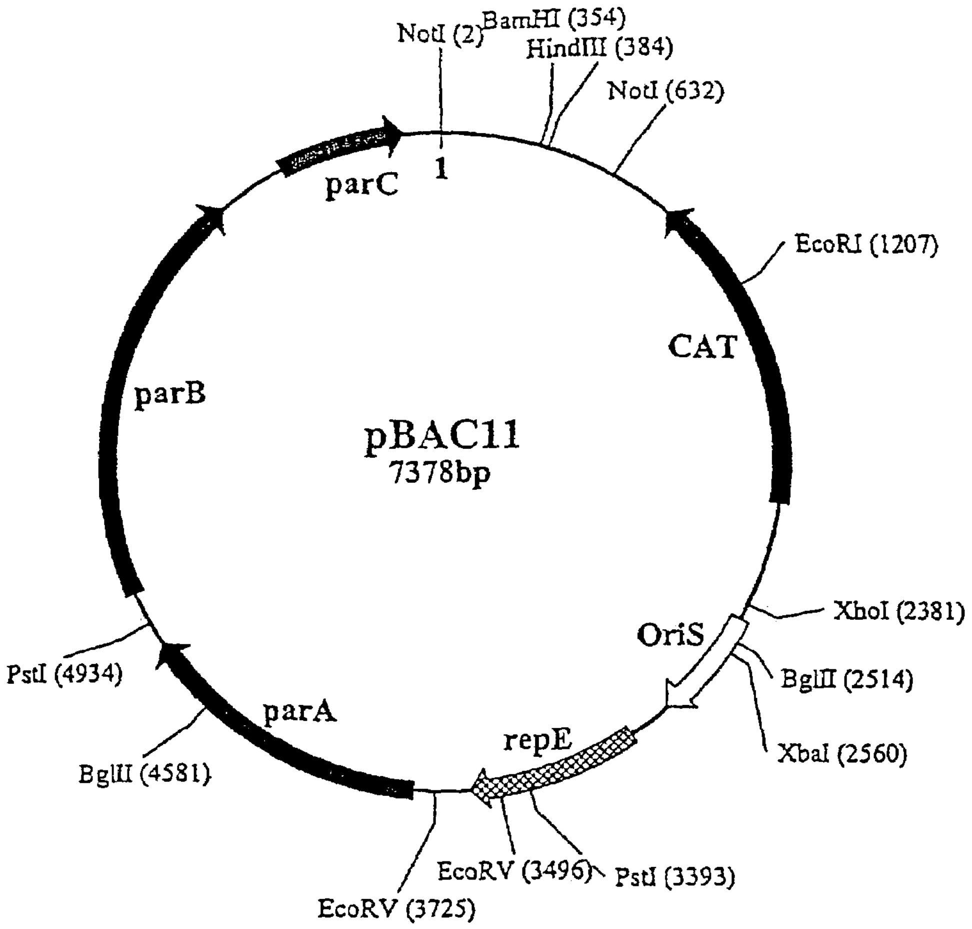
FIG. 20 represents a scheme of the vector pBAC11.

This last step of cloning into pBAC11 (represented in FIG. 20) gives the final plasmid BAC (Bacterial Artificial Chromosome) characteristics, in particular the ability to accept very large DNA inserts.

The PstI-PstI fragment of the vector pOSV014 carrying the set of elements and functions described previously is cloned into the plasmid pBAC11 (pBeloBAC11) digested with NotI. The ends are made compatible by treatment with the Klenow enzyme.

Figure 21:
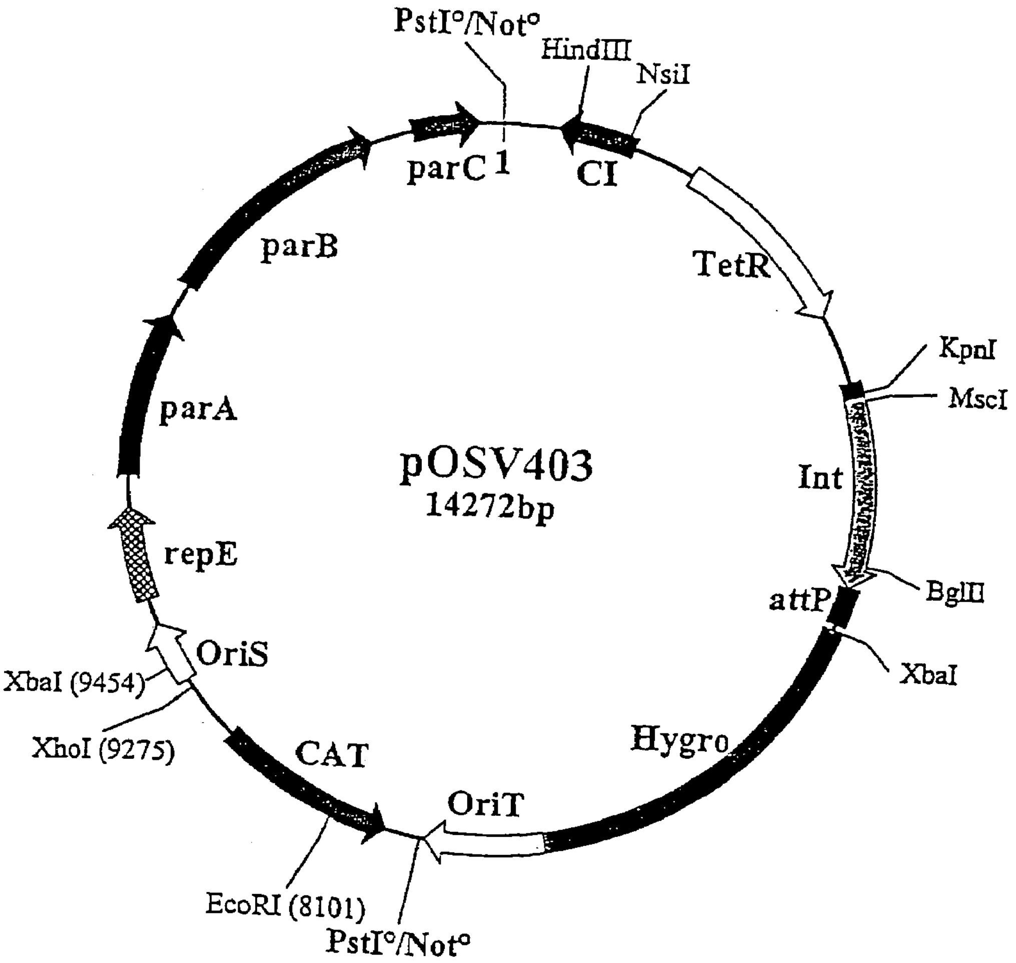
FIG. 21 represents a scheme of the vector pOSV403.

The map of the vector pOSV403 is represented in FIG. 21. The scheme of FIG. 21 indicates the orientation selected.

Step 6:

The vector pOSV403 contains the HindIII and NsiI sites. The NsiI site is quite rare in *Streptomyces* and has the advantage of being compatible with PstI. On the other hand, the PstI site is common in *Streptomyces* and can be used to carry out partial digestions.

The recombinant clones carrying an insert cloned into the Cl repressor, and thus inactivating this repressor, become tetracycline-resistant. Given that the BACs are present only at a rate of one copy per cell, it is necessary to select the recombinant clones with a lower dose of tetracycline than the usual dose of 20 μg/ml, for example with a dose of 5 μg/ml. Under these conditions, there is no background noise.

It is also possible to use the system developed and sold by the company InVitrogen, in which the insertion of DNA into the vector inactivates a gyrase inhibitor whose expression is toxic for *E. coli*. The fragment is preferentially isolated from the vector pZErO-2 (http://www.invitrogen.com/).

Example 9

Construction of an *S. alboniger* Library in the Integrative Cosmid (pOS7001) and the Replicative Cosmid (pOS700R)

1)—Construction of the Library

To evaluate the efficacy of the cloning system, the puromycin biosynthetic pathway of *Streptomyces alboniger* was cloned into the two shuttle cosmids pOS700I and pOS700R. The genes of the puromycin biosynthetic pathway are carried by a BamHI DNA fragment of about 15 kb.

The genomic DNA of *Streptomyces alboniger* was isolated. 90% of this DNA has a molecular weight of between 20 and 150 kb, determined by pulsed-field electrophoresis.

The two cosmids were digested with the enzyme BamHI (single cloning site).

The conditions of partial BamHI digestion of the genomic DNA were determined (50 μg of DNA and 12 units of enzyme, digestion for 5 minutes). After checking the size by agarose gel electrophoresis, the DNA partially digested was introduced into the vectors. In the ligation, 15 μg of genomic DNA+2 μg of the integrative vector or 5 μg of the replicative vector were used.

Each ligation mixture was used for the in vitro encapsidation of the DNA into the heads of bacteriophage lambda. The encapsidation mixtures (0.5 ml) were titrated (integrative vector pOS700I=$7.5\times10^5$ cosmids/ml, replicative vector=$5\times10^4$ cosmids/ml).

The cosmids were used to transfect *E. coli* and thus to generate libraries of about 25,000 ampicillin-resistant clones. The DNA from all of these clones was isolated and quantified.

To test the libraries, several clones were chosen, the DNA purified and digested with BamHI, in order to check the presence and size of the inserts. The clones tested contain between 20 and 35 Kb of *S. alboniger* insert.

2)—Identification of the Clones Containing the Puromycin Biosynthetic Pathway

The clones liable to contain the complete puromycin biosynthetic pathway were identified by hybridization with a probe corresponding to the puromycin-resistance gene, the 1.1 kb pac gene (Lacalle et al., Gene 1989; 79, 375-80).

Library Made in the Integrative Vector pOS 700I:

Among 2000 clones analysed, 9 clones were hybridized with the probe and they contain inserts of about 40 kb.

Library Made in the Replicative Vector pOS 700R:

Among 2000 clones analysed, 12 clones were hybridized with the probe; they contain inserts of about 40 kb.

Using the data published by Tercero et al. (J Biol. Chem. 1996; 271, 1579-90), the clones containing the entire biosynthetic pathway were identified, after hybridization with suitable probes. Certain integrative and replicative cosmids contain a 12,360-base pair fragment after ClaI-EcoRV digestion, which leads to the assumption of an insert containing the entire puromycin biosynthetic pathway.

4)—Checking the Production of Puromycin by the Resistant Clones (Rhône-Poulenc).

a) Materials and Methods

Strains and Culture Conditions:

Three resistant clones were selected to check the production of puromycin. They correspond to the *S. lividans* recombinants containing an insert in the integrative vector pOS700I (G 20) or an insert in the replicative vector (G21 and G22).

Reference strains were used to ensure that the culture media used allowed this production. They are the *S. alboniger* wild-type strain ATCC 12461, which produces puromycin, and the *S. lividans* recombinant strain containing the complete puromycin cluster cloned into the plasmid pRCP11 (Lacalle et al, 1992, the EMBO journal, 11, 785-792) (G23).

The strains were inoculated in a culture medium whose composition is as follows:

| | |
|---|---|
| Organotechnie bacteriological peptone | 5 g/l of final medium |
| Springer yeast extract | 5 |
| Liebig meat extract | 5 |
| Prolabo glucose | 15 |
| Prolabo $CaCO_3$ (1) | 3 |
| Prolabo NaCl | 5 |
| Difco agar (2) | 1 |

(1) The 3 g of carbonate are mixed with 200 ml of distilled water and then sterilized separately. The addition is carried out after sterilization.
(2) The agar is melted beforehand in 100 ml of distilled water, after which it is added to the other ingredients of the medium.
pH adjusted to 7.2 before sterilization
sterilization for 25 minutes at 121° C.

50 μg/l of hygromycin and 5 μg/l of thiostrepton are added to the medium after sterilization so as to maintain a selection pressure for the clones containing an insert by means of the marker gene present on the vector (the thiostrepton-resistance gene being carried by the plasmid pRCP11).

50 ml of liquid culture medium, distributed in 250 ml conical flasks, are inoculated with 2 ml of aqueous suspension of spores and mycelium of each of the strains. The cultures are incubated for 4 days at 28° C. with stirring at 220 rpm. 50 ml of production medium, distributed in 250 ml conical flasks, are then inoculated with 2 ml of these precultures. The production medium used is an industrial medium optimized for the production of pristinamycin (medium RPR 201). The cultures are incubated at 28° C., with stirring at 220 rpm. After different incubation times, a conical flask of each culture is brought to pH 11 and then extracted with twice 1 volume of dichloromethane. The organic phase is concentrated to dryness under reduced pressure and the extract is then taken up in 10 μl of methanol. 100 μl of the methanol solution are analysed by HPLC equipped with a diode-bar detector, in a water-acetonitrile 0.05% TFA VN gradient system on a C18 column for the detection of puromycin.

b) Results

Figure 23:
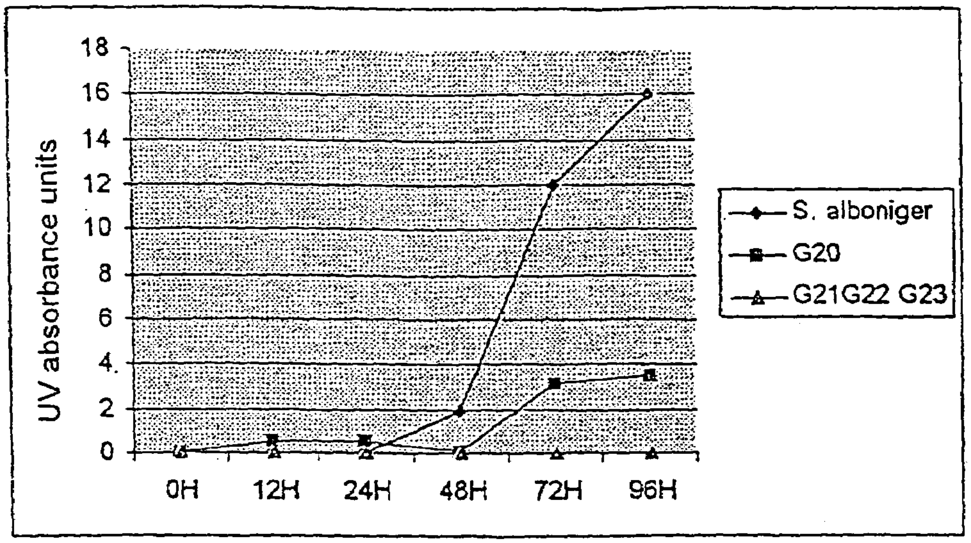
FIG. 23 illustrates the production of puromycin by the *S. lividans* recombinants compared with the production of the *S. alboniger* wild-type strain.

The comparative HPLC analyses from the cultures of the various strains show the production of puromycin in the culture of the wild-type strain at and above 24 h of incubation. A production, although lower, is also clearly detected at and above 48 h in the culture of the clone G20 containing the cosmid pOS700I (FIG. 23). Puromycin was also detected in trace amounts in the clone G23 containing the complete operon encoding the compound in the plasmid pRCP11. However, no production was observed in the cultures of the clones G21 and G22 containing the cosmid pOS700R. The results are given in FIG. 23.

c) Conclusions

The results obtained make it possible to demonstrate the efficacy of the cloning system developed in the cosmid pOS700I for expressing, in a heterologous host such as *S. lividans*, a complete biosynthetic pathway under the control of its own regulatory sequences. Moreover, these data also validate the screening of the libraries obtained on the basis of the resistance of the clones to puromycin since it leads to the identification, among a small number of clones, of a recombinant capable of expressing the biosynthetic pathway associated with the resistance gene. The absence of puromycin production in the other clones can probably be explained by the cloning of only a portion of the operon containing the resistance gene but devoid of certain regulatory, transduction or transcription sequences necessary for the synthesis of the compound.

Example 10

Cloning of Soil DNA into Vectors

1)—Preparation of the Soil DNA to be Cloned

The various DNA fragments need to be purified according to their destination:

Cosmids

The size of the molecules should be between 30 and 40 kb. Now, the DNA extracted from the soil is heterogeneous in size and comprises molecules of up to 200 or 300 kb. In order to homogenize the sizes, the DNA is broken mechanically by passing the solution through a needle 0.4 mm in diameter. The fragments of a size in the region of 30 kb are not affected by these repeated passages through a needle and it is thus not necessary to carry out a separation on the basis of size especially since the packaging in the particles automatically eliminates the short inserts.

BACs

Preparation of the DNA

The soil DNA is separated by pulsed-field electrophoresis (CHEF type) under conditions such that the fragments between 100 and 300 kb are concentrated in a band of about 5 mm. This is obtained by carrying out the migration in a gel containing 0.7% of normal agarose or 1% of agarose of low melting point with a pulsation time of 100 seconds, for 20 hours and at a temperature of 10° C.

Recovery of the DNA

Two methods are used, their choice depending on the size of the molecules it is desired to isolate, either up to 150 kb or higher.

Up to 150 kb

The porosity of a 0.7% agarose gel allows the exit of the DNA by electroelution on the condition that there is total absence of ethidium bromide. This DNA is then handled with hydrophobic and enlarged-orifice pipetting instruments in order to avoid mechanical fragmentation of the molecules.

Between 100 and 300 kb

The band containing the fragments between 100 and 300 kb in size is cut up. For the migration, a gel containing 1% of agarose of low melting point is used. This property makes it possible to melt the gel at a temperature of 65° C., which can be tolerated by the DNA, and then to digest it with agarase (Agarase sold by the company Boehringer) at a temperature of 45° C. according to the supplier's prescriptions.

2)—Use of the Integrative Cosmid pOS700I and the Replicative Cosmid pOS700R

Construction with polyA polyT Tails

Principle

A cosmid vector, opened at any cloning site, is modified at the 3' ends by adding a monotonous polynucleotide. Moreover, the DNA to be cloned is modified at the 3' ends by adding a monotonous polynucleotide which can pair up with the above polynucleotide.

The vector-fragment combination to be cloned is made with these polynucleotides and the cos sequence of the vector allows the in vitro packaging of the DNA into lambda phage capsids.

Preparation of the Vector

The vector used is a vector which is self-replicating in *E. coli* and integrative in *Streptomyces.*

For *E. coli*, the selection is made on the ampicillin resistance, and for *Streptomyces*, it is made on the hygromycin resistance.

The cosmid is opened at one of the 2 possible sites (BamHI or HindIII) and the 3' ends are extended with polyA with terminal transferase under the conditions in which the enzyme supplier envisages the addition of 50 to 100 nucleotides.

Preparation of the DNA to be Inserted

The 3' ends of the DNA are extended with polyT with terminal transferase under the conditions supplying an extension comparable to that of the vector. Under the experimental conditions described by the manufacturer, the polyA polyT tails are from 30 to 70 bases long.

Assembly of the Molecules and In Vitro Encapsidation

For the assembly of the molecules, one vector molecule is mixed per molecule of DNA inserted. The concentration of the DNA by mass is 500 $\mu g \cdot ml^{-1}$.

The mixture is encapsidated and the transfection efficacy depends on the strain used as recipient and the DNA inserted: zero with the test DNA and the strain DH5α, the efficacy is comparable for the SURE and DH10B strains; on extraction, the DNA yield is, however, higher with the strain DH10B.

Construction by Dephosphorylation

The soil DNA is rendered with blunt ends by removal of the protruding 3' sequences and filling in of the protruding 5' sequences. This operation is carried out with: Klenow enzyme, T4 polymerase, the 4 nucleotide triphosphates. The cosmid vector is digested with BamHI and then treated with the Klenow enzyme to make the ends blunt, then dephosphorylated to prevent it from closing up on itself. After ligation, the mixture is encapsidated and transfected as described previously.

3)—Use of pBACs

Principle

The conjugative and integrative plasmid pBAC contains the HindIII and NsiI sites as cloning sites. The insertion of a DNA sequence into these sites inactivates the lambda phage Cl repressor which controls the expression of the tetracycline-resistance gene. Inactivation of the repressor thus makes the cell resistant to this antibiotic (5 $\mu g \cdot ml^{-1}$). The cloning at these sites is facilitated by modifying the vector and preparing the DNA to be cloned.

Preparation of the Vector. HindIII Example

In order for the vector not to close up on itself, the Hind III site is modified: the first base (A) is reinserted to form a protruding 5' sequence, which cannot pair up with its partners. The operation is carried out with the Klenow enzyme in the presence of dATP.

The success of the operation is checked by carrying out a self-ligation of the vector before and after treatment with the Klenow enzyme. For an identical amount of test DNA, 3000 clones are obtained before treatment and 60 clones after treatment.

Preparation of the DNA (Size Between 100 and 300 kb)

Giving the DNA Blunt Ends

The DNA is given blunt ends by removing the protruding 3' sequences and filling in the protruding 5' sequences. This operation is carried out with: Klenow enzyme, T4 polymerase, the 4 nucleotide triphosphates.

Preparation of the Ends. HindIII Example

The addition of DNA to the vector is carried out by means of oligonucleotides which recognize the HindIII modified sequence of the vector. They contain rare restriction sites to allow the subsequent clonings (SwaI; NotI). This technique is derived from that of: Elledge S J, Mulligan J T, Ramer S W, Spottswood M, Davis R W. Proc. Natl. Acad. Sci. USA 1991 Mar. 1;88(5):1731-5

Two complementary oligonucleotides are used:

Oligo 1: 5'-GCTTATTTAAATATTAATGCGGCCGCCCGGG-3' (SEQ ID No 25)

Oligo 2: 5'-CCCGGGCGGCCGCATTAATATTTAAATA-3' (SEQ ID No 26)

They are phosphorylated at the 5' end with T4 polynucleotide kinase in the presence of ATP, after hybridization. This phosphorylation step can be eliminated by using the already-phosphorylated oligonucleotides. The ligation of this double-stranded adapter with the DNA to be inserted into a vector is carried out with T4 ligase in the presence of a very large excess of adapter (1000 adapter molecules per molecule of DNA to be inserted) over 15 hours at 14° C.

The excess adapter is removed by agarose gel electrophoresis and the molecules of interest are recovered from the gel by hydrolysing it with agarase or by electroelution.

Vector-DNA Ligation

The ligation is carried out at 14° C. over 15 hours with 10 molecules of vector per insert molecule.

Transformation

The recipient strain is the strain DH10B. The transformation is carried out by electroporation. To express the tetracycline resistance, the transformants are incubated at 37° C. for 1 hour in antibiotic-free medium. The clones are selected by culturing overnight on gelled LB medium supplemented with 5 μg·ml$^{-1}$ of tetracycline.

Example 11

Clone-to-Clone Conjugation Between *E. coli* and *Streptomyces*

Conjugation Between *E coli* Strain S17.1 Containing pPM803 and *Streptomyces lividans* TK 21

Introduction

It is possible to carry out conjugations between *E. coli* and *Streptomyces* (Mazodier et al, 1989). The adaptation of this method, by developing a so-called drop technique in which 10 μl of an *E. coli* culture containing a recombinant vector are mixed with one drop of recipient *S. lividans*, consists in carrying out a clone-to-clone transformation while ensuring that, at the end of the operation, all of the library constructed in *E. coli* is introduced into *S. lividans*. A bulk transformation would necessarily lead to a multiplication of the *Streptomyces* transformant clones in order to be sure in practice that the library in *E. coli* is fully represented in *S. lividans*. Furthermore, this method is easy to automate.

Preliminary Tests

Conjugation between *E. coli* strain S17.1 containing the vector pOSV303 and *S. lividans* TK21.

Under these conditions, 6×10$^6$ *E. coli* cells are mixed with 2×10$^6$ pre-germinated *S. lividans* spores in a final volume of 20 μl.

Development of the Method

It is known that the DNA extracted from certain actinomycetes is modified and, as a result, cannot be introduced into certain strains of *E. coli* without it being restricted. The *E. coli* strain DH10B which accepts these DNAs is not capable of transferring to *Streptomyces* a plasmid containing only oriT, and it is thus necessary to construct such a plasmid. A derivative of RP4 should be introduced therein by integration into the chromosome, this derivative being capable of trans-supplying all the functions required to ensure the transfer of the recombinant clones containing the transfer origin oriT.

Example 12

Construction of a Cosmid Library in *E. coli* and *Streptomyces lividans*: Cloning of the Soil DNA The object is to construct a library of large-sized environmental DNA, without a prior step of culturing the microorganisms, with the aim of gaining access to the metabolic genes of bacteria (or of any other organism) which it is not known how to culture under standard laboratory conditions.

The procedure described was used to generate a DNA library in *Escherichia coli* using the *E. coli-S. lividans* shuttle cosmid pOS700I and DNA extracted and purified from the bacterial fraction of a soil. This last method makes it possible to obtain DNA of high purity and with an average size of 40 kb. Also, in order to avoid a partial digestion of the extracted DNA in the cloning, an alternative strategy was adopted based on the use of the terminal transferase enzyme for adding polynucleotide tails to the 3' ends of the DNA and of the vector.

5 μg of DNA were extracted from 60 mg of "Saint-André coast" soil according to the protocol described in Example 3, and were treated with terminal transferase (Pharmacia) to extend the 3' ends with a monotonous polynucleotide (poly T) (Example 10).

The integrative cosmid pOS700I is prepared according to protocol B1, Orsay. After a standard step of purification in the presence of phenol/chloroform, the DNA and the vector are assembled by mixing one molecule of vector and one molecule of inserted DNA. The mixture is then encapsidated in the heads of lambda bacteriophages (Amersham kit) which serve to transfect *E. coli* DH10B. The cells transfected are then inoculated on LB agar medium in the presence of ampicillin for the selection of the recombinants resistant to this antibiotic.

A library of about 5000 ampicillin-resistant *E. coli* clones was obtained. Each clone was inoculated in LB or TB medium+ampicillin in a microplate well (96 wells) and stored at −80° C.

The sequence at the sites of insertion of the soil fragments into the vector, pOS700I, generated during the construction of the library was analysed. For this, 17 cosmids of the libraries were purified and sequenced with a primer, seq.5' CCGCGAATTCTCATGTTTGACCG 3', which hybridizes between the BamHI site and the HindIII cloning site present in the vector.

The sequences obtained made it possible to estimate that the length of the homopolymeric tails at the junction points is very variable, between 13 and 60 poly-dA/dT. Beyond the tails, the sequences of the soil fragments thus generated have a percentage of G+C of between 53 and 70%. Such high percentages were unexpected, but similar results have already been reported on crude preparations of soil DNA (Chatzinotas A. et al., 1998).

A strategy of "pooling" 48 or 96 clones was used to analyse the microbial and metabolic richness. The cosmid DNA extracted from these "pools" of clones was then used to carry out PCR or hybridization experiments.

Example 13

Diversity of the 16S Ribosomal DNA in the Cloned DNA a) Materials and Methods The cosmids of the library are extracted from pools of clones by alkaline lysis and are then purified on a caesium chloride gradient, in order to take up the band of cosmid DNA in supercoiled form and for the purpose of eliminating any *Escherichia coli* chromosomal DNA which might interfere in the study.

After linearization of the cosmids by the action of S1 nuclease, (50 units, 30 minutes at 37° C.), the 16S rDNA sequences contained in the pools of clones are amplified under the standard amplification conditions, using the universal primers 63f (5'-CAGGCCTAACACATGCAAGTC-3') and 1387r (5'-GGGCGGWGTGTACAAGGC-3') defined by Marchesi et al. (1998). The amplification products of about 1.5 kilobases are purified using the Qiaquik gel extraction kit (Qiagen) and then cloned directly into the vector pCR II (Invitrogen) in *Escherichia coli* TOP10, according to the manufacturer's instructions. The insert is then amplified using the primers M13 forward and M13 reverse specific for the cloning site of the vector pCR II. The amplification products of expected size (about 1.7 kb) are analysed by RFLP (Restriction Fragment Length Polymorphism) using the enzymes CfoI, MspI and BstUI (0.1 units) in order to select the clones to be sequenced. The restriction profiles obtained are separated on 2.5% Metaphore agarose gel (FMC Products) containing 0.4 mg of ethidium bromide per ml.

The 16S rDNA sequences are then determined directly using the PCR products purified with the "Qiaquick gel extraction" kit with the aid of the sequencing primers defined by Normand (1995). The phylogenetic analyses are obtained by comparing the sequences with the prokaryotic 16S rDNA sequences collated in the Ribosomal Database Project (RDP) database, version 7.0 (Maidak et al. (1999)) by means of the SIMILARITY MATCH program, which makes it possible to obtain the similarity values relative to the database sequences.

b) Results

To determine the phylogenetic diversity represented in the library, 47 sequences of the 16S rRNA gene were isolated from pools of 288 clones and were sequenced almost entirely. The results are given in Table 7.

Analysis of the sequences by interrogation of the databases reveals that most of the sequences (>61%) have percentages of similarity of less than or equal to 95% with identified bacterial species (Table 7). Out of the 47 sequences analysed, 28 sequences have non-cultured bacteria as closest neighbours, the sequences of which were obtained directly from DNA extracted from the environment. The majority of these sequences moreover have very low percentages of similarity (88-95%), 17 sequences out of 28 thus differing by more than 5% relative to their closest neighbours.

Among the sequences which can be classified in a phyletic group, a majority of sequences belong to the proteobacteria subclass a (18 sequences with a percentage of similarity of between 89 and 99%). A second group of sequences is represented by the proteobacteria subclass g, comprising 9 sequences whose percentages of, similarity range between 84 and 99%. The groups of b-proteobacteria and d-proteobacteria, which are Firmicutes with a low G+C % and a high G+C %, comprise 1, 4, 3 and 5 sequences, respectively. Only one sequence could not be classified among the major bacterial taxonomic groups defined: the sequence a22.1(19), its closest neighbour *Aerothermobacter marianas* (with a similarity of 89%) itself being a strain isolated from the marine environment and not classified at the current time. Finally, 6 sequences can be classified in the group of *Acidobacterium/Holophaga*. This group has the particular feature of being represented by only two cultured bacteria, *Acidobacterium capsulatum* and *Holophaga foetida*, this entire group being composed of bacteria for which only the 16S rRNA gene has been detected by amplification and cloning using DNA extracted from an environmental sample (mainly from soil) (Ludwig et al., (1997)). The low values of similarity between the different sequences composing this group makes it possible to predict great heterogeneity and diversity within this group.

The set of results is represented in Table 7.

These results show that the sequences contained in the cosmid library are thought to be derived from microorganisms that are not only phylogenetically diversified but above all from microorganisms which have never been isolated to date.

The results of the sequencing of the DNAs amplified allowed the establishment of a phylogenetic tree of the organisms present in the soil sample whose characterized sequences are novel.

The phylogenetic tree represented in FIG. 7 was produced from the alignment of the sequences by the MASE software (Faulner and Jurak, 1988) and corrected by the Kimura-2-parameter method (1980), and with the aid of the Neighbour Joining algorithm (Saitou and Nei, 1987). The phylogenetic analysis allowed comparison of the 16S rDNA sequences cloned in the soil DNA library, with sequences of prokaryotic 16S rDNA collated in the Ribosomal Database Project (RDP) databases (version 7.0, SIMILARITY-MATCH program, Maidak et al., 1999) and in the GenBank base by means of the BLAST 2.0 software (Atschul et al, 1997).

Example 14

Genetic Preselection of the Library to Evaluate the Metabolic Richness

To characterize the library obtained in terms of metabolic diversity and to identify the clones containing inserts carrying genes which may be involved in biosynthetic pathways, genetic screening techniques based on. PCR methods were developed according to the invention in order to detect and identify type I PKS genes.

1 Bacterial Strains, Plasmids and Culture Conditions

*S. coelicolor* ATCC101478, *S. ambofaciens* NRRL2420, *S. lactamandurans* ATCC27382, *S. rimosus* ATCC109610, *B. Subtilis* ATCC6633 and *B. licheniformis* THE1856 (collection RPR) were used as DNA sources for the PCR experiments. *S. lividans* TK24 is the host strain used for the shuttle cosmid POSI700.

For the preparation of genomic DNA, suspensions of spores and protoplasts and for the transformation of *S. lividans*, the standard protocols described in Hopwood et al. (1986) were followed.

*Escherichia coli* Top 10 (INVITROGEN) was used as host for the cloning of the PCR products and *E. coli* Sure (STRATAGENE) was used as host for the shuttle cosmid pOS700I. The *E. coli* culture conditions, the preparation of plasmids, the digestion of the DNA and the agarose gel electrophoresis were carried out according to the standard procedures (Sambrook et al., 1996).

2. PCR Primers:

The primer pairs a1-a2 and b1-b2 were defined by the team of N. Bamas-Jacques and their use was optimized for the screening of the DNA from the pure strains and of the soil library for the investigation of genes encoding PKSI.

TABLE 8

PCR primers that are homologous to the PKSI genes used for screening the library.

| | |
|---|---|
| a1 (+) | 5' CCSCAGSAGCGCSTSTTSCTSGA 3' |
| a2 (−) | 5' GTSCCSGTSCCGTGSGTSTCSA 3' |
| b1 | 5' CCSCAGSAGCGCSTSCTSCTSGA 3' |
| b2 | 5' GTSCCSGTSCCGTGSGCCTCSA 3' |

Amplification Conditions:

For the investigation of PKS I from the DNA of pure strains, the amplification mixture contained: in a final volume of 50 μl, between 50 and 150 ng of genomic DNA, 200 μM of dNTP, 5 mM of $MgCl_2$ final, 7% DMSO, 1× Appligene buffer, 0.4 μM of each primer and 2.5 U of Appligene Taq polymerase. The amplification conditions used are: denaturing at 95° C. for 2 minutes, hybridization at 65° C. for 1 minute, elongation at 72° C. for 1 minute, for the first cycle, followed by 30 cycles in which the temperature is reduced to 58° C., as described in K. Seow et al., 1997. The final extension step is carried out at 72° C. for 10 minutes.

For the investigation of PKS I from the DNA of the library, the PCR conditions are the same as above for the a1-a2 pair using between 100 and 500 ng of cosmid extracted from pools of 48 clones.

For the b1-b2 primer pair, 500 ng of cosmids derived from pools of 96 clones were used. The amplification mixture contained 200 μM of dNTP, 2.5 mM of $MgCl_2$ final, 7% DMSO, 1× Quiagen buffer, 0.4 μM of each primer and 2.5 U of hot-start Taq polymerase (Qiagen). The amplification conditions used are: denaturing for 15 minutes at 95° C. followed by 30 cycles: 1 minute of denaturing at 95° C.+1 minute of hybridization at 65° C. for the first cycle and 62° C. for the other cycles, 1 minute of elongation at 72° C., final extension step of 10 minutes at 72° C.

The identification of the positive clones from the pools of 48 or 96 clones is carried out using replicas of the corresponding parent microplates on solid medium or any other standard replication method.

3 Subcloning and Sequencing

The PCR products of the clones identified were sequenced according to the following protocol:

The fragments are purified on agarose gel (gel extraction kit (Qiagen)) and cloned into *E coli* TOP 10 (Invitrogen) using the TOPO TA cloning kit (Invitrogen). The plasmid DNA of subclones is extracted by alkaline lysis on a Biorobot (Qiagen) and dialysed for 2 h on a 0.025 μm VS membrane (Millipore). The samples are sequenced with the "universal" and "reverse" M13 primers on the ABI 377 96 sequencer (Perkin Elmer).

4) Results

Definition and Validation of the PCR Primers

Two highly conserved regions of actinomycetes type I PKS, comprising the active site of the enzyme, were targeted for the amplification of homologous genes with degenerate primers. These two regions correspond to the sequences PQQR(L)(L)LE and VE(A)HGTGT, respectively.

Primers (Table 8) were tested with the DNA of strains producing or not producing macrolides: *Streptomyces coelicolor*, *Streptomyces ambofaciens*, producing spiramycin, and *Saccharopolyspora erythraea*, producing erythromycin. Irrespective of the primers used, bands representing fragments of about 700 pb and corresponding to the length of the expected fragment were obtained with all the strains.

These results demonstrate the specificity of the primers a and b for the PKS I genes of productive strains or of silent genes in *S. coelicolor*.

The sequencing of the PCR products obtained with the a1-a2 primer pair made it possible to identify, from the *S. ambofaciens* strain, the sequence of a KS gene already described (European patent application No. EP 0 791 656) as belonging to the pathway for the biosynthesis of plantenolide, a macrolide precursor of spiramycin, and two sequences never described, Stramb 9 and Stramb 12 (see sequence listing).

As regards *S. erythraea*, the screening method allowed the identification of a sequence of KS (sacery17) which is identical to that of the KS of module 1 already published in Genebank (Access number M63677), encoding synthetase 1 (DEBS1) of 6-deoxyerythronolide B. Another sequence not correlated to the erythromycin biosynthetic pathway was identified and is the sequence SEQ ID No 32.

Conclusion

A method for analysing the presence of genes encoding type I PKSs by PCR from different microorganisms has been developed. The highly conserved structure of the type I keto-synthetase domain made it possible to produce a PCR method based on the use of GC-biased degenerate primers for the choice of the codons.

This approach shows the possibility of identifying genes or clusters involved in the biosynthetic pathway of type I polyketides. The cloning of these genes allows the creation of a collection which may then be used to construct polyketide hybrids. The same principle can be applied to other classes of antibiotics.

The results obtained here also show the presence of genes which may belong to silent clusters (SEQ ID No 30 to 32).

The presence of silent clusters has already been documented in *S. lividans* and their expressions are triggered by specific or pleiotropic regulators (Horinouchi et al.; Umeyama et al. 1996). These results suggest that the detection of genes belonging to so-called silent pathways in reality encode active enzymes capable of directing, in combination with the other specific enzymes of the pathway, the enzymatic steps required for the synthesis of the secondary metabolites.

Screening of the Library

The screening was carried out under the conditions described in the Materials and Methods section using the primer pairs validated from productive strains.

In the presence of the a1-a2 primer pair, the size of the PCR products obtained from cosmid DNA extracted from pools of 48 or 96 clones was about 700 bp, which is thus in agreement with the expected results.

The intensity of the bands obtained was variable, but only one amplification band was present for each pool of target DNA.

Under these conditions, 8 groups of target DNA were detected, corresponding to 9 positive clones after dereplication.

The screening carried out with the second primer pair, b1-b2, gave less specific amplification results since many satellite bands were observed alongside the 700 bp band. Nevertheless, 9 groups of target DNA were detected, corresponding to 14 positive clones after dereplication starting with these positive clones, and the DNA was extracted for the steps of sequencing and transformation of *S. lividans*.

Analysis of the Cosmids

Figure 22:
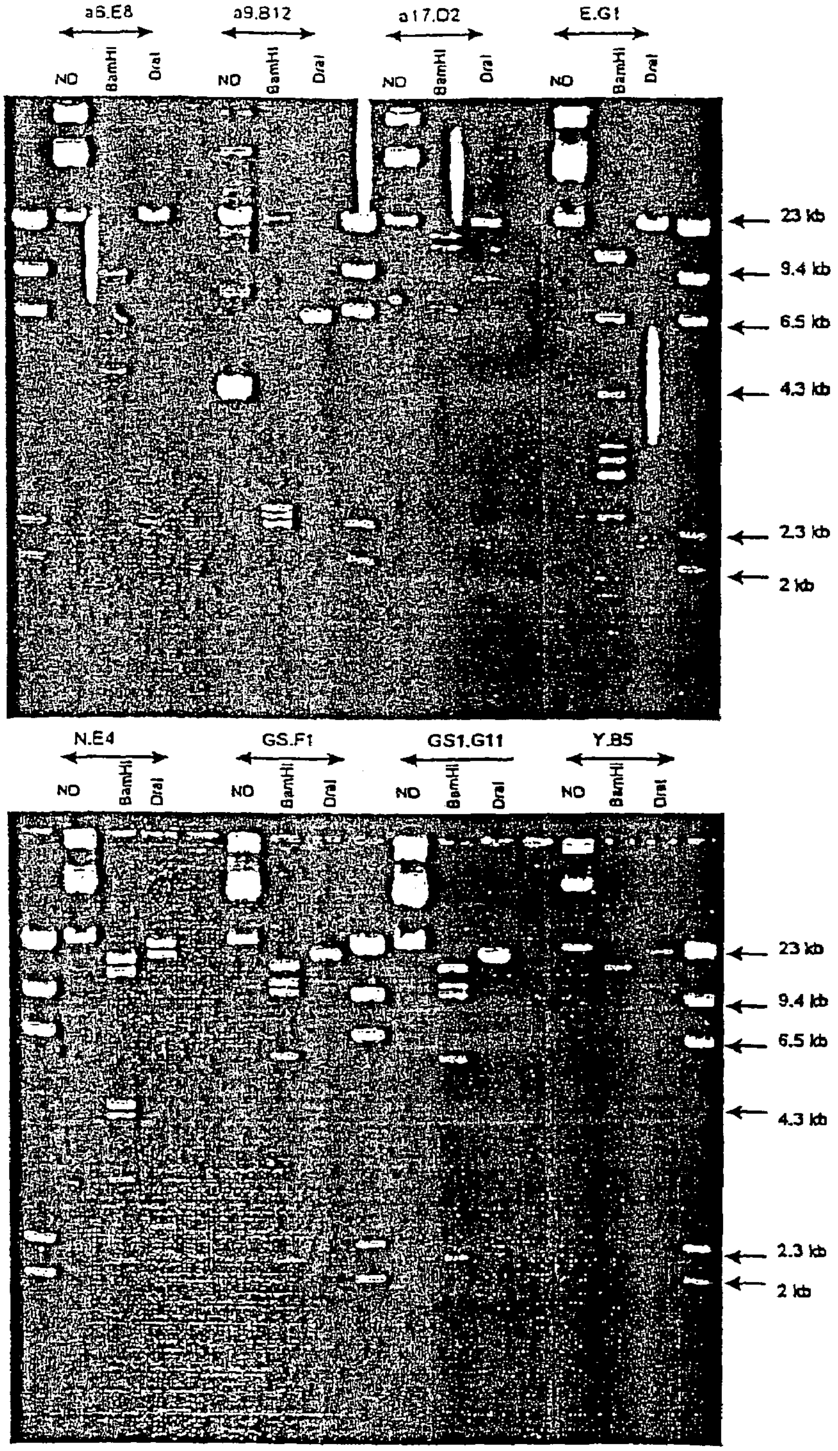
FIG. 22 represents the electrophoresis gels for DNA of the library after digestion with the enzymes BamHI and DraI of the positive clones of the library screened with the PKS-I oligonucleotides.

Digestion of the cosmids identified by PCR with the enzyme DraI, which recognizes an AT-rich site, frees a fragment greater than 23 kb (FIG. 22). This suggests that the PCR method preferentially targets soil DNA containing a high percentage of G+C. This result is the consequence of the degeneracy of the primers used, which are GC-biased, for the choice of the codons. The inserts, as expected in the case of cosmids, are larger than 23 kb in size, except in one case (clone a9B12), which might reflect a certain level of instability of the cosmids. Moreover, among all the clones selected, only two of them, GS.F1 and GS.G11, showed the same restriction profile, indicating a low level of redundancy in the library.

The cosmids selected were transferred into *Streptomyces lividans* by transformation of protoplasts in the presence of PEG 1000. The transformation efficacy ranges between 30 and 1000 transformants per μg of cosmid DNA used.

Sequencing and Phylogenetic Analysis of the Soil PKS I Genes

The PCR method developed on the pure strains was used as described on the cosmids of the library and 24 clones were thus identified.

The PCR products of about 700 bp obtained from the DNA of two pools (48 clones) and of 8 unique clones, were cloned, after purification on agarose gel, and sequenced. This allowed the identification of 11 sequences.

The alignment of the deduced protein sequences of soil PKSs I with other PKSs I present in different microorganisms (FIG. 24) shows the presence of a highly conserved region which corresponds to the consensus region of the active site of β-ketoacyl synthetase.

Analysis of the sequences obtained with the "codon preference" method (Gribskov et al., 1984; Bibb et al., 1984) revealed the presence of a strong bias in the use of codons rich in G+C in a single reading frame. The proteins deduced according to this reading frame show strong similarity with known type I KSs (Blast program). In particular, the similarity between the sequences of KSs from the soil and of KSs of the erythromycin cluster is about 53%.

After dereplication of a pool and identification of the unique clone, the sequence of the PCR product obtained from this clone is identical to that of the pool, which confirms the reliability of the method used.

Analysis of the sequence of the PCR product of a clone allowed the probable identification of 3 different KSI genes. One of these sequences (SEQ ID No 34) has a similarity of 98.7% with the sequence of another pool, suggesting that they encode the same enzyme. The other two sequences are different but strongly homologous.

The cloning and identification in a soil DNA library of pathways for the biosynthesis of secondary metabolites containing genes encoding type I KSs is described here for the first time.

The high percentage of G+C in the soil sequences suggests that they may derive from genomes having a codon use similar to that of actinomycetes.

Although the data available in the literature is limited, it is known that the genes encoding type I PKSs are highly diversified on account of their physical organization in the genome, size and the number of modules contained in each gene.

The presence of several domains originating from a single clone is confirmation that they belong to asymmetric polyketide clusters. In a single case, two clones appear to form a contiguum since they share the same sequence for the KS domain.

The size of the genetic regions involved in PKSI synthesis ranges between a few kb for penicillin to about 120 kb for rapamycin. The size of the cosmid inserts may thus not be sufficient for the expression of the most complex clusters.

Genes encoding PKSs I, capable of working iteratively like the PKSs II and of controlling the synthesis of aromatic polyketides, have been described (Jae-Hyuk et al., 1995). The study of soil PKS I clusters may provide further novelties in this field.

5. Identification of 6 Genes Encoding Polyketide Synthases

On continuing the screening of the cosmid library according to the protocols described in the present example, the inventors identified a cosmid clone containing a 34071-bp insertion containing several open reading frames encoding polypeptides of the polyketide synthase type.

More specifically, the cosmid thus identified by screening the library contains six open reading frames encoding polyketide synthase polypeptides or very closely related polypeptides, non-ribosomal synthase peptides. A detailed map of this cosmid is represented in FIG. 36.

The complete nucleotide sequence of the cosmid constitutes the sequence SEQ ID No. 113 of the sequence listing. The DNA insertion contained in the sequence SEQ ID No. 113 constitutes the complementary nucleotide sequence (−strand) of the nucleotide sequence encoding the various polyketide synthases.

The nucleotide sequence of the DNA insertion contained in the cosmid in FIG. 36 which comprises the open reading frames encoding the polyketide synthase polypeptides (+strand) is represented schematically in FIG. 37 and constitutes the sequence SEQ ID No. 114 of the sequence listing.

Furthermore, a detailed map of the various open reading frames contained in the DNA insertion of this cosmid is represented in FIG. 37.

The characteristics of the nucleotide sequences comprising open reading frames contained in the DNA insertion of this cosmid are detailed below.

ORF1 Sequence

The orf1 sequence comprises a partial open reading frame 4615 nucleotides long. This sequence constitutes the sequence SEQ ID No. 115, which starts at the nucleotide in position 1 and ends at the nucleotide in position 4615 of the sequence SEQ ID No. 114.

The sequence SEQ ID No. 115 encodes the 1537-amino acid ORF1 polypeptide, this polypeptide constituting the sequence SEQ ID No. 121.

The polypeptide of sequence SEQ ID No. 121 is related to the non-ribosomal synthase peptides. This polypeptide has a degree of amino acid identity of 37% with the synthase peptide of *Anabaena* sp.90 referenced under the access number "emb CACO1604.1" in the Genbank database.

ORF2 Sequence

The orf2 nucleotide sequence is 8301 nucleotides long and constitutes the sequence SEQ ID No. 116, which starts at the nucleotide in position 4633 and ends at the nucleotide in position 12933 of the sequence SEQ ID No. 114.

The ORF2 sequence encodes the 2766-amino acid ORF2 peptide, this polypeptide constituting the sequence SEQ ID No. 122.

The polypeptide of sequence SEQ ID No. 122 has an amino acid sequence identity of 41% with the MtaD sequence of *Stigmatella aurantiaca* referenced under the access number "gb AAF 19812.1" from the Genbank database.

The ORF2 polypeptide constitutes a polyketide synthase.

ORF3 Sequence

The orf3 nucleotide sequence is 5292 nucleotides long and constitutes the sequence SEQ ID No. 117. The sequence SEQ ID No. 117 corresponds to the sequence which starts at the nucleotide in position 12936 and which ends at the nucleotide in position 18227 of the sequence SEQ ID No. 114.

The nucleotide sequence SEQ ID No. 117 encodes the 1763-amino acid ORF3 polyketide synthase polypeptide, this polypeptide constituting the sequence SEQ ID No. 123 according to the invention.

The ORF3 polypeptide of sequence SEQ ID No. 123 has an amino acid identity of 42% with the MtaB sequence of *Stigmatella aurantiaca* referenced under the access number "gb AAF 19810.1" from the Genbank database.

ORF4 Sequence

The orf4 nucleotide sequence is 6462 nucleotides long and constitutes the sequence SEQ ID No. 118 according to the invention.

The nucleotide sequence SEQ ID No. 118 corresponds to the sequence starting at the nucleotide in position 18224 and ending at the nucleotide in position 24685 of the nucleotide sequence SEQ ID No. 114.

The nucleotide sequence SEQ ID No. 118 encodes the 2153-amino acid ORF4 polyketide synthase polypeptide, this polypeptide constituting the sequence SEQ ID No. 124 according to the invention.

The ORF4 polypeptide of sequence SEQ ID No. 124 has an amino acid sequence identity of 46% with the epoD sequence of *Sorangium cellulosum* referenced under the access number "gb AAF62883.1" of the Genbank database.

ORF5 Sequence

The orf5 nucleotide sequence is 5088 nucleotides long and constitutes the sequence SEQ ID No. 119 according to the invention.

The sequence SEQ ID No. 119 corresponds to the sequence starting at the nucleotide in position 24682 and ending at the nucleotide in position 29769 of the nucleotide sequence SEQ ID No. 114.

The nucleotide sequence SEQ ID No. 119 encodes the 1695-amino acid ORF5 polyketide synthase polypeptide, this polypeptide constituting the sequence SEQ ID No. 125 according to the invention.

The ORF5 polyketide synthase polypeptide of sequence SEQ ID No. 125 has an amino acid identity of 43% with the epod sequence of *Sorangium cellulosium* referenced under the access number "gb AAF 62883.1" of the Genbank database.

ORF6 Sequence

The orf6 nucleotide sequence is 4306 nucleotides long and constitutes the sequence SEQ ID No. 120 according to the invention. The nucleotide sequence SEQ ID No. 120 corresponds to the sequence starting at the nucleotide in position 29766 and ending at the nucleotide in position 34071 of the sequence SEQ ID No. 114.

The sequence SEQ ID No. 120 contains a partial open reading frame encoding the 1434-amino acid ORF6 polypeptide of the polyketide synthase type, this polypeptide constituting the sequence SEQ ID No. 126 according to the invention.

The polypeptide of sequence SEQ ID No. 126 has an amino acid identity of 43% with the epoD sequence of *Sorangium cellulosum* referenced under the access number "gb AAF 62883.1" of the Genbank database.

Example 15

Construction of Shuttle Vectors of Integrative BAC Type in *Streptomyces*

Construction of Shuttle Vectors of the Integrative and Conjugative BAC Type in *Streptomyces*

15.1 Construction of the Vector pMBD-1

The vector BAC pMBD-1 was obtained according to the following steps:

Step 1: The vector pOSVO10 was subjected to a digestion with the enzymes PsTI and BstZ171 in order to obtain a 6.3-kb nucleotide fragment.

Step 2: The vector pDNR-1 was digested with the enzymes PstI and PvuII in order to obtain a 4 145-kb nucleotide fragment.

Step 3: The 6.3-kb nucleotide fragment derived from the vector pOSV017 was fused by ligation with the 4.15-kb fragment derived from the vector pDNR-1, so as to produce the vector pMBD-1, as illustrated in FIG. 30.

15.2 Construction of the Vector pMBD-2

The vector pMBD-2 is a vector of the BAC type containing an "ϕc31 int-Ωhyg" integrative box.

ϕc31 is a broad host spectrum temperate phage whose site of attachment (attp) is well localized. The ϕc31 int fragment is the minimum fragment of the actinophage ϕc31 capable of inducing the integration of a plasmid into the chromosome of *Streptomyces Lividans*.

Ωhyg is a derivative of the Ω interposon capable of conferring hygromycin resistance in *E. coli* and *S. Lividans*.

BAC vectors containing the ϕc31 integration system are described by Sosio et al. (2000) and in PCT patent application. No. 99/6734 published on 29 Dec. 1999.

The vector BAC pmBD-2 was constructed according to the following steps:

Step 1: Construction of a ϕc31int Ωhyg integrative box in an *E. coli* multicopy plasmid.

The ϕc31int fragment was first amplified from the plasmid pOJ436 using the following pair of primers:

- The primer EVϕc31I (SEQ ID No.109) (which allows the introduction of an EcoRV site into the 5' end of the ϕc31 sequence) and the primer BIIϕc31F (SEQ ID No. 110) (which allows the introduction of a BgLII site into the 3' end of the ϕc31 sequence).

The Ωhyg fragment was obtained by digestion using the BamHI enzyme of the plasmid pHP45 Ωhyg described by Blondelet-Rouault (1997).

Next, the ϕc31 int-Ωhyg integrative box was cloned into the vector pMCS5 digested with the enzymes BglII and EcoRV.

Step 2: Construction of the Vector pMBD-2

The bacterial artificial chromosome pBAce3.6 described by Frengen et al. (1999) was digested with the enzyme NheI and then treated with the enzyme Eco polymerase.

Next, the vector pMCS5 ϕc31 int-Ωhyg was digested with the enzymes SnaBI and EcoRV so as to recover the integrative box.

The detailed map of the vector pMBD2 is represented in FIG. 31.

15.3 Construction of the Vector pMBD-3

The vector pMBD-3 is an integrative (ϕc31 int) and conjugative (OriT) vector of the BAC type, which comprises the selection marker Ωhyg.

The map of the vector pMBD-3 and also the method for constructing it are illustrated in FIG. 31.

The vector pMBD-3 was obtained by amplifying the OriT gene starting with the plasmid pOJ436 using the pair of primers of sequences SEQ ID No. 111 and SEQ ID No. 112 which contain pad restriction sites.

The nucleotide fragment amplified using the primers SEQ ID No. 111 and SEQ ID No. 112 was cloned into the vector pMBD2 predigested with the PacI enzyme. The scheme for constructing the vector pMBD-3 is illustrated in FIG. 31.

15.4 Construction of the Vector pMBD-4

The detailed map of the vector pMBD-4 is represented in FIG. 32.

The vector pMBD-4 was obtained by cloning the ϕc31 int-Ωhyg integrative box into the vector pCYTAC2.

15.5 Construction of the Vector pMBD-5

The scheme for constructing the vector pMBD-5 is illustrated in FIG. 33.

The vector pMBD-5 was constructed by recombination of the nucleotide fragment included between the two loxP sites of the vector pMBD-1 illustrated in FIG. 33 with the loxp site contained in the BAC vector designated pBTP3, a detailed map of the plasmid pBTP3 being represented in FIG. 34.

15.6 Construction of the Vector pMBD-6

The vector pMBD-6 was constructed by recombining the nucleotide fragment included between the two loxP sites of the vector pMBD-1 into the loxP site of the BAC pBeloBac11 vector, as represented in FIG. 35.

TABLE 1

Location of the sampling sites and characteristics of the soils used in the various experiments. The direct microbial counts using staining with acridine orange were carried out before and after grinding the soil.

| Number | Origin | Texture | Amount (%) of sand | loam | clay | Organic matter (g/kg of dry soil | pH | Number of cells before grinding[a] ($\times 10^9$/g dry weight of soil) | Number of cells after grinding[a] ($\times 10^9$/g dry weight of soil) |
|---|---|---|---|---|---|---|---|---|---|
| 1 | Australia | Sandy clay | 62 | 22 | 6 | 49.7 | 5.8 | 6.5 (0.9) | 2.9 (1.3) |
| 2 | Peyrat le Château, France | Sandy clay | 61 | 26 | 13 | 48.2 | 4.9 | 7.3 (0.6) | 5.4 (0.8) |
| 3 | St-André coast, France | Sandy compost | 50 | 41 | 9 | 40.6 | 5.6 | 10.0 (0.7) | 7.5 (1.4) |
| 4 | Chazay d'Azergue, France | Clayey sandy compost | 34 | 47 | 19 | 13.9 | 5.8 | 7.8 (1.1) | 4.2 (0.6) |
| 5 | Guadeloupe, France | Clay | 27 | 26 | 47 | 17.0 | 4.8 | 1.4 (0.4) | 0.5 (0.1) |
| 6 | Dombes, France | Clayey sandy compost | 20 | 67 | 13 | 30.3 | 4.3 | 7.5 (0.5) | 5.6 (0.9) |

[a]n = 3; standard deviation in parentheses

TABLE 2

Primers and probes used for the PCR amplification and the dot-blot hybridization

| Primer or probe | Target[a)] | Sequence (5' to 3') | Reference No. |
|---|---|---|---|
| FGPS431 probe | Universelle (1392-1406) | ACGGGCGGTGTGT(A/G)C | Amann et al., 1995 |
| FGPS122 primer | Bactéries (6-27) | GGAGAGTTTGATCATGGCTCAG | Amann et al., 1995 |
| FGPS350 primer | *Streptosporangium* (616-635) | CCTGGAGTTAAGCCCCCAAGC | This study |
| FGPS643 probe | *Streptosporangium* (122-142) | GTGAGTAACCTGCCCC(T/C)GACT | This study |
| R499 primer | *Bacillus anthracis* | TTAATTCACTTGCAACTGATGGG | Patra et al., 1996 |
| R500 primer | *Bacillus anthracis* | AACGATAGCTCCTACATTTGGAG | Patra et al., 1996 |
| C501 probe | *Bacillus anthracis* | TTGCTGATACGGTATAGAACCTGGC | Patra et al., 1996 |
| FGPS516 primer | *S. lividans* 0S48.3 | TCCAGATCCTTGACCCGCAG | This study |
| FGPS517 primer | *S. lividans* 0S48.3 | CACGACATTGCACTCCACCG | This study |
| FGPS518 probe | *S. lividans* 0s48.3 | CCGTGAGCCGGATCAG | This study |

[a)]The positions on the *E. coli* 16S rRNA gene are given in parentheses. For *B. anthracis* and *S. lividans*, the primers and probes target chromosomal sequences specific for the respective organisms. These sequences are not located in the 16S rRNA gene. The cassette containing the target region of *S. lividans* is described by Clerc-Bardin et al. (unpublished).

TABLE 3

Amount of DNA extracted from different soils after lysis treatments according to protocols 1 to 5 (μg ADN/g of weight of dry soil ± standard deviation)[a] Soils 1, 2, 3 and 6; n = 3; soil 4: n = 1.

| Soil | Lysis protocol number[b] | | | | | | |
|---|---|---|---|---|---|---|---|
| Number and origin | 1 | 2 | 3 | 4a | 4b | 5a | 5b |
| 1. Australia | 17 +/− 2 | 52 +/− 2 | 32 +/− 5 | 16 +/− 3 | 33 +/− 2 | 59 +/− 1 | 27 +/− 0 |
| 2. Peyrat | 29 +/− 2 | 58 +/− 1 | 40 +/− 2 | 29 +/− 2 | 18 +/3 | 56 +/− 1 | 15 +/− 1 |
| 3. St-André coast | 36 +/− 7 | 60 +/− 6 | 148 +/− 10 | 94 +/− 7 | 38 +/− 6 | 73 +/− 5 | 47 +/− 6 |
| 4. Chazay | 9 | 16 | ND | 32 | 15 | 15 | 70 |
| 6. Dombes | 4 +/− 2 | 26 +/− 3 | 43 +/− 1 | 61 +/− | 66 +/− 1 | 160 +/− 7 | 102 +/− 5 |

[a]Quantification by phosphorescence imaging after dot-blot hybridization with the universal probe FGPS431 (Table 2).

[b]1: no treatment; 2: dry-grinding of the soil (G); 3: Cr + Ultra-turrax homogenization (H); 4a: G + H + Microtip sonication (MT); 4b: G + H + Cup Horn sonications (CH); 5a: Cr + H + NT + chemical/enzymatic lysis.

See also FIG. 1.

[c]ND = not determined.

TABLE 4

Primers and probes used in the molecular characterization of the DNAs extracted from the soil

| | Target (primer or probe) | Sequence (5' - 3') | Position[a] |
|---|---|---|---|
| FGPS 612 | Eubacteria (primer) | C(C/T)AACT(T/C/A)CGTGCCAGCAGCC | 506-525 |
| FGPS 669 | Eubacteria (primer) | GACGTC(A/G)TCCCC(A/C)CCTTCCTC | 1174-1194 |
| FGPS 618 | Eubacteria (probe) | ATGG(T/C)TGTCGTCAGCTCG | 1056-1073 |
| FGPS 614 | a-Proteobacteria (probe) | GTGTAGAGGTGAAATTCGTAG | 683-703 |
| FGPS 615 | b-Proteobacteria (probe) | CGGTGGATGATGTGGATT | 939-956 |
| FGPS 616 | g-Proteobacteria (probe) | AGGTTAAAACTCAAATGA | 900-917 |
| FGPS 621 | Gram+ with low GC % (probe) | ATACGTAGGTGGCAAGCG | 532-549 |
| FGPS 617 | *Actinomycetes* (probe) | GCCGGGGTCAACTCGGAGG | 1159-1149 |
| FGPS 680 | *Streptomycetes* (probe) | TGAGTCCCCA(A/C/T)C(T/A)CCCCG | 1132-1149 |
| FGPS 619 | *Streptosporangium* (probe) | GCTTGGGGCTTAACTCCAGG | 609-628 |

[a]position on the *Escherichia coli* 16S rRNA gene

TABLE 5

Extraction efficacies of the bacterial cells on a Nycodenz gradient and amounts of DNA extracted. Effect of incubating the soil sample in a 6% yeast extract solution, prior to the dispersion and centrifugation on a density gradient.

| | Bacteria extracted Total microflora[a] bacteria/g dry soil | DNA extracted Culturable microflora[b] cfu/g dry soil | Culturable *actinomycetes*[c] cfu/g dry soil | Direct lysis[d] ng DNA/g dry soil | Lysis on agarose block[d,e] ng DNA/g dry soil |
|---|---|---|---|---|---|
| Without incubation | | | | | |
| Soil suspension | $1.3 \times 10^9$ (±0.1) | $6.9 \times 10^6$ (±0.2) | $8.6 \times 10^6$ (±1.2) | | |
| Cell extract | $1.9 \times 10^8$ (±0.2) | $4.1 \times 10^6$ (±1.5) | $2.5 \times 10^6$ (±0.7) | 333 (±35) | 221 (±70) |
| Extraction efficacy | 15% | 59% | 38% | | |
| With incubation in 6% yeast extract | | | | | |
| Soil suspension | $1.2 \times 10^9$ (±0.1) | $7.6 \times 10^7$ (±1.1) | $6.6 \times 10^7$ (±0.4) | | |
| Cell extract | $1.6 \times 10^8$ (±0.3) | $5.3 \times 10^6$ (±1.4) | $3.7 \times 10^6$ (±0.7) | 344 (±30) | 341 (±67) |
| Extraction efficacy | 13% | 7% | 5% | | |

[a]Counting by microscope after staining with acridine orange
[b]Counting on 10% Trypcase-Soja solid medium
[c]Counting on HV Agar solid medium, after enrichment for 20 minutes at 40° C. in a solution of 6% yeast extract - 0.05% SDS
[d]The amount of DNA extracted was evaluated on electrophoresis gel relative to a calibration range of calf thymus DNA.
[e]The quantification was carried out after digesting the agarose by the action of a β-agarase.

TABLE 6

Characterization of the DNAs extracted as a function of proteobacteria subclases a, b and g in Gram+ with low GC % and actinomycetes; the hybridization signal with the prokaryotic probe serving as 100% reference.

| | a-Proteobacteria | b-Proteobacteria | g-Proteobacteria | Gram+ low GC % | Actinomycetes | Streptomycetes |
|---|---|---|---|---|---|---|
| Direct extraction[a] | 7.7% (±1.4) | 5.3% (±0.5) | 3.3% (±0.9) | 3.1% (±1.7) | 14.7% (±0.6) | 0.8% (±0.1) |
| Indirect extraction | | | | | | |
| Lysis + CsCl | 10.9% (±1.4) | 6.4% (±1.4) | 14.3% (±1.4) | 7.9% (±1.4) | 8.5% (±1.4) | 3.0% (±1.4) |
| Block lysis | 2.9% (±1.4) | 5.4% (±1.4) | 11.1% (±1.4) | 8.0% (±1.4) | 11.3% (±1.4) | 2.6% (±1.4) |
| Block lysis + YE incubation | 6.3% (±1.4) | 7.5% (±1.4) | 17.0% (±1.4) | 18.1% (±1.4) | 19.4% (±1.4) | 4.6% (±1.4) |

[a]grinding in a centrifugal-force tungsten bead grinder (extraction protocol described in the article by Frostegard et al.)
YE: 6% yeast extract solution

TABLE 7

Diversity of the 16S rDNA sequences contained in the cosmid library

| Pool No. (clone No.) | Closest neighbour identified | % of similarity | Closest neighbour (classification, reference) | % of similarity |
|---|---|---|---|---|
| α-Proteobacteria | | | | |
| a24.1 (2) | *Azospirillum brasilense* | 97.7% | | |
| a4-a6-a7 (7) | *Azospirillum brasilense* | 95.4% | | |
| a4-a6-a7 (23) | *Azospirillum brasilense* | 88.9% | Str L-87 (a-proteobacteria)[1] | 89.8% |
| a52-a53-a5 (15) | *Azospirillum lipoferum* | 97.6% | | |
| a49-a50-a51 (22) | *Agrobacterium tumefaciens* | 95.0% | Clone JN15d (unpublished) | 95.5% |
| a49-a50-a51 (11) | *Rhizobium* sp | 99.7% | | |
| a4-a6-a7 (14) | *Rhizobium* sp | 99.7% | | |
| a30-a31-a32 (7) | *Bradyrhizobium japonicum* | 99.4% | | |
| a19-a20-a26 (5) | *Bradyrhizobium genosp* | 93.3% | Clone DA122 (unpublished) | 95.9% |
| a37-a38-a39 (6) | *Mesorhizobium* sp. | 98.9% | | |
| a19-a20-a26 (9) | *Bradyrhizobium* sp | 90.2% | Clone S-26 (a-proteobacteria)[2] | 95.9% |
| a46-a47-a48 (14) | *Phyllobacterium rubiacearum* | 97.6% | | |
| a49-a50-a51 (1) | *Caulobacter henricii* | 97.0% | | |
| a1-a2-a3 (13) | *Caulobacter* sp. | 96.3% | | |
| a52-a53-a5 (8) | *Mesorhyzobium mediterraneum* | 92.1% | Clone DA122 (unpublished) | 94.8% |
| a34-a35-a36 (3) | *Rhodobium orientis* | 91.8% | Clone (unpublished) | 95.1% |
| a1-a2-a3 (4) | *Sphingomonas* sp. | 94.7% | Clone PAD23 (unpublished) | 95.1% |
| a8-a9-a10 (13) | *Sphingomonas* sp. | 94.0% | | |
| γ-Proteobacteria | | | | |
| a40-a41-a42 (13) | *Pseudomonas* sp | 98.9% | clone G26 (g-proteobacteria)[3] | 99.7% |
| a15-a16-a17 (12) | *Lysobacter antibioticus* | 94.4% | clone vadin HA77 (g-Proteo)[4] | 93.6% |
| a15-a16-a17 (5) | *Xanthomonas* sp | 93.4% | clone vadin HA77 (g-Proteo)[4] | 94.6% |
| a19-a20-a26 (13) | *Luteimonas mephitis* | 92.9% | Strain rJ15 (unpublished) | 93.5% |
| a46-a47-a48 (6) | *Methylobacter whittenburyi* | 88.3% | soil clone S-43 (g-Proteo)[2] | 88.9% |
| a11-a12-a13 (11) | *Methylobacter whittenburyi* | 88.3% | soil clone S-43 (g-Proteo)[2] | 88.9% |
| a34-a35-a36 (5) | *Methylococcus capsulatus* | 84.9% | soil clone S-12 (d-Proteo)[2] | 85.6% |
| a43-a44-a45 (10) | *Legionella birminghamensis* | 88.9% | | |
| A8-a9-a10 (2) | *Lamprocystis roseopersicina* | 87.5% | Clone 2-100C14 (unpublished) | 95.1% |
| β-Proteobacteria | | | | |
| a27-a28-a29 (5) | *Rhodocyclus tenuis* | 90.2% | Clone OPB37 (b-proteo)[5] | 91% |
| δ-Proteobacteria | | | | |
| a8-a9-a10 (18) | *Nannocystis exedens* | 92.0% | | |
| a11-a12-a13 (5) | *Geobacter sulfurreducens* | 91.5% | | |
| a27-a28-a29 (8) | *Desulfoacinum infernum* | 88.4% | Clone S-31 (d-Proteo)[2] | 89.1% |
| a40-a41-a42 (6) | *Desulfivibrio aminophilus* | 85.3% | Clone S-34 (d-Proteo)[2] | 86.2% |
| G+ with low GC % | | | | |
| a23.1 | *Kurthia zopfii* | 97.3% | | |
| a25.1 | *Kurthia zopfii* | 97.2% | | |
| a18.1 (22) | *Kurthia gipsonii* | 94.4% | G+ low GC % not identified RS19 (unpublished) | 94.8% |
| *Actinomycetes* | | | | |
| a33.1 | *Cellulomonas* sp | 99.5% | | |
| a14.7 | *Streptosporangium longisporum* | 99.8% | | |
| a21.7 | *Arthrobacter polychromogenes* | 99.2% | | |
| a8-a9-a10 (7) | *Arthrobacter oxydans* | 98.3% | *actinomycete* not identified RSW1 (unpublished) | 98.5% |
| a27-a28-a29 (3) | *Arthrobacter oxydans* | 98.9% | *actinomycete* not identified RSW1 (unpublished) | 99.3% |
| *Acidobacterium*? | | | | |
| a43-a44-a45 (4) | *Holophaga foetida* | 87.3% | Clone 32-10 (*Acidobacterium phylum*)[6] | 95.0% |
| a27-a28-a29 (12) | *Desulfuromonas acetexigens* | 88.8% | Clone Sva0515 (*Acidobacterium phylum*)[6] | 91.0% |
| a37-a38-a39 (12) | *Desulfuromonas palmitatis* | 90.3% | Clone Sva0515 (*Acidobacterium phylum*)[6] | 91.5% |
| a37-a38-a39 (14) | *Halothermothrix orenii* | 87.5% | Clone ii3-7 (*Acidobacterium phylum*)[6] | 93.3% |
| a8-a9-a10 (9) | *Pelobacter carbinolicus* | 86.5% | Clone ii3-15 (*Acidobacterium phylum*)[6] | 92.6% |
| a34-a35-a36 (10) | *Nitrococcus mobilis* | 90.6% | Clone RB43 (*Acidobacterium phylum*)[6] | 93.7% |

TABLE 7-continued

Diversity of the 16S rDNA sequences contained in the cosmid library

| Pool No. (clone No.) | Closest neighbour identified | % of similarity | Closest neighbour (classification, reference) | % of similarity |
|---|---|---|---|---|
| Not classified | | | | |
| a22.1 (19) | *Aerothermobacter marianas* | 89.1% | Eubacteria not identified (unpublished) | 93.4% |

[1]GONZALEZ et al. (1996)
[2]Zhou et al. (1997)
[3]Pederson et al. (1996)
[4]Godon et al. (1997)
[5]Hugenholtz et al. (1998)
[6]Ludwig (1997)

TABLE 9

Sequences

| Name | SEQ ID No. |
|---|---|
| Probes and primers | |
| FGPS431 | 1 |
| FGPS122 | 2 |
| FGPS350 | 3 |
| FGPS643 (T) | 4 |
| FGPS643 (C) | 5 |
| R499 | 6 |
| R500 | 7 |
| C501 | 8 |
| FGPS516 | 9 |
| FGPS517 | 10 |
| FGPS518 | 11 |
| FGPS612 | 12 |
| FGPS669 | 13 |
| FGPS618 | 14 |
| FGPS614 | 15 |
| FGPS615 | 16 |
| FGPS616 | 17 |
| FGPS621 | 18 |
| FGPS617 | 19 |
| FGPS680 | 20 |
| FGPS619 | 21 |
| 63f | 22 |
| 1387r | 23 |
| Oligo-1 (Example 10) | 24 |
| Oligo-2 (Example 10) | 25 |
| A1 | 26 |
| A2 | 27 |
| B1 | 28 |
| B2 | 29 |
| PKS-I nucleic acids | |
| Amb9 | 30 |
| Amb12 | 31 |
| Ery19 | 32 |
| A9b12 | 33 |
| A23G1 1-1 | 34 |
| A26G1 1-2 | 35 |
| A26G1-10 | 36 |
| A35 E4-16 | 37 |
| A49F1-32 | 38 |
| A17d2-3 | 39 |
| A53F11-13 | 40 |
| A53F11-14 | 41 |
| A22A 2-11 | 42 |
| A36E8-1 | 43 |
| A52E8-2 | 44 |
| PKS-I amino acid sequences | |
| Amb9 | 45 |
| Amb12 | 46 |
| Ery19 | 47 |

TABLE 9-continued

Sequences

| Name | SEQ ID No. |
|---|---|
| A9b12 | 48 |
| A23G1 1-1 | 49 |
| A26G1 1-2 | 50 |
| A26G1-10 | 51 |
| A35 E4-16 | 52 |
| A49F1-32 | 53 |
| A17d2-3 | 54 |
| A53F11-13 | 55 |
| A53F11-14 | 56 |
| A22A 2-11 | 57 |
| A36E8-1 | 58 |
| A52E8-2 | 59 |
| 16S rDNA sequences | |
| a24.1(2), | 60 |
| a4.a6.a7 (7) | 61 |
| a52.a53.a5(15) | 62 |
| a49.a50.a51(11) | 63 |
| a4.a6.a7(14) | 64 |
| a30.a31.a32(7) | 65 |
| a37.a38.a39(6) | 66 |
| a46.a47.a48(14) | 67 |
| a49.a50.a51(1) | 68 |
| a52.a53.a5(8) | 69 |
| a8.a9.a10(13) | 70 |
| a1.a2.a3(13) | 71 |
| a43.a44.a45(10) | 72 |
| a27.a28.a29(5) | 73 |
| a23.1 | 74 |
| a25.1 | 75 |
| a18.1(22) | 76 |
| a33.1 | 77 |
| a14.7 | 78 |
| a21.7 | 79 |
| a8.a9.a10(7) | 80 |
| a8.a9.a10(18) | 81 |
| a27.a28.a29(3) | 82 |
| a34.a35.a36(5) | 83 |
| a22.1(19) | 84 |
| a11.a12.a13(5) | 85 |
| a19.a20.a26(9) | 86 |
| a40.a41.a42(6) | 87 |
| a27.a28.a29(8) | 88 |
| a27.a28.a29(12) | 89 |
| a37.a38.a39(12) | 90 |
| a46.a47.a48(6) | 91 |
| a11.a12.a13(11) | 92 |
| a15.a16.a17(12) | 93 |
| a15.a16.a17(5) | 94 |
| a19.a20.a26(13) | 95 |
| a37.a38.a39(14) | 96 |
| a8.a9.a10(9) | 97 |
| a19.a20.a26(5) | 98 |

TABLE 9-continued

| Name | SEQ ID No. |
|---|---|
| Sequences | |
| a43.a44.a45(4) | 99 |
| a1.a2.a3(4) | 100 |
| a4.a6.a7(23) | 101 |
| a49.a50.a51(22) | 102 |
| a8.a9.a10(2) | 103 |
| a34.a35.a36(3) | 104 |
| a34.a35.a36(10) | 105 |
| a40.a41.a42(13) | 106 |
| Primers | |
| cos 1 n (Example 5) | 107 |
| cos 2 n (Example 5) | 108 |
| Evϕc 31I (Example 15) | 109 |
| BIIϕc 31F (Example 15) | 110 |
| Primer 1 (Example 15) | 111 |
| Primer 2 (Example 15) | 112 |
| PKS-I nucleic acids | |
| Cosmid a2641 (vector + (−) strand insertion | 113 |
| Cosmid a2641 (insertion − (+) strand | 114 |
| orf1 | 115 |
| orf2 | 116 |
| orf3 | 117 |
| orf4 | 118 |
| orf5 | 119 |
| orf6 | 120 |
| PKS-I amino acid sequences | |
| ORF1 | 121 |
| ORF2 | 122 |
| ORF3 | 123 |
| ORF4 | 124 |
| ORE5 | 125 |
| ORF6 | 126 |

REFERENCES

Amann, R. I., W. Ludwig, and K.-H. Schleifer. 1995. Phylogenetic identification and in situ detection of individual microbial cells without cultivation. Microbiol. Rev. 59:143-169.

Atschul S. F., Madden T. L., Schäffer A. A., Zhang J., Zhang Z., Miller W., Lipman D. J. (1997) "Gapped BLAST and PSI-BLAST: a next generation of protein database search programs" *Nucleic Acid Research* Vol 25: 3389-3404

Atschul S F et al., 1990, J. Mol. Biol, 215: 403-410.

Bakken, L. R. 1985. Separation and purification of bacteria from soil. Appl. Environ. Microbiol. 49:1482-1487.

Bibb M J, Findlay P R, Johnson M W, The relationship between base composition and codon usage in bacterial genes and its use for the simple and reliable identification of protein-coding sequences. Gene 30: 1-3, 157-66, October, 1984.

Biesiekierska-Galguen M. (1997) "Atténuation biologique de contaminant xénobiotiques dans le sol—modèle lindane [Biological attenuation of xenobiotic contaminants in soil—lindane model]" National DEP Diploma in Toxicology, Université Claude Bernard Lyons I.

Blondelet-Rouault M H, Weiser J, Lebrihi A, Branny P, Pernodet J L. Institute of Genetics and Microbiology, URA CNRS 2225, Universite Paris XI, Orsay, France. Gene 1997 May 6;190(2):315-7

Borchert S et al., 1992, Microbiology Letters, 92: 175-180

Blondelet-Rouault, 1997, Gene, 315-317

Boccard, F., Smokvina T., Pernodet J. L., Friedmann, A. & Guerineau M. (1989). The integrated conjugative plasmid pSAM2 of *Streptomyces ambofaciens* is related to temperature bacteriophages. Embo J 8,973-80

Chatzinotas A., Sandaa R-A., Schönhuber W., Amanna R., Daae F. L., Torsvik V., Zeyer J., Hahn D. (1998) "Analysis of broad-scale differences in microbial community composition of two pristine forest soils" *Systematic and Applied Microbiology* Vol 21: 579-587

Clegg, C. D., K. Ritz, and B. S. Griffiths. 1997. Direct extraction of microbial community DNA from humified upland soils. Lett. Appi. Microbiol. 25:30-33.

Clerc-Bardin, S., J.-L. Pernodet, Å. Frostegård, and P. Simonet. Development of a conditional suicide system for a *Streptomyces lividans* strain and its use to investigate conjugative transfer in soil. Submitted.

Elledge S J, Mulligan J T, Ramer S W, Spottswood M, Davis R W. Department of Biochemistry, Baylor College of Medicine, Houston, Tex. 77030. Proc Natl Acad Sci U S A 1991 Mar. 1;88(5):1731-5

Engelen, B., K. Meinken, F. Von Wintzingerode, H. Heuer, H.-P. Malkomes, and H. Backhaus. 1998. Monitoring impact of a pesticide treatment on bacterial soil communities by metabolic and genetic fingerprinting in addition to conventional testing procedures. Appi. Environ. Microbiol. 64:2814-2821.

Farrelly, V., F. A. Rainey, and E. Stackebrandt. 1995. Effect of genome size and rrn gene copy number on PCR amplification of 16S rRNA genes from a mixture of bacterial species. Appl. Environ. Microbiol. 61:2798-2801.

Faulkner D. V., Jurka J. (1988) "Multiple Aligned Sequence Editor (MASE)" Trends in Biochemical Sciences Vol 13: 321-322

Frengen et al., 1999, Genomics, 58: 250-258

Frostegård, Å., Tunlid, A., and Bååth, E. 1991. Microbial biomass measured as total lipid phosphate in soils of different organic content. J. Microbiol. Meth. 14:151-163.

Giddings, G. 1998. The release of genetically engineered micro-organisms and viruses into the environment. New Phytol. 140:173-184.

Gladek, A., and J. Zakrzewska. 1984. Genome size of *Streptomyces*. FEMS Microbiol. Lett. 24:73-76.

Gribskov M, Devereux J, Burgess R R, The codon preference plot: graphic analysis of protein coding sequences and prediction of gene expression. Nucleic Acids Res 12: 1 Pt 2, 539-49, Jan. 11, 1984.

Guiney et al., 1983, Proc. Natl. Acad. Sci USA, (12): 3595-3598.

Gourmelen A., Blondelet-Rouault, M. H. & Pernodet, J. L. (1998). Characterization of a glycosyl transferase inactivating macrolide, encoded by gimA from *Streptomyces ambofaciens*, Antimicrob Agents Chemother 42, 2612-9.

Hayakawa, M., and H. Nonomura. 1987. Humic acid-vitamin agar, a new medium for the selective isolation of soil actinomycetes. J. Ferment. Technol. 65:501-509.

Hayakawa, M., Ishizawa K., and H. Nonomura. 1988. Distribution of rare actinomycetes in Japanese soils. J. Ferment. Technol. 66:367-373.

Hickey, R. J., and H. D. Tresner. 1952. A cobalt containing medium for sporulation of *Streptomyces* species. J. Bacteriol. 64:891-892.

Hintermann, G., R., Crameri, Kieser, T., and R. Hütter. 1981. Restriction analysis of the *Streptomyces glaucescens* genome by agarose gel electrophoresis. Arch. Microbiol. 130:218-222.

Holben, W. E., J. K. Jansson, B. K. Chelm, and J. M. Tiedje. 1988. DNA probe method for the detection of specific microorganisms in the soil bacterial community. Appl. Environ. Microbiol. 54:703-711.

Hong Fu et al., 1995, Molecular diversity, 1: 121-124

Hopwood D A, Bibb M J, Chater K F, Kieser T., Bruton C. J., Kieser H. M., Lydiate D. J., Smith C. P., Ward J. M. and Scrempf H. 1985. Genetic Manipulation of *Streptomyces*. A Laboratory manual. The John Innes Foundation, Norwich, U.K.

Hopwood, D. A., M. J. Bibb, K. F. Chater, T. Kieser, C. J. Bruton, H. M. Kieser, D. J. Lydiate, C. P. Smith, J. M. Ward, and H. Schrempf. 1985. Genetic manipulation of *streptomyces*—a laboratory manual. The John Innes Foundation, Norwich, United Kingdom.

Hohm B. and Collins J., 1980, Gene, 11: 291-298

Horinouchi S., Malpartida F., Hopwood D. et Beppu T., Mol. Gen. Genet. (1989) 215: 355-357.

Imai R., Nagata Y., Fukuda M., Takagi M., Yano K. (1991) "Molecular cloning of a *Pseudomonas paucimobilis* gene encoding a 17-kilodalton polypeptide that eliminates HCl molecules from ?-Hexachlorocyclohexane" *Journal of Bacteriology* Vol 17", No 21: 6811-6819

Jacobsen, C. S., and O. F. Rasmussen. 1992. Development and application of a new method to extract bacterial DNA from soil based on separation of bacteria from soil with cation-exchange resin. Appl. Environ. Microbiol. 58:2458-2462.

Jae-Hyuk Y. U. and Leonard T. J., 1995. Sterigmetscytin biosynthesis in *Aspergilus nidulans* requires a . . . type I polyketide synthase. J. Bacteriol, (August): 4792-4800.

Ka, J. O., W. E. Holben, and J. M. Tiedje. 1994. Analysis of competition in soil among 2,4-dichlorophenoxyacetic acid-degrading bacteria. Appl. Environ. Microbiol. 60:1121-1128.

Kah-Tong S et al., 1997, J Bacteriol, G179(23): 7360-7368

Kimura M. (1980) "A simple method for estimating evolutionary rates of base substitutions through comparative studies of nucleotide sequences" *Journal of Molecular Evolution* Vol 16: 111-120

Kuske, C. R., K. L. Banton, D. L. Adorada, P. C. Stark, K. K. Hill, and P. J. Jackson. 1998. Small-scale DNA sample preparation method for field PCR detection of microbial cells and spores in soil. Appl. Environ. Microbiol. 64:2463-2472.

Lacalle R A, Pulido D, Vara J, Zalacain M, Jimenez A. Centro de Biologia Molecular (CSIC-UAM), Universidad Autonoma, Canto Blanco, Madrid, Spain. Gene 1989 Jul. 15;79(2):375-80

Lee, S.-Y., J. Bollinger, D. Bezdicek, and A. Ogram. 1996. Estimation of the abundance of an uncultured soil bacterial strain by a competitive quantitative PCR method. Appl. Environ. Microbiol. 62:3787-3793.

Leff, L. G., J. R. Dana, J. V. McArthur, and L. J. Shimkets. 1995. Comparison of methods of DNA extraction from stream sediments. Appl. Environ. Microbiol. 61:1141-1143.

Liesack, W., and E. Stackebrandt. 1992. Occurrence of novel groups of the domain Bacteria as revealed by analysis of genetic material isolated from an Australian terrestrial environment. J. Bacteriol. 174:5072-5078.

Liesack, W., P. H. Janssen, F. A. Rainey, N. L. Ward-Rainey, and E. Stackebrandt. 1997. Microbial diversity in soil: the need for a combined approach using molecular and cultivation techniques. In J. D. Van Elsas, J. T. Trevors, and E. M. H. Wellington (ed.), Modern soil microbiology, Marcel Dekker, Inc., New York. (p 375-439)

Lorentz, M. G., and W. Wackernagel. 1994. Bacterial gene transfer by natural genetic transformation in the environment. Microbiol. Reviews 58:563-602.

Maidak B. L., Cole J. R., Parker C. T., Garrity G. M., Larsen N., Li B., Lilburn T. G., McCaughey M. J., Olsen G. J., Overbeek R., Pramanik S., Schmidt T. M., Tiedje J. M., Woese C. R. (1999) "A new project of the RDP (Ribosomal Database Project)" *Nucleic Acids Research* Vol 27: 171-173

Mazodier P. et al., 1989, J. Bacteriol., 171(6): 3583-3585.

Moré, M. I., J. B. Herrick, M. C. Silva, W. C. Ghiorse, and E. L. Madsen. 1994. Quantitative cell lysis of indigenous microorganisms and rapid extraction of microbial DNA from sediment. Appl. Environ. Microbiol. 60:1572-1580.

Murakami T, Holt T G, Thompson C J, Microbiological Engineering Unit, Institute Pasteur, Paris, France. J. Bacteriol 1989 March;171(3):1459-66

Nagata Y., Hatta T., Imai R., Kimbara K., Fukuda M., Yano K., Takagi M. (1993) "Purification and characterization of ?-Hexachlorocyclohexane (?-HCH)dehydrochlorinase (LinA) from *Pseudomonas paucimobilis*" Bioscience, Biotechnology and Biochemistry Vol 57 No 9: 1582-1583

Nalin R., Simonet P., Vogel T. M., Normand P. (1999) "Rhodanobacter lindaniclasticus gen.nov., sp., nov., a lindane-degrading bacterium" *International Journal of Systematic Bacteriology* Vol 49: 19-23

Nesme, X., C. Picard, and P. Simonet. 1995. Specific DNA sequences for detection of soil bacteria. In J. T. Trevors, and J. D. van Elsas (ed.), Nucleic acids in the environment, methods and application. Springer Lab Manual. (p 111-139)

Nilsson B, Uhlen M, Josephson S, Gatenbeck S, Philipson L. Nucleic Acids Res 1983 Nov. 25;11(22):8019-30

Normand P. et al., 1995, Océanis, 21(1): 31-56

Ogram, A. V., M. L. Mathot, J. B. Harsh, J. Boyle, and C. A. Pettigrew, JR. 1994. Effects of DNA polymer length on its adsorption to soils. Appl. Environ. Microbiol. 60:393-396.

Ogram, A., G. S. Sayler, and T. Barkay. 1987. The extraction and purification of microbial DNA from sediments. J. Microbiol. Methods 7:57-66.

Olsen, R. A., and Bakken, L. R. 1987. Viability of soil bacteria: optimization of the plate-counting technique. Microb. Ecol. 13:59-74.

Paget, E., L. Jocteur Monrozier, and P. Simonet. 1992. Adsorption of DNA on clay minerals: protection against DNaseI and influence on gene transfer. FEMS Microbiol. Lett. 97:31-40.

Patra, G., P. Sylvestre, V. Ramisse, J. Thérasse, and J.-L. Guesdon. 1996. Isolation of a specific chromosomic DNA sequence of *Bacillus anthrasis* and its possible use in diagnosis. FEMS Immunol. Medical Microbiology 15:223-231.

Pernodet J. L. Fish, S. Blondelet-Rouault, M. H. & Cundliffe, E. (1996). The macrolide-lincosamide-streptogramin B resistance phenotypes characterized by using a specifically deleted, antibiotic-sensitive strain of *Streptomyces lividans*. Antimicrob Agents Chemother 40, 581, 5.

Pernodet J. L., Gourmelen, A., Blondelet-Rouault, M. H. & Cundliffe, E. (1999). Dispensable ribosomal resistance to spiramycin conferred by srmA in the spiramycin producer *Streptomyces ambofaciens*. 145, 2355-64.

Picard, C., C. Ponsonnet, X. Nesme, and P. Simonet. 1992. Detection and enumeration of bacteria in soil by direct DNA extraction and polymerase chain reaction. Appl. Environ. Microbiol. 58:2717-2722.

Preud'homme, J., Belloc, A., Charpentié, Y., and Tarridec, P. 1965. Un antibiotique formé de deux groupes de composants à synergie d'action: la pristinamycine [An antibiotic formed from two groups of components with synergistic action: pristinamycin] C. R. Acad. Sci. 260: 1309-1312.

Priemé, A., J. I. B. Sitaula, Å. K. Klemedtsson, and L. R. Bakken. 1996. Extraction of methane-oxidizing bacteria from soil particles. FEMS Microbiol. Ecol. 21: 59-68.

Prosser, J. 1994. Molecular marker systems for detection of genetically engineered micro-organisms in the environment. Microbiol. 140:5-17.

Raynal A, Tuphile K, Gerbaud C, Luther T, Guérineau M, Pernodet J L; Laboratory of Biology and Molecular Genetics, Institute of Genetics and Microbiology, URA CNRS 2225, Université Paris-Sud, Orsay, France. Mol Microbiol 1998 April;28(2):333-42

Raynald A. Tuphile, K. Gerbaud, C., Luther, T. Guerineau, M. & Pernodet, J. L. (1998). Structure of the chromosomal insertion site for pSAM2: functional analysis in *Escherichia coli*. Mol. Microbiol 28, 333-42.

Richard, G. M. 1974. Modifications of the diphenylamine reaction giving increased sensitivity and simplicity in the estimation of DNA. Analytical Biochem. 57:369-376.

Romanowski, G., M. G. Lorentz, and W. Wackernagel. 1993. Use of polymerase chain reaction and electroporation of *Escherichia coli* to monitor the persistence of extracellular plasmid DNA introduced into natural soils. Appl. Environ. Microbiol. 59:3438-3446.

Saitou N., Nei M. (1987) "The Neighbour-Joining method: a new method for reconstructing phylogenetic trees" *Molecular and Biological Evolution* Vol 2: 112-118

Sambrook J., Fritsch E. F. et Maniatis T. 1996. Molecular cloning: a laboratory manual, 2nd ed. Cold spring Harbor Laboratory Press, Cold Spring Harbor, N.Y.

Sambrook, J., E. F. Fritsch, and T. Maniatis. 1989. Molecular cloning: a laboratory manual, 2nd ed. Cold Spring Harbor Laboratory, Cold Spring Harbor, N.Y.

Senoo K., Wada H. (1989) "Isolation and identification of an aerobic ?-HCH-decomposing bacterium from soil" *Soil Science, Plant Nutrition* Vol 35, No 1: 79-87.

Sezonov, G., Blanc, V., Bamas-Jacques, N., Friedmann, A. Pernodet, J. L. & Guerineau, M. (1997). Complete conversion of antibiotic precursor to pristinamycin IIA by overexpression of *Streptomyces pristinae* biosynthetic genes. Nat Biotechnol 15,349-53.

Shirling, E. B., and D. Gottlieb. 1966. Methods for characterization of *Streptomyces* species. Int. J. Syst. Bacteriol. 16:313-340.

Shizuga et al., 1992, Proc. Natl. Acad. Sci USA, 89: 8794-8797.

Siefert, J. L., and G. E. Fox. 1998. Phylogenetic mapping of bacterial morphology. Microbiology 144:2803-2808.

Simonet, P., P. Normand, A. Moiroud, and R. Bardin. 1990. Identification of *Frankia* strains in nodules by hybridization of polymerase chain reaction products with strain-specific oligonucleotide probes. Arch. Microbiol. 153: 235-240.

Smalla, K., N. Cresswell, L. Mendonca-Hagler, A. Wolters, and D. J. van Elsas. 1993. Rapid DNA extraction protocol from soil for polymerase chain reaction-mediated amplification. J. Appl. Bacteriol. 74:78-85.

Sosio M. et al., 2000, Nature Biotechnology, vol 18: 343-345

Smit, E., P. Leeflang, and K. Wernars. 1997. Detection of shifts in microbial community structure and diversity in soil caused by copper contamination using amplified ribosomal DNA restriction analysis. FEMS Microbiol. Ecol. 23:249-261.

Smokvina T, Mazodier P, Boccard F, Thompson C J, Guerineau M. Laboratory of Biology and Molecular Genetics, Universite Paris-Sud, Orsay, France. Gene 1990 Sep. 28;94(1):53-9

Smolvina, T., Mazodier, P. Boccard, F. Thompson, C. J. & Guerineau, M. (1990). Construction of a series of pSAM2-based integrative vectors for use in actinomycetes. Gene 94, 53-9.

Stackebrandt, E. 1988. Phylogenetic relationships vs. phenotypic diversity: how to achieve a phylogenetic classification system of the eubacteria. Can. J. Microbiol. 34:552-556.

Staneck, J. L., and G. D. Roberts. 1974. Simplified approach to identification of aerobic Actinomycetes by thin-layer chromatography. Appl. Microbiol. 28:226-231.

Stapleton, R. D., S. Ripp, L. Jimenez, S. Cheol-Koh, J. T. Fleming, I. R. Gregory, and G. S. Sayler. 1998. Nucleic acid analytical approaches in bioremediation: site assessment and characterization. J. Microbiol. Methods 32:165-178.

Steffan, R. J., J. Goksoyr, A. K. Bej, and R. Atlas. 1988. Recovery of DNA from soils and sediments. Appl. Environ. Microbiol. 54:2908-2915.

Tebbe, C. C., and W. Vahjen. 1993. Interference of humic acids and DNA extracted directly from soil in detection and transformation of recombinant DNA from bacteria and a yeast. Appl. Environ. Microbiol. 59:2657-2665.

Tercero J A, Espinosa J C, Lacalle R A, Jimenez A. Centro de Biologia Molecular Severo Ochoa, Consejo Superior de Investigaciones Cientificas, Madrid, Spain. J Biol Chem 1996 Jan. 19;271(3):1579-90

Thomas J-C., Berger F., Jacquier M., Bernillon D., Baud-Grasset F., Truffaut N., Normand P., Vogel T. M., Simonet P. (1996) "Isolation and Characterisation of a novel ?-Hexachlorocyclohexane-degrading bacterium" *Journal of Bacteriology Vol* 178, No 20: 6049-6055

Torsvik, V. L. 1980. Isolation of bacterial DNA from soil. Soil Biol. Biochem. 12:15-21.

Torsvik, V., R. Sørheim, and J. Goksøyr. 1996. Total bacterial diversity in soil and sediment communities—a review. J. Ind. Microbiol. 17:170-178.

Tsai, Y.-L., and B. Olson. 1991. Rapid method for direct extraction of DNA from soil and sediments. Appl. Environ. Microbiol. 57:1070-1074.

Umeyama T., Tanabe Y., Aigle B. D. et Horinuochi S., FEMS (1996) 144: 177-184.

Van Elsas, J. D., G. F. Duarte, A. S. Rosado, and K. Smalla. 1998. Microbiological and molecular biological methods for monitoring microbial inoculants and their effects in the soil environment. J. Microbiol. Methods 32:133-154.

Van Elsas, J. D., V. Mäntynen, and A. C. Wolters. 1997. Soil DNA extraction and assessment of the fate of *Mycobacterium chlorophenolicum* strain PCP-1 in different soils by 16S ribosomal RNA gene sequence based most-probable-number PCR and immunofluorescence. Biol. Fert. Soils 24:188-195.

Volff J N et al., 1996, Mol. Microbiol., 21(5): 1037-1047.

Volossiouk, T., E. J. Robb, and R. N. Nazar. 1995. Direct DNA extraction for PCR-mediated assays. Appl. Environ. Microbiol. 61:3972-3976.

Wahl G M, Lewis K A, Ruiz J C, Rothenberg B, Zhao J, Evans G A. Proc Natl Acad Sci U S A 1987 April;84(8): 2160-4

Waksman, S. A. 1961. Williams and Wilkins (ed.) The actinomycetes. Classification, identification and description of genera and species. Vol 2. Baltimore.

Ward, D. M., R. Weller, and M. M. Bateson. 1990. 16S rRNA sequences reveal numerous uncultured microorganisms in a natural community. Nature 344:63-65.

Widmer, F., R. J. Seidler, and L. S. Watrud. 1996. Sensitive detection of transgenic plant marker gene persistence in soil microcosms. Mol. Ecol. 5:603-613.

Williams, S. T., R. Locci, A. Beswick, D. I. Kurtboke, V. D. Kuznetsov, F. J. Le Monnier, P. F. Long, K. A. Maycroft, R. A. Palma, B. Petrolini, S. Quaroni, J. I. Todd, and M. West. 1993. Detection and identification of novel actinomycetes. Res. Microbiol. 144:653-656.

Wilson, I. G. 1997. Inhibition and facilitation of nucleic acid amplification. Appl. Environ. Microbiol. 63:3741-3751.

Woese, C. R. 1987. Bacterial evolution. Microbiol. Rev. 51:221-271.

Yannish-Perron et al., 1985, Gene, 33(1) 103-119.

Zaslavsky, B. Y. 1995. Separation of biomolecules, p. 503-667. In Aqueous two-phase partitioning. Boris Y. Zaslavsky (ed.) Physical Chemistry and Bioanalytical Applications, Marcel Dekker, Inc., New York.

Zhou, J., M. A. Bruns, and J. M. Tiedje. 1996. DNA recovery from soils of diverse composition. Appl. Environ. Microbiol. 62:316-322.

---

We claim:

1. A method for collecting nucleic acids from organisms in a soil sample comprising:

(a) grinding a pre-dried or pre-desiccated soil sample containing organisms is to produce microparticles;

(b) suspending the microparticles in a liquid buffer medium;

(c) extracting nucleic acids from the organisms in the suspension of microparticles;

(d) passing the extracted nucleic acids over a molecular sieve to produce elution fractions enriched in nucleic acids;

(e) passing the elution fractions enriched in nucleic acids over an anion-exchange chromatography support to produce fractions containing substantially purified nucleic acids; and (f) recovering the elution fractions containing the substantially purified nucleic acids;

wherein the nucleic acids are DNA comprising at least one operon or part of an operon;

wherein the operon encodes all or part of a metabolic pathway;

wherein the metabolic pathway is the polyketide synthesis pathway; and wherein the DNA comprises SEQ ID No.:34.

2. The method for collecting nucleic acids from organisms in a soil sample comprising:

(a) grinding a pre-dried or pre-desiccated soil sample containing organisms to produce microparticles;

(b) suspending the microparticles in a liquid buffer medium;

(c) extracting nucleic acids from the organisms in the suspension of microparticles;

(d) passing the extracted nucleic acids over a molecular sieve to produce elution fractions enriched in nucleic acids;

(e) passing the elution fractions enriched in nucleic acids over an anion-exchange chromatography support to produce fractions containing substantially purified nucleic acids; and recovering the elution fractions containing the substantially purified nucleic acids; wherein:

step (b) further comprises:

homogenizing the microparticles by vigorous mixing followed by simple stirring;

incubating the suspension at 37° C., after sonication, in the presence of lysozyme and achromopeptidase; and adding SDS to the suspension; wherein:

the one or more purified nucleic acids in the vector comprise SEQ ID No.: 34; and the host cell is cultured under conditions suitable to produce a polypeptide encoded by the nucleic acid in the vector; and wherein the vector is inserted into a host cell.

3. The method of claim 2, wherein the polypeptide produced is recovered.

4. The method of claim 2, wherein the polypeptide produced is purified.

* * * * *

SEQUENCE LISTING

<160> NUMBER OF SEQ ID NOS: 126

<210> SEQ ID NO 1
<211> LENGTH: 15
<212> TYPE: DNA
<213> ORGANISM: Artificial sequence
<220> FEATURE:
<223> OTHER INFORMATION: Description of the artificial sequence: probe
FGPS431

<400> SEQUENCE: 1
acgggcggtg tgtrc 15

<210> SEQ ID NO 2
<211> LENGTH: 22
<212> TYPE: DNA
<213> ORGANISM: Artificial sequence
<220> FEATURE:
<223> OTHER INFORMATION: Description of the artificial sequence: primer
FGPS122

<400> SEQUENCE: 2
ggagagtttg atcatggctc ag 22

<210> SEQ ID NO 3
<211> LENGTH: 20
<212> TYPE: DNA
<213> ORGANISM: Artificial sequence
<220> FEATURE:
<223> OTHER INFORMATION: Description of the artificial sequence: primer
FGPS350

<400> SEQUENCE: 3
cctggagtta agccccaagc 20

<210> SEQ ID NO 4
<211> LENGTH: 24
<212> TYPE: DNA
<213> ORGANISM: Artificial sequence
<220> FEATURE:
<223> OTHER INFORMATION: Description of the artificial sequence: probe
FGPS643
<220> FEATURE:
<221> NAME/KEY: modified_base
<222> LOCATION: (7)..(9)
<223> OTHER INFORMATION: variable nucleotide

<400> SEQUENCE: 4
gtgagtnnna acctgccccy gact 24

-continued

<210> SEQ ID NO 5
<211> LENGTH: 21
<212> TYPE: DNA
<213> ORGANISM: Artificial sequence
<220> FEATURE:
<223> OTHER INFORMATION: Description of the artificial sequence: probe
FGPS643-2

<400> SEQUENCE: 5
gtgagtaacc tgcccccgac t 21

<210> SEQ ID NO 6
<211> LENGTH: 23
<212> TYPE: DNA
<213> ORGANISM: Artificial sequence
<220> FEATURE:
<223> OTHER INFORMATION: Description of the artificial sequence: primer
R499

<400> SEQUENCE: 6
ttaattcact tgcaactgat ggg 23

<210> SEQ ID NO 7
<211> LENGTH: 23
<212> TYPE: DNA
<213> ORGANISM: Artificial sequence
<220> FEATURE:
<223> OTHER INFORMATION: Description of the artificial sequence: primer
R500

<400> SEQUENCE: 7
aacgatagct cctacatttg gag 23

<210> SEQ ID NO 8
<211> LENGTH: 25
<212> TYPE: DNA
<213> ORGANISM: Artificial sequence
<220> FEATURE:
<223> OTHER INFORMATION: Description of the artificial sequence: probe
C501

<400> SEQUENCE: 8
ttgctgatac ggtatagaac ctggc 25

<210> SEQ ID NO 9
<211> LENGTH: 20
<212> TYPE: DNA
<213> ORGANISM: Artificial sequence
<220> FEATURE:
<223> OTHER INFORMATION: Description of the artificial sequence: primer
FGPS516

<400> SEQUENCE: 9
tccagatcct tgacccgcag 20

<210> SEQ ID NO 10
<211> LENGTH: 20
<212> TYPE: DNA
<213> ORGANISM: Artificial sequence
<220> FEATURE:
<223> OTHER INFORMATION: Description of the artificial sequence: primer
FGPS517

<400> SEQUENCE: 10
cacgacattg cactccaccg 20

-continued

<210> SEQ ID NO 11
<211> LENGTH: 16
<212> TYPE: DNA
<213> ORGANISM: Artificial sequence
<220> FEATURE:
<223> OTHER INFORMATION: Description of the artificial sequence: probe
FGPS518

<400> SEQUENCE: 11
ccgtgagccg gatcag 16

<210> SEQ ID NO 12
<211> LENGTH: 20
<212> TYPE: DNA
<213> ORGANISM: Artificial sequence
<220> FEATURE:
<223> OTHER INFORMATION: Description of the artificial sequence: probe
FGPS612

<400> SEQUENCE: 12
cyaacthcgt gccagcagcc 20

<210> SEQ ID NO 13
<211> LENGTH: 21
<212> TYPE: DNA
<213> ORGANISM: Artificial sequence
<220> FEATURE:
<223> OTHER INFORMATION: Description of the artificial sequence: probe
FGPS669

<400> SEQUENCE: 13
gacgtcrtcc ccmccttcct c 21

<210> SEQ ID NO 14
<211> LENGTH: 18
<212> TYPE: DNA
<213> ORGANISM: Artificial sequence
<220> FEATURE:
<223> OTHER INFORMATION: Description of the artificial sequence: probe
FGPS618

<400> SEQUENCE: 14
atggytgtcg tcagctcg 18

<210> SEQ ID NO 15
<211> LENGTH: 21
<212> TYPE: DNA
<213> ORGANISM: Artificial sequence
<220> FEATURE:
<223> OTHER INFORMATION: Description of the artificial sequence: probe
FGPS614

<400> SEQUENCE: 15
gtgtagaagt gaaattcgat t 21

<210> SEQ ID NO 16
<211> LENGTH: 18
<212> TYPE: DNA
<213> ORGANISM: Artificial sequence
<220> FEATURE:
<223> OTHER INFORMATION: Description of the artificial sequence: probe
FGPS615

<400> SEQUENCE: 16
cggtggatga tgtggatt 18

<210> SEQ ID NO 17

-continued

<211> LENGTH: 18
<212> TYPE: DNA
<213> ORGANISM: Artificial sequence
<220> FEATURE:
<223> OTHER INFORMATION: Description of the artificial sequence: probe FGPS616

<400> SEQUENCE: 17
aggttaaaac tcaaatga 18

<210> SEQ ID NO 18
<211> LENGTH: 18
<212> TYPE: DNA
<213> ORGANISM: Artificial sequence
<220> FEATURE:
<223> OTHER INFORMATION: Description of the artificial sequence: probe FGPS621

<400> SEQUENCE: 18
atacgtaggt ggcaagcg 18

<210> SEQ ID NO 19
<211> LENGTH: 19
<212> TYPE: DNA
<213> ORGANISM: Artificial sequence
<220> FEATURE:
<223> OTHER INFORMATION: Description of the artificial sequence: probe FGPS617

<400> SEQUENCE: 19
gccggggtca actcggagg 19

<210> SEQ ID NO 20
<211> LENGTH: 18
<212> TYPE: DNA
<213> ORGANISM: Artificial sequence
<220> FEATURE:
<223> OTHER INFORMATION: Description of the artificial sequence: probe FGPS680

<400> SEQUENCE: 20
tgagtcccca hcwccccg 18

<210> SEQ ID NO 21
<211> LENGTH: 20
<212> TYPE: DNA
<213> ORGANISM: Artificial sequence
<220> FEATURE:
<223> OTHER INFORMATION: Description of the artificial sequence: probe FGPS619

<400> SEQUENCE: 21
gcttggggct taactccagg 20

<210> SEQ ID NO 22
<211> LENGTH: 21
<212> TYPE: DNA
<213> ORGANISM: Artificial sequence
<220> FEATURE:
<223> OTHER INFORMATION: Description of the artificial sequence: primer 63f

<400> SEQUENCE: 22
caggcctaac acatgcaagt c 21

<210> SEQ ID NO 23
<211> LENGTH: 18

-continued

<212> TYPE: DNA
<213> ORGANISM: Artificial sequence
<220> FEATURE:
<223> OTHER INFORMATION: Description of the artificial sequence: primer 1387r
<220> FEATURE:
<221> NAME/KEY: modified_base
<222> LOCATION: (7)
<223> OTHER INFORMATION: variable nucleotide

<400> SEQUENCE: 23
gggcggngtg tacaaggc 18

<210> SEQ ID NO 24
<211> LENGTH: 30
<212> TYPE: DNA
<213> ORGANISM: Artificial sequence
<220> FEATURE:
<223> OTHER INFORMATION: Description of the artificial sequence: oligo-1

<400> SEQUENCE: 24
gcttatttaa atattaagcg gccgcccggg 30

<210> SEQ ID NO 25
<211> LENGTH: 28
<212> TYPE: DNA
<213> ORGANISM: Artificial sequence
<220> FEATURE:
<223> OTHER INFORMATION: Description of the artificial sequence: oligo-2

<400> SEQUENCE: 25
cccgggcggc cgcattaata tttaaata 28

<210> SEQ ID NO 26
<211> LENGTH: 23
<212> TYPE: DNA
<213> ORGANISM: Artificial sequence
<220> FEATURE:
<223> OTHER INFORMATION: Description of the artificial sequence: primer a1
<220> FEATURE:
<221> NAME/KEY: modified_base
<222> LOCATION: (3)
<223> OTHER INFORMATION: variable nucleotide
<220> FEATURE:
<221> NAME/KEY: modified_base
<222> LOCATION: (7)
<223> OTHER INFORMATION: variable nucleotide
<220> FEATURE:
<221> NAME/KEY: modified_base
<222> LOCATION: (13)
<223> OTHER INFORMATION: variable nucleotide
<220> FEATURE:
<221> NAME/KEY: modified_base
<222> LOCATION: (15)
<223> OTHER INFORMATION: variable nucleotide
<220> FEATURE:
<221> NAME/KEY: modified_base
<222> LOCATION: (18)
<223> OTHER INFORMATION: variable nucleotide
<220> FEATURE:
<221> NAME/KEY: modified_base
<222> LOCATION: (21)
<223> OTHER INFORMATION: variable nucleotide

<400> SEQUENCE: 26
ccncagnagc gcntnttnct nga 23

<210> SEQ ID NO 27
<211> LENGTH: 22
<212> TYPE: DNA

-continued

```
<213> ORGANISM: Artificial sequence
<220> FEATURE:
<223> OTHER INFORMATION: Description of the artificial sequence: primer
      a2
<220> FEATURE:
<221> NAME/KEY: modified_base
<222> LOCATION: (3)
<223> OTHER INFORMATION: variable nucleotide
<220> FEATURE:
<221> NAME/KEY: modified_base
<222> LOCATION: (6)
<223> OTHER INFORMATION: variable nucleotide
<220> FEATURE:
<221> NAME/KEY: modified_base
<222> LOCATION: (9)
<223> OTHER INFORMATION: variable nucleotide
<220> FEATURE:
<221> NAME/KEY: modified_base
<222> LOCATION: (15)
<223> OTHER INFORMATION: variable nucleotide
<220> FEATURE:
<221> NAME/KEY: modified_base
<222> LOCATION: (18)
<223> OTHER INFORMATION: variable nucleotide
<220> FEATURE:
<221> NAME/KEY: modified_base
<222> LOCATION: (21)
<223> OTHER INFORMATION: variable nucleotide

<400> SEQUENCE: 27

gtnccngtnc cgtgngtntc na                                              22


<210> SEQ ID NO 28
<211> LENGTH: 23
<212> TYPE: DNA
<213> ORGANISM: Artificial sequence
<220> FEATURE:
<223> OTHER INFORMATION: Description of the artificial sequence: primer
      b1
<220> FEATURE:
<221> NAME/KEY: modified_base
<222> LOCATION: (3)
<223> OTHER INFORMATION: variable nucleotide
<220> FEATURE:
<221> NAME/KEY: modified_base
<222> LOCATION: (7)
<223> OTHER INFORMATION: variable nucleotide
<220> FEATURE:
<221> NAME/KEY: modified_base
<222> LOCATION: (13)
<223> OTHER INFORMATION: variable nucleotide
<220> FEATURE:
<221> NAME/KEY: modified_base
<222> LOCATION: (15)
<223> OTHER INFORMATION: variable nucleotide
<220> FEATURE:
<221> NAME/KEY: modified_base
<222> LOCATION: (18)
<223> OTHER INFORMATION: variable nucleotide
<220> FEATURE:
<221> NAME/KEY: modified_base
<222> LOCATION: (21)
<223> OTHER INFORMATION: variable nucleotide

<400> SEQUENCE: 28

ccncagnagc gcntnctnct nga                                             23


<210> SEQ ID NO 29
<211> LENGTH: 22
<212> TYPE: DNA
<213> ORGANISM: Artificial sequence
<220> FEATURE:
<223> OTHER INFORMATION: Description of the artificial sequence: primer
      b2
<220> FEATURE:
```

-continued

<221> NAME/KEY: modified_base
<222> LOCATION: (3)
<223> OTHER INFORMATION: variable nucleotide
<220> FEATURE:
<221> NAME/KEY: modified_base
<222> LOCATION: (6)
<223> OTHER INFORMATION: variable nucleotide
<220> FEATURE:
<221> NAME/KEY: modified_base
<222> LOCATION: (9)
<223> OTHER INFORMATION: variable nucleotide
<220> FEATURE:
<221> NAME/KEY: modified_base
<222> LOCATION: (15)
<223> OTHER INFORMATION: variable nucleotide
<220> FEATURE:
<221> NAME/KEY: modified_base
<222> LOCATION: (21)
<223> OTHER INFORMATION: variable nucleotide

<400> SEQUENCE: 29
gtnccngtnc cgtgngcctc na 22

<210> SEQ ID NO 30
<211> LENGTH: 672
<212> TYPE: DNA
<213> ORGANISM: Streptomyces ambofaciens

<400> SEQUENCE: 30
ccccagcagc acgtgttcct cgagacggtg tgggagacct tcgaatccgc cggagtggac 60
ccgcgcgcgg tacgcggtcg ttccgtcggg atgttcgtcg gcaccaacgg acaggactac 120
ccggtggtgt tggccggatc cgccgacgag ggcctggacg cccacgcggc caccggtaac 180
gcggcggcgg tgctgtccgg ccgggtctcg tacgccttcg gcctggaagg gccggcggtc 240
accgtcgaca cggcgtgttc gtcgtcgctg gtggcccttc acctggccgc gcaggcgctg 300
cggcgcggcg agtgcgatct ggcactcgcc ggcggtgtgt cggagatgtc caccgaggcg 360
gcgttcaccg agttcgcccg gcagggcggc ctggccgacg acggccgctg caaggccttc 420
tcggccgacg ccgacggcac gggctggggc gagggcgtcg gcgtcctgct ggtggagcgg 480
ctggcggacg cccgccgcaa cgggcaccgg gccctcgcgc tggtacgggg cagcgcggtc 540
aaccaggacg gcgcctccaa cggtctgacg gcacccaacg gcccgtccca gcagcgagtc 600
atccggcagg cactggcgga cgcccggctg tcgccgtcgg aggtcgacgc ggtcgagacc 660
cacggcaccg gc 672

<210> SEQ ID NO 31
<211> LENGTH: 665
<212> TYPE: DNA
<213> ORGANISM: Streptomyces ambofaciens

<400> SEQUENCE: 31
ccccagcagc gcgtgttcct ggaagcgtcc tgggaggcgg tcgagcgggc aggcatcgac 60
atgcgcaccc tgcgcggtgg acgcaccggc gtcttcgccg gcgtgatgta ccacgactac 120
ccgtcggtgg tcgaccccga agcgctcgac ggctacctgg gcacggccaa cgccggcagc 180
gttctctccg gccgcatcgc ctacaccttc gggcttcagg gaccggcggt caccgtggac 240
acggcctgct cctcgtccct ggtggcgctg cacctcgccg cccaggcgct gcccgccggc 300
gagtgcgaac tcgccctggt cggtggggtc acggtcatgt ccggcccgat gatgttcgcg 360
ggcttcggcc tggaagacgg ctctgccgcc gacggccgct gcaaggcgtt cgccgccgcc 420
gccgacggca ccggctgggg cgagggtgtc ggtgtgctgc tggtggagcg gctgtcggac 480

-continued gcccggcgcc acgggcaccg ggtgctggcc gtggtgcgcg gtagcgcggt caaccaggac 540
ggtgcctccg gcggcctcac cgcccccaac ggacctgccc agcagcgcgt catccgtcag 600
gccctggcga gcgcggcact cgtaccggcc gaggtcgacg cggtcgagac ccacggcacc 660
gggac 665

<210> SEQ ID NO 32
<211> LENGTH: 671
<212> TYPE: DNA
<213> ORGANISM: Saccharopolyspora erythraea

<400> SEQUENCE: 32
ccgcaggagc gcgtgttcct ggaactcgct tgggaagcac ttgataacgc gggcatcgca 60
ccgcacagcc tcagggacag ccggacgggc gtgttcttcg gagctatgtg gcacggctac 120
gcgcagttcg cagccggagc cgtcgaccgc atcacccagc acaccgcgac cgggcacgac 180
ctgagcatca tcccggccag gatcgcctac ttcctgggct tgcgcggccc ggacatgacc 240
ctgaacaccg cgtgctcatc ggctttggtg gccatgcacc aggcacgcca aagcatcctg 300
ctgggcgaat cctcggtcgc cttggtcggc gggatcagct tgttggtcgc gctggacagc 360
atggtcgcca tgtcgcggtt cggagcgatg gccccggacg gccggtgcaa ggcattcgac 420
tctcgcgcga acggctacgt gcgcggcgaa ggcggcggtg tcgtggtgct caaaccgctg 480
tcgcgcgctc tggccgatgg caacccggtc tactgcgtcc tgcgcggcag cgcggtcaac 540
aacgacggct tcagcaatgg ccttaccgcg ccgagcccgg cggcgcagga gcaggtactg 600
cgcgacgcct acgccaacgc cggggtcgat ccggcacagg tcgactacgt cgagacccac 660
gggaccggca c 671

<210> SEQ ID NO 33
<211> LENGTH: 686
<212> TYPE: DNA
<213> ORGANISM: Unknown organism
<220> FEATURE:
<223> OTHER INFORMATION: Origin of the sequence: soil organism

<400> SEQUENCE: 33
ccgcaggagc gcgtgttcct cgagtcgtgc tgggaggcgc tggagcatgc tggatacgat 60
actgcacgct accccggccg catcgggctg tgggccggcg cgggcttcaa cagctacctc 120
ctgaccaatc tcatgaacaa ccgcgccttt ttagagagcg tgggcatgta ccagatcttt 180
ctgagcaacg acaaggactt catcgccacc cgcacggctt acaagttaaa cctgcgcggt 240
ccggcgatgg ccgtcggcac cgcctgttcc acatcgctgg tggcggttca cgaagcttgc 300
caggcgctgc ggctgggcga gtgtgacatg gcactggccg gtgctgcgtc tgtcagcacg 360
cccctccggg agggctacct ctaccaggaa ggcatgatta tgagccgtga cggcgtctgc 420
cgcccgtttg acgccgacgc cgatggcacg gtgctgggca atggcgtggc ggtcgtggtg 480
ctcaagcggc tggacgaagc gctccgggac ggtgacacgg tctacgccgt gattcgtggc 540
acggcggtca acaacgacgg ctctgtcaag atcgggttca cggcgcccag cgccgagggg 600
cagagccggg tcgtgcggga cgccctgcgg gcggccgcgg tcccggcgga gagcgtgacc 660
tacgtcgaca cgcacggcac cggcac 686

<210> SEQ ID NO 34
<211> LENGTH: 689
<212> TYPE: DNA

-continued

<213> ORGANISM: Unknown organism
<220> FEATURE:
<223> OTHER INFORMATION: Origin of the sequence: soil organism

<400> SEQUENCE: 34
ccccagcagc gcctgttcct cgagtgcgcg tgggaagcga tggagaacgc gggatatgcg 60
gcgcgaagct ataagggttc gatcggcgtt ttcgcgggat gcggcgtcaa tacctacctg 120
ctgaacaacc tcgccaccgc ggagccgttc gatttctcac gcccctccgc gtaccagctg 180
ctgacggcca acgacaagga tttcctggcc acgcgtgtct cttacaagct gaacctccgc 240
gggcccagcc tgacggttca gacggcgtgc tccacctcgc tggtgtcggt ggtgatggca 300
tgcgagagct tgcagcgcgg cgcctcggac attgccttgg ccgggggagt tgccatcaat 360
gttccgcagt ccgtggggta cctgcaccag ccgggcatga tcctgtcgcc cgacgggcgc 420
tgccgcgcct tcgatgagtc cgctcaaggc acggtgccgg gcaacggcgc gggtgtggtc 480
gtcctcaagc gcttgagccg cgctctggcc gatggcgaca cgatctacgc cgtcattcgc 540
ggagcggcta ttaataatga tggcgccgag cgcatggggt ttaccgctcc aggtgtggac 600
ggtcagacgc gattgattcg gcgcactcaa gagatggcgg gcgtgaagcc ggagtccatc 660
ggctacatgg acacccacgg caccggcac 689

<210> SEQ ID NO 35
<211> LENGTH: 671
<212> TYPE: DNA
<213> ORGANISM: Unknown organism
<220> FEATURE:
<223> OTHER INFORMATION: Origin of the sequence: soil organism

<400> SEQUENCE: 35
ccgcagcagc gcctcttcct cgaggtggca tgggaagctt tggagcgtgc gggtcggccg 60
cccgacagtc tcgcgggcag cgacaccgga gtgttcatcg ggatcagcac cgacgactac 120
agccggctga aacctaccga tccggcgctc attgacgcct ataccggtac cggaaccgcg 180
ttcagcactg ccgccggacg gatctcctat ctgctggggt tgcagggacc gaacttcccc 240
gtcgacacgg cgtgctcttc ctcactcgtg gcggttcatc tggcgtgccg cagcttgcag 300
tcgcgagagt gcagcatggc gctggccggc ggcgtgaacc tgattctggc gccggaaagc 360
acgatctact tctgccgcct gcgggccatg gcggccgatg gccgttgcaa aagtttcgct 420
gcctccgccg acggttacgg ccgcggcgag ggatgcggaa tgctggtgct gaagcggctg 480
tccgatgcga cgcgtgacgg cgatcgtatt ctggcgctga ttcgcggatc ggccgtcaac 540
cacggcggcc gcagcaacgg cctcacggcg ccgaacggtc cggcgcagga agccgtgatt 600
cgggcggcgc tcaagaacgc cggcatggcc cccgccgatg tcgattacgt ggacacccac 660
ggcaccggca c 671

<210> SEQ ID NO 36
<211> LENGTH: 758
<212> TYPE: DNA
<213> ORGANISM: Unknown organism
<220> FEATURE:
<223> OTHER INFORMATION: Origin of the sequence: soil organism

<400> SEQUENCE: 36
ccgcaggagc gcgtcttcct cgaacgcatt gacggtttcg atgcggaatt cttcggcatc 60
tccccccgcg aagctctgaa catggatccg cagcagcggc tgctgctgga agtgtgctgg 120
gaagcggcag aggacgccgg catctctccc ggccctctgg cgggcagcgc gaccggcgtc 180

-continued

```
tttgccggct cctgcgccca ggacttcgga ctgtttcagt acgccgaccc tgcccgcatc    240
ggagcttggt cgggttccgg cgtggcgcat agcatgttgg ccaatcgcat ctcctatctg    300
ctcgacctgc gcggtccgag catggcggtc gatacggcct gctcctccgc gctcgtcgcc    360
gtccatctgg cttgccaaag cctgcgccgg cgcgaatgcg atgcggcatt cgccggcgga    420
gtgaacttga tcctgactcc cgagggcatg atcgctttgt cgaaggctcg catgttggcg    480
cccgacggac gctgcaagac gttcgacgcc gcagccgacg gttatgtgcg cggcgagggc    540
tgcggcatcg tgctgctgaa gcggctctcc gatgcgctgg ccgatggcga tgccatctgt    600
gcagtcatcc gcggctcggc aatcaatcag gacggacgga gcaatggcat cacggcgccg    660
aatctgcagg cgcagaaggc ggtcctgcaa gaggcggtgg ccaacgcgca catcgatcca    720
tcccacgtat cgttgatcga cacgcacggc accggcac                            758
```

<210> SEQ ID NO 37
<211> LENGTH: 704
<212> TYPE: DNA
<213> ORGANISM: Unknown organism
<220> FEATURE:
<223> OTHER INFORMATION: Origin of the sequence: soil organism

<400> SEQUENCE: 37

```
ccgcagcagc gcgtgttcct cgagtgcgcc tgggaggcgg tggaaagcgc gggctacgat     60
cccgaaaaat atcccggcct gatcggagtt ttcgccgggg ccagcatcaa cagctatttc    120
ctttataacc tcgcgcacaa ccgggaattc gtcgcccgca tggcggggga gtaccaagtg    180
ggcgagtacc agacgatcct cggaaacgac aaggactacc tccccactcg cgtctcctac    240
aaattgaacc tgcgcggccc cagcctggcc gtgcagtccg cctgctcgac cggcctcgtc    300
gccgtttgtc aggccattca aaatctgcag acttatcagt gcgatatggc cctcgcgggc    360
ggcatctcga tttcgtttcc gcaaaagcgc gactaccgct tcaccgacga aggaatggtc    420
tctcgcgacg gtcactgccg cccgttcgac gccagcgcgc aaggcacggt cttcggcaac    480
ggggccggcg tcgtcctgat gaaaagattg gccgacgcag tgaccgatcg ggacacgatc    540
ctcgccgtga ttaggggcgc tgccgtgaac aacgacggcg gcgtcaaaat gggttacacg    600
gcgcccagtg ccgaaggtca ggcggaggcc atcaccctgg ccctcgcgct cgctggcgtc    660
agcccggaga ccatcacttg catggacacc cacggcaccg gcac                     704
```

<210> SEQ ID NO 38
<211> LENGTH: 680
<212> TYPE: DNA
<213> ORGANISM: Unknown organism
<220> FEATURE:
<223> OTHER INFORMATION: Origin of the sequence: soil organism

<400> SEQUENCE: 38

```
ccccagcagc gcgtgttcct cgaatgcgcc tgggcggcgc tggagcgccg ccggatatca     60
gggcgacacc ttccacggtg tccatcggcg gtctatgcct caagcggctt taacacctat    120
cttctgaacc tgcatgccaa tgccgcggtg cgccaatcga tcagcccgtt tgaactgttc    180
gtcgccaacg acaaggattt tctggcgacg cgcacggctt acaagctcaa tctgcgcggc    240
ccggccatga cagtgcagac ggcctgctcc tcatcgttgg ttgccgttca tgtcgccgcg    300
caaagcctcc tagcgggcga atgcgatatt gcgctcgcgg gcggcatcac ggtttcccgt    360
tcgcatggat atgtggcgcg cgaaggtgga atattgtctc ctgacgggca ttgccgggcg    420
```

-continued

```
ttcgatgcgg atgccggcgg aaccgttcca ggcagcggcg tcggcgttgt cgtgctcaag    480

cgtctcgaag atgcgcttgc agacggcgat acgatcgacg ccgtcatcat cggttcggcc    540

atcaacaatg atggcgcgct gaaggcgagc tttaccgcac cgcaggtgga cagccaggcc    600

ttggtcatca gcgaggccca tgcagctgcc ggaatatcgg ccgattccat cggttatatg    660

gacacccacg gcaccgggac                                                680
```

<210> SEQ ID NO 39
<211> LENGTH: 671
<212> TYPE: DNA
<213> ORGANISM: Unknown organism
<220> FEATURE:
<223> OTHER INFORMATION: Origin of the sequence: soil organism

<400> SEQUENCE: 39

```
ccgcagcagc gcctcttcct cgagctcacc tgggaagcgc tggaagatgc cggcatcccg     60

ccgtccacga ttgccggcac gaatgtcggc gttttcatgg gcgcgtcgca ggctgactac    120

ggccacaagt tcttcagcga ccacgccgtc gcggattccc atttcgccac cggcacctcg    180

ctggcggtcg tcgccaatcg catttcctac atctacgacc tgcgcggccc aagcctcact    240

gtagacacgg cgtgctcgtc gtcgctcgtc gcgctgcatc aggcggtgga agcgctccgc    300

tcggggcgga tcgaaacagc cattgtcggc ggcattaacg ttatcgccag cccggcgtcc    360

ttcatcgcct tctcgcaggc ctcgatgctg tcgccgacgg ggttgtgcca ggctttctcc    420

gccaaggccg atggctttgt ccgcggcgag ggcggcacgg ttttcgtcct gcgcaaggcg    480

gcgcatgcgc atggcagccg caacccggtg cgcgggctca ttctcgccac cgacgtcaat    540

tccgacgggc gtaccaacgg catctcgctg ccatcggccg aagcgcagga agtcctcctg    600

caacgcgtct attcacgcgc atcgatcgat ccgaaccgcc tggctttcgt cgacacccac    660

gggaccggca c                                                         671
```

<210> SEQ ID NO 40
<211> LENGTH: 764
<212> TYPE: DNA
<213> ORGANISM: Unknown organism
<220> FEATURE:
<223> OTHER INFORMATION: Origin of the sequence: soil organism

<400> SEQUENCE: 40

```
ccgcagcagc gcgtgttcct cgacggcatc gaccggttcg atccgcgtca cttcgcgatc     60

acgccgcgcg aggcgatcag catggacccg cagcagcggc tcctgctcga ggtcacgtgg    120

gaagcgctgg agcgcgccgg cgtggcgccc gatcgcctga ccggatccga caccggcgtc    180

ttcatcggca tcagcaccaa cgactacggc cagatcctgc tgcgcgcctc ggaccagatc    240

gatccgggga tgtacttcgg caccggcaac ctgttgaacg cggcggcggg acgcctctcg    300

tacgtcctcg gcctgcaggg tccgagcatg gcggtcgaca ccgcatgtcc gtcgtcgctg    360

gtggcgattc atctcgcgtg tcagagcctg cgcaaccgcg agtgccgcat ggcgctcgcc    420

ggcggcgcca acctggtgct cgtcccggaa gtgacggtca actgctgccg cgccaagatg    480

ctcgcgcctg acgggcgctg caagacgttc gacgccgcgg cggacggcta cgtccgcggc    540

gaaggggccg cggtgatcgt gctgaagcgg ctctccgacg cgctggcgga cggcgatccg    600

atcgtcgcgc tgatccgcgg atccgcggtc aatcaggacg gccgcagcgg cggcttcacc    660

gcgccgaacg aactggcgca gcaggcggtg atccggaccg cgctcgcggc agcgggcgtc    720

gccgcgtccg acatcggcta cgtggacacg cacggcaccg ggac                     764
```

-continued

<210> SEQ ID NO 41
<211> LENGTH: 763
<212> TYPE: DNA
<213> ORGANISM: Unknown organism
<220> FEATURE:
<223> OTHER INFORMATION: Origin of the sequence: soil organism

<400> SEQUENCE: 41
ccgcagcagc gcgtgttcct cgacggcatc gaccgcttcg atccgcagtt tttcgggatc 60
gcgccgcgcg aagcggccgg catcgatccg cagcagcggc tgctgctcga gacgacgtgg 120
gaagcgctgg aagacgccgg gacgtcgccg gaaaagctgc agggaacccc ggccggcgtg 180
ttcgtcggca tcaacagcat cgactacgcg acgctgcagc tgcagaactg cgatctggcc 240
agcatcgacg cctattcgct ctccggcagc gcgcacagca tcgcggccgg gcggctcgcc 300
tacgtgctcg gcctgcaggg gccggcgatg gcggtcgaca ccgcctgctc gtcgtcgctg 360
gtcgcgatcc acctggcgtg ccagagcctg cgcaacgacg actgccgcgt cgccgtggcc 420
ggcggcgtgc acgtcacgct gacgccgatc aacatggtcg tgttctcgaa gctgcgcatg 480
ctggcggcgg acggcaagtg caagacgttc gacggccgcg gcgacggatt cgtcgaaggc 540
gagggctgcg cggtcatcgt cctcaagcgg ttgtcgcacg cgcttgccga caaggatcgg 600
atcctcgcgc tggtgcgcgg ttcggcggtc aaccaggacg gcgcgagcag cggtctcacc 660
gcgccgaacg gtccggcgca ggaagcggtc atccgcgcgg cgttgaagcg ggccggcgtg 720
cagccggcgg aggtcggcta cgtggacacc cacggcaccg gca 763

<210> SEQ ID NO 42
<211> LENGTH: 668
<212> TYPE: DNA
<213> ORGANISM: Unknown organism
<220> FEATURE:
<223> OTHER INFORMATION: Origin of the sequence: soil organism
<220> FEATURE:
<221> NAME/KEY: modified_base
<222> LOCATION: (507)
<223> OTHER INFORMATION: variable nucleotide

<400> SEQUENCE: 42
ccgcaggagc gcgtgctgct ggaatcctcg tggcatgcgc tggaagacgc cggctatgcc 60
ggcgaaagca tcgccggcgc gcgctgcggc gtgtacatgg gcttcaacgg cggcgactac 120
ggcgacctgc tgtacggcca gccgtcgctg ccgccgcacg cgatgtgggg caacgccgcc 180
tcggtgctgt cggcgcgcat cgcctattac ctggacctgc aaggcccggc gatcaccctc 240
gacaccgcct gttcgagctc gttggtcgcg gtgcatctgg cctgccaggg gctgtggacc 300
ggcgagaccg atctggccct ggccggcggc gtgtggatcc agtgcacgcc cggattcctg 360
atctcctcca gccgcgccgg catgctctcg ccgaccggcc agtgccgcgc gttcggcgcc 420
ggcgccgacg gcttcgtgcc gtccgaaggc gtcggcgtgg tcgtgctcaa gcgcctgcag 480
gacgcgctcg acgccggcga ccacatntac ggcgtgatcc gcggcagcgc gatcaaccag 540
gacggcgcca gcaacggcat caccgcgccg agcgccgccg cccaggagcg cttgcagcgc 600
cacgtctacg acagcttcgg catcgacgcc tcgcgcctgc agatgatcga ggcccacggc 660
accggcac 668

<210> SEQ ID NO 43
<211> LENGTH: 671
<212> TYPE: DNA

-continued

<213> ORGANISM: Unknown organism
<220> FEATURE:
<223> OTHER INFORMATION: Origin of the sequence: soil organism

<400> SEQUENCE: 43
ccgcaggagc gcgtgctgct ggaggtgact tgggaggcac tcgaagacgc cggccaagac 60
gtggaccgtc tggccgggcg gcccgtcggc gtcttcgtcg ggatctcgtc gaacgattac 120
ggccagcttc agaacggcga cccggccgac gtggacgcct acgtcggcac cggtaacgcg 180
ctgagcatcg ccgccaaccg actcagctac acgtttgact ttcgcggccc gagtctggcg 240
gtggacacgg cgtgctcgtc ttcactcgtc gcgatccatc tcgcctgcca gagcgttcgc 300
cgcggtgaag cggaactcgc cgtcgcggcc ggcgtcaact tgattctgac ccccggcctg 360
acggtgaatt tcacccgcgc cggcatgatg gcgcctgacg gccggtgcaa gacgttcgac 420
gcggccgcca acggctacgt gcgcggcgaa ggcgccggcg tcgtcgtgct caagccgctg 480
gcccaggcta tcgccgacgg cgacccgatc tacgcgatcg tccgtggcag cgccgtcaac 540
caggacggcc gttccaacgg cctcaccgcc ccgaaccgac aggcccaaga ggtcgtgctg 600
cgggccgcgt atcgtgacgc gggcatcagc ccggccgatg tcgacgccgt cgaggcccac 660
ggcaccggca c 671

<210> SEQ ID NO 44
<211> LENGTH: 707
<212> TYPE: DNA
<213> ORGANISM: Unknown organism
<220> FEATURE:
<223> OTHER INFORMATION: Origin of the sequence: soil organism

<400> SEQUENCE: 44
ccccagcagc gcgtgttcct cgaggacgcg actgaggtcg acgtggatgc gctttcagac 60
ggcgaagacg tcgtgatcgc cggcatcatg cagcacatcg aggaggccgg catccactcg 120
ggcgattcat cgtgcgtgct tccgccggtc gacatcccgc cgaaggcgct gcagacgatc 180
cgcgatcaca cgttcaagct cgcgcgcgcg ttgaaggtca tcggcctgat gaacgtgcag 240
tacgcgattc agcgcgacaa ggtctacgtg attgaggtaa accctagggc ttctcgaact 300
gtcccgtatg tctcgaaggc gacaggcgtg ccgctggcga aggtcgcgtc acgcttgatg 360
accggacgca aactgcacga gctgttgccg gaaggggtcg agcgcggctg gatcaccacc 420
gcgggcgaga atttctacgt gaagtcgccg gtcttcccgt ggggtaagtt cccgggcgtt 480
gacactgtgc tcgggccgga gatgaaatcg accggcgaag tcatgggcgt cgccgacaac 540
ttcggcgagg ccttcgccaa ggcacagatc gccgccggca catacctgcc gaccgaaggt 600
accgtcttca tctcggtcaa cgaccgtgac aaaggcaacg tcattcagct ggcgcagcgt 660
ttctccgaac tcggtttcgg cattgtcgac acgcacggca ccgggac 707

<210> SEQ ID NO 45
<211> LENGTH: 225
<212> TYPE: PRT
<213> ORGANISM: Streptomyces ambofaciens

<400> SEQUENCE: 45

Pro Gln Gln His Val Phe Leu Glu Thr Val Trp Glu Thr Phe Glu Ser
1 5 10 15

Ala Gly Val Asp Pro Arg Ala Val Arg Gly Arg Ser Val Gly Met Phe
20 25 30

Val Gly Thr Asn Gly Gln Asp Tyr Pro Val Val Leu Ala Gly Ser Ala

-continued 35 40 45

Asp Glu Gly Leu Asp Ala His Ala Ala Thr Gly Asn Ala Ala Ala Val
50 55 60

Leu Ser Gly Arg Val Ser Tyr Ala Phe Gly Leu Glu Gly Pro Ala Val
65 70 75 80

Thr Val Asp Thr Ala Cys Ser Ser Ser Leu Val Ala Leu His Leu Ala
85 90 95

Ala Gln Ala Leu Arg Arg Gly Glu Cys Asp Leu Ala Leu Ala Gly Gly
100 105 110

Val Ser Glu Met Ser Thr Glu Ala Ala Phe Thr Glu Phe Ala Arg Gln
115 120 125

Gly Gly Leu Ala Asp Asp Gly Arg Cys Lys Ala Phe Ser Ala Asp Ala
130 135 140

Asp Gly Thr Gly Trp Gly Glu Gly Val Gly Val Leu Leu Val Glu Arg
145 150 155 160

Leu Ala Asp Ala Arg Arg Asn Gly His Arg Ala Leu Ala Leu Val Arg
165 170 175

Gly Ser Ala Val Asn Gln Asp Gly Ala Ser Asn Gly Leu Thr Ala Pro
180 185 190

Asn Gly Pro Ser Gln Gln Arg Val Ile Arg Gln Ala Leu Ala Asp Ala
195 200 205

Arg Leu Ser Pro Ser Glu Val Asp Ala Val Glu Thr His Gly Thr Gly
210 215 220

Thr
225

<210> SEQ ID NO 46
<211> LENGTH: 207
<212> TYPE: PRT
<213> ORGANISM: Streptomyces ambofaciens

<400> SEQUENCE: 46

Ala Ser Trp Glu Ala Val Glu Arg Ala Gly Ile Asp Met Arg Thr Leu
1 5 10 15

Arg Gly Gly Arg Thr Gly Val Phe Ala Gly Val Met Tyr His Asp Tyr
20 25 30

Pro Ser Val Val Asp Pro Glu Ala Leu Asp Gly Tyr Leu Gly Thr Ala
35 40 45

Asn Ala Gly Ser Val Leu Ser Gly Arg Ile Ala Tyr Thr Phe Gly Leu
50 55 60

Gln Gly Pro Ala Val Thr Val Asp Thr Ala Cys Ser Ser Ser Leu Val
65 70 75 80

Ala Leu His Leu Ala Ala Gln Ala Leu Pro Ala Gly Glu Cys Glu Leu
85 90 95

Ala Leu Val Gly Gly Val Thr Val Met Ser Gly Pro Met Met Phe Ala
100 105 110

Gly Phe Gly Leu Glu Asp Gly Ser Ala Ala Asp Gly Arg Cys Lys Ala
115 120 125

Phe Ala Ala Ala Ala Asp Gly Thr Gly Trp Gly Glu Gly Val Gly Val
130 135 140

Leu Leu Val Glu Arg Leu Ser Asp Ala Arg Arg His Gly His Arg Val
145 150 155 160

Leu Ala Val Val Arg Gly Ser Ala Val Asn Gln Asp Gly Ala Ser Gly
165 170 175

-continued

```
Gly Leu Thr Ala Pro Asn Gly Pro Ala Gln Gln Arg Val Ile Arg Gln
            180                 185                 190

Ala Leu Ala Ser Ala Ala Leu Val Pro Ala Glu Val Asp Ala Val
        195                 200                 205


<210> SEQ ID NO 47
<211> LENGTH: 223
<212> TYPE: PRT
<213> ORGANISM: Saccharopolyspora erythraea

<400> SEQUENCE: 47

Pro Gln Glu Arg Val Phe Leu Glu Leu Ala Trp Glu Ala Leu Asp Asn
  1               5                  10                  15

Ala Gly Ile Ala Pro His Ser Leu Arg Asp Ser Arg Thr Gly Val Phe
             20                  25                  30

Phe Gly Ala Met Trp His Gly Tyr Ala Gln Phe Ala Ala Gly Ala Val
         35                  40                  45

Asp Arg Ile Thr Gln His Thr Ala Thr Gly His Asp Leu Ser Ile Ile
     50                  55                  60

Pro Ala Arg Ile Ala Tyr Phe Leu Gly Leu Arg Gly Pro Asp Met Thr
 65                  70                  75                  80

Leu Asn Thr Ala Cys Ser Ser Ala Leu Val Ala Met His Gln Ala Arg
                 85                  90                  95

Gln Ser Ile Leu Leu Gly Glu Ser Ser Val Ala Leu Val Gly Gly Ile
            100                 105                 110

Ser Leu Leu Val Ala Leu Asp Ser Met Val Ala Met Ser Arg Phe Gly
        115                 120                 125

Ala Met Ala Pro Asp Gly Arg Cys Lys Ala Phe Asp Ser Arg Ala Asn
    130                 135                 140

Gly Tyr Val Arg Gly Glu Gly Gly Gly Val Val Val Leu Lys Pro Leu
145                 150                 155                 160

Ser Arg Ala Leu Ala Asp Gly Asn Pro Val Tyr Cys Val Leu Arg Gly
                165                 170                 175

Ser Ala Val Asn Asn Asp Gly Phe Ser Asn Gly Leu Thr Ala Pro Ser
            180                 185                 190

Pro Ala Ala Gln Glu Gln Val Leu Arg Asp Ala Tyr Ala Asn Ala Gly
        195                 200                 205

Val Asp Pro Ala Gln Val Asp Tyr Val Glu Thr His Gly Thr Gly
    210                 215                 220


<210> SEQ ID NO 48
<211> LENGTH: 211
<212> TYPE: PRT
<213> ORGANISM: Unknown organism
<220> FEATURE:
<223> OTHER INFORMATION: Origin of the sequence: soil organism

<400> SEQUENCE: 48

Ser Cys Trp Glu Ala Leu Glu His Ala Gly Tyr Asp Thr Ala Arg Tyr
  1               5                  10                  15

Pro Gly Arg Ile Gly Leu Trp Ala Gly Ala Gly Phe Asn Ser Tyr Leu
             20                  25                  30

Leu Thr Asn Leu Met Asn Asn Arg Ala Phe Leu Glu Ser Val Gly Met
         35                  40                  45

Tyr Gln Ile Phe Leu Ser Asn Asp Lys Asp Phe Ile Ala Thr Arg Thr
     50                  55                  60

Ala Tyr Lys Leu Asn Leu Arg Gly Pro Ala Met Ala Val Gly Thr Ala
```

-continued

```
 65                  70                  75                  80

Cys Ser Thr Ser Leu Val Ala Val His Glu Ala Cys Gln Ala Leu Arg
                 85                  90                  95

Leu Gly Glu Cys Asp Met Ala Leu Ala Gly Ala Ala Ser Val Ser Thr
            100                 105                 110

Pro Leu Arg Glu Gly Tyr Leu Tyr Gln Glu Gly Met Ile Met Ser Arg
        115                 120                 125

Asp Gly Val Cys Arg Pro Phe Asp Ala Asp Ala Asp Gly Thr Val Leu
    130                 135                 140

Gly Asn Gly Val Ala Val Val Val Leu Lys Arg Leu Asp Glu Ala Leu
145                 150                 155                 160

Arg Asp Gly Asp Thr Val Tyr Ala Val Ile Arg Gly Thr Ala Val Asn
                165                 170                 175

Asn Asp Gly Ser Val Lys Ile Gly Phe Thr Ala Pro Ser Ala Glu Gly
            180                 185                 190

Gln Ser Arg Val Val Arg Asp Ala Leu Arg Ala Ala Ala Val Pro Ala
        195                 200                 205

Glu Ser Val
    210


<210> SEQ ID NO 49
<211> LENGTH: 229
<212> TYPE: PRT
<213> ORGANISM: Unknown organism
<220> FEATURE:
<223> OTHER INFORMATION: Origin of the sequence: soil organism

<400> SEQUENCE: 49

Pro Gln Gln Arg Leu Phe Leu Glu Cys Ala Trp Glu Ala Met Glu Asn
  1               5                  10                  15

Ala Gly Tyr Ala Ala Arg Ser Tyr Lys Gly Ser Ile Gly Val Phe Ala
             20                  25                  30

Gly Cys Gly Val Asn Thr Tyr Leu Leu Asn Asn Leu Ala Thr Ala Glu
         35                  40                  45

Pro Phe Asp Phe Ser Arg Pro Ser Ala Tyr Gln Leu Leu Thr Ala Asn
     50                  55                  60

Asp Lys Asp Phe Leu Ala Thr Arg Val Ser Tyr Lys Leu Asn Leu Arg
 65                  70                  75                  80

Gly Pro Ser Leu Thr Val Gln Thr Ala Cys Ser Thr Ser Leu Val Ser
                 85                  90                  95

Val Val Met Ala Cys Glu Ser Leu Gln Arg Gly Ala Ser Asp Ile Ala
            100                 105                 110

Leu Ala Gly Gly Val Ala Ile Asn Val Pro Gln Ser Val Gly Tyr Leu
        115                 120                 125

His Gln Pro Gly Met Ile Leu Ser Pro Asp Gly Arg Cys Arg Ala Phe
    130                 135                 140

Asp Glu Ser Ala Gln Gly Thr Val Pro Gly Asn Gly Ala Gly Val Val
145                 150                 155                 160

Val Leu Lys Arg Leu Ser Arg Ala Leu Ala Asp Gly Asp Thr Ile Tyr
                165                 170                 175

Ala Val Ile Arg Gly Ala Ala Ile Asn Asn Asp Gly Ala Glu Arg Met
            180                 185                 190

Gly Phe Thr Ala Pro Gly Val Asp Gly Gln Thr Arg Leu Ile Arg Arg
        195                 200                 205

Thr Gln Glu Met Ala Gly Val Lys Pro Glu Ser Ile Gly Tyr Met Asp
```

-continued

```
    210                 215                 220

Thr His Gly Thr Gly
225


<210> SEQ ID NO 50
<211> LENGTH: 223
<212> TYPE: PRT
<213> ORGANISM: Unknown organism
<220> FEATURE:
<223> OTHER INFORMATION: Origin of the sequence: soil organism

<400> SEQUENCE: 50

Pro Gln Gln Arg Leu Phe Leu Glu Val Ala Trp Glu Ala Leu Glu Arg
  1               5                  10                  15

Ala Gly Arg Pro Pro Asp Ser Leu Ala Gly Ser Asp Thr Gly Val Phe
             20                  25                  30

Ile Gly Ile Ser Thr Asp Asp Tyr Ser Arg Leu Lys Pro Thr Asp Pro
         35                  40                  45

Ala Leu Ile Asp Ala Tyr Thr Gly Thr Gly Thr Ala Phe Ser Thr Ala
     50                  55                  60

Ala Gly Arg Ile Ser Tyr Leu Leu Gly Leu Gln Gly Pro Asn Phe Pro
 65                  70                  75                  80

Val Asp Thr Ala Cys Ser Ser Ser Leu Val Ala Val His Leu Ala Cys
                 85                  90                  95

Arg Ser Leu Gln Ser Arg Glu Cys Ser Met Ala Leu Ala Gly Gly Val
            100                 105                 110

Asn Leu Ile Leu Ala Pro Glu Ser Thr Ile Tyr Phe Cys Arg Leu Arg
        115                 120                 125

Ala Met Ala Ala Asp Gly Arg Cys Lys Ser Phe Ala Ala Ser Ala Asp
    130                 135                 140

Gly Tyr Gly Arg Gly Glu Gly Cys Gly Met Leu Val Leu Lys Arg Leu
145                 150                 155                 160

Ser Asp Ala Thr Arg Asp Gly Asp Arg Ile Leu Ala Leu Ile Arg Gly
                165                 170                 175

Ser Ala Val Asn His Gly Gly Arg Ser Asn Gly Leu Thr Ala Pro Asn
            180                 185                 190

Gly Pro Ala Gln Glu Ala Val Ile Arg Ala Ala Leu Lys Asn Ala Gly
        195                 200                 205

Met Ala Pro Ala Asp Val Asp Tyr Val Asp Thr His Gly Thr Gly
    210                 215                 220


<210> SEQ ID NO 51
<211> LENGTH: 252
<212> TYPE: PRT
<213> ORGANISM: Unknown organism
<220> FEATURE:
<223> OTHER INFORMATION: Origin of the sequence: soil organism

<400> SEQUENCE: 51

Pro Gln Glu Arg Val Phe Leu Glu Arg Ile Asp Gly Phe Asp Ala Glu
  1               5                  10                  15

Phe Phe Gly Ile Ser Pro Arg Glu Ala Leu Asn Met Asp Pro Gln Gln
             20                  25                  30

Arg Leu Leu Leu Glu Val Cys Trp Glu Ala Ala Glu Asp Ala Gly Ile
         35                  40                  45

Ser Pro Gly Pro Leu Ala Gly Ser Ala Thr Gly Val Phe Ala Gly Ser
     50                  55                  60
```

-continued

Cys Ala Gln Asp Phe Gly Leu Phe Gln Tyr Ala Asp Pro Ala Arg Ile
65 70 75 80

Gly Ala Trp Ser Gly Ser Gly Val Ala His Ser Met Leu Ala Asn Arg
85 90 95

Ile Ser Tyr Leu Leu Asp Leu Arg Gly Pro Ser Met Ala Val Asp Thr
100 105 110

Ala Cys Ser Ser Ala Leu Val Ala Val His Leu Ala Cys Gln Ser Leu
115 120 125

Arg Arg Arg Glu Cys Asp Ala Ala Phe Ala Gly Gly Val Asn Leu Ile
130 135 140

Leu Thr Pro Glu Gly Met Ile Ala Leu Ser Lys Ala Arg Met Leu Ala
145 150 155 160

Pro Asp Gly Arg Cys Lys Thr Phe Asp Ala Ala Ala Asp Gly Tyr Val
165 170 175

Arg Gly Glu Gly Cys Gly Ile Val Leu Leu Lys Arg Leu Ser Asp Ala
180 185 190

Leu Ala Asp Gly Asp Ala Ile Cys Ala Val Ile Arg Gly Ser Ala Ile
195 200 205

Asn Gln Asp Gly Arg Ser Asn Gly Ile Thr Ala Pro Asn Leu Gln Ala
210 215 220

Gln Lys Ala Val Leu Gln Glu Ala Val Ala Asn Ala His Ile Asp Pro
225 230 235 240

Ser His Val Ser Leu Ile Asp Thr His Gly Thr Gly
245 250

<210> SEQ ID NO 52
<211> LENGTH: 234
<212> TYPE: PRT
<213> ORGANISM: Unknown organism
<220> FEATURE:
<223> OTHER INFORMATION: Origin of the sequence: soil organism

<400> SEQUENCE: 52

Pro Gln Gln Arg Val Phe Leu Glu Cys Ala Trp Glu Ala Val Glu Ser
1 5 10 15

Ala Gly Tyr Asp Pro Glu Lys Tyr Pro Gly Leu Ile Gly Val Phe Ala
20 25 30

Gly Ala Ser Ile Asn Ser Tyr Phe Leu Tyr Asn Leu Ala His Asn Arg
35 40 45

Glu Phe Val Ala Arg Met Ala Gly Glu Tyr Gln Val Gly Glu Tyr Gln
50 55 60

Thr Ile Leu Gly Asn Asp Lys Asp Tyr Leu Pro Thr Arg Val Ser Tyr
65 70 75 80

Lys Leu Asn Leu Arg Gly Pro Ser Leu Ala Val Gln Ser Ala Cys Ser
85 90 95

Thr Gly Leu Val Ala Val Cys Gln Ala Ile Gln Asn Leu Gln Thr Tyr
100 105 110

Gln Cys Asp Met Ala Leu Ala Gly Gly Ile Ser Ile Ser Phe Pro Gln
115 120 125

Lys Arg Asp Tyr Arg Phe Thr Asp Glu Gly Met Val Ser Arg Asp Gly
130 135 140

His Cys Arg Pro Phe Asp Ala Ser Ala Gln Gly Thr Val Phe Gly Asn
145 150 155 160

Gly Ala Gly Val Val Leu Met Lys Arg Leu Ala Asp Ala Val Thr Asp
165 170 175

-continued

```
Arg Asp Thr Ile Leu Ala Val Ile Arg Gly Ala Ala Val Asn Asn Asp
            180                 185                 190

Gly Gly Val Lys Met Gly Tyr Thr Ala Pro Ser Ala Glu Gly Gln Ala
        195                 200                 205

Glu Ala Ile Thr Leu Ala Leu Ala Leu Ala Gly Val Ser Pro Glu Thr
    210                 215                 220

Ile Thr Cys Met Asp Thr His Gly Thr Gly
225                 230
```

<210> SEQ ID NO 53
<211> LENGTH: 226
<212> TYPE: PRT
<213> ORGANISM: Unknown organism
<220> FEATURE:
<223> OTHER INFORMATION: Origin of the sequence: soil organism

<400> SEQUENCE: 53

```
Pro Gln Gln Arg Val Phe Leu Glu Cys Ala Trp Ala Ala Leu Glu Arg
  1               5                  10                  15

Arg Arg Ile Ser Gly Arg His Leu Pro Arg Cys Pro Ser Ala Val Tyr
             20                  25                  30

Ala Ser Ser Gly Phe Asn Thr Tyr Leu Leu Asn Leu His Ala Asn Ala
         35                  40                  45

Ala Val Arg Gln Ser Ile Ser Pro Phe Glu Leu Phe Val Ala Asn Asp
     50                  55                  60

Lys Asp Phe Leu Ala Thr Arg Thr Ala Tyr Lys Leu Asn Leu Arg Gly
 65                  70                  75                  80

Pro Ala Met Thr Val Gln Thr Ala Cys Ser Ser Ser Leu Val Ala Val
                 85                  90                  95

His Val Ala Ala Gln Ser Leu Leu Ala Gly Glu Cys Asp Ile Ala Leu
            100                 105                 110

Ala Gly Gly Ile Thr Val Ser Arg Ser His Gly Tyr Val Ala Arg Glu
        115                 120                 125

Gly Gly Ile Leu Ser Pro Asp Gly His Cys Arg Ala Phe Asp Ala Asp
    130                 135                 140

Ala Gly Gly Thr Val Pro Gly Ser Gly Val Gly Val Val Val Leu Lys
145                 150                 155                 160

Arg Leu Glu Asp Ala Leu Ala Asp Gly Asp Thr Ile Asp Ala Val Ile
                165                 170                 175

Ile Gly Ser Ala Ile Asn Asn Asp Gly Ala Leu Lys Ala Ser Phe Thr
            180                 185                 190

Ala Pro Gln Val Asp Ser Gln Ala Leu Val Ile Ser Glu Ala His Ala
        195                 200                 205

Ala Ala Gly Ile Ser Ala Asp Ser Ile Gly Tyr Met Asp Thr His Gly
    210                 215                 220

Thr Gly
225
```

<210> SEQ ID NO 54
<211> LENGTH: 223
<212> TYPE: PRT
<213> ORGANISM: Unknown organism
<220> FEATURE:
<223> OTHER INFORMATION: Origin of the sequence: soil organism

<400> SEQUENCE: 54

```
Pro Gln Gln Arg Leu Phe Leu Glu Leu Thr Trp Glu Ala Leu Glu Asp
  1               5                  10                  15
```

-continued

```
Ala Gly Ile Pro Pro Ser Thr Ile Ala Gly Thr Asn Val Gly Val Phe
            20                  25                  30

Met Gly Ala Ser Gln Ala Asp Tyr Gly His Lys Phe Phe Ser Asp His
        35                  40                  45

Ala Val Ala Asp Ser His Phe Ala Thr Gly Thr Ser Leu Ala Val Val
    50                  55                  60

Ala Asn Arg Ile Ser Tyr Ile Tyr Asp Leu Arg Gly Pro Ser Leu Thr
 65                  70                  75                  80

Val Asp Thr Ala Cys Ser Ser Ser Leu Val Ala Leu His Gln Ala Val
                85                  90                  95

Glu Ala Leu Arg Ser Gly Arg Ile Glu Thr Ala Ile Val Gly Gly Ile
            100                 105                 110

Asn Val Ile Ala Ser Pro Ala Ser Phe Ile Ala Phe Ser Gln Ala Ser
        115                 120                 125

Met Leu Ser Pro Thr Gly Leu Cys Gln Ala Phe Ser Ala Lys Ala Asp
    130                 135                 140

Gly Phe Val Arg Gly Glu Gly Gly Thr Val Phe Val Leu Arg Lys Ala
145                 150                 155                 160

Ala His Ala His Gly Ser Arg Asn Pro Val Arg Gly Leu Ile Leu Ala
                165                 170                 175

Thr Asp Val Asn Ser Asp Gly Arg Thr Asn Gly Ile Ser Leu Pro Ser
            180                 185                 190

Ala Glu Ala Gln Glu Val Leu Leu Gln Arg Val Tyr Ser Arg Ala Ser
        195                 200                 205

Ile Asp Pro Asn Arg Leu Ala Phe Val Asp Thr His Gly Thr Gly
    210                 215                 220
```

<210> SEQ ID NO 55
<211> LENGTH: 254
<212> TYPE: PRT
<213> ORGANISM: Unknown organism
<220> FEATURE:
<223> OTHER INFORMATION: Origin of the sequence: soil organism

<400> SEQUENCE: 55

```
Pro Gln Gln Arg Val Phe Leu Asp Gly Ile Asp Arg Phe Asp Pro Arg
  1               5                  10                  15

His Phe Ala Ile Thr Pro Arg Glu Ala Ile Ser Met Asp Pro Gln Gln
            20                  25                  30

Arg Leu Leu Leu Glu Val Thr Trp Glu Ala Leu Glu Arg Ala Gly Val
        35                  40                  45

Ala Pro Asp Arg Leu Thr Gly Ser Asp Thr Gly Val Phe Ile Gly Ile
    50                  55                  60

Ser Thr Asn Asp Tyr Gly Gln Ile Leu Leu Arg Ala Ser Asp Gln Ile
 65                  70                  75                  80

Asp Pro Gly Met Tyr Phe Gly Thr Gly Asn Leu Leu Asn Ala Ala Ala
                85                  90                  95

Gly Arg Leu Ser Tyr Val Leu Gly Leu Gln Gly Pro Ser Met Ala Val
            100                 105                 110

Asp Thr Ala Cys Pro Ser Ser Leu Val Ala Ile His Leu Ala Cys Gln
        115                 120                 125

Ser Leu Arg Asn Arg Glu Cys Arg Met Ala Leu Ala Gly Gly Ala Asn
    130                 135                 140

Leu Val Leu Val Pro Glu Val Thr Val Asn Cys Cys Arg Ala Lys Met
145                 150                 155                 160
```

-continued

```
Leu Ala Pro Asp Gly Arg Cys Lys Thr Phe Asp Ala Ala Ala Asp Gly
                165                 170                 175

Tyr Val Arg Gly Glu Gly Ala Ala Val Ile Val Leu Lys Arg Leu Ser
            180                 185                 190

Asp Ala Leu Ala Asp Gly Asp Pro Ile Val Ala Leu Ile Arg Gly Ser
        195                 200                 205

Ala Val Asn Gln Asp Gly Arg Ser Gly Gly Phe Thr Ala Pro Asn Glu
    210                 215                 220

Leu Ala Gln Gln Ala Val Ile Arg Thr Ala Leu Ala Ala Ala Gly Val
225                 230                 235                 240

Ala Ala Ser Asp Ile Gly Tyr Val Asp Thr His Gly Thr Gly
                245                 250


<210> SEQ ID NO 56
<211> LENGTH: 254
<212> TYPE: PRT
<213> ORGANISM: Unknown organism
<220> FEATURE:
<223> OTHER INFORMATION: Origin of the sequence: soil organism

<400> SEQUENCE: 56

Pro Gln Gln Arg Val Phe Leu Asp Gly Ile Asp Arg Phe Asp Pro Gln
  1               5                  10                  15

Phe Phe Gly Ile Ala Pro Arg Glu Ala Ala Gly Ile Asp Pro Gln Gln
            20                  25                  30

Arg Leu Leu Leu Glu Thr Thr Trp Glu Ala Leu Glu Asp Ala Gly Thr
        35                  40                  45

Ser Pro Glu Lys Leu Gln Gly Thr Pro Ala Gly Val Phe Val Gly Ile
    50                  55                  60

Asn Ser Ile Asp Tyr Ala Thr Leu Gln Leu Gln Asn Cys Asp Leu Ala
 65                  70                  75                  80

Ser Ile Asp Ala Tyr Ser Leu Ser Gly Ser Ala His Ser Ile Ala Ala
                85                  90                  95

Gly Arg Leu Ala Tyr Val Leu Gly Leu Gln Gly Pro Ala Met Ala Val
            100                 105                 110

Asp Thr Ala Cys Ser Ser Ser Leu Val Ala Ile His Leu Ala Cys Gln
        115                 120                 125

Ser Leu Arg Asn Asp Asp Cys Arg Val Ala Val Ala Gly Gly Val His
    130                 135                 140

Val Thr Leu Thr Pro Ile Asn Met Val Val Phe Ser Lys Leu Arg Met
145                 150                 155                 160

Leu Ala Ala Asp Gly Lys Cys Lys Thr Phe Asp Gly Arg Gly Asp Gly
                165                 170                 175

Phe Val Glu Gly Glu Gly Cys Ala Val Ile Val Leu Lys Arg Leu Ser
            180                 185                 190

His Ala Leu Ala Asp Lys Asp Arg Ile Leu Ala Leu Val Arg Gly Ser
        195                 200                 205

Ala Val Asn Gln Asp Gly Ala Ser Ser Gly Leu Thr Ala Pro Asn Gly
    210                 215                 220

Pro Ala Gln Glu Ala Val Ile Arg Ala Ala Leu Lys Arg Ala Gly Val
225                 230                 235                 240

Gln Pro Ala Glu Val Gly Tyr Val Asp Thr His Gly Thr Gly
                245                 250


<210> SEQ ID NO 57
```

-continued

<211> LENGTH: 222
<212> TYPE: PRT
<213> ORGANISM: Unknown organism
<220> FEATURE:
<223> OTHER INFORMATION: Origin of the sequence: soil organism
<220> FEATURE:
<221> NAME/KEY: MOD_RES
<222> LOCATION: (169)
<223> OTHER INFORMATION: any amino acid

<400> SEQUENCE: 57

```
Pro Gln Glu Arg Val Leu Leu Glu Ser Ser Trp His Ala Leu Glu Asp
  1               5                  10                  15

Ala Gly Tyr Ala Gly Glu Ser Ile Ala Gly Ala Arg Cys Gly Val Tyr
             20                  25                  30

Met Gly Phe Asn Gly Gly Asp Tyr Gly Asp Leu Leu Tyr Gly Gln Pro
         35                  40                  45

Ser Leu Pro Pro His Ala Met Trp Gly Asn Ala Ala Ser Val Leu Ser
     50                  55                  60

Ala Arg Ile Ala Tyr Tyr Leu Asp Leu Gln Gly Pro Ala Ile Thr Leu
 65                  70                  75                  80

Asp Thr Ala Cys Ser Ser Ser Leu Val Ala Val His Leu Ala Cys Gln
                 85                  90                  95

Gly Leu Trp Thr Gly Glu Thr Asp Leu Ala Leu Ala Gly Gly Val Trp
            100                 105                 110

Ile Gln Cys Thr Pro Gly Phe Leu Ile Ser Ser Ser Arg Ala Gly Met
        115                 120                 125

Leu Ser Pro Thr Gly Gln Cys Arg Ala Phe Gly Ala Gly Ala Asp Gly
    130                 135                 140

Phe Val Pro Ser Glu Gly Val Gly Val Val Val Leu Lys Arg Leu Gln
145                 150                 155                 160

Asp Ala Leu Asp Ala Gly Asp His Xaa Tyr Gly Val Ile Arg Gly Ser
                165                 170                 175

Ala Ile Asn Gln Asp Gly Ala Ser Asn Gly Ile Thr Ala Pro Ser Ala
            180                 185                 190

Ala Ala Gln Glu Arg Leu Gln Arg His Val Tyr Asp Ser Phe Gly Ile
        195                 200                 205

Asp Ala Ser Arg Leu Gln Met Ile Glu Ala His Gly Thr Gly
    210                 215                 220
```

<210> SEQ ID NO 58
<211> LENGTH: 223
<212> TYPE: PRT
<213> ORGANISM: Unknown organism
<220> FEATURE:
<223> OTHER INFORMATION: Origin of the sequence: soil organism

<400> SEQUENCE: 58

```
Pro Gln Glu Arg Val Leu Leu Glu Val Thr Trp Glu Ala Leu Glu Asp
  1               5                  10                  15

Ala Gly Gln Asp Val Asp Arg Leu Ala Gly Arg Pro Val Gly Val Phe
             20                  25                  30

Val Gly Ile Ser Ser Asn Asp Tyr Gly Gln Leu Gln Asn Gly Asp Pro
         35                  40                  45

Ala Asp Val Asp Ala Tyr Val Gly Thr Gly Asn Ala Leu Ser Ile Ala
     50                  55                  60

Ala Asn Arg Leu Ser Tyr Thr Phe Asp Phe Arg Gly Pro Ser Leu Ala
 65                  70                  75                  80
```

-continued

```
Val Asp Thr Ala Cys Ser Ser Ser Leu Val Ala Ile His Leu Ala Cys
                 85                  90                  95

Gln Ser Val Arg Arg Gly Glu Ala Glu Leu Ala Val Ala Ala Gly Val
            100                 105                 110

Asn Leu Ile Leu Thr Pro Gly Leu Thr Val Asn Phe Thr Arg Ala Gly
        115                 120                 125

Met Met Ala Pro Asp Gly Arg Cys Lys Thr Phe Asp Ala Ala Ala Asn
    130                 135                 140

Gly Tyr Val Arg Gly Glu Gly Ala Gly Val Val Val Leu Lys Pro Leu
145                 150                 155                 160

Ala Gln Ala Ile Ala Asp Gly Asp Pro Ile Tyr Ala Ile Val Arg Gly
                165                 170                 175

Ser Ala Val Asn Gln Asp Gly Arg Ser Asn Gly Leu Thr Ala Pro Asn
            180                 185                 190

Arg Gln Ala Gln Glu Val Val Leu Arg Ala Ala Tyr Arg Asp Ala Gly
        195                 200                 205

Ile Ser Pro Ala Asp Val Asp Ala Val Glu Ala His Gly Thr Gly
    210                 215                 220


<210> SEQ ID NO 59
<211> LENGTH: 235
<212> TYPE: PRT
<213> ORGANISM: Unknown organism
<220> FEATURE:
<223> OTHER INFORMATION: Origin of the sequence: soil organism

<400> SEQUENCE: 59

Pro Gln Gln Arg Val Phe Leu Glu Asp Ala Thr Glu Val Asp Val Asp
  1               5                  10                  15

Ala Leu Ser Asp Gly Glu Asp Val Val Ile Ala Gly Ile Met Gln His
             20                  25                  30

Ile Glu Glu Ala Gly Ile His Ser Gly Asp Ser Ser Cys Val Leu Pro
         35                  40                  45

Pro Val Asp Ile Pro Pro Lys Ala Leu Gln Thr Ile Arg Asp His Thr
     50                  55                  60

Phe Lys Leu Ala Arg Ala Leu Lys Val Ile Gly Leu Met Asn Val Gln
 65                  70                  75                  80

Tyr Ala Ile Gln Arg Asp Lys Val Tyr Val Ile Glu Val Asn Pro Arg
                 85                  90                  95

Ala Ser Arg Thr Val Pro Tyr Val Ser Lys Ala Thr Gly Val Pro Leu
            100                 105                 110

Ala Lys Val Ala Ser Arg Leu Met Thr Gly Arg Lys Leu His Glu Leu
        115                 120                 125

Leu Pro Glu Gly Val Glu Arg Gly Trp Ile Thr Thr Ala Gly Glu Asn
    130                 135                 140

Phe Tyr Val Lys Ser Pro Val Phe Pro Trp Gly Lys Phe Pro Gly Val
145                 150                 155                 160

Asp Thr Val Leu Gly Pro Glu Met Lys Ser Thr Gly Glu Val Met Gly
                165                 170                 175

Val Ala Asp Asn Phe Gly Glu Ala Phe Ala Lys Ala Gln Ile Ala Ala
            180                 185                 190

Gly Thr Tyr Leu Pro Thr Glu Gly Thr Val Phe Ile Ser Val Asn Asp
        195                 200                 205

Arg Asp Lys Gly Asn Val Ile Gln Leu Ala Gln Arg Phe Ser Glu Leu
    210                 215                 220
```

Gly Phe Gly Ile Val Asp Thr His Gly Thr Gly
225                 230                 235

<210> SEQ ID NO 60
<211> LENGTH: 1269
<212> TYPE: DNA
<213> ORGANISM: Unknown organism
<220> FEATURE:
<223> OTHER INFORMATION: Origin of the sequence: soil organism

<400> SEQUENCE: 60

| | | | | | |
|---|---|---|---|---|---|
| taacaggaag | aagcttgctt | ctttgctgac | gagtggcgga | cgggtgagta | acacgtggga | 60 |
| acctgcctta | tggttcggga | taacgtctgg | aaacggacgc | taacaccgga | tgtgcccttc | 120 |
| gggggaaagt | ttacgccatg | agaggggccc | gcgtccgatt | aggtagttgg | tggggtaatg | 180 |
| gcccaccaag | ccgacgatcg | gtagctggtc | tgagaggatg | atcagccaca | ctgggactga | 240 |
| gacacggccc | agactcctac | gggaggcagc | agtggggaat | attggacaat | ggggcaacc | 300 |
| ctgatccagc | aatgccgcgt | gagtgatgaa | ggccttaggg | ttgtaaagct | ctttcgcacg | 360 |
| cgacgatgat | gacggtagcg | tgagaagaag | ccccggctaa | cttcgtgcca | gcagccgcgg | 420 |
| taatacgaag | ggggcgagcg | ttgttcggaa | ttactgggcg | taaagggcgc | gtaggcggcc | 480 |
| cgatcagtca | gatgtgaaag | ccccgggctc | aacctgggaa | ctgcatttga | tactgtcggg | 540 |
| cttgagttcc | ggagaggatg | gtggaattcc | cagtgtagag | gtgaaattcg | tagatattgg | 600 |
| gaagaacacc | ggtggcgaag | gcggccatct | ggacggacac | tgacgctgag | gcgcgaaagc | 660 |
| gtggggagca | aacaggatta | gataccctgg | tagtccacgc | cgtaaacgat | gaatgctaga | 720 |
| cgctggggtg | catgcacttc | ggtgtcgccg | ctaacgcatt | aagcattccg | cctggggagt | 780 |
| acggccgcaa | ggttaaaact | caaaggaatt | gacgggggcc | cgcacaagcg | gtggagcatg | 840 |
| tggtttaatt | cgaagcaacg | cgcagaacct | taccaaccct | tgacatgtcc | attgccggtc | 900 |
| cgagagattg | gaccttcagt | tcggctggat | ggaacacagg | tgctgcatgg | ctgtcgtcag | 960 |
| ctcgtgtcgt | gagatgttgg | gttaagtccc | gcaacgagcg | caacccctac | cgccagttgc | 1020 |
| catcattcag | ttgggcactc | tggtggaact | gccggtgaca | agccggagga | aggcggggat | 1080 |
| gacgtcaagt | cctcatggcc | cttatgggtt | gggctacaca | cgtgctacaa | tagcggtgac | 1140 |
| agtgggacgc | gaagtcgcaa | gatggagcaa | atccccaaaa | gccgtctcag | ttcggattgc | 1200 |
| actctgcaac | tcgggtgcat | gaagttggaa | tcgctagtaa | tcgcggatca | gcacgccgcg | 1260 |
| gtgaatacg | | | | | | 1269 |

<210> SEQ ID NO 61
<211> LENGTH: 1500
<212> TYPE: DNA
<213> ORGANISM: Unknown organism
<220> FEATURE:
<223> OTHER INFORMATION: Origin of the sequence: soil organism

<400> SEQUENCE: 61

| | | | | | |
|---|---|---|---|---|---|
| ttttaaaacg | acggccagtg | aattgtaata | cgactcacta | tagggcgaat | tgggccctct | 60 |
| agatgcatgc | tcgagcggcc | gccagtgtga | tggatatctg | cagaattcgc | ccttcaggcc | 120 |
| taacacatgc | aagtcgaacg | agggcttcgg | ccctagtggc | gcacgggtga | gtaacacgtg | 180 |
| ggaacctgcc | ttatggttcg | ggataacgtc | tggaaacgga | cgctaacacc | ggatgtgccc | 240 |
| ttcgggggaa | agtttacgcc | atgagagggg | cccgcgtccg | attaggtagt | tggtggggta | 300 |
| atggcccacc | aagccgacga | tcggtagctg | gtctgagagg | atgatcagcc | acactgggac | 360 |

-continued

```
tgagacacgg cccagactcc tacgggaggc agcagtgggg aatattggac aatgggggca    420

accctgatcc agcaatgccg cgtgagtgat gaaggcctta gggttgtaaa gctctttcgc    480

acgcgacgat gatgacggta gcgtgagaag aagccccggc taacttcgtg ccagcagccg    540

cggtaatacg aaggggcga gcgttgttcg gaattactgg gcgtaaaggg cgcgtaggcg    600

gcccgatcag tcagatgtga aagccccggg ctcaacctgg gaactgcatt tgatactgtc    660

gggcttgagt tccggagagg atggtggaat tcccagtgta gaggtgaaat tcgtagatat    720

tgggaagaac accggtggcg aaggcggcca tctggacgga cactgacgct gaggcgcgaa    780

agcgtgggga gcaaacagga ttagataccc tggtagtcca cgccgtaaac gatgaatgct    840

agacgctggg gtgcatgcac ttcggtgtcg ccgctaacgc attaagcatt ccgcctgggg    900

agtacggccg caaggttaaa actcaaagga attgacgggg gcccgcacaa gcggtggagc    960

atgtggttta attcgaagca acgcgcagaa ccttaccaac ccttgacatg tccattgccg   1020

gtccgagaga ttggaccttc agttcggctg gatggaacac aggtgctgca tggctgtcgt   1080

cagctcgtgt cgtgagatgt tgggttaagt cccgcaacga gcgcaacccc taccgccagt   1140

tgccatcatt cagttgggca ctctggtgga actgccggtg acaagccgga ggaaggcggg   1200

gatgacgtca agtcctcatg gcccttatgg gttgggctac acacgtgcta caatggcggt   1260

gacagtggga cgcgaagtcg caagatggag caaatcccca aaagccgtct cagttcggat   1320

tgcactctgc aactcgggtg catgaagttg gaatcgctag taatcgcgga tcagcacgcc   1380

gcggtgaata cgttcccggg ccttgtacac accgcccaag ggcgaattcc agcacactgg   1440

cggccgttac tagtggatcc gagctcggta ccaagcttgg cgtaatcatg gtcatagctg   1500
```

```
<210> SEQ ID NO 62
<211> LENGTH: 1366
<212> TYPE: DNA
<213> ORGANISM: Unknown organism
<220> FEATURE:
<223> OTHER INFORMATION: Origin of the sequence: soil organism

<400> SEQUENCE: 62

acgacggcca gtgaattgta atacgactca ctatagggcg aattgggccc tctagatgca     60

tgctcgagcg gccgccagtg tgatggatat ctgcagaatt cgcccttcag gcctaacaca    120

tgcaagtcga acgaaggctt cggccttagt ggcgcacggg tgagtaacac gtgggaacct    180

gcctttcggt tcggaataac gtctggaaac ggacgctaac accggatacg cccttcgggg    240

gaaagttcac gccgagagag gggcccgcgt cggattaggt agttggtgag gtaatggctc    300

accaagcctt cgatccgtag ctggtctgag aggatgatca gccacactgg gactgagaca    360

cggcccagac tcctacggga ggcagcagtg gggaatattg gacaatgggc gcaagcctga    420

tccagcaatg ccgcgtgagt gatgaaggcc ttagggttgt aaagctcttt cgcacgcgac    480

gatgatgacg gtagcgtgag aagaagcccc ggctaacttc gtgccagcag ccgcggtaat    540

acgaaggggg ctagcgttgt tcggaattac tgggcgtaaa gggcgcgtag gcggcctgct    600

tagtcagaag tgaaagcccc gggctcaacc tgggaatagc ttttgatact ggcaggcttg    660

agttccggag aggatggtgg aattcccagt gtagaggtga aattcgtaga tattgggaag    720

aacaccggtg gcgaaggcgg ccatctggac ggacactgac gctgaggcgc gaaagcgtgg    780

ggagcaaaca ggattagata ccctggtagt ccacgccgta aacgatgaat gctagacgtc    840

ggggtgcatg cacttcggtg tcgccgctaa cgcattaagc attccgcctg gggagtacgg    900

ccgcaaggtt aaaactcaaa ggaattgacg ggggcccgca caagcggtgg agcatgtggt    960
```

-continued

```
ttaattcgaa gcaacgcgca gaaccttacc aacccttgac atgtccatta tgggcttcag   1020

agatgaggtc cttcagttcg gctgggtgga acacaggtgc tgcatggctg tcgtcagctc   1080

gtgtcgtgag atgttgggtt aagtcccgca acgagcgcaa cccctaccgt cagttgccat   1140

cattcagttg ggcactctgg tggaaccgcc ggtgacaagc cggaggaagg cggggatgac   1200

gtcaagtcct catggccctt atgggttggg ctacacacgt gctacaatgg cggtgacagt   1260

gggaagcgaa gtcgcgagat ggagcaaatc cccaaaagcc gtctcagttc ggatcgcact   1320

ctgcaactcg agtgcgtgaa gttggaatcg ctagtaatcg cggatc                  1366
```

<210> SEQ ID NO 63
<211> LENGTH: 1360
<212> TYPE: DNA
<213> ORGANISM: Unknown organism
<220> FEATURE:
<223> OTHER INFORMATION: Origin of the sequence: soil organism

<400> SEQUENCE: 63

```
acagctatga ccatgattac gccaagcttg gtaccgagct cggatccact agtaacggcc     60

gccagtgtgc tggaattcgc ccttcaggcc taacacatgc aagtcgaacg ccccgcaagg    120

ggagtggcag acgggtgagt aacgcgtggg aacataccct ttcctgcgga atagctccgg    180

gaaactggaa ttaataccgc atacgcccta cgggggaaag atttatcggg gaaggattgg    240

cccgcgttgg attagctagt tggtggggta aaggcctacc aaggcgacga tccatagctg    300

gtctgagagg atgatcagcc acattgggac tgagacacgg cccaaactcc tacgggaggc    360

agcagtgggg aatattggac aatgggcgca agcctgatcc agccatgccg cgtgagtgat    420

gaaggcctta gggttgtaaa gctctttcac cggagaagat aatgacggta tccggagaag    480

aagccccggc taacttcgtg ccagcagccg cggtaatacg aagggggcta gtgttgttcg    540

gaattactgg gcgtaaagcg cacgtaggcg gatatttaag tcaggggtga aatcccagag    600

ctcaactctg gaactgcctt tgatactggg tatcttgagt atggaagagg taagtggaat    660

tccgagtgta gaggtgaaat tcgtagatat tcggaggaac accagtggcg aaggcggctt    720

actggtccat tactgacgct gaggtgcgaa agcgtgggga gcaaacagga ttagataccc    780

tggtagtcca cgccgtaaac gatgaatgtt agccgtcggg cagtatactg ttcggtggcg    840

cagctaacgc attaaacatt ccgcctgggg agtacggtcg caagattaaa actcaaagga    900

attgacgggg gcccgcacaa gcggtggagc atgtggttta attcgaagca acgcgcagaa    960

ccttaccagc tcttgacatt cggggtttgg gcagtggaga cattgtcctt cagttaggct   1020

ggccccagaa caggtgctgc atggctgtcg tcagctcgcg tcgtgagatg ttgggttaag   1080

tcccgcaacg agcgcaaccc tcgcccttag ttgccagcat ttagttgggc actctaaggg   1140

gactgccggt gataagccga gaggaaggtg gggacgacgt caagtcctca tggcccttac   1200

gggctgggct acacacgtgc tacaatggtg gtgacagtgg gcagcgagac agcgatgtcg   1260

agctaatctc caaaagccat ctcagttcgg attgcactct gcaactcgag tgcatgaagt   1320

tggaatcgct agtaatcgca gatcagcatg tgcggtgaat                         1360
```

<210> SEQ ID NO 64
<211> LENGTH: 1288
<212> TYPE: DNA
<213> ORGANISM: Unknown organism
<220> FEATURE:
<223> OTHER INFORMATION: Origin of the sequence: soil organism
<220> FEATURE:

-continued

<221> NAME/KEY: modified_base
<222> LOCATION: (1195)
<223> OTHER INFORMATION: variable nucleotide

<400> SEQUENCE: 64
tccaggaaac agctatgacc atgattacgc caagcttggt accgagctcg gatccactag 60
taacggccgc cagtgtgctg gaattcgccc ttcaggccta acacatgcaa gtcgagcgcc 120
ccgcaagggg agcggcagac gggtgagtaa cgcgtgggaa tctacccatc cctacggaac 180
aactccggga aactggagct aataccgtat acgccctttg ggggaaagat ttatcgggga 240
tggatgagcc cgcgttggat tagctagttg gtggggtaaa ggcctaccaa ggcgacgatc 300
catagctggt ctgagaggat gatcagccac attgggactg agacacggcc caaactccta 360
cgggaggcag cagtggggaa tattggacaa tgggcgcaag cctgatccag ccatgcccgc 420
gtgagtgatg aaggtcttag gattgtaaag ctctttcacc ggagaagata atgacggtat 480
ccggagaaga agccccggct aactttcgtg ccagcagccg cggtaatacg aaggggggcta 540 gcgttgttcg gaattactgg gcgtaaagcg cacgtaggcg gatatttaag tcaggggtga 600
aatcccagag ctcaactctg gaactgcctt tgatactggg tatcttgagt atggaagagg 660
taagtggaat tgcgagtgta gaggtgaaat tcgtagatat tcgcaggaac accagtggcg 720
aaggcggctt actggtccat tactgacgct gaggtgcgaa agcgtgggga gcaaacagga 780
ttagataccc tggtagtcca cgccgtaaac gatgaatgtt agccgtcggc aagtttactt 840
gtcggtggcg cagctaacgc attaaacatt ccgcctgggg agtacggtcg caagattaaa 900
actcaaagga attgacgggg gcccgcacaa gcggtggagc atgtggttta attcgaagca 960
acgcgcagaa ccttaccagc ccttgacatg cccggacagc tacagagatg tagtgttccc 1020
ttcggggacc gggacacagg tgctgcatgg ctgtcgtcag ctcgtgtcgt gagatgttgg 1080
gttaagtccc gcaacgagcg caaccctcgc ccttagttgc cagcattcag ttgggcactc 1140
taaggggact gccggtgata agccgagagg aagtggggat gacgtcaagt cctnatggcc 1200
cttacgggct gggctacaca cgtgctacaa tgggtggtga cagtgggcag cgaaggaacg 1260
atcccgagct aatctccaaa agccatct 1288

<210> SEQ ID NO 65
<211> LENGTH: 1386
<212> TYPE: DNA
<213> ORGANISM: Unknown organism
<220> FEATURE:
<223> OTHER INFORMATION: Origin of the sequence: soil organism

<400> SEQUENCE: 65
cgacggccag tgaattgtaa tacgactcac tatagggcga attgggccct ctagatgcat 60
gctcgagcgg ccgccagtgt gatggatatc tgcagaattc gcccttcagg cctaacacat 120
gcaagtcgag cgggcgtagc aatacgtcag cggcagacgg gtgagtaacg cgtgggaaca 180
taccttttgg ttcggaacaa cacagggaaa cttgtgctaa taccggataa gcccttacgg 240
ggaaagattt atcgccgaaa gattggcccg cgtctgatta gctagttggt agggtaatgg 300
cctaccaagg cgacgatcag tagctggtct gagaggatga tcagccacat tgggactgag 360
acacggccca aactcctacg ggaggcagca gtggggaata ttggacaatg ggcgcaagcc 420
tgatccagcc atgccgcgtg agtgatgaag gccctagggt tgtaaagctc ttttgtgcgg 480
gaagataatg acggtaccgc aagaataagc cccggctaac ttcgtgccag cagccgcggt 540
aatacgaagg gggctagcgt tgctcggaat cactgggcgt aaagggtgcg taggcgggtc 600

```
tttaagtcag gggtgaaatc ctggagctca actccagaac tgcctttgat actgaagatc    660

ttgagttcgg gagaggtgag tggaactgcg agtgtagagg tgaaattcgt agatattcgc    720

aagaacacca gtgggcgaag gcggctcact ggcccgatac tgacgctgag gcacgaaagc    780

gtggggagca aacaggatta gataccctgg tagtccacgc cgtaaacgat gaatgccagc    840

cgttagtggg tttactcact agtggcgcag ctaacgcttt aagcattccg cctggggagt    900

acggtcgcaa gattaaaact caaaggaatt gacgggggcc cgcacaagcg gtggagcatg    960

tggtttaatt cgacgcaacg cgcagaacct taccagccct tgacatgtcc aggaccggtc   1020

gcagagatgt gaccttctct tcggagcctg gagcacaggt gctgcatggc tgtcgtcagc   1080

tcgtgtcgtg agatgttggg ttaagtcccg caacgagcgc aaccccccgtc cttagttgct   1140

accatttagt tgagcactct aaggagactg ccggtgataa gccgcgagga aggtggggat   1200

gacgtcaagt cctcatggcc cttacgggct gggctacaca cgtgctacaa tggcggtgac   1260

aatgggacgc taaggggcaa cccttcgcaa atctcaaaaa gcccgtctca gttcggattg   1320

ggctctgcaa ctcgagccca tgaagttgga atcgctagta atcgtggatc agcacgccac   1380

ggtgaa                                                               1386
```

<210> SEQ ID NO 66
<211> LENGTH: 1223
<212> TYPE: DNA
<213> ORGANISM: Unknown organism
<220> FEATURE:
<223> OTHER INFORMATION: Origin of the sequence: soil organism

<400> SEQUENCE: 66

```
agcggcagag ggtgagtaac gcgtgggaat ctacccatct ctacggaaca actccgggaa     60

actggagcta ataccgtata cgtccttcgg gagaaagatt tatcggagat ggatgagccc    120

gcgttggatt agctagttgg tggggtaatg gcctaccaag gcgacgatcc atagctggtc    180

tgagaggatg atcagccaca ctgggactga gacacggccc agactcctac gggaggcagc    240

agtggggaat attggacaat gggcgaaagc ccgatccagc catgccgcgt gagtgatgaa    300

ggccctaggg ttgtaaagct ctttcaacgg tgaggataat gacggtaacc gtagaagaag    360

ccccggctaa cttcgtgcca gcagccgcgg taatacgaag gggctagcg ttgttcggaa    420

ttactgggcg taaagcgcac gtaggcggac tattaagtca ggggtgaaat cccggggctc    480

aaccccggaa ctgcctttga tactggtagt ctcgagtccg gaagaggtga gtggaattcc    540

gagtgtagag gtgaaattcg tagatattcg gaggaacacc agtggcgaag gcggctcact    600

ggtccggtac tgacgctgag gtgcgaaagc gtggggagca aacaggatta gataccctgg    660

tagtccacgc cgtaaacgat ggaagctagc cgttggcaag tttacttgtc ggtggcgcag    720

ctaacgcatt aagcttcccg cctggggagt acggtcgcaa gattaaaact caaaggaatt    780

gacgggggcc cgcacaagcg gtggagcatg tggtttaatt cgaagcaacg cgcagaacct    840

taccagccct tgacatcccg gtcgcggtta ccagagatgg tatccttcag ttcggctgga    900

ccggtgacag gtgctgcatg gctgtcgtca gctcgtgtcg tgagatgttg ggttaagtcc    960

cgcaacgagc gcaaccctcg cccttagttg ccagcattca gttgggcact ctaaggggac   1020

tgccggtgat aagccgagag gaaggtgggg atgacgtcaa gtcctcatgg cccttacggg   1080

ctgggctaca cacgtgctac aatggtggtg acagtgggca gcgagaccgc gaggtcgagc   1140

taatctccaa aagccatctc agttcggatt gcactctgca actcgagtgc atgaagttgg   1200
```

-continued aatcgctagt aatcgcggat cag 1223

<210> SEQ ID NO 67
<211> LENGTH: 1237
<212> TYPE: DNA
<213> ORGANISM: Unknown organism
<220> FEATURE:
<223> OTHER INFORMATION: Origin of the sequence: soil organism

<400> SEQUENCE: 67
cccgcagggg agtggcagag ggtgagtaac gcgtgggaat ctaccctttt ctacggaaca 60
actgagggaa acttcagcta ataccgtata cggccgagag gcgaaagatt tatcggagaa 120
ggatgagccc gcgttggatt agctagttgg tggggtaaag gcctaccaag gcgacgatcc 180
atagctggtc tgagaggatg atcagccaca ctgggactga gacacggccc agactcctac 240
gggaggcagc agtggggaat attggacaat gggcgcaagc ctgatccagc catgccgcgt 300
gagtgatgaa ggccctaggg ttgtaaagct ctttcaccgg tgaagataat gacggtaacc 360
ggagaagaag ccccggctaa cttcgtgcca gcagccgcgg taatacgaag gggctagcg 420 ttgttcggat ttactgggcg taaagcgcac gtaggcggac tattaagtca ggggtgaaat 480
cccggggctc aaccccggaa ctgcctttga tactggtagt cttgagttcg aaagaggtga 540
gtggaattcc gagtgtagag gtgaaattcg tagatattcg gaggaacacc agtggcgaag 600
gcggctcact ggctcgatac tgacgctgag gtgcgaaagc gtggggagca aacaggatta 660
gataccctgg tagtccacgc cgtaaactat gagagctagg cgtcgggcag tatactgttc 720
ggtggcgcag ctaacgcatt aagctcttcg cctggggagt acggtcgcaa gattaaaact 780
caaaggaatt gacgggggcc cgcacaagcg gtggagcatg tggtttaatt cgaagcaacg 840
cgcagaacct taccagccct tgacatcccg atcgcggtta ccagagatgg tatccttcag 900
ttaggctgga tcggtgacag gtgctgcatg gctgtcgtca gctcgtgtcg tgagatgttg 960
ggttaagtcc cgcaacgagc gcaaccctcg cccttagttg ccatcattca gttgggcact 1020
ctaaggggac tgccggtgat aagccgagag gaaggtgggg atgacgtcaa gtcctcatgg 1080
cccttacggg ctgggctaca cacgtgctac aatggtggcg acagtgggca gcgagaccgc 1140
gaggtcgagc taatctccaa aagccatctc agttcggatt gcactctgca actcgagtgc 1200
atgaagttgg aatcgctagt aatcgtggat cagaatg 1237

<210> SEQ ID NO 68
<211> LENGTH: 1346
<212> TYPE: DNA
<213> ORGANISM: Unknown organism
<220> FEATURE:
<223> OTHER INFORMATION: Origin of the sequence: soil organism

<400> SEQUENCE: 68
acgacgggcc agtgaattgt aatacgactc actatagggc gaattgggcc ctctagatgc 60
atgctcgagc ggccgccagt gtgatggata tctgcagaat tcgcccttca ggcctaacac 120
atgcaagtcg aacggatccc ttcggattag tggcggacgg gtgagtaaca cgcgggaacg 180
tgccctttgg ttcggaacaa ctcagggaaa cttgagctaa taccggataa gcctttcgag 240
ggaaagattt atcgccattg gagcggcccg cgtaggatta gctagttggt gaggtaaaag 300
ctcaccaagg cgacgatcct tagctggtct gagaggatga tcagccacat tgggactgag 360
acacggccca aactcctacg ggaggcagca gtggggaatc ttgcgcaatg ggcgaaagcc 420
tgacgcagcc atgccgcgtg aatgatgaag gtcttaggat tgtaaaattc tttcaccggg 480

-continued

```
gacgataatg acggtacccg gagaagaagc cccggctaac ttcgtgccag cagccgcggt    540
aatacgaagg gggctagcgt tgctcggaat tactgggcgt aaagggagcg taggcggata    600
gtttagtcag aggtgaaagc ccagggctca accttggaat tgcctttgat actggctatc    660
ttgagtacgg aagaggtatg tggaactccg agtgtagagg tgaaattcgt agatattcgg    720
aagaacacca gtggcgaagg cgacatactg gtccgttact gacgctgagg ctcgaaagcg    780
tggggagcaa acaggattag ataccctggt agtccacgct gtaaacgatg agtgctagtt    840
gtcggcatgc atgcatgtcg gtggcgcagc taacgcatta agcactccgc ctggggagta    900
cggtcgcaag attaaaactc aaaggaattg acgggggccc gcacaagcgg tggagcatgt    960
ggtttaattc gaagcaacgc gcagaacctt accacctttt gacatgcccg gaccgctcca   1020
gagatggagc tttcccttcg ggactgggga cacaggtgct gcatggctgt cgtcagctcg   1080
tgtcgtgaga tgttgggtta agtcccgcaa cgagcgcaac cctcgctatt agttgccatc   1140
aggtttggct gggcactcta ataggaccgc cggtggtaag ccggaggaag gtggggatga   1200
cgtcaagtcc tcatggccct tacaaggtgg gctacacacg tgctacaatg gcgactacag   1260
agggctgcaa tcccgcgagg gggagccaat ccctaaaagt cgtctcagtt cggattgcac   1320
tctgcaactc gagtgcatga agttgg                                        1346
```

```
<210> SEQ ID NO 69
<211> LENGTH: 1500
<212> TYPE: DNA
<213> ORGANISM: Unknown organism
<220> FEATURE:
<223> OTHER INFORMATION: Origin of the sequence: soil organism

<400> SEQUENCE: 69
```

```
acagctatga ccatgattac gccaagcttg gtaccgagct cggatccact agtaacggcc     60
gccagtgtgc tggaattcgc ccttcaggcc taacacatgc aagtcgaacg ccgtagcaat    120
acggagtggc agacgggtga gtaacacgtg ggaacgtgcc ctttggttcg gaacaacaca    180
gggaaacttg tgctaatacc gaataagccc ttacggggaa agatttatcg ccaaaggatc    240
ggcccgcgtc tgattagcta gttggtgggg taacggccca ccaaggctac gatcagtagc    300
tggtctgaga ggatgatcag ccacactggg actgagacac ggcccagact cctacgggag    360
gcagcagtta ggaatcttgg acaatgggcg caagcctgat ccagccatgc cgcgtgagtg    420
atgaaggcct tagggttgta aagctctttc agcggggaag ataatgacgg tacccgcaga    480
agaagccccg gctaacttcg tgccagcagc cgcggtaata cgaagggggc tagcgttgct    540
cggaatcact gggcgtaaag cgcacgtagg cggatcttta agtcaggggt gaaatcctgg    600
agctcaactc cagaactgcc tttgatactg gggatctcga gtccggaaga ggtgagtgga    660
actccgagtg tagaggtgaa attcgtagat attcggaaga acaccagtgg cgaaggcggc    720
tcactggtcc ggtactgacg ctgaggtgcg aaagcgtggg gagcaaacag gattagatac    780
cctggtagtc cacgccgtaa acgatggatg ctagccgttg gcgggtttac tcgtcagtgg    840
cgcagctaac gcattaagca tcccgcctgg ggagtacggt cgcaagatta aaactcaaag    900
gaattgacgg gggcccgcac aagcggtgga gcatgtggtt caattcgaag caacgcgcag    960
aaccttacca gcccttgaca tgtcccgtat ggacttcaga gatgaggtcc ttcagttcgg   1020
ctggcgggaa cacaggtgct gcatggctgt cgtcagctcg tgtcgtgaga tgttgggtta   1080
agtcccgcaa cgagcgcaac cctcgccctt agttgccatc atttagttgg gcactctaag   1140
```

-continued

```
gggactgccg gtgataagcc gcgaggaagg tggggatgac gtcaagtcct catggccctt   1200

acgggctggg ctacacacgt gctacaatgg cggtgacagt gggacgcaat ggagcaatcc   1260

tgcgcaaatc tcaaaaagcc gtctcagttc ggattggggt ctgcaactcg accccatgaa   1320

gtcggaatcg ctagtaatcg cagatcagca cgctgcggtg aatacgttcc cgggccttgt   1380

acacaccgcc caagggcgaa ttctgcagat atccatcaca ctggcggccg ctcgagcatg   1440

catctagagg gcccaattcg ccctatagtg agtcgtatta caattcactg gccgtcgttt   1500
```

<210> SEQ ID NO 70
<211> LENGTH: 1113
<212> TYPE: DNA
<213> ORGANISM: Unknown organism
<220> FEATURE:
<223> OTHER INFORMATION: Origin of the sequence: soil organism

<400> SEQUENCE: 70

```
gagctaatac cgtataatga cttcggtcca aagatttatc gcctgaggat gagcccgcgt     60

cggattagct agttggtagg gtaaaagcct accaaggcga cgatccgtag ctggtctgag    120

aggatgatca gccacactgg gactgagaca cggcccagac tcctacggga ggcagcagtg    180

gggaatattg gacaatgggc gcaagcctga tccagcaatg ccgcgtgagt gatgaaggcc    240

ttagggttgt aaagctcttt tacccgggaa gataatgact gtaccgggag aataagcccc    300

ggctaactcc gtgccagcag ccgcggtaat acggaggggg ctagcgttgt tcggaattac    360

tgggcgtaaa gcgcacgtag gcggctttgt aagttagagg tgaaagcccg gggctcaact    420

ccggaattgc ctttaagact gcatcgctcg aattgtggag aggtaagtgg aattccgagt    480

gtagaggtga aattcgtaga tattcggaag aacaccagtg gcgaaggcga cttactggac    540

acatattgac gctgaggtgc gaaagcgtgg ggagcaaaca ggattagata ccctggtagt    600

ccacgccgta aacgatgatg actagctgtc ggggcgctta gcgtttcggt ggcgcagcta    660

acgcgttaag tcatccgcct ggggagtacg gccgcaaggt taaactcaaa gaaattgacg    720

ggggcctgca caagcggtgg agcatgtggt ttaattcgaa gcaacgcgca gaaccttacc    780

agcgtttgac atgccaggac ggtttccaga gatggattcc ttcccttacg ggacctggac    840

acaggtgctg catggctgtc gtcagctcgt gtcgtgagat gttgggttaa gtcccgcaac    900

gagcgcaacc ctcgtcttta gttgctacca tttagttgag cactctagag aaactgccgg    960

tgataagccg gaggaaggtg gggatgacgt caagtcctca tggcccttac gcgctgggct   1020

acacacgtgc tacaatggcg gtgacaacgg gcagcaaact cgcgagagtg agcaaatccc   1080

gaaaagccgt ctcagttcgg attgttctct gca                                1113
```

<210> SEQ ID NO 71
<211> LENGTH: 1225
<212> TYPE: DNA
<213> ORGANISM: Unknown organism
<220> FEATURE:
<223> OTHER INFORMATION: Origin of the sequence: soil organism

<400> SEQUENCE: 71

```
ggagcggcgg acgggtgagt aacgcgtggg aacgtgccct ttggtacgga acaactgagg     60

gaaacttcag ctaataccgt atgtgccctt cgggggaaag atttatcgcc attggagcgg    120

cccgcgttgg attaggtagt tggtggggta aaggcctacc aagcctacga tccatagctg    180

gtctgagagg atgatcagcc acactgggac tgagacacgg cccagactcc tacgggaggc    240

agcagtaggg aatcttgcgc aatgggcgaa agcctgacgc agccatgccg cgtgtatgat    300
```

-continued

```
gaaggtctta ggattgtaaa atactttcac cggggaagat aatgacggta cccggagaag    360

aagccccggc taacttcgtg ccagcagccg cggtaatacg aagggggcta gcgttgctcg    420

gaattactgg gcgtaaaggg cgcgtaggcg gatatttaag tcgggggtga aagcccaggg    480

ctcaaccctg gaattgcctt cgatactgga tatcttgagt tcgggagagg tgagtggaat    540

gccgagtgta gaggtgaaat tcgtagatat tcggcggaac accagtggcg aaggcgactc    600

actggcccga tactgacgct gaggcgcgaa agcgtgggga gcaaacagga ttagataccc    660

tggtagtcca cgctgtaaac gatgagtgct agttgtcggc atgcatgcat gtcggtgacg    720

cagctaacgc attaagcact ccgcctgggg agtacggtcg caagattaaa actcaaagga    780

attgacgggg gcccgcacaa gcggtggagc atgtggttta attcgaagca acgcgcagaa    840

ccttaccacc ttttgacatg ccctgatcgc tggagagatc cagttttccc ttcggggaca    900

gggacacagg tgctgcatgg ctgtcgtcag ctcgtgtcgt gagatgttgg gttaagtccc    960

gcaacgagcg caaccctcgc cattagttgc catcattaag ttgggcactc taatgggacc   1020

gccggtggta agccggagga aggtggggat gacgtcaagt cctcatggcc cttacggggt   1080

gggctacaca cgtgctacaa tggcgactac agagggttgc aaacctgcga aggggagcta   1140

atccctaaaa gtcgtctcag ttcggattgc actctgcaac tcgagtgcat gaagtcggaa   1200

tcgctagtaa tcgcggatca gcatg                                         1225
```

```
<210> SEQ ID NO 72
<211> LENGTH: 1286
<212> TYPE: DNA
<213> ORGANISM: Unknown organism
<220> FEATURE:
<223> OTHER INFORMATION: Origin of the sequence: soil organism

<400> SEQUENCE: 72
```

```
atgattagta gcaatactaa tcgatgacga gcggcggacg ggtgagtaat acgtaggaac     60

ctgcccttaa gcgggggata actaagggaa actttagcta ataccgcata aactcgagag    120

agaaaagctg cagcaatgtg gcacttgagg aggggcctgc gtcagattag ctagttggtg    180

aggtaatagc tcaccaaggc gatgatctgt aactggtctg agaggacgac cagtcacact    240

gggactgaga cacggcccag actcctacgg gaggcagcag tggggaatat tggacaatgg    300

gggcaaccct gatccagcga tgccgcgtgg gtgaagaagg ccttcgggtt gtaaagccct    360

ttaggtcggg aagaaggtta gtagaggaaa tgctattaac ttgacggtac cgacagaata    420

agcaccggca aactctgtgc cagcagccgc ggtaatacag agggtgcgag cgttaatcgg    480

atttactggg cgtaaagggc gcgtaggcgg tgagatgtgt gtgatgtgaa agccccaggc    540

tcaacctggg aagtgcatcg caaactgtct gactggagta tatgagaggg tggcggaatt    600

tccggtgtag cggtgaaatg cgtagagatc ggaaggaacg tcgatggcga aggcagccac    660

ctggcataat actgacgctg aggcgcgaaa gcgtggggat cgaacaggat tagataccct    720

ggtagtccac gctgtaaact atgagtacta gatgttggta ggggaaccta tcggtatcga    780

agctaacgcg ataagtattc cgcctgggaa gtacggccgc aaggttgaaa ctcaaatgaa    840

ttgacggggg cccgcacaag cggtggagca tgtggtttaa ttcgatgcaa cgcgaagaac    900

cttacctacc cttgacatcc tgagaatctg gcttagtagc tggagtgccg aaaggagctc    960

agagacaggt gctgcatggc tgtcgtcagc tcgtgttgtg agatgttggg ttaagtcccg   1020

taacgagcgc aacccttgcc cttagttgcc atcatttagt tggggactct aaggggaccg   1080
```

-continued

```
ccagtgatga actggaggaa ggcggggacg acgtcaagtc atcatggcct ttatgggtag   1140

ggccacacac gtgctacaat ggggcgtacg gagggtcgca aacccgcgag gggagctaa   1200

tctcataaag cgtctcgtag tccggattgg agtctgcaac tcgactccat gaagttggaa   1260

tcgctagtaa tcgcgaatca gcattg                                         1286
```

<210> SEQ ID NO 73
<211> LENGTH: 1288
<212> TYPE: DNA
<213> ORGANISM: Unknown organism
<220> FEATURE:
<223> OTHER INFORMATION: Origin of the sequence: soil organism

<400> SEQUENCE: 73

```
cggggcaacc ctggcggcga gcggcgaacg ggtgagtaat gcatcggaac gtgtcctctt     60

gtgggggata accagtcgaa agactggcta ataccgcatg agatcgaaag atgaaagcag    120

gggaccgcaa ggccttgcgc gagaggagca gccgatgccg gattagctag ttggtggggt    180

aaaagcctac caaggcgacg atccgtagct ggtctgagag gacgaccagc cacactggga    240

ctgagacacg gcccagactc ctacgggagg cagcagtggg gaattttgga cagtgggggc    300

aaccctgatc cagccatgcc gcgtgtgtga agaaggcctt cgggttgtaa agcactttcg    360

gacggaacga aatcgcgcga gttaatagtt cgcgtggatg acggtaccgt aagaagaagc    420

accggctaac tacgtgccag cagccgcggt aatacgtagg gtgcgagcgt taatcggaat    480

tactgggcgt aaagtgtgcg caggcggctt cgcaagtcga gtgtgaaatc cccgagctta    540

acttgggaat tgcgctcgaa actacggagc cggagtgtgg cagaggaagg tggaattcca    600

cgtgtagcgg tgaaatgcgt agagatgtgg aggaacaccg atggcgaagg cggccttctg    660

ggccaacact gacgctcatg cacgaaagcg tggggagcaa acaggattag ataccctggt    720

agtccacgcc ctaaacgatg atgactagtt gttggaggag ttaaatcctt tagtaacgca    780

gctaacgcgt gaagtcatcc gcctggggag tacggtcgca agattaaaac tcaaaggaat    840

tgacgggggc ccgcacaagc ggtggatgat gtggtttaat tcgatgcaac gcgaaaaacc    900

ttacctaccc ttgacatgct aggaacgctg cagaaatgta gcggtgcccg aaagggaacc    960

tagacacagg tgctgcatgg ctgtcgtcag ctcgtgtcgt gagatgttgg gttaagtccc   1020

gcaacgagcg caacccctgc cattagttgc tacattcagt tgagcactct aatgggactg   1080

ccggtgacaa accggaggaa ggtggggatg acgtcaagtc ctcatggccc ttatgggtag   1140

ggctacacac gtcatacaat ggcgcgtaca gagggttgcc aacccgcgag ggggagccaa   1200

tcccagaaag cgcgtcgtag tccggattgg agtctgcaac tcgactccca tgaagtcgga   1260

atcgctagta atcgcggatc agcatgtc                                       1288
```

<210> SEQ ID NO 74
<211> LENGTH: 600
<212> TYPE: DNA
<213> ORGANISM: Unknown organism
<220> FEATURE:
<223> OTHER INFORMATION: Origin of the sequence: soil organism
<220> FEATURE:
<221> NAME/KEY: modified_base
<222> LOCATION: (494)
<223> OTHER INFORMATION: variable nucleotide

<400> SEQUENCE: 74

```
cgtgccagca gccgcggtaa tacgtaggtg gcaagcgttg tccggaatta ttgggcgtaa     60

agcgcgcgca ggtggtttct taagtctgat gtgaaagccc acggcttaac cgtggagggt    120
```

-continued

```
cattggaaac tgggagactt gagtgcagaa gaggaaagtg gaattccaag tgtagcggtg    180

aaatgcgtag agatttggag gaacaccagt ggcgaaggcg actttctggt ctgcaactga    240

cgctgaggcg cgaaagcatg gggagcaaac aggattagat accctggtag tccatgccgt    300

aaacgatgag tgctaagtgt taggggggttt ccgcccctta gtgctgcagc taacgcatta    360

agcactccgc ctggggagta cgaccgcaag gttgaaactc aaaggaattg acgggggccc    420

gcacaagcgg tggagcatgt ggtttaattc gaagcaacgc gaagaacctt accaggtctt    480

gacatcccga tgancgctct agagatagag ttttcccttc ggggacattg gtgacaggtg    540

gtgcatggtt gtcgtcagct cgtgtcgtga gatgttgggt taagtcccgc aacgagcgca    600
```

```
<210> SEQ ID NO 75
<211> LENGTH: 601
<212> TYPE: DNA
<213> ORGANISM: Unknown organism
<220> FEATURE:
<223> OTHER INFORMATION: Origin of the sequence: soil organism

<400> SEQUENCE: 75

cgtgccagca gccgcggtaa tacgtaggtg gcaagcgttg tccggaatta ttgggcgtaa     60

agcgcgcgca ggtggtttct taagtctgat gtgaaagccc acggcttaac cgtggagggt    120

cattggaaac tgggagactt gagtgcagaa gaggaaagtg gaattccaag tgtagcggtg    180

aaatgcgtag agatttggag gaacaccagt ggcgaaggcg actttctggt ctgcaactga    240

cgctgaggcg cgaaagcatg gggagcaaac aggattagat accctggtag tccatgccgt    300

aaacgatgag tgctaagtgt taggggggttt ccgcccctta gtgctgagct aacgcattaa    360

gcactccgcc tggggagtac gaccgcaagg ttgaaactca aaggaattga cgggggcccg    420

cacaagcggt ggagcatgtg gtttaattcg aagcaacgcg aagaacctta ccaggtcttg    480

acatcccgat gacgctctag agatagagtt ttcccttcgg ggacattggt gacaggtggt    540

gcatggttgt cgtcagctcg tgtcgtgaga tgttgggtta agtcccgcaa cgagcgcacc    600

c                                                                    601
```

```
<210> SEQ ID NO 76
<211> LENGTH: 1236
<212> TYPE: DNA
<213> ORGANISM: Unknown organism
<220> FEATURE:
<223> OTHER INFORMATION: Origin of the sequence: soil organism

<400> SEQUENCE: 76

tgccctgtag acggggataa cttcgggaaa ccggagctaa taccggataa tcctcttccc     60

cacatgggga agagttgaaa ggcgctttcg cgtcactaca ggatgggccc gcggtgcatt    120

agctagttgg tagggtaacg gcctaccaag gcgacgatgc atagccgacc tgagagggtg    180

atcggccaca ttgggactga gacacggccc aaactcctac gggaggcagc agtagggaat    240

cttccacaat ggacgaaagt ctgatggagc aacgccgcgt gagtgatgaa ggttttcgga    300

tcgtaaaact ctgttgtaag ggaagaacca gtacgtcagg caatggacgt accttgacgg    360

taccttatta gaaagccacg gctaactacg tgccagcagc cgcggtaata cgtaggtggc    420

aagcgttgtc cggaattatt gggcgtaaag cgcgcgcagg tggtttctta agtctgatgt    480

gaaagcccac ggcttaaccg tggagggtca ttggaaactg ggagacttga gtgcagaaga    540

ggaaagtgga attccaagtg tagcggcgaa atgcgtagag atttggagga acaccagtgg    600
```

-continued

```
cgaaggcgac tttctggtct gcaactgacg ctgaggcgcg aaagcatggg gagcaaacag    660

gattagatac cctggtagtc catgctgtaa acgatgagtg ctaagtgtta ggggggtttcc   720

gccccttagt gctgcagcta acgcattaag cactccgcct ggggagtacg accgcaaggt    780

tgaaactcaa aggaattgac gggggcccgc acaagcggtg gagcatgtgg tttaattcga    840

agcaacgcga agaaccttac caggtcttga catcccgatg atcgctctgg agatagagtt    900

ttcccttcgg ggacattggt gacaggtggt gcatggttgt cgtcagctcg tgtcgtgaga    960

tgttgggtta agtcccgcaa cgagcgcaac ccttaatctt agttgccatc atttagttgg   1020

gcactctaag gtgactgccg gtgataaacc ggaggaaggt ggggatgacg tcaaatcatc   1080

atgcccctta tgacctgggc tacacacgtg ctacaatgga cggtacaaag agtcgctaac   1140

tcgcgagagt atgctaatct catagaaccg ttctcagttc ggattgtagg ctgcaactcg   1200

cctacatgaa gccggaatcg ctagtaatcg cggatc                             1236
```

<210> SEQ ID NO 77
<211> LENGTH: 815
<212> TYPE: DNA
<213> ORGANISM: Unknown organism
<220> FEATURE:
<223> OTHER INFORMATION: Origin of the sequence: soil organism

<400> SEQUENCE: 77

```
caagcgttgt ccggaattat tgggcgtaaa gagctcgtag gcggtttgtc gcgtctgctg     60

tgaaaactcg aggctcaacc tcgggcttgc agtgggtacg ggcagactag agtgcggtag    120

gggtgactgg aattcctggt gtagcggtgg aatgcgcaga tatcaggagg aacaccgatg    180

gcgaaggcag gtcactgggc cgcaactgac gctgaggagc gaaagcatgg ggagcgaaca    240

ggattagata ccctggtagt ccatgccgta aacgttgggc actaggtgtg ggctcattc     300

cacgagttcc gtgccgcagc aaacgcatta agtgccccgc ctggggagta cggccgcaag    360

gcttaaaact caaagaaatt gacgggggcc cgcacaagcg gcggagcatg cggattaatt    420

cgatgcaacg cgaagaacct taccaaggct tgacatacac cggaaacttc cagagatggt    480

tgccccgcaa ggtcggtgta caggtggtgc atggttgtcg tcagctcgtg tcgtgaagat    540

gttgggttaa gtcccgcaac gagcgcaacc ctcgtcctat gttgccagca cgtgatggtg    600

gggactcata ggagactgcc ggggtcaact cggaggaagg tggggatgac gtcaaatcat    660

catgcccctt atgtcttggg cttcacgcat gctacaatgg ccggtacaaa gggctgcgat    720

accgcaaggt ggagcgaatc ccaaaaagcc ggtctcagtt cggattgggg tctgcaactc    780

gaccccatga agtcggagtc gctagtaatc gcaga                               815
```

<210> SEQ ID NO 78
<211> LENGTH: 826
<212> TYPE: DNA
<213> ORGANISM: Unknown organism
<220> FEATURE:
<223> OTHER INFORMATION: Origin of the sequence: soil organism

<400> SEQUENCE: 78

```
tcgtaggtgg cttgtcacgt cgggtgtgaa agcttggggc ttaactccag gtctgcattc     60

gatacgggct ggctagaggt aggtagggga gaacggaatt cctggtgtag cggtgaaatg    120

cgcagatatc aggaggaaca ccggtggcga aggcggttct ctgggcctta cctgacgctg    180

aggagcgaaa gcgtggggag cgaacaggat tagataccct ggtagtccac gctgtaaacg    240

ttgggcgcta ggtgtgggga ccttccacgg tttccgcgcc gtagctaacg cattaagcgc    300
```

-continued

```
cccgcctggg gagtacggcc gcaaggctaa aactcaaagg aattgacggg ggcccgcaca    360

agcggcggag catgttgctt aattcgacgc aacgcgaaga accttaccaa ggcttgacat    420

cgcccggaaa gcttcagaga tggagccctc ttcggactgg gtgacaggtg gtgcatggct    480

gtcgtcagct cgtgtcgtga gatgttgggt taagtcccgc aacgagcgca acccttgttc    540

aatgttgcca gcaacatcct tcggggtggt tggggactca ttggagactg ccggggtcaa    600

ctcggaggaa ggtggggacg acgtcaagtc atcatgcccc ttatgtcttg ggctgcaaac    660

atgctacaat ggccggtaca gagggttgcg ataccgcaag gtggagcgaa tccctaaaag    720

ccggtctcag ttcggattgg ggtctgcaac tcgaccccat gaagtcggag tcgctagtaa    780

tcgcagatca gcaacgctgc ggtgaatacg ttcccgggcc ttgtac                   826
```

<210> SEQ ID NO 79
<211> LENGTH: 799
<212> TYPE: DNA
<213> ORGANISM: Unknown organism
<220> FEATURE:
<223> OTHER INFORMATION: Origin of the sequence: soil organism

<400> SEQUENCE: 79

```
cgtaggcggt ttgtcgcgtc tgccgtgaaa gtccggggct caactccgga tctgcggtgg     60

gtacgggcag actagagtga tgtaggggag actggaattc ctggtgtagc ggtgaaatgc    120

gcagatatca ggaggaacac cgatggcgaa ggcaggtctc tgggcattaa ctgacgctga    180

ggagcgaaag catggggagc gaacaggatt agataccctg gtagtccatg ccgtaaacgt    240

tgggcactag gtgtggggga cattccacgt tttccgcgcc gtagctaacg cattaagtgc    300

cccgcctggg gagtacggcc gcaaggctaa aactcaaagg aattgacggg ggcccgcaca    360

agcggcggag catgcggatt aattcgatgc aacgcgaaga accttaccaa ggcttgacat    420

gaaccggaaa cacctggaaa caggtgcccc gcttgcggtc ggtttacagg tggtgcatgg    480

ttgtcgtcag ctcgtgtcgt gagatgttgg gttaagtccc gcaacgagcg caaccctcgt    540

tctatgttgc cagcgcgtta tggcggggac tcataggaga ctgccggggt caactcggag    600

gaaggtgggg acgacgtcaa atcatcatgc cccttatgtc ttgggcttca cgcatgctac    660

aatggccggt acaaagggtt gcgatactgt gaggtggagc taatcccaaa aagccggtct    720

cagttcggat tggggtctgc aactcgaccc catgaagtcg gagtcgctag taatcgcaga    780

tcagcaacgc tgcggtgaa                                                 799
```

<210> SEQ ID NO 80
<211> LENGTH: 1250
<212> TYPE: DNA
<213> ORGANISM: Unknown organism
<220> FEATURE:
<223> OTHER INFORMATION: Origin of the sequence: soil organism

<400> SEQUENCE: 80

```
tgccagcttg ctggtggatt agtggcgaac gggtgagtaa cacgtgagta acctgccctt     60

aactctggga taagcctggg aaactgggtc taatgccgga tatgactcct catcgcatgg    120

tgggggtgg aaagcttttt gtggttttgg atggactcgc ggcctatcag cttgttggtg    180

aggtaatggc tcaccaaggc gacgacgggt agccggcctg agagggtgac cggccacact    240

gggactgaga cacggcccag acttctacgg gaggcagcag tggggaatat tgcacaatgg    300

gcgaaagcct gatgcagcga cgccgcgtga gggatgacgg ccttcgggtt gtaaacctct    360
```

-continued

```
ttcagtaggg aagaagcgaa agtgacggta cctgcagaag aagcgccggc taactacgtg    420

ccagcagccg cggtaatacg tagggcgcaa gcgttatccg gaattattgg gcgtaaagag    480

ctcgtaggcg gtttgtcgcg tctgccgtga aagtccgggg ctcaactccg gatctgcggt    540

gggtacgggc agactagagt gatgtagggg agactggaat tcctggtgta gcggtgaaat    600

gcgcagatat caggaggaac accgatggcg aaggcaggtc tctgggcatt aactgacgct    660

gaggagcgaa agcatgggga gcgaacagga ttagataccc tggtagtcca tgccgtaaac    720

gttgggcact aggtgtgggg gacattccac gttttccgcg ccgtagctaa cgcattaagt    780

gccccgcctg gggagtacgg ccgcaaggct aaaactcaaa ggaattgacg gggcccgca    840

caagcggcgg agcatgcgga ttaattcgat gcaacgcgag gaaccttacc aaggcttgac    900

atgaaccgga aatacctgga aacaggtgcc ccgcttgcgg tcggtttaca ggtggtgcat    960

ggttgccgtc agctcgtgtc gtgagatgtt gggttaagtc ccgcaacgag cgcaaccctc   1020

gttctatgtt gccagcgcgt tatggcgggg actcatagga gactgccggg gtcaactcgg   1080

aggaaggtgg ggacgacgtc aaatcatcat gccccttatg tcttgggctt cacgcatgct   1140

acaatggccg gtacaaaggg ttgcgatact gtgaggtgga gctaatccca aaaagccggt   1200

ctcagttcgg attggggtct gcaactcgac cccatgaagt cggagtcgct              1250
```

<210> SEQ ID NO 81
<211> LENGTH: 1210
<212> TYPE: DNA
<213> ORGANISM: Unknown organism
<220> FEATURE:
<223> OTHER INFORMATION: Origin of the sequence: soil organism

<400> SEQUENCE: 81

```
cgctaatacc ggatacggcg cgagagtctt cggactttcg cgagaaagat tcgcaaggat     60

cactgaggga cgagcctgcg gcccatcagc tagttggtga ggtaagagct caccaaggct    120

aagacgggta gctggtctga gaggatgatc agccacactg gaactgagac acggtccaga    180

ctcctacggg aggcagcagt ggggaatatt gcgcaatggg cgaaagcctg acgcagccac    240

gccgcgtgag cgatgagggc cttcgggtcg taaagctctg tggggagaga cgaataaggc    300

cggtgaagag tcggccttga cggtatctcc ttagcaagca ccggctaact ccgtgccagc    360

agccgcggta atacggaggg tgcaaacgtt gctcggaatc attgggcgta aagcgcacgt    420

aggcggcgtg ataagttggg tgtgaaagcc ctgggctcaa cccaggaagt gcattcaaaa    480

ctgtcacgct tgaatctcgg agggggtcag agaattcccg gtgtagaggt gaaattcgta    540

gatatcggga ggaataccag tggcgaaggc gctggcctgg acgaagattg acgctgaggt    600

gcgaaagcgc ggggagcaaa caggattaga taccctggta gtccgcgctg taaacgatga    660

gtgctagacg gggaggtat tgaccccttc gctgccgaag ctaacgcgtt aagcactccg    720

cctggggagt acggtcgcaa gactaaaact caaaggaatt gacgggggcc cgcacaagcg    780

gtggagcatg tggtttaatt cgacgcaacg cgcaaaacct tacctgggtt aaatccgccg    840

gaacctggct gaaaggctgg ggtgccctcc ggggaatcgg tgagaaggtg ctgcatggct    900

gtcgtcagct cgtgtcgtga gatgttgggt taagtcccgc aacgagcgca acccctatcg    960

tcagttgcca acattaaggt gggaactctg gcgagactgc cggtctaaac cggaggaagg   1020

tggggacgac gtcaagtcct catggccctt atgcccaggg ctacacacgt gctacaatgg   1080

ctggtacaat gagccgcaaa accgcgaggt caagctaatc tcaaaaaacc agtctcagtt   1140

cggatcggag tctgcaactc gactccgtga agctggaatc gctagtaatc gaagatcagc   1200
```

-continued

```
acgctttcgg                                                          1210

<210> SEQ ID NO 82
<211> LENGTH: 1272
<212> TYPE: DNA
<213> ORGANISM: Unknown organism
<220> FEATURE:
<223> OTHER INFORMATION: Origin of the sequence: soil organism

<400> SEQUENCE: 82

gatgccagct tgctggtgga ttagtggcga acgggtgagt aacacgtgag taacctgccc     60

ttaactctgg gataagcctg ggaaactggg tctaataccg gatatgactc ctcatcgcat    120

ggtggggggt ggaaagcttt ttgtggtttt ggatggactc gcggcctatc agcttgttgg    180

tgaggtaatg gctcaccaag gcgacgacgg gtagccggcc tgagagggtg accggccaca    240

ctgggactga gacacggccc agactcctac gggaggcagc agtggggaat attgcacaat    300

gggcgaaagc ctgatgcagc gacgccgcgt gagggatgac ggccttcggg ttgtaaacct    360

ctttcagtag ggaagaagcg aaagtgacgg tacctgcaga agaagcgccg gctaactacg    420

tgccagcagc cgcggtaata cgtagggcgc aagcgttatc cggaattatt gggcgtaaag    480

agctcgtagg cggtttgtcg cgtctgccgt gaaagtccgg ggctcaactc cggatctgcg    540

gtgggtacgg gcagactaga gtgatgtagg ggagactgga attcctggtg tagcggtgaa    600

atgcgcagat atcaggagga acaccgatgg cgaaggcagg tctctgggca ttaactgacg    660

ctgaggaacg aaagcatggg gagcgaacag gattagatac cctggtagtc catgccgtaa    720

acgttgggca ctaggtgtgg gggacattcc acgttttccg cgccgtagct aacgcattaa    780

gtgccccgcc tggggagtac ggccgcaagg ctaaaactca aaggaattga cgggggcccg    840

cacaagcggc ggagcatgcg gattaattcg atgcaacgcg aagaacctta ccaaggcttg    900

acatgaaccg gaaatacctg gaaacaggtg ccccgcttgc ggtcggttta caggtggtgc    960

atggttgtcg tcagctcgtg tcgtgagatg ttgggttaag tcccgcaacg agcgcaaccc   1020

tcgttctatg ttgccagcgc gttatggcgg ggactcatag gagactgccg gggtcaactc   1080

ggaggaaggt ggggacgacg tcaaatcatc atgcccctta tgtcttgggc ttcacgcatg   1140

ctacaatggc cggtacaaag ggttgcgata ctgtgaggtg gagctgatcc caaaaagccg   1200

gtcccagttc ggattggggt ctgcaactcg accccatgaa gtcggagtcg ctagtaatcg   1260

cagatcagca ac                                                       1272

<210> SEQ ID NO 83
<211> LENGTH: 1247
<212> TYPE: DNA
<213> ORGANISM: Unknown organism
<220> FEATURE:
<223> OTHER INFORMATION: Origin of the sequence: soil organism

<400> SEQUENCE: 83

tgtttagtag caatactaaa tgatgacgag cggcggacgg gtgaggaaca cgtaggaacc     60

tgcccaagag agggggacaa ccaagggaaa ctttggctaa taccgcataa tctctacgga    120

gaaaagttgc ccgtaagggt ggcgcttttg gaggggcctg cgtccgatta gttagttggt    180

gaggtaatag ctcaccaaga ctgtgatcgg taactggtct gagaggacga ccagtcacac    240

tgggactgag acacggccca gactcctacg ggaggcagca gtggggaatc ttggacaatg    300

ggggcaaccc tgatccagcg atgccgcgtg ggtgaagaag gccttcgggt tgtaaagccc    360
```

-continued

```
tttaggcggg gaagaaggat atgggatgaa taagcctgta ttttgacggt acccgcagaa    420

taagcaccgg caaactctgt gccagcagcc gcggtaatac agagggtgcg agcgttaatc    480

ggatttactg ggcgtaaagg gcgcgtaggc ggttgtgtga gtgtgatgtg aaagccccgg    540

gctcaacctg ggaagtgcat cgcaaacgac acaactggag tatatgagag ggtggcggaa    600

tttccggtgt agcggtgaaa tgcgtagaga tcggaaggaa cgtcgatggc gaaggcagcc    660

acctggcata atactggcgc tgaggcgcga aagcgtgggg agcgaacagg attagatacc    720

ctggtagtca cgcccgtaaa cgatgagaac tagatgttgg agggggaacc cttcagtatc    780

gaagctaacg cgataagttc tccgcctggg aagtacagtc gcaagactga aactcaaaag    840

aattgacggg ggcccgcaca agcggtggag catgtggttt aattcgatgc aacgcgaaga    900

accttacctg cccttgacat cctgcgaatc ttgccgagag gtgagagtgc cgcagggagc    960

gcagagacag gtgctgcatg gctgtcgtca gctcgtgttg tgagatgttg ggttaagtcc   1020

cgtaacgagc gcaacccttg tccttagttg ccatcattta gttggggact ctaaggagac   1080

cgccggtgat gaaccggagg aaggcgggga cgacgtcaag tcatcatggc ctttatgggt   1140

agggctacac acgtgctaca atggggcgta cagagggtcg ccaacccgcg agggggagcc   1200

aatctcttaa agcgtctcgt agtccggatt ggagtctgca actcgac                 1247
```

```
<210> SEQ ID NO 84
<211> LENGTH: 1292
<212> TYPE: DNA
<213> ORGANISM: Unknown organism
<220> FEATURE:
<223> OTHER INFORMATION: Origin of the sequence: soil organism

<400> SEQUENCE: 84

ggctcgcaag agcaaccggc gaacgggtgc gtaacacgtg aacaacctgc cctcgtgtgg     60

gggatagccg ggctaacgcc cgggtaatac cgcatacgtt ctctctgggg agtcctgggg    120

agaggaaagc tccggcgcac ggggaggggt tcgcggccta tcagctagtt ggcggggtaa    180

tggcccacca aggcgacgac gggtagctgg tctgagagga tggccagcca cattgggact    240

gagagacggc ccagactcct acgggaggca gcagtgggga atcttgcgca atggccgaaa    300

ggctgacgca gcgacgccgc gtgtgggagg acgcctttcg ggtgtaaac cactgttgcc     360

cgggacgaac agcctctttc gagaggtctg acggtaccgg gtgaggaagc accggctaac    420

tccgtgccag cagccgcggt aatacggagg gtgcgagcgt tgtccggaat cattgggcgt    480

aaagggcgcg taggtggccc ggtcagttcg tggtgaaagc gcggggctca accctgcgtc    540

ggccatgaat actgccgcgg ctggagcact gtagaggcag gcggaattcc gggtgtagcg    600

gtggaatgcg tagagatccg gaagaacacc ggtggcgaag gcggcctgct gggcagtagc    660

tgacactgag gcgcgacagc gtggggagca aacaggatta gataccctgg tagtccacgc    720

cgtaaacgat gggcactagg cgcttggggg agcgaccccc cgagggccgg cgctaacgca    780

ttaagtgccc cgcctgggga gtacggccgc aaggctgaaa ctcaaaggaa ttgacggggg    840

cccgcacaag cggtggagca tgtggtttaa ttcgacgcaa cgcgaagaac cttacctagg    900

cttgacatac acgggaaacc ggtcagaaac ggccggccct cttcggagcc cgtgcacagg    960

tgctgcatgg ctgtcgtcag ctcgtgtcgt gagatgttgg gttaagtccc gcaacgagcg   1020

caacccctgt ctctagttgc cagcgcgtca tggcggggac tctagagaga ctgccggtgc   1080

caaaccggag gaaggtgggg atgacgtcaa gtcatcatgg tccttacgtc tagggctaca   1140

cacgtgctac aatggcgggg acagagggtc gcgagccggc aacggcaagc caatcccgta   1200
```

-continued

```
aaccccgcct cagttcggat tgtcgtctgc aactcgacgg catgaagctg gaatcgctag   1260

taatcgtgga tcagctacgc cacggtgaat ac                                 1292
```

<210> SEQ ID NO 85
<211> LENGTH: 1300
<212> TYPE: DNA
<213> ORGANISM: Unknown organism
<220> FEATURE:
<223> OTHER INFORMATION: Origin of the sequence: soil organism
<220> FEATURE:
<221> NAME/KEY: modified_base
<222> LOCATION: (1104)
<223> OTHER INFORMATION: variable nucleotide

<400> SEQUENCE: 85

```
tcccttcggg agcaagtaca gcggcgaacg ggtgagtaac acgtaggtaa cctaccctgg     60

agactgggat aacctgccga aaggcgggct aataccagat aagaccacga gggctgcggc    120

ccttggggca aaaggtggcc tctacttgta agctaccact ccgggatggg cctgcgcgcc    180

attagctagt tggcggggta acggcccacc aaggcagaga tggctagctg gtctgagagg    240

atggccagcc acacagggac tgagacacgg cccagactcc tacgggaggc agcagtgggg    300

aatattgcgc aatgggcgaa agcctgacgc agcgacgccg cgtgggtgat gaaggccttc    360

gggtcgtaaa gccctgtcaa gagggacgaa accttgtcga cctaacacgt cggcaacctg    420

acggtacctc tgaaggaagc accggctaac tccgtgccag cagccgcggt aatacggagg    480

gtgcgagcgt tgttcggaat tactgggcgt aaagcgcgtg taggcggcct cttcagtctg    540

gtgtgaaagc ccggggctca accccggaag tgcattggat actgggaggc tggagtaccg    600

gagaggaggg tggaattcct ggtgtagcgg tgaaatgcgt agatatcagg aggaacacct    660

gtggcgaagg cggccctctg gacggatact gacgctgaga cgcgaaagcg tggggagcaa    720

acaggattag ataccctggt agtccacgct gtaaacgatg ggcactaggt gttcggggta    780

ttgaccccct gagtgccgca gctaacgcat taagtgcccc gcctggggaa tacggccgca    840

aggttaaaac tcaaaggaat tgacgggggc ccgcacaagc ggtggagcat gtggtttaat    900

tcgacgcaac gcgaagaacc ttacctgggc tagacaacat cggacagcct cagaaatgag    960

gtctccccgc aaggggccgg tggttcaggt gctgcatggc tgtcgtcagc tcgtgtcgtg   1020

agatgttggg ttaagtcccg caacgagcgc aacccctgtc tctagttgct accattcagt   1080

tgagcactct agagagactg cccngtgtta aacgggagga aggtggggac gacgtcaagt   1140

cctcatggcc cttatgtcca gggctacaca cgtgctacaa tgggcgatac aaagggctgc   1200

gaacccgcga ggggaagcca atcccaaaaa gtcgctctca gttcggattg gagtctgcaa   1260

ctcgactcca tgaaggcgga atcgctagta atcgcggatc                         1300
```

<210> SEQ ID NO 86
<211> LENGTH: 1186
<212> TYPE: DNA
<213> ORGANISM: Unknown organism
<220> FEATURE:
<223> OTHER INFORMATION: Origin of the sequence: soil organism

<400> SEQUENCE: 86

```
caatgggcag cggcggacgg gtgagtaaca cgtgggaatg tacctttcgg tgcggaacaa     60

ctcagggaaa cttgagctaa tgccgcatac gcccttacgg ggaaagattt atcgccgaaa    120

gatcagcccg cgttggatta gctagttggt gaggtaatgg cccaccaagg cgacgatcca    180
```

-continued

```
tagctggttt gagagaacga ccagcctcac tgggactgag acacggccca gactcctacg    240
ggaggcagca gttgggaatc ttggacaatg ggggaaaccc tgatccagcc atgccgcgtg    300
agtgatgaag gccttcgggt tgtaaaactc tttcgacggg gacgataatg acggtacccg    360
tagaagaagc tccggctaac ttcgtgccag cagccgcggt aatacgaagg gggctagcgt    420
tgttcggaat tactgggcgt aaagcgtgcg caggcggcta tccaagtcag tggtgaaagc    480
ccggagctca actccggaat tgccattgaa actgtttagc ttgagtacga gagaggtgag    540
tggaataccc agtgtagagg tgaaattcgt agatattggg tagaacaccg gtggcgaagg    600
cggctcactg gctcgtaact gacgctcagg cacgacagcg tggggatcaa acaggattag    660
ataccctggt agtccacgcc gtaaacgatg aacgctagcc gttggatagc ttgctattca    720
gtggcgcagc taacgcatta agcgttccgc ctggggagta cggccgcaag gttgagactc    780
agaggaattg acgggggccc gcacaagcgg tggagcatgt ggtttaattc gacgcaacgc    840
gcagaacctt accagggttt gacatcctgt gctcgccggt gaaagccggt tttcccgcaa    900
gggacgcaga gacaggtgct gcatggctgt cgtcagctcg tgtcgtgaga tgttgggtta    960
agtcccgcaa cgagcgcaac cctcgccttt agttgccatc attcagttgg gcactctaga   1020
gggaccgccg gcgacaagcc ggaggaaggt ggggatgacg tcaagtcccc atggccctta   1080
caccctgggc tacacacgtg ctacaatggc ggtgacagtg ggcacgagct cgcgagagtc   1140
agctaatccc aaaaaaccgt cccagttcag attgcactct gcaact                  1186
```

<210> SEQ ID NO 87
<211> LENGTH: 1454
<212> TYPE: DNA
<213> ORGANISM: Unknown organism
<220> FEATURE:
<223> OTHER INFORMATION: Origin of the sequence: soil organism
<220> FEATURE:
<221> NAME/KEY: modified_base
<222> LOCATION: (1333)
<223> OTHER INFORMATION: variable nucleotide

<400> SEQUENCE: 87

```
cgacggccag tgaattgtaa tacgactcac tatagggcga attgggccct ctagatgcat     60
gctcgagcgg ccgccagtgt gatggatatc tgcagaattc gcccttcagg cctaacacat    120
gcaagtcgag cgagaaaggg cgcttcggcg cctgagtaca gcggcgcacg ggtgcgtaac    180
acgtgggcaa tctgtccttg agatggggat aacccagcga aagttgggct aataccgaat    240
aagactacag gaggcaactc ccgtggttaa agggtgctct ctgcggggag catgcgcttg    300
aggaggagcc cgcggcctat cagctagttg gtagggtcac ggcctaccaa ggcgaagacg    360
ggtagctggt ctgagaggat gaccagccac acggggactg agacacggcc ccgactccta    420
cgggaggcag cagtggggaa tattgggcaa tgggggaaac cctgacccag cgacgccgcg    480
tgggtgatga aggccttcgg gtcgtaaagc cctgtcgggc ggaacgaagg ttctcacggc    540
aaatagccgt gagaggtgac ggtaccgccg aaggaagcac cggccaactc cgtgccagca    600
gccgcggtaa gacggagggt gcaagcgttg ctcggaatca ctgggcgtaa agggtgcgta    660
ggcggtctcg caagtctggc gtgaaagccc aaggctcagc cttggaagtg cgctcgaaac    720
tgcgaggctg gagtgccgga ggggagagtg gaattcccgg tgtagcggtg aaatgcgtag    780
agatcgggag gaataccggt ggcgaaagcg actctctgga cggcaactga cgctgaggca    840
cgaaagcgtg gggagcaaac aggattagat accctggtag tccacgccgt aaacgatgga    900
cactaggtgt cgggggtatc cactccctcg gtgccgccgc taacgcagta agtgtcccgc    960
```

-continued

```
ctgggaagta cggtcgcaag attaaaactc aaaggaattg acgggggccc gcacaagcgg   1020

tggagcatgt ggttcaattc gatgcaacgc gaagaacctt acctgggttt gacatctggc   1080

gaatctctgg gaaaccagag agtgcccgca ggggagcgcc aagacaggtg ctgcatggct   1140

gtcgtcagct cgtgccgtga ggtgttgggt taagtcccgc aacgagcgca acccttaccc   1200

ttagttgccc ccgggtcaag ccgtggcact ccaagggaac tgcccgtgtt aagcgggagg   1260

aaggtgggga cgacgtcaag tcatcatggc ctttatatcc agggctacac acgtgctaca   1320

atggctggga canagcgtgg ccaacgcgcg agcgggagct aatcgcaaaa ccccagcctc   1380

agttcggatc ggagtctgca actcgactcc gtgaagctgg aatcgctagt aatcgcggat   1440

cagcatgccg cggt                                                     1454
```

```
<210> SEQ ID NO 88
<211> LENGTH: 1307
<212> TYPE: DNA
<213> ORGANISM: Unknown organism
<220> FEATURE:
<223> OTHER INFORMATION: Origin of the sequence: soil organism

<400> SEQUENCE: 88

cccttcgggg agcgagtaca gcggcgaacg ggtgagtaac acgtaggtaa cctaccctgg     60

tgactgggat aacttgccga aaggcgggct aataccagat aagaccacga gggctgcggc    120

ctttggggta aaagatggcc tctgcttgca tgctatcacg ccgggatggg cctgcgcgcc    180

attagctagt tggtgaggta acggctcacc aaggcagaga tggctagctg gtctgagagg    240

atggccagcc acactgggac tgagacacgg cccagactcc tacgggaggc agcagtgggg    300

aatattgcgc aatgggcgaa agcctgacgc agcgacgccg cgtgggtgat gaaggccttc    360

gggtcgtaaa gccctgtcaa gagggacgaa acctcgccga cccaatacgt cggcgacctg    420

acggtacctc tgaaggaagc accggctaac tccgtgccag cagccgcggt aatacggagg    480

gtgcaagcgt tgttcggaat cactgggcgt aaagcgcgtg taggcggcct tcttagtctg    540

gtgtgaaagc ccggggctca accccggaag agcattggat actggaaggc tggagtaccg    600

gagaggaggg tggaattcct ggtgtagcgg tgaaatgcgt agatatcagg aggaacaccg    660

gtggcgaagg cggccctctg gacggatact gacgctgaga cgcgacagcg tggggagcaa    720

acaggattag ataccctggt agtccacgcc gtaaacgatg ggtactaggt gttcggggta    780

ttgacccccct gagtgccgca gctaacgcat taagtacccc gcctggggac tacggccgca    840

aggctaaaac tcaaaggaat tgacgggggc ccgcacaagc ggtggagcat gtggtttaat    900

tcgacgcaac gcgaagaacc ttacctgggc tagacaacac tggacagccc cagaaatggg    960

gtcttcccgc aagggactgg tggttcaggt gctgcatggc tgtcgtcagc tcgtgtcgtg   1020

agatgttggg ttaagtcccg caacgagcgc aacccctgtc tctagttgct accattaagt   1080

tgagcactct agagagactg cccgtgttaa acgggaggaa ggtggggacg acgtcaagtc   1140

ctcatggccc ttatgtccag ggctacacac gtgctacaat ggacagtaca aagggctgcg   1200

aacccgtgag gggagccaa tcccaaaaag ctgttctcag ttcggattgg agtctgcaac   1260

tcgactccat gaaggcggaa tcgctagtaa tcgcggatca gcatgcc                 1307
```

```
<210> SEQ ID NO 89
<211> LENGTH: 1305
<212> TYPE: DNA
<213> ORGANISM: Unknown organism
<220> FEATURE:
```

-continued

<223> OTHER INFORMATION: Origin of the sequence: soil organism

<400> SEQUENCE: 89

```
gggagcaatc cccaagtaga gcggcgaacg ggtgagtaac gcgtgggtaa tctgcctccg     60
agtggggaac aacatcggga aactggtgct aataccgcat aacatcgttg ggtcttcgga    120
tctgacgatc aaagccgggg accgcaaggc ctggcgcttg gagaggagcc cgcgtccgat    180
tagctagttg gtggggtaat ggcccaccaa ggcttcgatc ggtagccggc ctgagagggc    240
ggacggccac actgggactg agacacggcc cagactccta cgggaggcag cagtggggaa    300
tttttcgcaa tgggcgaaag cctgacgaag caacgccgcg tggaggatga gggccttcgg    360
gtcgtaaact cctgtcgacc gggacgaaag taggatggcc taatacgccg atctattgac    420
tgtaccggtg gaggaagcca cggctaactc tgtgccagca gccgcggtaa tacagaggtg    480
gcaagcgttg ttcggaatta ctgggcgtaa agggcgcgta ggcggcttgg tcagtcccgt    540
gtgaaatccc tcggctcaac tgaggaactg cacgggaaac tgcctggctt gagttcggga    600
gagggaagtg gaattccggg tgtagcggtg aaatgcgtag atatccggag gaacaccggt    660
ggcgaaggcg gcttcctgga ccgacactga cgctgaggcg cgaaagctag gggagcaaac    720
gggattagat accccggtag tcctagctgt aaacgatgag tgctgggtgt agggggtatc    780
aacccccccct gtgccgaagc taacgcatta agcactccgc ctggggagta cggtcgcaag    840
gctgaaactc aaaggaattg acgggggccc gcacaagcgg tggagcatgt ggttcaattc    900
gacgcaacgc gaagaacctt accggggttt gaactgtacg ggacagctct agagatagag    960
tcttccttcg ggacccgtac agaggtgctg catggctgtc gtcagctcgt gtcgtgagat   1020
gttgggttaa gtcccgcaac gagcgcaacc cttgcctcct gttgccatca ggtaaagctg   1080
ggcactctgg agagactgcc ggtgataaac cggaggaagg tggggatgac gtcaagtcct   1140
catggccttt atgccccggg ctacacacgt gctacaatgg ccggtacaaa gggtcgcaaa   1200
accgcgaggt ggagctaatc ccaaaaagcc ggtcccagtt cggattgcag tctgcaactc   1260
gactgcatga agttggaatc gctagtaatc gcggatcagc atgcc                   1305
```

<210> SEQ ID NO 90
<211> LENGTH: 1299
<212> TYPE: DNA
<213> ORGANISM: Unknown organism
<220> FEATURE:
<223> OTHER INFORMATION: Origin of the sequence: soil organism

<400> SEQUENCE: 90

```
gggctttcgg gtcctgagta aagtggcgaa cgggtgagta acgcgtaggt aacctgacct     60
cgagtgtgga ataacctggc gaaagccggg ctaataccgc atgacgtctt cgggtcttcg    120
gacttgagga ccaaaggtgg cgagctttga gcgctgtcgc tcgagaaggg gcctgcgtcc    180
cattagctag ttggtggggt gatggcctac caaggcgacg atgggtagcc gggctgagag    240
gctgtccggc cacactggaa ccgagacacg gtccagactc ctacgggagg cagcagtggg    300
gaatcttgcg caatggggga aaccctgacg caacgacgcc gcgtgggcga tgaaggcctt    360
cgggtcgtaa agccctgtcg agcgggacga accgtgcgag ctctaacata gctcgtgcct    420
gacggtaccg ctagaggaag ccccggctaa ctccgtgcca gcagccgcgg taatacggag    480
ggggctagcg ttattcggaa ttattgggcg taaagggcgt gtaggcggct ctgtgtgtcc    540
catgtgaaag ccctcggctc aaccggggaa ctgcatggga aactgcggag cttgagtccg    600
ggagaggtga gtggaattcc cagtgtagcg gtgaaatgcg tagatattgg gaggaacacc    660
```

-continued

```
agtggcgaag gcggctcact ggaccggtac tgacgctgag acgcgaaagc caggggagca    720

aacgggatta gataccccgg tagtcctggc tgtaaacgat gagcacttgg tgtggcgggt    780

atcgacccct gccgtgctga agctaacgca ttaagtgctc cgcctgggga gtacggccgc    840

aaggctgaaa ctcaaaggaa ttgacggggg cccgcacaag cggtggagca tgtggttcaa    900

ttcgacgcaa cgcgaagaac cttacctggg tttgaactgc aggtgacagc ccctgaaagg    960

gggtcttcct tcgggacacc tgtagaggtg ccgcatggct gtcgtcagct cgtgtcgtga   1020

gatgttgggt taagtcccgc aacgagcgca acccctactc ctagttgcca gcggctcggc   1080

cgggaactct agggggaccg ccggtgataa accggaggaa ggtggggatg acgtcaagtc   1140

ctcatggcct ttatgtccag ggctacacac gtgctacaac ggacggtaca aagggctgcg   1200

aaggcgcgag ccggagccaa tcccaaaaag ccgttctcca gtgcggattg cagtctgcaa   1260

ctcgactgca tgaaggtgga atcgctagta atcgcggat                          1299
```

<210> SEQ ID NO 91
<211> LENGTH: 1296
<212> TYPE: DNA
<213> ORGANISM: Unknown organism
<220> FEATURE:
<223> OTHER INFORMATION: Origin of the sequence: soil organism

<400> SEQUENCE: 91

```
atgtctggta gcaataccag atgatggcaa gtggcggacg ggtgagtaat acgtagggat     60

ctgcccagaa gaggggggaca acccggggaa actcgggcta ataccgcata ctattctgag    120

gaagaaagct tggcgcaagc caggcgcttt tggaggaacc tacgtccgat tagctagttg    180

gtgaggtaaa ggctcaccaa ggcagagatc ggtagctggt ctgagaggat gaccagccac    240

actgggactg agacacggcc cagactccta cgggaggcag cagtggggaa tattggacaa    300

tgggggcaac cctgatccag cgatgccgcg tgtgtgaaga aggccttcgg gttgtaaagc    360

actttagttg gggaagaagt aatgtttttt aatagagagc attgttgacg gtacccaaag    420

aataagcacc ggctaactct gtgccagcag ccgcggtaat acagagggtg caagcgttaa    480

tcggagttac tgggcgtaaa gggcgcgtag gcggtgttgc aagtgagatg tgaaatccct    540

gggcttaacc taggaaccgc attttagact gcaatgctag agtacagtag agggtagtgg    600

aatttccggt gtagcggtga aatgcgtaga gatcggaagg aacaccagtg gcgaaggcga    660

ctacctggac tgacactgac gctgaggcgc gagagcgtgg ggagcaaaca ggattagata    720

ccctggtagt ccacgctgta aacgatgaga actagatgtt ggtgcgcgcg agcgcacaag    780

tatcgaagct aacgcgataa gttctccgcc tggggagtac ggccgcaagg ttaaaactca    840

aaggaattga cgggggcccg cacaagcggt ggagcatgtg gtttaattcg atgcaacgcg    900

aggaacctta cctacccttg acatccacag aatttgatag agatatcgaa gtgccgaaag    960

gaactgtgag acaggtgctg catggctgtc gtcagctcgt gttgtgagat gttgggttaa   1020

gtcccgtaac gagcgcaacc cttatcctta gttgccaaca cgtaatggtg ggactctaa   1080

ggagactgcc ggtgaagaac cggaggaagg tggggacgac gtcaagtcat catggccttt   1140

atgggtaggg ctacacacgt gctacaatgg ggcgtacaga gggttgccaa cctgcgaagg   1200

ggagccaatc ccggaaagcg cctcgtagtc cagattgaag tctgcaactc gacttcatga   1260

agtcggaatc gctagtaatc gcgaatcaga acgtcc                             1296
```

<210> SEQ ID NO 92

-continued

<211> LENGTH: 1250
<212> TYPE: DNA
<213> ORGANISM: Unknown organism
<220> FEATURE:
<223> OTHER INFORMATION: Origin of the sequence: soil organism

<400> SEQUENCE: 92
gtctggtagc aataccagat gatggcaagt ggcggacggg tgagtaatac gtagggatct 60
gcccagaaga gggggacaac ccggggaaac tcgggctaat accgcatact attctgagga 120
aaaaagcttg gcgcaagcca ggcgcttttg gaggaaccta cgtccgatta gctagttggt 180
gaggtaaagg ctcaccaagg cagagatcgg tagctggtct gagaggatga ccagccacac 240
tgggactgag acacggccca gactcctacg ggaggcagca gtggggaata ttggacaatg 300
ggggcaaccc tgatccagcg atgccgcgtg tgtgaagaag gccttcgggt tgtaaagcac 360
tttagttggg gaagaagtaa tgttttttaa tagagagcat tgttgacggt acccaaagaa 420
taagcaccgg ctaactctgt gccagcagcc gcggtaatac agagggtgca agcgttaatc 480
ggagttactg ggcgtaaagg gcgcgtaggc ggtgttgcaa gtgagatgtg aaatccctgg 540
gcttaaccta ggaaccgcat ttagactgc aatgctagag tacagtagag ggtagtggaa 600
tttccggtgt agcggtgaaa tgcgtagaga tcggaaggaa caccagtggc gaaggcgact 660
acctggactg acactgacgc tgaggcgcga gagcgtgggg agcaaacagg attagatacc 720
ctggtagtcc acgctgtaaa cgatgagaac tagatgttgg tgcgcgcgag cgcacaagta 780
tcgaagctaa cgcgataagt tctccgcctg gggagtacgg ccgcaaggtt aaaactcaaa 840
ggaattgacg gggcccgca caagcggtgg agcatgtggt ttaattcgat gcaacgcgaa 900
gaaccttacc taccttgac atccacagaa tttgatagag atatcgaagt gccgaaagga 960
actgtgagac aggtgctgca tggctgtcgt cagctcgtgt tgtgagatgt tgggttaagt 1020
cccgtaacgg gcgcaaccct tatccttagt tgccaacacg taatggtggg gactctaagg 1080
agactgccgg tgaagaaccg gaggaaggtg gggacgacgt caagtcatca tggcctttat 1140
gggtagggct acacacgtgc tacaatgggg cgtacagagg gttgccaacc tgcgaagggg 1200
agccaatccc ggaaagcgcc tcgtagtcca gattgaagtc tgcaactcga 1250

<210> SEQ ID NO 93
<211> LENGTH: 1545
<212> TYPE: DNA
<213> ORGANISM: Unknown organism
<220> FEATURE:
<223> OTHER INFORMATION: Origin of the sequence: soil organism
<220> FEATURE:
<221> NAME/KEY: modified_base
<222> LOCATION: (1084)
<223> OTHER INFORMATION: variable nucleotide

<400> SEQUENCE: 93
ccaggaaaca gctatgacca tgattacgcc aagcttggta ccgagctcgg atccactagt 60
aacggccgcc agtgtgctgg aattcgccct tcaggcctaa cacatgcaag tcgaacggca 120
gcacagggga gcttgctccc tgggtggcga gtggcggacg ggtgaggaat acatcggaat 180
ctgcccagtc gtgggggata acctcgggaa accgggacta ataccgcata cgaccttagg 240
gtgaaagcgg aggaccgcaa ggcttcgcgc gattggatga gccgatgtcg gattagcttg 300
ttggcggggt aacggcccac caaggcgacg atccgtagct ggtctgagag gatgatcagc 360
cacactggaa ctgagacacg gtccagactc ctacgggagg cagcagtggg gaatattgga 420
caatgggcgc aagcctgatc cagccatgcc gcgtgagtga agaaggcctt cgggttgtaa 480

-continued agctcttttg tccggaaaga aaagctttcg gttaataccc ggaagtcctg acggtaccgg 540
aagaataagc accggctaac ttcgtgccag cagccgcggt aatacgaagg gtgcaagcgt 600
tactcggaat tactgggcgt aaagcgtgcg taggtggttt gttaagtctg atgtgaaagc 660
cctgggctca acctgggaat tgcactggat actggcaggc tagagtgcgg tagaggatgg 720
cggaattccc ggtgtagcag tgaaatgcgt agagatcggg aggaacatct gtggcgaagg 780
cggccatctg gaccagcact gacactgagg cacgaaagcg tggggagcaa acaggattag 840
ataccctggt agtccacgcc ctaaacgatg cgaactggat gttgggagca actaggctct 900
cagtatcgaa gctaacgcgt taagttcgcc gcctggggag tacggtcgca agactgaaac 960
tcaaaggaat tgacgggggc ccgcacaagc ggtggagtat gtggtttaat tcgatgcaac 1020
gcgaagaacc ttacctggcc ttgacatcca cggaacttac cagagatggt ttggtgcctt 1080
cggnaaccgt gagacaggtg ctgcatggct gtcgtcagct cgtgtcgtga gatgttgggt 1140
taagtcccgc aacgagcgca acccttgtcc ttagttgcca gcacgtaatg gtgggaactc 1200
taaggagact gccggtgaca aaccggagga aggtggggat gacgtcaagt catcatggcc 1260
cttacggcca gggctacaca cgtactacaa tggtcggtac agagggttgc aaagccgcga 1320
ggtagagcca atcccagaaa accgatccca gtccggatcg aagtctgcaa ctcgacttcg 1380
tgaagtcgga atcgctagta atcgcggatc agaatgccgc ggtgaatacg ttcccgggcc 1440
ttgtacacac cgcccaaggg cgaattctgc agatatccat cacactggcg gccgctcgag 1500
catgcatcta gagggcccaa ttcgccctat agtgagtcgt attac 1545

<210> SEQ ID NO 94
<211> LENGTH: 1549
<212> TYPE: DNA
<213> ORGANISM: Unknown organism
<220> FEATURE:
<223> OTHER INFORMATION: Origin of the sequence: soil organism

<400> SEQUENCE: 94
ttttaaaccg acggccagtg aattgtaata cgactcacta tagggcgaat tgggccctct 60
agatgcatgc tcgagcggcc gccagtgtga tggatatctg cagaattcgc ccttcaggcc 120
taacacatgc aagtcgagcg gcagcgcggg gcaacctggc ggcgagcggc ggacgggtga 180
ggaatgcatc ggaatctacc ctgtcgtggg ggataacgta gggaaactta cgctaatacc 240
gcatacgacc gagaggtgaa agtgggggac cgcaaggcct cacgcgatag gatgagccga 300
tgccggatta gctagttggt gaggtaaagg ctcaccaagg cgacgatccg tagctggtct 360
gagaggatga tcagccacat tggactgag acacggccca aactcctacg ggaggcagca 420
gtggggaata ttggacaatg ggcgcaagcc tgatccagcc atgccgcgtg tgtgaagaag 480
gccttcgggt tgtaaagcac ttttgttcgg gaagaaatcg tgcgggttaa tacccagtac 540
ggatgacggt accgaaagaa taagcaccgg ctaacttcgt gccagcagcc gcggtaatac 600
gaagggtgca agcgttactc ggaatcactg ggcgtaaagc gtgcgtaggc ggttggttaa 660
gtctgctgtg aaagccctgg gctcaacctg ggaactgcag tggatactgg ccagctagag 720
tgtgatagag gatggtggaa ttcccggtgt agcggtgaaa tgcgtagaga tcgggaggaa 780
caccagtggc gaaggcggcc atctggatca acactgacgc tgaggcacga aagcgtgggg 840
agcaaacagg attagatacc ctggtagtcc acgccctaaa cgatgcgaac tggacgttgg 900
gagcaacttg gctctcagtg tcgaagctaa cgcgctaagt tcgccgcctg gggagtacgg 960

-continued

```
tcgcaagact gaaactcaaa ggaattgacg ggggcccgca caagcggtgg agtatgtggt   1020

ttaattcgat gcaacgcgaa gaaccttacc tggccttgac atccacggaa cttaccagag   1080

atggtttggt gccttcggaa ccgtgagaca ggtgctgcat ggctgtcgtc agctcgtgtc   1140

gtgagatgtt gggttaagtc ccgcaacgag cgcaaccctt gtccttagtt gccagcacgt   1200

aatggtggga actctaagga gactgccggt gacaaaccgg aggaaggtgg ggatgacgtc   1260

aagtcatcat ggcccttacg gccagggcta cacacgtact acaatggtcg gtacaagagg   1320

gttgcaaagc ccgcgaggta gagccaatcc cagaaaaccc gatcccagtc ccggatcgaa   1380

gtctgcaact cgacttcgtg aagtcggaat cgctagtaat cgcggatcag aatgccgcgg   1440

tgaatacgtt cccgggcctt gtacacaccg cccaagggcg aattccagca cactggcggc   1500

cgttactagt ggatccgagc tcggtaccaa gcttggcgta atcatggtc              1549
```

<210> SEQ ID NO 95
<211> LENGTH: 1276
<212> TYPE: DNA
<213> ORGANISM: Unknown organism
<220> FEATURE:
<223> OTHER INFORMATION: Origin of the sequence: soil organism

<400> SEQUENCE: 95

```
ctggcggcga gcggcggacg ggtgaggaat acatcggaat ctacccagtc gtgggggata     60

acgtagggaa acttacgcta ataccgcata cgacctgagg gtgaaagcag gggatcgcaa    120

gaccttgcgc gattggatga gccgatgtcc gattagctag ttggtgaggt aaaggctcac    180

caaggcgacg atcggtagct ggtctgagag ggtgatcagc cacactggaa ctgagacacg    240

gtccagactc ctacgggagg cagcagtggg gaatattgga caatgggcgc aagcctgatc    300

cagccatgcc gcgtgtgtga agaaggcctt cgggttgtaa agcacttttg ttcgggaaga    360

aatcttccga gttaatacct cgggaggatg acggtaccgg aagaataagc accggctaac    420

ttcgtgccag cagccgcggt aatacgaagg gtgcaagcgt tactcggaat tactgggcgt    480

aaagcgtgcg taggtggttc gttaagtctg ccgtgaaagc cccgggctca acctgggaat    540

tgcggtggat actggcggac tagagtgcgg tagagggtgg tggaattccc ggtgtagcag    600

tgaaatgcgt agagatcggg aggaacatct gtggcgaagc ggccacctgg accagcactg    660

acactgaggc acgaaagcgt ggggagcaaa caggattaga taccctggta gtccacgccc    720

taaacgatgc gaactggacg ttgggagcaa ctaggctctc agtgtcgaag ctaacgcgtt    780

aagttcgccg cctggggagt acggtcgcaa gactgaaact caaaggaatt gacgggggcc    840

cgcacaagcg gtggagtgtg tggtttaatt cgatgcaacg cgaagaacct tacctggcct    900

tgacatccac ggaatccttt agagatagag gagtgccttc gggaaccgtg agacaggtgc    960

tgcatggctg tcgtcagctc gtgtcgtgag atgttgggtt aagtcccgca acgagcgcaa   1020

cccttgtcct tagttgccag cgcgtaatgg cgggaactct aaggagactg ccggtgacaa   1080

accggaggaa ggtggggatg acgtcaagtc atcatggccc ttacggccag ggctacacac   1140

gtactacaat ggtggggaca gagggtcgcg aagccgcgag gtggagccaa tcccagaaac   1200

cccatcctag tccggatcgg agtctgcaac tcgactccgt gaagtcggaa tcgctagtaa   1260

tcgcggtcag catgcc                                                   1276
```

<210> SEQ ID NO 96
<211> LENGTH: 1306
<212> TYPE: DNA
<213> ORGANISM: Unknown organism
<220> FEATURE:
<223> OTHER INFORMATION: Origin of the sequence: soil organism

<400> SEQUENCE: 96
cagggatcag tagagtggca aacgggtgag taacgcgtgg gcgacctacc ttcgagtggg 60
ggataacctt ccgaaaggag ggctaatacc gcatgacatc ccgtgtttgg atacacggac 120
atcaaagccg gggatcgcaa gacctggcgc ttggagaggg gcccgcgtcc gattagctag 180
ttggtgaggt cacggctcac caaggctccg atcggtatcc ggcctgagag ggcggacgga 240
cacactggga ctgagacacg gcccagactc ctacgggagg cagcagtggg gaattgttcg 300
caatgggcgc aagcctgacg acgcaacgcc gcgtggagga tgaagacctt cgggtcgtaa 360
actcctttcg accgagatga agacccgccg gcctaatacg ccggcggatt gacagtatcg 420
agggaagaag ccccggctaa ctccgtgcca gcagccgcgg taatacgggg ggggcaagcg 480
ttgttcggaa ttactgggcg taaagggttc gtaggtggct cgctaagtca gacgtgaaat 540
ccctcagctc aactggggaa ctgcgtctga gactggcaag cttgagtgca ggagaggaac 600
gcggaattcc aggtgtagcg gtgaaatgcg tagatatctg gaggaacacc ggtggcgaag 660
gcggcgttct ggactgcaac tgacactgag gaacgaaagc taggggagca aacgggatta 720
gataccccgg tagtcctagc cctaaacgat gaatgcttgg tgtggcgggt atcgatccct 780
gccgtgccgc agttaacgcg ataagcattc cgcctgggga gtacggtcgc aaggctgaaa 840
ctcaaaggaa ttgacggggg cccgcacaag cggtggagca tgtggttcaa ttcgacgcaa 900
cgcgaagaac cttacctagg ctcgaagtgc agatgaccat cggtgaaagc cgactttcgc 960
aagaacatct gtagaggtgc tgcatggctg tcgtcagctc gtgtcgtgag atgttgggtt 1020
aagtcccgca acgagcgcaa cccttgtttc ctgttgccat caggttaagc tgggcactct 1080
ggagagactg ccggtgacaa accggaggaa ggtggggatg acgtcaagtc agcatggcct 1140
ttatgtctag ggctacacac gtgctacaat ggccggtaca aagcgctgca aacccgcgag 1200
ggtgagccaa tcgcagaaag ccggtctcag ttcggatagc aggctgcaac tcgcctgctt 1260
gaagttggaa tcgctagtaa tcgcggatca gcatgccgcg gtgaat 1306

<210> SEQ ID NO 97
<211> LENGTH: 1300
<212> TYPE: DNA
<213> ORGANISM: Unknown organism
<220> FEATURE:
<223> OTHER INFORMATION: Origin of the sequence: soil organism

<400> SEQUENCE: 97
cccgcagggt gagtagatgg caaacgggtg agtaacacgt gggtgacctg cctcagagtg 60
ggggataacg acccgaaagg gtcgctaata ccgcataaca tcctgtcttt ggatagacgg 120
agatcaaagc cggggatcgc aagacctggc gcttagagag gggcccgcgg ccgattagct 180
agttggtgag gtaacggctc accaaggcaa cgatcggtat ccggcctgag agggcggacg 240
gacacactgg gactgagaca cggcccagac tcctacggga ggcagcagtg gggaattgtt 300
cgcaatgggc gcaagcctga cgacgcaacg ccgcgtggag gatgaagatc ttcgggtcgt 360
aaactccttt cgatcgggaa gaacgcctct ggtgtgaaca ccatcagagg gtgacggtac 420
cgagagaaga agccccggct aactctgtgc cagcagccgc ggtaatacag ggggggcaag 480
cgttgttcgg aattactggg cgtaaagggc tcgtaggcgg ccggctaagt ccgacgtgaa 540
atccccaggc ttaacctggg aactgcgtcg gatactggcg ggcttgaatc cgggagaggg 600

-continued

```
atgcggaatt ccaggtgtag cggtgaaatg cgtagatatc tggaggaaca ccggtggcga    660

aggcggcatc ctggaccggt attgacgctg aatagcgaaa gccaggggag caaacgggat    720

tagatacccc ggtagtcctg gccctaaacg atgaatgttt ggtgtggcgg gtatcgatcc    780

ctgccgtgcc gaagctaacg cattaaacat tccgcctggg gagtacggtc gcaaggctga    840

aactcaaagg aattgacggg ggcccgcaca agcggtggag catgtggttc aattcgacgc    900

aacgcgaaga accttaccca ggctcgaacg gcattggaca tccggcgaaa gccggctccc    960

gcaagggccg atgtcgaggt gctgcatggc tgtcgtcagc tcgtgtcgtg agatgttggg   1020

ttaagtcccg caacgagcgc aacccttgtc cgctgttgcc atcacgttat ggtgggcact   1080

ctgcggagac tgccggtgat aaaccggagg aaggtgggga tgacgtcaag tcagcatggc   1140

ctttatgtct ggggctacac acgtgctaca atggccggta caaaccgttg cgatctcgca   1200

agagtgagct aatcggagaa agccggtctc agttcggatt gcaggctgca actcgcctgc   1260

atgaagttgg aatcgctagt aatcgcggat cagcacgccg                         1300
```

<210> SEQ ID NO 98
<211> LENGTH: 1233
<212> TYPE: DNA
<213> ORGANISM: Unknown organism
<220> FEATURE:
<223> OTHER INFORMATION: Origin of the sequence: soil organism
<220> FEATURE:
<221> NAME/KEY: modified_base
<222> LOCATION: (435)
<223> OTHER INFORMATION: variable nucleotide

<400> SEQUENCE: 98

```
acggagcggc agacgggaga gtaacacgtg ggaacgtgcc ctttggttcg gaacaacaca     60

gggaaacttg tgctaatacc ggataagccc ttacggggaa agatttatcg ccaaaggatc    120

ggcccgcgtc tgattagcta gttggtgagg taacggctca ccaaggcgac gatcagtagc    180

tggtctgaga ggatgatcag cctcactggg actgagacac ggcccagact cctacgggag    240

gcagcagtgg ggaatattgg acaatgggcg caagcctgat ccagccatgc cgcgtggatg    300

atgaaggccc tagggttgta aagtcctttc ggcggggaag ataatgacgg tacccgcaga    360

agaagccccg gctaacttcg tgccagcagc cgcggtaata cgaagggggc tagcgttgct    420

cggaatcact gggcngtaaa gcgcacgtag gcggcttttt aagtcagggg tgaaatcctg    480

gagctcaact ccagaactgc ctttgatact gagaagcttg agtccgggag aggtgagtgg    540

aactgcgagt gtagaggtga aattcgtaga tattcgcaag aacaccagtg gcgaaggcgg    600

ctcactggcc cggtactgac gctgaggtgc gaaagcgtgg ggagcaaaca ggattagata    660

ccctggtagt ccacgctgta aacgatggat gctagccgtt gtcgggttta ctcgtcagtg    720

gcgcagctaa cgcattaagc atcccgcctg gggagtacgg tcgcaagatt aaaactcaaa    780

ggaattgacg gggcccgca caagcggtgg agcatgtggt tcaattcgaa gcaacgcgca    840

gaaccttacc agcccttgac atgtcccgta tgagtaccag agatggaact cttcagttcg    900

gctggcggga acacaggtgc tgcatggctg tcgtcagctc gtgtcgtgag atgttgggtt    960

aagtcccgca acgagcgcaa ccctcgccct tagttgccat catttagttg ggcactctaa   1020

ggggactgcc ggtgataagc cgcgaggaag gtggggatga cgtcaagtcc tcatggccct   1080

tacgggctgg gctacacacg tgctacaatg gcggtgacag tgggatgcag aggggtaacc   1140

ccgagcaaat ctcaaaaagc cgtctcagtt cggattgtgc tctgcaactc gagcacatga   1200

agttggaatc gctagtaatc gcagatcagc acg                                1233
```

-continued

<210> SEQ ID NO 99
<211> LENGTH: 1304
<212> TYPE: DNA
<213> ORGANISM: Unknown organism
<220> FEATURE:
<223> OTHER INFORMATION: Origin of the sequence: soil organism

<400> SEQUENCE: 99
cgaaatcccg cagggatcag tagagtggca aacgggtgag taacacgtgg gtgacctgcc 60
ttcgagtggg ggataacgtc ccgaaaggga cgctaatacc gcatgacatc ctgctcttga 120
acgagtggag atcaaagctg gggatcgcaa gacctagcgc tcaaagaggg gcccgcgcct 180
gattagctag ttggtggggt aacggctcac caaggcgacg atcagtatcc ggcctgagag 240
ggcggacgga cacactggga ctgagacacg gcccagactc ctacgggagg cagcagtggg 300
gaattgttcg caatgggcgc aagcctgacg acgcaacgcc gcgtggagga tgaagatctt 360
cgggtcgtaa actcctttcg atcgagacga acggcctccg ggtgaacaat ccggaggagt 420
gacggtaccg agagaagaag ccccggctaa ctccgtgcca gcagccgcgg taatacgggg 480
ggggcaagcg ttgttcggaa ttactgggcg taaagggctc gtaggcggcc aactaagtca 540
gacgtgaaat ccctcggctt aaccggggaa ctgcgtctga tactggatgg ctagaggttg 600
ggagagggat gcggaattcc aggtgtagcg gtgaaatgcg tagatatctg gaggaacacc 660
ggtggcgaag gcggcatcct ggaccaattc tgacgctgag gagcgaaagc caggggagca 720
aacgggatta gataccccgg tagtcctggc cctaaacgat gaatgcttgg tgtggcgggt 780
atcgatccct gccgtgccga agctaacgca ttaagcattc cgcctgggga gtacggtcgc 840
aaggctgaaa ctcaaaggaa ttgacggggg cccgcacaag cggtggagca tgtggttcaa 900
ttcgacgcaa cgcgaagaac cttacccagg cttgaacagc gagtgaccac tcctgaaaag 960
gagcttccgc aaggacactc gtagaggtgc tgcatggctg tcgtcagctc gtgtcgtgag 1020
atgttgggtt aagtcccgca acgagcgcaa cccttgtttg ctgttgccat cacgttatgg 1080
tgggcactct gcaaagactg ccggtgataa accggaggaa ggtggggatg acgtcaagtc 1140
agcatggcct ttatgtctgg ggctacacac gtgctacaat ggccggtaca aaccgtcgca 1200
aaaccgtaag gtcgagctaa tcggagaaag ccggtctcag ttcggatcgt cggctgcaac 1260
tcgccggcgt gaagttggaa tcgctagtaa tcgcggatca gcac 1304

<210> SEQ ID NO 100
<211> LENGTH: 1197
<212> TYPE: DNA
<213> ORGANISM: Unknown organism
<220> FEATURE:
<223> OTHER INFORMATION: Origin of the sequence: soil organism

<400> SEQUENCE: 100
tctagtggcg cacgggtgcg taacgcgtgg gaatctgccc ttgggttcgg gataacagtt 60
ggaaacgact gctaataccg gatgatgtct tcggaccaaa gatttatcgc ccagggatga 120
gcccgcgtcg gattagctag ttggtgaggt aaaggctcac caaggcgacg atccgtagct 180
ggtctgagag gatgatcagc cacactggga ctgagacacg gcccagactc ctacgggagg 240
cagcagtggg gaatattgga caatgggcga aagcctgatc cagcaatgcc gcgtgagtga 300
tgaaggcctt agggttgtaa agctcttttg cccgggatga taatgacagt accgggagaa 360
taagccccgg ctaactccgt gccagcagcc gcggtaatac ggagggggct agcgttgttc 420

-continued

```
ggaattactg ggcgtaaagc gcacgtaggc ggctttgtaa gttagaggtg aaagcccgga    480

gctcaactcc ggaactgcct ttaagactgc atcgcttgaa cgtcggagag gtaagtggaa    540

ttccgagtgt agaggtgaaa ttcgtagata ttcggaagaa caccagtggc gaaggcgact    600

tactggacga ctgttgacgc tgaggtgcga aagcgtgggg agcaaacagg attagatacc    660

ctggtagtcc acgccgtaaa cgatgatgac tagctgtcgg ggctcatgga gtttcggtgg    720

cgcagctaac gcgttaagtc atccgcctgg ggagtacggc cgcaaggtta aaactcaaag    780

aaattgacgg gggcctgcac aagcggtgga gcatgtggtt taattcgaag caacgcgcag    840

aaccttacca gcgtttgaca tggtaggacg gtttccagag atggattcct tcccttacgg    900

gacctacaca caggtgctgc atggctgtcg tcagctcgtg tcgtgagatg ttgggttaag    960

tcccgcaacg agcgcaaccc tcgtctttag ttgctaccat ttagttgggc actctaaaga   1020

aactgccggt gataagccgg aggaaggtgg ggatgacgtc aagtcctcat ggcccttacg   1080

cgctgggcta cacacgtgct acaatggcgg tgacagtggg cagcaaactc gcgagagtga   1140

gcaaatcccc aaaaaccgtc tcagttcgga ttgttctctg caactcgaga gcatgaa      1197
```

<210> SEQ ID NO 101
<211> LENGTH: 1352
<212> TYPE: DNA
<213> ORGANISM: Unknown organism
<220> FEATURE:
<223> OTHER INFORMATION: Origin of the sequence: soil organism

<400> SEQUENCE: 101

```
cgacggccag tgaattgtaa tacgactcac tatagggcga attgggccct ctagatgcat     60

gctcgagcgg ccgccagtgt gatggatatc tgcagaattc gcccttcagg cctaacacat    120

gcaagtcgca cgagaaaggg cttcggcccc ggtacagtgg cgcacgggtg agtaacacgt    180

aggcaatctc ccctcgagtg gtggataacc ttccgaaagg agggctaata cagcatgaga    240

ccacgagctc gcagagcttg tggccaaagc ggacctcttc ttgaaagttc gcgcttgagg    300

atgagcctgc ggcccatcag ctagttggta gggtaatggc ctaccaaggc taagacgggt    360

agctggtctg agaggacgga cagccacact ggaactgaga cacggtccag actcctacgg    420

gaggcagcag tggggaatct tgcgcaatgg acgaaagtct gacgcagcga cgccgcgtga    480

gcgatgaagg ccttcgggtt gtaaagctct gtggggagag acgaataagg tgcagctaat    540

acctgcatcg atgacggtat ctccttagca agcaccggct aactctgtgc cagcagccgc    600

ggtaagacag agggtgcaaa cgttgttcgg aattactggg cgtaaagcgc gtgtaggcgg    660

ctgtgtaagt cgggcgtgaa atcccatggc tcaaccatgg aagtgcaccc gaaactgcgt    720

agctagagtc ctggagagga aggtggaatg cttggtgtag aggtgaaatt cgtagatatc    780

aagcggaaca ccggtggcga agcggccttc tggacagtga ctgacgctga gacgcgaaag    840

cgtggggagc aaacaggatt agataccctg gtagtccacg ccgtaaacga tgaatgctag    900

acgctggggt gcatgcactt cggtgtcgcc gctaacgcat taagcattcc gcctggggag    960

tacggccgca aggttaaaac tcaaaggaat tgacgggggc ccgcacaagc ggtggagcat   1020

gtggtttaat tcgaagcaac gcgcaaacct taccaaccct tgacatgtcc attgccggtc   1080

cgagagattg gaccttcagt tcggctggat ggaacacagg tgctgcatgg ctgtcgtcag   1140

ctcgtgtcgt gagatgttgg gttaagtccc gcaacgagcg caacccctac cgccagttgc   1200

catcattcag ttgggcactc tggtggaact gccggtgaca agccggagga agcggggatg   1260

acgtcaagtc ctcatggccc ttatgggttg ggctacacac gtgctacaat ggcggtgaca   1320
```

-continued

```
gtgggacgcg aagtccaaga tggacaaatc cc                                  1352

<210> SEQ ID NO 102
<211> LENGTH: 1361
<212> TYPE: DNA
<213> ORGANISM: Unknown organism
<220> FEATURE:
<223> OTHER INFORMATION: Origin of the sequence: soil organism

<400> SEQUENCE: 102

aacagctatg accatgatta cgccaagctt ggtaccgagc tcggatccac tagtaacggc      60
cgccagtgtg ctggaattcg cccttcaggc ctaacacatg caagtcgaac ggatccttcg     120
ggattagtgg cggacgggtg agtaacacgt gggaacgtgc cctttggttc ggaacaactc     180
agggaaactt gagctaatac cggataagcc tttcgaggga aagatttatc gccattggag     240
cggcccgcgt aggattagct agttggtgag gtaaaagctc accaaggcga cgatccttag     300
ctggtctgag aggatgatca gccacattgg gactgagaca cggcccaaac tcctacggga     360
ggcagcagtg gggaatcttg cgcaatgggc gcaagcctga tccagccatg ccgcgtgagt     420
gatgaaggcc ttagggttgt aaagctcttt caccggagaa gataatgacg gtatccggag     480
aagaagcccc ggctaacttc gtgccagcag ccgcggtaat acgaaggggg ctagcgttgt     540
tcggaattac tgggcgtaaa gcgcacgtag gcggatattt aagtcagggg tgaaatccca     600
gagctcaact ctggaactgc ctttgatact gggtatcttg agtatggaag aggtaagtgg     660
aattccgagt gtagaggtga aattcgtaga tattcggagg aacaccagtg gcgaaggcgg     720
cttactggtc cattactgac gctgaggtgc gaaagcgtgg ggagcaaaca ggattagata     780
ccctggtagt ccacgccgta aacgatgaat gttagccgtc gggcagtata ctgttcggtg     840
gcgcagctaa cgcattaaac attccgcctg gggagtacgg tcgcaagatt aaaactcaaa     900
ggaattgacg gggcccgca caagcggtgg agcatgtggt ttaattcgaa gcaacgcgca      960
gaaccttacc agctcttgac attcggggtt tgggcagtgg agacattgtc cttcagttag    1020
gctggcccca gaacaggtgc tgcatggctg tcgtcagctc gtgtcgtgag atgttgggtt    1080
aagtcccgca acgagcgcaa ccctcgccct tagttgccag catttagttg ggcactctaa    1140
ggggactgcc ggtgataagc cgagaggaag gtggggatga cgtcaagtcc tcatggccct    1200
tacgggctgg gctacacacg tgctacaatg gtggtgacag tgggcagcga gacagcgatg    1260
tcgagctaat ctccaaaagc catctcagtt cggattgcat ctgcaactcg agtgcatgaa    1320
gttggaatcg ctagtaatcg cagatcagca tgctgcggtg a                        1361

<210> SEQ ID NO 103
<211> LENGTH: 1300
<212> TYPE: DNA
<213> ORGANISM: Unknown organism
<220> FEATURE:
<223> OTHER INFORMATION: Origin of the sequence: soil organism

<400> SEQUENCE: 103

catgtttagt agcaatacta aatgatgacg agcggcggac gggtgaggaa cacgtaggaa      60
cctgcccaag agagggggac aaccaaggga aactttggct aataccgcat aatctctacg     120
gagaaaagtt gcccgtaagg gtggcgcttt tggagggggcc tgcgtccgat tagttagttg    180
gtgaggtaat agctcaccaa gactgtgatc ggtaactggt ctgagaggac gaccagtcac     240
actgggactg agacacggcc cagactccta cgggaggcag cagtggggaa tcttggacaa     300
```

-continued

```
tgggggcaac cctgatccag cgatgccgcg tgggtgaaga aggccttcgg gttgtaaagc    360
cctttaggcg gggaagaagg atatgggatg aataagcctg tattttgacg gtacccgcag    420
aataagcacc ggcaaactct gtgccagcag ccgcggtaat acagagggtg cgagcgttaa    480
tcggatttac tgggcgtaaa gggcgcgtag gcggttgtgt gagtgtgatg tgaaagcccc    540
gggctcaacc tgggaagtgc atcgcaaacg acacaactgg agtatatgag agggtggcgg    600
aatttccggt gtagcggtga aatgcgtaga gatcggaagg aacgtcgatg gcgaaggcag    660
ccacctggca taatactgac gctgaggcgc gaaagcgtgg ggagcgaaca ggattagata    720
ccctggtagt ccacgccgta aacgatgaga actagatgtt ggaggggggaa cccttcagta   780
tcgaagctaa cgcgataagt tctccgcctg ggaagtacag tcgcaagact gaaactcaaa    840
agaattgacg gggcccgca caagcggtgg agcatgtggt ttaattcgat gcaacgcgaa    900
gaaccttacc taccettgac atcctgcgaa tcttgccgag aggtgagagt gccgcaagga    960
gcgcagagac aggtgctgca tggctgtcgt cagctcgtgt tgtgagatgt tgggttaagt   1020
cccgtaacga gcgcaaccct tgtccttagt tgccatcatt tagttgggga ctctaaggag   1080
accgccggtg atgaaccgga ggaaggcggg gacgacgtca agtcatcatg gcctttatgg   1140
gtagggctac acacgtgcta caatggggcg tacagagggt cgccaacccg cgaggggggag  1200
ccaatctctt aaagcgtctc gtagtccgga ttggagtctg caactcgact ccatgaagtc   1260
ggaatcgcta gtaatcgcgg atcagcagtg ccgcggtgaa                         1300
```

<210> SEQ ID NO 104
<211> LENGTH: 1250
<212> TYPE: DNA
<213> ORGANISM: Unknown organism
<220> FEATURE:
<223> OTHER INFORMATION: Origin of the sequence: soil organism

<400> SEQUENCE: 104

```
tgtagcaata catcagtggc agacgggtga gtaacacgtg ggaaccttcc tcgttgtacg     60
ggacaactca gggaaacttg agctaatacc gtatacgtcc gagaggagaa agatttatcg    120
caatgagacg ggcccgcgtc ggattagcta gttggtaagg taacggctta ccaaggcgac    180
gatccgtagc tgatctgaga ggatgatcag ccacactggg actgagacac ggcccagact    240
cctacgggag gcagcagtgg ggaatcttgg acaatgggcg caagcctgat ccagccatgc    300
cgcgtgagtg aagaaggcct tagggttgta aagctctttt gccagggacg ataatgacgg    360
tacctgagaa taagccccgg caaacttcgt gccagcagcc gcggtaatac gaaggggggct   420
agcgttgttc ggatttactg ggcgtaaagc gcacgtaggc gggtcgttaa gtcaggggtg    480
aaatcccgga gctcaactcc ggaactgcct ttgatactgg cgaccttgag gctggaagag    540
gttagtggaa ttcccagtgt agaggtgaaa ttcgtagata ttgggaagaa caccagtggc    600
gaaggcggct aactggtcca gatctgacgc tgaggtgcga aagcgtgggg agcaaacagg    660
attagatacc ctggtagtcc acgccgtaaa ctatgggtgc tagctgtcag cgggcttgct    720
cgttggtggc gcagctaacg cattaagcac cccgcctggg gagtacggtc gcaagattaa    780
aacttaaagg aattgacggg ggcccgcaca agcggtggag catgtggttt aattcgaagc    840
aacgcgcaga accttaccaa cccttgacat cccgatcgcg gacaccagag atggagtcct    900
tcagttcggc tggatcggag acaggtgctg catggctgtc gtcagctcgt gtcgtgagat    960
gttgggttaa gtcccgcaac gagcgcaacc ctcgcccttta gttgccatca tttagttggg  1020
cactctaaag ggactgccgg tgataagccg gaggaaggtg ggatgacgt caagtcctca    1080
```

-continued tggcccttac gggttgggct acacacgtgc tacaatggcg gtgacaatgg gcagctactt 1140
cgcaaggaga agctaatccc aaaaagccgt ctcagttcag attgcactct gcaactcggg 1200
tgcatgaagt tggaatcgct agtaatcgct aatcagcagg tagcggtgaa 1250

<210> SEQ ID NO 105
<211> LENGTH: 1302
<212> TYPE: DNA
<213> ORGANISM: Unknown organism
<220> FEATURE:
<223> OTHER INFORMATION: Origin of the sequence: soil organism

<400> SEQUENCE: 105
ggcttcggct ccccggtaga gtggcggacg ggtgagtaac acgtgggtaa tctgcctttg 60
ggtggggaat aacccttcga aagaggggct aataccgcat aacgcagcgg caccgaatgg 120
tgacagttgt taaagtgggg gatcgcaaga cctcacgcct gaagaggagc ccgcgcccga 180
ttagctagtt ggtgcggtaa tggcgtacca aggcggcgat cggtagccgg cctgagaggg 240
cggacggcca cactggcact gagagacggg ccagactcct acgggaggca gcagtgggga 300
attttgggca atgggcgcaa gcctgaccca gcaacgccgc gtgaaggacg aaatccctct 360
gggatgtaaa cttcgaaagt tggggaagaa atccgtgtga ggataatgca cacgggatga 420
cggtacccaa cgtaagcccc ggctaactac gtgccagcag ccgcggtaat acgtaggggg 480
caagcgttgt tcggaattac tgggcgtaaa gggcgcgtag gcggtacgac aagtctggag 540
tgaaagcccg gggctcaacc ccggaatgtc tttggaaact gtcgaacttg agtgcggaag 600
aggcatctgg aattcccagt gtagcggtga aatgcgtaga tattgggaag aacacctgag 660
gcgaaggcgg gatgctgggc cgacactgac gctgaggcgc gaaagccagg ggagcgaacg 720
ggattagata ccccggtagt cctggcccta aacgatggat acttggtgtg tggggttctc 780
gaagtccccg cgtgccggag ctaacgcggt aagtatcccg cctggggagt acggtcgcaa 840
ggctgaaact caaaggaatt gacggggacc cgcacaagcg gtggagcatg tggttcaatt 900
cgacgcaacg cgaagaacct tacctgggtt aaatcctacc tcgtcgcctc agagatgagg 960
tttcccttcg gggaggtag gacggtgctg catggctgtc gtcagctcgt gccgtgaggt 1020
gttgggttaa gtcccgcaac gagcgcaacc cttaccacta gttgccagcg gttcggccgg 1080
gcactctatt gggactgccg gtgacaaacc ggaggaaggt ggggatgacg tcaagtcatc 1140
atggccttta tgtccagggc tacacacgtg ctacaatggc cggaacaaag cgcagcaaac 1200
ccgcgagggg gagccaatcg caaaaatccg gtctcagttc ggattggagt ctgcaactcg 1260
actccatgaa gttggaatcg ctagtaatcg cggatcagca tg 1302

<210> SEQ ID NO 106
<211> LENGTH: 1281
<212> TYPE: DNA
<213> ORGANISM: Unknown organism
<220> FEATURE:
<223> OTHER INFORMATION: Origin of the sequence: soil organism

<400> SEQUENCE: 106
tgcttctctt gagagcggcg gacgggtgag taatgcctag gaatctgcct ggtagtgggg 60
gataacgttc ggaaacggac gctaataccg catacgtcct acgggagaaa gcaggggacc 120
ttcgggcctt gcgctatcag atgagcctag gtcggattag ctagttggtg aggtaatggc 180
tcaccaaggc gacgatccgt aactggtctg agaggatgat cagtcacact ggaactgaga 240

-continued

```
cacggtccag actcctacgg gaggcagcag tggggaatat tggacaatgg gcgaaagcct    300

gatccagcca tgccgcgtgt gtgaagaagg tcttcggatt gtaaagcact ttaagttgga    360

aggaagggca gtaaattaat actttgctgt tttgacgtta ccgacagaat aagcaccggc    420

taactctgtg ccagcagccg cggtaataca gagggtgcaa gcgttaatcg gaattactgg    480

gcgtaaagcg cgcgtaggtg gtttgttaag ttggatgtga aatccccggg ctcaacctgg    540

gaactgcatt caaaactgac tgactagagt atggtagagg gtggtggaat ttcctgtgta    600

gcggtgaaat gcgtagatat aggaaggaac accagtggcg aaggcgacca cctggactaa    660

tactgacact gaggtgcgaa agcgtgggga gcaaacagga ttagataccc tggtagtcca    720

cgccgtaaac gatgtcaact agccgttgga agccttgagc ttttagtggc gcagctaacg    780

cattaagttg accgcctggg gagtacggcc gcaaggttaa aactcaaatg aattgagggg    840

ggcccgcaca agcggtggag catgtggttt aattcgaagc aacgcgaaga accttaccag    900

gccttgacat ccaatgaact ttctagagat agattggtgc cttcgggaac attgagacag    960

gtgctgcatg gctgtcgtca gctcgtgtcg tgagatgttg ggttaagtcc cgtaacgagc   1020

gcaacccttg tccttagtta ccagcacgac atggtgggca ctctaaggag actgccggtg   1080

acaaaccgga ggaaggtggg gatgacgtca agtcatcatg gcccttacgg cctgggctac   1140

acacgtgcta caatggtcgg tacagagggt tgccaagccg cgaggtggag ctaatcccac   1200

aaaaccgatc gtagtccgga tcgcagtctg caactcgact gcgtgaagtc ggaatcgcta   1260

gtaatcgcga atcagaaatg t                                             1281
```

<210> SEQ ID NO 107
<211> LENGTH: 43
<212> TYPE: DNA
<213> ORGANISM: Artificial sequence
<220> FEATURE:
<223> OTHER INFORMATION: Description of the artificial sequence: primer

<400> SEQUENCE: 107

```
cgctgcagat ttaaatatgc aacgcgtaag tcgatggcgt tcg                       43
```

<210> SEQ ID NO 108
<211> LENGTH: 51
<212> TYPE: DNA
<213> ORGANISM: Artificial sequence
<220> FEATURE:
<223> OTHER INFORMATION: Description of the artificial sequence: primer

<400> SEQUENCE: 108

```
cggtcaactt aattaagata tctcgagaga tctattaata cgatacctgc g              51
```

<210> SEQ ID NO 109
<211> LENGTH: 29
<212> TYPE: DNA
<213> ORGANISM: Artificial sequence
<220> FEATURE:
<223> OTHER INFORMATION: Description of the artificial sequence: primer

<400> SEQUENCE: 109

```
aaaaagatat ctgacgtccc gaaggcgtg                                       29
```

<210> SEQ ID NO 110
<211> LENGTH: 32
<212> TYPE: DNA
<213> ORGANISM: Artificial sequence
<220> FEATURE:
<223> OTHER INFORMATION: Description of the artificial sequence: primer

<400> SEQUENCE: 110
aaaaaagatc tggctaacta actaaaccga ga 32

<210> SEQ ID NO 111
<211> LENGTH: 36
<212> TYPE: DNA
<213> ORGANISM: Artificial sequence
<220> FEATURE:
<223> OTHER INFORMATION: Description of the artificial sequence: primer

<400> SEQUENCE: 111
gtgccgttaa ttaagctccg cgaagtcgct cttctt 36

<210> SEQ ID NO 112
<211> LENGTH: 36
<212> TYPE: DNA
<213> ORGANISM: Artificial sequence
<220> FEATURE:
<223> OTHER INFORMATION: Description of the artificial sequence: primer

<400> SEQUENCE: 112
gtgccgttaa ttaaccgctg cataaccctg cttcgg 36

<210> SEQ ID NO 113
<211> LENGTH: 42717
<212> TYPE: DNA
<213> ORGANISM: Artificial sequence
<220> FEATURE:
<223> OTHER INFORMATION: Description of the artificial sequence: cosmid a26g1 noncoding strand
<220> FEATURE:
<221> NAME/KEY: modified_base
<222> LOCATION: (37391)
<223> OTHER INFORMATION: variable nucleotide

<400> SEQUENCE: 113
aaaaaaaaaa aaaaaaaaaa aaaaaaaaaa aaaaaaaaaa aaaaaaaacc gggccctgac 60
gttcagaact ccccgcgaga atctctcggc agagcgcctg cacctcgact tcaccggcag 120
tgtcgagatc gatgcaggtg caagcgaact cgggatgctc ggccgcgatg gtacgtccca 180
gaccccacac cggtgcccgc gcgggcacca ccggcatctg cagatgctcc gcatgaacgc 240
ccgccgtaat cagccagatt cgcggatgct gcgattcggc gtcggacgct tgtttcgtca 300
gctgtatgcg tcccactccg aattcttgaa cgatgcgcaa aatgtcttcg caggcggttc 360
cccccgcagc cgacggatcg gtctcatcct cggtctcatc caggctcccg cagtgaatga 420
cgccccggta aggctgatcc ggtatctcgg catcgcgacc cgaaatcaca accgtgtttg 480
tgcccagccc tcgcgccacc gcggctgcga tgccgccggc atcggcaatg accagccatg 540
cacccgacac cgttgccgtt ggactctcgg ccagcagctg cggctcccat tccatagcgt 600
ggaaccattc ggattggcgc tccagttcct gggcacgcag gccttggacc tcgaggatga 660
cgtggccttc cgcatcacac agggtgacat cgccctcgag ccgcccccgtc agccgcgcat 720 gcaccctaag atcgccggcg ggtctgccga aacagtgcaa ccgttcgatg gcgacaggca 780
cgcaaggacc ggcgctgcct tcgccgccaa gcgtcgcgcc cagcacctgc aaacaggcat 840
cgagcaaggc aggatgaagc gtgtaaccgg actctgcttc gcgaacggca tccggcacgc 900
tcagtcgcgc cactgcctcg ccgtcgcgcc gccacacttc cgcgatgccg cggaaggtgt 960
cgccgtaatg catcccctgc gatgcgaagg ccgcatagaa gtcatcgccc tcgatgcgat 1020
ccccaagtgt gggcaggctc accgtgggcg cgaccttgtc cggcgccgca gccatggtgc 1080

-continued

```
cgcgcgcgtg ctcggtccaa tcggaaccgc cttcggccag actggagatg cggaatgcgt   1140
gtccctcgag tatgacctgc actcgcgagg cgcccgcgga aggaacaacc agcatttgtt   1200
caaaccggat ctcttccagg ctgcagccac ccgcgaacac ttccttggct gcggccagcg   1260
ccatctccac ataagcggca ccgggaagca cccacaagctc gttgagccgg tgatcggcga   1320
gaaacggcag cgcatccaga gagagcacgg actcccagac gtgtgtgtcc ggcgccagcg   1380
caatctcgac cttgcgaccg agcagcggat gaccgccaac tgccggcaaa cttcgccgcg   1440
tcgaggtcgc gaaccagaag cgctcgcgct gccagggata cgtcggcaga tccaggcgcg   1500
tgtcgggaga cgaagcgagc gcgcgccagt ccggacgctg cccattcacg tagagcgcgg   1560
cgagcaactc gagcagctca cgccgctccg gttcgtcgcg gcgcagtacg gggcgaacca   1620
gtccgtttat gccgagcgtc cgcagactat cctcgatcga cggcgtcagc acaggatgcg   1680
gactgatctc caggaactgc gtgaactcat caccagccat cgcctgcaac gactcccaga   1740
aacggactgg ctgtcgcaga ttggctaccc agtacgacgc gtcgcacgcc tcgcccgtgc   1800
tcaactgtcc ttcaaccgtg gagaagaacg gcacggcgga acgttttgca ataacgcggc   1860
cgagttcctg gcgcaattcg ttctcgagcg ggtccacctg cgagctgtgt gaagcgacat   1920
ccacctgaat cagccggcag aagacgccgc gcctctcgaa gtcgtccttc aaatgctcga   1980
gagccacacg gtctcccgag aacaccgtgc tgcgtggtcc gttgctggcc gcgacagaaa   2040
cagtagtgag accgcgttca gcgagcacgg ccttcgcccg atcgagcggc agttcgacca   2100
gagccatcgc tccccggccg cgaagtccga gcaacagccg gctgcggcga cagatgatgc   2160
gggccgcgtc ctccagggtg agaatgcctg cgacatgggc cgccgccact tctcccatgc   2220
tgtgtccggc cacgccgtcc gggcgaattc cccaggattg cagcagttcg accagcgcga   2280
tttgaacggc gaacagcgca ggctgcacgc gatcgatctg gctcagccat gctcccgact   2340
cgtcggcgag caggtccgca agccgccatt ccacgaagct gcggaaggcg gcgtcgcaac   2400
gttcgatcgc cgatcggaag acaggctcgt cggaatacag gcgatacgcc atgcgcgggt   2460
actgtccgcc ctggccggaa aagatgaagg cgagtttcgg acgaactccg ggatcggcga   2520
aaccggtggc gacgccgcga ttggtttcat tgcgccggaa ggcctcgagc aattgattga   2580
actcgggcag ggatgaggcc acaaacgctg cgcgatgttc gtagtgactg cgcgtcaggc   2640
tggcggcgga acacagcgcg gagagcggag cgtgaaagcg cccatcgcga taggcgccgg   2700
cgagatcgcg cagagcctgc ggatggcgcg ccgaaagcgg taggaggtat tcgcggccgt   2760
cttcggcatg gagttgatcc gggaccggca cttcctcgcg gctgggcggc cggcccgacc   2820
ccccgccgcc gcttcgcggg cggctgtccc cctcgaggag ggggacacta gcactagcct   2880
tagcctccac attccctttg gcctctacac tcgccttgac ctcttcactc gtcttcgcct   2940
ctacattcgt cttcgcctct acattcgtct tcgcttctac attcgtcttc gcttctgcga   3000
ggacgacgtg cgaattggtg ccactgattc cgaacgagct caccccggca actcgggggc   3060
ggccgttgga gggccatggc gaacatgcgg tggctatctt tagcggcagc tcattccaga   3120
gtacgtgcgg gttgggcgcg ttgaaatgca gatggggcgg aatctctcgg tgctgcaggg   3180
cgagaatggt cttgatcagg ccggcgatac ctgccgccgc ctccaggtgg ccgaagttgg   3240
ttttcaccga cccgacgatc aacggagaat cgacggcacg cccctcgccc agcaccgctg   3300
ccatcgcccg cagttcgatg ggatctccca gcggcgtccc ggttccgtgg gcttccacgt   3360
aatcgacatc ggcgggggcc atgccggcgt tcttgagcgc cgcccgaatc acggcttcct   3420
```

-continued gcgccggacc gttcggcgcc gtgaggccgt tgctgcggcc gccgtggttg acggccgatc 3480
cgcgaatcag cgccagaata cgatcgccgt cacgcgtcgc atcggacagc cgcttcagca 3540
ccagcattcc gcatccctcg ccgcggccgt aaccgtcggc ggaggcagcg aaacttttgc 3600
aacggccatc ggccgccatg gcccgcaggc ggcagaagta gatcgtgctt tccggcgcca 3660
gaatcaggtt cacgccgccg gccagcgcca tgctgcactc tcgcgactgc aagctgcggc 3720
acgccagatg aaccgccacg agtgaggaag agcacgccgt gtcgacgggg aagttcggtc 3780
cctgcaaccc cagcagatag gagatccgtc cggcggcagt gctgaacgcg gttccggtac 3840
cggtataggc gtcaatgagc gccggatcgg taggtttcag ccggctgtag tcgtcggtgc 3900
tgatcccgat gaacactccg gtgtcgctgc ccgcgagact gtcgggcggc cgacccgcac 3960
gctccaaagc ttcccatgcc acctcgagca gcaggcgctg ctgcggatcc agaccggcga 4020
cctcgcgcgg cgtgattccg aagaagccgg cgtcgaagcc gtcgacggca ccatcgagga 4080
atccgcccag acgcgtgtac atctttcccg gcgcgttggg atcgggatcg taaaacgcat 4140
cggcatccca acggcccgca ggaatttcgc ggatggcatc gatgccatcg tgcaggagct 4200
gccaaaatgc ttccggcgag tccgcgccgg gaaagcggca agccatgccg acgatcgcga 4260
tgggttcgtt gtggacgctc tccagttcgt cgagacgcgc tcgcgtgcgc ttgagcgcca 4320
ggaccgcctg ttgaagagga gtgagatcgc tcatcgttcc tctcccagat ggtgcaaggt 4380
ttccgtgatg aacgccgcca tctcctgctc ggacagctgc cgcacttcat cgacgaggga 4440
atcgctgggg acgtcgagtc cgagttcgcg gaggacatgg ccggccaatt tctcgacggt 4500
cggatggtcg tatagcaatg tcgcgggaag gctcttgcgc accagctctc cgatggcgcg 4560
cgccagatcc agcgccatca gcgaatcgag tccgtattcc ttgagcggcc ggcgcgggtc 4620
gagcgtcttg gacgcatcga gcgccagcac gccgccggcc tgcttgcgga tgcgcatctg 4680
cagcagttcc tgccgccgct ccggcgcagc ttcggtgagt tgctggatga agccgggatc 4740
gctcgccggg ctccgccttt tttcggcgga gacttggaac accgcgatct gagcggcagt 4800
ctcgcccagc agatcgccga agatgcgcgc acccacttcc ggcggcagca gcggtacccc 4860
cggcaggcct tgccgcgcga tgcgcgcggc catgccttcg cccgcccatg gtccccaatt 4920
gatgctcagc gccggtagtc cttgcgcgcg gcgcatgtgg gcaaggctgt cgagaaatgc 4980
gttggccgcc gagtaattgc tctgtccggc ggaaccgagc agcgaagcgg cggaagagaa 5040
gagtacgaaa aagtcgagcg catggtggcg agtgagctgg tgaagattcc aggcaccctg 5100
cagcttcggc gccagcacct tctcgaaacg agcccacgtc tgttctgtaa ctaccccgtc 5160
atcgagcacg cctgcggcat gcacgactcc acgcagcggc tgggtgcgcg ggtccgccag 5220
cagcgccgcc agctgttgct cggaactcac atcgcaagca gcaaccatga ctgcagcccc 5280
gagttgctcg agatcggcaa ctgcctccgt atgccggccg accagtacca gacggcgcgc 5340
gccttgctcg atcaagcggc gtgccaccct tcgtcctaat gcgccgagac cgccggtgat 5400
cagatagacg ccgtcggctg aaatggcagg cggccgcttc gacgtttcct tgtgccgcac 5460
cagccggcga acgtagcggc gtccgttgcg caatgcgatc gctttgtcgt cgccggcata 5520
acggatttca tccagcagca tggcggcggc gatgtcggca ttgtcgcaac cgaggtcgat 5580
caggccgccc cacagctcgg gatgctcgcg cgcgatcgcc tgcccgagtc cccacagtgg 5640
agcctggaaa ggatcgacgg gagtcgcatc gtcatcactg atgcgatgca cgccgcgcgt 5700
gatcagccag agccgcgccg ggcggccgac caaagtctgg gtctgttcca gcgcctggcg 5760
gagagtgacg ccggacacga cgcgcagctc ttgcggcatc aaaccggcga catcgtctgc 5820

-continued

```
gccggcacac agcaaccagt cctccggctt gccagggccg tcggacttca acgttgtcga   5880
tcgctcgcac tcctgccact gcacatcctg cagccacgac tgtgcggatt gcagcgtacc   5940
ggcatgcatt acagccagtc cggaaaactc ggcgatgacc gcgccggtct cttcaaccag   6000
cgtcagatca ccgacgaacg ggccgctcga gctcgggcgc agacgcgcat gacagcgcag   6060
agaacctgcc ggcggacggt agaagcgcac cgcttcgatc ccgaccggca cgtatgcgcc   6120
gggctggcaa cgctccgcgg gccaagtcgc tccgaatact tgaaaacaag aatcgatcag   6180
gccggggtgc agccggtaag cgttcgcgcc atcctcagcc accggcagac gcattcgccc   6240
cagcgcctcg ccatcgcgac gccagacttc ttccacccaa ctgaaggcgg ggccaagatc   6300
gacgccgcgt gcgttcatcg cgccgtagaa cgcatcgccg gaaatgactt cggaaggctg   6360
cgccggcagc tcgaaatgaa cggcgccggc agtcgccgcg cgcagactgg ctgccgtgtg   6420
gagcttccac gaatcgccat cctggctgaa gacctgcacc tttgcttcgc cgtcctcgcc   6480
gggtgtgaca atcgcttgca ccgtgaccgg cgtatccggc gggatggcca gtgcctgccg   6540
catcatgaca tcggagacgg cgcagggaac cggaccgaag acttcctgtg ccgcttcgag   6600
aaatgccgac acgtgccagg cgccgggcac aatgaccgcg tcgtagatca cgtgctcatg   6660
gagcagaggc gtctccgtgg ttagcgaatt ttcgaagatg acatcgccca acgcgctgtt   6720
gaggcgcgct cccaacatgc cgccgcgcgc cggctctctc gcgggtacgc gtctcaggct   6780
gaaggtgtca cgctgaaacg gatacgtcgg cagcgcgacg cggctgggtg attccccggc   6840
atagagaccg cgccagtcgg gattcacgcc cgcggtaaac aggccgccaa gactttccag   6900
cagcacggac caatccgatc gtcccttaga tagggagtgc agccagaccg cgccgtcatc   6960
gggcagacaa tatcgcccca gcgtggtgag cgtgggatgc gggccgattt ccagaaacag   7020
cttgcactcg cggtccgcca gggttcgcat cgcgctttca aactgcacgg tttcgcgcaa   7080
ctgtcgccgc cagtagcggg cgtcgagtgt cgtgcctttc ggcaatacgg ctccgctgac   7140
gttcgacacc agcgggatcg ccagcggctg atacgcgatc gcacctgcaa gcgcttcgaa   7200
cttgtccaaa atcggatcca tcagcggcga atggaacgca tgcgatacgt tcagctctcg   7260
cgtttccacg ccggcgcgat gcaggtcatc ttgcgcttcc gcgatttctg cagccgtgcc   7320
ggagatcacg gtgcggtccg gcgcattcga tgcggcgact gccaccttgg cggcgagcgc   7380
cgcgatgcgg ctcggattgg cgtgaacgat gaccgctttg ccgcggggaa gcgcattgac   7440
cagccgcccc ctggcggtca ccagccgcag gccgtcctcc acgctaaagg cgccggccac   7500
acacgccgca acatactcgc cgagactgtg gcccagcacg tagtccggcc ggacgccgag   7560
cgacagccag aactgagcca gagcccattc cagggcaaac attgccggct gggtatacgc   7620
cgtctcgtgc aacggcgaaa ccgactcgaa caagagaacg gtcagcggaa catcgagctg   7680
gggacggagc caatcggcgc aacgatcgag cgcgtcgcga aaaacaggct gcgttttata   7740
aagctctgcg cccatgccgg cgtactgcgc gccctggccg gtgaagagaa aagcgattgc   7800
cggccgccgg cgcaacgata cttcgcgccg cggcgccgcg gccaatgccg ctacagcctc   7860
tgccgcatct gcggcggtga tcgccaagcg gtgactatat gcgtcgcgcc caacctgact   7920
ggtgaagcaa acgtcggaca gcaacgcatt cgggtgcgac tgcaggaact ccgcgaagtg   7980
gccggccagt tcgccgagcg cttcgtcggt gcgcgccgac agagtgagaa gctgcgggcg   8040
tgtgaccggc ttcggcaaag ggagtgcagg cgcctcttcg aggatgacgt gcgcgttgct   8100
ccctccaaaa ccgaacgagc tgacgccggc cagacgcggc cgtccttccg acgtccacgg   8160
```

-continued

```
cgacgattcc gtggcgatgc gaaaccggct gccgtccagt gagatgttcg gattcagccg   8220
gcgaaaatgc aggtgcggag gaatggtgcg atgctgcagg gcgagtacgg ctttgatcag   8280
cccggcgatt cccgccgcgc cctccagatg cccgatgttg gtctttacgg aacccagcag   8340
acaaggcgca gagtccggcg cgtcgtagac cgactgcagg gcctcgatct cgataggatc   8400
gcccagcgac gtgcccgtgc catgcgcctc gatcaacgat acgtgggatg gatcgatgtg   8460
cgcgttggcc accgcctctt gcaggaccgc cttctgcgcc tgcagattcg gcgccgtgat   8520
gccattgctc cgtccgtcct gattgattgc cgagccgcgg atgactgcac ggatggcatc   8580
gccatcggcc agcgcatcgg agagccgctt cagcagcacg atgccgcagc cctcgccgcg   8640
cacataaccg tcggctgcgg cgtcgaacgt cttgcagcgt ccgtcgggcg ccaacatgcg   8700
agccttcgac aaagcgatca tgccctcggg agtcaggatc aagttcactc cgccggcgaa   8760
tgccgcatcg cattcgcgcc ggcgcaggct ttggcaagcc agatggacgg cgacgagcgc   8820
ggaggagcag gccgtatcga ccgccatgct cggaccgcgc aggtcgagca gataggagat   8880
gcgattggcc aacatgctat gcgccacgcc ggaacccgac caagctccga tgcgggcagg   8940
gtcggcgtac tgaaacagtc cgaagtcctg ggcgcaggag ccggcaaaga cgccggtcgc   9000
gctgcccgcc agagggccgg gagagatgcc ggcgtcctct gccgcttccc agcacacttc   9060
cagcagcagc cgctgctgcg gatccatgtt cagagcttcg cggggggaga tgccgaagaa   9120
ttccgcatcg aaaccgtcaa tgcgttcgag gaaggcggca tatcgcgcat acgccttgcc   9180
cggagcatcg ggatcggagg agtagtactg gtccgagttc cagcggtctg gcggcacctc   9240
ggtgacaccg tcgacaccgt tcttcaacag cgtccagaag gcgtccggat tcttcgcgcc   9300
gcccggaaaa cgacacgcca tgccgacgat ggcgatgggt tcggcgtgaa ccaggtcgaa   9360
gcctgcgatg ttttgccgca tgttccgcgc caatagcgcg agtttgaccg acgacatggg   9420
cgcaattttt tccctcacga ccttgctcct cggagcgcag ccacggctgc ttcttccgac   9480
atgtcgtcca acccgctgag tgcagttttc atggcgcggc tgtctccttc cgcagcagcc   9540
gcggcctgcg cttcgaccag cggcagtccc atttgcgacg ccaggtgcgg ggcaagaccg   9600
gccagcgtgg gatgacccca aatcagggtc gcggggagcg tgagacccag tgtgagttcg   9660
agacggttgc gaaactccag ggccatgagg gaatcgaagc cgagttcctt cagcgggcgc   9720
aggggatcga tagtttgaga gtcgatgcgc agcacgcgcg ccagctgctg ctgtagatgt   9780
tcttcgagca atgtcctgcg ggtctgaggc tcggccgatt gcagccgcgc gcgcaacgcg   9840
tttggcgcat cggcttcgct cgccgcgtcg tcatgcaaaa gctcgaacag tgcagactgc   9900
gccgccttgg gatagaactg ccgccactgg cggacattga tgggcatcgc ggcgacgtgg   9960
caagccgagc tgttcagcag ctgttccaga atagcgaggc cgtgttgcgg cgtcaggttt  10020
tccatgccgc gcaaagccag ccgcgatccg cgattgtcct gcgcggcagc cagcccgacc  10080
tccgaccacg caccccaacc gatgctcagc gccggcaggc cttgggcctt ccggtagtag  10140
gccagcgcgt caagaaaggc gttcgcggcc gcgtagtttc cctgggcggg cgcgcccagc  10200
agtcctgcag cggaggagaa gagcacgaaa tgatcgagcg ggcagtcgcg ggtgagcaag  10260
tgcaggttcc aggcaccgtc gattttcgcg gccatcacgt tgcggaaatg cgcttccgtc  10320
tggttcagta gcagcgcatc gtcgagaacg gctgcggcat gaatcacgcc gcgcaatcga  10380
tcgatggaag agatcacgcg ctcgagttca tcgcgctgag aaacatcggc ctgcaccgtc  10440
cggacatctg cgtccatgac ggcgatggct tgctggacct cgggtgaagg cgcgcggcgg  10500
ctcagcagca ccagccgccg ggcgccgcgt ccgatcatcc agcgtgcgac ggtaagaccg  10560
```

-continued

```
agcccgccaa gtccgccggt aatcaagtag gttccctcgc tatcgaacgc cgagcgtagg  10620
ggtgcgatgg gcgcattggc gcaatctcgc atcgccatga cgattttgcc gatgtgccgc  10680
gcctgcgcca tggtgcgaaa cgcctccacc gattcggtga tggtcgtcac tcgcgtttcc  10740
aggggccgcc aggtttccga ttcgaatttt gcgaccatct cctgcagcag ctcccgggtc  10800
aatgccgggc gcttcaggga catgccgagc aaatcgacca gcgtgtacga gaggttcttc  10860
aggaacgggc gaagccccag cttgcggccg gcatagtaat cgcgcttgcc gatctcgatg  10920
aaccgtccat gatcgcgcag cagatcgaag ctcgcctcca gcagatcgcc ggaaagcgaa  10980
ttcaggacga cgtctactcc ttcttgattc gtccaattgc ggatgtcgtc cacgaaagcc  11040
atcgagcgcg aatccgaaac atgcgcgatg cccagcgagc gcagatacgc tcgtttttcc  11100
ggactcccgg cagtagcgaa gatctccgcg cccgcacgct gtgcgatctg gattgccgcc  11160
aatcccacac cgccggtggc agcgtgaatc aggactcgtt cgccgggcgc cagccgcgcc  11220
gctcgcgaga gcgcgtaatc ggcggtgaga aacgcgatag gcagggcggc ggcctgttcg  11280
gcgggaatgt tggccggctt caaggcaacg cggaaggcgg gcgtggtgac gaagcgaccg  11340
aaactgcaag gcgcaagggc cacgacttca tctccgatgc gaaagtcggt gacgcctttc  11400
cccatggcca cgatacggcc cgagcattcg ccgcccaggc gcgggctgcc ggcaatcgcg  11460
ccgggcgcat cgtcgggcat aacgccgagg gcgagcagaa cgtcgaggaa gttcaggccc  11520
gcggcgcaga cttcaatctc cacttcaccg gcttgcgggg ggcggcgcga tgtggcccgc  11580
aagcgcagcc ggtcgaggac tccgggggca tcgatctcga gccggaacgg ccgatcgccg  11640
gccttgaaca tggcgggttg catatccgct tcgtgccgag ccacgcgcgc gacgtaacgc  11700
gcgccgccgc gaaaggcgat ttgattctcg ccgttgttcg tcagcagttc gtgcaggagt  11760
tcctcttcgc cgccggcggg atcgagatcg atcagcgtgc agttcagttc cggatgttcg  11820
taatgcacgg tccggcccaa accccagaaa ggcgcctgag cgataccggc ttgcaggatc  11880
tgtccatcga ccggctgcgc gccgcgcgtg accagccata ggcgcggtgc ttgacgccag  11940
ggcgtgcgcc ccagggtctg gaggagatgc agaatgcggt cgcatgaggg ttcgtgctcg  12000
agcaaaaaca cgatttcctc gagcggcggc tggagttcat cgagcttttc cggcgaggtc  12060
tgcgtcacgc ggttgccggt agcgcgcagc catgcggtga gcgcgctatc cacagcgccg  12120
acaatgagcc atgaccgcgc cgctcgcgcc gccggcggct ctgcagcggc gtgcggctga  12180
gcgacccagc gcagttcgtg caaccagccg cgcatgtcga tgcgctccga cgcatccagg  12240
cgctgcagcc gcagaccctc gatgcgggcg accagttgtc cctctccgtc cagcagcgac  12300
agatcggcga taggtccttc cagccgcgca tgcgtccaca ccacggaacg tgcgggatgc  12360
agccagcgca tccggtcgat gccggcgggc agccaggttc caccggcggg accaaacgcc  12420
gcggcgatga tctgcagaca tgcatcgagg aacgccggcg cagtggaacg cgtttccgag  12480
ctacgcagac gcccgatcgc ctcacctgga caactccaga tctgctcgag cgcgcggaaa  12540
gccggaccat actcgacgcc gtgctccgcc atctgacgcc acagctccgc cgccggcacc  12600
actgtggggc agcgggcctg caccgtctcc gcagaatccg gcgggacggt cgatgcatcc  12660
gcaggcgtct gacgaatgtc cccggaagca tgcaggaccc atgtcgatgc ctgccggctg  12720
gaaatccgaa acgacgccat cccgggtcta tcgaccgcga tggccagctg caacgtcatg  12780
ctgccgtcgc gcggcacaat gagcatctgt gtgaaagtca catgctccag cacgcacgga  12840
ctttcaccga aggtctcgga agttccggcc agagccatat cgagatacgc agtagccggc  12900
```

-continued aagacgactt cgccctgcac gcgatggtct gccagccaag gcacggaagc gagactgagt 12960
tccgtctccc agaagaaagt gccgggttgc gtcgaggctt cgacgcgttt tcccaacagc 13020
ggattgccca acgtgatcgc gtgtcgcgcg ggggaagcgt cgagccagaa acgacgacgc 13080
tgccagggat accggggcag gcgcacgcaa ttgccggaag ggtacacggt ccgccatgcg 13140
acagtgtgcc cagcctcata gagggcgccc agcgacgtga gcatggaacc gcgttcgtcc 13200
tggtcgcggc gcagagacgg aaccagcgcc gcattgccgc cgatggcggg cagcaggatg 13260
ggatgagggc tgatctcgag aaagacatcg tgcccgctgt cggcaagatg gcggatgccc 13320
tgccagaaca gaaccggcga tcgcagattg cgagcccagt acgtgctgtc gaggctggtg 13380
gtctccagcg tcgcgccggt caccgtggag taaaaaggta tggtcgcggg ccgcggttga 13440
atcccgtcga gcgactgcag gagttcgtcg cacaatgggt ccacttgcgg gctatgcgcg 13500
gcgaagtcca ctttcaccgg ccggcaagac acgcctcgcc gctccagcgt cgcgacgacc 13560
tcggccaggg cttcgacttc accggagatg acggtggagt tgggtccgtt cgacaccgcg 13620
ggcgatagtc gttccgtgta agtcgacagc acggcctcac attccgcgag cggcagctcc 13680
accatcgcca tcccgcccag gccgctgatc cggctcaaca gccggctgcg gctgcaaatg 13740
atccgcgccg catcctgcag cgtcagcgca cccgcgacat gagcggcggc gacctctccc 13800
atgctgtgcc cgatgacggc atccggctcg attccccagg aacgccacaa tgcggcgatg 13860
gcgacctgca gcgcgaagag cgcaggctga atgacctcga cgcggtcgag cttcgccagt 13920
tcttctttca gcgaccagtc cacataaggc cgcatggcgg cctcgcagcg ttccaacgcc 13980
tcgcgaataa cgggttcgcg gtccatccag ctgcgcccca ttccgatcca ttgcgatccc 14040
tgtcccgaga agacgaatac cgtcttccgt cgctgggaag ggatcgtgat cccctggagc 14100
tgcgccgcca gttcttcagc cgttctgccg gaaacagcga gccggcatcg gtgatgcgtg 14160
cggcggactg cggccgtgta gcaaagatca cgcaggctcg gtgcgtgcga cgctgtcagc 14220
aattccccgt atgcccgcgc cacccgacgc agttcgtccg caccatgcgc ggacagcgga 14280
agcacataca tcgcgtctgc aatgcccgta gttgccgcag tgcctgcagt ccctgcaatg 14340
tcgggagtgt ctgcagtgtc gggagtgtct gcagtgtcgg gagtgcctgc aatgtcggga 14400
gtgcccccag tgtccccctc cgcgaggggg acagccgccc gcgcagcggc ggcggggggt 14460
cgggaatgga acccgctcgc agcttcgcct ctaccagtcg gcgccgcttc ttcaagaacg 14520
acatgcgcgt tcgtgccgga ccaaccaaac gcgctgacgc ccgcaaacct tcgtctcgaa 14580
cccgcgggcc acggccggac ttccttcaca atgtcgagcg acgttccctc caaccggata 14640
ttcgggttca gctgtctcac gtgtaagctc ggcggtatcg tctcgtgact caatgcgagc 14700
accgctttaa tcaatcccgc tatgcctgcc gctccctcca ggtggccgat gttcgatttc 14760
agggacccga ccgcgcacac atcgccgaca ggtcgcggga ggccgacggt ttccgccagc 14820
gcctcgatct cgatgggatc gccgagcgga gtccccgtgc catgggcttc gatgtaaccg 14880
atctgctgcg ccgcgacgcc cgcattggcc aatgccgacc ggatgacgac ctgctgagac 14940
acgacattgg gagcggtgag cccggccgag cggccatcct gattgaccgc ggagccgcgc 15000
accacggccc acacccggtc tccggccgcg agtgcatcgg acaggcgctt cagcaccacc 15060
acgccgcagc cttctccgaa cacgatgccg tccgccgccg cgtcgaaggc gcggcagcga 15120
ccgctgggcg aggcggttcc catcttcgag gtggcgtaca taaactccgg cgagaagcgc 15180
agattcactc cgccggccac ggccagcgta cactcgccgc tgcgcaggct ctggcacgcc 15240
agatgaaccg ccgccagcga agacgagcag gccgtgtcga gcgcgatgct gggtccttgc 15300

-continued

```
aagttcagca aataggaaag tcggccggcg atcacgctat gcgccgtgcc ggtggcggta  15360
tacggatcga tgcgcgcgcc atcggcggtc tgcatccaga aatagtcgct gctttggctg  15420
tggatcccga cgaagacgcc cgtgcggctg ccggagagcc cttccatcgt ctgccccgca  15480
tcctccagtg cctcccacgc cacttccaac agcagccgct gctgcggatc aatgctgacg  15540
gcctcgcgtg gcgaaatgcc gaaaaaatcg ttgtcgaaac catcgatgga atcgagaaat  15600
ccggcttgaa tcttcaccgg cgtggcgggg ttcaacgatt tcaggatgcg ccggaccgac  15660
tcctcgtccc atcgtccagg cggtacctca cgaatagcat cgactccact gcgcaacatc  15720
tgccagaact catcgggccc atcgccgccc ggaaaccggc agcccagacc cacgatcgcg  15780
atgggttcgc gcgcgtcgcg ttcggccgca tcgagacgtc gctgcatgtg ctccagcgtc  15840
aggtacgcct gctgcaacgg cgtaaggttg gggaatcgct cggatatcga actcactcgg  15900
aggctcctga aaaatgagcg aacttctgtt tcaacaaagc ttcgatttct ttgtccccca  15960
acccggcgat ctggtttgcg acggcgtcga gatcgtctgc agcggcggga ctccggtcct  16020
cgcccgcggc ggtgccaacg gtagcaaggg tagcaacggc agcaacggtc gaaggttcag  16080
cattgccggc catgctttcc agcggcaggc cgagcttgtc ggcgagatgc tgcgccaggg  16140
cggagaatgt cgggtaacgc cagatcaggg tggcagaaag cttgacgcgc agcccggctt  16200
ccagacggtt gcgaaactcg agggccatca acgaatcgaa tccgagatca cccagcgtcg  16260
ctctgccgtc gagtttcgct ggatcgaagc gcagcacgtg tccggcttcg tgcatcagca  16320
gcgtttccag ccgcgcgcgg cgctgccgcc cggctggaac tgccaggagc tcgctgcgca  16380
tgtcggccgc cggtttggtg tccgcggccg cgggtgcgat gccggccagc agggacatcg  16440
atgcggccga cggatagtaa cggagccact gcgcgatatc gaagttcatg acagcgacgt  16500
gcggccgaat ctgcgtcaat gctttgtaga gcgcgcgcaa tccctgttgc ggttgaataa  16560
ccgagatgcc gcgcgcggcc agacggtctc cgcggttcgc ctgtgcggcc aaaccaacct  16620
gtgtccacgg tccccacgcg atgctgacgg cgggaagacc ctgggcgcgg cgcagatgag  16680
ccagcgcgtc gagaaatgaa ttgccggcgg cgtagttgcc ctggccggga gatcccactg  16740
tcgcgctggc ggaagagaag agaacaaaat gatccagcgg ccggccggcg gtgagttcgt  16800
gcaggttcca cgcgccggct actttcggag ccatggcggc ttcgaagcgt tcggtcgtga  16860
gattgagcag catgccgtcg gccagcgtgc ctgccagatg gaacacgccc cgcaacggcg  16920
gcatgtcgcg atcgatgatc gcgagcgcat ccgatagctg ctgccggtcc gccacgtccg  16980
catggatgat cttgacgttg acaccttcca gttgtggccg aggacgctcg ctgcgtccca  17040
gcagaacgag atggcgcgct ccggcggcgg cgagccatcc cgccacctgc agtccgagtc  17100
cgccgagccc gcccgtgatc agataggttg cgtcggcacg gaacgccaca tcgggtgcgg  17160
atgggatctt gtgaagactg aggcgcggcg cccataccgt gccttgccgg atcgcaactt  17220
gatcctctgc gatattcgac agcatcagcg tcgcgagatg cccgcagtcg ttgctgtgcg  17280
catcgagatc gacgagcgtg cagcgcagct cgggatgctc ataggcaatc gtccgcccaa  17340
ttccgtgcag ccaggcttgt cgaatatcaa tatctttgtc ggagttgaga accgcggcag  17400
atccgcgcgt cagcagccac aggcgcggcg gctcaggcca gcccgcttgc acgatgctgc  17460
gcaatacgga aagcaggtcg tcgatgcgcg gcgagggaca gtacacaatt tgacggcacg  17520
gcggacccga gcacgtatcg gccgtgcggc aggtttggcc gcgcttttgc agagtctcgg  17580
caatcgccgg ctcgccgatg acgagccaag gtccgccagc attgccggca ttggcatcgc  17640
```

-continued

```
cgcggcgaac cgacgcggtc cattgcaccg tccaggtggg aatctccgat tcgccgagct  17700
ggccgctatg ggcgactctc gactgcagcc ccaccaattc cgccaccacg ctgccggtgc  17760
cggtgacgag acggacatcc accgtggaat ccggccgcaa gaccgcgtat ccccagaccg  17820
ggccagtggg cacttcagcg agcgagaatc ggtccagacc taccggcaca tgcacatctt  17880
tcaaatcgtc gtgatggacg agggccgcgg gcaactgcag acagcagtcg atcgtctgca  17940
tttccgtcag cggaatgtcc acgcgacaaa gcacctcacc gttgccgcgc cagatggggc  18000
cgatggttcg gaaggtggga ccgaagtgat agccgcgatc ccacagtcgc gaatagaagg  18060
catcggctgt gagctccgcc gtgcagcggg cgcgaatcgc atccagatcg atggatgccg  18120
tggaatcgcc cgcctgcagc atgccttcgc tgtgcagctt ccaggaatcc tcgcggctgt  18180
agatgcggaa ggaagctccg ccgccctctt catgacggag taccagttga acctgcctgg  18240
cagcatcgtt ttccggcagc gtcagcgcgc ccgtcaatga cacgtgttcg acatggtgag  18300
gcccggcgcc gagaccttgg cgcgcagcgg cgagcgccat tgccaggtgc cacgctcccg  18360
gagtcacgat cacatcgtgc agccggtgat ccgcgaaatc tttcgcctcc acagtggact  18420
cgaactgcat ctccggcagc ggcgacggga tccgccggcc aggcaaagcc tgagactcga  18480
cctgcggcgg acggatatcg atccaataac gctcacgctg ccagggatag ttgggcagcc  18540
ggcgagtttg gccgccgttg ggataaatac gagaccagtc cggagtgact ccgttagtca  18600
gcagcgctcc cagcgtccgg cgcagtgcga ggtttccgtc ttcatcgcgc cgcaacgagg  18660
cagcggcaat cgctgcccga tctccgagcg tttcctggat cggctggacc aacaacgggt  18720
ggggactcag ttccagaaac acatcatgac cacccgccgc ggctgcggcg acggccgtcg  18780
acagcatcac gggttggcga agattacgag cccagtacgc agaaaccagc tcttcaccgc  18840
taatcgctgc gccggtgacg gtggagtaca tgccaagggc ggccggccgc ggctgaagcg  18900
ctcccaccac gcccggcaac gccgcgcaca cggagtccat cagatggctg tgcgaggcaa  18960
tgtccacttt cacgcgacgg cagaagacgt ctttcgcctc cagttcccgc agcagttcgc  19020
ccagagctgc gctgtcgccc gacaggacgg tgctgcgcgg gctgttgctg gcggcaatcg  19080
agacccgatc cgagcgcccg gcgatggcag cgatggcctc gtccagcgct aattccacga  19140
cagccatttc tccctggccg cgtactccgg cgagcatccg gctgcgcagg caaatcaccc  19200
gagcggcttc atcgagagtc agcgcacctg caatgtgcgc tgccgcgact tcgcccatgc  19260
tgtggccgat cacggcgtcc ggctcgattc cccaatggcg ccacagtccg gccaaggcga  19320
ccccgactgc gaacagggcc ggttgaatca cgtcgatgcg gtcgagcggc ccctgcaact  19380
cttgcgtcag cgaccagtcg acgtaaggct gcatggcgcg gccgcactct tcgatggcgg  19440
cacggaacac cggttcagaa gccatcaggt cgcggcccat gccgggccac tgcgatcctt  19500
gtcccggcaa aacgaaaacg acttttcgct tctggccgcg cggcacaaaa cctgtggcgg  19560
tatcgcggtt cgggttgccc gccagaaaac tgtccagccc ggccatcaag tcctgcgcgt  19620
tcgtcccggt gaatgccgcg cggtgttcgt atgaagtgcg gcgagcgcac gccgtgtagc  19680
aggtgtcggc ggggttgtcg ttcaccacgt cgcggtatgc gcgcgccaga tcacgcagcg  19740
cctccggact gcgcgccgat agcggaagca ggtacggtgc gggcgtactg gacgcggcct  19800
gttgcggcgc ctgctcgatg agcacgtgcg cattcgtacc gctcaagccg aacgagttga  19860
tgccggcgac gcgccgcccg ccgggtgcaa ccggccaggg ggtgagccgt gccgggattt  19920
cgaggggaag cgtgttccaa tcgatgtgcg ggctgggcgt ggtcagattc agatggggcg  19980
gaatggcttc gttctgcagc atcagcgcca ccttgatcag tgcggccacg cccgctgccg  20040
```

-continued

```
cctcgaggtg gccgaagttg gtcttcaccg acccgagctt cagcttgttg ccgttggtgc  20100
gccccgctcc cagcgcggcc gcaagggctc cggcttcgat gggatcgccc agcggcgtgc  20160
cggttccgtg cgcctcgaca tagctcacat ccagcgtctg caagcgcgcg tctcccacag  20220
cctggcggat cacggcttcc tgtgcgggcc cgttcggcgc cgtcagtcca ttgctgcgtc  20280
cgtcctggtt gattgccgtg ccgcgaatca ccgccatcac cggatcgcga tcgcgcagcg  20340
cgtcggagag tcgcttcagc acaaccacac cgcagccctc accgcggacg tagccgtctg  20400
ctgcggcatc gaatgcctta cagcgaccgt cggctgccat cgccttcagc ttgcagaagt  20460
agatcgtccg atccggcgag agaatcagat tgacgccgcc cgccagcgcg aggtcgcttt  20520
cacctgagcg caggctctga caggcaaggt gcaccgcgac cagcgatgac gagcatgccg  20580
tgtcgatcgc catgttcggg ccctgcagcc cgaggatgta cgagagacgc ccggcggcaa  20640
cgctggccgt attgcccgtg ccggtgtacg cgtcgatatg cgcatccccg ccgcgcattt  20700
gcaggttgta ataatcgttg gaaaagatcc ccatgaagac gccggtccgg ctccccgcca  20760
gccggtcggg tggaagcccg gcgttctcga tcgcctccca ggtgacttcc agaagcagcc  20820
gctgctgtgg atccaggctg atcgcctcgc gcggagcgat gccgaagaac cgggcgtcaa  20880
aacggtcaac ctgatcgatg aagccgccgt accgcgtgta cattcggccc gtcgcgccgg  20940
gatccggatc gtagtaggca tcgatgtccc agcggtcggg tggaacttca cgtaccgcgc  21000
tgcggccctc gcgcagcaac gaccaatagg catcgagatt ggatgcgccg gggaagcggc  21060
agcccgcgcc gatgagggcg atgggctcgc tgcgcgcgct ctccagctgg tcgatgcgtt  21120
tctgcacctt gtcgagcgca atcacggcgc ggcgaagctt gctgagatcg tctgacccgc  21180
tcatgtttat tgcgtctcca accactggtc gacctgcgcc agccgcgaat cgagcagcgc  21240
ttccagttct tcgcgggcga ggttctcaaa ctccggcgct tccaccggtg atgcttcggg  21300
tggaaatacc gcatggagca cgtaactgac gatcgcatcg agcgacggat agtcgaacag  21360
cagactcgcg ggcaaaggct gccccagtga ttgggagagc gagttgcgaa gttctatggc  21420
cattagcgaa tcgagtccca gttcacccaa aggctgctgt ggatcgagcg gtgtggaagt  21480
cgcgatgccg acaaagcgcg ccagtgactc cctgatgtgc gcaatgagga tggcttcgcg  21540
ctgccggggt gtggcttcgt tcaagcgggt gcgcagttga ggtgaaggca gcgcggcggg  21600
acgcagcaac tcgccggtaa tcgagcccgc cggtagcgcg gcaatctgaa tggggcattc  21660
atgcaggacg gcctcgagaa tgtgtagacc ctcgtccacg gagaggctcg ccacgccggc  21720
catcgactgg ctggtgcgcg cggccattcc ggctcccgac cagcgccccc agttaatgct  21780
ggtcgccggc aaacccagtc cgcgccggtg atgcgccagc gcatcgagaa cggcgttggc  21840
cgcggcgtag cctgcctgcc cggcaggacc taagagcgag gatgccgatg aaaagagcac  21900
gaagaagtcg agcggcagat cgcgggtgtg atgatggagg tgtacagcgc cttccgcctt  21960
cggcgccatg acgcttgcga tccgcgtcca gtcctgattc agcagtacgc cgtcgtccag  22020
cacacccgcg gcatggataa cgccgcgcag cggtgacgtt tcggtgtgga tgcggcgaat  22080
gagatccgcg acctcttctt cccggctgac gtcgaccgtc tctgccgtcg caccaatctg  22140
ttgcagcacg cgctgctgct cctcgtttgg aggccggcgc ccggccagca cgacgcgagt  22200
ggcgccgtgc tccaccatcc atttcgcgac tgtaagtccc agggctccga gcccgccggt  22260
gatcaaataa gtcgcgcccg aaaccagacg gactgccgct cgcgcgctgg gtcggcgggt  22320
cagtcgcggc acgtagcgcc ggttgcttct ccacgccgac tgatcttcgc cgtcgaaatc  22380
```

-continued

```
acgcatctgc gcggccgcgc cggccgccga agcatgcgca tcgtcgggat ccagatcgat  22440
gagcccgccc cacagatccg ggtgctcgcg cgcgatcacc cggccgaagc cccagagcgc  22500
ggcctgcatg ggattgtgca ccgcactggt cgcctgcgcg ccggccgtta ccagccatag  22560
ccgcggaccg gacttcaggg acttcaccag ggccagagtg ctgcggcagc cgagctcata  22620
atcatcgaga ctgtacaggt tgacgatccc gcgccagtca cgctcaccga ctagggacat  22680
gtactcgccg gctggcggca cggtaacgca catctcgccc tgagctgtga gcgcatctgc  22740
cagagcgcgg gccgcgccgc cactgtcggc caggatcagc catgccccag gctgtagcgt  22800
tcgcgaaggc tggcggagcg gttcgggccg ccactcgacc tcatacaatt cgggcttccg  22860
ttccgagcgc tgcgcccatg cgcgagtgac gcgccggaaa ctcacgccct gaagttcccc  22920
gagaacgcag ccctccgagt ccagcaactg cgcctcgccg gtaaagccgt ccggcgaatg  22980
ccggagaatt tgcgcggccc cccatacggc gccctccagg ctgccgtaaa aacaaacgcg  23040
atcgataccg agcggagcga atatcggatg ttcggcgcca tccgcaagcg cgggactcgc  23100
cgcggcgcta agcaattgca ggccggcttc cgccaattca caacggggat tgagcggcgt  23160
tgcggaatca atcgcggcca gcgcttcctg ttcaccgaaa tgaatgcgct gtatgcggcg  23220
gtagctcggc cccagttcta tctcgaggtg gcgcagcagc gaatagtacg tgtctccatc  23280
caccgcaggc cggcgttcat cgaccagtcg gggcacggga gcgacaccag cgtgggcggc  23340
aatattgccg gcagcatgta agttccacga gccgtcggac aagctgagta tgcggaacga  23400
ggcatgccgg tcatcgctct gtgaaagcac gagctgaaca gccgtgtcgc gctccgctga  23460
aaggatcaga gggtgcgcga agttcacgtt ttccagcgtg tgccggccgg cgccaaacac  23520
ctccgccgac gcctcgagcg ccatggccag gaagtacacg gccggggcca ccaccgaacc  23580
gtaatatcgg tggtctgaga gtagaggcga agccgtcgat agtttcgact cgaagataac  23640
gtctgccacc ggtagcgaca gccggcaccc gacgagacca ctcgcaaccg ctacaggttc  23700
cggtctggaa ctccgctcga tccaatggcg gcgtctctcg aaaggatagg ccggcagggc  23760
gacacgcctt cgcgaatacg gacggtcgaa ctcctgccaa tcgatgtcga acccaccctg  23820
atatagcgtc gccacactgc tgagaatcgt ctcccactca tcgcggcctt tacgcagcga  23880
cggcagccac tgcttggcgt cgtcgggcag gcacttttgg cccatgccga gtagaaccgg  23940
cttaggaccg atctcgagaa acacgtcgca gccttcgtcc ttgagcgttt ggataccgtc  24000
ggcgaaacgg acagggtttc gagcgtgatc tcgccagtac agcggattcg ccagctgtcc  24060
ctcgccggcc agtttgcccg tgaggttcga aaccaagccg atcgaaggat tgcgccacgc  24120
gatcgccgcc gcccggcgtt gcaggtccgc cagaatcgga tccatgctcg agctgtgaaa  24180
ggcgcgcgca acggccagca tctgcgtttt gatgccctcc gcacgtagag ttgccagcgc  24240
gctctcaata tcctgcggcg cacccgaaat cacgacctca gcgggtccgt tgatggccgc  24300
aatggagacg cgcgaggtga tcgctgcggc acagcgctgc tcgccggcgc tgaccgcagc  24360
catcgcacct tccggcaggt tctgcatgag ccggccgcgt tcggcaacta agccgagcgc  24420
atccggcagg ctgacggcgc cggcaataca cgccgccgcg tattcgccga cgctgtgtcc  24480
catcaccagg tcgggcgtca caccccagga cttccacaac tgcgccaagg cccactgcaa  24540
agcaaacagc gcgggctgcg cgccggcggt cgcgtcgagc aacgcgtcat cggccaacag  24600
cgccggcaga tcgagccgtc cattcagcag agctgcgcat tcatccatgg cggcgcgaaa  24660
caccggctgc gactcgtaga actggcggcc catgcccgcg tattgcgcac cttgcccggt  24720
gaaaagaaac gcaatcttgg ggcgcgtctg ggcgatgcga acccgtcgtg cctccgtcag  24780
```

-continued

```
tcgttggcga gcctcgtcgc tcgaccgggc cacaatgcag atacggtgcg ggaagtgcac  24840
gcgccctgca ttggccgtga atgcgacatc gccgaacgac aaaccgggct ggttgtccat  24900
atggccgcga tacgagcgca ccagttcttc gagggccgcg tctgtattgg cggacaggca  24960
aagcacatgt gcggatcgtt cgggcgcagc tgcggccggc gtcaccggcg gcgcttgctc  25020
cagaatcacg tgagcgttgg tgccgccgat cccgaacgaa ctgactgccg ctcgtctcgg  25080
ggtctttccg gcgggccagt cgagcagccg cgtactcaca cgaaacggag tgtttgcgaa  25140
atcaattcgc ggattcggac gctggaaatt caggctggga ggaatctggc cgcgatggac  25200
ggcaagcacc gtcttgatca gcccggccac accggccgcg acgtctagat gaccgatgtt  25260
ggtcttgacg gatccgatat acacatcgcc gcttccgttt ttcggaaagt tggcagcgat  25320
ggcggcgatc tccaccggat cgccgagcgg cgtggctgtt ccgtgggcct cgatgtagcc  25380
gatggactcc ggcttcacgc ccgccatctc ttgagtgcgc cgaatcaatc gcgtctgacc  25440
gtccacacct ggagcggtaa accccatgcg ctcggcgcca tcattattaa tagccgctcc  25500
gcgaatgacg gcgtagatcg tgtcgccatc ggccagagcg cggctcaagc gcttgaggac  25560
gaccacaccc gcgccgttgc ccggcaccgt gccttgagcg gactcatcga aggcgcggca  25620
gcgcccgtcg ggcgacagga tcatgcccgg ctggtgcagg taccccacgg actgcggaac  25680
attgatggca actcccccgg ccaaggcaat gtccgaggcg ccgcgctgca agctctcgca  25740
tgccatcacc accgacacca gcgaggtgga gcacgccgtc tgaaccgtca ggctgggccc  25800
gcggaggttc agcttgtaag agacacgcgt ggccaggaaa tccttgtcgt tggccgtcag  25860
cagctggtac gcggaggggc gtgagaaatc gaacggctcc gcggtggcga ggttgttcag  25920
caggtaggta ttgacgccgc atcccgcgaa aacgccgatc gaacccttat agcttcgcgc  25980
cgcatatccc gcgttctcca tcgcttccca cgcgcactcg agaaacacgc gatgctgcgg  26040
gtccatgatc tccgcttcgc gcggactgta gccgaagaac gcggcatcga aaaactcgat  26100
gccgtccagc agacccttgg ccggcacgta gctcgggtcc tggaagacct ccgggctgat  26160
gccgcccgcc agcagatctt ccggcgaaag cctggcgatg gaatccacac cgtcgcgcag  26220
attgcgccag aactcctcca cattgcgcgc ccccgggaac cggccggcca tcccgataac  26280
tgcgatccga tcttctgcga ccgcagccgc aggttccgca gcggcgggtt cggatttttc  26340
tgccaggccg gcaagcgact cgatcgtcgt atgccggaac agatcgacga cggagagcgt  26400
caaccccagg cgctcctcga gcagtccgcg cacccgtgtg agcattagcg agtgcccgcc  26460
gacatcaaag aagttctgcc gatagtcgac gtgctccacg cgcagaactt cacgccagat  26520
ggacgcaatc gtctccacca catcgccgcg catcggctcg cgagcagcaa ccggcgttgt  26580
gggcaaaccg ggaagcgcgt tcgcgtcgat tttgccgttg ggcgtcagcg gaagggagga  26640
caggctgaca aacgccgagg ggatcatgta atcgggaagg cgcgttgcca gccacgaccg  26700
caaatcgctc tgcagatcgc gcacgtcgcc cgttgccgga acgagatagg cgatcagccg  26760
atcgtccttc acgaccgtaa tcgcctgctt cacggcaatg tgcgtctcga tcgcggcctc  26820
aatctcggcc ggttcgatgc gaaacccgcg cagcttgatc tggcgatcga ctcgtcccag  26880
gcactcgact gcgccgtcgg aacggtagcg agccagatcg ccggtagagt aaatgcgtcc  26940
tcgatcacgc cactcgcgga atttctcacg cgtgagctcg gggttgcgat gatagccccg  27000
cgccagtccc gctcctccga tgtacagctc tcccggaact ccggggggaa ccggctccat  27060
gcgcgaatcc aggatgtata actgcgtgtt gtcgatggga tggccgatcg gcacgatgct  27120
```

-continued

```
atcggaggca cccagtcttt gtgtcttgtg cacggccgac catatggtgg tctccgtcgg  27180
tccgtaaaga ttccacagct ctacgccact atcgagaatg cggcgcgcca gttccggcgg  27240
cagagcttca ccgccgcaga aaacacggaa gcctttaccc ggcttccagc ccgaatccag  27300
caattgccgc caaccgctcg ggtcgcctg catgaccgta gcgcccgact tatccagcag  27360
ggtggtgagc cgctcgccgt caaccacgat ctcgcgggtg gcgacgatga cgcgggcgcc  27420
ggtgatcaac ggcagccaga tctccagtcc ggcaatatcg aatgacacgg tggtgacggc  27480
gaccagccca tcggcggctg tcagacccgg ctcgcgctgc atggagcgca gcagattgac  27540
tagcgacgag tggcggatct ccacgccctt cggtcgcccc gtcgatccgg aggtatatat  27600
gatgtaggcg agatcgtcgg gcttgctgcc gctgacgaga ttcgcagctt ctggttcgac  27660
ggcgaccgcc atcatcgcca tcatcgccat catctcagcc accgcctcct gcgtgaggac  27720
cgcgtgcggt tgcacttcat cgagaatccg ggcgagacga tccttggggt gcgcgggatc  27780
gagaggcagg tacgcgctgc cggacttcag aatcgcaagc agcgcaatca ccatctccag  27840
cgagcgctcc atcgccagag cgatgatctt tcccgggccc gcgccggatg cgctcagacg  27900
atgagccagg cggttggccc gcgcattcag ctcggcgtag gtcaactgat ggtcttcgaa  27960
gacaacggcg acggcgtgcg gagtgcgttc cgcctgagct tcgaccagtt catgcgcaca  28020
cccgttcgga ccggcatcgc gccgtgtcgc attgtgctgc tcgagcatcc ggcttcggac  28080
cgcgggggac aacagcgcag cggttgaaat gcggacgtcg ggatccgtca ccacgctcgc  28140
cagcagggtt cggtacgcat cgagcaggga ggcgatggtt gccgcatcga acaaatcggt  28200
gttgtattcg gcggacgcca tcagtccatc gccggatggc tcgagggtca cgccgaggtc  28260
gagtttggat ccgccgttgt gcatgtactc gcgcgagatg gtgagcccag gcatgacggt  28320
gatggccggc gcatcgggca gcagcgcgaa ggagacctga aatacaggcg accggctcag  28380
gtcccgcgga ggatgcagtt cctcaaccag gcgttcgaaa ggaaagtcct gatgagagag  28440
ggcgctcaaa gcggtgtcgc gggtgcgggc gagaagactg cgaaacgacg gatcgtcgcg  28500
cagatcgccg cgcaggacga tcatgttggc gaaacaaccg acgagacctt ccgtttctcg  28560
ttgtgtacgg cccgcgactg gaaccccgat aaggatgtct tcctgcgcgg tatagcgatg  28620
cagcagcacc tgaaacgccg cgattgccgt catgaacacc gtcgctcctt cacgcaaggc  28680
aaacgcgtgg agtccatcgg tcaaatcacg gccgagggct gtggtctcca cggcgccccg  28740
ccaggtctgc tgcgcgggcc gggggcgatc ggtaggaagg tcgaggaaag gcaaggtgcc  28800
cgacagctgt ttcttccagt actgctgcgc ggtttggttc agcgacgtct gctgatggac  28860
ggcccagtcg ccatactgaa tcggcagttc catgagcggc gatggccgcc cctgcacgaa  28920
cgcttcgtac gatcgcgtca ggtcgcggac gaacgtctcg accgaccacg catccgcgat  28980
gatgtggctc aacgtcagca ggagaatctg ctgcttgtca tcgaggcaga tcagcttggt  29040
ccgcagaagc gggggtttc gcaggtcgaa cgggatctgg gcatcacgca aggccatttg  29100
ccgcgcttct gcgattccgt cagcctgaac aaccggaagt tccagtgtca ctcgcgccag  29160
gaggctctgg cgcgcctctc catccacacc gccaatgcag ctgcgcaggc tctcgtgccg  29220
ctgcaccacg gcctccagac tccgcaggag gacgcgaata tccagcggac ctcggatatg  29280
cagcgctatg ggaatgttgt aggcgggaga atccgggtcg agctgatgga gaaaccaaag  29340
ccgctgctgg gccagcgaca agggtgcggc atcccggttt tcacgccgcg ggatgcgatg  29400
ttcggggctg ttttcctgca gcagacggtc gagcaattgg cggcgggcga gcgagaggtc  29460
tatggtattt ggcgacgaat tctgcattac aacccgctgt gttcctagtc ttgggcggcg  29520
```

-continued

```
ctcatcatac gctcgatttg aacatctgac atttgggaaa cagcgatcag caaatcggcg  29580
gctcgccttg cccatcctgg gtctacgccg tcctgaatag cgacggcgaa gcctcgaacc  29640
gtgggggcgt taaacacggt tcgaaagggc acttccacgt ggagcatgtc gcgcacgcgg  29700
gcgatcatct gcgtgaccag cagcgaatgt cctccagagt cgaagaagtg atcatggacg  29760
ccgatgccat ccatgccgag cacctcgccc caaatgtggg cgagtacctg ttccaccgga  29820
gtttccggag gcgtgaatgc ttcggcgtgg gctcgccggc tgggctcggg atcgggcagg  29880
gcgttacggt cgatttttcc gttgggcgtc agcggcattt cgtggagcac gacccacgcg  29940
gtcgggatca tgtagtcggg cagcttctcc ttcagatgag tacgcaactg cggcacaacc  30000
gtgcgcgtat agacggctcg cagcggatcg ttcgtatacg ggccggccag gcggcgtcgc  30060
ggacgggaag ccggcggacc ggccgccgca cggcagaagg tcgcgtcgaa gcgtccgtgt  30120
ggcccatgac tgctccagtc gattgccacg cggtacggca ggtcttcgtc catacgccat  30180
agatcggcgg gatcgacgcc ggaaggcgac gtctggcgca gccggtcccg caactccccg  30240
agtgtctctg gagcttcgtc accgttcatc caggtcacaa tggcgctttc ggcggtcaac  30300
cgtgcgttcg gaatctcggt aaatgcggcc aactccggct gagcgtccgt cagtactctg  30360
cgtatttcgg ccgcggtctg gcaacgcctg cgatccgatt ccggctcctc cgcttcccgc  30420
gatccgatat gcaggatcgc ctggtagcgg aagcgggtca gctcgttatg cgaccggccg  30480
cgacgcggca ggatttcaat ccggccgatc tccggaatct gttcgcggag agcaaagaag  30540
aacgcgggat cgaccacgag ttcctcttcc tgcgacgcga gcgaacgcac gcgttgccga  30600
aactcattcc gggtcaacga cgcgggtgcg cgctgaactt ctaaagaagc gtaaaacgtc  30660
tccagcagcg ggagactgcg gacatcgccg acaaatacga tgccgcccgg tttgaccaca  30720
cgcaccgcct cggccagcac gcgccgcaga tacgcttcgc cggggaagta ctggataacg  30780
gagttcagaa caaccgcatc gcacgagcga ctgtcgatct cgcacgcgtc gtcggccgcc  30840
tgccggaacg tgcggacatt tgccaggccg gtgcggtccg cgtgagcggc gatgtagtcc  30900
agcgccttct gcgaaaagtc cgtggcccag tactccgaac agtggggagc gacgcggaag  30960
agcagcagtc ccgtaccaca gccaatctcg agcacgcgac gcggccgcga ggccaggatg  31020
cgatcgacgg aatcctgcac ccactcccgc atctcggcag ctggaatcgg ctctccggta  31080
acactgcttc tccagccgac gatgttgaac tccggatccg cgttcggcgc attctgttca  31140
tatgtggtgt cccagacgga ttgccactgc gtcacgtgct cggactcgac tcggtcgtgg  31200
aatgtgtcgg cggctgccgt cgcgcgatgc ccgtcagcaa gggggacaat gtaggccgcc  31260
agatacttac cggccgcgtc attttctctg gcggtgacca cagcatgtcg gaccgccggg  31320
tgactgcgga ccgcggcctc gatctcgccg gtttcgatgc ggaacccgcg tatcttcacc  31380
tggtggtcga tccggccgag atactcgagc gcgccgtcgc gttggcggcg ggcgagatct  31440
cccgtgcgat acagccgagt gccatgaggg tcgaacgaat tggcgacgaa cttgtccgcg  31500
ctgagttccg gacgattcag gtatccacgg gcgagcccgg cgccgccgat gtacagttcg  31560
cccgcaacac cgatgggtgc gggctgcatc cgatcgtcaa gcacatagag ctgagtgttt  31620
gcgatggggc ggccaatcga aaccggtccg tcacctgtcg tcacccgttg gatggcggac  31680
caaattgtcg tttcggtagg tccgtaaaga ttccatagcg ccgcggttcg ttgcaggagc  31740
cggtcggcaa gatcgcgagg aagggcttca ccgccgcaga gcgccgtcag gcggcggtcg  31800
ccgggccagc cggatgcgag cagcagacgc caggtggcgg gagttgcctg catcattgtc  31860
```

-continued

```
gctttgctgc gcgcgagttc cctcgccagc ctctcaccat cgacggccgt ctcctggttc  31920
gccaccacga cgcgcgcgcc ggcgctcaag ggcaaaaaga tctcgagcgc ggaaatgtcg  31980
aacatgaacg tcgtgagggc gagcagcgta tcgcggtcgc tgatgcccgg ctcatgccgc  32040
atcgacgaaa gaaaattgac gacggcctgg tgtgtgattt gcacgccttt cggccggccg  32100
gtcgaaccgg aggtgtacag gacataggcg agatcggcgg gagtcgcgag cgggttcgga  32160
ttggtgtcgg gctgcgtcca tacttccgat tccgtgacat tcagcacaac gaccggcctg  32220
gtctcttcca gcatcagccg aagacgttgc gccggatatt ccggttccag cggaacgtag  32280
gccgcgccgg ccttcaggac gcccaacagc cctgcgacgg tttcgagcga ccgcgtgaca  32340
tggatgccaa ccatttcgcc gggtccagcg ccgcgcgagc ggagatagtg cgcgatccgg  32400
ttggcgctcc cgttgagttc gcgatatgtc agattctgct caccgaagct caacgcgatg  32460
gcgtcgggcg tcaactccac ctgagcttcg aacagctcgt gcacgcattg ggacgggaat  32520
tccgcggcgg tcgcattcca ctcttcgagc agctggatgc gttcccgggt tgtcagcagc  32580
ggtagatcga caactggaca ggcgggattc tccgcgattc cttccagcag cacggcgaag  32640
tgcaaggaga gacgttcaat cgtggcagca tcaaaaatgt ccgtgttgta ttgcagaaag  32700
gcggagaggc ctccatcggt ttcgaccatc atcagatcca ggtcaaaccg gctctgtcgc  32760
agcggcatcg ccagggactc cagtgtgagg ctgccccagg ccatgcgacc gccggactga  32820
cccaacatga acggcacgga ttcgggaatg cgatgaggct gctggagcac gaatagaacc  32880
cgcagtccgg gacccaaccg ctccacgatc cgggcatacg ggtactcctg gtgctcgatc  32940
gcgccgagaa gcgtttgccg aatccgggcg agcaccgtat tgaaatccgg atcgcctgaa  33000
agttctcctc gcaggattac gggattcacg aagtatccga cgagatcggc gaattccggt  33060
tgcgtccgac cgttggtgag ggtgccggtc aggatctctt cttgtgaggt ccaacgggag  33120
agaagcactt gaaacgccgc catcagcgtc gcatgcagcg tcgcgttctg ccgccgcgcg  33180
agcgccttca gtttcgcagt cagcgcgggt tcgattcgga acgagtgaga gtttccccgg  33240
aaactctgca ccggcggact gggacgatcc gacgggagat tcagaaccgg aagctggccg  33300
gaaagctgcg aggaccagta gttccaaagc cgctcgccct cggttccggc caacagttcg  33360
ttctgccagc ggacgaaagc ggcgaagctc gcgaccggcg gcgcgacagg cggaccgcca  33420
gctgtcctcg cgaggtagat actgcggagt tcatccacca tcaccagcag tgaccagaag  33480
tcggcgagga tgtgatgcac cacgatggcc agaacctgat ccttccccga ctgcaccagg  33540
agacgcgagc ggaaacagtt ttcgccgaga ttgaagggcg cgtggaagac gccgtcgatc  33600
agcaccgcct catcgtccgg cgaacacggg atcacttcga aatccaccgg gacgctgctg  33660
tggaccgttt gaacgggtgc gccgccactc tccgcaatcg tcgttcgcag cgccggatga  33720
cgatccacca ggtcctgcag cgaacggcgc aacgcctgcg gatcgaaagc gcctctcgcg  33780
cgcgcgatcc acgcgatgtt gtatgcggga ctttccggcg cgcttcggta aataaaccaa  33840
agcgcctgct ggccggcgct gagagggtag gagagggcag gaaccgaggc ctgcgccgca  33900
ggttccggcg ccaccgtcgt gcgttcgctg aggccgctta gatcgcttag atccctggcc  33960
agttccgcaa cgctggggcc gtctagaaat cggaccatgg gcagcaagac gcgcagatcc  34020
gtatcgatcc ggttgcgtaa ttgcaccgcc atgagcgagt ccaatcccat acgcaccagc  34080
ggctgctgta agtccaccgc cgattccggg cactgcagtt tttttttttt tttttttttt  34140
tttttttttt tttttttttt tttttttttt tttttttttt ttttaatgcg gtagtttatc  34200
acagttaaat tgctaacgca gtcaggcacc gtgtatgaaa tctaacaatg cgctcatcgt  34260
```

-continued

```
catcctcggc accgtcaccc tggatgctgt aggcataggc ttggttatgc cggtactgcc  34320
gggcctcttg cgggatgatc cctgtcagtc atgcgggcaa cttagccgag ccctacgaca  34380
ccgcccgtgg gaaggtgagt gtctaactgc gtgacaacgc cagcgcacag cggcggacaa  34440
ccgcgagcac ccatggactg gcgccgcagg tgagaagcac actggcccaa ggtcgagcgc  34500
ccacccaagt tgcttcggga cgaagaggtc gtgggttcaa atcccgccac cccgacagag  34560
aaacaccagg tgaggcagac cgtaacgtta cggtctgcct cacctgtttt ctgtgcgtgt  34620
ctatctgcgt gactatcgcg ccggaccccg cttgaagatg ccgtccatga ccacagcgcc  34680
ggtctggatg acgggccgga tctgcttccg gtagacctcc tcagtcacgg ccgtaccgga  34740
gtgtccgacg agccgggaga tctcctccag cgggacgccg cggtcggaca gcagggacac  34800
gaagctgtgc ctcagctccc tcggtgtcca ctcgtcggcg ttgatcccgt tggcatcctt  34860
gagcgcctgg cggaaggcgc gccggacgtt agtcgcgtcg agcggcttgc caacggccga  34920
cgagaagacc aggccgtgtt cctcccactt gtcaccggcg gcgagccgtt cccagccctg  34980
gtcctcaaag tgctgccaga ggacctccac gcaacgcgcc ggcagggcga gcgttcgccg  35040
agacttccgg gttttcgtgt ccccaccgcg ccggaccgag cgccagacgg cgatgtgcgg  35100
aggctgcggc ggctcaacgt ccggacttcc cttgaggaag acgtggtccc aggtcagcgc  35160
ccgcagctcc tcggtgcgcg caccggtcag cagggcgacg acgatgtagg cgtgcatcga  35220
cgtgccctcg gcagcattca gcaccgcctc ggcctgggcg aaggtgagcg ccttggacgg  35280
ccggccaggc tggccctggg gcacagagca cagctccacc acgttgcgct tcaccttgtc  35340
acgcgccatg gcccgcttga ccgcccggtt caggcaggag tggaccgcct gaaggctgcg  35400
cgtgctcaga gtctgagcct tggcggccag ccagcggtcg acgtcctctg cgctgaggtc  35460
acgcagcttc cgggcaccca aacccggtat gacgtgcttc tggcttaggt gggtgcagtt  35520
ctcgacggtg cgctggtcac ggccagcgag accgtaggca agccagtcgt tcaccgcgtc  35580
ggcgacggtg taccccgtgg gtgcgatcgc gagaccgtct tcgtggtcac gcagaacctc  35640
tttgagcttg ttcttagcct ccgtcttggt cttgccactc ccccgcttga cgatccgctt  35700
accgctcgga tcgaagccga ggttcgccgt ggcgatccag cgctgtctct tctcgtccca  35760
gtggaggccg ccgtcacccc ggctacgtcg cttggccatg gatcgatccc ctgcccggca  35820
aaatagagtg ttcctctgcc ctctttagca ttcagtgtat ccattaccgt catcaattgc  35880
tcactcccgg ggcgcggtgc gttgtcatcg aataaattga gctgcgcgac tccctgactg  35940
aagaaatccc ccagcatcac gcccgctttt tggtaacgat ggcccgcttg ccagatggca  36000
tccagagatc gcgtagcagc gttaatgata tccctgctgt cctgagtggg cgtcagcagt  36060
tttaccgacg cgctattgcc gtaataaggt tcattgagcg caaatggtga cgtcttaata  36120
aacgtggaga taaaccgaca atattgatgc tcgctgcgaa gtttttccgc cgcccgggca  36180
gcgtaactac aaatggcctg ccgcatcgac ggataatccg tgatgcgttc accaaacgag  36240
cgggaacaga taatttcctg cttcgtcggt gcaaactctt ccagttgcaa acagggttcg  36300
ccgcgcagtt cacgcaccgt tctttcgagc acgacattaa aatgtttacg gataaaccgg  36360
atatctgtat ccgccaaatc gagaacggtt ttgatcccca tcgcgtccag ttttttgctg  36420
atccgccgtc caatccccca gacgtcatcc acggggagag cagacattaa tttacgctgg  36480
cgttccagat ttgataaatc caccacccca cccgtctgcc gctgccattt ttttgccgca  36540
tgattggcaa gctagcttta tgcttgtaaa ccgttttgtg aaaaaatttt taaaataaaa  36600
```

-continued

```
aaggggacct ctagggtccc caattaatta gtaatataat ctattaaagg tcattcaaaa  36660
ggtcatccac cggatcagct tagtaaagcc ctcgctagat tttaatgcgg atgttgcgat  36720
tacttcgcca actattgcga taacaagaaa aagccagcct ttcatgatat atctcccaat  36780
ttgtgtaggg cttattatgc acgcttaaaa ataataaaag cagacttgac ctgatagttt  36840
ggctgtgagc aattatgtgc ttagtgcatc taacgcttga gttaagccgc gccgcgaagc  36900
ggcgtcggct tgaacgaatt gttagacatt atttgccgac taccttggtg atctcgcctt  36960
tcacgtagtg gacaaattct tccaactgat ctgcgcggat cgatccttgc cgagctggga  37020
tggaagcccg gccgacccac cctggaggag atgatcgagg atgccagggc ctttcacgcc  37080
cgccgctgct gagcgtccgc cgccgggccc gcaccgccgt cggccggccc gctccgggct  37140
cgcagcagcg ggcttcggcg cgggcccggg gctcccgggc cgccgggcgg ggctccgccc  37200
ggcggccgcc gggggccggg ggcggcgccg ggcggcccgg ggcgtcaggc gccgggggcg  37260
gtgtccggcg gcccccagag gaactgcgcc agttcctccg gatcggtgaa gccggagaga  37320
tccagcgggg tctcctcgaa cacctcgaag tcgtgcagga aggtgaaggc gagcagttcg  37380
cgggcgaagt nctcggtccg cttccactgc gccccgtcga gcagcgcggc caggatctcg  37440
cggtcgcccc ggaaggcgtt gagatgcagt tgcaccaggc tgtagcggga gtctcccgca  37500
tagacgtcgg tgaagtcgac gatcccggtg acctcggtcg cggccaggtc cacgaagatg  37560
ttggtcccgt gcaggtcgcc gtggacgaac cggggttcgc ggccggccag cagcgtgtcc  37620
acgtccggca gccagtcctc caggcggtcc agcagccggg gcgagaggta gccccacccg  37680
cggtggtcct cgacggtcgc cgcgcggcgt tcccgcagca gttccgggaa gacctcggaa  37740
tggggggtga gcacggtgtt cccggtcagc ggcaccctgt gcagccggcc gagcacccgg  37800
ccgagttcgc gggccagggc gagcagcgcg ttccggtcgg tcgtgccgtc catcgcggac  37860
cgccaggtgg tgccggtcat ccggctcatc accaggtagg gccacggcca ggctccggtg  37920
ccgggccgca gctcgccgcg gccgaggagg cggggcaccg gcaccggggc gtccgccagg  37980
accgcgtacg cctccgactc cgacgcgagg ctctccggac cgcaccagtg ctcgccgaac  38040
agcttgatca ccgggccggg ctcgccgacc agtacggggt tggtgctctc gccgggcacc  38100
cgcagcaccg gcggcaccgg cagcccgagc tcctccaggg ctcggcgggc cagcggctcc  38160
cagaattcct ggtcgttccg caggctcgcg taggaatcat ccgaatcaat acggtcgaga  38220
agtaacaggg attcttgtgt cacagcggac ctctattcac agggtacggg ccggcttaat  38280
tccgcacggc cggtcgcgac acggcctgtc cgcaccgcgg atcaggcgtt gacgatgacg  38340
ggctggtcgg ccacgtcggg gacgttctcg gtggtgctgc ggtcgggatc gccaatctct  38400
acgggccgac cgaggcgacg gtgtacgcca cagcttggcg taatcatggt catagctgtt  38460
tcctgtgtga aattgttatc cgctcacaat tccacacaac atacgagccg gaagcataaa  38520
gtgtaaagcc tggggtgcct aatgagtgag ctaactcaca ttacggatca gtgagggttt  38580
gcaactgcgg gtcaaggatc tggatttcga tcacggcacg atcatcgtgc gggagggcaa  38640
gggctccaag gatcgggcct tgatgttacc cgagagcttg gcacccagcc tgcgcgagca  38700
ggggaattga tccggtggat gaccttttga atgaccttta atagattata ttactaatta  38760
attggggacc ctagaggtcc ccttttttat tttaaaaatt ttttcacaaa acggtttaca  38820
agcataaagc tatcgtccat tccgacagca tcgccagtca ctatggcgtg ctgctagcgc  38880
tatatgcgtt gatgcaattt ctatgcgcac ccgttctcgg agcactgtcc gaccgctttg  38940
gccgccgccc agtcctgctc gcttcgctac ttggagccac tatcgactac gcgatcatgg  39000
```

-continued cgaccacacc cgtcctgtgg atctgcctcg ctggcctgcc gcagttcttc aacctcccgg 39060
cgcagctttt cgttctcaat ttcagcatcc ctttcggcat accattttat gacggcggca 39120
gagtcataaa gcacctcatt acccttgcca ccgcctcgca gaacgggcat tccctgttcc 39180
tgccagttct gaatggtacg gatactcgca ccgaaaatgt cagccagctg ctttttgttg 39240
acttccattg ttcattccac ggacaaaaac agagaaagga aacgacagag gccaaaaagc 39300
tcgctttcag cacctgtcgt ttcctttctt ttcagagggt attttaaata aaaacattaa 39360
gttatgacga agaagaacgg aaacgcctta aaccggaaaa ttttcataaa tagcgaaaac 39420
ccgcgaggtc gccgccccgt aacaaggcgg atcgccggaa aggacccgca aatgataata 39480
attatcaatt gcatactatc gacggcactg ctgccagata acaccaccgg ggaaacattc 39540
catcatgatg gccgtgcgga cataggaagc cagttcatcc atcgctttct tgtctgctgc 39600
catttgcttt gtgacatcca gcgccgcaca ttcagcagcg tttttcagcg cgttttcgat 39660
caacgtttca atgttggtat caacaccagg tttaactttg aacttatcgg cactgacggt 39720
taccttgttc tgcgctggct catcacgctg gataccaagg ctgatgttgt agatattggt 39780
caccggctga ggtgtttcga ttgccgctgc gtggatagca ccatttgcga tagcggcgtc 39840
cttgatgaat gacactccat tgcgaataag ttcgaaggag acggtgtcac gaatgcgctg 39900
gtccagctcg tcgattgcct tttgtgcagc agaggtatca atctcaacgc caagcgtcat 39960
cgaagcgcaa tattgctgct caccaaaacg cgtattgacc aggtgttcaa cggcaaattt 40020
ctgcccttct gatgtcagaa aggtaaagtg attttctttc tggtattcag ttgctgtgtg 40080
tctggtttca gcaaaaccaa gctcgcgcaa ttcggctgtg ccagatttag aaggcagatc 40140
accagacagc aacgcgccac ggaaaaacag cgcatacaga acatccgtcg ccgcgccgga 40200
caacgtgata attttatgac ccatgattta tttcctttta gacgtgagcc tgtcgcacag 40260
caaagccgcc gaaagttaac ttgtttattg cagcttataa tggttacaaa taaagcaata 40320
gcatcacaaa tttcacaaat aaagcatttt tttcactgca ttctagttgt ggtttgtcca 40380
aactcatcaa tgtatcttat catgtctgga tctgacgggt gcgcatgatc gtgctcctgt 40440
cgttgaggac ccggctaggc tggcggggtt gccttactgg ttagcagaat gaatcaccga 40500
tacgcgagcg aacgtgaagc gactgctgct gcaaaacgtc tgcgacctga gcaacaacat 40560
gaatggtctt cggtttccgt gtttcgtaaa gtctggaaac gcggaagtca gcgctcttcc 40620
gcttcctcgc tcactgactc gctgcgctcg gtcgttcggc tgcggcgagc ggtatcagct 40680
cactcaaagg cggtaatacg gttatccaca gaatcagggg ataacgcagg aaagaacatg 40740
tgagcaaaag gccagcaaaa ggccaggaac cgtaaaaagg ccgcgttgct ggcgtttttc 40800
cataggctcc gcccccctga cgagcatcac aaaaatcgac gctcaagtca gaggtggcga 40860
aacccgacag gactataaag ataccaggcg tttccccctg gaagctccct cgtgcgctct 40920
cctgttccga ccctgccgct taccggatac ctgtccgcct ttctcccttc gggaagcgtg 40980
gcgctttctc atagctcacg ctgtaggtat ctcagttcgg tgtaggtcgt tcgctccaag 41040
ctgggctgtg tgcacgaacc ccccgttcag cccgaccgct gcgccttatc cggtaactat 41100
cgtcttgagt ccaacccggt aagacacgac ttatcgccac tggcagcagc cactggtaac 41160
aggattagca gagcgaggta tgtaggcggt gctacagagt tcttgaagtg gtggcctaac 41220
tacggctaca ctagaaggac agtatttggt atctgcgctc tgctgaagcc agttaccttc 41280
ggaaaaagag ttggtagctc ttgatccggc aaacaaacca ccgctggtag cggtggtttt 41340

-continued

```
tttgtttgca agcagcagat tacgcgcaga aaaaaaggat ctcaagaaga tcctttgatc  41400

ttttctacgg ggtctgacgc tcagtggaac gaaaactcac gttaagggat tttggtcatg  41460

agattatcaa aaaggatctt cacctagatc cttttaaatt aaaaatgaag ttttaaatca  41520

atctaaagta tatatgagta aacttggtct gacagttacc aatgcttaat cagtgaggca  41580

cctatctcag cgatctgtct atttcgttca tccatagttg cctgactccc cgtcgtgtag  41640

ataactacga tacgggaggg cttaccatct ggccccagtg ctgcaatgat accgcgagac  41700

ccacgctcac cggctccaga tttatcagca ataaaccagc cagccggaag ggccgagcgc  41760

agaagtggtc ctgcaacttt atccgcctcc atccagtcta ttaattgttg ccgggaagct  41820

agagtaagta gttcgccagt taatagtttg cgcaacgttg ttgccattgc tgcaggcatc  41880

gtggtgtcac gctcgtcgtt tggtatggct tcattcagct ccggttccca acgatcaagg  41940

cgagttacat gatcccccat gttgtgcaaa aaagcggtta gctccttcgg tcctccgatc  42000

gttgtcagaa gtaagttggc cgcagtgtta tcactcatgg ttatggcagc actgcataat  42060

tctcttactg tcatgccatc cgtaagatgc ttttctgtga ctggtgagta ctcaaccaag  42120

tcattctgag aatagtgtat gcggcgaccg agttgctctt gcccggcgtc aacacgggat  42180

aataccgcgc cacatagcag aactttaaaa gtgctcatca ttggaaaacg ttcttcgggg  42240

cgaaaactct caaggatctt accgctgttg agatccagtt cgatgtaacc cactcgtgca  42300

cccaactgat cttcagcatc ttttactttc accagcgttt ctgggtgagc aaaaacagga  42360

aggcaaaatg ccgcaaaaaa gggaataagg gcgacacgga aatgttgaat actcatactc  42420

ttcctttttc aatattattg aagcatttat cagggttatt gtctcatgag cggatacata  42480

tttgaatgta tttagaaaaa taaacaaata ggggttccgc gcacatttcc ccgaaaagtg  42540

ccacctgacg tctaagaaac cattattatc atgacattaa cctataaaaa taggcgtatc  42600

acgaggccct ttcgtcttca agaattcgcg gccgcaatta accctcacta aagggatccc  42660

tatagtgagt cgtattatgc ggccgcgaat tctcatgttt gaccgcttat catcgat     42717
```

```
<210> SEQ ID NO 114
<211> LENGTH: 34071
<212> TYPE: DNA
<213> ORGANISM: Artificial sequence
<220> FEATURE:
<223> OTHER INFORMATION: Description of the artificial sequence: DNA
      insert of the cosmid a26g1 coding strand

<400> SEQUENCE: 114

actgcagtgc ccggaatcgg cggtggactt acagcagccg ctggtgcgta tgggattgga     60

ctcgctcatg gcggtgcaat tacgcaaccg gatcgatacg gatctgcgcg tcttgctgcc    120

catggtccga tttctagacg gccccagcgt tgcggaactg gccagggatc taagcgatct    180

aagcggcctc agcgaacgca cgacggtggc gccggaacct gcggcgcagg cctcggttcc    240

tgccctctcc taccctctca gcgccggcca gcaggcgctt tggtttattt accgaagcgc    300

gccggaaagt cccgcataca acatcgcgtg gatcgcgcgc gcgagaggcg ctttcgatcc    360

gcaggcgttg cgccgttcgc tgcaggacct ggtggatcgt catccggcgc tgcgaacgac    420

gattgcggag agtggcggcg cacccgttca aacggtccac agcagcgtcc cggtggattt    480

cgaagtgatc ccgtgttcgc cggacgatga ggcggtgctg atcgacggcg tcttccacgc    540

gcccttcaat ctcggcgaaa actgtttccg ctcgcgtctc ctggtgcagt cggggaagga    600

tcaggttctg gccatcgtgg tgcatcacat cctcgccgac ttctggtcac tgctggtgat    660
```

-continued

```
ggtggatgaa ctccgcagta tctacctcgc gaggacagct ggcggtccgc ctgtcgcgcc    720
gccggtcgcg agcttcgccg ctttcgtccg ctggcagaac gaactgttgg ccggaaccga    780
gggcgagcgg ctttggaact actggtcctc gcagctttcc ggccagcttc cggttctgaa    840
tctcccgtcg gatcgtccca gtccgccggt gcagagtttc cggggaaact ctcactcgtt    900
ccgaatcgaa cccgcgctga ctgcgaaact gaaggcgctc gcgcggcggc agaacgcgac    960
gctgcatgcg acgctgatgg cggcgtttca agtgcttctc tcccgttgga cctcacaaga   1020
agagatcctg accggcaccc tcaccaacgg tcggacgcaa ccggaattcg ccgatctcgt   1080
cggatacttc gtgaatcccg taatcctgcg aggagaactt tcaggcgatc cggatttcaa   1140
tacggtgctc gcccggattc ggcaaacgct tctcggcgcg atcgagcacc aggagtaccc   1200
gtatgcccgg atcgtggagc ggttgggtcc cggactgcgg gttctattcg tgctccagca   1260
gcctcatcgc attcccgaat ccgtgccgtt catgttgggt cagtccggcg gtcgcatggc   1320
ctggggcagc ctcacactgg agtccctggc gatgccgctg cgacagagcc ggtttgacct   1380
ggatctgatg atggtcgaaa ccgatggagg cctctccgcc tttctgcaat acaacacgga   1440
catttttgat gctgccacga ttgaacgtct ctccttgcac ttcgccgtgc tgctggaagg   1500
aatcgcggag aatcccgcct gtccagttgt cgatctaccg ctgctgacaa cccgggaacg   1560
catccagctg ctcgaagagt ggaatgcgac cgccgcggaa ttcccgtccc aatgcgtgca   1620
cgagctgttc gaagctcagg tggagttgac gcccgacgcc atcgcgttga gcttcggtga   1680
gcagaatctg acatatcgcg aactcaacgg gagcgccaac cggatcgcgc actatctccg   1740
ctcgcgcggc gctggacccg gcgaaatggt tggcatccat gtcacgcggt cgctcgaaac   1800
cgtcgcaggg ctgttgggcg tcctgaaggc cggcgcggcc tacgttccgc tggaaccgga   1860
atatccggcg caacgtcttc ggctgatgct ggaagagacc aggccggtcg ttgtgctgaa   1920
tgtcacggaa tcggaagtat ggacgcagcc cgacaccaat ccgaacccgc tcgcgactcc   1980
cgccgatctc gcctatgtcc tgtacacctc cggttcgacc ggccggccga aaggcgtgca   2040
aatcacacac caggccgtcg tcaattttct ttcgtcgatg cggcatgagc cgggcatcag   2100
cgaccgcgat acgctgctcg ccctcacgac gttcatgttc gacatttccg cgctcgagat   2160
ctttttgccc ttgagcgccg gcgcgcgcgt cgtggtggcg aaccaggaga cggccgtcga   2220
tggtgagagg ctggcgaggg aactcgcgcg cagcaaagcg acaatgatgc aggcaactcc   2280
cgccacctgg cgtctgctgc tcgcatccgg ctggcccggc gaccgccgcc tgacggcgct   2340
ctgcggcggt gaagcccttc ctcgcgatct tgccgaccgg ctcctgcaac gaaccgcggc   2400
gctatggaat ctttacggac ctaccgaaac gacaatttgg tccgccatcc aacgggtgac   2460
gacaggtgac ggaccggttt cgattggccg ccccatcgca aacactcagc tctatgtgct   2520
tgacgatcgg atgcagcccg cacccatcgg tgttgcgggc gaactgtaca tcggcggcgc   2580
cgggctcgcc cgtggatacc tgaatcgtcc ggaactcagc gcggacaagt tcgtcgccaa   2640
ttcgttcgac cctcatggca ctcggctgta tcgcacggga gatctcgccc gccgccaacg   2700
cgacggcgcg ctcgagtatc tcggccggat cgaccaccag gtgaagatac gcgggttccg   2760
catcgaaacc ggcgagatcg aggccgcggt ccgcagtcac ccggcggtcc gacatgctgt   2820
ggtcaccgcc agagaaaatg acgcggccgg taagtatctg gcggcctaca ttgtccccct   2880
tgctgacggg catcgcgcga cggcagccgc cgacacattc cacgaccgag tcgagtccga   2940
gcacgtgacg cagtggcaat ccgtctggga caccacatat gaacagaatg cgccgaacgc   3000
ggatccggag ttcaacatcg tcggctggag aagcagtgtt accggagagc cgattccagc   3060
```

-continued

```
tgccgagatg cgggagtggg tgcaggattc cgtcgatcgc atcctggcct cgcggccgcg   3120
tcgcgtgctc gagattggct gtggtacggg actgctgctc ttccgcgtcg ctccccactg   3180
ttcggagtac tgggccacgg acttttcgca gaaggcgctg gactacatcg ccgctcacgc   3240
ggaccgcacc ggcctggcaa atgtccgcac gttccggcag gcggccgacg acgcgtgcga   3300
gatcgacagt cgctcgtgcg atgcggttgt tctgaactcc gttatccagt acttccccgg   3360
cgaagcgtat ctgcggcgcg tgctggccga ggcggtgcgt gtggtcaaac cgggcggcat   3420
cgtatttgtc ggcgatgtcc gcagtctccc gctgctggag acgttttacg cttctttaga   3480
agttcagcgc gcacccgcgt cgttgacccg gaatgagttt cggcaacgcg tgcgttcgct   3540
cgcgtcgcag gaagaggaac tcgtggtcga tcccgcgttc ttctttgctc tccgcgaaca   3600
gattccggag atcggccgga ttgaaatcct gccgcgtcgc ggccggtcgc ataacgagct   3660
gacccgcttc cgctaccagg cgatcctgca tatcggatcg cgggaagcgg aggagccgga   3720
atcggatcgc aggcgttgcc agaccgcggc cgaaatacgc agagtactga cggacgctca   3780
gccggagttg gccgcattta ccgagattcc gaacgcacgg ttgaccgccg aaagcgccat   3840
tgtgacctgg atgaacggtg acgaagctcc agagacactc ggggagttgc gggaccggct   3900
gcgccagacg tcgccttccg gcgtcgatcc cgccgatcta tggcgtatgg acgaagacct   3960
gccgtaccgc gtggcaatcg actggagcag tcatgggcca cacggacgct tcgacgcgac   4020
cttctgccgt gcggcggccg gtccgccggc ttcccgtccg cgacgccgcc tggccggccc   4080
gtatacgaac gatccgctgc gagccgtcta tacgcgcacg gttgtgccgc agttgcgtac   4140
tcatctgaag gagaagctgc ccgactacat gatcccgacc gcgtgggtcg tgctccacga   4200
aatgccgctg acgcccaacg gaaaaatcga ccgtaacgcc ctgcccgatc ccgagcccag   4260
ccggcgagcc cacgccgaag cattcacgcc tccggaaact ccggtggaac aggtactcgc   4320
ccacatttgg ggcgaggtgc tcggcatgga tggcatcggc gtccatgatc acttcttcga   4380
ctctggagga cattcgctgc tggtcacgca gatgatcgcc cgcgtgcgcg acatgctcca   4440
cgtggaagtg ccctttcgaa ccgtgtttaa cgccccccacg gttcgaggct tcgccgtcgc   4500
tattcaggac ggcgtagacc caggatgggc aaggcgagcc gccgatttgc tgatcgctgt   4560
ttcccaaatg tcagatgttc aaatcgagcg tatgatgagc gccgcccaag actaggaaca   4620
cagcgggttg taatgcagaa ttcgtcgcca aataccatag acctctcgct cgcccgccgc   4680
caattgctcg accgtctgct gcaggaaaac agccccgaac atcgcatccc gcggcgtgaa   4740
aaccgggatg ccgcaccctt gtcgctggcc cagcagcggc tttggtttct ccatcagctc   4800
gacccggatt ctcccgccta caacattccc atagcgctgc atatccgagg tccgctggat   4860
attcgcgtcc tcctgcggag tctggaggcc gtggtgcagc ggcacgagag cctgcgcagc   4920
tgcattggcg gtgtggatgg agaggcgcgc cagagcctcc tggcgcgagt gacactggaa   4980
cttccggttg ttcaggctga cggaatcgca gaagcgcggc aaatggcctt gcgtgatgcc   5040
cagatcccgt tcgacctgcg aaaacccccg cttctgcgga ccaagctgat ctgcctcgat   5100
gacaagcagc agattctcct gctgacgttg agccacatca tcgcggatgc gtggtcggtc   5160
gagacgttcg tccgcgacct gacgcgatcg tacgaagcgt tcgtgcaggg gcggccatcg   5220
ccgctcatgg aactgccgat tcagtatggc gactgggccg tccatcagca gacgtcgctg   5280
aaccaaaccg cgcagcagta ctggaagaaa cagctgtcgg gcaccttgcc tttcctcgac   5340
cttcctaccg atcgcccccg gcccgcgcag cagacctggc ggggcgccgt ggagaccaca   5400
```

-continued

```
gccctcggcc gtgatttgac cgatggactc cacgcgtttg ccttgcgtga aggagcgacg   5460
gtgttcatga cggcaatcgc ggcgtttcag gtgctgctgc atcgctatac cgcgcaggaa   5520
gacatcctta tcggggttcc agtcgcgggc cgtacacaac gagaaacgga aggtctcgtc   5580
ggttgtttcg ccaacatgat cgtcctgcgc ggcgatctgc gcgacgatcc gtcgtttcgc   5640
agtcttctcg cccgcacccg cgacaccgct ttgagcgccc tctctcatca ggactttcct   5700
ttcgaacgcc tggttgagga actgcatcct ccgcgggacc tgagccggtc gcctgtattt   5760
caggtctcct tcgcgctgct gcccgatgcg ccggccatca ccgtcatgcc tgggctcacc   5820
atctcgcgcg agtacatgca caacggcgga tccaaactcg acctcggcgt gaccctcgag   5880
ccatccggcg atggactgat ggcgtccgcc gaatacaaca ccgatttgtt cgatgcggca   5940
accatcgcct ccctgctcga tgcgtaccga accctgctgg cgagcgtggt gacggatccc   6000
gacgtccgca tttcaaccgc tgcgctgttg tcccccgcgg tccgaagccg gatgctcgag   6060
cagcacaatg cgacacggcg cgatgccggt ccgaacgggt gtgcgcatga actggtcgaa   6120
gctcaggcgg aacgcactcc gcacgccgtc gccgttgtct tcgaagacca tcagttgacc   6180
tacgccgagc tgaatgcgcg ggccaaccgc ctggctcatc gtctgagcgc atccggcgcg   6240
ggcccgggaa agatcatcgc tctggcgatg gagcgctcgc tggagatggt gattgcgctg   6300
cttgcgattc tgaagtccgg cagcgcgtac ctgcctctcg atcccgcgca ccccaaggat   6360
cgtctcgccc ggattctcga tgaagtgcaa ccgcacgcgg tcctcacgca ggaggcggtg   6420
gctgagatga tggcgatgat ggcgatgatg gcggtcgccg tcgaaccaga agctgcgaat   6480
ctcgtcagcg gcagcaagcc cgacgatctc gcctacatca tatatacctc cggatcgacg   6540
gggcgaccga agggcgtgga gatccgccac tcgtcgctag tcaatctgct gcgctccatg   6600
cagcgcgagc cgggtctgac agccgccgat gggctggtcg ccgtcaccac cgtgtcattc   6660
gatattgccg gactggagat ctggctgccg ttgatcaccg gcgcccgcgt catcgtcgcc   6720
acccgcgaga tcgtggttga cggcgagcgg ctcaccaccc tgctggataa gtcgggcgct   6780
acggtcatgc aggcgacccc gagcggttgg cggcaattgc tggattcggg ctggaagccg   6840
ggtaaaggct tccgtgtttt ctgcggcggt gaagctctgc cgccggaact ggcgcgccgc   6900
attctcgata gtggcgtaga gctgtggaat ctttacggac cgacggagac caccatatgg   6960
tcggccgtgc acaagacaca aagactgggt gcctccgata gcatcgtgcc gatcggccat   7020
cccatcgaca acacgcagtt atacatcctg gattcgcgca tggagccggt tccccccgga   7080
gttccgggag agctgtacat cggaggagcg ggactggcgc ggggctatca tcgcaacccc   7140
gagctcacgc gtgagaaatt ccgcgagtgg cgtgatcgag gacgcattta ctctaccggc   7200
gatctggctc gctaccgttc cgacggcgca gtcgagtgcc tgggacgagt cgatcgccag   7260
atcaagctgc gcgggtttcg catcgaaccg gccgagattg aggccgcgat cgagacgcac   7320
attgccgtga agcaggcgat tacggtcgtg aaggacgatc ggctgatcgc ctatctcgtt   7380
ccggcaacgg gcgacgtgcg cgatctgcag agcgatttgc ggtcgtggct ggcaacgcgc   7440
cttcccgatt acatgatccc ctcggcgttt gtcagcctgt cctcccttcc gctgacgccc   7500
aacggcaaaa tcgacgcgaa cgcgcttccc ggtttgccca caacgccggt tgctgctcgc   7560
gagccgatgc gcggcgatgt ggtggagacg attgcgtcca tctggcgtga agttctgcgc   7620
gtggagcacg tcgactatcg gcagaacttc tttgatgtcg gcgggcactc gctaatgctc   7680
acacgggtgc gcggactgct cgaggagcgc ctggggttga cgctctccgt cgtcgatctg   7740
ttccggcata cgacgatcga gtcgcttgcc ggcctggcag aaaaatccga acccgccgct   7800
```

-continued gcggaacctg cggctgcggt cgcagaagat cggatcgcag ttatcgggat ggccggccgg 7860
ttcccggggg cgcgcaatgt ggaggagttc tggcgcaatc tgcgcgacgg tgtggattcc 7920
atcgccaggc tttcgccgga agatctgctg gcgggcggca tcagcccgga ggtcttccag 7980
gacccgagct acgtgccggc caagggtctg ctggacggca tcgagttttt cgatgccgcg 8040
ttcttcggct acagtccgcg cgaagcggag atcatggacc cgcagcatcg cgtgtttctc 8100
gagtgcgcgt gggaagcgat ggagaacgcg ggatatgcgg cgcgaagcta taagggttcg 8160
atcggcgttt tcgcgggatg cggcgtcaat acctacctgc tgaacaacct cgccaccgcg 8220
gagccgttcg atttctcacg cccctccgcg taccagctgc tgacggccaa cgacaaggat 8280
ttcctggcca cgcgtgtctc ttacaagctg aacctccgcg ggcccagcct gacggttcag 8340
acggcgtgct ccacctcgct ggtgtcggtg gtgatggcat gcgagagctt gcagcgcggc 8400
gcctcggaca ttgccttggc cgggggagtt gccatcaatg ttccgcagtc cgtggggtac 8460
ctgcaccagc cgggcatgat cctgtcgccc gacgggcgct gccgcgcctt cgatgagtcc 8520
gctcaaggca cggtgccggg caacggcgcg ggtgtggtcg tcctcaagcg cttgagccgc 8580
gctctggccg atggcgacac gatctacgcc gtcattcgcg gagcggctat taataatgat 8640
ggcgccgagc gcatggggtt taccgctcca ggtgtggacg gtcagacgcg attgattcgg 8700
cgcactcaag agatggcggg cgtgaagccg gagtccatcg gctacatcga ggcccacgga 8760
acagccacgc cgctcggcga tccggtggag atcgccgcca tcgctgccaa ctttccgaaa 8820
aacggaagcg gcgatgtgta tatcggatcc gtcaagacca acatcggtca tctagacgtc 8880
gcggccggtg tggccgggct gatcaagacg gtgcttgccg tccatcgcgg ccagattcct 8940
cccagcctga atttccagcg tccgaatccg cgaattgatt tcgcaaacac tccgtttcgt 9000
gtgagtacgc ggctgctcga ctggcccgcc ggaaagaccc cgagacgagc ggcagtcagt 9060
tcgttcggga tcggcggcac caacgctcac gtgattctgg agcaagcgcc gccggtgacg 9120
ccggccgcag ctgcgcccga acgatccgca catgtgcttt gcctgtccgc caatacagac 9180
gcggccctcg aagaactggt gcgctcgtat cgcggccata tggacaacca gcccggtttg 9240
tcgttcggcg atgtcgcatt cacggccaat gcagggcgcg tgcacttccc gcaccgtatc 9300
tgcattgtgg cccggtcgag cgacgaggct cgccaacgac tgacggaggc acgacgggtt 9360
cgcatcgccc agacgcgccc caagattgcg tttcttttca ccgggcaagg tgcgcaatac 9420
gcgggcatgg gccgccagtt ctacgagtcg cagccggtgt ttcgcgccgc catggatgaa 9480
tgcgcagctc tgctgaatgg acggctcgat ctgccggcgc tgttggccga tgacgcgttg 9540
ctcgacgcga ccgccggcgc gcagcccgcg ctgtttgctt tgcagtgggc cttggcgcag 9600
ttgtggaagt cctggggtgt gacgcccgac ctggtgatgg gacacagcgt cggcgaatac 9660
gcggcggcgt gtattgccgg cgccgtcagc ctgccggatg cgctcggctt agttgccgaa 9720
cgcggccggc tcatgcagaa cctgccggaa ggtgcgatgg ctgcggtcag cgccggcgag 9780
cagcgctgtg ccgcagcgat cacctcgcgc gtctccattg cggccatcaa cggacccgct 9840
gaggtcgtga tttcgggtgc gccgcaggat attgagagcg cgctggcaac tctacgtgcg 9900
gagggcatca aaacgcagat gctggccgtt gcgcgcgcct ttcacagctc gagcatggat 9960
ccgattctgg cggacctgca acgccgggcg gcggcgatcg cgtggcgcaa tccttcgatc 10020
ggcttggttt cgaacctcac gggcaaactg gccggcgagg gacagctggc gaatccgctg 10080
tactggcgag atcacgctcg aaaccctgtc cgtttcgccg acggtatcca aacgctcaag 10140

-continued

```
gacgaaggct gcgacgtgtt tctcgagatc ggtcctaagc cggttctact cggcatgggc  10200
caaaagtgcc tgcccgacga cgccaagcag tggctgccgt cgctgcgtaa aggccgcgat  10260
gagtgggaga cgattctcag cagtgtggcg acgctatatc agggtgggtt cgacatcgat  10320
tggcaggagt tcgaccgtcc gtattcgcga aggcgtgtcg ccctgccggc ctatcctttc  10380
gagagacgcc gccattggat cgagcggagt tccagaccgg aacctgtagc ggttgcgagt  10440
ggtctcgtcg ggtgccggct gtcgctaccg gtggcagacg ttatcttcga gtcgaaacta  10500
tcgacggctt cgcctctact ctcagaccac cgatattacg gttcggtggt ggccccggcc  10560
gtgtacttcc tggccatggc gctcgaggcg tcggcggagg tgtttggcgc cggccggcac  10620
acgctggaaa acgtgaactt cgcgcaccct ctgatccttt cagcggagcg cgacacggct  10680
gttcagctcg tgctttcaca gagcgatgac cggcatgcct cgttccgcat actcagcttg  10740
tccgacggct cgtggaactt acatgctgcc ggcaatattg ccgcccacgc tggtgtcgct  10800
cccgtgcccc gactggtcga tgaacgccgg cctgcggtgg atggagacac gtactattcg  10860
ctgctgcgcc acctcgagat agaactgggg ccgagctacc gccgcataca gcgcattcat  10920
ttcggtgaac aggaagcgct ggccgcgatt gattccgcaa cgccgctcaa tccccgttgt  10980
gaattggcgg aagccggcct gcaattgctt agcgccgcgg cgagtcccgc gcttgcggat  11040
ggcgccgaac atccgatatt cgctccgctc ggtatcgatc gcgtttgttt ttacggcagc  11100
ctggagggcg ccgtatgggg ggccgcgcaa attctccggc attcgccgga cggctttacc  11160
ggcgaggcgc agttgctgga ctcggagggc tgcgttctcg gggaacttca gggcgtgagt  11220
ttccggcgcg tcactcgcgc atgggcgcag cgctcggaac ggaagcccga attgtatgag  11280
gtcgagtggc ggcccgaacc gctccgccag ccttcgcgaa cgctacagcc tggggcatgg  11340
ctgatcctgg ccgacagtgg cggcgcggcc cgcgctctgg cagatgcgct cacagctcag  11400
ggcgagatgt gcgttaccgt gccgccagcc ggcgagtaca tgtccctagt cggtgagcgt  11460
gactggcgcg ggatcgtcaa cctgtacagt ctcgatgatt atgagctcgg ctgccgcagc  11520
actctggccc tggtgaagtc cctgaagtcc ggtccgcggc tatggctggt aacggccggc  11580
gcgcaggcga ccagtgcggt gcacaatccc atgcaggccg cgctctgggg cttcggccgg  11640
gtgatcgcgc gcgagcaccc ggatctgtgg ggcgggctca tcgatctgga tcccgacgat  11700
gcgcatgctt cggcggccgg cgcggccgcg cagatgcgtg atttcgacgg cgaagatcag  11760
tcggcgtgga gaagcaaccg gcgctacgtg ccgcgactga cccgccgacc cagcgcgcga  11820
gcggcagtcc gtctggtttc gggcgcgact tatttgatca ccggcgggct cggagccctg  11880
ggacttacag tcgcgaaatg gatggtggag cacggcgcca ctcgcgtcgt gctggccggg  11940
cgccggcctc caaacgagga gcagcagcgc gtgctgcaac agattggtgc gacggcagag  12000
acggtcgacg tcagccggga agaagaggtc gcggatctca ttcgccgcat ccacaccgaa  12060
acgtcaccgc tgcgcggcgt tatccatgcc gcgggtgtgc tggacgacgg cgtactgctg  12120
aatcaggact ggacgcggat cgcaagcgtc atggcgccga aggcggaagg cgctgtacac  12180
ctccatcatc acacccgcga tctgccgctc gacttcttcg tgctcttttc atcggcatcc  12240
tcgctcttag gtcctgccgg gcaggcaggc tacgccgcgg ccaacgccgt tctcgatgcg  12300
ctggcgcatc accggcgcgg actgggtttg ccggcgacca gcattaactg gggcgctgg   12360
tcgggagccg gaatggccgc gcgcaccagc cagtcgatgg ccggcgtggc gagcctctcc  12420
gtggacgagg gtctacacat tctcgaggcc gtcctgcatg aatgccccat tcagattgcc  12480
gcgctaccgg cgggctcgat taccggcgag ttgctgcgtc ccgccgcgct gccttcacct  12540
```

-continued

```
caactgcgca cccgcttgaa cgaagccaca ccccggcagc gcgaagccat cctcattgcg  12600
cacatcaggg agtcactggc gcgctttgtc ggcatcgcga cttccacacc gctcgatcca  12660
cagcagcctt tgggtgaact gggactcgat tcgctaatgg ccatagaact tcgcaactcg  12720
ctctcccaat cactggggca gcctttgccc gcgagtctgc tgttcgacta tccgtcgctc  12780
gatgcgatcg tcagttacgt gctccatgcg gtatttccac ccgaagcatc accggtggaa  12840
gcgccggagt ttgagaacct cgcccgcgaa gaactggaag cgctgctcga ttcgcggctg  12900
gcgcaggtcg accagtggtt ggagacgcaa taaacatgag cgggtcagac gatctcagca  12960
agcttcgccg cgccgtgatt gcgctcgaca aggtgcagaa acgcatcgac cagctggaga  13020
gcgcgcgcag cgagcccatc gccctcatcg gcgcgggctg ccgcttcccc ggcgcatcca  13080
atctcgatgc ctattggtcg ttgctgcgcg agggccgcag cgcggtacgt gaagttccac  13140
ccgaccgctg ggacatcgat gcctactacg atccggatcc cggcgcgacg ggccgaatgt  13200
acacgcggta cggcggcttc atcgatcagg ttgaccgttt tgacgcccgg ttcttcggca  13260
tcgctccgcg cgaggcgatc agcctggatc cacagcagcg gctgcttctg gaagtcacct  13320
gggaggcgat cgagaacgcc gggcttccac ccgaccggct ggcggggagc cggaccggcg  13380
tcttcatggg gatcttttcc aacgattatt acaacctgca aatgcgcggc ggggatgcgc  13440
atatcgacgc gtacaccggc acgggcaata cggccagcgt tgccgccggg cgtctctcgt  13500
acatcctcgg gctgcagggc ccgaacatgg cgatcgacac ggcatgctcg tcatcgctgg  13560
tcgcggtgca ccttgcctgt cagagcctgc gctcaggtga aagcgacctc gcgctggcgg  13620
gcggcgtcaa tctgattctc tcgccggatc ggacgatcta cttctgcaag ctgaaggcga  13680
tggcagccga cggtcgctgt aaggcattcg atgccgcagc agacggctac gtccgcggtg  13740
agggctgcgg tgtggttgtg ctgaagcgac tctccgacgc gctgcgcgat cgcgatccgg  13800
tgatggcggt gattcgcggc acggcaatca accaggacgg acgcagcaat ggactgacgg  13860
cgccgaacgg gcccgcacag gaagccgtga tccgccaggc tgtgggagac gcgcgcttgc  13920
agacgctgga tgtgagctat gtcgaggcgc acggaaccgg cacgccgctg ggcgatccca  13980
tcgaagccgg agcccttgcg gccgcgctgg gagcggggcg caccaacggc aacaagctga  14040
agctcgggtc ggtgaagacc aacttcggcc acctcgaggc ggcagcgggc gtggccgcac  14100
tgatcaaggt ggcgctgatg ctgcagaacg aagccattcc gccccatctg aatctgacca  14160
cgcccagccc gcacatcgat tggaacacgc ttcccctcga aatcccggca cggctcaccc  14220
cctggccggt tgcacccggc gggcggcgcg tcgccggcat caactcgttc ggcttgagcg  14280
gtacgaatgc gcacgtgctc atcgagcagg cgccgcaaca ggccgcgtcc agtacgcccg  14340
caccgtacct gcttccgcta tcggcgcgca gtccggaggc gctgcgtgat ctggcgcgcg  14400
cataccgcga cgtggtgaac gacaaccccg ccgacacctg ctacacggcg tgcgctcgcc  14460
gcacttcata cgaacaccgc gcggcattca ccgggacgaa cgcgcaggac ttgatggccg  14520
ggctggacag ttttctggcg ggcaacccga accgcgatac cgccacaggt tttgtgccgc  14580
gcggccagaa gcgaaaagtc gttttcgttt tgccgggaca aggatcgcag tggcccggca  14640
tgggccgcga cctgatggct tctgaaccgg tgttccgtgc cgccatcgaa gagtgcggcc  14700
gcgccatgca gccttacgtc gactggtcgc tgacgcaaga gttgcagggg ccgctcgacc  14760
gcatcgacgt gattcaaccg gccctgttcg cagtcggggt cgccttggcc ggactgtggc  14820
gccattgggg aatcgagccg gacgccgtga tcggccacag catgggcgaa gtcgcggcag  14880
```

-continued

```
cgcacattgc aggtgcgctg actctcgatg aagccgctcg ggtgatttgc ctgcgcagcc  14940
ggatgctcgc cggagtacgc ggccagggag aaatggctgt cgtggaatta gcgctggacg  15000
aggccatcgc tgccatcgcc gggcgctcgg atcgggtctc gattgccgcc agcaacagcc  15060
cgcgcagcac cgtcctgtcg ggcgacagcg cagctctggg cgaactgctg cgggaactgg  15120
aggcgaaaga cgtcttctgc cgtcgcgtga aagtggacat tgcctcgcac agccatctga  15180
tggactccgt gtgcgcggcg ttgccgggcg tggtgggagc gcttcagccg cggccggccg  15240
cccttggcat gtactccacc gtcaccggcg cagcgattag cggtgaagag ctggtttctg  15300
cgtactgggc tcgtaatctt cgccaacccg tgatgctgtc gacggccgtc gccgcagccg  15360
cggcgggtgg tcatgatgtg tttctggaac tgagtcccca cccgttgttg gtccagccga  15420
tccaggaaac gctcggagat cgggcagcga ttgccgctgc ctcgttgcgg cgcgatgaag  15480
acggaaacct cgcactgcgc cggacgctgg gagcgctgct gactaacgga gtcactccgg  15540
actggtctcg tatttatccc aacggcggcc aaactcgccg gctgcccaac tatccctggc  15600
agcgtgagcg ttattggatc gatatccgtc cgccgcaggt cgagtctcag gctttgcctg  15660
gccggcggat cccgtcgccg ctgccggaga tgcagttcga gtccactgtg gaggcgaaag  15720
atttcgcgga tcaccggctg cacgatgtga tcgtgactcc gggagcgtgg cacctggcaa  15780
tggcgctcgc cgctgcgcgc caaggtctcg gcgccgggcc tcaccatgtc gaacacgtgt  15840
cattgacggg cgcgctgacg ctgccggaaa acgatgctgc caggcaggtt caactggtac  15900
tccgtcatga agagggcggc ggagcttcct tccgcatcta cagccgcgag gattcctgga  15960
agctgcacag cgaaggcatg ctgcaggcgg gcgattccac ggcatccatc gatctggatg  16020
cgattcgcgc ccgctgcacg gcggagctca cagccgatgc cttctattcg cgactgtggg  16080
atcgcggcta tcacttcggt cccaccttcc gaaccatcgg ccccatctgg cgcggcaacg  16140
gtgaggtgct ttgtcgcgtg gacattccgc tgacggaaat gcagacgatc gactgctgtc  16200
tgcagttgcc cgcggccctc gtccatcacg acgatttgaa agatgtgcat gtgccggtag  16260
gtctggaccg attctcgctc gctgaagtgc ccactggccc ggtctgggga tacgcggtct  16320
tgcggccgga ttccacggtg gatgtccgtc tcgtcaccgg caccggcagc gtggtggcgg  16380
aattggtggg gctgcagtcg agagtcgccc atagcggcca gctcggcgaa tcggagattc  16440
ccacctggac ggtgcaatgg accgcgtcgg ttcgccgcgg cgatgccaat gccggcaatg  16500
ctggcggacc ttggctcgtc atcggcgagc cggcgattgc cgagactctg caaaagcgcg  16560
gccaaacctg ccgcacggcc gatacgtgct cgggtccgcc gtgccgtcaa attgtgtact  16620
gtccctcgcc gcgcatcgac gacctgcttt ccgtattgcg cagcatcgtg caagcgggct  16680
ggcctgagcc gccgcgcctg tggctgctga cgcgcggatc tgccgcggtt ctcaactccg  16740
acaaagatat tgatattcga caagcctggc tgcacggaat tgggcggacg attgcctatg  16800
agcatcccga gctgcgctgc acgctcgtcg atctcgatgc gcacagcaac gactgcgggc  16860
atctcgcgac gctgatgctg tcgaatatcg cagaggatca agttgcgatc cggcaaggca  16920
cggtatgggc gccgcgcctc agtcttcaca agatcccatc cgcacccgat gtggcgttcc  16980
gtgccgacgc aacctatctg atcacgggcg ggctcggcgg actcggactg caggtggcgg  17040
gatggctcgc cgccgccgga gcgcgccatc tcgttctgct gggacgcagc gagcgtcctc  17100
ggccacaact ggaaggtgtc aacgtcaaga tcatccatgc ggacgtggcg gaccggcagc  17160
agctatcgga tgcgctcgcg atcatcgatc gcgacatgcc gccgttgcgg ggcgtgttcc  17220
atctggcagg cacgctggcc gacggcatgc tgctcaatct cacgaccgaa cgcttcgaag  17280
```

-continued ccgccatggc tccgaaagta gccggcgcgt ggaacctgca cgaactcacc gccggccggc 17340
cgctggatca ttttgttctc ttctcttccg ccagcgcgac agtgggatct cccggccagg 17400
gcaactacgc cgccggcaat tcatttctcg acgcgctggc tcatctgcgc cgcgcccagg 17460
gtcttcccgc cgtcagcatc gcgtggggac cgtggacaca ggttggtttg gccgcacagg 17520
cgaaccgcgg agaccgtctg gccgcgcgcg gcatctcggt tattcaaccg caacagggat 17580
tgcgcgcgct ctacaaagca ttgacgcaga ttcggccgca cgtcgctgtc atgaacttcg 17640
atatcgcgca gtggctccgt tactatccgt cggccgcatc gatgtccctg ctggccggca 17700
tcgcacccgc ggccgcggac accaaaccgg cggccgacat gcgcagcgag ctcctggcag 17760
ttccagccgg gcggcagcgc cgcgcgcggc tggaaacgct gctgatgcac gaagccggac 17820
acgtgctgcg cttcgatcca gcgaaactcg acggcagagc gacgctgggt gatctcggat 17880
tcgattcgtt gatggccctc gagtttcgca accgtctgga agccgggctg cgcgtcaagc 17940
tttctgccac cctgatctgg cgttacccga cattctccgc cctggcgcag catctcgccg 18000
acaagctcgg cctgccgctg gaaagcatgg ccggcaatgc tgaaccttcg accgttgctg 18060
ccgttgctac ccttgctacc gttggcaccg ccgcgggcga ggaccggagt cccgccgctg 18120
cagacgatct cgacgccgtc gcaaaccaga tcgccgggtt gggggacaaa gaaatcgaag 18180
ctttgttgaa acagaagttc gctcattttt caggagcctc cgagtgagtt cgatatccga 18240
gcgattcccc aaccttacgc cgttgcagca ggcgtacctg acgctggagc acatgcagcg 18300
acgtctcgat gcggccgaac gcgacgcgcg cgaacccatc gcgatcgtgg gtctgggctg 18360
ccggtttccg ggcggcgatg ggcccgatga gttctggcag atgttgcgca gtggagtcga 18420
tgctattcgt gaggtaccgc ctggacgatg ggacgaggag tcggtccggc gcatcctgaa 18480
atcgttgaac ccccgccacgc cggtgaagat tcaagccgga tttctcgatt ccatcgatgg 18540
tttcgacaac gatttttttcg gcatttcgcc acgcgaggcc gtcagcattg atccgcagca 18600
gcggctgctg ttggaagtgg cgtgggaggc actggaggat gcgggggcaga cgatggaagg 18660 gctctccggc agccgcacgg gcgtcttcgt cgggatccac agccaaagca gcgactattt 18720
ctggatgcag accgccgatg gcgcgcgcat cgatccgtat accgccaccg gcacggcgca 18780
tagcgtgatc gccggccgac tttcctattt gctgaacttg caaggaccca gcatcgcgct 18840
cgacacggcc tgctcgtctt cgctggcggc ggttcatctg gcgtgccaga gcctgcgcag 18900
cggcgagtgt acgctggccg tggccggcgg agtgaatctg cgcttctcgc cggagtttat 18960
gtacgccacc tcgaagatgg gaaccgcctc gcccagcggt cgctgccgcg ccttcgacgc 19020
ggcggcggac ggcatcgtgt tcggagaagg ctgcggcgtg gtggtgctga agcgcctgtc 19080
cgatgcactc gcggccggag accgggtgtg ggccgtggtg cgcggctccg cggtcaatca 19140
ggatggccgc tcggccgggc tcaccgctcc caatgtcgtg tctcagcagg tcgtcatccg 19200
gtcggcattg gccaatgcgg gcgtcgcggc gcagcagatc ggttacatcg aagcccatgg 19260
cacggggact ccgctcggcg atcccatcga gatcgaggcg ctggcggaaa ccgtcggcct 19320
cccgcgacct gtcggcgatg tgtgcgcggt cgggtccctg aaatcgaaca tcggccacct 19380
ggagggagcg gcaggcatag cgggattgat taaagcggtg ctcgcattga gtcacgagac 19440
gataccgccg agcttacacg tgagacagct gaacccgaat atccggttgg agggaacgtc 19500
gctcgacatt gtgaaggaag tccggccgtg gcccgcgggt tcgagacgaa ggtttgcggg 19560
cgtcagcgcg tttggttggt ccggcacgaa cgcgcatgtc gttcttgaag aagcggcgcc 19620

-continued

```
gactggtaga ggcgaagctg cgagcgggtt ccattcccga ccccccgccg ccgctgcgcg  19680
ggcggctgtc cccctcgcgg agggggacac tgggggcact cccgacattg caggcactcc  19740
cgacactgca gacactcccg acactgcaga cactcccgac attgcaggga ctgcaggcac  19800
tgcggcaact acgggcattg cagacgcgat gtatgtgctt ccgctgtccg cgcatggtgc  19860
ggacgaactg cgtcgggtgg cgcgggcata cggggaattg ctgacagcgt cgcacgcacc  19920
gagcctgcgt gatctttgct acacggccgc agtccgccgc acgcatcacc gatgccggct  19980
cgctgtttcc ggcagaacgg ctgaagaact ggcggcgcag ctccagggga tcacgatccc  20040
ttcccagcga cggaagacgg tattcgtctt ctcgggacag ggatcgcaat ggatcggaat  20100
ggggcgcagc tggatggacc gcgaacccgt tattcgcgag gcgttggaac gctgcgaggc  20160
cgccatgcgg ccttatgtgg actggtcgct gaaagaagaa ctggcgaagc tcgaccgcgt  20220
cgaggtcatt cagcctgcgc tcttcgcgct gcaggtcgcc atcgccgcat tgtggcgttc  20280
ctggggaatc gagccggatg ccgtcatcgg gcacagcatg ggagaggtcg ccgccgctca  20340
tgtcgcgggt gcgctgacgc tgcaggatgc ggcgcggatc atttgcagcc gcagccggct  20400
gttgagccgg atcagcggcc tgggcgggat ggcgatggtg gagctgccgc tcgcggaatg  20460
tgaggccgtg ctgtcgactt acacggaacg actatcgccc gcggtgtcga acggacccaa  20520
ctccaccgtc atctccggtg aagtcgaagc cctggccgag gtcgtcgcga cgctggagcg  20580
gcgaggcgtg tcttgccggc cggtgaaagt ggacttcgcc gcgcatagcc cgcaagtgga  20640
cccattgtgc gacgaactcc tgcagtcgct cgacgggatt caaccgcggc ccgcgaccat  20700
acctttttac tccacggtga ccggcgcgac gctggagacc accagcctcg acagcacgta  20760
ctgggctcgc aatctgcgat cgccggttct gttctggcag ggcatccgcc atcttgccga  20820
cagcgggcac gatgtctttc tcgagatcag ccctcatccc atcctgctgc ccgccatcgg  20880
cggcaatgcg gcgctggttc cgtctctgcg ccgcgaccag gacgaacgcg gttccatgct  20940
cacgtcgctg ggcgccctct atgaggctgg gcacactgtc gcatggcgga ccgtgtaccc  21000
ttccggcaat tgcgtgcgcc tgccccggta tccctggcag cgtcgtcgtt tctggctcga  21060
cgcttccccc gcgcgacacg cgatcacgtt gggcaatccg ctgttgggaa aacgcgtcga  21120
agcctcgacg caacccggca ctttcttctg ggagacggaa ctcagtctcg cttccgtgcc  21180
ttggctggca gaccatcgcg tgcagggcga agtcgtcttg ccggctactg cgtatctcga  21240
tatggctctg gccggaactt ccgagacctt cggtgaaagt ccgtgcgtgc tggagcatgt  21300
gactttcaca cagatgctca ttgtgccgcg cgacggcagc atgacgttgc agctggccat  21360
cgcggtcgat agacccggga tggcgtcgtt tcggatttcc agccggcagg catcgacatg  21420
ggtcctgcat gcttccgggg acattcgtca gacgcctgcg gatgcatcga ccgtcccgcc  21480
ggattctgcg gagacggtgc aggcccgctg ccccacagtg gtgccggcgg cggagctgtg  21540
gcgtcagatg gcggagcacg gcgtcgagta tggtccggct ttccgcgcgc tcgagcagat  21600
ctggagttgt ccaggtgagg cgatcgggcg tctgcgtagc tcggaaacgc gttccactgc  21660
gccggcgttc ctcgatgcat gtctgcagat catcgccgcg gcgtttggtc ccgccggtgg  21720
aacctggctg cccgccggca tcgaccggat gcgctggctg catcccgcac gttccgtggt  21780
gtggacgcat gcgcggctgg aaggacctat cgccgatctg tcgctgctgg acggagaggg  21840
acaactggtc gcccgcatcg agggtctgcg gctgcagcgc ctggatgcgt cggagcgcat  21900
cgacatgcgc ggctggttgc acgaactgcg ctgggtcgct cagccgcacg ccgctgcaga  21960
gccgccggcg gcgcgagcgg cgcggtcatg gctcattgtc ggcgctgtgg atagcgcgct  22020
```

-continued

```
caccgcatgg ctgcgcgcta ccggcaaccg cgtgacgcag acctcgccgg aaaagctcga 22080
tgaactccag ccgccgctcg aggaaatcgt gtttttgctc gagcacgaac cctcatgcga 22140
ccgcattctg catctcctcc agaccctggg gcgcacgccc tggcgtcaag caccgcgcct 22200
atggctggtc acgcgcggcg cgcagccggt cgatggacag atcctgcaag ccggtatcgc 22260
tcaggcgcct ttctggggtt tgggccggac cgtgcattac gaacatccgg aactgaactg 22320
cacgctgatc gatctcgatc ccgccggcgg cgaagaggaa ctcctgcacg aactgctgac 22380
gaacaacggc gagaatcaaa tcgcctttcg cggcggcgcg cgttacgtcg cgcgcgtggc 22440
tcggcacgaa gcggatatgc aacccgccat gttcaaggcc ggcgatcggc cgttccggct 22500
cgagatcgat gcccccggag tcctcgaccg gctgcgcttg cgggccacat cgcgccgccc 22560
cccgcaagcc ggtgaagtgg agattgaagt ctgcgccgcg ggcctgaact tcctcgacgt 22620
tctgctcgcc ctcggcgtta tgcccgacga tgcgcccggc gcgattgccg gcagcccgcg 22680
cctgggcggc gaatgctcgg gccgtatcgt ggccatgggg aaaggcgtca ccgactttcg 22740
catcggagat gaagtcgtgg cccttgcgcc ttgcagtttc ggtcgcttcg tcaccacgcc 22800
cgccttccgc gttgccttga agccggccaa cattcccgcc gaacaggccg ccgccctgcc 22860
tatcgcgttt ctcaccgccg attacgcgct ctcgcgagcg gcgcggctgg cgcccggcga 22920
acgagtcctg attcacgctg ccaccggcgg tgtgggattg gcggcaatcc agatcgcaca 22980
gcgtgcgggc gcggagatct tcgctactgc cgggagtccg gaaaaacgag cgtatctgcg 23040
ctcgctgggc atcgcgcatg tttcggattc gcgctcgatg gctttcgtgg acgacatccg 23100
caattggacg aatcaagaag gagtagacgt cgtcctgaat tcgctttccg gcgatctgct 23160
ggaggcgagc ttcgatctgc tgcgcgatca tggacggttc atcgagatcg gcaagcgcga 23220
ttactatgcc ggccgcaagc tggggcttcg cccgttcctg aagaacctct cgtacacgct 23280
ggtcgatttg ctcggcatgt ccctgaagcg cccggcattg acccgggagc tgctgcagga 23340
gatggtcgca aaattcgaat cggaaacctg gcggcccctg gaaacgcgag tgacgaccat 23400
caccgaatcg gtggaggcgt ttcgcaccat ggcgcaggcg cggcacatcg gcaaaatcgt 23460
catggcgatg cgagattgcg ccaatgcgcc catcgcaccc ctacgctcgg cgttcgatag 23520
cgagggaacc tacttgatta ccggcggact tggcgggctc ggtcttaccg tcgcacgctg 23580
gatgatcgga cgcggcgccc ggcggctggt gctgctgagc cgccgcgcgc cttcacccga 23640
ggtccagcaa gccatcgccg tcatggacgc agatgtccgg acggtgcagg ccgatgtttc 23700
tcagcgcgat gaactcgagc gcgtgatctc ttccatcgat cgattgcgcg gcgtgattca 23760
tgccgcagcc gttctcgacg atgcgctgct actgaaccag acggaagcgc atttccgcaa 23820
cgtgatggcc gcgaaaatcg acggtgcctg gaacctgcac ttgctcaccc gcgactgccc 23880
gctcgatcat ttcgtgctct tctcctccgc tgcaggactg ctgggcgcgc ccgcccaggg 23940
aaactacgcg gccgcgaacg cctttcttga cgcgctggcc tactaccgga aggcccaagg 24000
cctgccggcg ctgagcatcg gttggggtgc gtggtcggag gtcgggctgg ctgccgcgca 24060
ggacaatcgc ggatcgcggc tggctttgcg cggcatggaa aacctgacgc cgcaacacgg 24120
cctcgctatt ctggaacagc tgctgaacag ctcggcttgc cacgtcgccg cgatgcccat 24180
caatgtccgc cagtggcggc agttctatcc caaggcggcg cagtctgcac tgttcgagct 24240
tttgcatgac gacgcggcga gcgaagccga tgcgccaaac gcgttgcgcg cgcggctgca 24300
atcggccgag cctcagaccc gcaggacatt gctcgaagaa catctacagc agcagctggc 24360
```

-continued

```
gcgcgtgctg cgcatcgact ctcaaactat cgatcccctg cgcccgctga aggaactcgg  24420
cttcgattcc ctcatggccc tggagtttcg caaccgtctc gaactcacac tgggtctcac  24480
gctccccgcg accctgattt ggggtcatcc cacgctggcc ggtcttgccc cgcacctggc  24540
gtcgcaaatg ggactgccgc tggtcgaagc gcaggccgcg gctgctgcgg aaggagacag  24600
ccgcgccatg aaaactgcac tcagcgggtt ggacgacatg tcggaagaag cagccgtggc  24660
tgcgctccga ggagcaaggt cgtgagggaa aaaattgcgc ccatgtcgtc ggtcaaactc  24720
gcgctattgg cgcggaacat gcggcaaaac atcgcaggct tcgacctggt tcacgccgaa  24780
cccatcgcca tcgtcggcat ggcgtgtcgt tttccgggcg gcgcgaagaa tccggacgcc  24840
ttctggacgc tgttgaagaa cggtgtcgac ggtgtcaccg aggtgccgcc agaccgctgg  24900
aactcggacc agtactactc ctccgatccc gatgctccgg gcaaggcgta tgcgcgatat  24960
gccgccttcc tcgaacgcat tgacggtttc gatgcggaat tcttcggcat ctcccccgc  25020
gaagctctga acatggatcc gcagcagcgg ctgctgctgg aagtgtgctg ggaagcggca  25080
gaggacgccg gcatctctcc cggccctctg gcgggcagcg cgaccggcgt ctttgccggc  25140
tcctgcgccc aggacttcgg actgtttcag tacgccgacc ctgcccgcat cggagcttgg  25200
tcgggttccg gcgtggcgca tagcatgttg gccaatcgca tctcctatct gctcgacctg  25260
cgcggtccga gcatggcggt cgatacggcc tgctcctccg cgctcgtcgc cgtccatctg  25320
gcttgccaaa gcctgcgccg gcgcgaatgc gatgcggcat tcgccggcgg agtgaacttg  25380
atcctgactc ccgagggcat gatcgctttg tcgaaggctc gcatgttggc gcccgacgga  25440
cgctgcaaga cgttcgacgc cgcagccgac ggttatgtgc gcggcgaggg ctgcggcatc  25500
gtgctgctga agcggctctc cgatgcgctg gccgatggcg atgccatccg tgcagtcatc  25560
cgcggctcgg caatcaatca ggacggacgg agcaatggca tcacggcgcc gaatctgcag  25620
gcgcagaagg cggtcctgca agaggcggtg gccaacgcgc acatcgatcc atcccacgta  25680
tcgttgatcg aggcgcatgg cacgggcacg tcgctgggcg atcctatcga gatcgaggcc  25740
ctgcagtcgg tctacgacgc gccggactct gcgccttgtc tgctgggttc cgtaaagacc  25800
aacatcgggc atctggaggg cgcggcggga atcgccgggc tgatcaaagc cgtactcgcc  25860
ctgcagcatc gcaccattcc tccgcacctg cattttcgcc ggctgaatcc gaacatctca  25920
ctggacggca gccggtttcg catcgccacg gaatcgtcgc cgtggacgtc ggaaggacgg  25980
ccgcgtctgg ccggcgtcag ctcgttcggt tttggaggga gcaacgcgca cgtcatcctc  26040
gaagaggcgc ctgcactccc tttgccgaag ccggtcacac gcccgcagct tctcactctg  26100
tcggcgcgca ccgacgaagc gctcggcgaa ctggccggcc acttcgcgga gttcctgcag  26160
tcgcacccga atgcgttgct gtccgacgtt tgcttcacca gtcaggttgg gcgcgacgca  26220
tatagtcacc gcttggcgat caccgccgca gatgcggcag aggctgtagc ggcattggcc  26280
gcggcgccgc ggcgcgaagt atcgttgcgc cggcggccgg caatcgcttt tctcttcacc  26340
ggccagggcg cgcagtacgc cggcatgggc gcagagcttt ataaaacgca gcctgttttt  26400
cgcgacgcgc tcgatcgttg cgccgattgg ctccgtcccc agctcgatgt tccgctgacc  26460
gttctcttgt tcgagtcggt ttcgccgttg cacgagacgg cgtataccca gccggcaatg  26520
tttgccctgg aatgggctct ggctcagttc tggctgtcgc tcggcgtccg gccggactac  26580
gtgctgggcc acagtctcgg cgagtatgtt gcggcgtgtg tggccggcgc ctttagcgtg  26640
gaggacggcc tgcggctggt gaccgccagg gggcggctgg tcaatgcgct tccccgcggc  26700
aaagcggtca tcgttcacgc caatccgagc cgcatcgcgg cgctcgccgc caaggtggca  26760
```

-continued

```
gtcgccgcat cgaatgcgcc ggaccgcacc gtgatctccg gcacggctgc agaaatcgcg  26820
gaagcgcaag atgacctgca tcgcgccggc gtggaaacgc gagagctgaa cgtatcgcat  26880
gcgttccatt cgccgctgat ggatccgatt ttggacaagt tcgaagcgct tgcaggtgcg  26940
atcgcgtatc agccgctggc gatcccgctg gtgtcgaacg tcagcggagc cgtattgccg  27000
aaaggcacga cactcgacgc ccgctactgg cggcgacagt tgcgcgaaac cgtgcagttt  27060
gaaagcgcga tgcgaaccct ggcggaccgc gagtgcaagc tgtttctgga aatcggcccg  27120
catcccacgc tcaccacgct ggggcgatat tgtctgcccg atgacggcgc ggtctggctg  27180
cactccctat ctaagggacg atcggattgg tccgtgctgc tggaaagtct tggcggcctg  27240
tttaccgcgg gcgtgaatcc cgactggcgc ggtctctatg ccggggaatc acccagccgc  27300
gtcgcgctgc cgacgtatcc gtttcagcgt gacaccttca gcctgagacg cgtacccgcg  27360
agagagccgg cgcgcggcgg catgttggga gcgcgcctca acagcgcgtt gggcgatgtc  27420
atcttcgaaa attcgctaac cacggagacg cctctgctcc atgagcacgt gatctacgac  27480
gcggtcattg tgcccggcgc ctggcacgtg tcggcatttc tcgaagcggc acaggaagtc  27540
ttcggtccgg ttccctgcgc cgtctccgat gtcatgatgc ggcaggcact ggccatcccg  27600
ccggatacgc cggtcacggt gcaagcgatt gtcacacccg gcgaggacgg cgaagcaaag  27660
gtgcaggtct tcagccagga tggcgattcg tggaagctcc acacggcagc cagtctgcgc  27720
gcggcgactg ccggcgccgt tcatttcgag ctgccggcgc agccttccga agtcatttcc  27780
ggcgatgcgt tctacggcgc gatgaacgca cgcggcgtcg atcttggccc cgccttcagt  27840
tgggtggaag aagtctggcg tcgcgatggc gaggcgctgg ggcgaatgcg tctgccggtg  27900
gctgaggatg gcgcgaacgc ttaccggctg caccccggcc tgatcgattc ttgttttcaa  27960
gtattcggag cgacttggcc cgcggagcgt tgccagcccg gcgcatacgt gccggtcggg  28020
atcgaagcgg tgcgcttcta ccgtccgccg gcaggttctc tgcgctgtca tgcgcgtctg  28080
cgcccgagct cgagcggccc gttcgtcggt gatctgacgc tggttgaaga gaccggcgcg  28140
gtcatcgccg agttttccgg actggctgta atgcatgccg gtacgctgca atccgcacag  28200
tcgtggctgc aggatgtgca gtggcaggag tgcgagcgat cgacaacgtt gaagtccgac  28260
ggccctggca agccggagga ctggttgctg tgtgccggcg cagacgatgt cgccggtttg  28320
atgccgcaag agctgcgcgt cgtgtccggc gtcactctcc gccaggcgct ggaacagacc  28380
cagactttgg tcggccgccc ggcgcggctc tggctgatca cgcgcggcgt gcatcgcatc  28440
agtgatgacg atgcgactcc cgtcgatcct ttccaggctc cactgtgggg actcgggcag  28500
gcgatcgcgc gcgagcatcc cgagctgtgg ggcggcctga tcgacctcgg ttgcgacaat  28560
gccgacatcg ccgccgccat gctgctggat gaaatccgtt atgccggcga cgacaaagcg  28620
atcgcattgc gcaacggacg ccgctacgtt cgccggctgg tgcggcacaa ggaaacgtcg  28680
aagcggccgc ctgccatttc agccgacggc gtctatctga tcaccggcgg tctcggcgca  28740
ttaggacgaa gggtggcacg ccgcttgatc gagcaaggcg cgcgccgtct ggtactggtc  28800
ggccggcata cggaggcagt tgccgatctc gagcaactcg gggctgcagt catggttgct  28860
gcttgcgatg tgagttccga gcaacagctg gcggcgctgc tggcggaccc gcgcacccag  28920
ccgctgcgtg gagtcgtgca tgccgcaggc gtgctcgatg acggggtagt tacagaacag  28980
acgtgggctc gtttcgagaa ggtgctggcg ccgaagctgc agggtgcctg gaatcttcac  29040
cagctcactc gccaccatgc gctcgacttt ttcgtactct tctcttccgc cgcttcgctg  29100
```

-continued

```
ctcggttccg ccggacagag caattactcg gcggccaacg catttctcga cagccttgcc  29160
cacatgcgcc gcgcgcaagg actaccggcg ctgagcatca attggggacc atgggcgggc  29220
gaaggcatgg ccgcgcgcat cgcgcggcaa ggcctgccgg gggtaccgct gctgccgccg  29280
gaagtgggtg cgcgcatctt cggcgatctg ctgggcgaga ctgccgctca gatcgcggtg  29340
ttccaagtct ccgccgaaaa aaggcggagc ccggcgagcg atcccggctt catccagcaa  29400
ctcaccgaag ctgcgccgga gcggcggcag gaactgctgc agatgcgcat ccgcaagcag  29460
gccggcggcg tgctggcgct cgatgcgtcc aagacgctcg acccgcgccg gccgctcaag  29520
gaatacggac tcgattcgct gatggcgctg gatctggcgc gcgccatcgg agagctggtg  29580
cgcaagagcc ttcccgcgac attgctatac gaccatccga ccgtcgagaa attggccggc  29640
catgtcctcc gcgaactcgg actcgacgtc cccagcgatt ccctcgtcga tgaagtgcgg  29700
cagctgtccg agcaggagat ggcggcgttc atcacggaaa ccttgcacca tctgggagag  29760
gaacgatgag cgatctcact cctcttcaac aggcggtcct ggcgctcaag cgcacgcgag  29820
cgcgtctcga cgaactggag agcgtccaca acgaacccat cgcgatcgtc ggcatggctt  29880
gccgctttcc cggcgcggac tcgccggaag cattttggca gctcctgcac gatggcatcg  29940
atgccatccg cgaaattcct gcgggccgtt gggatgccga tgcgttttac gatcccgatc  30000
ccaacgcgcc gggaaagatg tacacgcgtc tgggcggatt cctcgatggt gccgtcgacg  30060
gcttcgacgc cggcttcttc ggaatcacgc cgcgcgaggt cgccggtctg gatccgcagc  30120
agcgcctgct gctcgaggtg gcatgggaag ctttggagcg tgcgggtcgg ccgcccgaca  30180
gtctcgcggg cagcgacacc ggagtgttca tcgggatcag caccgacgac tacagccggc  30240
tgaaacctac cgatccggcg ctcattgacg cctataccgg taccggaacc gcgttcagca  30300
ctgccgccgg acggatctcc tatctgctgg ggttgcaggg accgaacttc cccgtcgaca  30360
cggcgtgctc ttcctcactc gtggcggttc atctggcgtg ccgcagcttg cagtcgcgag  30420
agtgcagcat ggcgctggcc ggcggcgtga acctgattct ggcgccggaa agcacgatct  30480
acttctgccg cctgcgggcc atggcggccg atggccgttg caaaagtttc gctgcctccg  30540
ccgacggtta cggccgcggc gagggatgcg gaatgctggt gctgaagcgg ctgtccgatg  30600
cgacgcgtga cggcgatcgt attctggcgc tgattcgcgg atcggccgtc aaccacggcg  30660
gccgcagcaa cggcctcacg gcgccgaacg gtccggcgca ggaagccgtg attcgggcgg  30720
cgctcaagaa cgccggcatg gcccccgccg atgtcgatta cgtggaagcc cacggaaccg  30780
ggacgccgct gggagatccc atcgaactgc gggcgatggc agcggtgctg ggcgaggggc  30840
gtgccgtcga ttctccgttg atcgtcgggt cggtgaaaac caacttcggc cacctggagg  30900
cggcggcagg tatcgccggc ctgatcaaga ccattctcgc cctgcagcac cgagagattc  30960
cgccccatct gcatttcaac gcgcccaacc cgcacgtact ctggaatgag ctgccgctaa  31020
agatagccac cgcatgttcg ccatggccct ccaacggccg cccccgagtt gccggggtga  31080
gctcgttcgg aatcagtggc accaattcgc acgtcgtcct cgcagaagcg aagacgaatg  31140
tagaagcgaa gacgaatgta gaggcgaaga cgaatgtaga ggcgaagacg agtgaagagg  31200
tcaaggcgag tgtagaggcc aaagggaatg tggaggctaa ggctagtgct agtgtccccc  31260
tcctcgaggg ggacagccgc ccgcgaagcg gcggcggggg gtcgggccgg ccgcccagcc  31320
gcgaggaagt gccggtcccg gatcaactcc atgccgaaga cggccgcgaa tacctcctac  31380
cgctttcggc gcgccatccg caggctctgc gcgatctcgc cggcgcctat cgcgatgggc  31440
gctttcacgc tccgctctcc gcgctgtgtt ccgccgccag cctgacgcgc agtcactacg  31500
```

-continued

```
aacatcgcgc agcgtttgtg gcctcatccc tgcccgagtt caatcaattg ctcgaggcct  31560
tccggcgcaa tgaaaccaat cgcggcgtcg ccaccggttt cgccgatccc ggagttcgtc  31620
cgaaactcgc cttcatcttt tccggccagg gcggacagta cccgcgcatg gcgtatcgcc  31680
tgtattccga cgagcctgtc ttccgatcgg cgatcgaacg ttgcgacgcc gccttccgca  31740
gcttcgtgga atggcggctt gcggacctgc tcgccgacga gtcgggagca tggctgagcc  31800
agatcgatcg cgtgcagcct gcgctgttcg ccgttcaaat cgcgctggtc gaactgctgc  31860
aatcctgggg aattcgcccg gacggcgtgg ccggacacag catgggagaa gtggcggcgg  31920
cccatgtcgc aggcattctc accctggagg acgcggcccg catcatctgt cgccgcagcc  31980
ggctgttgct cggacttcgc ggccggggag cgatggctct ggtcgaactg ccgctcgatc  32040
gggcgaaggc cgtgctcgct gaacgcggtc tcactactgt ttctgtcgcg gccagcaacg  32100
gaccacgcag cacggtgttc tcgggagacc gtgtggctct cgagcatttg aaggacgact  32160
tcgagaggcg cggcgtcttc tgccggctga ttcaggtgga tgtcgcttca cacagctcgc  32220
aggtggaccc gctcgagaac gaattgcgcc aggaactcgg ccgcgttatt gcaaaacgtt  32280
ccgccgtgcc gttcttctcc acggttgaag gacagttgag cacgggcgag gcgtgcgacg  32340
cgtcgtactg ggtagccaat ctgcgacagc cagtccgttt ctgggagtcg ttgcaggcga  32400
tggctggtga tgagttcacg cagttcctgg agatcagtcc gcatcctgtg ctgacgccgt  32460
cgatcgagga tagtctgcgg acgctcggca taaacggact ggttcgcccc gtactgcgcc  32520
gcgacgaacc ggagcggcgt gagctgctcg agttgctcgc cgcgctctac gtgaatgggc  32580
agcgtccgga ctggcgcgcg ctcgcttcgt ctcccgacac gcgcctggat ctgccgacgt  32640
atccctggca gcgcgagcgc ttctggttcg cgacctcgac gcggcgaagt ttgccggcag  32700
ttggcggtca tccgctgctc ggtcgcaagg tcgagattgc gctggcgccg gacacacacg  32760
tctgggagtc cgtgctctct ctggatgcgc tgccgtttct cgccgatcac cggctcaacg  32820
agcttgtggt gcttcccggt gccgcttatg tggagatggc gctggccgca gccaaggaag  32880
tgttcgcggg tggctgcagc ctggaagaga tccggtttga acaaatgctg gttgttcctt  32940
ccgcgggcgc ctcgcgagtg caggtcatac tcgagggaca cgcattccgc atctccagtc  33000
tggccgaagg cggttccgat tggaccgagc acgcgcgcgg caccatggct gcggcgccgg  33060
acaaggtcgc gcccacggtg agcctgccca cacttgggga tcgcatcgag ggcgatgact  33120
tctatgcggc cttcgcatcg caggggatgc attacggcga caccttccgc ggcatcgcgg  33180
aagtgtggcg gcgcgacggc gaggcagtgg cgcgactgag cgtgccggat gccgttcgcg  33240
aagcagagtc cggttacacg cttcatcctg ccttgctcga tgcctgtttg caggtgctgg  33300
gcgcgacgct tggcggcgaa ggcagcgccg gtccttgcgt gcctgtcgcc atcgaacggt  33360
tgcactgttt cggcagaccc gccggcgatc ttagggtgca tgcgcggctg acggggcggc  33420
tcgagggcga tgtcaccctg tgtgatgcgg aaggccacgt catcctcgag gtccaaggcc  33480
tgcgtgccca ggaactggag cgccaatccg aatggttcca cgctatggaa tgggagccgc  33540
agctgctggc cgagagtcca acggcaacgg tgtcgggtgc atggctggtc attgccgatg  33600
ccggcggcat cgcagccgcg gtggcgcgag ggctgggcac aaacacggtt gtgatttcgg  33660
gtcgcgatgc cgagataccg gatcagcctt accggggcgt cattcactgc gggagcctgg  33720
atgagaccga ggatgagacc gatccgtcgg ctgcgggggg aaccgcctgc gaagacattt  33780
tgcgcatcgt tcaagaattc ggagtgggac gcatacagct gacgaaacaa gcgtccgacg  33840
```

-continued

```
ccgaatcgca gcatccgcga atctggctga ttacggcggg cgttcatgcg gagcatctgc  33900

agatgccggt ggtgcccgcg cgggcaccgg tgtggggtct gggacgtacc atcgcggccg  33960

agcatcccga gttcgcttgc acctgcatcg atctcgacac tgccggtgaa gtcgaggtgc  34020

aggcgctctg ccgagagatt ctcgcgggga gttctgaacg tcagggcccg g           34071
```

<210> SEQ ID NO 115
<211> LENGTH: 4615
<212> TYPE: DNA
<213> ORGANISM: Unknown organism
<220> FEATURE:
<223> OTHER INFORMATION: Origin of the sequence: Undetermined bacterium

<400> SEQUENCE: 115

```
actgcagtgc ccggaatcgg cggtggactt acagcagccg ctggtgcgta tgggattgga    60

ctcgctcatg gcggtgcaat tacgcaaccg gatcgatacg gatctgcgcg tcttgctgcc   120

catggtccga tttctagacg gccccagcgt tgcggaactg gccagggatc taagcgatct   180

aagcggcctc agcgaacgca cgacggtggc gccggaacct gcggcgcagg cctcggttcc   240

tgccctctcc taccctctca gcgccggcca gcaggcgctt tggtttattt accgaagcgc   300

gccggaaagt cccgcataca acatcgcgtg gatcgcgcgc gcgagaggcg ctttcgatcc   360

gcaggcgttg cgccgttcgc tgcaggacct ggtggatcgt catccggcgc tgcgaacgac   420

gattgcggag agtggcggcg cacccgttca aacggtccac agcagcgtcc cggtggattt   480

cgaagtgatc ccgtgttcgc cggacgatga ggcggtgctg atcgacggcg tcttccacgc   540

gcccttcaat ctcggcgaaa actgtttccg ctcgcgtctc ctggtgcagt cggggaagga   600

tcaggttctg gccatcgtgg tgcatcacat cctcgccgac ttctggtcac tgctggtgat   660

ggtggatgaa ctccgcagta tctacctcgc gaggacagct ggcggtccgc ctgtcgcgcc   720

gccggtcgcg agcttcgccg ctttcgtccg ctggcagaac gaactgttgg ccggaaccga   780

gggcgagcgg ctttggaact actggtcctc gcagctttcc ggccagcttc cggttctgaa   840

tctcccgtcg gatcgtccca gtccgccggt gcagagtttc cggggaaact ctcactcgtt   900

ccgaatcgaa cccgcgctga ctgcgaaact gaaggcgctc gcgcggcggc agaacgcgac   960

gctgcatgcg acgctgatgg cggcgtttca agtgcttctc tcccgttgga cctcacaaga  1020

agagatcctg accggcaccc tcaccaacgg tcggacgcaa ccggaattcg ccgatctcgt  1080

cggatacttc gtgaatcccg taatcctgcg aggagaactt tcaggcgatc cggatttcaa  1140

tacggtgctc gcccggattc ggcaaacgct tctcggcgcg atcgagcacc aggagtaccc  1200

gtatgcccgg atcgtggagc ggttgggtcc cggactgcgg gttctattcg tgctccagca  1260

gcctcatcgc attcccgaat ccgtgccgtt catgttgggt cagtccggcg gtcgcatggc  1320

ctggggcagc ctcacactgg agtccctggc gatgccgctg cgacagagcc ggtttgacct  1380

ggatctgatg atggtcgaaa ccgatggagg cctctccgcc tttctgcaat acaacacgga  1440

catttttgat gctgccacga ttgaacgtct ctccttgcac ttcgccgtgc tgctggaagg  1500

aatcgcggag aatcccgcct gtccagttgt cgatctaccg ctgctgacaa cccgggaacg  1560

catccagctg ctcgaagagt ggaatgcgac cgccgcggaa ttcccgtccc aatgcgtgca  1620

cgagctgttc gaagctcagg tggagttgac gcccgacgcc atcgcgttga gcttcggtga  1680

gcagaatctg acatatcgcg aactcaacgg gagcgccaac cggatcgcgc actatctccg  1740

ctcgcgcggc gctggacccg gcgaaatggt tggcatccat gtcacgcggt cgctcgaaac  1800

cgtcgcaggg ctgttgggcg tcctgaaggc cggcgcggcc tacgttccgc tggaaccgga  1860
```

-continued

```
atatccggcg caacgtcttc ggctgatgct ggaagagacc aggccggtcg ttgtgctgaa   1920
tgtcacggaa tcggaagtat ggacgcagcc cgacaccaat ccgaacccgc tcgcgactcc   1980
cgccgatctc gcctatgtcc tgtacacctc cggttcgacc ggccggccga aaggcgtgca   2040
aatcacacac caggccgtcg tcaattttct ttcgtcgatg cggcatgagc cgggcatcag   2100
cgaccgcgat acgctgctcg ccctcacgac gttcatgttc gacatttccg cgctcgagat   2160
ctttttgccc ttgagcgccg gcgcgcgcgt cgtggtggcg aaccaggaga cggccgtcga   2220
tggtgagagg ctggcgaggg aactcgcgcg cagcaaagcg acaatgatgc aggcaactcc   2280
cgccacctgg cgtctgctgc tcgcatccgg ctggcccggc gaccgccgcc tgacggcgct   2340
ctgcggcggt gaagcccttc ctcgcgatct tgccgaccgg ctcctgcaac gaaccgcggc   2400
gctatggaat ctttacggac ctaccgaaac gacaatttgg tccgccatcc aacgggtgac   2460
gacaggtgac ggaccggttt cgattggccg ccccatcgca aacactcagc tctatgtgct   2520
tgacgatcgg atgcagcccg cacccatcgg tgttgcgggc gaactgtaca tcggcggcgc   2580
cgggctcgcc cgtggatacc tgaatcgtcc ggaactcagc gcggacaagt tcgtcgccaa   2640
ttcgttcgac cctcatggca ctcggctgta tcgcacggga gatctcgccc gccgccaacg   2700
cgacggcgcg ctcgagtatc tcggccggat cgaccaccag gtgaagatac gcgggttccg   2760
catcgaaacc ggcgagatcg aggccgcggt ccgcagtcac ccggcggtcc gacatgctgt   2820
ggtcaccgcc agagaaaatg acgcggccgg taagtatctg gcggcctaca ttgtccccct   2880
tgctgacggg catcgcgcga cggcagccgc cgacacattc cacgaccgag tcgagtccga   2940
gcacgtgacg cagtggcaat ccgtctggga caccacatat gaacagaatg cgccgaacgc   3000
ggatccggag ttcaacatcg tcggctggag aagcagtgtt accggagagc cgattccagc   3060
tgccgagatg cgggagtggg tgcaggattc cgtcgatcgc atcctggcct cgcggccgcg   3120
tcgcgtgctc gagattggct gtggtacggg actgctgctc ttccgcgtcg ctccccactg   3180
ttcggagtac tgggccacgg acttttcgca gaaggcgctg gactacatcg ccgctcacgc   3240
ggaccgcacc ggcctggcaa atgtccgcac gttccggcag gcggccgacg acgcgtgcga   3300
gatcgacagt cgctcgtgcg atgcggttgt tctgaactcc gttatccagt acttccccgg   3360
cgaagcgtat ctgcggcgcg tgctggccga ggcggtgcgt gtggtcaaac cgggcggcat   3420
cgtatttgtc ggcgatgtcc gcagtctccc gctgctggag acgttttacg cttctttaga   3480
agttcagcgc gcacccgcgt cgttgacccg gaatgagttt cggcaacgcg tgcgttcgct   3540
cgcgtcgcag gaagaggaac tcgtggtcga tcccgcgttc ttctttgctc tccgcgaaca   3600
gattccggag atcggccgga ttgaaatcct gccgcgtcgc ggccggtcgc ataacgagct   3660
gacccgcttc cgctaccagg cgatcctgca tatcggatcg cgggaagcgg aggagccgga   3720
atcggatcgc aggcgttgcc agaccgcggc cgaaatacgc agagtactga cggacgctca   3780
gccggagttg gccgcattta ccgagattcc gaacgcacgg ttgaccgccg aaagcgccat   3840
tgtgacctgg atgaacggtg acgaagctcc agagacactc ggggagttgc gggaccggct   3900
gcgccagacg tcgccttccg gcgtcgatcc cgccgatcta tggcgtatgg acgaagacct   3960
gccgtaccgc gtggcaatcg actggagcag tcatgggcca cacggacgct tcgacgcgac   4020
cttctgccgt gcggcggccg gtccgccggc ttcccgtccg cgacgccgcc tggccggccc   4080
gtatacgaac gatccgctgc gagccgtcta tacgcgcacg gttgtgccgc agttgcgtac   4140
tcatctgaag gagaagctgc ccgactacat gatcccgacc gcgtgggtcg tgctccacga   4200
```

-continued

```
aatgccgctg acgcccaacg gaaaaatcga ccgtaacgcc ctgcccgatc ccgagcccag   4260
ccggcgagcc cacgccgaag cattcacgcc tccggaaact ccggtggaac aggtactcgc   4320
ccacatttgg ggcgaggtgc tcggcatgga tggcatcggc gtccatgatc acttcttcga   4380
ctctggagga cattcgctgc tggtcacgca gatgatcgcc cgcgtgcgcg acatgctcca   4440
cgtggaagtg ccctttcgaa ccgtgtttaa cgccccccacg gttcgaggct tcgccgtcgc   4500
tattcaggac ggcgtagacc caggatgggc aaggcgagcc gccgatttgc tgatcgctgt   4560
ttcccaaatg tcagatgttc aaatcgagcg tatgatgagc gccgcccaag actag        4615
```

<210> SEQ ID NO 116
<211> LENGTH: 8301
<212> TYPE: DNA
<213> ORGANISM: Unknown organism
<220> FEATURE:
<223> OTHER INFORMATION: Origin of the sequence: Undetermined bacterium

<400> SEQUENCE: 116

```
atgcagaatt cgtcgccaaa taccatagac ctctcgctcg cccgccgcca attgctcgac     60
cgtctgctgc aggaaaacag ccccgaacat cgcatcccgc ggcgtgaaaa ccgggatgcc    120
gcacccttgt cgctggccca gcagcggctt tggtttctcc atcagctcga cccggattct    180
cccgcctaca acattcccat agcgctgcat atccgaggtc cgctggatat tcgcgtcctc    240
ctgcggagtc tggaggccgt ggtgcagcgg cacgagagcc tgcgcagctg cattggcggt    300
gtggatggag aggcgcgcca gagcctcctg gcgcgagtga cactggaact tccggttgtt    360
caggctgacg gaatcgcaga agcgcggcaa atggccttgc gtgatgccca gatcccgttc    420
gacctgcgaa aacccccgct tctgcggacc aagctgatct gcctcgatga caagcagcag    480
attctcctgc tgacgttgag ccacatcatc gcggatgcgt ggtcggtcga gacgttcgtc    540
cgcgacctga cgcgatcgta cgaagcgttc gtgcaggggc ggccatcgcc gctcatggaa    600
ctgccgattc agtatggcga ctgggccgtc catcagcaga cgtcgctgaa ccaaaccgcg    660
cagcagtact ggaagaaaca gctgtcgggc accttgcctt tcctcgacct tcctaccgat    720
cgcccccggc ccgcgcagca gacctggcgg ggcgccgtgg agaccacagc cctcggccgt    780
gatttgaccg atggactcca cgcgtttgcc ttgcgtgaag gagcgacggt gttcatgacg    840
gcaatcgcgg cgtttcaggt gctgctgcat cgctataccg cgcaggaaga catccttatc    900
ggggttccag tcgcgggccg tacacaacga gaaacggaag gtctcgtcgg ttgtttcgcc    960
aacatgatcg tcctgcgcgg cgatctgcgc gacgatccgt cgtttcgcag tcttctcgcc   1020
cgcacccgcg acaccgcttt gagcgccctc tctcatcagg actttccttt cgaacgcctg   1080
gttgaggaac tgcatcctcc gcgggacctg agccggtcgc ctgtatttca ggtctccttc   1140
gcgctgctgc ccgatgcgcc ggccatcacc gtcatgcctg ggctcaccat ctcgcgcgag   1200
tacatgcaca acggcggatc caaactcgac ctcggcgtga ccctcgagcc atccggcgat   1260
ggactgatgg cgtccgccga atacaacacc gatttgttcg atgcggcaac catcgcctcc   1320
ctgctcgatg cgtaccgaac cctgctggcg agcgtggtga cggatcccga cgtccgcatt   1380
tcaaccgctg cgctgttgtc ccccgcggtc cgaagccgga tgctcgagca gcacaatgcg   1440
acacggcgcg atgccggtcc gaacgggtgt gcgcatgaac tggtcgaagc tcaggcggaa   1500
cgcactccgc acgccgtcgc cgttgtcttc gaagaccatc agttgaccta cgccgagctg   1560
aatgcgcggg ccaaccgcct ggctcatcgt ctgagcgcat ccggcgcggg cccgggaaag   1620
atcatcgctc tggcgatgga gcgctcgctg gagatggtga ttgcgctgct tgcgattctg   1680
```

-continued

```
aagtccggca gcgcgtacct gcctctcgat cccgcgcacc ccaaggatcg tctcgcccgg   1740
attctcgatg aagtgcaacc gcacgcggtc ctcacgcagg aggcggtggc tgagatgatg   1800
gcgatgatgg cgatgatggc ggtcgccgtc gaaccagaag ctgcgaatct cgtcagcggc   1860
agcaagcccg acgatctcgc ctacatcata tatacctccg gatcgacggg gcgaccgaag   1920
ggcgtggaga tccgccactc gtcgctagtc aatctgctgc gctccatgca gcgcgagccg   1980
ggtctgacag ccgccgatgg gctggtcgcc gtcaccaccg tgtcattcga tattgccgga   2040
ctggagatct ggctgccgtt gatcaccggc gcccgcgtca tcgtcgccac ccgcgagatc   2100
gtggttgacg gcgagcggct caccaccctg ctggataagt cgggcgctac ggtcatgcag   2160
gcgaccccga gcggttggcg gcaattgctg gattcgggct ggaagccggg taaaggcttc   2220
cgtgttttct gcggcggtga agctctgccg ccggaactgg cgcgccgcat tctcgatagt   2280
ggcgtagagc tgtggaatct ttacggaccg acggagacca ccatatggtc ggccgtgcac   2340
aagacacaaa gactgggtgc ctccgatagc atcgtgccga tcggccatcc catcgacaac   2400
acgcagttat acatcctgga ttcgcgcatg gagccggttc cccccggagt tccgggagag   2460
ctgtacatcg gaggagcggg actggcgcgg ggctatcatc gcaaccccga gctcacgcgt   2520
gagaaattcc gcgagtggcg tgatcgagga cgcatttact ctaccggcga tctggctcgc   2580
taccgttccg acggcgcagt cgagtgcctg ggacgagtcg atcgccagat caagctgcgc   2640
gggtttcgca tcgaaccggc cgagattgag gccgcgatcg agacgcacat tgccgtgaag   2700
caggcgatta cggtcgtgaa ggacgatcgg ctgatcgcct atctcgttcc ggcaacgggc   2760
gacgtgcgcg atctgcagag cgatttgcgg tcgtggctgg caacgcgcct tcccgattac   2820
atgatcccct cggcgtttgt cagcctgtcc tcccttccgc tgacgcccaa cggcaaaatc   2880
gacgcgaacg cgcttcccgg tttgcccaca acgccggttg ctgctcgcga gccgatgcgc   2940
ggcgatgtgg tggagacgat tgcgtccatc tggcgtgaag ttctgcgcgt ggagcacgtc   3000
gactatcggc agaacttctt tgatgtcggc gggcactcgc taatgctcac acgggtgcgc   3060
ggactgctcg aggagcgcct ggggttgacg ctctccgtcg tcgatctgtt ccggcatacg   3120
acgatcgagt cgcttgccgg cctggcagaa aaatccgaac ccgccgctgc ggaacctgcg   3180
gctgcggtcg cagaagatcg gatcgcagtt atcgggatgg ccggccggtt cccgggggcg   3240
cgcaatgtgg aggagttctg gcgcaatctg cgcgacggtg tggattccat cgccaggctt   3300
tcgccggaag atctgctggc gggcggcatc agcccggagg tcttccagga cccgagctac   3360
gtgccggcca agggtctgct ggacggcatc gagtttttcg atgccgcgtt cttcggctac   3420
agtccgcgcg aagcggagat catggacccg cagcatcgcg tgtttctcga gtgcgcgtgg   3480
gaagcgatgg agaacgcggg atatgcggcg cgaagctata agggttcgat cggcgttttc   3540
gcgggatgcg gcgtcaatac ctacctgctg aacaacctcg ccaccgcgga gccgttcgat   3600
ttctcacgcc cctccgcgta ccagctgctg acggccaacg acaaggattt cctggccacg   3660
cgtgtctctt acaagctgaa cctccgcggg cccagcctga cggttcagac ggcgtgctcc   3720
acctcgctgg tgtcggtggt gatggcatgc gagagcttgc agcgcggcgc ctcggacatt   3780
gccttggccg gggagttgc catcaatgtt ccgcagtccg tggggtacct gcaccagccg   3840
ggcatgatcc tgtcgcccga cgggcgctgc cgcgccttcg atgagtccgc tcaaggcacg   3900
gtgccgggca acggcgcggg tgtggtcgtc ctcaagcgct tgagccgcgc tctggccgat   3960
ggcgacacga tctacgccgt cattcgcgga gcggctatta ataatgatgg cgccgagcgc   4020
```

-continued

```
atggggttta ccgctccagg tgtggacggt cagacgcgat tgattcggcg cactcaagag   4080
atggcgggcg tgaagccgga gtccatcggc tacatcgagg cccacggaac agccacgccg   4140
ctcggcgatc cggtggagat cgccgccatc gctgccaact ttccgaaaaa cggaagcggc   4200
gatgtgtata tcggatccgt caagaccaac atcggtcatc tagacgtcgc ggccggtgtg   4260
gccgggctga tcaagacggt gcttgccgtc catcgcggcc agattcctcc cagcctgaat   4320
ttccagcgtc cgaatccgcg aattgatttc gcaaacactc cgtttcgtgt gagtacgcgg   4380
ctgctcgact ggcccgccgg aaagaccccg agacgagcgg cagtcagttc gttcgggatc   4440
ggcggcacca acgctcacgt gattctggag caagcgccgc cggtgacgcc ggccgcagct   4500
gcgcccgaac gatccgcaca tgtgctttgc ctgtccgcca atacagacgc ggccctcgaa   4560
gaactggtgc gctcgtatcg cggccatatg gacaaccagc ccggtttgtc gttcggcgat   4620
gtcgcattca cggccaatgc agggcgcgtg cacttcccgc accgtatctg cattgtggcc   4680
cggtcgagcg acgaggctcg ccaacgactg acggaggcac gacgggttcg catcgcccag   4740
acgcgcccca agattgcgtt tcttttcacc gggcaaggtg cgcaatacgc gggcatgggc   4800
cgccagttct acgagtcgca gccggtgttt cgcgccgcca tggatgaatg cgcagctctg   4860
ctgaatggac ggctcgatct gccggcgctg ttggccgatg acgcgttgct cgacgcgacc   4920
gccggcgcgc agcccgcgct gtttgctttg cagtgggcct tggcgcagtt gtggaagtcc   4980
tggggtgtga cgcccgacct ggtgatggga cacagcgtcg gcgaatacgc ggcggcgtgt   5040
attgccggcg ccgtcagcct gccggatgcg ctcggcttag ttgccgaacg cggccggctc   5100
atgcagaacc tgccggaagg tgcgatggct gcggtcagcg ccggcgagca gcgctgtgcc   5160
gcagcgatca cctcgcgcgt ctccattgcg gccatcaacg gacccgctga ggtcgtgatt   5220
tcgggtgcgc cgcaggatat tgagagcgcg ctggcaactc tacgtgcgga gggcatcaaa   5280
acgcagatgc tggccgttgc gcgcgccttt cacagctcga gcatggatcc gattctggcg   5340
gacctgcaac gccgggcggc ggcgatcgcg tggcgcaatc cttcgatcgg cttggtttcg   5400
aacctcacgg gcaaactggc cggcgaggga cagctggcga atccgctgta ctggcgagat   5460
cacgctcgaa accctgtccg tttcgccgac ggtatccaaa cgctcaagga cgaaggctgc   5520
gacgtgtttc tcgagatcgg tcctaagccg gttctactcg gcatgggcca aaagtgcctg   5580
cccgacgacg ccaagcagtg gctgccgtcg ctgcgtaaag gccgcgatga gtgggagacg   5640
attctcagca gtgtggcgac gctatatcag ggtgggttcg acatcgattg gcaggagttc   5700
gaccgtccgt attcgcgaag gcgtgtcgcc ctgccggcct atcctttcga gagacgccgc   5760
cattggatcg agcggagttc cagaccggaa cctgtagcgg ttgcgagtgg tctcgtcggg   5820
tgccggctgt cgctaccggt ggcagacgtt atcttcgagt cgaaactatc gacggcttcg   5880
cctctactct cagaccaccg atattacggt tcggtggtgg ccccggccgt gtacttcctg   5940
gccatggcgc tcgaggcgtc ggcggaggtg tttggcgccg gccggcacac gctggaaaac   6000
gtgaacttcg cgcaccctct gatcctttca gcggagcgcg acacggctgt tcagctcgtg   6060
ctttcacaga gcgatgaccg gcatgcctcg ttccgcatac tcagcttgtc cgacggctcg   6120
tggaacttac atgctgccgg caatattgcc gcccacgctg gtgtcgctcc cgtgccccga   6180
ctggtcgatg aacgccggcc tgcggtggat ggagacacgt actattcgct gctgcgccac   6240
ctcgagatag aactggggcc gagctaccgc cgcatacagc gcattcattt cggtgaacag   6300
gaagcgctgg ccgcgattga ttccgcaacg ccgctcaatc cccgttgtga attggcggaa   6360
gccggcctgc aattgcttag cgccgcggcg agtcccgcgc ttgcggatgg cgccgaacat   6420
```

-continued

```
ccgatattcg ctccgctcgg tatcgatcgc gtttgttttt acggcagcct ggagggcgcc   6480
gtatgggggg ccgcgcaaat tctccggcat tcgccggacg gctttaccgg cgaggcgcag   6540
ttgctggact cggagggctg cgttctcggg gaacttcagg gcgtgagttt ccggcgcgtc   6600
actcgcgcat gggcgcagcg ctcggaacgg aagcccgaat tgtatgaggt cgagtggcgg   6660
cccgaaccgc tccgccagcc ttcgcgaacg ctacagcctg ggcatggct gatcctggcc   6720
gacagtggcg gcgcggcccg cgctctggca gatgcgctca cagctcaggg cgagatgtgc   6780
gttaccgtgc cgccagccgg cgagtacatg tccctagtcg gtgagcgtga ctggcgcggg   6840
atcgtcaacc tgtacagtct cgatgattat gagctcggct gccgcagcac tctggccctg   6900
gtgaagtccc tgaagtccgg tccgcggcta tggctggtaa cggccggcgc gcaggcgacc   6960
agtgcggtgc acaatcccat gcaggccgcg ctctggggct tcggccgggt gatcgcgcgc   7020
gagcacccgg atctgtgggg cgggctcatc gatctggatc ccgacgatgc gcatgcttcg   7080
gcggccggcg cggccgcgca gatgcgtgat ttcgacggcg aagatcagtc ggcgtggaga   7140
agcaaccggc gctacgtgcc gcgactgacc cgccgaccca gcgcgcgagc ggcagtccgt   7200
ctggtttcgg gcgcgactta tttgatcacc ggcgggctcg gagccctggg acttacagtc   7260
gcgaaatgga tggtggagca cggcgccact cgcgtcgtgc tggccgggcg ccggcctcca   7320
aacgaggagc agcagcgcgt gctgcaacag attggtgcga cggcagagac ggtcgacgtc   7380
agccgggaag aagaggtcgc ggatctcatt cgccgcatcc acaccgaaac gtcaccgctg   7440
cgcggcgtta tccatgccgc gggtgtgctg gacgacggcg tactgctgaa tcaggactgg   7500
acgcggatcg caagcgtcat ggcgccgaag gcggaaggcg ctgtacacct ccatcatcac   7560
acccgcgatc tgccgctcga cttcttcgtg ctcttttcat cggcatcctc gctcttaggt   7620
cctgccgggc aggcaggcta cgccgcggcc aacgccgttc tcgatgcgct ggcgcatcac   7680
cggcgcggac tgggtttgcc ggcgaccagc attaactggg ggcgctggtc gggagccgga   7740
atggccgcgc gcaccagcca gtcgatggcc ggcgtggcga gcctctccgt ggacgagggt   7800
ctacacattc tcgaggccgt cctgcatgaa tgccccattc agattgccgc gctaccggcg   7860
ggctcgatta ccggcgagtt gctgcgtccc gccgcgctgc cttcacctca actgcgcacc   7920
cgcttgaacg aagccacacc ccggcagcgc gaagccatcc tcattgcgca catcagggag   7980
tcactggcgc gctttgtcgg catcgcgact tccacaccgc tcgatccaca gcagcctttg   8040
ggtgaactgg gactcgattc gctaatggcc atagaacttc gcaactcgct ctcccaatca   8100
ctggggcagc ctttgcccgc gagtctgctg ttcgactatc cgtcgctcga tgcgatcgtc   8160
agttacgtgc tccatgcggt atttccaccc gaagcatcac cggtggaagc gccggagttt   8220
gagaacctcg cccgcgaaga actggaagcg ctgctcgatt cgcggctggc gcaggtcgac   8280
cagtggttgg agacgcaata a                                             8301
```

<210> SEQ ID NO 117
<211> LENGTH: 5292
<212> TYPE: DNA
<213> ORGANISM: Unknown organism
<220> FEATURE:
<223> OTHER INFORMATION: Origin of the sequence: Undetermined bacterium

<400> SEQUENCE: 117

```
atgagcgggt cagacgatct cagcaagctt cgccgcgccg tgattgcgct cgacaaggtg     60
cagaaacgca tcgaccagct ggagagcgcg cgcagcgagc ccatcgccct catcggcgcg    120
```

-continued ggctgccgct tccccggcgc atccaatctc gatgcctatt ggtcgttgct gcgcgagggc 180
cgcagcgcgg tacgtgaagt tccacccgac cgctgggaca tcgatgccta ctacgatccg 240
gatcccggcg cgacgggccg aatgtacacg cggtacggcg gcttcatcga tcaggttgac 300
cgttttgacg cccggttctt cggcatcgct ccgcgcgagg cgatcagcct ggatccacag 360
cagcggctgc ttctggaagt cacctgggag gcgatcgaga acgccgggct tccacccgac 420
cggctggcgg ggagccggac cggcgtcttc atggggatct tttccaacga ttattacaac 480
ctgcaaatgc gcggcgggga tgcgcatatc gacgcgtaca ccggcacggg caatacggcc 540
agcgttgccg ccgggcgtct ctcgtacatc ctcgggctgc agggcccgaa catggcgatc 600
gacacggcat gctcgtcatc gctggtcgcg gtgcaccttg cctgtcagag cctgcgctca 660
ggtgaaagcg acctcgcgct ggcgggcggc gtcaatctga ttctctcgcc ggatcggacg 720
atctacttct gcaagctgaa ggcgatggca gccgacggtc gctgtaaggc attcgatgcc 780
gcagcagacg gctacgtccg cggtgagggc tgcggtgtgg ttgtgctgaa gcgactctcc 840
gacgcgctgc gcgatcgcga tccggtgatg gcggtgattc gcggcacggc aatcaaccag 900
gacggacgca gcaatggact gacggcgccg aacgggcccg cacaggaagc cgtgatccgc 960
caggctgtgg gagacgcgcg cttgcagacg ctggatgtga gctatgtcga ggcgcacgga 1020
accggcacgc cgctgggcga tcccatcgaa gccggagccc ttgcggccgc gctgggagcg 1080
gggcgcacca acggcaacaa gctgaagctc gggtcggtga agaccaactt cggccacctc 1140
gaggcggcag cgggcgtggc cgcactgatc aaggtggcgc tgatgctgca gaacgaagcc 1200
attccgcccc atctgaatct gaccacgccc agcccgcaca tcgattggaa cacgcttccc 1260
ctcgaaatcc cggcacggct cacccccctgg ccggttgcac ccggcgggcg gcgcgtcgcc 1320
ggcatcaact cgttcggctt gagcggtacg aatgcgcacg tgctcatcga gcaggcgccg 1380
caacaggccg cgtccagtac gcccgcaccg tacctgcttc cgctatcggc gcgcagtccg 1440
gaggcgctgc gtgatctggc gcgcgcatac cgcgacgtgg tgaacgacaa ccccgccgac 1500
acctgctaca cggcgtgcgc tcgccgcact tcatacgaac accgcgcggc attcaccggg 1560
acgaacgcgc aggacttgat ggccgggctg gacagttttc tggcgggcaa cccgaaccgc 1620
gataccgcca caggttttgt gccgcgcggc cagaagcgaa aagtcgtttt cgttttgccg 1680
ggacaaggat cgcagtggcc cggcatgggc cgcgacctga tggcttctga accggtgttc 1740
cgtgccgcca tcgaagagtg cggccgcgcc atgcagcctt acgtcgactg gtcgctgacg 1800
caagagttgc aggggccgct cgaccgcatc gacgtgattc aaccggccct gttcgcagtc 1860
ggggtcgcct tggccggact gtggcgccat tggggaatcg agccggacgc cgtgatcggc 1920
cacagcatgg gcgaagtcgc ggcagcgcac attgcaggtg cgctgactct cgatgaagcc 1980
gctcgggtga tttgcctgcg cagccggatg ctcgccggag tacgcggcca gggagaaatg 2040
gctgtcgtgg aattagcgct ggacgaggcc atcgctgcca tcgccgggcg ctcggatcgg 2100
gtctcgattg ccgccagcaa cagcccgcgc agcaccgtcc tgtcgggcga cagcgcagct 2160
ctgggcgaac tgctgcggga actggaggcg aaagacgtct tctgccgtcg cgtgaaagtg 2220
gacattgcct cgcacagcca tctgatggac tccgtgtgcg cggcgttgcc gggcgtggtg 2280
ggagcgcttc agccgcggcc ggccgccctt ggcatgtact ccaccgtcac cggcgcagcg 2340
attagcggtg aagagctggt ttctgcgtac tgggctcgta atcttcgcca acccgtgatg 2400
ctgtcgacgg ccgtcgccgc agccgcggcg ggtggtcatg atgtgtttct ggaactgagt 2460
ccccacccgt tgttggtcca gccgatccag gaaacgctcg gagatcgggc agcgattgcc 2520

-continued gctgcctcgt tgcggcgcga tgaagacgga aacctcgcac tgcgccggac gctgggagcg 2580
ctgctgacta acggagtcac tccggactgg tctcgtattt atcccaacgg cggccaaact 2640
cgccggctgc ccaactatcc ctggcagcgt gagcgttatt ggatcgatat ccgtccgccg 2700
caggtcgagt ctcaggcttt gcctggccgg cggatcccgt cgccgctgcc ggagatgcag 2760
ttcgagtcca ctgtggaggc gaaagatttc gcggatcacc ggctgcacga tgtgatcgtg 2820
actccgggag cgtggcacct ggcaatggcg ctcgccgctg cgcgccaagg tctcggcgcc 2880
gggcctcacc atgtcgaaca cgtgtcattg acgggcgcgc tgacgctgcc ggaaaacgat 2940
gctgccaggc aggttcaact ggtactccgt catgaagagg gcggcggagc ttccttccgc 3000
atctacagcc gcgaggattc ctggaagctg cacagcgaag gcatgctgca ggcgggcgat 3060
tccacggcat ccatcgatct ggatgcgatt cgcgcccgct gcacggcgga gctcacagcc 3120
gatgccttct attcgcgact gtgggatcgc ggctatcact tcggtcccac cttccgaacc 3180
atcggcccca tctggcgcgg caacggtgag gtgctttgtc gcgtggacat tccgctgacg 3240
gaaatgcaga cgatcgactg ctgtctgcag ttgcccgcgg ccctcgtcca tcacgacgat 3300
ttgaaagatg tgcatgtgcc ggtaggtctg gaccgattct cgctcgctga agtgcccact 3360
ggcccggtct ggggatacgc ggtcttgcgg ccggattcca cggtggatgt ccgtctcgtc 3420
accggcaccg gcagcgtggt ggcggaattg gtggggctgc agtcgagagt cgcccatagc 3480
ggccagctcg gcgaatcgga gattcccacc tggacggtgc aatggaccgc gtcggttcgc 3540
cgcggcgatg ccaatgccgg caatgctggc ggaccttggc tcgtcatcgg cgagccggcg 3600
attgccgaga ctctgcaaaa gcgcggccaa acctgccgca cggccgatac gtgctcgggt 3660
ccgccgtgcc gtcaaattgt gtactgtccc tcgccgcgca tcgacgacct gctttccgta 3720
ttgcgcagca tcgtgcaagc gggctggcct gagccgccgc gcctgtggct gctgacgcgc 3780
ggatctgccg cggttctcaa ctccgacaaa gatattgata ttcgacaagc ctggctgcac 3840
ggaattgggc ggacgattgc ctatgagcat cccgagctgc gctgcacgct cgtcgatctc 3900
gatgcgcaca gcaacgactg cgggcatctc gcgacgctga tgctgtcgaa tatcgcagag 3960
gatcaagttg cgatccggca aggcacggta tgggcgccgc gcctcagtct tcacaagatc 4020
ccatccgcac ccgatgtggc gttccgtgcc gacgcaacct atctgatcac gggcgggctc 4080
ggcggactcg gactgcaggt ggcgggatgg ctcgccgccg ccggagcgcg ccatctcgtt 4140
ctgctgggac gcagcgagcg tcctcggcca caactggaag gtgtcaacgt caagatcatc 4200
catgcggacg tggcggaccg gcagcagcta tcggatgcgc tcgcgatcat cgatcgcgac 4260
atgccgccgt tgcggggcgt gttccatctg gcaggcacgc tggccgacgg catgctgctc 4320
aatctcacga ccgaacgctt cgaagccgcc atggctccga aagtagccgg cgcgtggaac 4380
ctgcacgaac tcaccgccgg ccggccgctg gatcattttg ttctcttctc ttccgccagc 4440
gcgacagtgg gatctcccgg ccagggcaac tacgccgccg gcaattcatt tctcgacgcg 4500
ctggctcatc tgcgccgcgc ccagggtctt cccgccgtca gcatcgcgtg gggaccgtgg 4560
acacaggttg gtttggccgc acaggcgaac cgcggagacc gtctggccgc gcgcggcatc 4620
tcggttattc aaccgcaaca gggattgcgc gcgctctaca aagcattgac gcagattcgg 4680
ccgcacgtcg ctgtcatgaa cttcgatatc gcgcagtggc tccgttacta tccgtcggcc 4740
gcatcgatgt ccctgctggc cggcatcgca cccgcggccg cggacaccaa accggcggcc 4800
gacatgcgca gcgagctcct ggcagttcca gccgggcggc agcgccgcgc gcggctggaa 4860

-continued

```
acgctgctga tgcacgaagc cggacacgtg ctgcgcttcg atccagcgaa actcgacggc   4920

agagcgacgc tgggtgatct cggattcgat tcgttgatgg ccctcgagtt tcgcaaccgt   4980

ctggaagccg ggctgcgcgt caagctttct gccaccctga tctggcgtta cccgacattc   5040

tccgccctgg cgcagcatct cgccgacaag ctcggcctgc cgctggaaag catggccggc   5100

aatgctgaac cttcgaccgt tgctgccgtt gctacccttg ctaccgttgg caccgccgcg   5160

ggcgaggacc ggagtcccgc cgctgcagac gatctcgacg ccgtcgcaaa ccagatcgcc   5220

gggttggggg acaaagaaat cgaagctttg ttgaaacaga agttcgctca tttttcagga   5280

gcctccgagt ga                                                        5292
```

<210> SEQ ID NO 118
<211> LENGTH: 6462
<212> TYPE: DNA
<213> ORGANISM: Unknown organism
<220> FEATURE:
<223> OTHER INFORMATION: Origin of the sequence: Undetermined bacterium

<400> SEQUENCE: 118

```
gtgagttcga tatccgagcg attccccaac cttacgccgt tgcagcaggc gtacctgacg     60

ctggagcaca tgcagcgacg tctcgatgcg gccgaacgcg acgcgcgcga acccatcgcg    120

atcgtgggtc tgggctgccg gtttccgggc ggcgatgggc ccgatgagtt ctggcagatg    180

ttgcgcagtg gagtcgatgc tattcgtgag gtaccgcctg gacgatggga cgaggagtcg    240

gtccggcgca tcctgaaatc gttgaacccc gccacgccgg tgaagattca agccggattt    300

ctcgattcca tcgatggttt cgacaacgat tttttcggca tttcgccacg cgaggccgtc    360

agcattgatc cgcagcagcg gctgctgttg gaagtggcgt gggaggcact ggaggatgcg    420

gggcagacga tggaagggct ctccggcagc cgcacgggcg tcttcgtcgg gatccacagc    480

caaagcagcg actatttctg gatgcagacc gccgatggcg cgcgcatcga tccgtatacc    540

gccaccggca cggcgcatag cgtgatcgcc ggccgacttt cctatttgct gaacttgcaa    600

ggacccagca tcgcgctcga cacggcctgc tcgtcttcgc tggcggcggt tcatctggcg    660

tgccagagcc tgcgcagcgg cgagtgtacg ctggccgtgg ccggcggagt gaatctgcgc    720

ttctcgccgg agtttatgta cgccacctcg aagatgggaa ccgcctcgcc cagcggtcgc    780

tgccgcgcct tcgacgcggc ggcggacggc atcgtgttcg gagaaggctg cggcgtggtg    840

gtgctgaagc gcctgtccga tgcactcgcg gccggagacc gggtgtgggc cgtggtgcgc    900

ggctccgcgg tcaatcagga tggccgctcg gccgggctca ccgctcccaa tgtcgtgtct    960

cagcaggtcg tcatccggtc ggcattggcc aatgcgggcg tcgcggcgca gcagatcggt   1020

tacatcgaag cccatggcac ggggactccg ctcggcgatc ccatcgagat cgaggcgctg   1080

gcggaaaccg tcggcctccc gcgacctgtc ggcgatgtgt gcgcggtcgg gtccctgaaa   1140

tcgaacatcg gccacctgga gggagcggca ggcatagcgg gattgattaa agcggtgctc   1200

gcattgagtc acgagacgat accgccgagc ttacacgtga gacagctgaa cccgaatatc   1260

cggttggagg gaacgtcgct cgacattgtg aaggaagtcc ggccgtggcc cgcgggttcg   1320

agacgaaggt ttgcgggcgt cagcgcgttt ggttggtccg gcacgaacgc gcatgtcgtt   1380

cttgaagaag cggcgccgac tggtagaggc gaagctgcga gcgggttcca ttcccgaccc   1440

cccgccgccg ctgcgcgggc ggctgtcccc ctcgcggagg gggacactgg gggcactccc   1500

gacattgcag gcactcccga cactgcagac actcccgaca ctgcagacac tcccgacatt   1560

gcagggactg caggcactgc ggcaactacg ggcattgcag acgcgatgta tgtgcttccg   1620
```

-continued

```
ctgtccgcgc atggtgcgga cgaactgcgt cgggtggcgc gggcatacgg ggaattgctg   1680
acagcgtcgc acgcaccgag cctgcgtgat ctttgctaca cggccgcagt ccgccgcacg   1740
catcaccgat gccggctcgc tgtttccggc agaacggctg aagaactggc ggcgcagctc   1800
caggggatca cgatcccttc ccagcgacgg aagacggtat tcgtcttctc gggacaggga   1860
tcgcaatgga tcggaatggg gcgcagctgg atggaccgcg aacccgttat tcgcgaggcg   1920
ttggaacgct gcgaggccgc catgcggcct tatgtggact ggtcgctgaa agaagaactg   1980
gcgaagctcg accgcgtcga ggtcattcag cctgcgctct tcgcgctgca ggtcgccatc   2040
gccgcattgt ggcgttcctg gggaatcgag ccggatgccg tcatcgggca cagcatggga   2100
gaggtcgccg ccgctcatgt cgcgggtgcg ctgacgctgc aggatgcggc gcggatcatt   2160
tgcagccgca gccggctgtt gagccggatc agcggcctgg gcgggatggc gatggtggag   2220
ctgccgctcg cggaatgtga ggccgtgctg tcgacttaca cggaacgact atcgcccgcg   2280
gtgtcgaacg gacccaactc caccgtcatc tccggtgaag tcgaagccct ggccgaggtc   2340
gtcgcgacgc tggagcggcg aggcgtgtct tgccggccgg tgaaagtgga cttcgccgcg   2400
catagcccgc aagtggaccc attgtgcgac gaactcctgc agtcgctcga cgggattcaa   2460
ccgcggcccg cgaccatacc tttttactcc acggtgaccg gcgcgacgct ggagaccacc   2520
agcctcgaca gcacgtactg ggctcgcaat ctgcgatcgc cggttctgtt ctggcagggc   2580
atccgccatc ttgccgacag cgggcacgat gtctttctcg agatcagccc tcatcccatc   2640
ctgctgcccg ccatcggcgg caatgcggcg ctggttccgt ctctgcgccg cgaccaggac   2700
gaacgcggtt ccatgctcac gtcgctgggc gccctctatg aggctgggca cactgtcgca   2760
tggcggaccg tgtacccttc cggcaattgc gtgcgcctgc cccggtatcc ctggcagcgt   2820
cgtcgtttct ggctcgacgc ttcccccgcg cgacacgcga tcacgttggg caatccgctg   2880
ttgggaaaac gcgtcgaagc ctcgacgcaa cccggcactt tcttctggga gacggaactc   2940
agtctcgctt ccgtgccttg gctggcagac catcgcgtgc agggcgaagt cgtcttgccg   3000
gctactgcgt atctcgatat ggctctggcc ggaacttccg agaccttcgg tgaaagtccg   3060
tgcgtgctgg agcatgtgac tttcacacag atgctcattg tgccgcgcga cggcagcatg   3120
acgttgcagc tggccatcgc ggtcgataga cccgggatgg cgtcgtttcg gatttccagc   3180
cggcaggcat cgacatgggt cctgcatgct tccggggaca ttcgtcagac gcctgcggat   3240
gcatcgaccg tcccgccgga ttctgcggag acggtgcagg cccgctgccc cacagtggtg   3300
ccggcggcgg agctgtggcg tcagatggcg gagcacggcg tcgagtatgg tccggctttc   3360
cgcgcgctcg agcagatctg gagttgtcca ggtgaggcga tcgggcgtct gcgtagctcg   3420
gaaacgcgtt ccactgcgcc ggcgttcctc gatgcatgtc tgcagatcat cgccgcggcg   3480
tttggtcccg ccggtggaac ctggctgccc gccggcatcg accggatgcg ctggctgcat   3540
cccgcacgtt ccgtggtgtg gacgcatgcg cggctggaag gacctatcgc cgatctgtcg   3600
ctgctggacg gagagggaca actggtcgcc cgcatcgagg gtctgcggct gcagcgcctg   3660
gatgcgtcgg agcgcatcga catgcgcggc tggttgcacg aactgcgctg ggtcgctcag   3720
ccgcacgccg ctgcagagcc gccggcggcg cgagcggcgc ggtcatggct cattgtcggc   3780
gctgtggata gcgcgctcac cgcatggctg cgcgctaccg gcaaccgcgt gacgcagacc   3840
tcgccggaaa agctcgatga actccagccg ccgctcgagg aaatcgtgtt tttgctcgag   3900
cacgaaccct catgcgaccg cattctgcat ctcctccaga ccctggggcg cacgccctgg   3960
```

-continued

```
cgtcaagcac cgcgcctatg gctggtcacg cgcggcgcgc agccggtcga tggacagatc   4020
ctgcaagccg gtatcgctca ggcgcctttc tggggtttgg gccggaccgt gcattacgaa   4080
catccggaac tgaactgcac gctgatcgat ctcgatcccg ccggcggcga agaggaactc   4140
ctgcacgaac tgctgacgaa caacggcgag aatcaaatcg cctttcgcgg cggcgcgcgt   4200
tacgtcgcgc gcgtggctcg gcacgaagcg gatatgcaac ccgccatgtt caaggccggc   4260
gatcggccgt tccggctcga gatcgatgcc cccggagtcc tcgaccggct gcgcttgcgg   4320
gccacatcgc gccgcccccc gcaagccggt gaagtggaga ttgaagtctg cgccgcgggc   4380
ctgaacttcc tcgacgttct gctcgccctc ggcgttatgc ccgacgatgc gcccggcgcg   4440
attgccggca gcccgcgcct gggcggcgaa tgctcgggcc gtatcgtggc catggggaaa   4500
ggcgtcaccg actttcgcat cggagatgaa gtcgtggccc ttgcgccttg cagtttcggt   4560
cgcttcgtca ccacgcccgc cttccgcgtt gccttgaagc cggccaacat tcccgccgaa   4620
caggccgccg ccctgcctat cgcgtttctc accgccgatt acgcgctctc gcgagcggcg   4680
cggctggcgc ccggcgaacg agtcctgatt cacgctgcca ccggcggtgt gggattggcg   4740
gcaatccaga tcgcacagcg tgcgggcgcg gagatcttcg ctactgccgg gagtccggaa   4800
aaacgagcgt atctgcgctc gctgggcatc gcgcatgttt cggattcgcg ctcgatggct   4860
ttcgtggacg acatccgcaa ttggacgaat caagaaggag tagacgtcgt cctgaattcg   4920
ctttccggcg atctgctgga ggcgagcttc gatctgctgc gcgatcatgg acggttcatc   4980
gagatcggca agcgcgatta ctatgccggc cgcaagctgg ggcttcgccc gttcctgaag   5040
aacctctcgt acacgctggt cgatttgctc ggcatgtccc tgaagcgccc ggcattgacc   5100
cgggagctgc tgcaggagat ggtcgcaaaa ttcgaatcgg aaacctggcg gcccctggaa   5160
acgcgagtga cgaccatcac cgaatcggtg gaggcgtttc gcaccatggc gcaggcgcgg   5220
cacatcggca aaatcgtcat ggcgatgcga gattgcgcca atgcgcccat cgcaccccta   5280
cgctcggcgt tcgatagcga gggaacctac ttgattaccg gcggacttgg cgggctcggt   5340
cttaccgtcg cacgctggat gatcggacgc ggcgcccggc ggctggtgct gctgagccgc   5400
cgcgcgcctt cacccgaggt ccagcaagcc atcgccgtca tggacgcaga tgtccggacg   5460
gtgcaggccg atgtttctca gcgcgatgaa ctcgagcgcg tgatctcttc catcgatcga   5520
ttgcgcggcg tgattcatgc cgcagccgtt ctcgacgatg cgctgctact gaaccagacg   5580
gaagcgcatt tccgcaacgt gatggccgcg aaaatcgacg gtgcctggaa cctgcacttg   5640
ctcacccgcg actgcccgct cgatcatttc gtgctcttct cctccgctgc aggactgctg   5700
ggcgcgcccg cccagggaaa ctacgcggcc gcgaacgcct ttcttgacgc gctggcctac   5760
taccggaagg cccaaggcct gccggcgctg agcatcggtt ggggtgcgtg gtcggaggtc   5820
gggctggctg ccgcgcagga caatcgcgga tcgcggctgg ctttgcgcgg catggaaaac   5880
ctgacgccgc aacacggcct cgctattctg gaacagctgc tgaacagctc ggcttgccac   5940
gtcgccgcga tgcccatcaa tgtccgccag tggcggcagt tctatcccaa ggcggcgcag   6000
tctgcactgt tcgagctttt gcatgacgac gcggcgagcg aagccgatgc gccaaacgcg   6060
ttgcgcgcgc ggctgcaatc ggccgagcct cagacccgca ggacattgct cgaagaacat   6120
ctacagcagc agctggcgcg cgtgctgcgc atcgactctc aaactatcga tcccctgcgc   6180
ccgctgaagg aactcggctt cgattccctc atggccctgg agtttcgcaa ccgtctcgaa   6240
ctcacactgg gtctcacgct ccccgcgacc ctgatttggg gtcatcccac gctggccggt   6300
cttgccccgc acctggcgtc gcaaatggga ctgccgctgg tcgaagcgca ggccgcggct   6360
```

-continued gctgcggaag gagacagccg cgccatgaaa actgcactca gcgggttgga cgacatgtcg 6420
gaagaagcag ccgtggctgc gctccgagga gcaaggtcgt ga 6462

<210> SEQ ID NO 119
<211> LENGTH: 5088
<212> TYPE: DNA
<213> ORGANISM: Unknown organism
<220> FEATURE:
<223> OTHER INFORMATION: Origin of the sequence: Undetermined bacterium

<400> SEQUENCE: 119
gtgagggaaa aaattgcgcc catgtcgtcg gtcaaactcg cgctattggc gcggaacatg 60
cggcaaaaca tcgcaggctt cgacctggtt cacgccgaac ccatcgccat cgtcggcatg 120
gcgtgtcgtt ttccgggcgg cgcgaagaat ccggacgcct tctggacgct gttgaagaac 180
ggtgtcgacg gtgtcaccga ggtgccgcca gaccgctgga actcggacca gtactactcc 240
tccgatcccg atgctccggg caaggcgtat gcgcgatatg ccgccttcct cgaacgcatt 300
gacggtttcg atgcggaatt cttcggcatc tccccccgcg aagctctgaa catggatccg 360
cagcagcggc tgctgctgga agtgtgctgg gaagcggcag aggacgccgg catctctccc 420
ggccctctgg cgggcagcgc gaccggcgtc tttgccggct cctgcgccca ggacttcgga 480
ctgtttcagt acgccgaccc tgcccgcatc ggagcttggt cgggttccgg cgtggcgcat 540
agcatgttgg ccaatcgcat ctcctatctg ctcgacctgc gcggtccgag catggcggtc 600
gatacggcct gctcctccgc gctcgtcgcc gtccatctgg cttgccaaag cctgcgccgg 660
cgcgaatgcg atgcggcatt cgccggcgga gtgaacttga tcctgactcc cgagggcatg 720
atcgctttgt cgaaggctcg catgttggcg cccgacggac gctgcaagac gttcgacgcc 780
gcagccgacg gttatgtgcg cggcgagggc tgcggcatcg tgctgctgaa gcggctctcc 840
gatgcgctgg ccgatggcga tgccatccgt gcagtcatcc gcggctcggc aatcaatcag 900
gacggacgga gcaatggcat cacggcgccg aatctgcagg cgcagaaggc ggtcctgcaa 960
gaggcggtgg ccaacgcgca catcgatcca tcccacgtat cgttgatcga ggcgcatggc 1020
acgggcacgt cgctgggcga tcctatcgag atcgaggccc tgcagtcggt ctacgacgcg 1080
ccggactctg cgccttgtct gctgggttcc gtaaagacca acatcgggca tctggagggc 1140
gcggcgggaa tcgccgggct gatcaaagcc gtactcgccc tgcagcatcg caccattcct 1200
ccgcacctgc attttcgccg gctgaatccg aacatctcac tggacggcag ccggtttcgc 1260
atcgccacgg aatcgtcgcc gtggacgtcg gaaggacggc cgcgtctggc cggcgtcagc 1320
tcgttcggtt ttggagggag caacgcgcac gtcatcctcg aagaggcgcc tgcactccct 1380
ttgccgaagc cggtcacacg cccgcagctt ctcactctgt cggcgcgcac cgacgaagcg 1440
ctcggcgaac tggccggcca cttcgcggag ttcctgcagt cgcacccgaa tgcgttgctg 1500
tccgacgttt gcttcaccag tcaggttggg cgcgacgcat atagtcaccg cttggcgatc 1560
accgccgcag atgcggcaga ggctgtagcg gcattggccg cggcgccgcg gcgcgaagta 1620
tcgttgcgcc ggcggccggc aatcgctttt ctcttcaccg gccagggcgc gcagtacgcc 1680
ggcatgggcg cagagcttta taaaacgcag cctgtttttc gcgacgcgct cgatcgttgc 1740
gccgattggc tccgtcccca gctcgatgtt ccgctgaccg ttctcttgtt cgagtcggtt 1800
tcgccgttgc acgagacggc gtatacccag ccggcaatgt ttgccctgga atgggctctg 1860
gctcagttct ggctgtcgct cggcgtccgg ccggactacg tgctgggcca cagtctcggc 1920

-continued

```
gagtatgttg cggcgtgtgt ggccggcgcc tttagcgtgg aggacggcct gcggctggtg   1980
accgccaggg ggcggctggt caatgcgctt ccccgcggca aagcggtcat cgttcacgcc   2040
aatccgagcc gcatcgcggc gctcgccgcc aaggtggcag tcgccgcatc gaatgcgccg   2100
gaccgcaccg tgatctccgg cacggctgca gaaatcgcgg aagcgcaaga tgacctgcat   2160
cgcgccggcg tggaaacgcg agagctgaac gtatcgcatg cgttccattc gccgctgatg   2220
gatccgattt tggacaagtt cgaagcgctt gcaggtgcga tcgcgtatca gccgctggcg   2280
atcccgctgg tgtcgaacgt cagcggagcc gtattgccga aaggcacgac actcgacgcc   2340
cgctactggc ggcgacagtt gcgcgaaacc gtgcagtttg aaagcgcgat gcgaaccctg   2400
gcggaccgcg agtgcaagct gtttctggaa atcggcccgc atcccacgct caccacgctg   2460
gggcgatatt gtctgcccga tgacggcgcg gtctggctgc actccctatc taagggacga   2520
tcggattggt ccgtgctgct ggaaagtctt ggcggcctgt ttaccgcggg cgtgaatccc   2580
gactggcgcg gtctctatgc cggggaatca cccagccgcg tcgcgctgcc gacgtatccg   2640
tttcagcgtg acaccttcag cctgagacgc gtacccgcga gagagccggc gcgcggcggc   2700
atgttgggag cgcgcctcaa cagcgcgttg ggcgatgtca tcttcgaaaa ttcgctaacc   2760
acggagacgc ctctgctcca tgagcacgtg atctacgacg cggtcattgt gcccggcgcc   2820
tggcacgtgt cggcatttct cgaagcggca caggaagtct tcggtccggt tccctgcgcc   2880
gtctccgatg tcatgatgcg gcaggcactg gccatcccgc cggatacgcc ggtcacggtg   2940
caagcgattg tcacacccgg cgaggacggc gaagcaaagg tgcaggtctt cagccaggat   3000
ggcgattcgt ggaagctcca cacggcagcc agtctgcgcg cggcgactgc cggcgccgtt   3060
catttcgagc tgccggcgca gccttccgaa gtcatttccg gcgatgcgtt ctacggcgcg   3120
atgaacgcac gcggcgtcga tcttggcccc gccttcagtt gggtggaaga agtctggcgt   3180
cgcgatggcg aggcgctggg gcgaatgcgt ctgccggtgg ctgaggatgg cgcgaacgct   3240
taccggctgc accccggcct gatcgattct tgttttcaag tattcggagc gacttggccc   3300
gcggagcgtt gccagcccgg cgcatacgtg ccggtcggga tcgaagcggt gcgcttctac   3360
cgtccgccgg caggttctct gcgctgtcat gcgcgtctgc gcccgagctc gagcggcccg   3420
ttcgtcggtg atctgacgct ggttgaagag accggcgcgg tcatcgccga gttttccgga   3480
ctggctgtaa tgcatgccgg tacgctgcaa tccgcacagt cgtggctgca ggatgtgcag   3540
tggcaggagt gcgagcgatc gacaacgttg aagtccgacg gccctggcaa gccggaggac   3600
tggttgctgt gtgccggcgc agacgatgtc gccggtttga tgccgcaaga gctgcgcgtc   3660
gtgtccggcg tcactctccg ccaggcgctg gaacagaccc agactttggt cggccgcccg   3720
gcgcggctct ggctgatcac gcgcggcgtg catcgcatca gtgatgacga tgcgactccc   3780
gtcgatcctt tccaggctcc actgtgggga ctcgggcagg cgatcgcgcg cgagcatccc   3840
gagctgtggg gcggcctgat cgacctcggt tgcgacaatg ccgacatcgc cgccgccatg   3900
ctgctggatg aaatccgtta tgccggcgac gacaaagcga tcgcattgcg caacggacgc   3960
cgctacgttc gccggctggt gcggcacaag gaaacgtcga agcggccgcc tgccatttca   4020
gccgacggcg tctatctgat caccggcggt ctcggcgcat taggacgaag ggtggcacgc   4080
cgcttgatcg agcaaggcgc gcgccgtctg gtactggtcg gccggcatac ggaggcagtt   4140
gccgatctcg agcaactcgg ggctgcagtc atggttgctg cttgcgatgt gagttccgag   4200
caacagctgg cggcgctgct ggcggacccg cgcacccagc cgctgcgtgg agtcgtgcat   4260
gccgcaggcg tgctcgatga cggggtagtt acagaacaga cgtgggctcg tttcgagaag   4320
```

-continued

```
gtgctggcgc cgaagctgca gggtgcctgg aatcttcacc agctcactcg ccaccatgcg   4380
ctcgactttt tcgtactctt ctcttccgcc gcttcgctgc tcggttccgc cggacagagc   4440
aattactcgg cggccaacgc atttctcgac agccttgccc acatgcgccg cgcgcaagga   4500
ctaccggcgc tgagcatcaa ttggggacca tgggcgggcg aaggcatggc cgcgcgcatc   4560
gcgcggcaag gcctgccggg ggtaccgctg ctgccgccgg aagtgggtgc gcgcatcttc   4620
ggcgatctgc tgggcgagac tgccgctcag atcgcggtgt tccaagtctc cgccgaaaaa   4680
aggcggagcc cggcgagcga tcccggcttc atccagcaac tcaccgaagc tgcgccggag   4740
cggcggcagg aactgctgca gatgcgcatc cgcaagcagg ccggcggcgt gctggcgctc   4800
gatgcgtcca agacgctcga cccgcgccgg ccgctcaagg aatacggact cgattcgctg   4860
atggcgctgg atctggcgcg cgccatcgga gagctggtgc gcaagagcct tcccgcgaca   4920
ttgctatacg accatccgac cgtcgagaaa ttggccggcc atgtcctccg cgaactcgga   4980
ctcgacgtcc ccagcgattc cctcgtcgat gaagtgcggc agctgtccga gcaggagatg   5040
gcggcgttca tcacggaaac cttgcaccat ctgggagagg aacgatga                5088
```

<210> SEQ ID NO 120
<211> LENGTH: 4306
<212> TYPE: DNA
<213> ORGANISM: Unknown organism
<220> FEATURE:
<223> OTHER INFORMATION: Origin of the sequence: Undetermined bacterium

<400> SEQUENCE: 120

```
atgagcgatc tcactcctct tcaacaggcg gtcctggcgc tcaagcgcac gcgagcgcgt     60
ctcgacgaac tggagagcgt ccacaacgaa cccatcgcga tcgtcggcat ggcttgccgc    120
tttcccggcg cggactcgcc ggaagcattt tggcagctcc tgcacgatgg catcgatgcc    180
atccgcgaaa ttcctgcggg ccgttgggat gccgatgcgt tttacgatcc cgatcccaac    240
gcgccgggaa agatgtacac gcgtctgggc ggattcctcg atggtgccgt cgacggcttc    300
gacgccggct tcttcggaat cacgccgcgc gaggtcgccg gtctggatcc gcagcagcgc    360
ctgctgctcg aggtggcatg ggaagctttg gagcgtgcgg gtcggccgcc cgacagtctc    420
gcgggcagcg acaccggagt gttcatcggg atcagcaccg acgactacag ccggctgaaa    480
cctaccgatc cggcgctcat tgacgcctat accggtaccg gaaccgcgtt cagcactgcc    540
gccggacgga tctcctatct gctggggttg cagggaccga acttccccgt cgacacggcg    600
tgctcttcct cactcgtggc ggttcatctg gcgtgccgca gcttgcagtc gcgagagtgc    660
agcatggcgc tggccggcgg cgtgaacctg attctggcgc cggaaagcac gatctacttc    720
tgccgcctgc gggccatggc ggccgatggc cgttgcaaaa gtttcgctgc ctccgccgac    780
ggttacggcc gcggcgaggg atgcggaatg ctggtgctga agcggctgtc cgatgcgacg    840
cgtgacggcg atcgtattct ggcgctgatt cgcggatcgg ccgtcaacca cggcggccgc    900
agcaacggcc tcacggcgcc gaacggtccg gcgcaggaag ccgtgattcg ggcggcgctc    960
aagaacgccg gcatggcccc cgccgatgtc gattacgtgg aagcccacgg aaccgggacg   1020
ccgctgggag atcccatcga actgcgggcg atggcagcgg tgctgggcga ggggcgtgcc   1080
gtcgattctc cgttgatcgt cgggtcggtg aaaaccaact tcggccacct ggaggcggcg   1140
gcaggtatcg ccggcctgat caagaccatt ctcgccctgc agcaccgaga gattccgccc   1200
catctgcatt tcaacgcgcc caacccgcac gtactctgga atgagctgcc gctaaagata   1260
```

-continued

```
gccaccgcat gttcgccatg gccctccaac ggccgccccc gagttgccgg ggtgagctcg   1320
ttcggaatca gtggcaccaa ttcgcacgtc gtcctcgcag aagcgaagac gaatgtagaa   1380
gcgaagacga atgtagaggc gaagacgaat gtagaggcga agacgagtga agaggtcaag   1440
gcgagtgtag aggccaaagg gaatgtggag gctaaggcta gtgctagtgt ccccctcctc   1500
gagggggaca gccgcccgcg aagcggcggc gggggtcgg gccggccgcc cagccgcgag   1560
gaagtgccgg tcccggatca actccatgcc gaagacggcc gcgaatacct cctaccgctt   1620
tcggcgcgcc atccgcaggc tctgcgcgat ctcgccggcg cctatcgcga tgggcgcttt   1680
cacgctccgc tctccgcgct gtgttccgcc gccagcctga cgcgcagtca ctacgaacat   1740
cgcgcagcgt ttgtggcctc atccctgccc gagttcaatc aattgctcga ggccttccgg   1800
cgcaatgaaa ccaatcgcgg cgtcgccacc ggtttcgccg atcccggagt tcgtccgaaa   1860
ctcgccttca tcttttccgg ccagggcgga cagtacccgc gcatggcgta tcgcctgtat   1920
tccgacgagc ctgtcttccg atcggcgatc gaacgttgcg acgccgcctt ccgcagcttc   1980
gtggaatggc ggcttgcgga cctgctcgcc gacgagtcgg gagcatggct gagccagatc   2040
gatcgcgtgc agcctgcgct gttcgccgtt caaatcgcgc tggtcgaact gctgcaatcc   2100
tggggaattc gcccggacgg cgtggccgga cacagcatgg gagaagtggc ggcggcccat   2160
gtcgcaggca ttctcaccct ggaggacgcg gcccgcatca tctgtcgccg cagccggctg   2220
ttgctcggac ttcgcggccg gggagcgatg gctctggtcg aactgccgct cgatcgggcg   2280
aaggccgtgc tcgctgaacg cggtctcact actgtttctg tcgcggccag caacggacca   2340
cgcagcacgg tgttctcggg agaccgtgtg gctctcgagc atttgaagga cgacttcgag   2400
aggcgcggcg tcttctgccg gctgattcag gtggatgtcg cttcacacag ctcgcaggtg   2460
gacccgctcg agaacgaatt gcgccaggaa ctcggccgcg ttattgcaaa acgttccgcc   2520
gtgccgttct tctccacggt tgaaggacag ttgagcacgg gcgaggcgtg cgacgcgtcg   2580
tactgggtag ccaatctgcg acagccagtc cgtttctggg agtcgttgca ggcgatggct   2640
ggtgatgagt tcacgcagtt cctggagatc agtccgcatc ctgtgctgac gccgtcgatc   2700
gaggatagtc tgcggacgct cggcataaac ggactggttc gccccgtact gcgccgcgac   2760
gaaccggagc ggcgtgagct gctcgagttg ctcgccgcgc tctacgtgaa tgggcagcgt   2820
ccggactggc gcgcgctcgc ttcgtctccc gacacgcgcc tggatctgcc gacgtatccc   2880
tggcagcgcg agcgcttctg gttcgcgacc tcgacgcggc gaagtttgcc ggcagttggc   2940
ggtcatccgc tgctcggtcg caaggtcgag attgcgctgg cgccggacac acacgtctgg   3000
gagtccgtgc tctctctgga tgcgctgccg tttctcgccg atcaccggct caacgagctt   3060
gtggtgcttc ccggtgccgc ttatgtggag atggcgctgg ccgcagccaa ggaagtgttc   3120
gcgggtggct gcagcctgga agagatccgg tttgaacaaa tgctggttgt tccttccgcg   3180
ggcgcctcgc gagtgcaggt catactcgag ggacacgcat tccgcatctc cagtctggcc   3240
gaaggcggtt ccgattggac cgagcacgcg cgcggcacca tggctgcggc gccggacaag   3300
gtcgcgccca cggtgagcct gcccacactt ggggatcgca tcgagggcga tgacttctat   3360
gcggccttcg catcgcaggg gatgcattac ggcgacacct tccgcggcat cgcggaagtg   3420
tggcggcgcg acggcgaggc agtggcgcga ctgagcgtgc cggatgccgt tcgcgaagca   3480
gagtccggtt acacgcttca tcctgccttg ctcgatgcct gtttgcaggt gctgggcgcg   3540
acgcttggcg gcgaaggcag cgccggtcct tgcgtgcctg tcgccatcga acggttgcac   3600
tgtttcggca gacccgccgg cgatcttagg gtgcatgcgc ggctgacggg gcggctcgag   3660
```

-continued

```
ggcgatgtca ccctgtgtga tgcggaaggc cacgtcatcc tcgaggtcca aggcctgcgt   3720

gcccaggaac tggagcgcca atccgaatgg ttccacgcta tggaatggga gccgcagctg   3780

ctggccgaga gtccaacggc aacggtgtcg ggtgcatggc tggtcattgc cgatgccggc   3840

ggcatcgcag ccgcggtggc gcgagggctg ggcacaaaca cggttgtgat ttcgggtcgc   3900

gatgccgaga taccggatca gccttaccgg ggcgtcattc actgcgggag cctggatgag   3960

accgaggatg agaccgatcc gtcggctgcg gggggaaccg cctgcgaaga cattttgcgc   4020

atcgttcaag aattcggagt gggacgcata cagctgacga aacaagcgtc cgacgccgaa   4080

tcgcagcatc cgcgaatctg gctgattacg gcgggcgttc atgcggagca tctgcagatg   4140

ccggtggtgc ccgcgcgggc accggtgtgg ggtctgggac gtaccatcgc ggccgagcat   4200

cccgagttcg cttgcacctg catcgatctc gacactgccg gtgaagtcga ggtgcaggcg   4260

ctctgccgag agattctcgc ggggagttct gaacgtcagg gcccgg                  4306


<210> SEQ ID NO 121
<211> LENGTH: 1537
<212> TYPE: PRT
<213> ORGANISM: Unknown organism
<220> FEATURE:
<223> OTHER INFORMATION: Origin of the sequence: Undetermined bacterium

<400> SEQUENCE: 121

Leu Gln Cys Pro Glu Ser Ala Val Asp Leu Gln Gln Pro Leu Val Arg
1               5                   10                  15

Met Gly Leu Asp Ser Leu Met Ala Val Gln Leu Arg Asn Arg Ile Asp
            20                  25                  30

Thr Asp Leu Arg Val Leu Leu Pro Met Val Arg Phe Leu Asp Gly Pro
        35                  40                  45

Ser Val Ala Glu Leu Ala Arg Asp Leu Ser Asp Leu Ser Gly Leu Ser
    50                  55                  60

Glu Arg Thr Thr Val Ala Pro Glu Pro Ala Ala Gln Ala Ser Val Pro
65                  70                  75                  80

Ala Leu Ser Tyr Pro Leu Ser Ala Gly Gln Gln Ala Leu Trp Phe Ile
                85                  90                  95

Tyr Arg Ser Ala Pro Glu Ser Pro Ala Tyr Asn Ile Ala Trp Ile Ala
            100                 105                 110

Arg Ala Arg Gly Ala Phe Asp Pro Gln Ala Leu Arg Arg Ser Leu Gln
        115                 120                 125

Asp Leu Val Asp Arg His Pro Ala Leu Arg Thr Thr Ile Ala Glu Ser
    130                 135                 140

Gly Gly Ala Pro Val Gln Thr Val His Ser Ser Val Pro Val Asp Phe
145                 150                 155                 160

Glu Val Ile Pro Cys Ser Pro Asp Asp Glu Ala Val Leu Ile Asp Gly
                165                 170                 175

Val Phe His Ala Pro Phe Asn Leu Gly Glu Asn Cys Phe Arg Ser Arg
            180                 185                 190

Leu Leu Val Gln Ser Gly Lys Asp Gln Val Leu Ala Ile Val Val His
        195                 200                 205

His Ile Leu Ala Asp Phe Trp Ser Leu Leu Val Met Val Asp Glu Leu
    210                 215                 220

Arg Ser Ile Tyr Leu Ala Arg Thr Ala Gly Gly Pro Pro Val Ala Pro
225                 230                 235                 240

Pro Val Ala Ser Phe Ala Ala Phe Val Arg Trp Gln Asn Glu Leu Leu
```

-continued

```
                245                 250                 255

Ala Gly Thr Glu Gly Glu Arg Leu Trp Asn Tyr Trp Ser Ser Gln Leu
            260                 265                 270

Ser Gly Gln Leu Pro Val Leu Asn Leu Pro Ser Asp Arg Pro Ser Pro
        275                 280                 285

Pro Val Gln Ser Phe Arg Gly Asn Ser His Ser Phe Arg Ile Glu Pro
    290                 295                 300

Ala Leu Thr Ala Lys Leu Lys Ala Leu Ala Arg Arg Gln Asn Ala Thr
305                 310                 315                 320

Leu His Ala Thr Leu Met Ala Ala Phe Gln Val Leu Leu Ser Arg Trp
                325                 330                 335

Thr Ser Gln Glu Glu Ile Leu Thr Gly Thr Leu Thr Asn Gly Arg Thr
            340                 345                 350

Gln Pro Glu Phe Ala Asp Leu Val Gly Tyr Phe Val Asn Pro Val Ile
        355                 360                 365

Leu Arg Gly Glu Leu Ser Gly Asp Pro Asp Phe Asn Thr Val Leu Ala
    370                 375                 380

Arg Ile Arg Gln Thr Leu Leu Gly Ala Ile Glu His Gln Glu Tyr Pro
385                 390                 395                 400

Tyr Ala Arg Ile Val Glu Arg Leu Gly Pro Gly Leu Arg Val Leu Phe
                405                 410                 415

Val Leu Gln Gln Pro His Arg Ile Pro Glu Ser Val Pro Phe Met Leu
            420                 425                 430

Gly Gln Ser Gly Gly Arg Met Ala Trp Gly Ser Leu Thr Leu Glu Ser
        435                 440                 445

Leu Ala Met Pro Leu Arg Gln Ser Arg Phe Asp Leu Asp Leu Met Met
    450                 455                 460

Val Glu Thr Asp Gly Gly Leu Ser Ala Phe Leu Gln Tyr Asn Thr Asp
465                 470                 475                 480

Ile Phe Asp Ala Ala Thr Ile Glu Arg Leu Ser Leu His Phe Ala Val
                485                 490                 495

Leu Leu Glu Gly Ile Ala Glu Asn Pro Ala Cys Pro Val Val Asp Leu
            500                 505                 510

Pro Leu Leu Thr Thr Arg Glu Arg Ile Gln Leu Leu Glu Glu Trp Asn
        515                 520                 525

Ala Thr Ala Ala Glu Phe Pro Ser Gln Cys Val His Glu Leu Phe Glu
    530                 535                 540

Ala Gln Val Glu Leu Thr Pro Asp Ala Ile Ala Leu Ser Phe Gly Glu
545                 550                 555                 560

Gln Asn Leu Thr Tyr Arg Glu Leu Asn Gly Ser Ala Asn Arg Ile Ala
                565                 570                 575

His Tyr Leu Arg Ser Arg Gly Ala Gly Pro Gly Glu Met Val Gly Ile
            580                 585                 590

His Val Thr Arg Ser Leu Glu Thr Val Ala Gly Leu Leu Gly Val Leu
        595                 600                 605

Lys Ala Gly Ala Ala Tyr Val Pro Leu Glu Pro Glu Tyr Pro Ala Gln
    610                 615                 620

Arg Leu Arg Leu Met Leu Glu Glu Thr Arg Pro Val Val Val Leu Asn
625                 630                 635                 640

Val Thr Glu Ser Glu Val Trp Thr Gln Pro Asp Thr Asn Pro Asn Pro
                645                 650                 655

Leu Ala Thr Pro Ala Asp Leu Ala Tyr Val Leu Tyr Thr Ser Gly Ser
            660                 665                 670
```

-continued

```
Thr Gly Arg Pro Lys Gly Val Gln Ile Thr His Gln Ala Val Val Asn
        675                 680                 685

Phe Leu Ser Ser Met Arg His Glu Pro Gly Ile Ser Asp Arg Asp Thr
    690                 695                 700

Leu Leu Ala Leu Thr Thr Phe Met Phe Asp Ile Ser Ala Leu Glu Ile
705                 710                 715                 720

Phe Leu Pro Leu Ser Ala Gly Ala Arg Val Val Val Ala Asn Gln Glu
                725                 730                 735

Thr Ala Val Asp Gly Glu Arg Leu Ala Arg Glu Leu Ala Arg Ser Lys
            740                 745                 750

Ala Thr Met Met Gln Ala Thr Pro Ala Thr Trp Arg Leu Leu Leu Ala
        755                 760                 765

Ser Gly Trp Pro Gly Asp Arg Arg Leu Thr Ala Leu Cys Gly Gly Glu
    770                 775                 780

Ala Leu Pro Arg Asp Leu Ala Asp Arg Leu Leu Gln Arg Thr Ala Ala
785                 790                 795                 800

Leu Trp Asn Leu Tyr Gly Pro Thr Glu Thr Thr Ile Trp Ser Ala Ile
                805                 810                 815

Gln Arg Val Thr Thr Gly Asp Gly Pro Val Ser Ile Gly Arg Pro Ile
            820                 825                 830

Ala Asn Thr Gln Leu Tyr Val Leu Asp Asp Arg Met Gln Pro Ala Pro
        835                 840                 845

Ile Gly Val Ala Gly Glu Leu Tyr Ile Gly Gly Ala Gly Leu Ala Arg
    850                 855                 860

Gly Tyr Leu Asn Arg Pro Glu Leu Ser Ala Asp Lys Phe Val Ala Asn
865                 870                 875                 880

Ser Phe Asp Pro His Gly Thr Arg Leu Tyr Arg Thr Gly Asp Leu Ala
                885                 890                 895

Arg Arg Gln Arg Asp Gly Ala Leu Glu Tyr Leu Gly Arg Ile Asp His
            900                 905                 910

Gln Val Lys Ile Arg Gly Phe Arg Ile Glu Thr Gly Glu Ile Glu Ala
        915                 920                 925

Ala Val Arg Ser His Pro Ala Val Arg His Ala Val Val Thr Ala Arg
    930                 935                 940

Glu Asn Asp Ala Ala Gly Lys Tyr Leu Ala Ala Tyr Ile Val Pro Leu
945                 950                 955                 960

Ala Asp Gly His Arg Ala Thr Ala Ala Ala Asp Thr Phe His Asp Arg
                965                 970                 975

Val Glu Ser Glu His Val Thr Gln Trp Gln Ser Val Trp Asp Thr Thr
            980                 985                 990

Tyr Glu Gln Asn Ala Pro Asn Ala Asp Pro Glu Phe Asn Ile Val Gly
        995                 1000                1005

Trp Arg Ser Ser Val Thr Gly Glu Pro Ile Pro Ala Ala Glu Met Arg
   1010                 1015                1020

Glu Trp Val Gln Asp Ser Val Asp Arg Ile Leu Ala Ser Arg Pro Arg
1025                1030                1035                1040

Arg Val Leu Glu Ile Gly Cys Gly Thr Gly Leu Leu Leu Phe Arg Val
               1045                1050                1055

Ala Pro His Cys Ser Glu Tyr Trp Ala Thr Asp Phe Ser Gln Lys Ala
           1060                1065                1070

Leu Asp Tyr Ile Ala Ala His Ala Asp Arg Thr Gly Leu Ala Asn Val
       1075                1080                1085
```

-continued

Arg Thr Phe Arg Gln Ala Ala Asp Asp Ala Cys Glu Ile Asp Ser Arg
1090 1095 1100

Ser Cys Asp Ala Val Val Leu Asn Ser Val Ile Gln Tyr Phe Pro Gly
1105 1110 1115 1120

Glu Ala Tyr Leu Arg Arg Val Leu Ala Glu Ala Val Arg Val Val Lys
1125 1130 1135

Pro Gly Gly Ile Val Phe Val Gly Asp Val Arg Ser Leu Pro Leu Leu
1140 1145 1150

Glu Thr Phe Tyr Ala Ser Leu Glu Val Gln Arg Ala Pro Ala Ser Leu
1155 1160 1165

Thr Arg Asn Glu Phe Arg Gln Arg Val Arg Ser Leu Ala Ser Gln Glu
1170 1175 1180

Glu Glu Leu Val Val Asp Pro Ala Phe Phe Phe Ala Leu Arg Glu Gln
1185 1190 1195 1200

Ile Pro Glu Ile Gly Arg Ile Glu Ile Leu Pro Arg Arg Gly Arg Ser
1205 1210 1215

His Asn Glu Leu Thr Arg Phe Arg Tyr Gln Ala Ile Leu His Ile Gly
1220 1225 1230

Ser Arg Glu Ala Glu Glu Pro Glu Ser Asp Arg Arg Arg Cys Gln Thr
1235 1240 1245

Ala Ala Glu Ile Arg Arg Val Leu Thr Asp Ala Gln Pro Glu Leu Ala
1250 1255 1260

Ala Phe Thr Glu Ile Pro Asn Ala Arg Leu Thr Ala Glu Ser Ala Ile
1265 1270 1275 1280

Val Thr Trp Met Asn Gly Asp Glu Ala Pro Glu Thr Leu Gly Glu Leu
1285 1290 1295

Arg Asp Arg Leu Arg Gln Thr Ser Pro Ser Gly Val Asp Pro Ala Asp
1300 1305 1310

Leu Trp Arg Met Asp Glu Asp Leu Pro Tyr Arg Val Ala Ile Asp Trp
1315 1320 1325

Ser Ser His Gly Pro His Gly Arg Phe Asp Ala Thr Phe Cys Arg Ala
1330 1335 1340

Ala Ala Gly Pro Pro Ala Ser Arg Pro Arg Arg Arg Leu Ala Gly Pro
1345 1350 1355 1360

Tyr Thr Asn Asp Pro Leu Arg Ala Val Tyr Thr Arg Thr Val Val Pro
1365 1370 1375

Gln Leu Arg Thr His Leu Lys Glu Lys Leu Pro Asp Tyr Met Ile Pro
1380 1385 1390

Thr Ala Trp Val Val Leu His Glu Met Pro Leu Thr Pro Asn Gly Lys
1395 1400 1405

Ile Asp Arg Asn Ala Leu Pro Asp Pro Glu Pro Ser Arg Arg Ala His
1410 1415 1420

Ala Glu Ala Phe Thr Pro Pro Glu Thr Pro Val Glu Gln Val Leu Ala
1425 1430 1435 1440

His Ile Trp Gly Glu Val Leu Gly Met Asp Gly Ile Gly Val His Asp
1445 1450 1455

His Phe Phe Asp Ser Gly Gly His Ser Leu Leu Val Thr Gln Met Ile
1460 1465 1470

Ala Arg Val Arg Asp Met Leu His Val Glu Val Pro Phe Arg Thr Val
1475 1480 1485

Phe Asn Ala Pro Thr Val Arg Gly Phe Ala Val Ala Ile Gln Asp Gly
1490 1495 1500

Val Asp Pro Gly Trp Ala Arg Arg Ala Ala Asp Leu Leu Ile Ala Val

-continued 1505 1510 1515 1520

Ser Gln Met Ser Asp Val Gln Ile Glu Arg Met Met Ser Ala Ala Gln
1525 1530 1535

Asp

<210> SEQ ID NO 122
<211> LENGTH: 2766
<212> TYPE: PRT
<213> ORGANISM: Unknown organism
<220> FEATURE:
<223> OTHER INFORMATION: Origin of the sequence: Undetermined bacterium

<400> SEQUENCE: 122

Met Gln Asn Ser Ser Pro Asn Thr Ile Asp Leu Ser Leu Ala Arg Arg
1 5 10 15

Gln Leu Leu Asp Arg Leu Leu Gln Glu Asn Ser Pro Glu His Arg Ile
20 25 30

Pro Arg Arg Glu Asn Arg Asp Ala Ala Pro Leu Ser Leu Ala Gln Gln
35 40 45

Arg Leu Trp Phe Leu His Gln Leu Asp Pro Asp Ser Pro Ala Tyr Asn
50 55 60

Ile Pro Ile Ala Leu His Ile Arg Gly Pro Leu Asp Ile Arg Val Leu
65 70 75 80

Leu Arg Ser Leu Glu Ala Val Val Gln Arg His Glu Ser Leu Arg Ser
85 90 95

Cys Ile Gly Gly Val Asp Gly Glu Ala Arg Gln Ser Leu Leu Ala Arg
100 105 110

Val Thr Leu Glu Leu Pro Val Val Gln Ala Asp Gly Ile Ala Glu Ala
115 120 125

Arg Gln Met Ala Leu Arg Asp Ala Gln Ile Pro Phe Asp Leu Arg Lys
130 135 140

Pro Pro Leu Leu Arg Thr Lys Leu Ile Cys Leu Asp Asp Lys Gln Gln
145 150 155 160

Ile Leu Leu Leu Thr Leu Ser His Ile Ile Ala Asp Ala Trp Ser Val
165 170 175

Glu Thr Phe Val Arg Asp Leu Thr Arg Ser Tyr Glu Ala Phe Val Gln
180 185 190

Gly Arg Pro Ser Pro Leu Met Glu Leu Pro Ile Gln Tyr Gly Asp Trp
195 200 205

Ala Val His Gln Gln Thr Ser Leu Asn Gln Thr Ala Gln Gln Tyr Trp
210 215 220

Lys Lys Gln Leu Ser Gly Thr Leu Pro Phe Leu Asp Leu Pro Thr Asp
225 230 235 240

Arg Pro Arg Pro Ala Gln Gln Thr Trp Arg Gly Ala Val Glu Thr Thr
245 250 255

Ala Leu Gly Arg Asp Leu Thr Asp Gly Leu His Ala Phe Ala Leu Arg
260 265 270

Glu Gly Ala Thr Val Phe Met Thr Ala Ile Ala Ala Phe Gln Val Leu
275 280 285

Leu His Arg Tyr Thr Ala Gln Glu Asp Ile Leu Ile Gly Val Pro Val
290 295 300

Ala Gly Arg Thr Gln Arg Glu Thr Glu Gly Leu Val Gly Cys Phe Ala
305 310 315 320

Asn Met Ile Val Leu Arg Gly Asp Leu Arg Asp Asp Pro Ser Phe Arg
325 330 335

-continued

```
Ser Leu Leu Ala Arg Thr Arg Asp Thr Ala Leu Ser Ala Leu Ser His
            340                 345                 350

Gln Asp Phe Pro Phe Glu Arg Leu Val Glu Glu Leu His Pro Pro Arg
        355                 360                 365

Asp Leu Ser Arg Ser Pro Val Phe Gln Val Ser Phe Ala Leu Leu Pro
    370                 375                 380

Asp Ala Pro Ala Ile Thr Val Met Pro Gly Leu Thr Ile Ser Arg Glu
385                 390                 395                 400

Tyr Met His Asn Gly Gly Ser Lys Leu Asp Leu Gly Val Thr Leu Glu
                405                 410                 415

Pro Ser Gly Asp Gly Leu Met Ala Ser Ala Glu Tyr Asn Thr Asp Leu
            420                 425                 430

Phe Asp Ala Ala Thr Ile Ala Ser Leu Leu Asp Ala Tyr Arg Thr Leu
        435                 440                 445

Leu Ala Ser Val Val Thr Asp Pro Asp Val Arg Ile Ser Thr Ala Ala
    450                 455                 460

Leu Leu Ser Pro Ala Val Arg Ser Arg Met Leu Glu Gln His Asn Ala
465                 470                 475                 480

Thr Arg Arg Asp Ala Gly Pro Asn Gly Cys Ala His Glu Leu Val Glu
                485                 490                 495

Ala Gln Ala Glu Arg Thr Pro His Ala Val Ala Val Val Phe Glu Asp
            500                 505                 510

His Gln Leu Thr Tyr Ala Glu Leu Asn Ala Arg Ala Asn Arg Leu Ala
        515                 520                 525

His Arg Leu Ser Ala Ser Gly Ala Gly Pro Gly Lys Ile Ile Ala Leu
    530                 535                 540

Ala Met Glu Arg Ser Leu Glu Met Val Ile Ala Leu Leu Ala Ile Leu
545                 550                 555                 560

Lys Ser Gly Ser Ala Tyr Leu Pro Leu Asp Pro Ala His Pro Lys Asp
                565                 570                 575

Arg Leu Ala Arg Ile Leu Asp Glu Val Gln Pro His Ala Val Leu Thr
            580                 585                 590

Gln Glu Ala Val Ala Glu Met Met Ala Met Met Ala Met Met Ala Val
        595                 600                 605

Ala Val Glu Pro Glu Ala Ala Asn Leu Val Ser Gly Ser Lys Pro Asp
    610                 615                 620

Asp Leu Ala Tyr Ile Ile Tyr Thr Ser Gly Ser Thr Gly Arg Pro Lys
625                 630                 635                 640

Gly Val Glu Ile Arg His Ser Ser Leu Val Asn Leu Leu Arg Ser Met
                645                 650                 655

Gln Arg Glu Pro Gly Leu Thr Ala Ala Asp Gly Leu Val Ala Val Thr
            660                 665                 670

Thr Val Ser Phe Asp Ile Ala Gly Leu Glu Ile Trp Leu Pro Leu Ile
        675                 680                 685

Thr Gly Ala Arg Val Ile Val Ala Thr Arg Glu Ile Val Val Asp Gly
    690                 695                 700

Glu Arg Leu Thr Thr Leu Leu Asp Lys Ser Gly Ala Thr Val Met Gln
705                 710                 715                 720

Ala Thr Pro Ser Gly Trp Arg Gln Leu Leu Asp Ser Gly Trp Lys Pro
                725                 730                 735

Gly Lys Gly Phe Arg Val Phe Cys Gly Gly Glu Ala Leu Pro Pro Glu
            740                 745                 750
```

-continued

```
Leu Ala Arg Arg Ile Leu Asp Ser Gly Val Glu Leu Trp Asn Leu Tyr
        755                 760                 765

Gly Pro Thr Glu Thr Thr Ile Trp Ser Ala Val His Lys Thr Gln Arg
    770                 775                 780

Leu Gly Ala Ser Asp Ser Ile Val Pro Ile Gly His Pro Ile Asp Asn
785                 790                 795                 800

Thr Gln Leu Tyr Ile Leu Asp Ser Arg Met Glu Pro Val Pro Pro Gly
                805                 810                 815

Val Pro Gly Glu Leu Tyr Ile Gly Gly Ala Gly Leu Ala Arg Gly Tyr
            820                 825                 830

His Arg Asn Pro Glu Leu Thr Arg Glu Lys Phe Arg Glu Trp Arg Asp
        835                 840                 845

Arg Gly Arg Ile Tyr Ser Thr Gly Asp Leu Ala Arg Tyr Arg Ser Asp
    850                 855                 860

Gly Ala Val Glu Cys Leu Gly Arg Val Asp Arg Gln Ile Lys Leu Arg
865                 870                 875                 880

Gly Phe Arg Ile Glu Pro Ala Glu Ile Glu Ala Ala Ile Glu Thr His
                885                 890                 895

Ile Ala Val Lys Gln Ala Ile Thr Val Val Lys Asp Asp Arg Leu Ile
            900                 905                 910

Ala Tyr Leu Val Pro Ala Thr Gly Asp Val Arg Asp Leu Gln Ser Asp
        915                 920                 925

Leu Arg Ser Trp Leu Ala Thr Arg Leu Pro Asp Tyr Met Ile Pro Ser
    930                 935                 940

Ala Phe Val Ser Leu Ser Ser Leu Pro Leu Thr Pro Asn Gly Lys Ile
945                 950                 955                 960

Asp Ala Asn Ala Leu Pro Gly Leu Pro Thr Thr Pro Val Ala Ala Arg
                965                 970                 975

Glu Pro Met Arg Gly Asp Val Val Glu Thr Ile Ala Ser Ile Trp Arg
            980                 985                 990

Glu Val Leu Arg Val Glu His Val Asp Tyr Arg Gln Asn Phe Phe Asp
        995                 1000                1005

Val Gly Gly His Ser Leu Met Leu Thr Arg Val Arg Gly Leu Leu Glu
    1010                1015                1020

Glu Arg Leu Gly Leu Thr Leu Ser Val Val Asp Leu Phe Arg His Thr
1025                1030                1035                1040

Thr Ile Glu Ser Leu Ala Gly Leu Ala Glu Lys Ser Glu Pro Ala Ala
                1045                1050                1055

Ala Glu Pro Ala Ala Ala Val Ala Glu Asp Arg Ile Ala Val Ile Gly
            1060                1065                1070

Met Ala Gly Arg Phe Pro Gly Ala Arg Asn Val Glu Glu Phe Trp Arg
        1075                1080                1085

Asn Leu Arg Asp Gly Val Asp Ser Ile Ala Arg Leu Ser Pro Glu Asp
    1090                1095                1100

Leu Leu Ala Gly Gly Ile Ser Pro Glu Val Phe Gln Asp Pro Ser Tyr
1105                1110                1115                1120

Val Pro Ala Lys Gly Leu Leu Asp Gly Ile Glu Phe Phe Asp Ala Ala
                1125                1130                1135

Phe Phe Gly Tyr Ser Pro Arg Glu Ala Glu Ile Met Asp Pro Gln His
            1140                1145                1150

Arg Val Phe Leu Glu Cys Ala Trp Glu Ala Met Glu Asn Ala Gly Tyr
        1155                1160                1165

Ala Ala Arg Ser Tyr Lys Gly Ser Ile Gly Val Phe Ala Gly Cys Gly
```

-continued 1170 1175 1180

Val Asn Thr Tyr Leu Leu Asn Asn Leu Ala Thr Ala Glu Pro Phe Asp
1185 1190 1195 1200

Phe Ser Arg Pro Ser Ala Tyr Gln Leu Leu Thr Ala Asn Asp Lys Asp
1205 1210 1215

Phe Leu Ala Thr Arg Val Ser Tyr Lys Leu Asn Leu Arg Gly Pro Ser
1220 1225 1230

Leu Thr Val Gln Thr Ala Cys Ser Thr Ser Leu Val Ser Val Val Met
1235 1240 1245

Ala Cys Glu Ser Leu Gln Arg Gly Ala Ser Asp Ile Ala Leu Ala Gly
1250 1255 1260

Gly Val Ala Ile Asn Val Pro Gln Ser Val Gly Tyr Leu His Gln Pro
1265 1270 1275 1280

Gly Met Ile Leu Ser Pro Asp Gly Arg Cys Arg Ala Phe Asp Glu Ser
1285 1290 1295

Ala Gln Gly Thr Val Pro Gly Asn Gly Ala Gly Val Val Val Leu Lys
1300 1305 1310

Arg Leu Ser Arg Ala Leu Ala Asp Gly Asp Thr Ile Tyr Ala Val Ile
1315 1320 1325

Arg Gly Ala Ala Ile Asn Asn Asp Gly Ala Glu Arg Met Gly Phe Thr
1330 1335 1340

Ala Pro Gly Val Asp Gly Gln Thr Arg Leu Ile Arg Arg Thr Gln Glu
1345 1350 1355 1360

Met Ala Gly Val Lys Pro Glu Ser Ile Gly Tyr Ile Glu Ala His Gly
1365 1370 1375

Thr Ala Thr Pro Leu Gly Asp Pro Val Glu Ile Ala Ala Ile Ala Ala
1380 1385 1390

Asn Phe Pro Lys Asn Gly Ser Gly Asp Val Tyr Ile Gly Ser Val Lys
1395 1400 1405

Thr Asn Ile Gly His Leu Asp Val Ala Ala Gly Val Ala Gly Leu Ile
1410 1415 1420

Lys Thr Val Leu Ala Val His Arg Gly Gln Ile Pro Pro Ser Leu Asn
1425 1430 1435 1440

Phe Gln Arg Pro Asn Pro Arg Ile Asp Phe Ala Asn Thr Pro Phe Arg
1445 1450 1455

Val Ser Thr Arg Leu Leu Asp Trp Pro Ala Gly Lys Thr Pro Arg Arg
1460 1465 1470

Ala Ala Val Ser Ser Phe Gly Ile Gly Gly Thr Asn Ala His Val Ile
1475 1480 1485

Leu Glu Gln Ala Pro Pro Val Thr Pro Ala Ala Ala Ala Pro Glu Arg
1490 1495 1500

Ser Ala His Val Leu Cys Leu Ser Ala Asn Thr Asp Ala Ala Leu Glu
1505 1510 1515 1520

Glu Leu Val Arg Ser Tyr Arg Gly His Met Asp Asn Gln Pro Gly Leu
1525 1530 1535

Ser Phe Gly Asp Val Ala Phe Thr Ala Asn Ala Gly Arg Val His Phe
1540 1545 1550

Pro His Arg Ile Cys Ile Val Ala Arg Ser Ser Asp Glu Ala Arg Gln
1555 1560 1565

Arg Leu Thr Glu Ala Arg Arg Val Arg Ile Ala Gln Thr Arg Pro Lys
1570 1575 1580

Ile Ala Phe Leu Phe Thr Gly Gln Gly Ala Gln Tyr Ala Gly Met Gly
1585 1590 1595 1600

-continued

```
Arg Gln Phe Tyr Glu Ser Gln Pro Val Phe Arg Ala Ala Met Asp Glu
               1605                1610                1615

Cys Ala Ala Leu Leu Asn Gly Arg Leu Asp Leu Pro Ala Leu Leu Ala
           1620                1625                1630

Asp Asp Ala Leu Leu Asp Ala Thr Ala Gly Ala Gln Pro Ala Leu Phe
       1635                1640                1645

Ala Leu Gln Trp Ala Leu Ala Gln Leu Trp Lys Ser Trp Gly Val Thr
   1650                1655                1660

Pro Asp Leu Val Met Gly His Ser Val Gly Glu Tyr Ala Ala Ala Cys
1665                1670                1675                1680

Ile Ala Gly Ala Val Ser Leu Pro Asp Ala Leu Gly Leu Val Ala Glu
               1685                1690                1695

Arg Gly Arg Leu Met Gln Asn Leu Pro Glu Gly Ala Met Ala Ala Val
           1700                1705                1710

Ser Ala Gly Glu Gln Arg Cys Ala Ala Ala Ile Thr Ser Arg Val Ser
       1715                1720                1725

Ile Ala Ala Ile Asn Gly Pro Ala Glu Val Val Ile Ser Gly Ala Pro
   1730                1735                1740

Gln Asp Ile Glu Ser Ala Leu Ala Thr Leu Arg Ala Glu Gly Ile Lys
1745                1750                1755                1760

Thr Gln Met Leu Ala Val Ala Arg Ala Phe His Ser Ser Ser Met Asp
               1765                1770                1775

Pro Ile Leu Ala Asp Leu Gln Arg Arg Ala Ala Ala Ile Ala Trp Arg
           1780                1785                1790

Asn Pro Ser Ile Gly Leu Val Ser Asn Leu Thr Gly Lys Leu Ala Gly
       1795                1800                1805

Glu Gly Gln Leu Ala Asn Pro Leu Tyr Trp Arg Asp His Ala Arg Asn
   1810                1815                1820

Pro Val Arg Phe Ala Asp Gly Ile Gln Thr Leu Lys Asp Glu Gly Cys
1825                1830                1835                1840

Asp Val Phe Leu Glu Ile Gly Pro Lys Pro Val Leu Leu Gly Met Gly
               1845                1850                1855

Gln Lys Cys Leu Pro Asp Asp Ala Lys Gln Trp Leu Pro Ser Leu Arg
           1860                1865                1870

Lys Gly Arg Asp Glu Trp Glu Thr Ile Leu Ser Ser Val Ala Thr Leu
       1875                1880                1885

Tyr Gln Gly Gly Phe Asp Ile Asp Trp Gln Glu Phe Asp Arg Pro Tyr
   1890                1895                1900

Ser Arg Arg Arg Val Ala Leu Pro Ala Tyr Pro Phe Glu Arg Arg Arg
1905                1910                1915                1920

His Trp Ile Glu Arg Ser Ser Arg Pro Glu Pro Val Ala Val Ala Ser
               1925                1930                1935

Gly Leu Val Gly Cys Arg Leu Ser Leu Pro Val Ala Asp Val Ile Phe
           1940                1945                1950

Glu Ser Lys Leu Ser Thr Ala Ser Pro Leu Leu Ser Asp His Arg Tyr
       1955                1960                1965

Tyr Gly Ser Val Val Ala Pro Ala Val Tyr Phe Leu Ala Met Ala Leu
   1970                1975                1980

Glu Ala Ser Ala Glu Val Phe Gly Ala Gly Arg His Thr Leu Glu Asn
1985                1990                1995                2000

Val Asn Phe Ala His Pro Leu Ile Leu Ser Ala Glu Arg Asp Thr Ala
               2005                2010                2015
```

-continued

```
Val Gln Leu Val Leu Ser Gln Ser Asp Asp Arg His Ala Ser Phe Arg
            2020                2025                2030

Ile Leu Ser Leu Ser Asp Gly Ser Trp Asn Leu His Ala Ala Gly Asn
        2035                2040                2045

Ile Ala Ala His Ala Gly Val Ala Pro Val Pro Arg Leu Val Asp Glu
    2050                2055                2060

Arg Arg Pro Ala Val Asp Gly Asp Thr Tyr Tyr Ser Leu Leu Arg His
2065                2070                2075                2080

Leu Glu Ile Glu Leu Gly Pro Ser Tyr Arg Arg Ile Gln Arg Ile His
                2085                2090                2095

Phe Gly Glu Gln Glu Ala Leu Ala Ala Ile Asp Ser Ala Thr Pro Leu
            2100                2105                2110

Asn Pro Arg Cys Glu Leu Ala Glu Ala Gly Leu Gln Leu Leu Ser Ala
        2115                2120                2125

Ala Ala Ser Pro Ala Leu Ala Asp Gly Ala Glu His Pro Ile Phe Ala
    2130                2135                2140

Pro Leu Gly Ile Asp Arg Val Cys Phe Tyr Gly Ser Leu Glu Gly Ala
2145                2150                2155                2160

Val Trp Gly Ala Ala Gln Ile Leu Arg His Ser Pro Asp Gly Phe Thr
                2165                2170                2175

Gly Glu Ala Gln Leu Leu Asp Ser Glu Gly Cys Val Leu Gly Glu Leu
            2180                2185                2190

Gln Gly Val Ser Phe Arg Arg Val Thr Arg Ala Trp Ala Gln Arg Ser
        2195                2200                2205

Glu Arg Lys Pro Glu Leu Tyr Glu Val Glu Trp Arg Pro Glu Pro Leu
    2210                2215                2220

Arg Gln Pro Ser Arg Thr Leu Gln Pro Gly Ala Trp Leu Ile Leu Ala
2225                2230                2235                2240

Asp Ser Gly Gly Ala Ala Arg Ala Leu Ala Asp Ala Leu Thr Ala Gln
                2245                2250                2255

Gly Glu Met Cys Val Thr Val Pro Pro Ala Gly Glu Tyr Met Ser Leu
            2260                2265                2270

Val Gly Glu Arg Asp Trp Arg Gly Ile Val Asn Leu Tyr Ser Leu Asp
        2275                2280                2285

Asp Tyr Glu Leu Gly Cys Arg Ser Thr Leu Ala Leu Val Lys Ser Leu
    2290                2295                2300

Lys Ser Gly Pro Arg Leu Trp Leu Val Thr Ala Gly Ala Gln Ala Thr
2305                2310                2315                2320

Ser Ala Val His Asn Pro Met Gln Ala Ala Leu Trp Gly Phe Gly Arg
                2325                2330                2335

Val Ile Ala Arg Glu His Pro Asp Leu Trp Gly Gly Leu Ile Asp Leu
            2340                2345                2350

Asp Pro Asp Asp Ala His Ala Ser Ala Ala Gly Ala Ala Ala Gln Met
        2355                2360                2365

Arg Asp Phe Asp Gly Glu Asp Gln Ser Ala Trp Arg Ser Asn Arg Arg
    2370                2375                2380

Tyr Val Pro Arg Leu Thr Arg Arg Pro Ser Ala Arg Ala Ala Val Arg
2385                2390                2395                2400

Leu Val Ser Gly Ala Thr Tyr Leu Ile Thr Gly Gly Leu Gly Ala Leu
                2405                2410                2415

Gly Leu Thr Val Ala Lys Trp Met Val Glu His Gly Ala Thr Arg Val
            2420                2425                2430

Val Leu Ala Gly Arg Arg Pro Pro Asn Glu Glu Gln Gln Arg Val Leu
```

-continued 2435 2440 2445

Gln Gln Ile Gly Ala Thr Ala Glu Thr Val Asp Val Ser Arg Glu Glu
2450 2455 2460

Glu Val Ala Asp Leu Ile Arg Arg Ile His Thr Glu Thr Ser Pro Leu
2465 2470 2475 2480

Arg Gly Val Ile His Ala Ala Gly Val Leu Asp Asp Gly Val Leu Leu
2485 2490 2495

Asn Gln Asp Trp Thr Arg Ile Ala Ser Val Met Ala Pro Lys Ala Glu
2500 2505 2510

Gly Ala Val His Leu His His His Thr Arg Asp Leu Pro Leu Asp Phe
2515 2520 2525

Phe Val Leu Phe Ser Ser Ala Ser Ser Leu Leu Gly Pro Ala Gly Gln
2530 2535 2540

Ala Gly Tyr Ala Ala Ala Asn Ala Val Leu Asp Ala Leu Ala His His
2545 2550 2555 2560

Arg Arg Gly Leu Gly Leu Pro Ala Thr Ser Ile Asn Trp Gly Arg Trp
2565 2570 2575

Ser Gly Ala Gly Met Ala Ala Arg Thr Ser Gln Ser Met Ala Gly Val
2580 2585 2590

Ala Ser Leu Ser Val Asp Glu Gly Leu His Ile Leu Glu Ala Val Leu
2595 2600 2605

His Glu Cys Pro Ile Gln Ile Ala Ala Leu Pro Ala Gly Ser Ile Thr
2610 2615 2620

Gly Glu Leu Leu Arg Pro Ala Ala Leu Pro Ser Pro Gln Leu Arg Thr
2625 2630 2635 2640

Arg Leu Asn Glu Ala Thr Pro Arg Gln Arg Glu Ala Ile Leu Ile Ala
2645 2650 2655

His Ile Arg Glu Ser Leu Ala Arg Phe Val Gly Ile Ala Thr Ser Thr
2660 2665 2670

Pro Leu Asp Pro Gln Gln Pro Leu Gly Glu Leu Gly Leu Asp Ser Leu
2675 2680 2685

Met Ala Ile Glu Leu Arg Asn Ser Leu Ser Gln Ser Leu Gly Gln Pro
2690 2695 2700

Leu Pro Ala Ser Leu Leu Phe Asp Tyr Pro Ser Leu Asp Ala Ile Val
2705 2710 2715 2720

Ser Tyr Val Leu His Ala Val Phe Pro Pro Glu Ala Ser Pro Val Glu
2725 2730 2735

Ala Pro Glu Phe Glu Asn Leu Ala Arg Glu Glu Leu Glu Ala Leu Leu
2740 2745 2750

Asp Ser Arg Leu Ala Gln Val Asp Gln Trp Leu Glu Thr Gln
2755 2760 2765

<210> SEQ ID NO 123
<211> LENGTH: 1763
<212> TYPE: PRT
<213> ORGANISM: Unknown organism
<220> FEATURE:
<223> OTHER INFORMATION: Origin of the sequence: Undetermined bacterium

<400> SEQUENCE: 123

Met Ser Gly Ser Asp Asp Leu Ser Lys Leu Arg Arg Ala Val Ile Ala
1 5 10 15

Leu Asp Lys Val Gln Lys Arg Ile Asp Gln Leu Glu Ser Ala Arg Ser
20 25 30

Glu Pro Ile Ala Leu Ile Gly Ala Gly Cys Arg Phe Pro Gly Ala Ser

-continued

```
        35                  40                  45

Asn Leu Asp Ala Tyr Trp Ser Leu Leu Arg Glu Gly Arg Ser Ala Val
    50                  55                  60

Arg Glu Val Pro Pro Asp Arg Trp Asp Ile Asp Ala Tyr Tyr Asp Pro
65                  70                  75                  80

Asp Pro Gly Ala Thr Gly Arg Met Tyr Thr Arg Tyr Gly Gly Phe Ile
                85                  90                  95

Asp Gln Val Asp Arg Phe Asp Ala Arg Phe Phe Gly Ile Ala Pro Arg
            100                 105                 110

Glu Ala Ile Ser Leu Asp Pro Gln Gln Arg Leu Leu Leu Glu Val Thr
        115                 120                 125

Trp Glu Ala Ile Glu Asn Ala Gly Leu Pro Pro Asp Arg Leu Ala Gly
    130                 135                 140

Ser Arg Thr Gly Val Phe Met Gly Ile Phe Ser Asn Asp Tyr Tyr Asn
145                 150                 155                 160

Leu Gln Met Arg Gly Gly Asp Ala His Ile Asp Ala Tyr Thr Gly Thr
                165                 170                 175

Gly Asn Thr Ala Ser Val Ala Ala Gly Arg Leu Ser Tyr Ile Leu Gly
            180                 185                 190

Leu Gln Gly Pro Asn Met Ala Ile Asp Thr Ala Cys Ser Ser Ser Leu
        195                 200                 205

Val Ala Val His Leu Ala Cys Gln Ser Leu Arg Ser Gly Glu Ser Asp
    210                 215                 220

Leu Ala Leu Ala Gly Gly Val Asn Leu Ile Leu Ser Pro Asp Arg Thr
225                 230                 235                 240

Ile Tyr Phe Cys Lys Leu Lys Ala Met Ala Ala Asp Gly Arg Cys Lys
                245                 250                 255

Ala Phe Asp Ala Ala Ala Asp Gly Tyr Val Arg Gly Glu Gly Cys Gly
            260                 265                 270

Val Val Val Leu Lys Arg Leu Ser Asp Ala Leu Arg Asp Arg Asp Pro
        275                 280                 285

Val Met Ala Val Ile Arg Gly Thr Ala Ile Asn Gln Asp Gly Arg Ser
    290                 295                 300

Asn Gly Leu Thr Ala Pro Asn Gly Pro Ala Gln Glu Ala Val Ile Arg
305                 310                 315                 320

Gln Ala Val Gly Asp Ala Arg Leu Gln Thr Leu Asp Val Ser Tyr Val
                325                 330                 335

Glu Ala His Gly Thr Gly Thr Pro Leu Gly Asp Pro Ile Glu Ala Gly
            340                 345                 350

Ala Leu Ala Ala Ala Leu Gly Ala Gly Arg Thr Asn Gly Asn Lys Leu
        355                 360                 365

Lys Leu Gly Ser Val Lys Thr Asn Phe Gly His Leu Glu Ala Ala Ala
    370                 375                 380

Gly Val Ala Ala Leu Ile Lys Val Ala Leu Met Leu Gln Asn Glu Ala
385                 390                 395                 400

Ile Pro Pro His Leu Asn Leu Thr Thr Pro Ser Pro His Ile Asp Trp
                405                 410                 415

Asn Thr Leu Pro Leu Glu Ile Pro Ala Arg Leu Thr Pro Trp Pro Val
            420                 425                 430

Ala Pro Gly Gly Arg Arg Val Ala Gly Ile Asn Ser Phe Gly Leu Ser
        435                 440                 445

Gly Thr Asn Ala His Val Leu Ile Glu Gln Ala Pro Gln Gln Ala Ala
    450                 455                 460
```

-continued

```
Ser Ser Thr Pro Ala Pro Tyr Leu Leu Pro Leu Ser Ala Arg Ser Pro
465                 470                 475                 480

Glu Ala Leu Arg Asp Leu Ala Arg Ala Tyr Arg Asp Val Val Asn Asp
                485                 490                 495

Asn Pro Ala Asp Thr Cys Tyr Thr Ala Cys Ala Arg Arg Thr Ser Tyr
            500                 505                 510

Glu His Arg Ala Ala Phe Thr Gly Thr Asn Ala Gln Asp Leu Met Ala
        515                 520                 525

Gly Leu Asp Ser Phe Leu Ala Gly Asn Pro Asn Arg Asp Thr Ala Thr
    530                 535                 540

Gly Phe Val Pro Arg Gly Gln Lys Arg Lys Val Val Phe Val Leu Pro
545                 550                 555                 560

Gly Gln Gly Ser Gln Trp Pro Gly Met Gly Arg Asp Leu Met Ala Ser
                565                 570                 575

Glu Pro Val Phe Arg Ala Ala Ile Glu Glu Cys Gly Arg Ala Met Gln
            580                 585                 590

Pro Tyr Val Asp Trp Ser Leu Thr Gln Glu Leu Gln Gly Pro Leu Asp
        595                 600                 605

Arg Ile Asp Val Ile Gln Pro Ala Leu Phe Ala Val Gly Val Ala Leu
    610                 615                 620

Ala Gly Leu Trp Arg His Trp Gly Ile Glu Pro Asp Ala Val Ile Gly
625                 630                 635                 640

His Ser Met Gly Glu Val Ala Ala Ala His Ile Ala Gly Ala Leu Thr
                645                 650                 655

Leu Asp Glu Ala Ala Arg Val Ile Cys Leu Arg Ser Arg Met Leu Ala
            660                 665                 670

Gly Val Arg Gly Gln Gly Glu Met Ala Val Val Glu Leu Ala Leu Asp
        675                 680                 685

Glu Ala Ile Ala Ala Ile Ala Gly Arg Ser Asp Arg Val Ser Ile Ala
    690                 695                 700

Ala Ser Asn Ser Pro Arg Ser Thr Val Leu Ser Gly Asp Ser Ala Ala
705                 710                 715                 720

Leu Gly Glu Leu Leu Arg Glu Leu Glu Ala Lys Asp Val Phe Cys Arg
                725                 730                 735

Arg Val Lys Val Asp Ile Ala Ser His Ser His Leu Met Asp Ser Val
            740                 745                 750

Cys Ala Ala Leu Pro Gly Val Val Gly Ala Leu Gln Pro Arg Pro Ala
        755                 760                 765

Ala Leu Gly Met Tyr Ser Thr Val Thr Gly Ala Ala Ile Ser Gly Glu
    770                 775                 780

Glu Leu Val Ser Ala Tyr Trp Ala Arg Asn Leu Arg Gln Pro Val Met
785                 790                 795                 800

Leu Ser Thr Ala Val Ala Ala Ala Ala Ala Gly Gly His Asp Val Phe
                805                 810                 815

Leu Glu Leu Ser Pro His Pro Leu Leu Val Gln Pro Ile Gln Glu Thr
            820                 825                 830

Leu Gly Asp Arg Ala Ala Ile Ala Ala Ala Ser Leu Arg Arg Asp Glu
        835                 840                 845

Asp Gly Asn Leu Ala Leu Arg Arg Thr Leu Gly Ala Leu Leu Thr Asn
    850                 855                 860

Gly Val Thr Pro Asp Trp Ser Arg Ile Tyr Pro Asn Gly Gly Gln Thr
865                 870                 875                 880
```

-continued

```
Arg Arg Leu Pro Asn Tyr Pro Trp Gln Arg Glu Arg Tyr Trp Ile Asp
                885                 890                 895

Ile Arg Pro Pro Gln Val Glu Ser Gln Ala Leu Pro Gly Arg Arg Ile
            900                 905                 910

Pro Ser Pro Leu Pro Glu Met Gln Phe Glu Ser Thr Val Glu Ala Lys
        915                 920                 925

Asp Phe Ala Asp His Arg Leu His Asp Val Ile Val Thr Pro Gly Ala
    930                 935                 940

Trp His Leu Ala Met Ala Leu Ala Ala Ala Arg Gln Gly Leu Gly Ala
945                 950                 955                 960

Gly Pro His His Val Glu His Val Ser Leu Thr Gly Ala Leu Thr Leu
                965                 970                 975

Pro Glu Asn Asp Ala Ala Arg Gln Val Gln Leu Val Leu Arg His Glu
            980                 985                 990

Glu Gly Gly Gly Ala Ser Phe Arg Ile Tyr Ser Arg Glu Asp Ser Trp
        995                 1000                1005

Lys Leu His Ser Glu Gly Met Leu Gln Ala Gly Asp Ser Thr Ala Ser
   1010                1015                1020

Ile Asp Leu Asp Ala Ile Arg Ala Arg Cys Thr Ala Glu Leu Thr Ala
1025                1030                1035                1040

Asp Ala Phe Tyr Ser Arg Leu Trp Asp Arg Gly Tyr His Phe Gly Pro
               1045                1050                1055

Thr Phe Arg Thr Ile Gly Pro Ile Trp Arg Gly Asn Gly Glu Val Leu
           1060                1065                1070

Cys Arg Val Asp Ile Pro Leu Thr Glu Met Gln Thr Ile Asp Cys Cys
       1075                1080                1085

Leu Gln Leu Pro Ala Ala Leu Val His His Asp Asp Leu Lys Asp Val
   1090                1095                1100

His Val Pro Val Gly Leu Asp Arg Phe Ser Leu Ala Glu Val Pro Thr
1105                1110                1115                1120

Gly Pro Val Trp Gly Tyr Ala Val Leu Arg Pro Asp Ser Thr Val Asp
               1125                1130                1135

Val Arg Leu Val Thr Gly Thr Gly Ser Val Val Ala Glu Leu Val Gly
           1140                1145                1150

Leu Gln Ser Arg Val Ala His Ser Gly Gln Leu Gly Glu Ser Glu Ile
       1155                1160                1165

Pro Thr Trp Thr Val Gln Trp Thr Ala Ser Val Arg Arg Gly Asp Ala
   1170                1175                1180

Asn Ala Gly Asn Ala Gly Gly Pro Trp Leu Val Ile Gly Glu Pro Ala
1185                1190                1195                1200

Ile Ala Glu Thr Leu Gln Lys Arg Gly Gln Thr Cys Arg Thr Ala Asp
               1205                1210                1215

Thr Cys Ser Gly Pro Pro Cys Arg Gln Ile Val Tyr Cys Pro Ser Pro
           1220                1225                1230

Arg Ile Asp Asp Leu Leu Ser Val Leu Arg Ser Ile Val Gln Ala Gly
       1235                1240                1245

Trp Pro Glu Pro Pro Arg Leu Trp Leu Leu Thr Arg Gly Ser Ala Ala
   1250                1255                1260

Val Leu Asn Ser Asp Lys Asp Ile Asp Ile Arg Gln Ala Trp Leu His
1265                1270                1275                1280

Gly Ile Gly Arg Thr Ile Ala Tyr Glu His Pro Glu Leu Arg Cys Thr
               1285                1290                1295

Leu Val Asp Leu Asp Ala His Ser Asn Asp Cys Gly His Leu Ala Thr
```

-continued

```
1300 1305 1310

Leu Met Leu Ser Asn Ile Ala Glu Asp Gln Val Ala Ile Arg Gln Gly
        1315                1320                1325

Thr Val Trp Ala Pro Arg Leu Ser Leu His Lys Ile Pro Ser Ala Pro
    1330                1335                1340

Asp Val Ala Phe Arg Ala Asp Ala Thr Tyr Leu Ile Thr Gly Gly Leu
1345                1350                1355                1360

Gly Gly Leu Gly Leu Gln Val Ala Gly Trp Leu Ala Ala Ala Gly Ala
                1365                1370                1375

Arg His Leu Val Leu Leu Gly Arg Ser Glu Arg Pro Arg Pro Gln Leu
            1380                1385                1390

Glu Gly Val Asn Val Lys Ile Ile His Ala Asp Val Ala Asp Arg Gln
        1395                1400                1405

Gln Leu Ser Asp Ala Leu Ala Ile Ile Asp Arg Asp Met Pro Pro Leu
    1410                1415                1420

Arg Gly Val Phe His Leu Ala Gly Thr Leu Ala Asp Gly Met Leu Leu
1425                1430                1435                1440

Asn Leu Thr Thr Glu Arg Phe Glu Ala Ala Met Ala Pro Lys Val Ala
                1445                1450                1455

Gly Ala Trp Asn Leu His Glu Leu Thr Ala Gly Arg Pro Leu Asp His
            1460                1465                1470

Phe Val Leu Phe Ser Ser Ala Ser Ala Thr Val Gly Ser Pro Gly Gln
        1475                1480                1485

Gly Asn Tyr Ala Ala Gly Asn Ser Phe Leu Asp Ala Leu Ala His Leu
    1490                1495                1500

Arg Arg Ala Gln Gly Leu Pro Ala Val Ser Ile Ala Trp Gly Pro Trp
1505                1510                1515                1520

Thr Gln Val Gly Leu Ala Ala Gln Ala Asn Arg Gly Asp Arg Leu Ala
                1525                1530                1535

Ala Arg Gly Ile Ser Val Ile Gln Pro Gln Gln Gly Leu Arg Ala Leu
            1540                1545                1550

Tyr Lys Ala Leu Thr Gln Ile Arg Pro His Val Ala Val Met Asn Phe
        1555                1560                1565

Asp Ile Ala Gln Trp Leu Arg Tyr Tyr Pro Ser Ala Ala Ser Met Ser
    1570                1575                1580

Leu Leu Ala Gly Ile Ala Pro Ala Ala Ala Asp Thr Lys Pro Ala Ala
1585                1590                1595                1600

Asp Met Arg Ser Glu Leu Leu Ala Val Pro Ala Gly Arg Gln Arg Arg
                1605                1610                1615

Ala Arg Leu Glu Thr Leu Leu Met His Glu Ala Gly His Val Leu Arg
            1620                1625                1630

Phe Asp Pro Ala Lys Leu Asp Gly Arg Ala Thr Leu Gly Asp Leu Gly
        1635                1640                1645

Phe Asp Ser Leu Met Ala Leu Glu Phe Arg Asn Arg Leu Glu Ala Gly
    1650                1655                1660

Leu Arg Val Lys Leu Ser Ala Thr Leu Ile Trp Arg Tyr Pro Thr Phe
1665                1670                1675                1680

Ser Ala Leu Ala Gln His Leu Ala Asp Lys Leu Gly Leu Pro Leu Glu
                1685                1690                1695

Ser Met Ala Gly Asn Ala Glu Pro Ser Thr Val Ala Ala Val Ala Thr
            1700                1705                1710

Leu Ala Thr Val Gly Thr Ala Ala Gly Glu Asp Arg Ser Pro Ala Ala
        1715                1720                1725
```

-continued

```
Ala Asp Asp Leu Asp Ala Val Ala Asn Gln Ile Ala Gly Leu Gly Asp
   1730                1735                1740

Lys Glu Ile Glu Ala Leu Leu Lys Gln Lys Phe Ala His Phe Ser Gly
1745               1750                1755                1760

Ala Ser Glu
```

<210> SEQ ID NO 124
<211> LENGTH: 2153
<212> TYPE: PRT
<213> ORGANISM: Unknown organism
<220> FEATURE:
<223> OTHER INFORMATION: Origin of the sequence: Undetermined bacterium

<400> SEQUENCE: 124

```
Met Ser Ser Ile Ser Glu Arg Phe Pro Asn Leu Thr Pro Leu Gln Gln
  1               5                  10                  15

Ala Tyr Leu Thr Leu Glu His Met Gln Arg Arg Leu Asp Ala Ala Glu
            20                  25                  30

Arg Asp Ala Arg Glu Pro Ile Ala Ile Val Gly Leu Gly Cys Arg Phe
        35                  40                  45

Pro Gly Gly Asp Gly Pro Asp Glu Phe Trp Gln Met Leu Arg Ser Gly
     50                  55                  60

Val Asp Ala Ile Arg Glu Val Pro Pro Gly Arg Trp Asp Glu Glu Ser
 65                  70                  75                  80

Val Arg Arg Ile Leu Lys Ser Leu Asn Pro Ala Thr Pro Val Lys Ile
                85                  90                  95

Gln Ala Gly Phe Leu Asp Ser Ile Asp Gly Phe Asp Asn Asp Phe Phe
            100                 105                 110

Gly Ile Ser Pro Arg Glu Ala Val Ser Ile Asp Pro Gln Gln Arg Leu
        115                 120                 125

Leu Leu Glu Val Ala Trp Glu Ala Leu Glu Asp Ala Gly Gln Thr Met
    130                 135                 140

Glu Gly Leu Ser Gly Ser Arg Thr Gly Val Phe Val Gly Ile His Ser
145                 150                 155                 160

Gln Ser Ser Asp Tyr Phe Trp Met Gln Thr Ala Asp Gly Ala Arg Ile
                165                 170                 175

Asp Pro Tyr Thr Ala Thr Gly Thr Ala His Ser Val Ile Ala Gly Arg
            180                 185                 190

Leu Ser Tyr Leu Leu Asn Leu Gln Gly Pro Ser Ile Ala Leu Asp Thr
        195                 200                 205

Ala Cys Ser Ser Ser Leu Ala Ala Val His Leu Ala Cys Gln Ser Leu
    210                 215                 220

Arg Ser Gly Glu Cys Thr Leu Ala Val Ala Gly Gly Val Asn Leu Arg
225                 230                 235                 240

Phe Ser Pro Glu Phe Met Tyr Ala Thr Ser Lys Met Gly Thr Ala Ser
                245                 250                 255

Pro Ser Gly Arg Cys Arg Ala Phe Asp Ala Ala Ala Asp Gly Ile Val
            260                 265                 270

Phe Gly Glu Gly Cys Gly Val Val Val Leu Lys Arg Leu Ser Asp Ala
        275                 280                 285

Leu Ala Ala Gly Asp Arg Val Trp Ala Val Val Arg Gly Ser Ala Val
    290                 295                 300

Asn Gln Asp Gly Arg Ser Ala Gly Leu Thr Ala Pro Asn Val Val Ser
305                 310                 315                 320
```

-continued

```
Gln Gln Val Val Ile Arg Ser Ala Leu Ala Asn Ala Gly Val Ala Ala
                325                 330                 335

Gln Gln Ile Gly Tyr Ile Glu Ala His Gly Thr Gly Thr Pro Leu Gly
            340                 345                 350

Asp Pro Ile Glu Ile Glu Ala Leu Ala Glu Thr Val Gly Leu Pro Arg
        355                 360                 365

Pro Val Gly Asp Val Cys Ala Val Gly Ser Leu Lys Ser Asn Ile Gly
    370                 375                 380

His Leu Glu Gly Ala Ala Gly Ile Ala Gly Leu Ile Lys Ala Val Leu
385                 390                 395                 400

Ala Leu Ser His Glu Thr Ile Pro Pro Ser Leu His Val Arg Gln Leu
                405                 410                 415

Asn Pro Asn Ile Arg Leu Glu Gly Thr Ser Leu Asp Ile Val Lys Glu
            420                 425                 430

Val Arg Pro Trp Pro Ala Gly Ser Arg Arg Arg Phe Ala Gly Val Ser
        435                 440                 445

Ala Phe Gly Trp Ser Gly Thr Asn Ala His Val Val Leu Glu Glu Ala
    450                 455                 460

Ala Pro Thr Gly Arg Gly Glu Ala Ala Ser Gly Phe His Ser Arg Pro
465                 470                 475                 480

Pro Ala Ala Ala Ala Arg Ala Ala Val Pro Leu Ala Glu Gly Asp Thr
                485                 490                 495

Gly Gly Thr Pro Asp Ile Ala Gly Thr Pro Asp Thr Ala Asp Thr Pro
            500                 505                 510

Asp Thr Ala Asp Thr Pro Asp Ile Ala Gly Thr Ala Gly Thr Ala Ala
        515                 520                 525

Thr Thr Gly Ile Ala Asp Ala Met Tyr Val Leu Pro Leu Ser Ala His
    530                 535                 540

Gly Ala Asp Glu Leu Arg Arg Val Ala Arg Ala Tyr Gly Glu Leu Leu
545                 550                 555                 560

Thr Ala Ser His Ala Pro Ser Leu Arg Asp Leu Cys Tyr Thr Ala Ala
                565                 570                 575

Val Arg Arg Thr His His Arg Cys Arg Leu Ala Val Ser Gly Arg Thr
            580                 585                 590

Ala Glu Glu Leu Ala Ala Gln Leu Gln Gly Ile Thr Ile Pro Ser Gln
        595                 600                 605

Arg Arg Lys Thr Val Phe Val Phe Ser Gly Gln Gly Ser Gln Trp Ile
    610                 615                 620

Gly Met Gly Arg Ser Trp Met Asp Arg Glu Pro Val Ile Arg Glu Ala
625                 630                 635                 640

Leu Glu Arg Cys Glu Ala Ala Met Arg Pro Tyr Val Asp Trp Ser Leu
                645                 650                 655

Lys Glu Glu Leu Ala Lys Leu Asp Arg Val Glu Val Ile Gln Pro Ala
            660                 665                 670

Leu Phe Ala Leu Gln Val Ala Ile Ala Ala Leu Trp Arg Ser Trp Gly
        675                 680                 685

Ile Glu Pro Asp Ala Val Ile Gly His Ser Met Gly Glu Val Ala Ala
    690                 695                 700

Ala His Val Ala Gly Ala Leu Thr Leu Gln Asp Ala Ala Arg Ile Ile
705                 710                 715                 720

Cys Ser Arg Ser Arg Leu Leu Ser Arg Ile Ser Gly Leu Gly Gly Met
                725                 730                 735

Ala Met Val Glu Leu Pro Leu Ala Glu Cys Glu Ala Val Leu Ser Thr
```

-continued

```
            740                 745                 750
Tyr Thr Glu Arg Leu Ser Pro Ala Val Ser Asn Gly Pro Asn Ser Thr
        755                 760                 765
Val Ile Ser Gly Glu Val Glu Ala Leu Ala Glu Val Val Ala Thr Leu
    770                 775                 780
Glu Arg Arg Gly Val Ser Cys Arg Pro Val Lys Val Asp Phe Ala Ala
785                 790                 795                 800
His Ser Pro Gln Val Asp Pro Leu Cys Asp Glu Leu Leu Gln Ser Leu
                805                 810                 815
Asp Gly Ile Gln Pro Arg Pro Ala Thr Ile Pro Phe Tyr Ser Thr Val
            820                 825                 830
Thr Gly Ala Thr Leu Glu Thr Thr Ser Leu Asp Ser Thr Tyr Trp Ala
        835                 840                 845
Arg Asn Leu Arg Ser Pro Val Leu Phe Trp Gln Gly Ile Arg His Leu
    850                 855                 860
Ala Asp Ser Gly His Asp Val Phe Leu Glu Ile Ser Pro His Pro Ile
865                 870                 875                 880
Leu Leu Pro Ala Ile Gly Gly Asn Ala Ala Leu Val Pro Ser Leu Arg
                885                 890                 895
Arg Asp Gln Asp Glu Arg Gly Ser Met Leu Thr Ser Leu Gly Ala Leu
            900                 905                 910
Tyr Glu Ala Gly His Thr Val Ala Trp Arg Thr Val Tyr Pro Ser Gly
        915                 920                 925
Asn Cys Val Arg Leu Pro Arg Tyr Pro Trp Gln Arg Arg Arg Phe Trp
    930                 935                 940
Leu Asp Ala Ser Pro Ala Arg His Ala Ile Thr Leu Gly Asn Pro Leu
945                 950                 955                 960
Leu Gly Lys Arg Val Glu Ala Ser Thr Gln Pro Gly Thr Phe Phe Trp
                965                 970                 975
Glu Thr Glu Leu Ser Leu Ala Ser Val Pro Trp Leu Ala Asp His Arg
            980                 985                 990
Val Gln Gly Glu Val Val Leu Pro Ala Thr Ala Tyr Leu Asp Met Ala
        995                 1000                1005
Leu Ala Gly Thr Ser Glu Thr Phe Gly Glu Ser Pro Cys Val Leu Glu
   1010                 1015                1020
His Val Thr Phe Thr Gln Met Leu Ile Val Pro Arg Asp Gly Ser Met
1025                1030                1035                1040
Thr Leu Gln Leu Ala Ile Ala Val Asp Arg Pro Gly Met Ala Ser Phe
               1045                1050                1055
Arg Ile Ser Ser Arg Gln Ala Ser Thr Trp Val Leu His Ala Ser Gly
           1060                1065                1070
Asp Ile Arg Gln Thr Pro Ala Asp Ala Ser Thr Val Pro Pro Asp Ser
       1075                1080                1085
Ala Glu Thr Val Gln Ala Arg Cys Pro Thr Val Val Pro Ala Ala Glu
   1090                1095                1100
Leu Trp Arg Gln Met Ala Glu His Gly Val Glu Tyr Gly Pro Ala Phe
1105                1110                1115                1120
Arg Ala Leu Glu Gln Ile Trp Ser Cys Pro Gly Glu Ala Ile Gly Arg
               1125                1130                1135
Leu Arg Ser Ser Glu Thr Arg Ser Thr Ala Pro Ala Phe Leu Asp Ala
           1140                1145                1150
Cys Leu Gln Ile Ile Ala Ala Ala Phe Gly Pro Ala Gly Gly Thr Trp
       1155                1160                1165
```

-continued

```
Leu Pro Ala Gly Ile Asp Arg Met Arg Trp Leu His Pro Ala Arg Ser
   1170                1175                1180

Val Val Trp Thr His Ala Arg Leu Glu Gly Pro Ile Ala Asp Leu Ser
1185                1190                1195                1200

Leu Leu Asp Gly Glu Gly Gln Leu Val Ala Arg Ile Glu Gly Leu Arg
               1205                1210                1215

Leu Gln Arg Leu Asp Ala Ser Glu Arg Ile Asp Met Arg Gly Trp Leu
           1220                1225                1230

His Glu Leu Arg Trp Val Ala Gln Pro His Ala Ala Ala Glu Pro Pro
       1235                1240                1245

Ala Ala Arg Ala Ala Arg Ser Trp Leu Ile Val Gly Ala Val Asp Ser
   1250                1255                1260

Ala Leu Thr Ala Trp Leu Arg Ala Thr Gly Asn Arg Val Thr Gln Thr
1265                1270                1275                1280

Ser Pro Glu Lys Leu Asp Glu Leu Gln Pro Pro Leu Glu Glu Ile Val
               1285                1290                1295

Phe Leu Leu Glu His Glu Pro Ser Cys Asp Arg Ile Leu His Leu Leu
           1300                1305                1310

Gln Thr Leu Gly Arg Thr Pro Trp Arg Gln Ala Pro Arg Leu Trp Leu
       1315                1320                1325

Val Thr Arg Gly Ala Gln Pro Val Asp Gly Gln Ile Leu Gln Ala Gly
   1330                1335                1340

Ile Ala Gln Ala Pro Phe Trp Gly Leu Gly Arg Thr Val His Tyr Glu
1345                1350                1355                1360

His Pro Glu Leu Asn Cys Thr Leu Ile Asp Leu Asp Pro Ala Gly Gly
               1365                1370                1375

Glu Glu Glu Leu Leu His Glu Leu Leu Thr Asn Asn Gly Glu Asn Gln
           1380                1385                1390

Ile Ala Phe Arg Gly Gly Ala Arg Tyr Val Ala Arg Val Ala Arg His
       1395                1400                1405

Glu Ala Asp Met Gln Pro Ala Met Phe Lys Ala Gly Asp Arg Pro Phe
   1410                1415                1420

Arg Leu Glu Ile Asp Ala Pro Gly Val Leu Asp Arg Leu Arg Leu Arg
1425                1430                1435                1440

Ala Thr Ser Arg Arg Pro Pro Gln Ala Gly Glu Val Glu Ile Glu Val
               1445                1450                1455

Cys Ala Ala Gly Leu Asn Phe Leu Asp Val Leu Leu Ala Leu Gly Val
           1460                1465                1470

Met Pro Asp Asp Ala Pro Gly Ala Ile Ala Gly Ser Pro Arg Leu Gly
       1475                1480                1485

Gly Glu Cys Ser Gly Arg Ile Val Ala Met Gly Lys Gly Val Thr Asp
   1490                1495                1500

Phe Arg Ile Gly Asp Glu Val Val Ala Leu Ala Pro Cys Ser Phe Gly
1505                1510                1515                1520

Arg Phe Val Thr Thr Pro Ala Phe Arg Val Ala Leu Lys Pro Ala Asn
               1525                1530                1535

Ile Pro Ala Glu Gln Ala Ala Ala Leu Pro Ile Ala Phe Leu Thr Ala
           1540                1545                1550

Asp Tyr Ala Leu Ser Arg Ala Ala Arg Leu Ala Pro Gly Glu Arg Val
       1555                1560                1565

Leu Ile His Ala Ala Thr Gly Gly Val Gly Leu Ala Ala Ile Gln Ile
   1570                1575                1580
```

-continued

Ala Gln Arg Ala Gly Ala Glu Ile Phe Ala Thr Ala Gly Ser Pro Glu
1585 1590 1595 1600

Lys Arg Ala Tyr Leu Arg Ser Leu Gly Ile Ala His Val Ser Asp Ser
1605 1610 1615

Arg Ser Met Ala Phe Val Asp Asp Ile Arg Asn Trp Thr Asn Gln Glu
1620 1625 1630

Gly Val Asp Val Val Leu Asn Ser Leu Ser Gly Asp Leu Leu Glu Ala
1635 1640 1645

Ser Phe Asp Leu Leu Arg Asp His Gly Arg Phe Ile Glu Ile Gly Lys
1650 1655 1660

Arg Asp Tyr Tyr Ala Gly Arg Lys Leu Gly Leu Arg Pro Phe Leu Lys
1665 1670 1675 1680

Asn Leu Ser Tyr Thr Leu Val Asp Leu Leu Gly Met Ser Leu Lys Arg
1685 1690 1695

Pro Ala Leu Thr Arg Glu Leu Leu Gln Glu Met Val Ala Lys Phe Glu
1700 1705 1710

Ser Glu Thr Trp Arg Pro Leu Glu Thr Arg Val Thr Thr Ile Thr Glu
1715 1720 1725

Ser Val Glu Ala Phe Arg Thr Met Ala Gln Ala Arg His Ile Gly Lys
1730 1735 1740

Ile Val Met Ala Met Arg Asp Cys Ala Asn Ala Pro Ile Ala Pro Leu
1745 1750 1755 1760

Arg Ser Ala Phe Asp Ser Glu Gly Thr Tyr Leu Ile Thr Gly Gly Leu
1765 1770 1775

Gly Gly Leu Gly Leu Thr Val Ala Arg Trp Met Ile Gly Arg Gly Ala
1780 1785 1790

Arg Arg Leu Val Leu Leu Ser Arg Arg Ala Pro Ser Pro Glu Val Gln
1795 1800 1805

Gln Ala Ile Ala Val Met Asp Ala Asp Val Arg Thr Val Gln Ala Asp
1810 1815 1820

Val Ser Gln Arg Asp Glu Leu Glu Arg Val Ile Ser Ser Ile Asp Arg
1825 1830 1835 1840

Leu Arg Gly Val Ile His Ala Ala Ala Val Leu Asp Asp Ala Leu Leu
1845 1850 1855

Leu Asn Gln Thr Glu Ala His Phe Arg Asn Val Met Ala Ala Lys Ile
1860 1865 1870

Asp Gly Ala Trp Asn Leu His Leu Leu Thr Arg Asp Cys Pro Leu Asp
1875 1880 1885

His Phe Val Leu Phe Ser Ser Ala Ala Gly Leu Leu Gly Ala Pro Ala
1890 1895 1900

Gln Gly Asn Tyr Ala Ala Ala Asn Ala Phe Leu Asp Ala Leu Ala Tyr
1905 1910 1915 1920

Tyr Arg Lys Ala Gln Gly Leu Pro Ala Leu Ser Ile Gly Trp Gly Ala
1925 1930 1935

Trp Ser Glu Val Gly Leu Ala Ala Ala Gln Asp Asn Arg Gly Ser Arg
1940 1945 1950

Leu Ala Leu Arg Gly Met Glu Asn Leu Thr Pro Gln His Gly Leu Ala
1955 1960 1965

Ile Leu Glu Gln Leu Leu Asn Ser Ser Ala Cys His Val Ala Ala Met
1970 1975 1980

Pro Ile Asn Val Arg Gln Trp Arg Gln Phe Tyr Pro Lys Ala Ala Gln
1985 1990 1995 2000

Ser Ala Leu Phe Glu Leu Leu His Asp Asp Ala Ala Ser Glu Ala Asp

-continued

```
            2005                2010                2015

Ala Pro Asn Ala Leu Arg Ala Arg Leu Gln Ser Ala Glu Pro Gln Thr
        2020                2025                2030

Arg Arg Thr Leu Leu Glu Glu His Leu Gln Gln Gln Leu Ala Arg Val
    2035                2040                2045

Leu Arg Ile Asp Ser Gln Thr Ile Asp Pro Leu Arg Pro Leu Lys Glu
   2050                2055                2060

Leu Gly Phe Asp Ser Leu Met Ala Leu Glu Phe Arg Asn Arg Leu Glu
2065                2070                2075                2080

Leu Thr Leu Gly Leu Thr Leu Pro Ala Thr Leu Ile Trp Gly His Pro
            2085                2090                2095

Thr Leu Ala Gly Leu Ala Pro His Leu Ala Ser Gln Met Gly Leu Pro
        2100                2105                2110

Leu Val Glu Ala Gln Ala Ala Ala Ala Ala Glu Gly Asp Ser Arg Ala
    2115                2120                2125

Met Lys Thr Ala Leu Ser Gly Leu Asp Asp Met Ser Glu Glu Ala Ala
   2130                2135                2140

Val Ala Ala Leu Arg Gly Ala Arg Ser
2145                2150


<210> SEQ ID NO 125
<211> LENGTH: 1695
<212> TYPE: PRT
<213> ORGANISM: Unknown organism
<220> FEATURE:
<223> OTHER INFORMATION: Origin of the sequence: Undetermined bacterium

<400> SEQUENCE: 125

Met Arg Glu Lys Ile Ala Pro Met Ser Ser Val Lys Leu Ala Leu Leu
  1               5                  10                  15

Ala Arg Asn Met Arg Gln Asn Ile Ala Gly Phe Asp Leu Val His Ala
            20                  25                  30

Glu Pro Ile Ala Ile Val Gly Met Ala Cys Arg Phe Pro Gly Gly Ala
        35                  40                  45

Lys Asn Pro Asp Ala Phe Trp Thr Leu Leu Lys Asn Gly Val Asp Gly
     50                  55                  60

Val Thr Glu Val Pro Pro Asp Arg Trp Asn Ser Asp Gln Tyr Tyr Ser
 65                  70                  75                  80

Ser Asp Pro Asp Ala Pro Gly Lys Ala Tyr Ala Arg Tyr Ala Ala Phe
                 85                  90                  95

Leu Glu Arg Ile Asp Gly Phe Asp Ala Glu Phe Phe Gly Ile Ser Pro
            100                 105                 110

Arg Glu Ala Leu Asn Met Asp Pro Gln Gln Arg Leu Leu Leu Glu Val
        115                 120                 125

Cys Trp Glu Ala Ala Glu Asp Ala Gly Ile Ser Pro Gly Pro Leu Ala
    130                 135                 140

Gly Ser Ala Thr Gly Val Phe Ala Gly Ser Cys Ala Gln Asp Phe Gly
145                 150                 155                 160

Leu Phe Gln Tyr Ala Asp Pro Ala Arg Ile Gly Ala Trp Ser Gly Ser
                165                 170                 175

Gly Val Ala His Ser Met Leu Ala Asn Arg Ile Ser Tyr Leu Leu Asp
            180                 185                 190

Leu Arg Gly Pro Ser Met Ala Val Asp Thr Ala Cys Ser Ser Ala Leu
        195                 200                 205

Val Ala Val His Leu Ala Cys Gln Ser Leu Arg Arg Arg Glu Cys Asp
```

-continued

```
    210                 215                 220

Ala Ala Phe Ala Gly Gly Val Asn Leu Ile Leu Thr Pro Glu Gly Met
225                 230                 235                 240

Ile Ala Leu Ser Lys Ala Arg Met Leu Ala Pro Asp Gly Arg Cys Lys
                245                 250                 255

Thr Phe Asp Ala Ala Ala Asp Gly Tyr Val Arg Gly Glu Gly Cys Gly
            260                 265                 270

Ile Val Leu Leu Lys Arg Leu Ser Asp Ala Leu Ala Asp Gly Asp Ala
        275                 280                 285

Ile Arg Ala Val Ile Arg Gly Ser Ala Ile Asn Gln Asp Gly Arg Ser
    290                 295                 300

Asn Gly Ile Thr Ala Pro Asn Leu Gln Ala Gln Lys Ala Val Leu Gln
305                 310                 315                 320

Glu Ala Val Ala Asn Ala His Ile Asp Pro Ser His Val Ser Leu Ile
                325                 330                 335

Glu Ala His Gly Thr Gly Thr Ser Leu Gly Asp Pro Ile Glu Ile Glu
            340                 345                 350

Ala Leu Gln Ser Val Tyr Asp Ala Pro Asp Ser Ala Pro Cys Leu Leu
        355                 360                 365

Gly Ser Val Lys Thr Asn Ile Gly His Leu Glu Gly Ala Ala Gly Ile
    370                 375                 380

Ala Gly Leu Ile Lys Ala Val Leu Ala Leu Gln His Arg Thr Ile Pro
385                 390                 395                 400

Pro His Leu His Phe Arg Arg Leu Asn Pro Asn Ile Ser Leu Asp Gly
                405                 410                 415

Ser Arg Phe Arg Ile Ala Thr Glu Ser Ser Pro Trp Thr Ser Glu Gly
            420                 425                 430

Arg Pro Arg Leu Ala Gly Val Ser Ser Phe Gly Phe Gly Gly Ser Asn
        435                 440                 445

Ala His Val Ile Leu Glu Glu Ala Pro Ala Leu Pro Leu Pro Lys Pro
    450                 455                 460

Val Thr Arg Pro Gln Leu Leu Thr Leu Ser Ala Arg Thr Asp Glu Ala
465                 470                 475                 480

Leu Gly Glu Leu Ala Gly His Phe Ala Glu Phe Leu Gln Ser His Pro
                485                 490                 495

Asn Ala Leu Leu Ser Asp Val Cys Phe Thr Ser Gln Val Gly Arg Asp
            500                 505                 510

Ala Tyr Ser His Arg Leu Ala Ile Thr Ala Ala Asp Ala Ala Glu Ala
        515                 520                 525

Val Ala Ala Leu Ala Ala Ala Pro Arg Arg Glu Val Ser Leu Arg Arg
    530                 535                 540

Arg Pro Ala Ile Ala Phe Leu Phe Thr Gly Gln Gly Ala Gln Tyr Ala
545                 550                 555                 560

Gly Met Gly Ala Glu Leu Tyr Lys Thr Gln Pro Val Phe Arg Asp Ala
                565                 570                 575

Leu Asp Arg Cys Ala Asp Trp Leu Arg Pro Gln Leu Asp Val Pro Leu
            580                 585                 590

Thr Val Leu Leu Phe Glu Ser Val Ser Pro Leu His Glu Thr Ala Tyr
        595                 600                 605

Thr Gln Pro Ala Met Phe Ala Leu Glu Trp Ala Leu Ala Gln Phe Trp
    610                 615                 620

Leu Ser Leu Gly Val Arg Pro Asp Tyr Val Leu Gly His Ser Leu Gly
625                 630                 635                 640
```

-continued

```
Glu Tyr Val Ala Ala Cys Val Ala Gly Ala Phe Ser Val Glu Asp Gly
                645                 650                 655

Leu Arg Leu Val Thr Ala Arg Gly Arg Leu Val Asn Ala Leu Pro Arg
            660                 665                 670

Gly Lys Ala Val Ile Val His Ala Asn Pro Ser Arg Ile Ala Ala Leu
        675                 680                 685

Ala Ala Lys Val Ala Val Ala Ala Ser Asn Ala Pro Asp Arg Thr Val
    690                 695                 700

Ile Ser Gly Thr Ala Ala Glu Ile Ala Glu Ala Gln Asp Asp Leu His
705                 710                 715                 720

Arg Ala Gly Val Glu Thr Arg Glu Leu Asn Val Ser His Ala Phe His
                725                 730                 735

Ser Pro Leu Met Asp Pro Ile Leu Asp Lys Phe Glu Ala Leu Ala Gly
            740                 745                 750

Ala Ile Ala Tyr Gln Pro Leu Ala Ile Pro Leu Val Ser Asn Val Ser
        755                 760                 765

Gly Ala Val Leu Pro Lys Gly Thr Thr Leu Asp Ala Arg Tyr Trp Arg
    770                 775                 780

Arg Gln Leu Arg Glu Thr Val Gln Phe Glu Ser Ala Met Arg Thr Leu
785                 790                 795                 800

Ala Asp Arg Glu Cys Lys Leu Phe Leu Glu Ile Gly Pro His Pro Thr
                805                 810                 815

Leu Thr Thr Leu Gly Arg Tyr Cys Leu Pro Asp Asp Gly Ala Val Trp
            820                 825                 830

Leu His Ser Leu Ser Lys Gly Arg Ser Asp Trp Ser Val Leu Leu Glu
        835                 840                 845

Ser Leu Gly Gly Leu Phe Thr Ala Gly Val Asn Pro Asp Trp Arg Gly
    850                 855                 860

Leu Tyr Ala Gly Glu Ser Pro Ser Arg Val Ala Leu Pro Thr Tyr Pro
865                 870                 875                 880

Phe Gln Arg Asp Thr Phe Ser Leu Arg Arg Val Pro Ala Arg Glu Pro
                885                 890                 895

Ala Arg Gly Gly Met Leu Gly Ala Arg Leu Asn Ser Ala Leu Gly Asp
            900                 905                 910

Val Ile Phe Glu Asn Ser Leu Thr Thr Glu Thr Pro Leu Leu His Glu
        915                 920                 925

His Val Ile Tyr Asp Ala Val Ile Val Pro Gly Ala Trp His Val Ser
    930                 935                 940

Ala Phe Leu Glu Ala Ala Gln Glu Val Phe Gly Pro Val Pro Cys Ala
945                 950                 955                 960

Val Ser Asp Val Met Met Arg Gln Ala Leu Ala Ile Pro Pro Asp Thr
                965                 970                 975

Pro Val Thr Val Gln Ala Ile Val Thr Pro Gly Glu Asp Gly Glu Ala
            980                 985                 990

Lys Val Gln Val Phe Ser Gln Asp Gly Asp Ser Trp Lys Leu His Thr
        995                1000                1005

Ala Ala Ser Leu Arg Ala Ala Thr Ala Gly Ala Val His Phe Glu Leu
   1010                1015                1020

Pro Ala Gln Pro Ser Glu Val Ile Ser Gly Asp Ala Phe Tyr Gly Ala
1025               1030                1035                1040

Met Asn Ala Arg Gly Val Asp Leu Gly Pro Ala Phe Ser Trp Val Glu
               1045                1050                1055
```

-continued

```
Glu Val Trp Arg Arg Asp Gly Glu Ala Leu Gly Arg Met Arg Leu Pro
            1060                1065                1070

Val Ala Glu Asp Gly Ala Asn Ala Tyr Arg Leu His Pro Gly Leu Ile
        1075                1080                1085

Asp Ser Cys Phe Gln Val Phe Gly Ala Thr Trp Pro Ala Glu Arg Cys
    1090                1095                1100

Gln Pro Gly Ala Tyr Val Pro Val Gly Ile Glu Ala Val Arg Phe Tyr
1105                1110                1115                1120

Arg Pro Pro Ala Gly Ser Leu Arg Cys His Ala Arg Leu Arg Pro Ser
                1125                1130                1135

Ser Ser Gly Pro Phe Val Gly Asp Leu Thr Leu Val Glu Glu Thr Gly
            1140                1145                1150

Ala Val Ile Ala Glu Phe Ser Gly Leu Ala Val Met His Ala Gly Thr
        1155                1160                1165

Leu Gln Ser Ala Gln Ser Trp Leu Gln Asp Val Gln Trp Gln Glu Cys
    1170                1175                1180

Glu Arg Ser Thr Thr Leu Lys Ser Asp Gly Pro Gly Lys Pro Glu Asp
1185                1190                1195                1200

Trp Leu Leu Cys Ala Gly Ala Asp Asp Val Ala Gly Leu Met Pro Gln
                1205                1210                1215

Glu Leu Arg Val Val Ser Gly Val Thr Leu Arg Gln Ala Leu Glu Gln
            1220                1225                1230

Thr Gln Thr Leu Val Gly Arg Pro Ala Arg Leu Trp Leu Ile Thr Arg
        1235                1240                1245

Gly Val His Arg Ile Ser Asp Asp Asp Ala Thr Pro Val Asp Pro Phe
    1250                1255                1260

Gln Ala Pro Leu Trp Gly Leu Gly Gln Ala Ile Ala Arg Glu His Pro
1265                1270                1275                1280

Glu Leu Trp Gly Gly Leu Ile Asp Leu Gly Cys Asp Asn Ala Asp Ile
                1285                1290                1295

Ala Ala Ala Met Leu Leu Asp Glu Ile Arg Tyr Ala Gly Asp Asp Lys
            1300                1305                1310

Ala Ile Ala Leu Arg Asn Gly Arg Arg Tyr Val Arg Arg Leu Val Arg
        1315                1320                1325

His Lys Glu Thr Ser Lys Arg Pro Pro Ala Ile Ser Ala Asp Gly Val
    1330                1335                1340

Tyr Leu Ile Thr Gly Gly Leu Gly Ala Leu Gly Arg Arg Val Ala Arg
1345                1350                1355                1360

Arg Leu Ile Glu Gln Gly Ala Arg Arg Leu Val Leu Val Gly Arg His
                1365                1370                1375

Thr Glu Ala Val Ala Asp Leu Glu Gln Leu Gly Ala Ala Val Met Val
            1380                1385                1390

Ala Ala Cys Asp Val Ser Ser Glu Gln Gln Leu Ala Ala Leu Leu Ala
        1395                1400                1405

Asp Pro Arg Thr Gln Pro Leu Arg Gly Val Val His Ala Ala Gly Val
    1410                1415                1420

Leu Asp Asp Gly Val Val Thr Glu Gln Thr Trp Ala Arg Phe Glu Lys
1425                1430                1435                1440

Val Leu Ala Pro Lys Leu Gln Gly Ala Trp Asn Leu His Gln Leu Thr
                1445                1450                1455

Arg His His Ala Leu Asp Phe Phe Val Leu Phe Ser Ser Ala Ala Ser
            1460                1465                1470

Leu Leu Gly Ser Ala Gly Gln Ser Asn Tyr Ser Ala Ala Asn Ala Phe
```

-continued

```
      1475                1480                1485

Leu Asp Ser Leu Ala His Met Arg Arg Ala Gln Gly Leu Pro Ala Leu
   1490                1495                1500

Ser Ile Asn Trp Gly Pro Trp Ala Gly Glu Gly Met Ala Ala Arg Ile
1505                1510                1515                1520

Ala Arg Gln Gly Leu Pro Gly Val Pro Leu Leu Pro Pro Glu Val Gly
               1525                1530                1535

Ala Arg Ile Phe Gly Asp Leu Leu Gly Glu Thr Ala Ala Gln Ile Ala
           1540                1545                1550

Val Phe Gln Val Ser Ala Glu Lys Arg Arg Ser Pro Ala Ser Asp Pro
       1555                1560                1565

Gly Phe Ile Gln Gln Leu Thr Glu Ala Ala Pro Glu Arg Arg Gln Glu
   1570                1575                1580

Leu Leu Gln Met Arg Ile Arg Lys Gln Ala Gly Gly Val Leu Ala Leu
1585                1590                1595                1600

Asp Ala Ser Lys Thr Leu Asp Pro Arg Arg Pro Leu Lys Glu Tyr Gly
               1605                1610                1615

Leu Asp Ser Leu Met Ala Leu Asp Leu Ala Arg Ala Ile Gly Glu Leu
           1620                1625                1630

Val Arg Lys Ser Leu Pro Ala Thr Leu Leu Tyr Asp His Pro Thr Val
       1635                1640                1645

Glu Lys Leu Ala Gly His Val Leu Arg Glu Leu Gly Leu Asp Val Pro
   1650                1655                1660

Ser Asp Ser Leu Val Asp Glu Val Arg Gln Leu Ser Glu Gln Glu Met
1665                1670                1675                1680

Ala Ala Phe Ile Thr Glu Thr Leu His His Leu Gly Glu Glu Arg
               1685                1690                1695


<210> SEQ ID NO 126
<211> LENGTH: 1434
<212> TYPE: PRT
<213> ORGANISM: Unknown organism
<220> FEATURE:
<223> OTHER INFORMATION: Origin of the sequence: Undetermined bacterium

<400> SEQUENCE: 126

Met Ser Asp Leu Thr Pro Leu Gln Gln Ala Val Leu Ala Leu Lys Arg
  1               5                  10                  15

Thr Arg Ala Arg Leu Asp Glu Leu Glu Ser Val His Asn Glu Pro Ile
             20                  25                  30

Ala Ile Val Gly Met Ala Cys Arg Phe Pro Gly Ala Asp Ser Pro Glu
         35                  40                  45

Ala Phe Trp Gln Leu Leu His Asp Gly Ile Asp Ala Ile Arg Glu Ile
     50                  55                  60

Pro Ala Gly Arg Trp Asp Ala Asp Ala Phe Tyr Asp Pro Asp Pro Asn
 65                  70                  75                  80

Ala Pro Gly Lys Met Tyr Thr Arg Leu Gly Gly Phe Leu Asp Gly Ala
                 85                  90                  95

Val Asp Gly Phe Asp Ala Gly Phe Phe Gly Ile Thr Pro Arg Glu Val
            100                 105                 110

Ala Gly Leu Asp Pro Gln Gln Arg Leu Leu Leu Glu Val Ala Trp Glu
        115                 120                 125

Ala Leu Glu Arg Ala Gly Arg Pro Pro Asp Ser Leu Ala Gly Ser Asp
    130                 135                 140

Thr Gly Val Phe Ile Gly Ile Ser Thr Asp Asp Tyr Ser Arg Leu Lys
```

-continued

```
145                 150                 155                 160

Pro Thr Asp Pro Ala Leu Ile Asp Ala Tyr Thr Gly Thr Gly Thr Ala
                165                 170                 175

Phe Ser Thr Ala Ala Gly Arg Ile Ser Tyr Leu Leu Gly Leu Gln Gly
            180                 185                 190

Pro Asn Phe Pro Val Asp Thr Ala Cys Ser Ser Ser Leu Val Ala Val
        195                 200                 205

His Leu Ala Cys Arg Ser Leu Gln Ser Arg Glu Cys Ser Met Ala Leu
    210                 215                 220

Ala Gly Gly Val Asn Leu Ile Leu Ala Pro Glu Ser Thr Ile Tyr Phe
225                 230                 235                 240

Cys Arg Leu Arg Ala Met Ala Ala Asp Gly Arg Cys Lys Ser Phe Ala
                245                 250                 255

Ala Ser Ala Asp Gly Tyr Gly Arg Gly Glu Gly Cys Gly Met Leu Val
            260                 265                 270

Leu Lys Arg Leu Ser Asp Ala Thr Arg Asp Gly Asp Arg Ile Leu Ala
        275                 280                 285

Leu Ile Arg Gly Ser Ala Val Asn His Gly Gly Arg Ser Asn Gly Leu
    290                 295                 300

Thr Ala Pro Asn Gly Pro Ala Gln Glu Ala Val Ile Arg Ala Ala Leu
305                 310                 315                 320

Lys Asn Ala Gly Met Ala Pro Ala Asp Val Asp Tyr Val Glu Ala His
                325                 330                 335

Gly Thr Gly Thr Pro Leu Gly Asp Pro Ile Glu Leu Arg Ala Met Ala
            340                 345                 350

Ala Val Leu Gly Glu Gly Arg Ala Val Asp Ser Pro Leu Ile Val Gly
        355                 360                 365

Ser Val Lys Thr Asn Phe Gly His Leu Glu Ala Ala Ala Gly Ile Ala
    370                 375                 380

Gly Leu Ile Lys Thr Ile Leu Ala Leu Gln His Arg Glu Ile Pro Pro
385                 390                 395                 400

His Leu His Phe Asn Ala Pro Asn Pro His Val Leu Trp Asn Glu Leu
                405                 410                 415

Pro Leu Lys Ile Ala Thr Ala Cys Ser Pro Trp Pro Ser Asn Gly Arg
            420                 425                 430

Pro Arg Val Ala Gly Val Ser Ser Phe Gly Ile Ser Gly Thr Asn Ser
        435                 440                 445

His Val Val Leu Ala Glu Ala Lys Thr Asn Val Glu Ala Lys Thr Asn
    450                 455                 460

Val Glu Ala Lys Thr Asn Val Glu Ala Lys Thr Ser Glu Glu Val Lys
465                 470                 475                 480

Ala Ser Val Glu Ala Lys Gly Asn Val Glu Ala Lys Ala Ser Ala Ser
                485                 490                 495

Val Pro Leu Leu Glu Gly Asp Ser Arg Pro Arg Ser Gly Gly Gly Gly
            500                 505                 510

Ser Gly Arg Pro Pro Ser Arg Glu Glu Val Pro Val Pro Asp Gln Leu
        515                 520                 525

His Ala Glu Asp Gly Arg Glu Tyr Leu Leu Pro Leu Ser Ala Arg His
    530                 535                 540

Pro Gln Ala Leu Arg Asp Leu Ala Gly Ala Tyr Arg Asp Gly Arg Phe
545                 550                 555                 560

His Ala Pro Leu Ser Ala Leu Cys Ser Ala Ala Ser Leu Thr Arg Ser
                565                 570                 575
```

-continued

His Tyr Glu His Arg Ala Ala Phe Val Ala Ser Ser Leu Pro Glu Phe
580 585 590

Asn Gln Leu Leu Glu Ala Phe Arg Arg Asn Glu Thr Asn Arg Gly Val
595 600 605

Ala Thr Gly Phe Ala Asp Pro Gly Val Arg Pro Lys Leu Ala Phe Ile
610 615 620

Phe Ser Gly Gln Gly Gly Gln Tyr Pro Arg Met Ala Tyr Arg Leu Tyr
625 630 635 640

Ser Asp Glu Pro Val Phe Arg Ser Ala Ile Glu Arg Cys Asp Ala Ala
645 650 655

Phe Arg Ser Phe Val Glu Trp Arg Leu Ala Asp Leu Leu Ala Asp Glu
660 665 670

Ser Gly Ala Trp Leu Ser Gln Ile Asp Arg Val Gln Pro Ala Leu Phe
675 680 685

Ala Val Gln Ile Ala Leu Val Glu Leu Leu Gln Ser Trp Gly Ile Arg
690 695 700

Pro Asp Gly Val Ala Gly His Ser Met Gly Glu Val Ala Ala Ala His
705 710 715 720

Val Ala Gly Ile Leu Thr Leu Glu Asp Ala Ala Arg Ile Ile Cys Arg
725 730 735

Arg Ser Arg Leu Leu Leu Gly Leu Arg Gly Arg Gly Ala Met Ala Leu
740 745 750

Val Glu Leu Pro Leu Asp Arg Ala Lys Ala Val Leu Ala Glu Arg Gly
755 760 765

Leu Thr Thr Val Ser Val Ala Ala Ser Asn Gly Pro Arg Ser Thr Val
770 775 780

Phe Ser Gly Asp Arg Val Ala Leu Glu His Leu Lys Asp Asp Phe Glu
785 790 795 800

Arg Arg Gly Val Phe Cys Arg Leu Ile Gln Val Asp Val Ala Ser His
805 810 815

Ser Ser Gln Val Asp Pro Leu Glu Asn Glu Leu Arg Gln Glu Leu Gly
820 825 830

Arg Val Ile Ala Lys Arg Ser Ala Val Pro Phe Phe Ser Thr Val Glu
835 840 845

Gly Gln Leu Ser Thr Gly Glu Ala Cys Asp Ala Ser Tyr Trp Val Ala
850 855 860

Asn Leu Arg Gln Pro Val Arg Phe Trp Glu Ser Leu Gln Ala Met Ala
865 870 875 880

Gly Asp Glu Phe Thr Gln Phe Leu Glu Ile Ser Pro His Pro Val Leu
885 890 895

Thr Pro Ser Ile Glu Asp Ser Leu Arg Thr Leu Gly Ile Asn Gly Leu
900 905 910

Val Arg Pro Val Leu Arg Arg Asp Glu Pro Glu Arg Arg Glu Leu Leu
915 920 925

Glu Leu Leu Ala Ala Leu Tyr Val Asn Gly Gln Arg Pro Asp Trp Arg
930 935 940

Ala Leu Ala Ser Ser Pro Asp Thr Arg Leu Asp Leu Pro Thr Tyr Pro
945 950 955 960

Trp Gln Arg Glu Arg Phe Trp Phe Ala Thr Ser Thr Arg Arg Ser Leu
965 970 975

Pro Ala Val Gly Gly His Pro Leu Leu Gly Arg Lys Val Glu Ile Ala
980 985 990

-continued

```
Leu Ala Pro Asp Thr His Val Trp Glu Ser Val Leu Ser Leu Asp Ala
        995                 1000                1005

Leu Pro Phe Leu Ala Asp His Arg Leu Asn Glu Leu Val Val Leu Pro
   1010                1015                1020

Gly Ala Ala Tyr Val Glu Met Ala Leu Ala Ala Ala Lys Glu Val Phe
1025                1030                1035                1040

Ala Gly Gly Cys Ser Leu Glu Glu Ile Arg Phe Glu Gln Met Leu Val
               1045                1050                1055

Val Pro Ser Ala Gly Ala Ser Arg Val Gln Val Ile Leu Glu Gly His
           1060                1065                1070

Ala Phe Arg Ile Ser Ser Leu Ala Glu Gly Gly Ser Asp Trp Thr Glu
       1075                1080                1085

His Ala Arg Gly Thr Met Ala Ala Ala Pro Asp Lys Val Ala Pro Thr
   1090                1095                1100

Val Ser Leu Pro Thr Leu Gly Asp Arg Ile Glu Gly Asp Asp Phe Tyr
1105                1110                1115                1120

Ala Ala Phe Ala Ser Gln Gly Met His Tyr Gly Asp Thr Phe Arg Gly
               1125                1130                1135

Ile Ala Glu Val Trp Arg Arg Asp Gly Glu Ala Val Ala Arg Leu Ser
           1140                1145                1150

Val Pro Asp Ala Val Arg Glu Ala Glu Ser Gly Tyr Thr Leu His Pro
       1155                1160                1165

Ala Leu Leu Asp Ala Cys Leu Gln Val Leu Gly Ala Thr Leu Gly Gly
   1170                1175                1180

Glu Gly Ser Ala Gly Pro Cys Val Pro Val Ala Ile Glu Arg Leu His
1185                1190                1195                1200

Cys Phe Gly Arg Pro Ala Gly Asp Leu Arg Val His Ala Arg Leu Thr
               1205                1210                1215

Gly Arg Leu Glu Gly Asp Val Thr Leu Cys Asp Ala Glu Gly His Val
           1220                1225                1230

Ile Leu Glu Val Gln Gly Leu Arg Ala Gln Glu Leu Glu Arg Gln Ser
       1235                1240                1245

Glu Trp Phe His Ala Met Glu Trp Glu Pro Gln Leu Leu Ala Glu Ser
   1250                1255                1260

Pro Thr Ala Thr Val Ser Gly Ala Trp Leu Val Ile Ala Asp Ala Gly
1265                1270                1275                1280

Gly Ile Ala Ala Ala Val Ala Arg Gly Leu Gly Thr Asn Thr Val Val
               1285                1290                1295

Ile Ser Gly Arg Asp Ala Glu Ile Pro Asp Gln Pro Tyr Arg Gly Val
           1300                1305                1310

Ile His Cys Gly Ser Leu Asp Glu Thr Glu Asp Glu Thr Asp Pro Ser
       1315                1320                1325

Ala Ala Gly Gly Thr Ala Cys Glu Asp Ile Leu Arg Ile Val Gln Glu
   1330                1335                1340

Phe Gly Val Gly Arg Ile Gln Leu Thr Lys Gln Ala Ser Asp Ala Glu
1345                1350                1355                1360

Ser Gln His Pro Arg Ile Trp Leu Ile Thr Ala Gly Val His Ala Glu
               1365                1370                1375

His Leu Gln Met Pro Val Val Pro Ala Arg Ala Pro Val Trp Gly Leu
           1380                1385                1390

Gly Arg Thr Ile Ala Ala Glu His Pro Glu Phe Ala Cys Thr Cys Ile
       1395                1400                1405

Asp Leu Asp Thr Ala Gly Glu Val Glu Val Gln Ala Leu Cys Arg Glu
```

-continued

```
1410                1415                1420

Ile Leu Ala Gly Ser Ser Glu Arg Gln Gly
1425                1430
```